(12) United States Patent
Chu et al.

(10) Patent No.: US 7,816,364 B2
(45) Date of Patent: Oct. 19, 2010

(54) GRP119 RECEPTOR AGONISTS IN METHODS OF INCREASING BONE MASS AND OF TREATING OSTEOPOROSIS AND OTHER CONDITIONS CHARACTERIZED BY LOW BONE MASS, AND COMBINATION THERAPY RELATING THERETO

(75) Inventors: Zhi-Liang Chu, San Diego, CA (US); James N. Leonard, San Diego, CA (US); Juerg Lehmann, San Diego, CA (US); Robert M. Jones, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 283 days.

(21) Appl. No.: 11/989,038

(22) PCT Filed: Apr. 10, 2007

(86) PCT No.: PCT/US2007/008926

§ 371 (c)(1),
(2), (4) Date: Jan. 22, 2008

(87) PCT Pub. No.: WO2007/120702

PCT Pub. Date: Oct. 25, 2007

(65) Prior Publication Data

US 2009/0270422 A1    Oct. 29, 2009

Related U.S. Application Data

(60) Provisional application No. 60/791,613, filed on Apr. 11, 2006, provisional application No. 60/834,737, filed on Jul. 31, 2006, provisional application No. 60/851,244, filed on Oct. 12, 2006.

(51) Int. Cl.
A61K 31/4965    (2006.01)
(52) U.S. Cl. .................................................. 514/256
(58) Field of Classification Search .................. 514/256
See application file for complete search history.

(56) References Cited

U.S. PATENT DOCUMENTS

| | | | |
|---|---|---|---|
| 4,166,452 A | 9/1979 | Generales, Jr. et al. |
| 4,256,108 A | 3/1981 | Theeuwes et al. |
| 4,265,874 A | 5/1981 | Bonsen et al. |
| 4,704,362 A | 11/1987 | Itakura et al. |
| 5,462,856 A | 10/1995 | Lerner et al. |
| 5,922,576 A | 7/1999 | He et al. |
| 6,040,145 A | 3/2000 | Huber |
| 6,051,386 A | 4/2000 | Lerner et al. |
| 6,100,042 A | 8/2000 | Fowlkes et al. |
| 6,100,234 A | 8/2000 | Huber |
| 6,166,063 A | 12/2000 | Villhauer |
| 6,183,974 B1 | 2/2001 | Bringhurst et al. |
| 6,221,660 B1 | 4/2001 | Bonini et al. |
| 6,242,422 B1 | 6/2001 | Karanewsky |
| 6,303,661 B1 | 10/2001 | Demuth et al. |
| 6,380,398 B2 | 4/2002 | Kanstrup et al. |
| 6,395,767 B2 | 5/2002 | Robl et al. |
| 6,410,508 B1 | 6/2002 | Isales et al. |
| 6,432,969 B1 | 8/2002 | Villhauer et al. |
| 6,468,756 B1 | 10/2002 | Bonini et al. |
| 6,573,287 B2 | 6/2003 | Sulsky et al. |
| 6,617,340 B1 | 9/2003 | Villhauer et al. |
| 6,645,995 B2 | 11/2003 | Kanstrup et al. |
| 6,653,064 B1 | 11/2003 | Jochum et al. |
| 6,699,871 B2 | 3/2004 | Edmondson et al. |
| 6,706,742 B2 | 3/2004 | de Nanteuil et al. |
| 6,710,040 B1 | 3/2004 | Hulin et al. |
| 6,716,843 B2 | 4/2004 | de Nanteuil et al. |
| 6,727,261 B2 | 4/2004 | Gobbi et al. |
| 6,800,650 B2 | 10/2004 | Boehringer et al. |
| 6,803,357 B1 | 10/2004 | Bachovchin et al. |
| 6,812,350 B2 | 11/2004 | Hulin et al. |
| 6,844,316 B2 | 1/2005 | Niestroj et al. |
| 6,849,622 B2 | 2/2005 | Yasuda et al. |
| 6,861,440 B2 | 3/2005 | Boehringer et al. |

(Continued)

FOREIGN PATENT DOCUMENTS

CA    2289124    11/1998

(Continued)

OTHER PUBLICATIONS

Abe et al., "First synethesis and determination of the absolute configuration of sulphostin, a novel inhibitor of dipeptidyl peptidasse IV," *J Nat Prod* (2004), 67:99-1004.

(Continued)

*Primary Examiner*—Raymond J Henley, III
(74) *Attorney, Agent, or Firm*—Fish & Richardson P.C.

(57) ABSTRACT

The present invention relates to the use of GPR119 receptor agonists for treating or preventing a condition characterized by low bone mass, such as osteoporosis, and for increasing bone mass in an individual. The present invention further relates to the use of a GPR119 receptor agonist in combination with a dipeptidyl peptidase IV (DPP-IV) inhibitor for treating or preventing a condition characterized by low bone mass, such as osteoporosis, and for increasing bone mass in an individual. A GPR119 receptor agonist and the combination of a GPR119 receptor agonist and a DPP-IV inhibitor promote bone formation in an individual.

171 Claims, 6 Drawing Sheets

U.S. PATENT DOCUMENTS

| | | |
|---|---|---|
| 6,867,205 B2 | 3/2005 | Boehringer et al. |
| 6,869,947 B2 | 3/2005 | Kanstrup et al. |
| 6,897,222 B2 | 5/2005 | Gobbi et al. |
| 6,946,480 B2 | 9/2005 | Demuth et al. |
| 6,949,515 B2 | 9/2005 | Demuth et al. |
| 6,995,183 B2 | 2/2006 | Hamann et al. |
| 7,008,957 B2 | 3/2006 | Wagner et al. |
| 7,022,718 B2 | 4/2006 | Boehringer et al. |
| 7,026,316 B2 | 4/2006 | Ashton et al. |
| 7,053,055 B2 | 5/2006 | Demuth et al. |
| 7,060,722 B2 | 6/2006 | Kitajima et al. |
| 7,074,794 B2 | 7/2006 | Kitajima et al. |
| 7,074,798 B2 | 7/2006 | Yoshikawa et al. |
| 7,083,933 B1 | 8/2006 | Griffin et al. |
| 7,084,120 B2 | 8/2006 | Demuth et al. |
| 7,094,800 B2 | 8/2006 | Schoenafinger et al. |
| 7,122,555 B2 | 10/2006 | Boehringer et al. |
| 7,132,426 B2 | 11/2006 | Jones et al. |
| 7,217,711 B2 | 5/2007 | Eckhardt et al. |
| 7,238,670 B2 | 7/2007 | Natarajan et al. |
| 7,238,671 B2 | 7/2007 | Natarajan et al. |
| 7,470,699 B2 | 12/2008 | Jones et al. |
| 7,495,002 B2 | 2/2009 | Langkopf et al. |
| 7,501,426 B2 | 3/2009 | Himmelsbach et al. |
| 7,550,455 B2 | 6/2009 | Himmelsbach et al. |
| 7,645,763 B2 | 1/2010 | Himmelsbach et al. |
| 2002/0006899 A1 | 1/2002 | Pospisilik et al. |
| 2002/0049164 A1 | 4/2002 | Demuth et al. |
| 2002/0103384 A1 | 8/2002 | Kanstrup et al. |
| 2002/0183367 A1 | 12/2002 | Sulsky et al. |
| 2002/0198205 A1 | 12/2002 | Himmelsbach et al. |
| 2003/0078247 A1 | 4/2003 | DeNanteuil et al. |
| 2003/0087950 A1 | 5/2003 | DeNanteuil et al. |
| 2003/0100563 A1 | 5/2003 | Edmondson et al. |
| 2003/0105077 A1 | 6/2003 | Kanstrup et al. |
| 2003/0119738 A1 | 6/2003 | Niestroj et al. |
| 2003/0119750 A1 | 6/2003 | Demuth et al. |
| 2003/0125304 A1 | 7/2003 | Demuth et al. |
| 2003/0125539 A1 | 7/2003 | Bonini et al. |
| 2003/0130199 A1 | 7/2003 | Von Hoersten et al. |
| 2003/0130281 A1 | 7/2003 | Boehringer et al. |
| 2003/0134802 A1 | 7/2003 | Demuth et al. |
| 2003/0162820 A1 | 8/2003 | Demuth et al. |
| 2003/0195188 A1 | 10/2003 | Boehringer et al. |
| 2003/0199528 A1 | 10/2003 | Kanstrup et al. |
| 2003/0216382 A1 | 11/2003 | Boehringer et al. |
| 2003/0216450 A1 | 11/2003 | Evans et al. |
| 2003/0225102 A1 | 12/2003 | Sankaranarayanan et al. |
| 2003/0232788 A1 | 12/2003 | Karanewsky et al. |
| 2004/0034014 A1 | 2/2004 | Kanstrup et al. |
| 2004/0063935 A1 | 4/2004 | Yasuda et al. |
| 2004/0072892 A1 | 4/2004 | Fukushima et al. |
| 2004/0077645 A1 | 4/2004 | Himmelsbach et al. |
| 2004/0082570 A1 | 4/2004 | Yoshikawa et al. |
| 2004/0087587 A1 | 5/2004 | Himmelsbach et al. |
| 2004/0097510 A1 | 5/2004 | Himmelsbach et al. |
| 2004/0106656 A1 | 6/2004 | Ashton et al. |
| 2004/0110817 A1 | 6/2004 | Hulin et al. |
| 2004/0116328 A1 | 6/2004 | Yoshikawa et al. |
| 2004/0138214 A1 | 7/2004 | Himmelsbach et al. |
| 2004/0176406 A1 | 9/2004 | Gobbi et al. |
| 2004/0180925 A1 | 9/2004 | Matsuno et al. |
| 2004/0229926 A1 | 11/2004 | Yasuda et al. |
| 2004/0242898 A1 | 12/2004 | Hulin et al. |
| 2004/0254226 A1 | 12/2004 | Feng et al. |
| 2004/0259883 A1 | 12/2004 | Sakashita et al. |
| 2004/0259902 A1 | 12/2004 | Boehringer et al. |
| 2004/0259903 A1 | 12/2004 | Boehringer et al. |
| 2005/0004205 A1 | 1/2005 | Evans et al. |
| 2005/0032804 A1 | 2/2005 | Cypes et al. |
| 2005/0038020 A1 | 2/2005 | Hamann et al. |
| 2005/0043292 A1 | 2/2005 | Parker et al. |
| 2005/0059650 A1 | 3/2005 | Jones et al. |
| 2005/0059724 A1 | 3/2005 | Schoenafinger et al. |
| 2006/0014764 A1 | 1/2006 | Feng et al. |
| 2006/0024313 A1 | 2/2006 | Chen et al. |
| 2006/0039974 A1 | 2/2006 | Akiyama et al. |
| 2006/0040963 A1 | 2/2006 | Mathvink et al. |
| 2006/0046978 A1 | 3/2006 | Pierau et al. |
| 2006/0052382 A1 | 3/2006 | Duffy et al. |
| 2006/0069116 A1 | 3/2006 | Ashton et al. |
| 2006/0074087 A1 | 4/2006 | Ashton et al. |
| 2006/0111336 A1 | 5/2006 | Duffy et al. |
| 2006/0135512 A1 | 6/2006 | Boehringer et al. |
| 2006/0135767 A1 | 6/2006 | Feng et al. |
| 2006/0142262 A1 | 6/2006 | Jones et al. |
| 2006/0142576 A1 | 6/2006 | Meng et al. |
| 2006/0154866 A1 | 7/2006 | Chu et al. |
| 2006/0217379 A1 | 9/2006 | Jones et al. |
| 2007/0032420 A1 | 2/2007 | Polidori et al. |
| 2007/0066590 A1 | 3/2007 | Jones et al. |
| 2007/0070562 A1 | 3/2007 | Jones et al. |
| 2007/0072803 A1 | 3/2007 | Chu et al. |
| 2007/0072804 A1 | 3/2007 | Chu et al. |
| 2007/0072844 A1 | 3/2007 | Jones et al. |
| 2007/0078150 A1 | 4/2007 | Jones et al. |
| 2007/0082874 A1 | 4/2007 | Jones et al. |
| 2007/0155763 A1 | 7/2007 | Jones et al. |
| 2007/0167473 A1 | 7/2007 | Jones et al. |
| 2007/0287670 A1 | 12/2007 | Natarajan et al. |
| 2008/0058339 A1 | 3/2008 | Brandt et al. |
| 2009/0036434 A1 | 2/2009 | Jones et al. |
| 2009/0253153 A1 | 10/2009 | Chu et al. |

FOREIGN PATENT DOCUMENTS

| | | |
|---|---|---|
| CA | 2289125 | 11/1998 |
| CA | 2339537 | 3/2000 |
| CA | 2433090 | 7/2002 |
| CA | 2 123 128 | 5/2003 |
| CA | 2466870 | 6/2003 |
| DE | 296075 | 11/1991 |
| DE | 19616486 | 10/1997 |
| DE | 19823831 | 12/1999 |
| DE | 19828113 | 1/2000 |
| DE | 19834591 | 2/2000 |
| DE | 10143840 | 3/2003 |
| DE | 10238243 | 3/2004 |
| DE | 10238470 | 3/2004 |
| DE | 10238477 | 3/2004 |
| DE | 10251927 | 5/2004 |
| DE | 10256264 | 6/2004 |
| DE | 10327439 | 1/2005 |
| DE | 10333935 | 2/2005 |
| DE | 200410032263 | 1/2006 |
| EP | 0995440 | 4/2000 |
| EP | 1043328 | 10/2000 |
| EP | 1050540 | 11/2000 |
| EP | 1092727 | 4/2001 |
| EP | 1215207 | 6/2002 |
| EP | 1 22 8061 | 8/2002 |
| EP | 1 248 604 | 10/2002 |
| EP | 1245568 | 10/2002 |
| EP | 1258476 | 11/2002 |
| EP | 1 280 797 | 2/2003 |
| EP | 1 296 974 | 4/2003 |
| EP | 1 301 187 | 4/2003 |
| EP | 1323710 | 7/2003 |
| EP | 1333025 | 8/2003 |
| EP | 1338592 | 8/2003 |
| EP | 1338651 | 8/2003 |
| EP | 1354882 | 10/2003 |
| EP | 1304327 | 4/2004 |
| EP | 1426366 | 4/2004 |

| | | | | | | |
|---|---|---|---|---|---|---|
| EP | 1 465 891 | 10/2004 | | WO | WO 01/81337 | 11/2001 |
| EP | 1 469 873 | 10/2004 | | WO | WO 01/87929 | 11/2001 |
| EP | 1 490 335 | 12/2004 | | WO | WO 01/96295 | 12/2001 |
| EP | 1489088 | 12/2004 | | WO | WO 01/97808 | 12/2001 |
| EP | 1538217 | 6/2005 | | WO | WO 02/02560 | 1/2002 |
| EP | 1 624 874 | 2/2006 | | WO | WO 02/14271 | 2/2002 |
| EP | 1627870 | 2/2006 | | WO | WO 02/30890 | 4/2002 |
| EP | 1659123 | 5/2006 | | WO | WO 02/30891 | 4/2002 |
| EP | 1664031 | 6/2006 | | WO | WO 02/34900 | 5/2002 |
| EP | 1671649 | 6/2006 | | WO | WO 02/38541 | 5/2002 |
| EP | 1287133 | 12/2006 | | WO | WO 02/42461 | 5/2002 |
| EP | 1 902 730 | 3/2008 | | WO | WO 02/44362 | 6/2002 |
| FR | 2822826 | 10/2002 | | WO | WO 02/49648 | 6/2002 |
| FR | 2824825 | 11/2002 | | WO | WO 02/51836 | 7/2002 |
| JP | 1998081666 | 3/1998 | | WO | WO 02/55088 | 7/2002 |
| JP | 1998182613 | 7/1998 | | WO | WO 02/62764 | 8/2002 |
| JP | 2000181616 | 7/2000 | | WO | WO 02/68420 | 9/2002 |
| JP | 200511559 | 9/2000 | | WO | WO 02/76450 | 10/2002 |
| JP | 2000327689 | 11/2000 | | WO | WO 02/083109 | 10/2002 |
| JP | 2001510442 | 7/2001 | | WO | WO 02/83128 | 10/2002 |
| JP | 2002265439 | 9/2002 | | WO | WO 03/000180 | 1/2003 |
| JP | 2002356471 | 12/2002 | | WO | WO 03/000181 | 1/2003 |
| JP | 2002356472 | 12/2002 | | WO | WO 03/000250 | 1/2003 |
| JP | 2002363157 | 12/2002 | | WO | WO 03/002530 | 1/2003 |
| JP | 2003238566 | 8/2003 | | WO | WO 03/002531 | 1/2003 |
| JP | 2003300977 | 10/2003 | | WO | WO 03/002553 | 1/2003 |
| JP | 2003327532 | 11/2003 | | WO | WO 03/002593 | 1/2003 |
| JP | 2004002367 | 1/2004 | | WO | WO 03/002595 | 1/2003 |
| JP | 2004002368 | 1/2004 | | WO | WO 03/002596 | 1/2003 |
| JP | 2004026678 | 1/2004 | | WO | WO 03/004496 | 1/2003 |
| JP | 2004026820 | 1/2004 | | WO | WO 03/004498 | 1/2003 |
| JP | 2004035574 | 2/2004 | | WO | WO 03/015775 | 2/2003 |
| JP | 2004043429 | 2/2004 | | WO | WO 03/022871 | 3/2003 |
| JP | 2004269469 | 3/2004 | | WO | WO 03/024942 | 3/2003 |
| JP | 2004244412 | 9/2004 | | WO | WO 03/024965 | 3/2003 |
| JP | 2004269468 | 9/2004 | | WO | WO 03/026661 | 4/2003 |
| JP | 2004315496 | 11/2004 | | WO | WO 03/035057 | 5/2003 |
| JP | 2005023038 | 1/2005 | | WO | WO 03/035067 | 5/2003 |
| WO | WO 91/16339 | 10/1991 | | WO | WO 03/037327 | 5/2003 |
| WO | WO 93/08259 | 4/1993 | | WO | WO 03/038123 | 5/2003 |
| WO | WO 93/10127 | 5/1993 | | WO | WO 03/040174 | 5/2003 |
| WO | WO 95/15309 | 6/1995 | | WO | WO 03/045228 | 6/2003 |
| WO | WO 95/29691 | 11/1995 | | WO | WO 03/045977 | 6/2003 |
| WO | WO 97/40832 | 11/1997 | | WO | WO 03/055881 | 7/2003 |
| WO | WO 98/18763 | 5/1998 | | WO | WO 03/057144 | 7/2003 |
| WO | WO 98/19998 | 5/1998 | | WO | WO 03/057666 | 7/2003 |
| WO | WO 98/50046 | 11/1998 | | WO | WO 03/068748 | 8/2003 |
| WO | WO 98/50066 | 11/1998 | | WO | WO 03/068757 | 8/2003 |
| WO | WO 99/14344 | 3/1999 | | WO | WO 03/072528 | 9/2003 |
| WO | WO 99/16864 | 4/1999 | | WO | WO 03/072556 | 9/2003 |
| WO | WO 99/25719 | 5/1999 | | WO | WO 03/074500 | 9/2003 |
| WO | WO 99/38501 | 8/1999 | | WO | WO 03/080633 | 10/2003 |
| WO | WO 99/56753 | 11/1999 | | WO | WO 03/082817 | 10/2003 |
| WO | WO 99/61431 | 12/1999 | | WO | WO 03/084940 | 10/2003 |
| WO | WO 99/62914 | 12/1999 | | WO | WO 03/095425 | 11/2003 |
| WO | WO 99/67278 | 12/1999 | | WO | WO 03/099279 | 12/2003 |
| WO | WO 00/10549 | 3/2000 | | WO | WO 03/101448 | 12/2003 |
| WO | WO 00/12704 | 3/2000 | | WO | WO 03/101958 | 12/2003 |
| WO | WO00/22129 | 4/2000 | | WO | WO 03/104229 | 12/2003 |
| WO | WO 00/23421 | 4/2000 | | WO | WO 03/105763 | 12/2003 |
| WO | WO 00/31258 | 6/2000 | | WO | WO 03/106456 | 12/2003 |
| WO | WO 00/34241 | 6/2000 | | WO | WO 2004/000327 | 12/2003 |
| WO | WO 00/50562 | 8/2000 | | WO | WO 2004/004661 | 1/2004 |
| WO | WO 00/53171 | 9/2000 | | WO | WO 2004/007446 | 1/2004 |
| WO | WO 00/56296 | 9/2000 | | WO | WO 2004/007468 | 1/2004 |
| WO | WO 00/56297 | 9/2000 | | WO | WO 2004/009544 | 1/2004 |
| WO | WO 00/69868 | 11/2000 | | WO | WO 2004/014860 | 2/2004 |
| WO | WO 00/71135 | 11/2000 | | WO | WO 2004/018467 | 3/2004 |
| WO | WO 01/34594 | 5/2001 | | WO | WO 2004/018468 | 3/2004 |
| WO | WO 01/52825 | 7/2001 | | WO | WO 2004/018469 | 3/2004 |
| WO | WO 01/55105 | 8/2001 | | WO | WO 2004/020407 | 3/2004 |
| WO | WO 01/68603 | 9/2001 | | WO | WO 2004/024943 | 3/2004 |
| WO | WO 01/81304 | 11/2001 | | WO | WO 2004/032836 | 4/2004 |

| | | |
|---|---|---|
| WO | WO 2004/033455 | 4/2004 |
| WO | WO 2004/037169 | 5/2004 |
| WO | WO 2004/037181 | 5/2004 |
| WO | WO 2004/041795 | 5/2004 |
| WO | WO 2004/041820 | 5/2004 |
| WO | WO 2004/043940 | 5/2004 |
| WO | WO 2004/046106 | 6/2004 |
| WO | WO 2004/048379 | 6/2004 |
| WO | WO 2004/050022 | 6/2004 |
| WO | WO 2004/050658 | 6/2004 |
| WO | WO 2004/052362 | 6/2004 |
| WO | WO 2004/052850 | 6/2004 |
| WO | WO 2004/058266 | 7/2004 |
| WO | WO 2004/064778 | 8/2004 |
| WO | WO 2004/065380 | 8/2004 |
| WO | WO 2004/069162 | 8/2004 |
| WO | WO 2004/071454 | 8/2004 |
| WO | WO 2004/8067509 | 8/2004 |
| WO | WO 2004/076413 | 9/2004 |
| WO | WO 2004/076433 | 9/2004 |
| WO | WO 2004/076434 | 9/2004 |
| WO | WO 2004/085378 | 10/2004 |
| WO | WO 2004/085661 | 10/2004 |
| WO | WO 2004/087053 | 10/2004 |
| WO | WO 2004/087650 | 10/2004 |
| WO | WO 2004/092128 | 10/2004 |
| WO | WO 2004/096806 | 11/2004 |
| WO | WO 2004/099134 | 11/2004 |
| WO | WO 2004/103276 | 12/2004 |
| WO | WO 2004/103993 | 12/2004 |
| WO | WO 2004/104215 | 12/2004 |
| WO | WO 2004/104216 | 12/2004 |
| WO | WO 2004/108730 | 12/2004 |
| WO | WO 2004/110375 | 12/2004 |
| WO | WO 2004/110436 | 12/2004 |
| WO | WO 2004/111041 | 12/2004 |
| WO | WO 2004/111051 | 12/2004 |
| WO | WO 2004/112701 | 12/2004 |
| WO | WO 2005/000846 | 1/2005 |
| WO | WO 2005/000848 | 1/2005 |
| WO | WO 2005/003135 | 1/2005 |
| WO | WO 2005/007647 | 1/2005 |
| WO | WO 2005/007658 | 1/2005 |
| WO | WO 2005/009956 | 2/2005 |
| WO | WO 2005/011581 | 2/2005 |
| WO | WO 2005/012249 | 2/2005 |
| WO | WO 2005/012308 | 2/2005 |
| WO | WO 2005/012312 | 2/2005 |
| WO | WO 2005/019168 | 3/2005 |
| WO | WO 2005/020920 | 3/2005 |
| WO | WO 2005/021536 | 3/2005 |
| WO | WO 2005/023762 | 3/2005 |
| WO | WO 2005/025554 | 3/2005 |
| WO | WO 2005/026148 | 3/2005 |
| WO | WO 2005/030127 | 4/2005 |
| WO | WO 2005/030751 | 4/2005 |
| WO | WO 2005/032590 | 4/2005 |
| WO | WO 2005/033099 | 4/2005 |
| WO | WO 2005/034940 | 4/2005 |
| WO | WO 2005/037779 | 4/2005 |
| WO | WO 2005/037828 | 4/2005 |
| WO | WO 2005/040095 | 5/2005 |
| WO | WO 2005/042488 | 5/2005 |
| WO | WO 2005/042533 | 5/2005 |
| WO | WO 2005/044195 | 5/2005 |
| WO | WO 2005/047297 | 5/2005 |
| WO | WO 2005/049022 | 6/2005 |
| WO | WO 2005/051950 | 6/2005 |
| WO | WO 2005/058849 | 6/2005 |
| WO | WO 2005/058901 | 6/2005 |
| WO | WO 2005/061489 | 7/2005 |
| WO | WO 2005/063750 | 7/2005 |
| WO | WO 2005/072530 | 8/2005 |
| WO | WO 2005/075426 | 8/2005 |
| WO | WO 2005/079795 | 9/2005 |
| WO | WO 2005/082348 | 9/2005 |
| WO | WO 2005/082849 | 9/2005 |
| WO | WO 2005/082906 | 9/2005 |
| WO | WO 2005/085246 | 9/2005 |
| WO | WO 2005/087235 | 9/2005 |
| WO | WO 2005/094323 | 10/2005 |
| WO | WO 2005/95339 | 10/2005 |
| WO | WO 2005/095381 | 10/2005 |
| WO | WO 2005/100334 | 10/2005 |
| WO | WO 2005/106011 | 11/2005 |
| WO | WO 2005/108382 | 11/2005 |
| WO | WO 2005/115982 | 12/2005 |
| WO | WO 2005/116014 | 12/2005 |
| WO | WO 2005/116029 | 12/2005 |
| WO | WO 2005/118555 | 12/2005 |
| WO | WO 2005/120494 | 12/2005 |
| WO | WO 2005/121089 | 12/2005 |
| WO | WO 2005/121121 | 12/2005 |
| WO | WO 2005/121131 | 12/2005 |
| WO | WO 2005/123685 | 12/2005 |
| WO | 2006/000576 | 1/2006 |
| WO | WO 2006/009886 | 1/2006 |
| WO | WO 2006/011035 | 2/2006 |
| WO | WO 2006/012395 | 2/2006 |
| WO | WO 2006/012441 | 2/2006 |
| WO | WO 2006/013104 | 2/2006 |
| WO | WO 2006/015691 | 2/2006 |
| WO | WO 2006/015699 | 2/2006 |
| WO | WO 2006/020017 | 2/2006 |
| WO | WO 2006/023750 | 3/2006 |
| WO | WO 2006/027204 | 3/2006 |
| WO | WO 2006/029769 | 3/2006 |
| WO | WO 2006/030847 | 3/2006 |
| WO | WO 2006/033848 | 3/2006 |
| WO | WO 2006/039325 | 4/2006 |
| WO | WO 2006/040625 | 4/2006 |
| WO | WO 2006/040966 | 4/2006 |
| WO | WO 2006/043490 | 4/2006 |
| WO | WO 2006/047248 | 5/2006 |
| WO | WO 2006/058064 | 6/2006 |
| WO | WO 2006/058628 | 6/2006 |
| WO | WO 2006/067531 | 6/2006 |
| WO | WO 2006/067532 | 6/2006 |
| WO | WO 2006/068163 | 6/2006 |
| WO | WO 2006/068978 | 6/2006 |
| WO | WO 2006/070208 | 6/2006 |
| WO | 2006/076231 | 7/2006 |
| WO | WO 2006/071752 | 7/2006 |
| WO | WO 2006/071762 | 7/2006 |
| WO | WO 2006/083491 | 8/2006 |
| WO | WO 2006/086727 | 8/2006 |
| WO | WO 2007/003960 | 1/2007 |
| WO | WO 2007/003961 | 1/2007 |
| WO | WO 2007/003962 | 1/2007 |
| WO | WO 2007/003964 | 1/2007 |
| WO | WO 2007/035355 | 3/2007 |
| WO | 2007/120689 | 10/2007 |
| WO | WO 2007/116229 | 10/2007 |
| WO | WO 2007/116230 | 10/2007 |
| WO | WO 2007/120702 | 10/2007 |
| WO | WO 2007/138362 | 12/2007 |
| WO | WO 2008/005569 | 1/2008 |
| WO | WO 2008/005576 | 1/2008 |
| WO | WO 2008/008895 | 1/2008 |
| WO | WO 2008/025798 | 3/2008 |
| WO | WO 2008/025799 | 3/2008 |
| WO | WO 2008/025800 | 3/2008 |
| WO | WO 2008/070692 | 6/2008 |
| WO | WO 2008/076243 | 6/2008 |

| WO | WO 2010/001166 | 1/2010 |

OTHER PUBLICATIONS

Adler, Claus-Peter, Bone Diseases, Springer-Verlag, Germany (2000).
Adult Treatment Panel III (ATP III: National Institutes of Health: Third Report of the National Cholesterol Education Program Expert Panel on Detection, Evaluation, and Treatment of High Blood Cholesterol in Adults (Adult Treatment Panel IIIJ), Executive Summary, Bethesda, MD., National Institutes of Health, National Heart, Lung and Blood Institute, 2001 (NIH pub. No. 01-3670).
Ahren et al., "Inhibition of Dipeptidyl Peptidase-4 Augments Insulin Secretion in Response to Exogenously Adminstered Glucagon-Like Peptide-1, Glucose-Dependent Inulinotropic Polypeptide, Pituitary Adenylate Cyclase-Activating Polypeptide, and Gastrin-Releasing Peptide in Mice," Endocrinology (2005) 146(4):2055-2059.
Ahren et al., "Inhibition of dipeptidyl peptidase-4 reduces glycemia, sustains insulin levels, and reduces glucagon levels in type 2 diabetes," *J Clin Endocrinol Metab* (2004), 89:2078-2084.
Ahren et al., "Inhibition of dipeptidyl peptidase IV improves metabolic control over a 4-week study period in type 2 diabetes." *Diabetes Care* (2002), 25:869-875.
Atik et al., "Burden of osteoporosis", *Clinical Orthopaedics and Related Research*, 443:19-24, (2006).
Bak et al., "The effect of aging on fracture healing in the rat", *Calcified Tissue International*, 45:292-297, (1989).
Berge et al., "Pharmaceutical salts," *Journal of Pharmaceutical Sciences* (1977) 66:1-19.
Bollag et al., "Osteoblast-derived cells express functional glucose-dependent insulinotropic peptide receptors", *Endocrinology*, 141:1228-1235, (2000).
Bollag, R.J., et al. "Glucose-dependent insulinotropic peptide is an integrative hormone with osteotropic effects" Molecular and Cellular Endocrinology, 177,(2001) pp. 35-41.
Bose et al., "Glucagon-like peptide 1 can directly protect the heart against ischemia/reperfusion injury," Diabetes (2005) 54:146-151.
Brubaker et al., "Regulation of glucagon-like peptide-1 synthesis and secretion in the GLUTag enteroendoctrine cell line," *Endocrinology* (1998), 139:4108-4114.
Caldwell et al., "Fluoropyrrolidine amides as dipeptidyl peptidase IV inhibitors," *Biorg Med Chem Lett* (2004) 14(5):1265-1268.
Campbell et al., "Selective $A_1$-adenosine receptor antagonists identified using yeast *Saccharomyces cerevisae* functional assays", *Bioorganic & Medicinal Chemistry Letters*, 9:2413-2418, (1999).
Cello et al., "Chemical synthesis of poliovirus cDNA: generation of infectious virus in the absence of natural template", *Science*, 297:1016-1018, (2002).
Chen et al., "CD26," J. Biol Regul Homest Agents (2004), 18:47-54.
Chen et al., "Glucose responsiveness of a reporter gene transduced into hepatocytic cells using a retroviral vector," FEBS Letters (1995) 365:223-226.
Chu et al., "A role for intestinal endocrine cell-expressed, GPR119 in glycemic control by enhancing GLP-1 and G IP release", *Endocrinology*, 2008.
Chu et al., "A role for β-cell-expressed G protein-coupled receptor 119 in glycemic control by enhancing glucose-dependent insulin release", *Endocrinology*, 148, p. 2601-2609, (2007).
Chu et al., "Agonists of the orphan GPCR 19AJ promote insulin secretion by stimulating both GLP-1—producing endocrine cells and pancreatic β-cell", Abstract #112, p. 42, *Diabetes Mellitus: Molecular Mechanisms, Genetics and New Therapies*, Keystone Symposia, Jan. 27-Feb. 2, 2005, Keystone, Colorado.
Chu et al., "AR231453 mediates improved glycemic control exclusively via GDIR/GPR119", Abstract # 117 & Poster, *Diabetes: Molecular Genetics, Signaling Pathways and Integrated Physiology*, Keystone Symposia, Jan. 14-19, 2007, Keystone, Colorado.
Chu et al., "Identification of an orphan, β-cell-specific GPCR that enhances glucose-dependent insulin release", Abstract #107, p. 56, *Toward Understanding Islet Biology*, Keystone Symposia, Jan. 21-26, 2003, Keystone, Colorado.
Chu et al., "Novel lipid amide activators of GDIR/GPR119 and their role in glucose homeostasis", Abstract # 230 & Poster, *Diabetes:*
*Molecular Genetics, Signaling Pathways and Integrated Physiology*, Keystone Symposia, Jan. 14-19, 2007, Keystone, Colorado.
Chu et al., "Transgenic mice with β-cell-targeted expression of the human orphan GPCR 19AJ are resistant to high fat diet-induced hyperglycemia", Abstract #228, p. 54, *Diabetes Mellitus: Molecular Mechanisms, Genetics and New Therapies*, Keystone Symposia, Jan. 27-Feb. 2, 2005, Keystone, Colorado.
Collier, T.L., et al., "Radiosynthesis and in-vivo evaluation of the pseudopeptide σ-opioid anatagonist [(125)ńITIPP(ψ)]," *J. Labelled Comd Radiopharm.* (1999), 42: 5264-5266.
Crespo et al., "Morphometric and mechanical properties of femora in young adult male turkeys with and without femoral fractures", *Poultry Science*, 79:602-608, (2000).
Deacon et al., "Degradation of endogenous and exogenous gastric inhibitory polypeptide in healthy and in type 2 diabetic subjects as revealed using a new assay for the intact peptide", *The Journal of Clinical Endocrinology & Metabolism*, 85:3575-3581, (2000).
Deacon et al., "Dipeptidyl peptidase IV inhibition potentiates the insulinotropic effect of glucagon-like peptide 1 in the anesthetized pig." *Diabetes* (1998), 47(5):764-769.
Deacon, Carolyn F., "What do we know about the secretion and degradation of incretin hormones", Regulatory Peptides, 128, (2005), pp. 117-124.
Ding et al., "Impact of glucose-dependent peptide on age-induced bone loss," *Journal of Bone and Mineral Research*, (published online Dec. 10, 2007).
Drucker, "The biology of incretin hormones", *Cell Metabolism*, 3:153-165, (2006).
Drucker, D.J., "Enhancing incretin action for the treatment of type 2 diabetes," *Diabetes Care* (2003), 26(10):2929-40.
During et al., "Glucagon-like peptide-1 receptor is involved in learning and neuroprotection," *Nat Med* (2003) 9:1173-1179.
Edmonson et al., "Potent and selective praline derived dipeptidyl peptidase IV inhibitors," *Bioorg Med Chem Lett* (2004) 14:5151-5155.
Endocrinology and Metabolism 4th Edition, Felig et al., Eds. (2001), McGraw-Hill Book Company.
Fredriksson R. et al., "Seven evolutionarily conserved human rhodopain G protein-coupled receptors lacking close relatives," *FEBS lett.* (2003) 20:554(3):381-8.
Fyfe et al., "GPR119 Agonists are Potential Novel Oral Agents for the Treatment of Diabesity", *Diabetes* (2007) 56 (Supplement 1):A142, (Abstract #532-P; American Diabetes Association).
GenBank ® Accession No. AY288423, Mus musculus G Protein-coupled receptor 119 (Gpr119) mRNA, complete cds., Dec. 8, 2003 date of last modification.
GenBank® Accession No. AAP72125, G Protein-coupled recetor 119 [*homo sapiens*], Dec. 8, 2003 date of last modification.
Greig et al., "New therapeutic strategies and drug candidates for neurodegenerative diseases: p. 53 and TNF-alpha inhibitors, and GLP-1 receptor agonists," *Ann NY Acad Sci* (2004) 1035:290-315.
Handbook of Pharmaceutical Excipients (Rowe et al., eds), 4th Edition, 2003, Pharmaceutical Press.
He et al., "A simplified system for generating recombinant adenoviruses," Proc. Natl. Acad. Sci. USA (Mar. 1998) 95:2509-2514.
Holz G.G., et al., "Glucagon-like peptide-1 synthetic analogs: new therapeutical agents for use in the treatment of diabetes mellitus," *Curr Med Chem* (2003), 10(22):2471-2483.
Jee et al., "Overview: animal models of osteopenia and osteoporosis," J Musculoskel Neuron Interact (2001) 1(3):193-207.
Karlin et al., "Methods for assessing the statistical significance of molecular sequence features by using general scoring schemes," Proc. Natl. Acad. Sci, USA (Mar. 1990) 87:2264-2268.
Kenakin, T., "Are receptors promiscuous? Intrinsic efficacy as a transduction phenomenon," 43 *Life Sciences* (1988) 1095-1101.
King et al. "Control of yeast mating signal transduction by a mammalian beta 2-adrenergic receptor and Gs alpha subunit," Science, New Sieres, vol. 250, No. 4977. (Oct. 5, 1990), pp. 121-123.
Kopelman P.G., "Obesity as a medical problem," *Nature* (2000), 404(6778):635-643.

Le Bas, M.D., et al., "Radioiodinated analogs of EP 00652218 for the exploration of the tachykinin NK1 receptor by spect," *J. Labelled Compd Radiopharm.* (2001), 44, S280-S282.

Leiting et al., "Catalytic properties and inhibition of proline-specific dipeptidyl peptidases II, IV and VII," Biochem. J. (2003) 371:525-532.

Mayet et al. Diabetologia, 2005, Abstract.

McCormack, J. ((OSI)™ Pharmaceuticals Inc.), "Update on PSN821", SEC file No. 0-15190; Accession No. 950123-7-16093, Nov. 29, 2007.

McIntosh et al., Dipeptidyl peptidase IV inhibitors: How do they work as new antidiabetic agents? *Regulatory Peptides* (2005), 128:159-165.

Mclean et al., "Visualizing Differences in Ligand Regulation of Wild-Type and Constitutively Active Mutant $\beta_2$—Adrenoceptor-Green Fluorescent Protein Fusion Proteins," Molecular Pharmacology (1999) 56:1182-1191.

MDS Pharma Services (Catalog # 163910; King of Prussia, PA).

Mentlein R., "Therapeutic assessment of glucagon-like peptide-1 agonists compared with dipeptidyl peptidase IV inhibitors as potential antidiabetic drugs," *Expert Opin Investig Drugs* (2005), 14:57-64.

Milligan et al., "Chimaeric G alpha proteins: their potential use in drug discovery," *Thrends in Pharmaceutical Sciences* (1999), 20:118-24.

Miret, Juan J., et al. "Functional Expression of Heteromeric Calcitonin Gene-related Peptide and Adrenomedullin Receptors in Yeast" The Journal of Biological Chemistry, vol. 277, No. 9, Mar. 1, 2002, pp. 6881-6887.

Mosekilde et al., "The effects of growth hormone on fracture healing in rats: a histological description", *Bone*, 14:19-27, (1993).

Mulcahy et al., "Sustained Glycaemic Control over 6 Years in a Large Outpatient Cohort Using a Repeatedly Implemented Aggressive Treatment Protocol," Abstract No. 531-P In Diabetes, Abstract Book 67th Scientific Session, Friday, Jun. 22-Tuesday, Jun. 26, 2007, Chicago, IL, vol. 56, supplement 1, Jun. 2007, p. A142.

Nauck et al., "Incretins and their analogues as new antidiabetic drugs," *Drug News Persepct* (2003) 16:413-422.

Nauck, et al., "Gastric inhibitory polypeptide and glucagon-like peptide-1 in the pathogenesis of type 2 diabetes," *Diabetes* (2004) 53 Suppl 3:S190-196.

Nichols, J.G. et al eds. Sinauer Associates, Inc. (1992), "Indirect Mechanisms of Synaptic Transmission," Chpt. 8 *From Neuron To Brain* (3rd Ed.).

Offermanns et al., "G alpha 15 and G alpha 16 couple a wide variety of receptors to phosphollpase C." *J Biol Chem* (1995), 270:15175-80.

Overton et al., "Deorphanization of a G protein-coupled receptor for oleoylethanolamide and its use in the discovery of small-molecule hypophagic agents", *Cell Metabolism*, 3:167-175, (2006).

Overton et al., "GPR119, a novel G protein-coupled receptor target for the treatment of type 2 diabetes and obesity", British Journal of Pharmacology, pp. 1-6, Nov. 26, 2007.

Pederson et al., "Improved glucose tolerance in Zucker fatty rats by oral adminstration of the dipeptidyl peptidase IV inhibitor isoleucine thiazolidide," *Diabetes* (1998) 47(8):1253-1258.

Peters et al., "Aminomethyl-pyrimides as novel DPP-IV inhibitors: a 10(5)-fold activity increase by optimization of aromatic substituents," *Bioorg Med Chem Lett* (2004), 14:1491-1493.

Polymorphism in Pharmaceutical Solids (1999) Britain,, ed., Marcel Dekker, Inc.

Potenza et al., "A rapid quantitative bioassay for evaluating the effects of ligands upon receptors that modulate cAMP levels in a melanophere cell line," *Pigment Cell Research* (1992) 5(6)-372-378.

Prevention and Management of Osteoporosis, ; *WHO Technical Report Series 921*, Geneva 2003.

Raisz, Lawrence G., "Pathogenesis of osteoporosis: concepts, conflicts, and prospects", The Journal of Clinical Investigation, vol. 115, No. 12, Dec. 2005, pp. 3318-3325.

Ramsay, Douglas et al., "Detection of receptor ligands by monitoring slecctive stabilization of a *Renilla* luciferase-tagged, constitutively active mutant, G-protein-coupled receptor", British Journal of Pharmacology (2001) pp. 315-323.

Remington: The Science and Practice of Pharmacy, (A.R. Gennaro, ed.), 20th Edition, 2000, Lippincott Williams & Wilkins.

Soga et al., 'Lysophosphatidylcholine enhances glucose-dependent insulin secretion via an orphan G-protein-coupled receptor, *Biochemical and Biophysica Research Communications*, 326: 744-751, (2005).

Sondhi, S. et al., "cDNA array reveals increased expression of glucose-dependent insulinotropic polypeptide following chronic clazapine treatment: role in atypical antipsychotic drug-induced adverse metabolic effects", The Pharmacogenomics Journal (2006) vol. 6, pp. 131-140.

Suzuki et al., "Regulatable promoters for use in gene therapy applications: modification of the 5'-flanking region of the CFTR gene with multiple cAMP response elements to support basal, low-level gene expression that can be upregulated by exogenous agents that raise intracellular levels of cAMP," *Hum. Gene Ther* (1996) 7:1883-1893.

Takasaki Kotoro et al., "Effects of combination treatment with dipeptidyl peptidase IV inhibitor and sulfonylurea on glucose levels in rats," *J. Pharmacol Sciences* (2004), 95(2):291-293.

Traynor et al., "Modulation by μ-Opioid Agonists of Guanosine-5'-O-(3-[35S]thio)triphosphate Binding to membranes from Human Neuroblastoma SH-SY5Y Cells," *Molecular Pharmacology* (1995), 47:848-854.

Tsukiyama, Katsushi et al., "Gastric Inhibitory Polypeptide as an endogenous Factor Promoting New bone Formation after Food Ingestion", Molecular Endocrinology 2006, 29(7): 1644-1651.

Villhauer et al., "1-[[(3-hydroxy-1-adamantyl)amino]acetyl]-2-cyano-(S)-pyrrolidine: a potent, selective, and orally bioavailable dipeptidyl peptidase IV inhibitor with antihyperglycemic properties," *J Med Chem* (2003) 46: 2774-2789.

Villhauer et al., " 1-[2-[(50Cyanopyridin-2-yl)aminoethylamino]acetyl-2-(S)-pyrrolidinecarbonitrile; a potent, selective and orally bioavailable dipeptidyl peptidase JV inhibitor with antihyperglycemic properties," *J Med Chem.* (2002), 45:2362-2365.

Weber A.E., "Dipeptidyl peptidase IV inhibitors for the treatment of diabetes," J med. Chem. (2004), 47(17): 4135-41 4135-4141.

Weber et al., "MK-0431 is a potent, selective, dipeptidyl peptidase IV inhibitor for the treatment of type 2 diabetes," Diabetes (2004) 53 (Suppl.2): A151, 633-P (Abstract).

Williams Textbook of Endocrinology, 10th Edition, Larsen et al., Eds. (2002), W.B. Saunders Company.

Wise et al., "The identification of ligands at orphan G-protein coupled receptors", *Annu. Rev. Pharmacol. Toxicol.*, 44:43-66, (2004).

Xie et al., "Glucose-dependent insulinotropic peptide-overexpressing transgenic mice having increased bone mass", *Bone xx* (2007).

Xie et al., "Glucose-dependent insulinotropic polypeptide receptor knockout mice have altered bone turnover", *Bone*, 37:759-769, (2005).

Xu J., "Metabolic Disease Drug Discovery-Strategic Research Institute's Third International World Summit, Dipeptidyl peptidase-IV inhibitors," IDrugs (2004), 7(9):839-40.

Zander et al., "Effect of 6-week course of glucagon-like peptide 1 on glycaemic control, insulin sensitivity, and beta-cell function in type 2 diabetes: a parallel-group study," *Lancet* (2002), 359:824-830.

Zhong et al., "Effects of glucose-dependent insulinotropic peptide on osteoclast function", *Am J Physiol Endocrinol Metab* 292: E543-E548, 2007.

Zhu, D.-G. et al., "Synthesis and mode of action of (125)I and (3)H-labeled thieno [2,3-c] pyridine antagonists of cell adhesions molecules expressions," *J. Org. Chem. 2002*, 67(3), 943-948.

Carpenter et al., "The in vitro and in vivo effects of a GPR119 agonist", Poster, *Diabetes Mellitus, Insulin Action and Resistance*, Keystone Symposia, Jan. 22-27, 2008, Breckenridge, Colorado.

U.S. Appl. No. 60/342,015, filed Oct. 18, 2001, Natarajan et al.

Abramowicz et al., "Drugs for diabetes," *Treatment Guidlines from the Medical Letter*, 3(36):57-62 (2005).

Abbott et al., "Blockade of the neuropeptide Y Y2 receptor with the specific antagonist BIIE0246 attenuates the effect of endogenous and exogenous peptide $YY_{(3-36)}$ on food intake," *Brain Res.*, 1043:139-144 (2005).

Adachi et al., "Free fatty acids adminstered into the colon promote the secretion of glucagon-like peptide-1 and insulin," *Biochem. Biophys. Res. Commun.*, 340:332-337 (2006).

Adrian et al., "Human distribution and release of a putative new gut hormone, peptide YY," *Gastroenterology*, 89:1070-1077 (1985).

Altschul et al., "Basic Local Alignment Search Tool," *J. Mol. Biol.*, 215:403-410 (1990).

Altschul et al., "Gapped Blast and PSI-Blast: a new generation of protein database search programs," *Nucleic Acids Research*, 25:3389-3402 (1997).

Ausubel et al., Short Protocols in Molecular Biology, 3$^{rd}$ Edition, Wiley & Sons (1995).

Anini Y. et al., "Role of leptin in the regulation of glucagon-like peptide-1 secretion," *Diabetes*, 52:252-259 (2003).

Arehart et al., "Acceleration of cardiovascular disease by a dysfunctional prostacyclin receptor mutation: potential implications for cyclooxygenase-2 inhibition," *Circ. Res.*, 102(8):986-993 (2008).

Balasubramamniam et al., "Structure-activity studies including a (CH-NH) scan of peptide YY (PYY) active site, PYY(22-36), for interaction with rat intestinal PYY receptors: development of analogues with potent in vivo activity in the intestine," *J. Med. Chem.*, 43:3420-3427 (2000).

Balasubramaniam et al., "Neuropeptide Y (NPY) $Y_2$ receptor-selective agonist inhibits food intake and promotes fat metabolism in mice: combined anorectic effects of $Y_2$ and $Y_4$ receptor-selective agonists," *Peptides*, 28:235-240.

Balena et al., "Eight Weeks of Treatment with the Long Acting, Human GLP-1 Analogue R1583 Improves Glycemic Control and Lowers Body Weight in Subjects with Type 2 Diabetes Mellitus (T2DM) Treated with Metformin: A Double-Blind Placebo-Controlled Phase 2 Study," *Diabetes* Abstract ADA08L-1604: contact View, [108-OR] (2008).

Barrish et al., "The use of stable isotope labeling and liquid chromatography/tandem mass spectrometry techniques to study the pharmacokinetics and bioavailability of the antimigraine drug, MK-0462 (rizatriptan) in dogs," *Rapid Commun. Mass Spectrom.*, 10:1033-1037 (1996).

Batterham et al., "Gut hormone $PYY_{3-36}$ physiologically inhibits food intake," *Nature*, 418:650-654 (2002).

Bas et al., "Radioiodinated Analogs of EP 00652218 for the Exploration of the Tackykinin NK1 Receptor by Spect," *J. Labelled Compd. Radiopharm.*, 44:S280-S282 (2001).

Beers et al., "The Merck Manual of Diagnosis and Therapy Seventeenth Edition," *Merck Research Laboratories*, Whitehouse Station, NJ, 469-471 (1999).

Behre, "Adiponectin, obesity and atherosclerosis," *Scand. J. Clin. Lab. Invest.*, 67:449-458 (2007).

Benoist et al., "In vivo sequence requirements of the SV40 early promoter region," *Nature*, 290:304-310 (1981).

Bilchik et al., "Peptide YY is a physiological regulator of water and electrolyte absorption in the canine small bowel in vivo," *Gastroenterology*, 105:1441-1448 (1993).

Bilchik et al., "Peptide YY augments postprandial small intestinal absorption in the conscious dog," *Am. J. Surg.*, 167:570-574 (1994).

Boey et al., "Peptide YY ablation in mice leads to the development of hyperinsulinaemia and obesity," *Diabetologia*, 49:1360-1370 (2006).

Boey et al., "PYY transgenic mice are protected against diet-induced and genetic obesity," *Neuropeptides*, 42:19-30 (2008).

Bradley, "TNF-mediated inflammatory disease,"*J. Pathol.*, 214:149-160 (2008).

Brutlag et al., "Improved sensitivity of biological sequence database searches" *Cabios Comput Appl. Biosci.*, 6(3):237-245 (1990).

Buchan et al., "Clinical pharmacokinetics of frovatriptan," *Headache Suppl.*, 42(suppl. 2):S54-S62 (2002).

Center Watch$^{SM}$, "Clinical Trial Result Information," dated May 7, 2007 [online]. Retrieved on Feb. 5, 2009]. Retrieved from the Internet: http://www.centerwatch.com/clinical-trials/results/db/stur10066.html.

Chavez-Eng et al., "High-performance liquid chromatographic-tandem mass spectrometric evaluation and determination of stable isotope labeled analogs of rofecoxib in human plasma samples from oral bioavailability studies," *J. Chromatogr. B. Analyt. Technol. Biomed. Life. Sci.*, 767:117-129 (2002).

Chaudhri et al., "Gastrointestinal satiety signals," *Annu. Rev. Physiol.*, 70:239-255 (2008).

Childs, "Diabetes medications update," *The Kansas Nurse*, 79(5):4-6 (2004).

ConjuChem Press Release Dec. 3, 2008 (3 pages).

Cox, "Peptide YY: a neuroendocrone neighbor of note," *Peptides*, 28:345-351 (2007).

Cruze et al., "The $Y_2$ receptor mediates increases in collateral-dependent blood flow in a model of peripheral arterial insufficiency," *Peptides*, 28:269-280 (2007).

D'Alessio et al., "Glucagon-like peptide 1: evolution of an incretin into a treatment of diabetes," *Am. J. Physiol. Endocrinol. Metab.*, 286(6):E882-E890 (2004).

E-mail communication, Deno Dialynas and Kellie McConnell (Aug. 14, 2006).

Eberlein et al., "A new molecular form of PYY: strctural characterization of human $PYY_{3-36}$ and $PYY_{1-36}$," *Peptides*, 10:797-803 (1989).

Ekstrand et al., "Deletion of neuropeptide Y (NPY) 2 receptor in mice results in blockage of NPY-induced angiogenesis and delayed wound healing," *Proc. Natl. Acad. Sci. USA*, 100:6033-6038 (2003).

Ekblad et al., "Distribution of pancreatic polypeptide and peptide YY," *Peptides*, 23-251-261 (2002).

El Bahh et al., "The anti-epileptic action of neuropeptide Y in the hippocampus are mediated by $Y_2$ and $Y_5$ receptors," *Eur. J. Neurosci.*, 22:1417-1430 (2005).

Engelstoft et al., "A gut feeling for obesity: 7TM sensors on enteroendocrine cells," *Cell Metabolism*, 8(6):447-449 (2008).

Fayad et al., "Noninvasive In vivo high-resolution magnetic resonance imaging of atherosclerotic lesions in genetically engineered mice," *Circulation*, 98:1541-1547 (1998).

Fyfe et al., "Synthesis, SAR, and in vivo efficacy of novel GPR119 agonists with a 4-[3-(4-methanesulfinylphenoxy)propyl]-1-Boc-piperidine core," Abstract # MEDI 62, Division of Medicinal Chemistry, 234th ACS National Meeting, Boston, MA (Aug. 19-23, 2007).

Fyfe et al., "Discovery of novel, orally active, synthetic GPR119 agonists as potential agents for treatment of obesity and associated metabolic disorders," *Diabetes*, 55 (Suppl. 1):p. A81 (Jun. 2006).

Fyfe et al., "New nonpeptide-binding GPCRs as targets for diabetes and the metabolic syndrome," *Ann. Rep. Med Chem.*, 42:129-145 (2007).

GenBank® Accession No. AAN95195, rat G Protein-coupled receptor 119 (Gpr119) protein (date of last modification: Dec. 20, 2002).

Gish et al., "Identification of protein coding regions by database similarity search," *Nature Genet,*, 3:266-272 (1993).

Gomez et al., "Intestinal peptide YY: ontogeny of gene expression in rat bowel and trophic actions on the rat and mouse bowel," *Am. J. Physiol.*, 268:G71-G81 (1995).

Gong et al., "An antagonist of monocyte chemoattractant protein 1 (MCP-1) inhibits arthritis in the MRL-]pr mouse model," *J. Exp. Med.*, 186:131-137 (1997).

Graham et al., "Characteristics of a human cell line transformed by DNA from human adenovirus type 5," *J. Gen Virol.*, 36:59 (1977).

Grandt et al., "Two molecular forms of peptide YY (PYY) are abundant in human blood: characterization of a radioimmunoassay recognizing PYY 1-36 and PYY 3-36," *Regul. Pept.*, 51:151-159 (1994).

Grise et al., "Peptide YY inhibits growth of human breast cancer in vitro and in vivo," *J. Surg. Res.*, 82:151-155 (1999).

Guerre-Millo, "Adipo9nectin: an update," *Diabetes & Metab.*, 34:12-18 (2008).

Gulyas et al., "Drug distribution in man: a positron emission tomography study after oral adminstration of the labelled neuroprotective drug vinpocetine," *Eur. J. Nucl. Med. Mol. Imaging*, 29:1031-1038 (2002).

Hamer et al., "Regulation in vivo of a cloned mammalian gene: cadmium induces the transcription of a mouse metallothionein gene in SV40 vectors," *J. Mol. Appl. Gen.*, 1(4):273-288 (1982).

Hansmann et al., "Pulmonary arterial hypertension is linked to insulin resistance and reversed by peroxisome proliferator-activated receptor-γ activation," *Circulation*, 115:1275-1284 (2007).

Hara et al., "Measurement of the high-molecular weight form of adiponectin in plasma is useful for the prediction of insulin resistance and metabolic syndrome," *Diabetes Care*, 29:1357-1362 (2006).

Hay et al., "Inflammatory bowel disease: costs-of-illness," *J. Clin. Gastroenterol.*, 14:309-317 (1992).

Hirasawa et al., "Free fatty acids regulate gut incretin glucagon-like peptide I secretion through GPR 120," *Nature Medicine*, 11(1):90-98 (2005).

Irwin et al., "Comparison of the metabolic effects of GIP receptor antagonism and PYY(3-36) receptor activation in high fat fed mice," *Peptides*, 28(11):2192-2198 (2007).

Jetter et al., "Effects of grapefruit juice on the pharmacokinetics of sildenafil," *Clin. Pharmacol. Ther.*, 71:21-29 (2002).

Johnston et al., "Isolation of the yeast regulatory gene GAL4 and analysis of its dosage effects on the galactose/melibiose regulon," *Proc. natl. Acad. Sci. USA*, 79:6971-6975 (1982).

Keighley et al., "Inflammatory bowel disease," *Ailment Pharmacol. Ther.*, 18:Suppl 3:66-70 (2003).

Keire et al., "Primary structures of PYY, [Pro$^{34}$]PYY, and PYY-(3-36) confer different conformations and receptors selectivity," *Am. J. Physiol. Castrointest. Liver Physiol.*, 279:G126-G131 (2000).

Kubota et al., "Disruption of adiponectin causes insulin resistance and neointimal formation," *J. Biol. Chem.*, 277:25863-25866 (2002).

Lumb et al., "Novel selective neuropeptide Y2 receptor PEGylated peptide agonists reduce food inktake and body weight in mice," *J. Med. Chem.*, 50:2264-2268 (2007).

Lauffer et al., "GRP119: GPR119: "double-dipping" for better glycemic control," *Endocrinology*, 149(5) 2035-2037 (2008).

Lee et al., "Impaired angiogenesis in neuropeptide Y (NPY)-Y2 receptor knockout mice," *Peptides*, 24:99-106 (2003).

Lee et al., "Neuropeptide Y induces ischemic angiogenesis and restores function of ischemic skeletal muscles," *J. Clin. Invest.*, 111:1853-1862 (2003).

Leonard, "GPR119—Overseer of Gut and Pancreatic Endocrine Systems in Glucose Homeostasis," 68$^{th}$ *Scientific Sessions, American DIabetes Association* (2008).

Lippincott William & Wilkins; and Handbook of Pharmaceutical Excipients (Rowe et al., eds), 4$^{th}$ Edition, *Pharmaceutical Press* (2003).

Liu et al., "Pancreatic peptide YY mRNA levels increase during adaptation after small intestinal resection," *J. Surg. Res.*, 58:6-11 (1995).

Liu et al., "Y2 receptors decrease human pancreatic cancer growth and intracellular cyclic adenosine monophosphate levels," *Surgery*, 118:229-236 (1995).

Liu et al., "Peptide YY: a potential proabsorptive hormone for the treatment of malabsorptive disorders," *Am. Surg.*, 62:232-236 (1996).

Lundberg et al., "Localization of peptide YY (PYY) in gastrointestinal endocrine cells and effects on intestinal blood flow and motility," *Proc. Natl. Acad. Sci.USA*, 79:4471-4475 (1982).

Maeda et al."Diet-induced insulin resistance in mice lacking adiponectin/ACRP30," *Nat. Med.*, 8:731-737 (2002).

Marsh et al., Role of the Y5 neuropeptide Y receptor in limbic seizures, *Proc. Natl. Acad. Sci. USA*, 96:13518-13523 (1999).

Marso et al., "Low adiponectin levels are associated with atherogenic dyslipidemia and lipid-rich plaque in nondiabetic coronary arteries," *Diabetes Care*, 31(5):989-994 (2008).

Mather, "Establishment and characterization of two distinct mouse testicular epithelial cell lines," *Biol. Reprod.*, 23:243-251 (1980).

Mather et al., "Culture of testicular cells in hormone-supplemented serum-free medium," *Ann. N.Y. Acad. Sci.*, 383:44-68 (1982).

Matsuda et al., "Role of adiponectin in preventing vascular stenosis, The missing link of adipo-vascular axis," *J. Biol. Chem.*, 277:37487-37491 (2002).

McFadden et al., "Peptide YY inhibits the growth of Barrett's esophageal adenocarcinoma in vitro," *Am. J. Surg.*, 188:516-519 (2004).

McGinnis et al., "Actual causes of death in the United States," *JAMA*, 270:2207-2212 (1993).

McKnight, "Functional relationships between transcriptional control signals of the thymidine kinase gene of herpes simplex virus," *Cell* 31:355-363 (1982).

Merck Sante S.A.S., "Glucovance, film-coated tablets" *Pediatric Public Assessment Report EU Working Sharing Procedure-Assessment of Pediatric data*, 1-8 (2008).

Morley et al., "An investigation of tolerance to the actions of leptogenic and anorexigenic drugs in mice," *Life Sci.*, 41:2157-2165 (1987).

Morris et al., "Hapten-induced model of chronic inflammation and ulceration in the rat colon," *Gastroenterology*, 96:795-803 (1989).

Nightingale et al., "Gastrointestinal hormones in short bowel syndrome. Peptide YY may be the 'colonic brake' to gastric emptying," *Gut*, 39:267-272 (1996).

Nishimura et al., "Adiponectin prevents cerebral ischemic injury through endothelial nitric oxide synthase dependent mechanisms," *Circulation*, 117:216-223 (2008).

Ohashi et al., "Adiponectin replenishment ameliorates obesity-related hypertension," *Hypertension*, 47:1108-1116 (2006).

Okada et al., "Program & Abstracts," *The Endocrine Society*, Supplement 180 (1993).

Okamoto et al., "Adiponectin reduces atherosclerosis in apolipoprotein E-deficient mice," *Circulation*, 106:2767-2770 (2002).

Oku et al., "Adiponectin deficiency suppresses ABCA1 expression and ApoA-I synthesis in the liver," *FEBS Lett.*, 581:5029-5033 (2007).

Ortiz et al., "A novel long-acting selective neuropeptide Y2 receptor polethylene glycol-conjugated peptide agonist reduces food intake and body weight and improves glucose metabolism in rodents," *J. Pharmacol. Exp. Ther.*, 323:692-700 (2007).

Ouchi et al., "Novel modulator for endothelial adhesion molecules: adipocyte-derived plasma protein adiponectin," *Circulation*, 100:2473-2476 (1999).

Ouchi et al., "Adiponectin as an anti-inflammatory factor," *Clin. Chim. Acta.*, 380:24-30 (2007).

Overton et al., "GRP119, a novel G protein-coupled receptor target for the treatment of type 2 diabetes and obesity," *Br. J. Pharmacol.*, 153:S76-S81 (2008).

Parker et al., "Neuropeptide Y Y2 receptor in helath and disease," *Br. J. Pharmacol.*, 153:420-431 (2008).

Pearson, "Inflammatory bowel disease," *Nurs. Times*, 100:86-90 (2004).

Pittner et al., "Effects of PYY[3-36] in rodent models of diabetes and obesity," *Int. J. Obes. Relat. Metab. Disord.*, 28:963-971 (2004).

Rendell et al., "Combination therapy with Pioglitazone plus metformin or sulfonylurea in pateints with Type 2 diabetes influence of prior antidiabetic drug regimen," *Journal of Diabetes and Its Complications*, 17:211-217 (2003).

Renshaw et al., "Peptide YY: a potential therapy for obesity," *Curr. Drug Targets*, 6:171-179 (2005).

Ruggeri, "Platelets in atherothrombosis," *Nat. Med.*, 8:1227-1234 (2002).

Sakamoto et al., "Expression and distribution of Gpr119 in the pancreatic islets of mice and rats: predominant localization in pancreatic polypeptide-secreting PP-cells," *Biochem. Biophys. Res. Commun.*, 351:474-480 (Dec. 2006).

Sambrook et al., Molecular Cloning: A Laboratory Manual, Second Edition, Cold-Spring Harbor, N.Y. (1989).

Sambrook, et al., Molecular Cloning: A Laboratory Manual, Third Edition, Cold-Spring Harbor, N.Y. (2001).

Sanofi Aventis *AVE0010-R&D Meeting* (Sep. 17, 2007).

Schwartz et al., "Safety profile and metabolic effects of 14 days of treatment with DIO-902: results of a phase IIa multicenter, randomized, double-blind, placebo-controlled, parallel-group trial in patients with type 2 diabetes mellitus," *Clin. Ther.*, 30(6):1081-1088 (2008).

Shibata et al., "Adiponectin stimulates angiogenesis in response to tissue ischemia through stimulation of amp-activated protein kinase signaling," *J. Biol. Chem.*, 279:28670-28674 (2004).

Shibata et al., "Adiponectin stimulates angiogenesis in response to tissue ischemia through stimulation of amp-activated protein kinase signaling," *Nat. Med.*, 11:1096-1103 (2005).

Shibata et al., "Adiponectin protects against the development of systolic dysfunction following myocardial infarction," *J. Mol. Cell. Cardiol.*, 42:1065-1074 (2007).

Shore et al., "Adiponectin attenuates allergen-induced airway inflammation and hyperresponseiveness in mice," *J. Allergy Clin. Immunol.*, 118:389-395 (2006).

Sierra-Ascencio, et al., "Exenatide: use in humans," *Gas Med Mex.*, 142(6):483-491 (2006) (English Abstract).

Silver et al., "Amino terminus of the yeast GAL4 gene product is sufficient for nuclear localization," *Proc. Natl. Acad. Sci. USA*, 81:5951-5955 (1984).

Souli et al., "Several receptors mediate the antisecretory effect of peptide YY, neuropeptide Y, and pancreatic polypeptide on VIP-induced fluid secretion in the rat jejunum in vivo,"*Peptides*, 18:551-557 (1997).

Stewart et al., Pharmacokinetics, Safety, and Tolerability of Albiglutide (Syncria®), a Long-Acting GLP-1 Mimetic, in Healthy Volunteers, Abstract ADA08L_1316: ContactView, [522-P] (2008).

Summer et al., "Alveolar macrophage activation and an emphysema-like phenotype in adiponectin-deficient mice," *Am. J. Physiol. Lung Cell Mol. Physiol.*, 294(6):L1035-L1042 (Epub. Mar. 7, 2008).

Tao et al., "Adiponectin cardioprotection after myocardial ischemia/reperfusion involves the reduction oxidative/nitrative stress," *Circulation*, 115:1408-1416 (2007).

Tatemoto et al., "Isolation of two novel candidate hormones using a chemical method for finding naturally occurring polypeptides," *Nature*, 285:417-418 (1980).

Tilg et al., "Adipocytokines: mediators linking adipose tissue, inflammation and immunity," *Nat. Rev. Immunol.*, 6:772-783 (2006).

Trümper, et al., "Glucose-Dependent Insulinotropic Polypeptide is a Growth Factor for β (INS-1) Cells by Pleicotropic Signaling," *Mol. Endocrinol.*, 15(9):1559-1570 (2001).

Tseng et al., "Peptide YY and cancer: current findings and potential clinical applicatiosn," *Peptides*, 23:389-395 (2002).

Euno et al., "The role of PYY in feeding regulation," *Regul. Pept.*, 145:12-16 (2008).

Urlaub and Chasin, "Isolation of Chinese hamster cell mutants deficient in dihydrofolate reductase activity," *Proc. Natl. Acad. Sci.* (USA), 77:4216 (1980).

Uttenthal, "The anorectic gut hormones: GLP-1 and co-secreted peptides," *CLI*, 4 pages (2007).

Vona-Davis et al., "PYY and the pancreas: inhibition of tumor growth and inflammation," *Peptides*, 28:334-338 (2007).

Wang Y. et al., "BI-1336. Dipeptidyl-Peptidase IV Inhibitor, Antidiabetic Agent," *Drugs of the Future*, 33(6):473-477 (2008).

Woldbye et al., "Differential suppression of siezures via Y2 and Y5 neuropeptide Y receptors," *Neurobiology of Dis.*, 20:760-772 (2005).

Wong et al., "Nonpeptide factor Xa inhibitors: DPC423, a highly potent and orally bioavailable pyrazole antithrombotic agent," *Cardiovasc.* Drug Rev., 20:137-52 (2002).

Wortley et al., "Peptide YY regulates bone turnover in rodents," *Gastroenterology*, 133:1534-1543 (2007).

Yamada et al., *Endocrinology & Diabetology*, 23:237-243 (Sep. 2006) [English Translation of Japanese article].

Yamamoto et al., "Correlation of the adipocyte-derived protein adiponectin with insulin resistance index and serum high-density lipoprotein-cholecterol, independent of body mass index, in the Japanese population," *Clin. Sci. (Lond)*, 103:134-142 (2002).

Yang et al. "Efficacy and specificity of bFGF increased collateral flwo in experimental peripheral arterial insufficiency," *Am. J. Physiol. Heart Circ. Physiol.*, 278:H1966-H1973 (2000).

Yasuda et al., "Metformin causes reduction of food intake and body weight gain and improvement of glucose intolerance in combination with dipeptidyl peptidase IV inhibitor in Zucker fa/fa rats," *J. Pharmacol. Exp. Ther.*, 310(2): 614-619 (2004).

Yasuda et al., "Enhanced secretion of glucagon-like peptide 1 by biguanide compounds," *Biochem. Biophys. Res. Commun.*, 298:779-784 (2002).

Yokota et al., "Adiponectin, a new member of the family of soluble defense collagens, negatively regulates the growth of myelomonocytic progenitors and the functions of macrophages," *Blood*, 96:1723-1732 (2000).

Zimmerman et al., "The effect of a high-fat meal on the oral bioavailability of the immunosuppressant sirolimus (rapamycin)," *J. Clin. Pharmacol.*, 39:1155-1161 (1999).

Deacon et al., "Inhibitors of dipeptidyl peptidase IV: a novel approach for the prevention and treatment of Type 2 diabetes?," *Expert Opin. Investig. Drugs*, 13(9):1091-1102 (2004).

Drucker, "Therapeutic potential of dipeptidyl peptidase IV inhibitors for the treatment of type 2 diabetes," *Expert Opin. Investig. Drugs*, 12(1):87-100 (2003).

Evans, "Dipeptidyl peptidase IV inhibitors" *IDrugs*, 5(6):577-585 (2002).

Wiedeman et al., "Dipeptidyl peptidase IV inhibitors for the treatment of impaired glucose tolerance and type 2 diabetes," *Curr. Opin. Investig. Drugs*, 4(4):412-420 (2003).

U.S. Appl. No. 60/486,728, Jones et al., filed Jul. 11, 2003.

U.S. Appl. No. 60/487,443, Jones et al., filed Jul. 14, 2003.

U.S. Appl. No. 60/577,354, Jones et al., filed Jun. 4, 2004.

U.S. Appl. No. 630/643,086, Chu, filed Jan. 10, 2005.

American Diabetes Association, "Implications of the United Kingdom Prospective Diabetes Study," *Diabetes Care*, 25 (Suppl 1), Jan. 2002, 5 pages.

Ammala et al., "GPR119 dependent hormone secretion: Insulin, GLP-1 and more," Keystone Symposia, Islet and Beta Cell Biology, Poster Presentation, Poster Session 1, Apr. 7, 2008.

Ammala et al., "GPR119 dependent hormone secretion: Insulin, GLP-1 and more," Abstract 102, Keystone Symposia, Islet and Beta Cell Biology, conference held Apr. 6-11, 2008 at Snowbird, Utah (according to conference organizers, the abstract was made available to attendees in an abstract book distributed at the conference).

Balkan et al , "Inhibition of dipeptidyl peptidase IV with NVP-DPP728 increases plasma GLP-1 (7-36 amide) concentrations and improves oral glucose tolerance in obese Zucker rats," *Diabetologia*, 42(11):1324-1331 (1999).

Balkan, "Effects of glucagon-like peptide-1 (GLP-1) on glucose homeostasis and food intake," *Appetite*, 35(3):269-270 (2000).

Charpentier, "Oral combination therapy for type 2 diabetes," *Diabetes Metab. Res. Rev.*, 18:S70-S76 (2002).

Deacon et al., "Preservation of active incretin hormones by inhibition of dipeptidyl peptidase IV suppresses meal-induced incretin secretion in dogs," *J. Endocrinol.*, 172(2):355-362 (2002).

Declaration of James N. Leonard, dated Dec. 12, 2008, 13 pages.

Duffy et al., "Effects of antidiabetic drugs on dipeptidyl peptidase IV activity: nateglinide is an inhibitor of DPP IV and augments the antidiabetic activity of glucagon-like peptide-1," *Eur. J. Pharmacol.*, 568:278-286 (2007).

Effects of a DPP4 Inhibitor and GPR 119 Azonist Alone or in Combination on Plasma Glucose in an OGTT in SD Rat—Study Protocol, 5 pages.

Effect of DPP4 Inhibitor and GPR 119 Agonists on Plasma Glucose in Male C57BL/6J Mouse—Study Protocol, 7 pages.

Findlay et al., "Mechanisms of bone loss in rheumatoid arthritis," *Mod. Rheumatol.*, 15:232-240 (2005).

Holst et al., "Inhibition of the Activity of Dipeptidyl-Peptidase IV as a Treatment for Type 2 Diabetes," *Diabetes*, 47:1663-1670 (1998).

Holst, "Treatment of Type 2 diabetes mellitus with agonists of the GLP-1 receptor or DPP-IV inhibitors," *Expert Opinion on Emerging Drugs*, 9(1):155-166 (2004).

Hughes et al., "NVP-DPP728 (1-[[[2-[(5-cyanopyridin-2-yl)amino]ethyl]amino]acetyl]-2-cyano-(S)- pyrrolidine), a slow-binding inhibitor of dipeptidyl peptidase IV," *Biochemistry*, 38(36):11597-11603 (1999).

Inzucchi, "Oral Antihyperglycemic Therapy for Type 2 Diabetes," *JAMA*, 287:360-372 (2002).

Jones et al., "GPR 119 agonists for the treatment of type 2 diabetes," *Expert Opinion Therapeutic Patents*, 19(10):1339-1359 (2009).

Kim et al.,"(2R)-4-oxo-4[3-(trifluoromethyl)-5,6-dihydro[1,2,4]triazolo[4,3-a]pyrazin-7(8H)-yl]-1- (2,4,5-trifluorophenyl)butan-2-amine: a potent, orally active dipeptidyl peptidase IV inhibitor for the treatment of type 2 diabetes," *J. Med. Chem.*, 48:141-151 (2005).

Lankas et al., "Dipeptidyl Peptidase IV Inhibition for the Treatment of Type 2 Diabetes," *Diabetes*, 54:2988-2994 (2005).

Milani et al., "Dipeptidyl peptidase IV inhibition improves impaired glucose tolerance in high-fat diet-fed rats: study using a Fischer 344 rat substrain deficient in its enzyme activity," *Jpn. J. Pharmacol.*, 88(4):442-450 (2002).

Ning et al., "Endogenous and synthetic agonists of GPR119 differ in signaling pathways and their effects on insulin secretion in MIN6c4 insulinoma cells," *Brit. J Pharmacol.*, 155:1056-1065 (2008).

Pei et al., "Discovery and Structure—Activity Relationships of Piperidinone- and Piperidine-Constrained Phenethylamines as Novel, Potent, and Selective Dipeptidyl Peptidase IV Inhibitors," *J. Med. Chem.*, 50:1983-1987 (2007).

Reimer et al., "Long-term inhibition of dipeptidyl peptidase IV improves glucose tolerance and preserves islet function in mice," *Eur. J Endocrinol.*, 146(5):717-727 (2002).

Rendell, "Advances in diabetes for the millennium: drug therapy of type 2 diabetes," *MedGenMed.*, 6(3 Suppl):9 (2004).

Riddle, "Oral pharmacologic management of type 2 diabetes," *Am. Pam. Physician*, 60(9):2613-2620 (1999).

Semple et al., "Discovery of the First Potent and Orally Efficacious Agonist of the Orphan G-Protein Coupled Receptor 119," *J Med. Chem.*, 51:5172-5175 (2008).

Sudre et al., "Chronic inhibition of circulating dipeptidyl peptidase IV by FE 999011 delays the occurrence of diabetes in male zucker diabetic fatty rats," *Diabetes*, 51(5):1461-1469 (2002).

Takasaki et al., "K579, a slow-binding inhibitor of dipeptidyl peptidase IV, is a long-acting hypoglycemic agent," *Eur. J Pharmacol.*, 486:335-342 (2004).

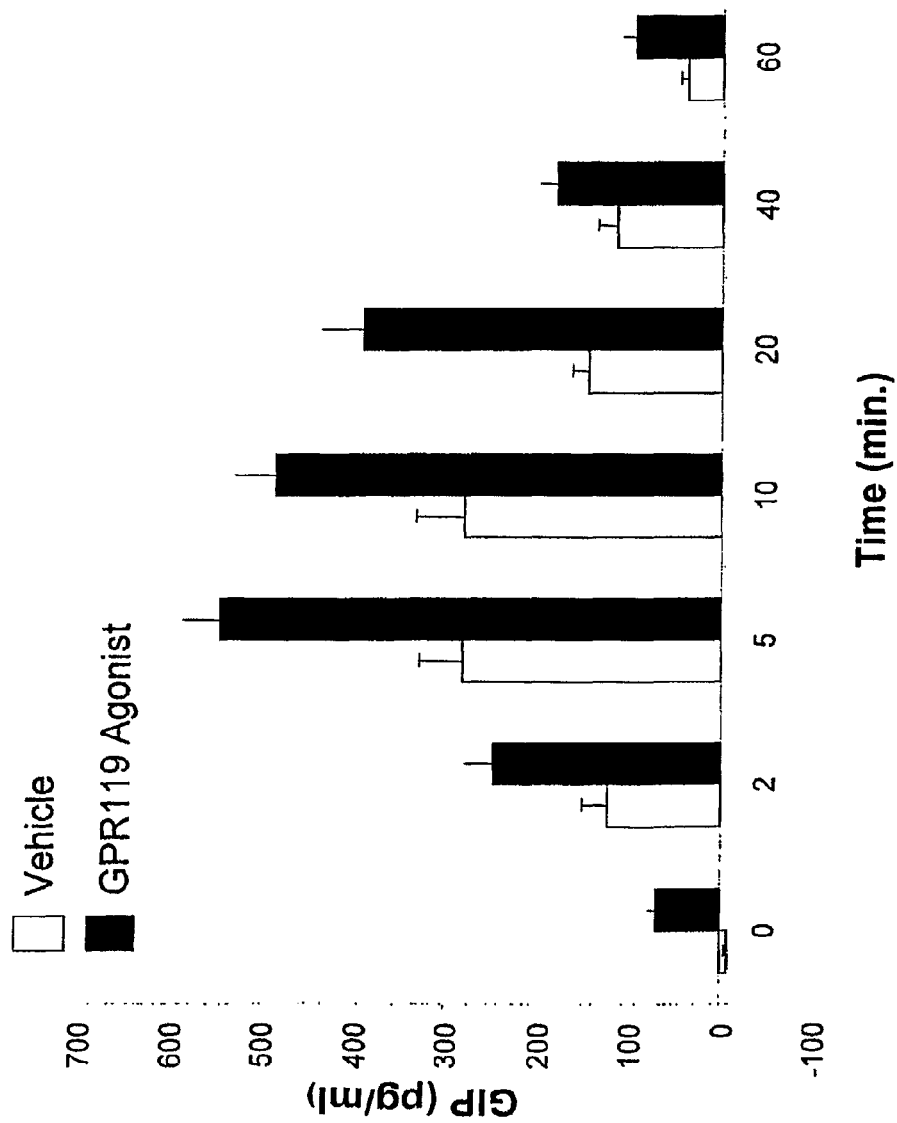

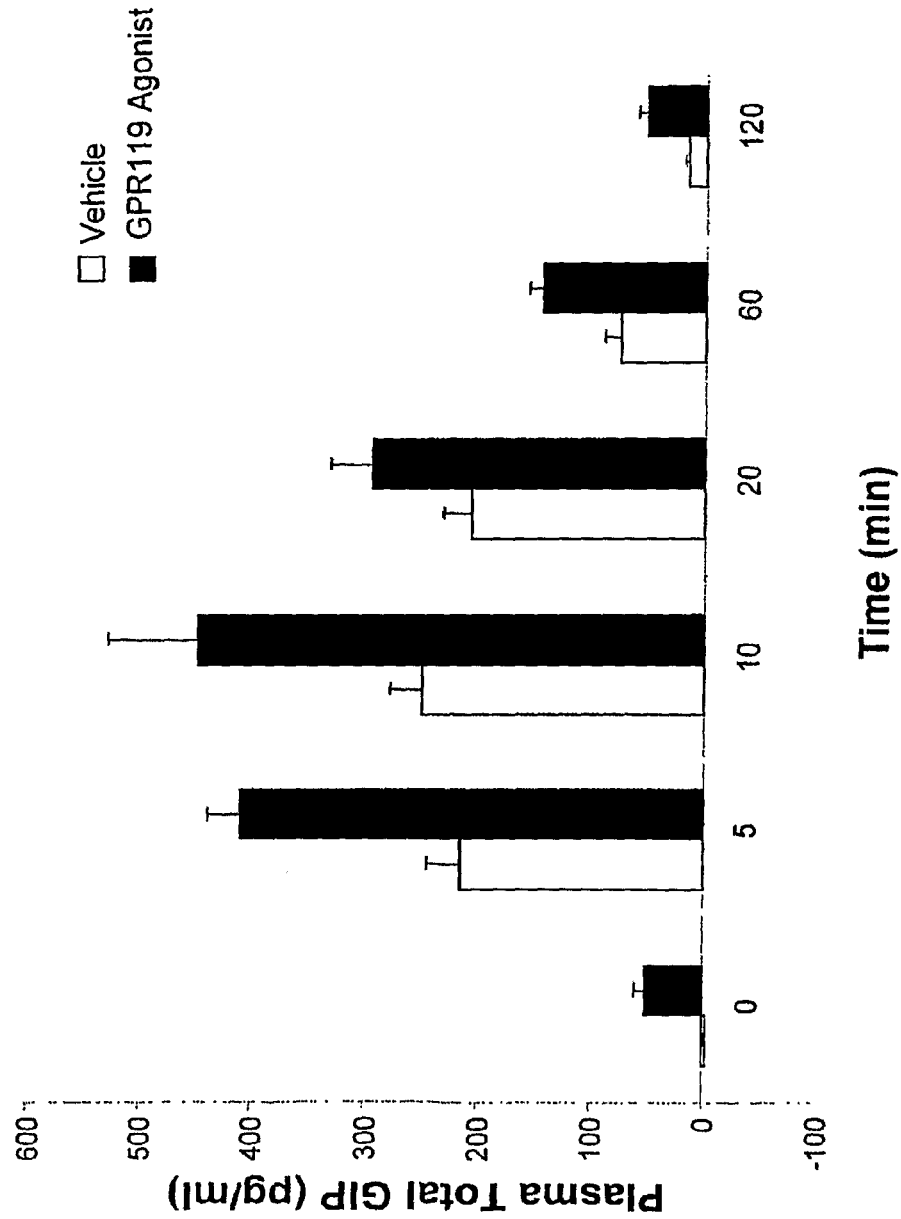

GPR119 Agonist Dose-Dependent Stimulation of Plasma Total GIP in Mice

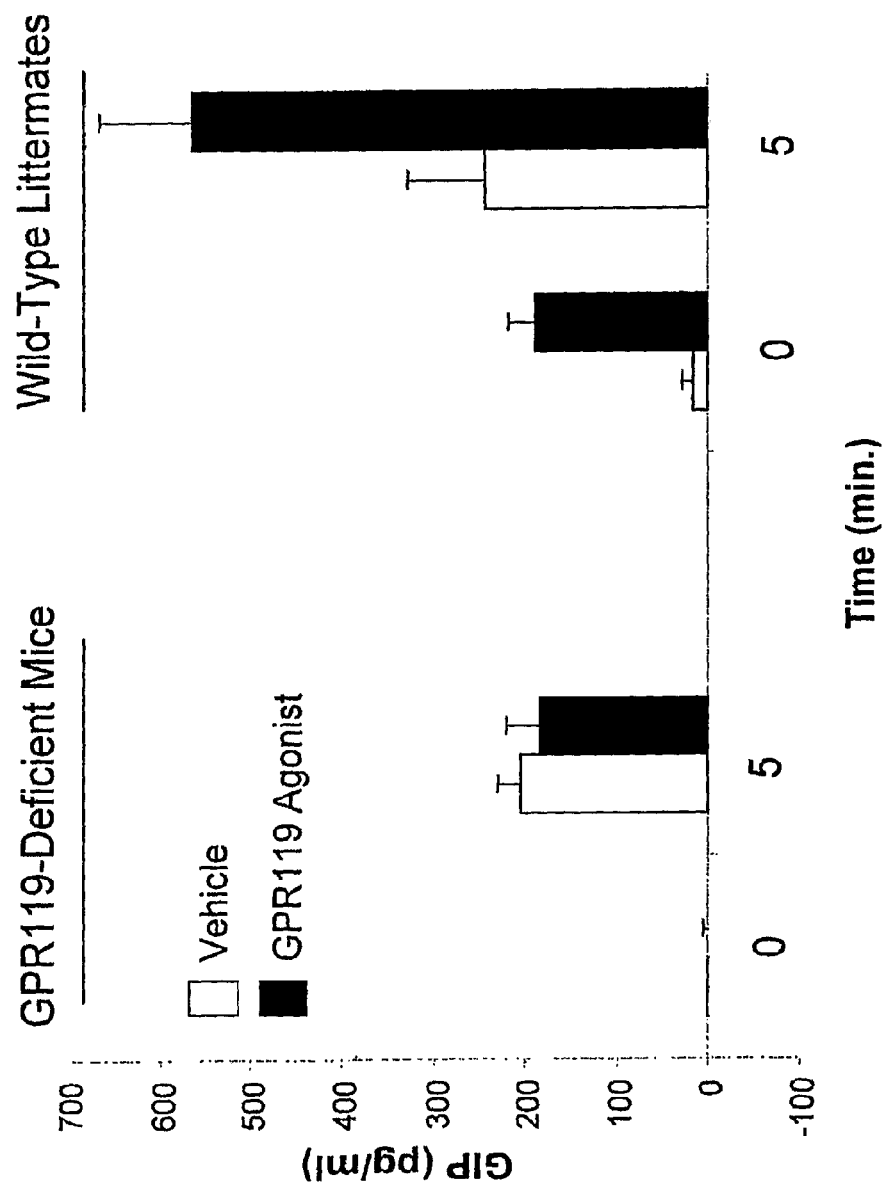

Loss of GPR119 Agonist Stimulation of Plasma Total GIP
In GPR119-Deficient (Knockout) Mice

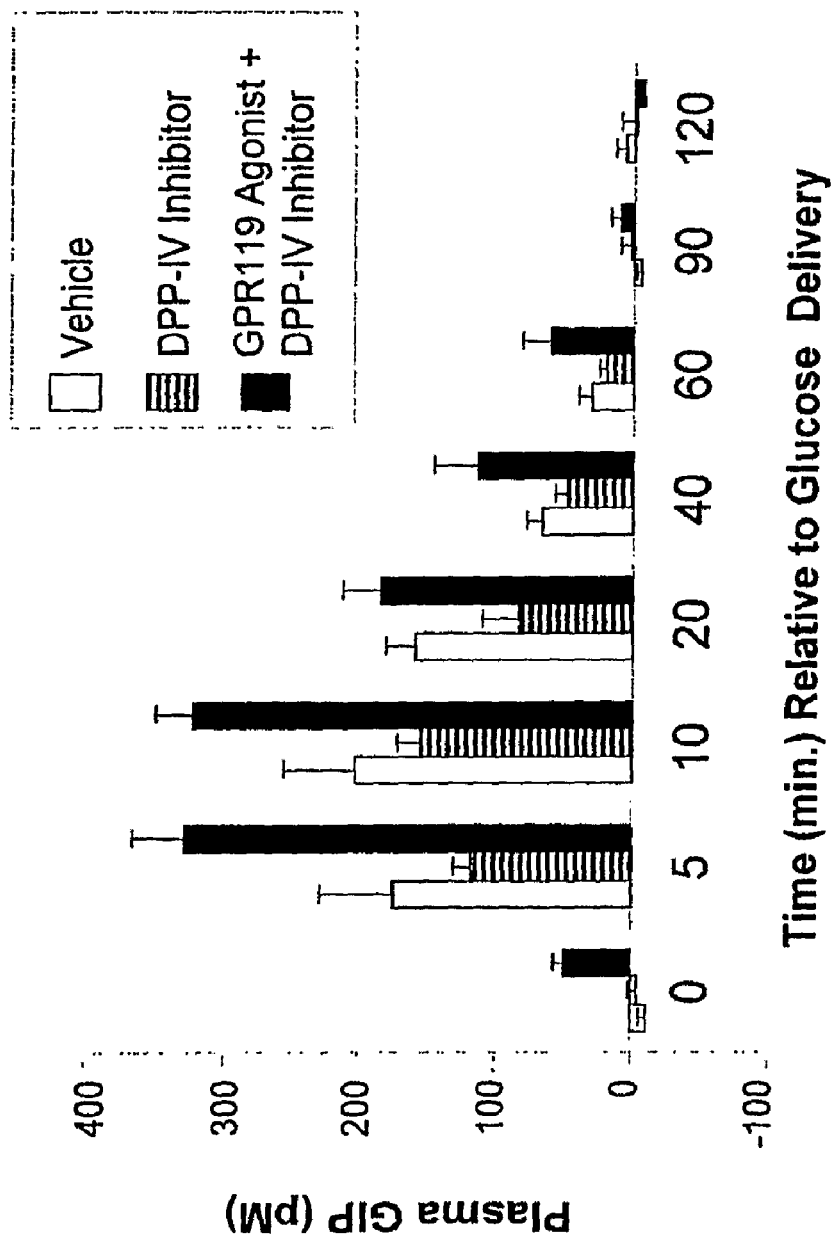

GRP119 RECEPTOR AGONISTS IN METHODS OF INCREASING BONE MASS AND OF TREATING OSTEOPOROSIS AND OTHER CONDITIONS CHARACTERIZED BY LOW BONE MASS, AND COMBINATION THERAPY RELATING THERETO

CROSS-REFERENCE TO RELATED APPLICATIONS

This application is a national phase filing under 35 U.S.C. §371 of International Application No. PCT/US2007/008926, filed on Apr. 10, 2007, which claims the benefit of priority of U.S. Application Ser. Nos. 60/791,613, filed on Apr. 11, 2006; 60/834,737 filed Jul. 31, 2006; and 60/851,244 filed Oct. 12, 2006. The disclosures of the prior applications are considered part of (and are incorporated by reference in) the disclosure of this application.

FIELD OF THE INVENTION

The present invention relates to the use of GPR119 receptor agonists for treating or preventing a condition characterized by low bone mass, such as osteoporosis, and for increasing bone mass in an individual. The present invention further relates to the use of a GPR119 receptor agonist in combination with a dipeptidyl peptidase IV (DPP-IV) inhibitor for treating or preventing a condition characterized by low bone mass, such as osteoporosis, and for increasing bone mass in an individual. A GPR119 receptor agonist and the combination of a GPR119 receptor agonist and a DPP-IV inhibitor promote bone formation in an individual.

BACKGROUND OF THE INVENTION

The following discussion is intended to facilitate the understanding of the invention, but is not intended nor admitted to be prior art to the invention.

A. Osteoporosis

Osteoporosis is a disabling disease characterized by the loss of bone mass and microarchitectural deterioration of skeletal structure leading to compromised bone strength, which predisposes a patient to increased risk of fragility fractures. Osteoporosis affects more than 75 million people in Europe, Japan and the United States, and causes more than 2.3 million fractures in Europe and the United States alone. In the United States, osteoporosis affects at least 25% of all post-menopausal white women, and the proportion rises to 70% in women older than 80 years. One in three women older than 50 years will have an osteoporotic fracture that causes a considerable social and financial burden on society. The disease is not limited to women; older men also can be affected. By 2050, the worldwide incidence of hip fracture in men is projected to increase by 310% and 240% in women. The combined lifetime risk for hip, forearm, and vertebral fractures presenting clinically is around 40%, equivalent to the risk for cardiovascular disease. Osteoporotic fractures therefore cause substantial mortality, morbidity, and economic cost. With an ageing population, the number of osteoporotic fractures and their costs will at least double in the next 50 years unless effective preventive strategies are developed. (See, e.g., Atik et al., Clin Orthop Relat Res (2006) 443:19-24; Raisz, J Clin Invest (2005) 115:3318-3325; and World Health Organization Technical Report Series 921 (2003), Prevention and Management of Osteoporosis.)

B. Glucose-Dependent Insulinotropic Polypeptide (GIP)

Glucose-dependent insulinotropic polypeptide (GIP, also known as gastric inhibitory polypeptide) is a peptide incretin hormone of 42 amino acids that is released from duodenal endocrine K cells after meal ingestion. The amount of GIP released is largely dependent on the amount of glucose consumed. GIP has been shown to stimulate glucose-dependent insulin secretion in pancreatic beta cells. GIP mediates its actions through a specific G protein-coupled receptor, namely GIPR.

As GIP contains an alanine at position 2, it is an excellent substrate for dipeptidyl peptidase-4 (DPP-IV), an enzyme regulating the degradation of GIP. Full-length GIP(1-42) is rapidly converted to bioinactive GIP(3-42) within minutes of secretion from the gut K cell. Inhibition of DPP-IV has been shown to augment GIP bioactivity. (See, e.g., Drucker, Cell Metab (2006) 3:153-165; McIntosh et al., Regul Pept (2005) 128:159-165; Deacon, Regul Pept (2005) 128:117-124; and Ahren et al., Endocrinology (2005) 146:2055-2059). Analysis of full length bioactive GIP, for example in blood, can be carried out using N-terminal-specific assays (see, e.g., Deacon et al, J Clin Endocrinol Metab (2000) 85:3575-3581).

Recently, GIP has been shown to promote bone formation. GIP has been shown to activate osteoblastic receptors, resulting in increases in collagen type I synthesis and alkaline phosphatase activity, both associated with bone formation. GIP has been shown to inhibit osteoclast activity and differentiation in vitro. GIP administration has been shown to prevent the bone loss due to ovariectomy. GIP receptor (GIPR) knockout mice evidence a decreased bone size, lower bone mass, altered bone microarchitecture and biochemical properties, and altered parameters for bone turnover, especially in bone formation. (See, e.g., Zhong et al, Am J Physiol Endocrinol Metab (2007) 292:E543-E548; Bollag et al., Endocrinology (2000) 141:1228-1235; Bollag et al.; Mol Cell Endocrinol (2001) 177:35-41; Xie et al., Bone (2005) 37:759-769; and Tsukiyama et al., Mol Endocrinol (2006) 20:1644-1651.)

The usefulness of GIP for maintaining or increasing bone density or formation has been acknowledged by the United State Trademark and Patent Office by issuance of U.S. Pat. No. 6,410,508 for the treatment of reduced bone mineralization by administration of GIP peptide. However, current GIP peptide agonists suffer from a lack of oral bioavailability, negatively impacting patient compliance. An attractive alternative approach is to develop an orally active composition for increasing an endogenous level of GIP activity.

C. GPR119

GPR119 is a G protein-coupled receptor (GPR119; e.g., human GPR119, GenBank® Accession No. AAP72125 and alleles thereof; e.g., mouse GPR119, GenBank® Accession No. AY288423 and alleles thereof). GPR119 activation as by an agonist leads to elevation of the level of intracellular cAMP, consistent with GPR119 being coupled to Gs. In the patent literature, GPR119 has been referred to as RUP3 (e.g., International Application No. PCT/US99/23687); GPR119 has also been referred to as Glucose-Dependent Insulinotropic Receptor (GDIR).

D. Dipeptidyl Peptidase IV (DPP-IV)

Dipeptidyl peptidase IV (DPP-IV, EC 3.4.14.5) exhibits catalytic activity against a broad range of peptide substrates that includes peptide hormones, neuropeptides, and chemokines. The incretins glucagon-like peptide 1 (GLP-1) and glucose-dependent insulinotropic polypeptide (GIP), which stimulate glucose-dependent insulin secretion and otherwise promote blood glucose homeostasis, are rapidly cleaved by DPP-IV at the position 2 alanine leading to inactivation of their biological activity. Both pharmacological and genetic attenuation of DPP-IV activity are associated with enhanced incretin action in vivo. A second-generation DPP-IV inhibitor, LAF237 (vildagliptin) (Ahren et al., J Clin Endocrinol Metab (2004) 89:2078-2084; and Villhauer et al., J Med Chem (2003) 46:2774-2789; the disclosure of each of which is herein incorporated by reference in its entirety), is currently in phase 3 clinical trials for Type 2 diabetes and additional DPP-IV inhibitors are in clinical development, including MK-0431 (sitagliptin), BMS-477118 (saxagliptin), PSN-9301, T-6666, PHX-1149 and SYR-322 (alogliptin). Sitagliptin (Januvia™; sitagliptin phosphate) has recently been approved by the U.S. Food and Drug Administration for use to improve blood sugar levels in patients with Type 2 diabetes.

Because the incretin hormones are not the only substrates for DPP-IV, there is concern that inhibition of the cleavage of other endogenous DPP-IV substrates may give rise to undesirable side effects (see, e.g., Chen et al, J Biol Regul Homeost Agents (2004) 18:47-54, the disclosure of which is herein incorporated by reference in its entirety). It therefore would be advantageous to identify a means for achieving increased levels of endogenous GIP activity independently of using a DPP-IV inhibitor or by using substantially lower concentrations of DPP-IV inhibitor than are presently contemplated.

SUMMARY OF THE INVENTION

The present invention relates to the unexpected discovery by Applicant that administration of a GPR119 agonist, such as by oral administration, can act at GPR119 receptor to increase a GIP level in an individual. Applicant has further shown that a GPR119 agonist in combination with a dipeptidyl peptidase IV (DPP-IV) inhibitor can provide an effect in increasing a GIP level in an individual over that provided by the DPP-IV inhibitor alone. The present invention concerns a GPR119 agonist as well as a combination of an amount of a GPR119 agonist with an amount of DPP-IV inhibitor such that the combination provides an effect in increasing a GIP level in an individual over that provided by the amount of the GPR119 agonist or the amount of the DPP-IV inhibitor alone. The present invention further concerns the use of a GPR119 agonist and the use of the combination of a GPR119 agonist with a DPP-IV inhibitor for treating or preventing a condition characterized by low bone mass, such as osteoporosis, and for increasing bone mass in an individual. A GPR119 agonist alone or in combination with a DPP-IV inhibitor is useful for promoting (e.g., increasing) bone formation in an individual. In certain embodiments, the individual is a human.

In a first aspect, the present invention features a method of treating or preventing a condition characterized by low bone mass comprising administering to an individual in need thereof a therapeutically effective amount of a composition comprising a GPR119 agonist. The present invention additionally features a method of treating or preventing a condition characterized by low bone mass comprising administering to an individual in need thereof a therapeutically effective amount of a pharmaceutical composition comprising a GPR119 agonist and a pharmaceutically acceptable carrier. In certain embodiments, the condition characterized by low bone mass is selected from the group consisting of osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height. In certain embodiments, the condition characterized by low bone mass is osteoporosis. In certain embodiments, osteoporosis is primary osteoporosis. In certain embodiments, osteoporosis is secondary osteoporosis.

The present invention features a method of increasing bone mass comprising administering to an individual in need thereof a therapeutically effective amount of a composition comprising a GPR119 agonist. The present invention additionally features a method of increasing bone mass comprising administering to an individual in need thereof a therapeutically effective amount of a pharmaceutical composition comprising a GPR119 agonist and a pharmaceutically acceptable carrier. In certain embodiments, the individual in need of increased bone mass has a bone mineral density (BMD) greater than 1 (T-score<−1) or greater than or equal to 1.5 (T-score≦−1.5), 2 (T-score≦−2) or 2.5 (T-score≦−2.5) standard deviations below the young adult reference mean. In certain embodiments, the individual in need of increased bone mass is in need of treatment of bone fracture. In certain embodiments, the individual has a traumatic bone fracture, a long-term bone fracture, or an osteoporotic fracture. In certain embodiments, the individual in need of increased bone mass is in need of treatment of a bone disease. In certain embodiments, the bone disease is selected from the group consisting of osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height. In certain embodiments, the bone disease is osteoporosis. In certain embodiments, osteoporosis is primary osteoporosis. In certain embodiments, osteoporosis is secondary osteoporosis. In certain embodiments, the individual in need of increased bone mass is in need of enhanced bone healing following facial reconstruction, maxillary reconstruction, mandibular reconstruction, periodontal disease or tooth extraction, enhanced long bone extension, enhanced prosthetic ingrowth or increased bone synostosis.

In certain embodiments, the GPR119 agonist is a selective GPR119 agonist. In certain embodiments, the GPR119 agonist is selected from the left column of Table D.

In certain embodiments, the administering is oral.

In certain embodiments, the GPR119 agonist is administered in an amount sufficient to increase a GIP level in the individual. In certain embodiments, the GIP level is a blood or plasma total GIP level. In certain embodiments, the GIP level is a blood or plasma bioactive GIP level.

In certain embodiments, the individual is a vertebrate. In certain embodiments, the individual is a mammal. In certain embodiments, the individual is a human.

In certain embodiments, the administering is carried out in a single dose.

In certain embodiments, the individual is not a human and the administering is carried out in a single dose.

In certain embodiments, the administering is carried out in multiple doses over a period of greater than 24 days, greater than 36 days, greater than 48 days or greater than 60 days. In certain embodiments, the multiple doses are consecutive daily doses. In certain embodiments, the individual is not a human and the administering is carried out in multiple doses over a period of greater than 24 days, greater than 36 days, greater than 48 days or great than 60 days. In certain embodiments, the individual is not a human and the multiple doses are consecutive daily doses.

In certain embodiments, the individual is a human and the administering is carried out in a single dose.

In certain embodiments, the individual is a human and the administering is carried out in consecutive daily doses over a period of at least 2 days, at least 7 days, at least 14 days, at least 30 days or at least 60 days.

In certain embodiments, the individual is a human and the administering is carried out in multiple doses over a period of greater than 8 weeks, greater than 12 weeks, greater than 16 weeks, greater than 20 weeks, greater than 24 weeks, greater than 28 weeks, greater than 32 weeks or greater than 36 weeks. In certain embodiments, the multiple doses are consecutive daily doses.

In a second aspect, the present invention features use of a GPR119 agonist to treat a condition characterized by low bone mass in the human or animal body by therapy. In certain embodiments, the human or animal body is a human body. In certain embodiments, the condition characterized by low bone mass is selected from the group consisting of osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height. In certain embodiments, the condition characterized by low bone mass is osteoporosis. In certain embodiments, osteoporosis is primary osteoporosis. In certain embodiments, osteoporosis is secondary osteoporosis.

The present invention features use of a GPR119 agonist to increase bone mass in the human or animal body by therapy. In certain embodiments, the human or animal body is a human body. In certain embodiments, the human or animal body has a bone mineral density (BMD) greater than 1 (T-score<−1) or greater than or equal to 1.5 (T-score≦−1.5), 2 (T-score≦−2) or 2.5 (T-score≦−2.5) standard deviations below the young adult reference mean. In certain embodiments, the human or animal body is in need of treatment of bone fracture. In certain embodiments, the human or animal body has a traumatic bone fracture, a long-term bone fracture, or an osteoporotic fracture. In certain embodiments, the human or animal body is in need of treatment of a bone disease. In certain embodiments, the bone disease is selected from the group consisting of osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height. In certain embodiments, the bone disease is osteoporosis. In certain embodiments, osteoporosis is primary osteoporosis. In certain embodiments, osteoporosis is secondary osteoporosis. In certain embodiments, the human or animal body is in need of enhanced bone healing following facial reconstruction, maxillary reconstruction, mandibular reconstruction, periodontal disease or tooth extraction, enhanced long bone extension, enhanced prosthetic ingrowth or increased bone synostosis.

In certain embodiments, the GPR119 agonist is a selective GPR119 agonist. In certain embodiments, the GPR119 agonist is selected from the left column of Table D.

In certain embodiments, the GPR119 agonist is provided in an amount sufficient to increase a GIP level in the human or animal body. In certain embodiments, the GIP level is a blood or plasma total GIP level. In certain embodiments, the GIP level is a blood or plasma bioactive GIP level.

In certain embodiments, the human or animal body is a human body.

In a third aspect, the present invention features use of a GPR119 agonist for the manufacture of a medicament for the treatment or prevention of a condition characterized by low bone mass in an individual. In certain embodiments, the condition characterized by low bone mass is selected from the group consisting of osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height. In certain embodiments, the condition characterized by low bone mass is osteoporosis. In certain embodiments, osteoporosis is primary osteoporosis. In certain embodiments, osteoporosis is secondary osteoporosis.

The present invention features use of a GPR119 agonist for the manufacture of a medicament for increasing bone mass in an individual. In certain embodiments, the individual has a bone mineral density (BMD) greater than 1 (T-score<−1) or greater than or equal to 1.5 (T-score≦−1.5), 2 (T-score≦−2) or 2.5 (T-score≦−2.5) standard deviations below the young adult reference mean. In certain embodiments, the individual is in need of treatment of bone fracture. In certain embodiments, the individual has a traumatic bone fracture, a long-term bone fracture, or an osteoporotic fracture. In certain embodiments, the individual is in need of treatment of a bone disease. In certain embodiments, the bone disease is selected from the group consisting of osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height. In certain embodiments, the bone disease is osteoporosis. In certain embodiments, osteoporosis is primary osteoporosis. In certain embodiments, osteoporosis is secondary osteoporosis. In certain embodiments, the individual is in need of enhanced bone healing following facial reconstruction, maxillary reconstruction, mandibular reconstruction, periodontal disease or tooth extraction, enhanced long bone extension, enhanced prosthetic ingrowth or increased bone synostosis.

In certain embodiments, the GPR119 agonist is a selective GPR119 agonist. In certain embodiments, the GPR119 agonist is selected from the left column of Table D.

In certain embodiments, the GPR119 agonist is provided in an amount sufficient to increase a GIP level in the individual. In certain embodiments, the GIP level is a blood or plasma total GIP level. In certain embodiments, the GIP level is a blood or plasma bioactive GIP level.

In certain embodiments, the individual is a vertebrate. In certain embodiments, the individual is a mammal. In certain embodiments, the individual is a human.

In a fourth aspect, the present invention features a method of treating or preventing a condition characterized by low bone mass comprising administering to an individual in need thereof a therapeutically effective amount of a composition comprising a GPR119 agonist and a DPP-IV inhibitor. The present invention additionally features a method of treating or preventing a condition characterized by low bone mass comprising administering to an individual in need thereof a therapeutically effective amount of a pharmaceutical composition comprising a GPR119 agonist and a DPP-IV inhibitor and a pharmaceutically acceptable carrier. In certain embodiments, the condition characterized by low bone mass is selected from the group consisting of osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height. In certain embodiments, the condition characterized by low bone mass is osteoporosis. In certain embodiments, osteoporosis is primary osteoporosis. In certain embodiments, osteoporosis is secondary osteoporosis.

The present invention features a method of increasing bone mass comprising administering to an individual in need thereof a therapeutically effective amount of a composition comprising a GPR119 agonist and a DPP-IV inhibitor. The present invention additionally features a method of increasing bone mass comprising administering to an individual in need thereof a therapeutically effective amount of a pharmaceutical composition comprising a GPR119 agonist and a DPP-IV inhibitor and a pharmaceutically acceptable carrier. In certain embodiments, the individual in need of increased bone mass has a bone mineral density (BMD) greater than 1 (T-score<−1) or greater than or equal to 1.5 (T-score≦−1.5), 2 (T-score≦−2) or 2.5 (T-score≦−2.5) standard deviations below the young adult reference mean. In certain embodiments, the individual in need of increased bone mass is in need of treatment of bone fracture. In certain embodiments, the individual has a traumatic bone fracture, a long-term bone fracture, or an osteoporotic fracture. In certain embodiments, the individual in need of increased bone mass is in need of treatment of a bone disease. In certain embodiments, the bone disease is selected from the group consisting of osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height. In certain embodiments, the bone disease is osteoporosis. In certain embodiments, osteoporosis is primary osteoporosis. In certain embodiments, osteoporosis is secondary osteoporosis. In certain embodiments, the individual in need of increased bone mass is in need of enhanced bone healing following facial reconstruction, maxillary reconstruction, mandibular reconstruction, periodontal disease or tooth extraction, enhanced long bone extension, enhanced prosthetic ingrowth or increased bone synostosis.

In certain embodiments, the GPR119 agonist is a selective GPR119 agonist. In certain embodiments, the GPR119 agonist is selected from the left column of Table D.

In certain embodiments, the DPP-IV inhibitor is a selective DPP-IV inhibitor. In certain embodiments, the DPP-IV inhibitor is selected from the right column of Table D.

In certain embodiments, the GPR119 agonist is selected from the left column of Table D and the DPP-IV inhibitor is selected from the right column of Table D.

In certain embodiments, the administering is oral.

In certain embodiments, the GPR119 agonist or the combination of the GPR119 agonist and the DPP-IV inhibitor is administered in an amount sufficient to increase a GIP level in the individual. In certain embodiments, the GIP level is a blood or plasma total GIP level. In certain embodiments, the GIP level is a blood or plasma bioactive GIP level.

In certain embodiments, the individual is a vertebrate. In certain embodiments, the individual is a mammal. In certain embodiments, the individual is a human.

In certain embodiments, the administering is carried out in a single dose.

In certain embodiments, the individual is not a human and the administering is carried out in a single dose.

In certain embodiments, the administering is carried out in multiple doses over a period of greater than 24 days, greater than 36 days, greater than 48 days or greater than 60 days. In certain embodiments, the multiple doses are consecutive daily doses. In certain embodiments, the individual is not a human and the administering is carried out in multiple doses over a period of greater than 24 days, greater than 36 days, greater than 48 days or great than 60 days. In certain embodiments, the individual is not a human and the multiple doses are consecutive daily doses.

In certain embodiments, the individual is a human and the administering is carried out in a single dose.

In certain embodiments, the individual is a human and the administering is carried out in consecutive daily doses over a period of at least 2 days, at least 7 days, at least 14 days, at least 30 days or at least 60 days.

In certain embodiments, the individual is a human and the administering is carried out in multiple doses over a period of greater than 8 weeks, greater than 12 weeks, greater than 16 weeks, greater than 20 weeks, greater than 24 weeks, greater than 28 weeks, greater than 32 weeks or greater than 36 weeks.

In a fifth aspect, the present invention features use of a GPR119 agonist in combination with a DPP-IV inhibitor to treat a condition characterized by low bone mass in the human or animal body by therapy. In certain embodiments, the human or animal body is a human body. In certain embodiments, the condition characterized by low bone mass is selected from the group consisting of osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height. In certain embodiments, the condition characterized by low bone mass is osteoporosis. In certain embodiments, osteoporosis is primary osteoporosis. In certain embodiments, osteoporosis is secondary osteoporosis.

The present invention features use of a GPR119 agonist in combination with a DPP-IV inhibitor to increase bone mass in the human or animal body by therapy. In certain embodiments, the human or animal body is a human body. In certain embodiments, the human or animal body has a bone mineral density (BMD) greater than 1 (T-score<−1) or greater than or equal to 1.5 (T-score≦−1.5), 2 (T-score≦−2) or 2.5 (T-score≦−2.5) standard deviations below the young adult reference mean. In certain embodiments, the human or animal body is in need of treatment of bone fracture. In certain embodiments, the human or animal body has a traumatic bone fracture, a long-term bone fracture, or an osteoporotic fracture. In certain embodiments, the human or animal body is in need of treatment of a bone disease. In certain embodiments, the bone disease is selected from the group consisting of osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height. In certain embodiments, the bone disease is osteoporosis. In certain embodiments, osteoporosis is primary osteoporosis. In certain embodiments, osteoporosis is secondary osteoporosis. In certain embodiments, the human or animal body is in need of enhanced bone healing following facial reconstruction, maxillary reconstruction, mandibular reconstruction, periodontal disease or tooth extraction, enhanced long bone extension, enhanced prosthetic ingrowth or increased bone synostosis.

In certain embodiments, the GPR119 agonist is a selective GPR119 agonist. In certain embodiments, the GPR119 agonist is selected from the left column of Table D.

In certain embodiments, the DPP-IV inhibitor is a selective DPP-IV inhibitor. In certain embodiments, the DPP-IV inhibitor is selected from the right column of Table D.

In certain embodiments, the GPR119 agonist is selected from the left column of Table D and the DPP-IV inhibitor is selected from the right column of Table D.

In certain embodiments, the GPR119 agonist or the combination of a GPR119 agonist and the DPP-IV inhibitor is provided in an amount sufficient to increase a GIP level in the human or animal body. In certain embodiments, the GIP level is a blood or plasma total GIP level. In certain embodiments, the GIP level is a blood or plasma bioactive GIP level.

In certain embodiments, the human or animal body is a human body.

In a sixth aspect, the present invention features use of a GPR119 agonist in combination with a DPP-IV inhibitor for the manufacture of a medicament for the treatment or prevention of a condition characterized by low bone mass in an individual. In certain embodiments, the condition characterized by low bone mass is selected from the group consisting of osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height. In certain embodiments, the condition characterized by low bone mass is osteoporosis. In certain embodiments, osteoporosis is primary osteoporosis. In certain embodiments, osteoporosis is secondary osteoporosis.

The present invention features use of a GPR119 agonist in combination with a DPP-IV inhibitor for the manufacture of a medicament for increasing bone mass in an individual. In certain embodiments, the individual has a bone mineral density (BMD) greater than 1 (T-score<−1) or greater than or equal to 1.5 (T-score≦−1.5), 2 (T-score≦−2) or 2.5 (T-score≦−2.5) standard deviations below the young adult reference mean. In certain embodiments, the individual is in need of treatment of bone fracture. In certain embodiments, the individual has a traumatic bone fracture, a long-term bone fracture, or an osteoporotic fracture. In certain embodiments, the individual is in need of treatment of a bone disease. In certain embodiments, the bone disease is selected from the group consisting of osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height. In certain embodiments, the bone disease is osteoporosis. In certain embodiments, osteoporosis is primary osteoporosis. In certain embodiments, osteoporosis is secondary osteoporosis. In certain embodiments, the individual is in need of enhanced bone healing following facial reconstruction, maxillary reconstruction, mandibular reconstruction, periodontal disease or tooth extraction, enhanced long bone extension, enhanced prosthetic ingrowth or increased bone synostosis.

In certain embodiments, the GPR119 agonist is a selective GPR119 agonist. In certain embodiments, the GPR119 agonist is selected from the left column of Table D.

In certain embodiments, the DPP-IV inhibitor is a selective DPP-IV inhibitor. In certain embodiments, the DPP-IV inhibitor is selected from the right column of Table D.

In certain embodiments, the GPR119 agonist is selected from the left column of Table D and the DPP-IV inhibitor is selected from the right column of Table D.

In certain embodiments, the GPR119 agonist or the combination of the GPR119 agonist and the DPP-IV inhibitor is provided in an amount sufficient to increase a GIP level in the individual. In certain embodiments, the GIP level is a blood or plasma total GIP level. In certain embodiments, the GIP level is a blood or plasma bioactive GIP level.

In certain embodiments, the individual is a vertebrate. In certain embodiments, the individual is a mammal. In certain embodiments, the individual is a human.

In a seventh aspect, the invention features a method according to the first aspect or to the fourth aspect, optionally further comprising the step of identifying the individual as an individual judged by a caregiver to require or benefit from said treating or preventing a condition characterized by low bone mass or from said increasing bone mass, and optionally further comprising the step of identifying achievement of therapeutic efficacy of said administering of said composition or said pharmaceutical composition.

In certain embodiments, the invention features a method of the first aspect, further comprising the step of identifying the individual as an individual judged by a caregiver to require or benefit from said treating or preventing a condition characterized by low bone mass or from said increasing bone mass.

In certain embodiments, the invention features a method of the fourth aspect, further comprising the step of identifying the individual as an individual judged by a caregiver to require or benefit from said treating or preventing a condition characterized by low bone mass or from said increasing bone mass.

In certain embodiments, the invention features a method of the first aspect, further comprising the step of identifying achievement of therapeutic efficacy of said administering of said composition or said pharmaceutical composition.

In certain embodiments, the invention features a method of the fourth aspect, further comprising the step of identifying achievement of therapeutic efficacy of said administering of said composition or said pharmaceutical composition.

In certain embodiments, the invention features a method of the first aspect, further comprising the step of identifying the individual as an individual judged by a caregiver to require or benefit from said treating or preventing a condition characterized by low bone mass or from said increasing bone mass, and further comprising the step of identifying achievement of therapeutic efficacy of said administering of said composition or said pharmaceutical composition.

In certain embodiments, the invention features a method of the fourth aspect, further comprising the step of identifying the individual as an individual judged by a caregiver to require or benefit from said treating or preventing a condition characterized by low bone mass or from said increasing bone mass, and further comprising the step of identifying achievement of therapeutic efficacy of said administering of said composition or said pharmaceutical composition.

In certain embodiments wherein the individual is a human, the caregiver is a physician, a nurse or a nurse practitioner. In certain embodiments wherein the individual is a non-human vertebrate, and in particular embodiment a non-human mammal, the caregiver is a veterinarian.

In certain embodiments, said identifying achievement of therapeutic efficacy of said administering comprises measuring a level of bone mass in the individual. In certain embodiments, said measuring a level of bone mass comprises measuring the level of bone mass using dual energy X-ray absorptiometry (DXA). In certain embodiments, said measuring a level of bone mass using DXA comprises measuring a T-score using DXA. In certain embodiments, said measuring a T-score using DXA comprises measuring a T-score at the hip using DXA. It is expressly contemplated that said measuring a level of bone mass may comprise measuring a level of bone mass using a technique other than DXA, such as single X-ray absorbtiometry (SXA) [see, e.g., World Health Organization Technical Report Series 921 (2003), Prevention and Management of Osteoporosis].

In some embodiments, said identifying achievement of therapeutic efficacy of said administering comprises measuring a GIP level in the individual. In certain embodiments, the GIP level is a blood or plasma total GIP level. In certain embodiments, the GIP level is a blood or plasma bioactive GIP level.

BRIEF DESCRIPTION OF THE DRAWINGS

The invention is illustrated in connection with the figures appended hereto in which:

FIG. 3 shows an effect of administration of a DPP-IV inhibitor in combination with a GPR119 agonist compared with the DPP-IV inhibitor alone on blood GIP level in wild-type mice. Compound 1Z was used as the GPR119 agonist. AR247810 was used as the DPP-IV inhibitor.

DETAILED DESCRIPTION OF THE INVENTION

Figure 1C:
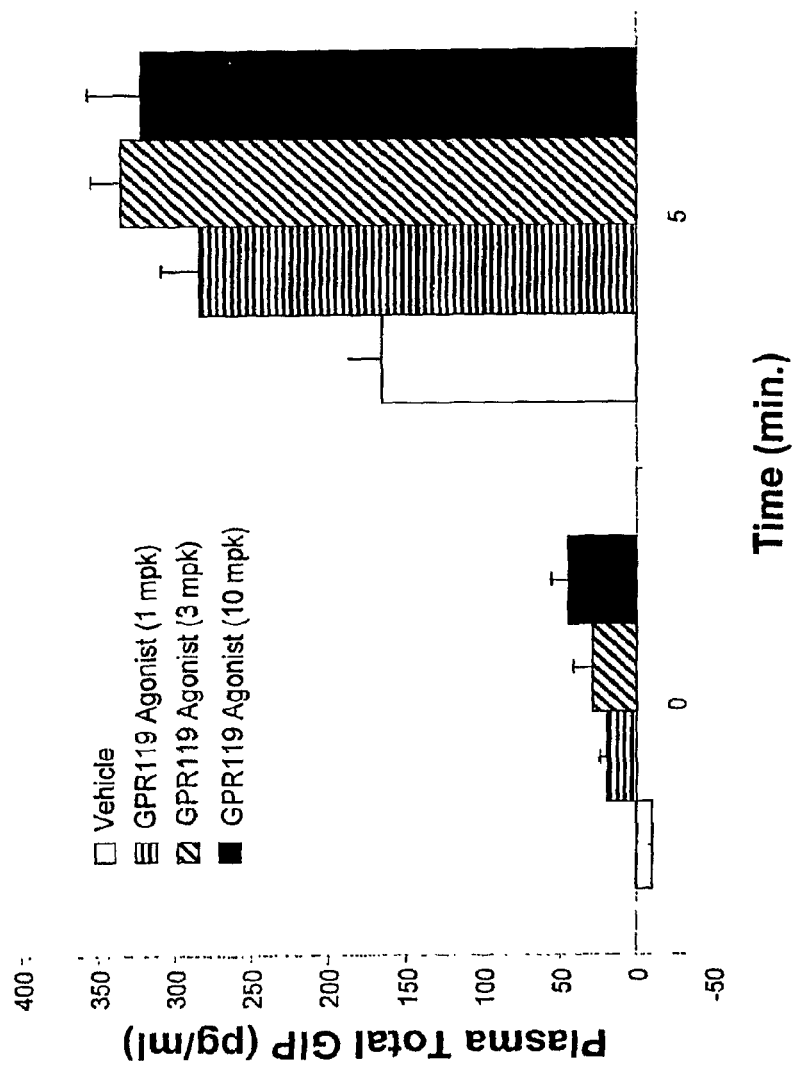
FIG. 1 shows a pharmacodynamic analysis of an effect of administration of GPR119 agonist on blood GIP level in wild-type mice. A. A time course analysis carried out using Compound 1Z as the GPR119 agonist. B. A time course analysis carried out using Compound 3Z as the GPR119 agonist. C. A dose titration analysis carried out using Compound 3Z as the GPR119 agonist.

This invention is concerned with certain compounds, or pharmaceutically acceptable salts thereof, for the treatment or prevention in an individual of a condition characterized by low bone mass, such as osteoporosis. This invention is further concerned with certain compounds, or pharmaceutically acceptable salts thereof, for increasing bone mass in an individual. Applicant has found that administering of a GPR119 agonist to an individual, such as by oral administration, can increase a GIP level in the individual. A GPR119 agonist is useful for treating or preventing a condition characterized by low bone mass, such as osteoporosis, and for increasing bone mass in an individual.

This invention is concerned with the combination of certain compounds, or pharmaceutically acceptable salts thereof, for the treatment or prevention in an individual of a condition characterized by low bone mass, such as osteoporosis. This invention is further concerned with the combination of certain compounds, or pharmaceutically acceptable salts thereof, for increasing bone mass in an individual. An amount of a GPR119 agonist in combination with an amount of a DPP-IV inhibitor can provide an effect in increasing a GIP level in an individual over that provided by the amount of the GPR119 agonist or the amount of the DPP-IV inhibitor alone. The combination of a GPR119 agonist and a DPP-IV inhibitor is useful for the treatment or prevention in an individual of a condition characterized by low bone mass, such as osteoporosis. The combination of a GPR119 agonist and a DPP-IV inhibitor is useful for increasing bone mass in an individual.

By the use of a combination of a GPR119 agonist and a DPP-IV inhibitor in accordance with the present invention, it is possible to treat or prevent a condition characterized by low bone mass more effectively than by use of a GPR119 agonist or a DPP-IV inhibitor alone, thereby reducing the likelihood of unwanted side-effects associated with inhibition of DPP-IV activity. By the use of a combination of a GPR119 agonist and a DPP-IV inhibitor in accordance with the present invention, it is possible to increase bone mass more effectively than by use of a GPR119 agonist or a DPP-IV inhibitor alone, thereby reducing the likelihood of unwanted side-effects associated with inhibition of DPP-IV activity. The present invention provides new, unexpected and advantageous approaches to treating or preventing a condition characterized by low bone mass, such as osteoporosis, and to increasing bone mass in an individual. The present invention additionally provides new, unexpected and advantageous approaches to increasing a GIP level in an individual.

The term "ligand", as used herein, shall mean a molecule (e.g., test compound) that specifically binds to a polypeptide, such as GPR119 or DPP-IV. A ligand may be, for example, a polypeptide, a lipid, a small molecule, an antibody. Compound 1Z is an exemplary ligand of GPR119 receptor polypeptide (see, Table E, which sets forth the chemical structure and chemical name of Compound 1Z). Compound 1Z is identical to a compound disclosed in International Patent Application No. PCT/US2004/001267 (published as WO 2004/065380). (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine (see, Table E) is an exemplary ligand of GPR119 receptor polypeptide. Compound 2Z is an exemplary ligand of GPR119 receptor polypeptide. Compound 2Z is identical to a compound disclosed in International Patent Application No. PCT/US2004/022417 (published as WO 2005/007658). Compound 3Z is an exemplary ligand of GPR119 receptor polypeptide. Compound 3Z is identical to a compound disclosed in International Patent Application No. PCT/US2004/022327 (published as WO 2005/007647). An endogenous ligand is a ligand that is an endogenous, natural ligand for a native polypeptide, such as GPR119 or DPP-IV. A ligand may be an "antagonist", "agonist", "partial agonist", or "inverse agonist", or the like. A ligand may be an "inhibitor."

TABLE E

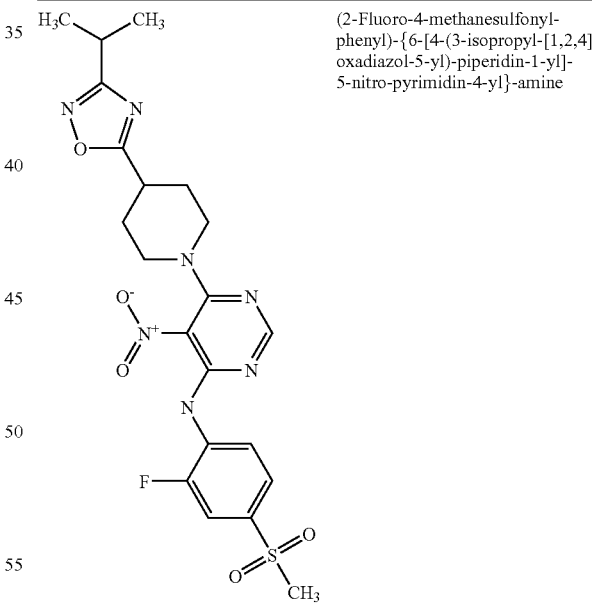

(2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine The term "agonist", as used herein, shall mean an agent (e.g., ligand) that by virtue of binding to a GPCR activates the GPCR so as to elicit an intracellular response mediated by the GPCR.

The term "partial agonist", as used herein, shall mean an agent (e.g., ligand) that by virtue of binding to a GPCR activates the GPCR so as to elicit an intracellular response mediated by the GPCR, albeit to a lesser extent or degree than does a full agonist.

The term "antagonist" shall mean an agent (e.g., ligand) that binds, and in particular embodiment binds competitively, to a GPCR at about the same site as an agonist or partial agonist but which does not activate an intracellular response initiated by the active form of the GPCR, and can thereby inhibit the intracellular response by agonist or partial agonist. An anatagonist typically does not diminish the baseline intracellular response in the absence of an agonist or partial agonist.

The term "inverse agonist" shall mean an agent (e.g., ligand) which binds to a GPCR and which inhibits the baseline intracellular response initiated by the active form of the receptor below the normal base level activity which is observed in the absence of an agonist or partial agonist.

The term "GPR119 agonist," as used herein, refers to a compound that binds to GPR119 receptor and acts as an agonist. Compound 1Z is an exemplary GPR119 agonist (see, Table E, which sets forth the chemical structure and chemical name of Compound 1Z). Compound 1Z is identical to a compound disclosed in International Patent Application No. PCT/US2004/001267 (published as WO 2004/065380). (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an exemplary GPR119 agonist. Compound 2Z is an exemplary GPR119 agonist. Compound 2Z is identical to a compound disclosed in International Patent Application No. PCT/US2004/022417 (published as WO 2005/007658). Compound 3Z is an exemplary GPR119 agonist. Compound 3Z is identical to a compound disclosed in International Patent Application No. PCT/US2004/022327 (published as WO 2005/007647).

The term "selective GPR119 agonist," as used herein, refers to a GPR119 agonist having selectivity for GPR119 receptor over one or more related receptors, such as corticotrophin-releasing factor-1 (CRF-1) receptor. Compound 1Z is an exemplary selective GPR119 agonist (see, Table E, which sets forth the chemical structure and chemical name of Compound 1Z). Compound 1Z is identical to a compound disclosed in International Patent Application No. PCT/US2004/001267 (published as WO 2004/065380). (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine is an exemplary selective GPR119 agonist. Compound 2Z is an exemplary selective GPR119 agonist. Compound 2Z is identical to a compound disclosed in International Patent Application No. PCT/US2004/022417 (published as WO 2005/007658). Compound 3Z is an exemplary selective GPR119 agonist. Compound 3Z is identical to a compound disclosed in International Patent Application No. PCT/US2004/022327 (published as WO 2005/007647).

The term "DPP-IV inhibitor," as used herein, refers to a compound that binds to DPP-IV and inhibits DPP-IV dipeptidyl peptidase activity. AR247810 is an exemplary DPP-IV inhibitor.

The term "selective DPP-IV inhibitor," as used herein, refers to a DPP-IV inhibitor having selectivity for DPP-IV over related peptidases, such as one or more of post-proline-cleaving enzyme (PPCE), dipeptidyl peptidase II (DPP-II), dipeptidyl peptidase 8 (DPP-8), and dipeptidyl peptidase 9 (DPP-9). AR247810 is an exemplary selective DPP-IV inhibitor.

The term "blood GIP level" shall mean blood GIP concentration. In certain embodiments, a blood GIP level is a blood total GIP level. In certain embodiments, a blood GIP level is a blood biologically active (bioactive) GIP level. In certain embodiments, bioactive GIP is GIP having agonist activity at GIPR. In certain embodiments, a blood GIP level is a plasma GIP level.

The term "individual," as used herein, refers to a vertebrate, including but not limited to fish (such as commercially farmed fish, pet fish, etc.), amphibians (such as frogs, toads, pet amphibians, etc.), reptiles (such as snakes, lizards, turtles, pet reptiles, etc.), birds (such as chickens, turkeys, pet birds, etc.) and mammals (such as mice, rats, hamsters, rabbits, pigs, dogs, cats, horses, cows, sheep, goats, non-human primates, non-human mammals, pet non-human mammals, humans, etc.). In certain embodiments, the individual is a fish. In certain embodiments, the individual is an amphibian. In certain embodiments, the individual is a reptile. In certain embodiments, the individual is a bird. In certain embodiments, the individual is a turkey. Over the past 25 yr, commercial selection pressure for turkeys with larger breast muscle mass has placed increasing demands on skeletal integrity. The increased breast muscle mass, however, has not been accompanied by compensatory changes in the skeleton, with the result that the turkey industry has experienced an increase in leg problems. Long bone fracture in young adult male turkeys has been reported. (See, e.g., Crespo et al, Poult Sci (2000) 79:602-608.) In certain embodiments, the individual is a mammal. In certain embodiments, the individual is a mouse, a rat, a hamster, a rabbit, a pig, a dog, a cat, a horse, a cow, a sheep, a goat, a non-human primate or a human (which may be included in embodiments of the invention individually or in any combination). In certain embodiments, the individual is a horse. Performance horses, which are horses involved in activities such as racing, pacing and other competitive events, are susceptible to bone fracture. In certain embodiments, the individual is a dog or a cat. In certain embodiments, the individual is a human companion animal (such as a dog, a cat, etc.), a farm animal (such as a cow, a sheep, a goat, a pig, a chicken, etc.), a sports animal (such as a horse, a dog, etc.), a beast of burden (such as a mule, a camel, etc.) or an exotic animal (such as an animal found in a zoo, etc.), which may be included in embodiments of the invention individually or in any combination. In certain embodiments, the individual is a non-human mammal. In certain embodiments, the individual is a non-human primate (such as a rhesus monkey, a chimpanzee, etc.). In certain embodiments, the individual is a human.

The term "in need of prevention or treatment" as used herein refers to a judgement made by a caregiver (e.g. physician, nurse, nurse practitioner in the case of humans; veterinarian in the case of non-human vertebrates, and in particular embodiment non-human mammals) that an individual requires or will benefit from treatment.

The term "therapeutically effective amount" or "therapeutically effective dose" as used herein refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

The term "therapeutic efficacy" as used herein refers to elicitation of the biological or medicinal response in a tissue, system, animal, individual or human that is being sought by a researcher, veterinarian, medical doctor or other clinician, which includes one or more of the following:

(1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

The term "amount that is effective to prevent" refers to that amount of drug that will prevent or reduce the risk of occurrence of the biological or medical event that is sought to be prevented. In many instances, the amount that is effective to prevent is the same as the therapeutically effective amount.

The term "composition" shall mean a material comprising at least one component.

The term "active ingredient" shall mean any component that provides pharmacological activity or other direct effect in the diagnosis, cure, mitigation, treatment, or prevention of disease.

The term "pharmaceutical composition" shall mean a composition comprising at least one active ingredient, whereby the composition is amenable to investigation and treatment in a mammal.

By "pharmaceutically acceptable" it is meant that the carrier, vehicle, diluent, excipients, and/or salt must be compatible with the other ingredients of the formulation, and not deleterious to the recipient thereof.

The term "dosage form" shall mean the physical form in which a drug is produced and dispensed, such as a tablet, capsule, or an injectable.

By "bone" is intended the dense, semi-rigid, porous, calcified connective tissue forming the major portion of the skeleton of most vertebrates, comprising a dense organic matrix and an inorganic, mineral component. Bone is any of numerous anatomically distinct structures making up the skeleton of a vertebrate.

The terms "bone mass" and "bone mineral density (BMD)" are used interchangeably herein. BMD in humans is usually measured by a standard radiographic technique, dual energy X-ray absorptiometry (DXA). Of the many techniques developed to assess BMD, DXA is the most highly developed technically and the most thoroughly validated biologically. DXA technology, with suitably adapted software, can also be used to reliably assess BMD in animal studies. DXA is used in the diagnosis of osteoporosis, prognosis (fracture prediction), monitoring the natural history of the disorder, and assessing response to treatment.

The term "low bone mass" as used herein refers to any decrease or reduction in bone mineral density (BMD) in an individual, and includes both osteoporosis and osteopenia as defined in proposals by the World Health Organization (WHO). The WHO has defined normal as a value of BMD within one standard deviation of the young adult reference mean (T-score$\geq$-1). The WHO has defined osteopenia as a value of BMD more than 1 standard deviation below the young adult mean, but less than 2.5 standard deviations below this value (T-score<-1 and >-2.5). The WHO has characterized osteoporosis as a more severe form of osteopenia, and has defined it by value of BMD 2.5 standard deviations or more blow the young adult mean (T-score $\leq$-2.5). (See, e.g., World Health Organization Technical Report Series 921 (2003), Prevention and Management of Osteoporosis, the disclosure of which is herein incorporated by reference in its entirety.) More commonly, osteopenia is defined as a T-score of less than -1 and greater than -2, and osteoporosis is defined as a T-score of less than or equal to -2. In certain embodiments of the present invention, the T-score is measured at the hip with DXA.

The term "osteoporosis" as used herein is defined by a value of BMD 2 standard deviations or more below the young adult reference mean (T-score$\leq$-2) or refers to a diagnosis made by a caregiver (e.g. physician, nurse, nurse practitioner in the case of humans; veterinarian in the case of non-human vertebrates).

Osteoporosis can be classified as either primary or secondary. (See, e.g., World Health Organization Technical Report Series 921 (2003), Prevention and Management of Osteoporosis.) As used herein, the term "osteoporosis" encompasses primary osteoporosis and secondary osteoporosis. In certain embodiments, osteoporosis is primary osteoporosis. In certain embodiments, osteoporosis is secondary osteoporosis.

"Primary osteoporosis" as used herein is associated with menopause (natural, premature, or surgical), aging, or both. It shall be understood that in the present invention, primary osteoporosis associated with menopause (natural, premature, or surgical), primary osteoporosis associated with aging, and primary osteoporosis associated with menopause and aging can be included in embodiments individually or in any combination.

"Secondary osteoporosis" as used herein refers to osteoporosis which is associated not with menopause or aging but rather with medical conditions or with the use of medications or drugs. An increased risk of osteoporosis is associated with a host of medical conditions, including but not limited to endocrine and metabolic disorders, and malignant disease, and with the use of certain medications and drugs, examples of which are well known to those skilled in the art (see, e.g., World Health Organization Technical Report Series 921 (2003), Prevention and Management of Osteoporosis; Williams Textbook of Endocrinology, $10^{th}$ Edition; the disclosure of which is herein incorporated by reference in its entirety.) Secondary osteoporosis can also be associated with immobilization. A diagnosis of osteoporosis secondary to a medical condition, to use of a medication or drug, or to immobilization can be made by a caregiver (e.g. physician, nurse, nurse practitioner in the case of humans; veterinarian in the case of non-human vertebrates).

By "bone fracture" is intended a complete or incomplete break, rupture or crack of a bone. Diagnosis of fractures normally depends upon clinical examination and radiological findings. In the invention, bone fractures include, but are not limited to, traumatic fractures, long-term fractures, and pathological fractures.

"Traumatic fracture" as used herein shall refer to an immediate fracture which involves a supraliminal trauma with a degree of local violence that exceeds the natural elasticity of the bone. It can be accompanied by simultaneous injury to the soft tissues and very often the skin. A traumatic fracture can be closed (the adjacent soft tissue can be injured but the covering soft parts are largely preserved). A traumatic fracture can be open (the broken ends of the bone are freed by extensive soft tissue injury so that pathogens from outside can enter the wound directly).

"Long-term fracture" as used herein shall refer to a chronic fracture, fatigue fracture, stress fracture or spontaneous fracture type I.

"Pathological fracture" as used herein shall refer to a spontaneous fracture type II. A pathological fracture arises spontaneously, without adequate trauma to account for it. The bone may have been previously damaged, either by a systemic disease (e.g., osteoporosis, osteodystrophy, or Paget's osteitis deformans) or by a local bone lesion (e.g., metastasis, radioosteonecrosis, or bone tumor). See, Adler, Claus-Peter, BONE DISEASES, p. 114 (Springer-Verlag, Germany 2000).

Fractures also include, but are not limited no, oblique torsion fracture, transverse fracture, comminuted fracture, compression fracture, rib fractures, creeping fracture, and fractured femoral neck (Adler, Claus-Peter, BONE DISEASES, Springer-Verlag. Germany (2000)).

As used herein, the term "condition characterized by low bone mass" includes but is not limited to osteopenia, osteoporosis, primary osteoporosis, secondary osteoporosis, rheumatoid arthritis, osteoarthritis, periodontal disease, alveolar bone loss, osteotomy bone loss, childhood idiopathic bone loss, curvature of the spine and loss of height. In certain embodiments, secondary osteoporosis is associated with a medical condition. In certain embodiments, secondary osteoporosis is associated with use of a medication or drug. In certain embodiments, secondary osteoporosis is associated with immobilization. Conditions characterized by low bone mass include but are not limited to Paget's disease, bone loss due to metastatic cancer, and osteolytic lesions such as those caused by neoplastic disease, radiotherapy, or chemotherapy. Conditions characterized by low bone mass also include but are not limited to long-term complications of osteoporosis such as curvature of the spine, loss of height and prosthetic surgery. It shall be understood that in the present invention, conditions characterized by low bone mass can be included in embodiments individually or in any combination. (See, e.g., World Health Organization Technical Report Series 921 (2003), Prevention and Management of Osteoporosis; Williams Textbook of Endocrinology, 10$^{th}$ Edition, Larsen et al, Eds. (2002), W.B. Saunders Company; and Endocrinology and Metabolism, 4$^{th}$ Edition, Felig et al, Eds. (2001), McGraw-Hill Book Company; the disclosure of each of which is herein incorporated by reference in its entirety.)

As used herein, "bone disease" refers to a disorder or condition relating to abnormality of the bone. Bone diseases that can be treated according to the invention, by increasing bone mass or bone growth, include but are not limited to osteopenia, osteoporosis, primary osteoporosis, secondary osteoporosis, rheumatoid arthritis, osteoarthritis, periodontal disease, alveolar bone loss, osteotomy bone loss, childhood idiopathic bone loss, curvature of the spine, and loss of height. In certain embodiments, secondary osteoporosis is associated with a medical conditions. In certain embodiments, secondary osteoporosis is associated with the use of a medication or drug. In certain embodiments, secondary osteoporosis is associated with immobilization. Bone diseases that can be treated according to the invention, by increasing bone mass or bone growth, also include but are not limited to Paget's disease and bone loss due to metastatic cancer. Destructive bone disorders that can be treated according to the invention, by increasing bone mass or growth, include but are not limited to osteoporosis, osteoarthritis, and osteolytic lesions such as those caused by neoplastic disease, radiotherapy, or chemotherapy. It shall be understood that in the present invention, bone diseases that can be treated according to the invention, by increasing bone mass or growth, can be included in embodiments individually or in any combination: (See, e.g., World Health Organization Technical Report Series 921 (2003), Prevention and Management of Osteoporosis; Williams Textbook of Endocrinology, 10$^{th}$ Edition, Larsen et al, Eds. (2002), W.B. Saunders Company; and Endocrinology and Metabolism, 4$^{th}$ Edition, Felig et at, Eds. (2001), McGraw-Hill Book Company; the disclosure of each of which is herein incorporated by reference in its entirety.)

The present invention also relates to the other conditions that derive benefit from treatment according to the invention, by increasing bone mass or bone growth, including but not limited to enhanced bone healing following facial reconstruction, maxillary reconstruction, mandibular reconstruction, periodontal disease or tooth extraction, enhanced long bone extension, enhanced prosthetic ingrowth and increased bone synostosis.

Chemical Group, Moiety or Radical

The term "$C_{1-5}$ acyl" denotes a $C_{1-5}$ alkyl radical attached to a carbonyl wherein the definition of alkyl has the same definition as described herein; some examples include but not limited to, acetyl, propionyl, n-butanoyl, iso-butanoyl, sec-butanoyl, t-butanoyl (i.e., pivaloyl), pentanoyl and the like.

The term "$C_{1-5}$ acyloxy" denotes an acyl radical attached to an oxygen atom wherein acyl has the same definition has described herein; some examples include but not limited to acetyloxy, propionyloxy, butanoyloxy, iso-butanoyloxy, sec-butanoyloxy, t-butanoyloxy and the like.

The term "$C_{1-6}$ acylsulfonamide" refers to a $C_{1-6}$ acyl attached directly to the nitrogen of the sulfonamide, wherein the definitions for $C_{1-6}$ acyl and sulfonamide have the same meaning as described herein, and a $C_{1-6}$ acylsulfonamide can be represented by the following formula:

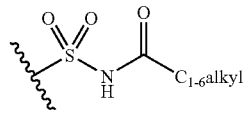

Some embodiments of the present invention are when acylsulfonamide is a $C_{1-5}$ acylsulfonamide, some embodiments are $C_{1-4}$ acylsulfonamide, some embodiments are $C_{1-3}$ acylsulfonamide, and some embodiments are $C_{1-2}$ acylsulfonamide. Examples of an acylsulfonamide include, but not limited to, acetylsulfamoyl [—S(=O)$_2$NHC(=O)Me], propionylsulfamoyl [—S(=O)$_2$NHC(=O)Et], isobutyrylsulfamoyl, butyrylsulfamoyl, 2-methyl-butyrylsulfamoyl, 3-methyl-butyrylsulfamoyl, 2,2-dimethyl-propionylsulfamoyl, pentanoylsulfamoyl, 2-methyl-pentanoylsulfamoyl, 3-methyl-pentanoylsulfamoyl, 4-methyl-pentanoylsulfamoyl, and the like.

The term "$C_{2-6}$ alkenyl" denotes a radical containing 2 to 6 carbons wherein at least one carbon-carbon double bond is present, some embodiments are 2 to 4 carbons, some embodiments are 2 to 3 carbons, and some embodiments have 2 carbons. Both E and Z isomers are embraced by the term "alkenyl." Furthermore, the term "alkenyl" includes di- and tri-alkenyls. Accordingly, if more than one double bond is present then the bonds may be all E or Z or a mixtures of E and Z. Examples of an alkenyl include vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2,4-hexadienyl and the like.

The term "$C_{1-4}$ alkoxy" as used herein denotes a radical alkyl, as defined herein, attached directly to an oxygen atom. Examples include methoxy, ethoxy, n-propoxy, iso-propoxy, n-butoxy, t-butoxy, iso-butoxy, sec-butoxy and the like.

The term "$C_{1-8}$ alkyl" denotes a straight or branched carbon radical containing 1 to 8 carbons, some embodiments are 1 to 6 carbons, some embodiments are 1 to 3 carbons, and some embodiments are 1 or 2 carbons. Examples of an alkyl include, but not limited to, methyl, ethyl, n-propyl, iso-propyl, n-butyl, sec-butyl, iso-butyl, t-butyl, pentyl, iso-pentyl, t-pentyl, neo-pentyl, 1-methylbutyl [i.e., —CH(CH$_3$)CH$_2$CH$_2$CH$_3$], 2-methylbutyl [i.e., —CH$_2$CH(CH$_3$)CH$_2$CH$_3$], n-hexyl and the like.

The term "$C_{1-4}$ alkylcarboxamido" or "$C_{1-4}$ alkylcarboxamide" denotes a single $C_{1-4}$ alkyl group attached to the nitrogen of an amide group, wherein alkyl has the same definition as found herein. The $C_{1-5}$ alkylcarboxamido may be represented by the following:

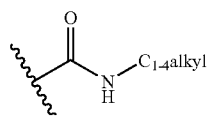 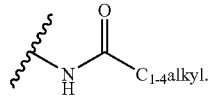

Examples include, but not limited to, N-methylcarboxamide, N-ethylcarboxamide, N-n-propylcarboxamide, N-iso-propylcarboxamide, N-n-butylcarboxamide, N-sec-butylcarboxamide, N-iso-butylcarboxamide, N-t-butylcarboxamide and the like.

The term "$C_{1-3}$ alkylene" refers to a $C_{1-3}$ divalent straight carbon group. In some embodiments $C_{1-3}$ alkylene refers to, for example, —CH$_2$—, —CH$_2$CH$_2$—, —CH$_2$CH$_2$CH$_2$—, and the like. In some embodiments, $C_{1-3}$ alkylene refers to —CH—, —CHCH$_2$—, —CHCH$_2$CH$_2$—, and the like wherein these examples relate generally to "A".

The term "$C_{1-4}$ alkylsulfinyl" denotes a $C_{1-4}$ alkyl radical attached to a sulfoxide radical of the formula: —S(O)— wherein the alkyl radical has the same definition as described herein. Examples include, but not limited to, methylsulfinyl, ethylsulfinyl, n-propylsulfinyl, iso-propylsulfinyl, n-butylsulfinyl, sec-butylsulfinyl, iso-butylsulfinyl, t-butyl, and the like.

The term "$C_{1-4}$ alkylsulfonamide" refers to the groups

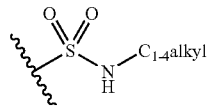 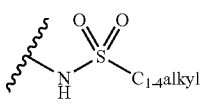

wherein $C_{1-4}$ alkyl has the same definition as described herein.

The term "$C_{1-4}$ alkylsulfonyl" denotes a $C_{1-4}$ alkyl radical attached to a sulfone radical of the formula: —S(O)$_2$— wherein the alkyl radical has the same definition as described herein. Examples include, but not limited to, methylsulfonyl, ethylsulfonyl, n-propylsulfonyl, iso-propylsulfonyl, n-butylsulfonyl, sec-butylsulfonyl, iso-butylsulfonyl, t-butyl, and the like.

The term "$C_{1-4}$ alkylthio" denotes a $C_{1-4}$ alkyl radical attached to a sulfide of the formula: —S— wherein the alkyl radical has the same definition as described herein. Examples include, but not limited to, methylsulfanyl (i.e., CH$_3$S—), ethylsulfanyl, n-propylsulfanyl, iso-propylsulfanyl, n-butylsulfanyl, sec-butylsulfanyl, iso-butylsulfanyl, t-butyl, and the like.

The term "$C_{1-4}$ alkylthiocarboxamide" denotes a thioamide of the following formulae:

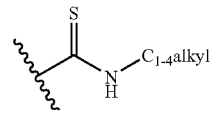 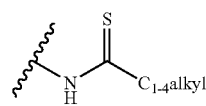

wherein $C_{1-4}$ alkyl has the same definition as described herein.

The term "$C_{1-4}$ alkylthioureyl" denotes the group of the formula: —NC(S)N— wherein one are both of the nitrogens are substituted with the same or different $C_{1-4}$ alkyl groups and alkyl has the same definition as described herein. Examples of an alkylthioureyl include, but not limited to, CH$_3$NHC(S)NH—, NH$_2$C(S)NCH$_3$—, (CH$_3$)$_2$N(S)NH—, (CH$_3$)$_2$N(S)NH—, (CH$_3$)$_2$N(S)NCH$_3$—, CH$_3$CH$_2$NHC(S)NH—, CH$_3$CH$_2$NHC(S)NCH$_3$—, and the like.

The term "$C_{1-4}$ alkylureyl" denotes the group of the formula: —NC(O)N— wherein one are both of the nitrogens are substituted with the same or different $C_{1-4}$ alkyl group wherein alkyl has the same definition as described herein. Examples of an alkylureyl include, but not limited to, CH$_3$NHC(O)NH—, NH$_2$C(O)NCH$_3$—, (CH$_3$)$_2$N(O)NH—, (CH$_3$)$_2$N(O)NH—, (CH$_3$)$_2$N(O)NCH$_3$—, CH$_3$CH$_2$NHC(O)NH—, CH$_3$CH$_2$NHC(O)NCH$_3$—, and the like.

The term "$C_{2-6}$ alkynyl" denotes a radical containing 2 to 6 carbons and at least one carbon-carbon triple bond, some embodiments are 2 to 4 carbons, some embodiments are 2 to 3 carbons, and some embodiments have 2 carbons. Examples of an alkynyl include, but not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

The term "amino" denotes the group —NH$_2$.

The term "$C_{1-4}$ alkylamino" denotes one alkyl radical attached to an amino radical wherein the alkyl radical has the same meaning as described herein. Some examples include, but not limited to, methylamino, ethylamino, n-propylamino, iso-propylamino, n-butylamino, sec-butylamino, iso-butylamino, t-butylamino, and the like. Some embodiments are "$C_{1-2}$ alkylamino."

The term "aryl" denotes an aromatic ring radical containing 6 to 10 ring carbons. Examples include phenyl and naphthyl.

The term "arylalkyl" defines a $C_1$-$C_4$ alkylene, such as —CH$_2$—, —CH$_2$CH$_2$— and the like, which is further substituted with an aryl group. Examples of an "arylalkyl" include benzyl, phenethylene and the like.

The term "arylcarboxamido" denotes a single aryl group attached to the nitrogen of an amide group, wherein aryl has the same definition as found herein. The example is N-phenylcarboxamide.

The term "arylureyl" denotes the group —NC(O)N— where one of the nitrogens are substituted with an aryl.

The term "benzyl" denotes the group —CH$_2$C$_6$H$_5$.

The term "carbo-C$_{1-6}$-alkoxy" refers to a C$_{1-6}$ alkyl ester of a carboxylic acid, wherein the alkyl group is as defined herein. In some embodiments, the carbo-C$_{1-6}$-alkoxy group is bonded to a nitrogen atom and together form a carbamate group (e.g., N—COO—C$_{1-6}$-alkyl). In some embodiments, the carbo-C$_{1-6}$-alkoxy group is an ester (e.g., —COO—C$_{1-6}$-alkyl). Examples include, but not limited to, carbomethoxy, carboethoxy, carbopropoxy, carboisopropoxy, carbobutoxy, carbo-sec-butoxy, carbo-iso-butoxy, carbo-t-butoxy, carbo-n-pentoxy, carbo-iso-pentoxy, carbo-t-pentoxy, carbo-neo-pentoxy, carbo-n-hexyloxy, and the like.

The term "carboxamide" refers to the group —CONH$_2$.

The term "carboxy" or "carboxyl" denotes the group —CO$_2$H; also referred to as a carboxylic acid group.

The term "cyano" denotes the group —CN.

The term "C$_{3-7}$ cycloalkenyl" denotes a non-aromatic ring radical containing 3 to 6 ring carbons and at least one double bond; some embodiments contain 3 to 5 carbons; some embodiments contain 3 to 4 carbons. Examples include cyclopropenyl, cyclobutenyl, cyclopentenyl, cyclopentenyl, cyclohexenyl, and the like.

The term "C$_{3-7}$ cycloalkyl" denotes a saturated ring radical containing 3 to 6 carbons; some embodiments contain 3 to 5 carbons; some embodiments contain 3 to 4 carbons. Examples include cyclopropyl, cyclobutyl, cyclopentyl, cyclopenyl, cyclohexyl, cycloheptyl and the like.

The term "C$_{4-8}$ diacylamino" denotes an amino group bonded with two acyl groups defined herein wherein the acyl groups may be the same or different, such as:

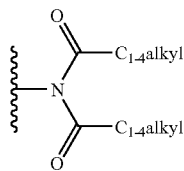

Examples of C$_{4-8}$ diacylamino groups include, but limited to, diacetylamino, dipropionylamino, acetylpropionylamino and the like.

The term "C$_{2-6}$ dialkylamino" denotes an amino substituted with two of the same or different alkyl radicals wherein alkyl radical has the same definition as described herein. Some examples include, but not limited to, dimethylamino, methylethylamino, diethylamino, methylpropylamino, methylisopropylamino, ethylpropylamino, ethylisopropylamino, dipropylamino, propylisopropylamino and the like. Some embodiments are "C$_{2-4}$ dialkylamino."

The term "C$_{1-4}$ dialkylcarboxamido" or "C$_{1-4}$ dialkylcarboxamide" denotes two alkyl radicals, that are the same or different, attached to an amide group, wherein alkyl has the same definition as described herein. A C$_{1-4}$ dialkylcarboxamido may be represented by the following groups:

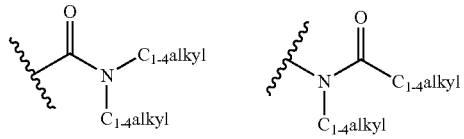

wherein C$_{1-4}$ has the same definition as described herein. Examples of a dialkylcarboxamide include, but not limited to, N,N-dimethylcarboxamide, N-methyl-N-ethylcarboxamide, N,N-diethylcarboxamide, N-methyl-N-isopropylcarboxamide, and the like.

The term "C$_{2-6}$ dialkylsulfonamide" refers to one of the following groups shown below:

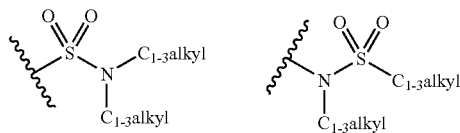

wherein C$_{1-3}$ has the same definition as described herein, for example but not limited to, methyl, ethyl, n-propyl, isopropyl, and the like.

The term "C$_{2-6}$ dialkylthiocarboxamido" or "C$_{2-6}$ dialkylthiocarboxamide" denotes two alkyl radicals, that are the same or different, attached to a thioamide group, wherein alkyl has the same definition as described herein. A C$_{1-4}$ dialkylthiocarboxamido may be represented by the following groups:

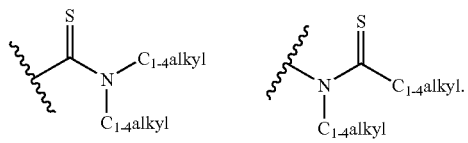

Examples of a dialkylthiocarboxamide include, but not limited to, N,N-dimethylthiocarboxamide, N-methyl-N-ethylthiocarboxamide and the like.

The term "C$_{2-6}$ dialkylsulfonylamino" refers to an amino group bonded with two C$_{1-3}$ alkylsulfonyl groups as defined herein.

The term "ethynylene" refers to the carbon-carbon triple bond group as represented below:

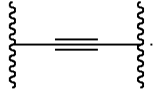

The term "formyl" refers to the group —CHO.

The term "C$_{1-4}$ haloalkoxy" denotes a haloalkyl, as defined herein, which is directly attached to an oxygen atom. Examples include, but not limited to, difluoromethoxy, trifluoromethoxy, 2,2,2-trifluoroethoxy, pentafluoroethoxy and the like.

The term "C$_{1-4}$ haloalkyl" denotes an C$_{1-4}$ alkyl group, defined herein, wherein the alkyl is substituted with one halogen up to fully substituted and a fully substituted C$_{1-4}$ haloalkyl can be represented by the formula $C_nL_{2n+1}$ wherein L is a halogen and "n" is 1, 2, 3 or 4; when more than one halogen is present then they may be the same or different and selected from the group consisting of F, Cl, Br and I, in particular embodiment F. Examples of $C_{1-4}$ haloalkyl groups include, but not limited to, fluoromethyl, difluoromethyl, trifluoromethyl, chlorodifluoromethyl, 2,2,2-trifluoroethyl, pentafluoroethyl and the like.

The term "$C_{1-4}$ haloalkylcarboxamide" denotes an alkylcarboxamide group, defined herein, wherein the alkyl is substituted with one halogen up to fully substituted represented by the formula $C_nL_{2n+1}$, wherein L is a halogen and "n" is 1, 2, 3 or 4. When more than one halogen is present they may be the same or different and selected from the group consisting of F, Cl, Br and I, in particular embodiment F.

The term "$C_{1-4}$ haloalkylsulfinyl" denotes a haloalkyl radical attached to a sulfoxide group of the formula: —S(O)— wherein the haloalkyl radical has the same definition as described herein. Examples include, but not limited to, trifluoromethylsulfinyl, 2,2,2-trifluoroethylsulfinyl, 2,2-difluoroethylsulfinyl and the like.

The term "$C_{1-4}$ haloalkylsulfonyl" denotes a haloalkyl radical attached to a sulfone group of the formula: —S(O)$_2$— wherein haloalkyl has the same definition as described herein. Examples include, but not limited to, trifluoromethylsulfonyl, 2,2,2-trifluoroethylsulfonyl, 2,2-difluoroethylsulfonyl and the like.

The term "$C_{1-4}$ haloalkylthio" denotes a haloalkyl radical directly attached to a sulfur wherein the haloalkyl has the same meaning as described herein. Examples include, but not limited to, trifluoromethylthio (i.e., $CF_3S$—), 1,1-difluoroethylthio, 2,2,2-trifluoroethylthio and the like.

The term "halogen" or "halo" denotes to a fluoro, chloro, bromo or iodo group.

The term "$C_{1-2}$ heteroalkylene" refers to a $C_{1-2}$ alkylene bonded to a heteroatom selected from O, S, S(O), S(O)$_2$ and NH. Some represented examples include, but not limited to, the groups of the following formulae:

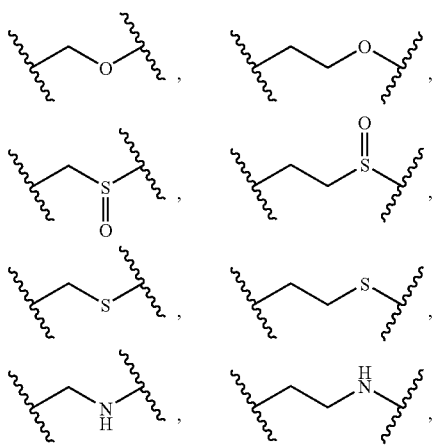

and the like.

The term "heteroaryl" denotes an aromatic ring system that may be a single ring, two fused rings or three fused rings wherein at least one ring carbon is replaced with a heteroatom selected from, but not limited to, the group consisting of O, S and N wherein the N can be optionally substituted with H, $C_{1-4}$ acyl or $C_{1-4}$ alkyl. Examples of heteroaryl groups include, but not limited to, pyridyl, benzofuranyl, pyrazinyl, pyridazinyl, pyrimidinyl, triazinyl, quinoline, benzoxazole, benzothiazole, 1H-benzimidazole, isoquinoline, quinazoline, quinoxaline and the like. In some embodiments, the heteroaryl atom is O, S, NH, examples include, but not limited to, pyrrole, indole, and the like.

The term "heterocyclic" denotes a non-aromatic carbon ring (i.e., cycloalkyl or cycloalkenyl as defined herein) wherein one, two or three ring carbons are replaced by a heteroatom selected from, but not limited to, the group consisting of O, S, N, wherein the N can be optionally substituted with H, $C_{1-4}$ acyl or $C_{1-4}$ alkyl, and ring carbon atoms optionally substituted with oxo or a thiooxo thus forming a carbonyl or thiocarbonyl group. The heterocyclic group is a 3-, 4-, 5-, 6- or 7-membered containing ring. Examples of a heterocyclic group include but not limited to aziridin-1-yl, aziridin-2-yl, azetidin-1-yl, azetidin-2-yl, azetidin-3-yl, piperidin-1-yl, piperidin-4-yl, morpholin-4-yl, piperazin-1-yl, piperazin-4-yl, pyrrolidin-1-yl, pyrrolidin-3-yl, [1,3]-dioxolan-2-yl and the like.

The term "heterocyclic-carbonyl" denotes a heterocyclic group, as defined herein, directly bonded to the carbon of a carbonyl group (i.e., C=O). In some embodiments, a ring nitrogen of the heterocyclic group is bonded to the carbonyl group forming an amide. Examples include, but not limited to,

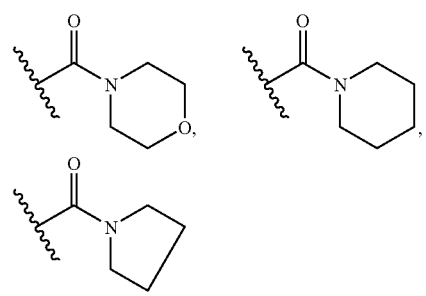

and the like.

In some embodiments, a ring carbon is bonded to the carbonyl group forming a ketone group.

Examples include, but not limited to,

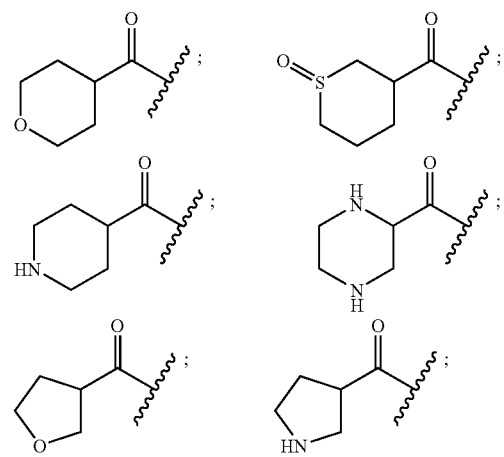

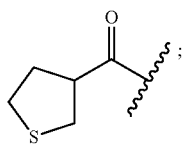

and the like.

The term "heterocyclic-oxy" refers to a heterocyclic group, as defined herein, that is directly bonded to an oxygen atom. Examples include the following:

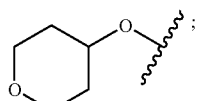 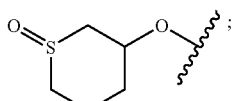

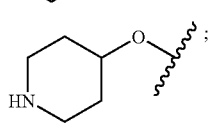 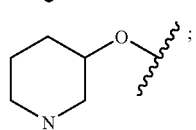

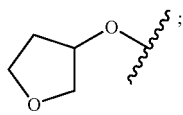 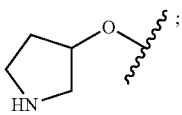

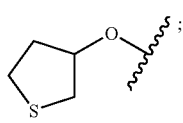

and the like.

The term "heterocycliccarboxamido" denotes a heterocyclic group, as defined herein, with a ring nitrogen where the ring nitrogen is bonded directly to the carbonyl forming an amide. Examples include, but not limited to,

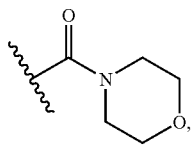 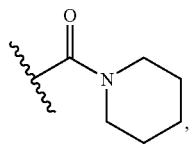

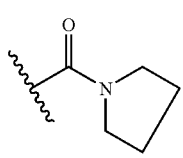

and the like.

The term "heterocyclicsulfonyl" denotes a heterocyclic group, as defined herein, with a ring nitrogen where the ring nitrogen is bonded directly to an SO$_2$ group forming an sulfonamide. Examples include, but not limited to,

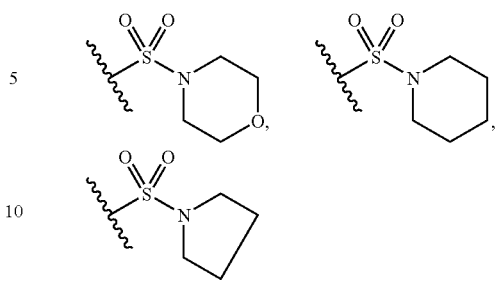

and the like.

The term "hydroxyl" refers to the group —OH.
The term "hydroxylamino" refers to the group —NHOH.
The term "nitro" refers to the group —NO$_2$.
The term "C$_{4-7}$ oxo-cycloalkyl" refers to a C$_{4-7}$ cycloalkyl, as defined herein, wherein one of the ring carbons is replaced with a carbonyl. Examples of C$_{4-7}$ oxo-cycloalkyl include, but are not limited to, 2-oxo-cyclobutyl, 3-oxo-cyclobutyl, 3-oxo-cyclopentyl, 4-oxo-cyclohexyl, and the like and represented by the following structures respectively:

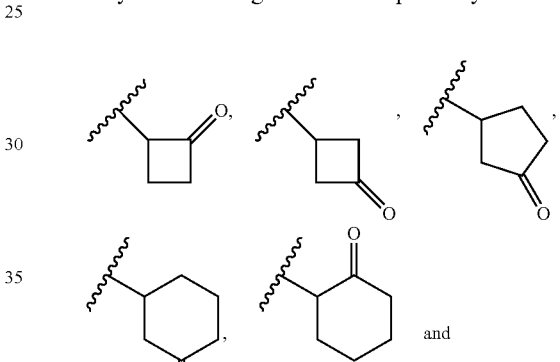

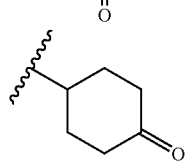

The term "perfluoroalkyl" denotes the group of the formula —C$_n$F$_{2n+1}$; stated differently, a perfluoroalkyl is an alkyl as defined herein wherein the alkyl is fully substituted with fluorine atoms and is therefore considered a subset of haloalkyl. Examples of perfluoroalkyls include CF$_3$, CF$_2$CF$_3$, CF$_2$CF$_2$CF$_3$, CF(CF$_3$)$_2$, CF$_2$CF$_2$CF$_2$CF$_3$, CF$_2$CF(CF$_3$)$_2$, CF(CF$_3$)CF$_2$CF$_3$ and the like.

The term "phenoxy" refers to the group C$_6$H$_5$O—.
The term "phenyl" refers to the group C$_6$H$_5$—.
The term "phosphonooxy" refers to a group with the following chemical structure:

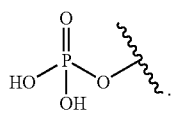

The term "sulfonamide" refers to the group —SO$_2$NH$_2$.
The term "sulfonic acid" refers to the group —SO$_3$H.

The term "tetrazolyl" refers to the five membered heteroaryl of the following formulae:

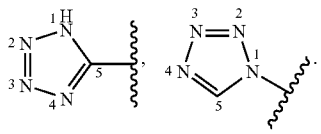

In some embodiments, the tetrazolyl group is further substituted at either the 1 or 5 position respectively with a group selected from the group consisting of $C_{1-3}$ alkyl, $C_{1-3}$ haloalkyl and $C_{1-3}$ alkoxy.

The term "thiol" denotes the group —SH.

The term "endogenous" shall mean a material that an individual (for example, and not limitation, a human) naturally produces. By contrast, "non-endogenous" shall mean that which is not naturally produced by an individual (for example, and not limitation, a human).

The term "host cell" shall mean a cell capable of having a vector incorporated therein. In the present context, the vector will typically contain nucleic acid encoding a GPCR or GPCR fusion protein in operable connection with a suitable promoter sequence to permit expression of the GPCR or GPCR fusion protein to occur. In particular embodiment, the host cell is a eukaryotic host cell. In certain embodiments, the eukaryotic host cell is a mammalian host cell. In certain embodiments, the eukaryotic host cell is a yeast host cell. In certain embodiments, the eukaryotic host cell is a melanophore host cell.

The term "contact" or "contacting" shall mean bringing at least two moieties together.

The terms "modulate" or "modify" shall be taken to refer to an increase or decrease in the amount, quality, or effect of a particular activity, function or molecule. By way of illustration and not limitation, agonists, partial agonists, inverse agonists, and antagonists of a G protein-coupled receptor are modulators of the receptor.

The term "small molecule" shall be taken to mean a compound having a molecular weight of less than about 10,000 grams per mole, including a peptide, peptidomimetic, amino acid, amino acid analogue, polynucleotide, polynucleotide analogue, nucleotide, nucleotide analogue, organic compound or inorganic compound (i.e. including a heterorganic compound or organometallic compound), and salts, esters and other pharmaceutically acceptable forms thereof. In certain embodiments, small molecules are organic or inorganic compounds having a molecular weight of less than about 5,000 grams per mole. In certain embodiments, small molecules are organic or inorganic compounds having molecular weight of less than about 1,000 grams per mole. In certain embodiments, small molecules are organic or inorganic compounds having a molecular weight of less than about 800 grams per mole. In certain embodiments, small molecules are organic or inorganic compounds having a molecular weight of less than about 600 grams per mole. In certain embodiments, small molecules are organic or inorganic compounds having a molecular weight of less than about 500 grams per mole.

Amino acid abbreviations used herein are set out in Table F:

TABLE F

| ALANINE | ALA | A |
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

The term "polypeptide" shall refer to a polymer of amino acids without regard to the length of the polymer. Thus, peptides, oligopeptides, and proteins are included within the definition of polypeptide. This term also does not specify or exclude post-expression modifications of polypeptides. For example, polypeptides that include the covalent attachment of glycosyl groups, acetyl groups, phosphate groups, lipid groups and the like are expressly encompassed by the term polypeptide.

The term "antibody" is intended herein to encompass monoclonal antibody and polyclonal antibody.

The term "second messenger" shall mean an intracellular response produced as a result of receptor activation. A second messenger can include, for example, inositol 1,4,5-triphosphate ($IP_3$), diacylglycerol (DAG), cyclic AMP (cAMP), cyclic GMP (cGMP), MAP kinase activity, MAPK/ERK kinase kinase-1 (MEKK1) activity, and $Ca^{2+}$. Second messenger response can be measured for a determination of receptor activation.

The term "receptor functionality" shall refer to the normal operation of a receptor to receive a stimulus and moderate an effect in the cell, including, but not limited to regulating gene transcription, regulating the influx or efflux of ions, effecting a catalytic reaction, and/or modulating activity through G-proteins, such as eliciting a second messenger response.

The term "stimulate" or "stimulating," in relationship to the term "response" or "functionality of the receptor" shall mean that a response or a functionality of the receptor is increased in the presence of a compound as opposed to in the absence of the compound.

The term "inhibit" or "inhibiting," in relationship to the term "response" or "functionality of the receptor" shall mean that a response a functionality of the receptor is decreased or prevented in the presence of a compound as opposed to in the absence of the compound.

Where a range of values is provided, it is understood that each intervening value, to the tenth of the lower limit unless the context clearly indicates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

GPR119 Agonists

In certain embodiments, GPR119 is mammalian GPR119. In certain embodiments, GPR119 is rodent or primate GPR119. In certain embodiments, GPR119 is human GPR119.

The class of GPR119 agonists useful in compositions and methods of the present invention including but not limited to the novel therapeutic combinations of the present invention include compounds which exhibit an acceptably high affinity for GPR119 receptor. The GPR119 agonist or pharmaceutically acceptable salt may be any agonist, and in particular embodiment a selective GPR119 agonist.

Examples of GPR119 agonists are described in International Application No. PCT/US2004/001267 (published as WO 04/065380), the disclosure of which is herein incorporated by reference in its entirety. Disclosed in International Application No. PCT/US2004/001267 as a GPR119 agonist is a compound of Formula (I):

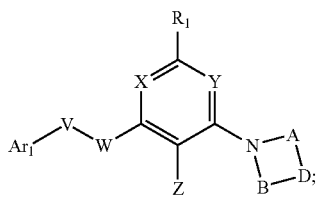

wherein:
A and B are independently $C_{1-3}$ alkylene optionally substituted with 1 to 4 methyl groups;
D is O, S, S(O), S(O)$_2$, CR$_2$R$_3$ or N—R$_2$;
V is selected from the group consisting of $C_{1-3}$ alkylene, ethynylene and $C_{1-2}$ heteroalkylene wherein each are optionally substituted with 1 to 4 substituents selected from the group consisting of $C_{1-3}$ alkyl, $C_{1-4}$ alkoxy, carboxy, cyano, $C_{1-3}$ haloalkyl and halogen; or
V is absent;
W is NR$_4$, O, S, S(O) or S(O)$_2$; or
W is absent;
X is N or CR$_5$;
Y is N or CR$_6$;
Z is selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, $C_{1-2}$ alkylamino, $C_{2-4}$ dialkylamino, carbo-$C_{1-6}$-alkoxy, carboxamide, carboxy, cyano, $C_{4-8}$ diacylamino, $C_{2-6}$ dialkylcarboxamide, $C_{1-4}$ dialkylthiocarboxamide, $C_{2-6}$ dialkylsulfonamide, $C_{1-4}$ dialkylsulfonylamino, formyl, $C_{1-4}$ haloalkoxy, $C_{1-4}$ haloalkyl, $C_{1-4}$ haloalkylcarboxamide, $C_{1-4}$ haloalkylsulfinyl, $C_{1-4}$ haloalkylsulfonyl, $C_{1-4}$ haloalkylthio, halogen, aryl, heterocyclic, heteroaryl, hydroxyl, hydroxylamino, nitro and tetrazolyl, wherein $C_{1-8}$ alkyl and $C_{1-5}$ acyl are each optionally substituted with 1, 2, 3 or 4 groups selected from the group consisting of $C_{1-5}$ acyl, $C_{1-5}$ acyloxy, $C_{1-4}$ alkoxy, $C_{1-8}$ alkylcarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-2}$ alkylamino, $C_{2-4}$ dialkylamino, carbo-$C_{1-6}$-alkoxy, carboxamide, carboxy, cyano, formyl, $C_{1-4}$ haloalkoxy, $C_{1-4}$ haloalkylsulfinyl, $C_{1-4}$ haloalkylsulfonyl, $C_{1-4}$ haloalkylthio, halogen, hydroxyl, hydroxylamino and nitro; or Z is a group of Formula (IA):

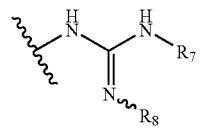

wherein:
$R_7$ is H, $C_{1-8}$ alkyl or $C_{3-6}$ cycloalkyl; and
$R_8$ is H, nitro or nitrile;
Ar$_1$ is aryl or heteroaryl wherein each are optionally substituted with $R_9$-$R_{13}$;
$R_1$ is selected from the group consisting of H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-6}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio and hydroxyl;
$R_2$ is selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, carbo-$C_{1-6}$-alkoxy, carboxamide, carboxy, cyano, $C_{3-6}$-cycloalkyl, $C_{2-6}$ dialkylcarboxamide, $C_{1-4}$ haloalkoxy, $C_{1-4}$ haloalkyl, halogen, heteroaryl, hydroxyl and phenyl; and wherein $C_{1-8}$ alkyl, heteroaryl and phenyl are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-alkylene, $C_{3-6}$-cycloalkyl-$C_{1-3}$-heteroalkylene, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro; or
$R_2$ is —Ar$_2$—Ar$_3$ wherein Ar$_2$ and Ar$_3$ are independently aryl or heteroaryl each optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, carbo-$C_{1-6}$-alkoxy, carboxamide, carboxy, cyano, $C_{3-6}$-cycloalkyl, $C_{2-6}$ dialkylcarboxamide, $C_{1-4}$ haloalkoxy, $C_{1-4}$ haloalkyl, halogen, hydroxyl and nitro; or $R_2$ is a group of Formula (IB):

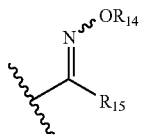

(IB)

wherein:
$R_{14}$ is $C_{1-8}$ alkyl or $C_{3-6}$ cycloalkyl; and $R_{15}$ is F, Cl, Br or CN; or $R_2$ is a group of Formula (IC):

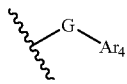

(IC)

wherein:
G is C=O, $CR_{16}R_{17}$, O, S, S(O), $S(O)_2$; where $R_{16}$ and $R_{17}$ are independently H or $C_{1-8}$ alkyl; and
$Ar_4$ is phenyl or heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{2-6}$ dialkylcarboxamide, $C_{1-4}$ dialkylthiocarboxamide, $C_{2-4}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, halogen, heteroaryl, hydroxyl, hydroxylamino and nitro;

$R_3$ is H, $C_{1-8}$ alkyl, $C_{1-4}$ alkoxy, halogen or hydroxyl;
$R_4$ is H or $C_{1-8}$ alkyl;
$R_5$ and $R_6$ are independently H, $C_{1-8}$ alkyl or halogen;
$R_9$ is selected from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylamino, $C_{1-4}$ alkylcarboxamide, $C_{2-4}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, arylsulfonyl, carbo-$C_{1-6}$-alkoxy, carboxamide, carboxy, cyano, $C_{3-6}$ cycloalkyl, $C_{2-6}$ dialkylamino, $C_{2-4}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclicsulfonyl, heteroaryl, hydroxyl, nitro, $C_{4-7}$ oxo-cycloalkyl, phenoxy, phenyl, sulfonamide and sulfonic acid, and wherein $C_{1-5}$ acyl, $C_{1-4}$ alkoxy, $C_{1-8}$ alkyl, $C_{1-4}$ alkylsulfonamide, alkylsulfonyl, arylsulfonyl, heteroaryl, phenoxy and phenyl are each optionally substituted with 1 to 5 substituents selected independently from the group consisting of $C_{1-5}$ acyl, $C_{1-5}$ acyloxy, $C_{2-4}$ alkenyl, $C_{1-4}$ alkoxy, $C_{1-8}$ alkyl, $C_{1-4}$ alkylcarboxamide, $C_{2-4}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro and phenyl; or $R_9$ is a group of Formula (ID):

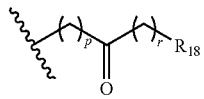

(ID)

wherein:
"p" and "r" are independently 0, 1, 2 or 3; and
$R_{18}$ is H, $C_{1-5}$ acyl, $C_{2-4}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-6}$ cycloalkyl, $C_{2-6}$ dialkylcarboxamide, halogen, heteroaryl or phenyl, and wherein the heteroaryl and phenyl are each optionally substituted with 1 to 5 substituents selected independently from the group consisting of $C_{1-4}$ alkoxy, amino, $C_{1-4}$ alkylamino, $C_{2-6}$ alkynyl, $C_{2-6}$ dialkylamino, halogen, $C_{1-4}$ haloalkoxy, $C_{1-4}$ haloalkyl and hydroxyl; and
$R_{10}$-$R_{13}$ are independently selected form the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl and nitro; or
two adjacent $R_{10}$-$R_{11}$ groups together with $Ar_1$ form a 5, 6 or 7 membered cycloalkyl, cycloalkenyl or heterocyclic group wherein the 5, 6 or 7 membered group is optionally substituted with halogen.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Specific examples of GPR119 agonists disclosed in International Application No. PCT/US2004/001267 include the following compounds according to Formula (I) (referred to herein as Group A1): [6-(4-Benzenesulfonyl-piperidin-1-yl)-5-nitro-pyrimidin-4-yl]-(4-methanesulfonyl-phenyl)-amine; {4-[6-(4-Methanesulfonyl-phenylamino)-5-nitro-pyrimidin-4-yl]-piperazin-1-yl}-acetic acid ethyl ester; (2-Fluoro-phenyl)-{5-nitro-6-[4-(pyridin-2-ylsulfanyl)-piperidin-1-yl]-pyrimidin-4-yl}-amine; 1-[6-(4-Imidazol-1-yl-phenoxy)-5-nitro-pyrimidin-4-yl]-piperidine-4-carboxylic acid ethyl ester; 1-[5-Nitro-6-(4-[1,2,4]triazol-1-yl-phenoxy)-pyrimidin-4-yl]-piperidine-4-carboxylic acid ethyl ester; {6-[4-(4-Fluoro-phenoxy)-piperidin-1-yl]-5-nitro-pyrimidin-4-yl}-(4-methanesulfonyl-phenyl)-amine; {6-[4-(3-Isopropyl-[1,2,4]oxadiazol-5-yl)-piperidin-1-yl]-5-nitro-pyrimidin-4-yl}-(4-methanesulfonyl-phenyl)-amine; {6-[4-(3-Cyclopropyl-[1,2,4]oxadiazol-5-yl)-piperidin-1-yl]-5-nitro-pyrimidin-4-yl}-(4-methanesulfonyl-phenyl)-amine; (4-Methanesulfonyl-phenyl)-(5-nitro-6-{4-[3-(3-trifluoromethyl-phenyl)-[1,2,4]oxadiazol-5-yl]-piperidin-1-yl}-pyrimidin-4-yl)-amine; {6-[4-(3-Ethyl-[1,2,4]oxadiazol-5-yl)-piperidin-1-yl]-5-nitro-pyrimidin-4-yl}-(2-fluoro-phenyl)-amine; (2-Fluoro-4-methanesulfonyl-phenyl)-{6-[4-(3-isopropyl-[1,2,4]oxadiazol-5-yl)-piperidin-1-yl]-5-nitropyrimidin-4-yl}-amine; {6-[4-(3-Ethyl-[1,2,4]oxadiazol-5-yl)-piperidin-1-yl]-5-nitro-pyrimidin-4-yl}-(2-fluoro-4-methanesulfonyl-phenyl)-amine; (4-Methanesulfonyl-phenyl)-{5-nitro-6-[4-(3-propyl-[1,2,4]oxadiazol-5-yl)-piperidin-1-yl]-pyrimidin-4-yl}-amine; {6-[4-(3-Cyclopropylmethyl-[1,2,4]oxadiazol-5-yl)-piperidin-1-yl]-5-nitro-pyrimidin-4-yl}-(4-methanesulfonyl-phenyl)-amine; (4-Methanesulfonyl-phenyl)-{5-nitro-6-[4-(pyridin-4-yloxy)-piperidin-1-yl]-pyrimidin-4-yl}-amine; (4-Methanesulfonyl-phenyl)-{5-nitro-6-[4-(pyrimidin-2-yloxy)-piperidin-1-yl]-pyrimidin-4-yl}-amine; 1-[6-(4-Carbamoylmethyl-phenoxy)-5-nitro-pyrimidin-4-yl]-piperidine-4-carboxylic acid ethyl ester; 1-{6-[4-(1,3-Dioxo-1,3-dihydro-isoindol-2-yl)-phenoxy]-5-nitro-pyrimidin-4-yl}-piperidine-4-carboxylic acid ethyl ester; 4'-[4-(2-Methoxycarbonyl-acetyl)-phenoxy]-3'-nitro-3,4,5,6-tetrahydro-2H-[1,2']bipyridinyl-4-carboxylic acid ethyl ester; {6-[4-(2-Methoxy-phenylsulfanyl)-piperidin-1-yl]-5-nitro-pyrimidin-4-yl}-(4-[1,2,4]triazol-1-yl-phenyl)-amine; 4'-(2-Amino-4-ethanesulfonyl-phenoxy)-3'-nitro-3,4,5,6-tetrahydro-2H-[1,2']bipyridinyl-4-carboxylic acid ethyl ester; 4'-(4-Imidazol-1-yl-phenoxy)-3'-nitro-3,4,5,6-tetrahydro-2H-[1,2']bipyridinyl-4-carboxylic acid ethyl ester; (4-Methoxy-2-{5-nitro-6-[4-(pyridin-2-ylsulfanyl)-piperidin-1-yl]-pyrimidin-4-yloxy}-phenyl)-phenyl-methanone; 4-{4-[6-(4-Cyclopropylmethoxymethyl-piperidin-1-yl)-5-nitro-pyrimidin-4-yloxy]-phenyl}-butan-2-one; 4-{4-[5-Nitro-6-(4-propoxymethyl-piperidin-1-yl)-pyrimidin-4-yloxy]-phenyl}-butan-2-one; 4-{4-[6-(4-Butoxymethyl-piperidin-1-yl)-5-nitro-pyrimidin-4-yloxy]-phenyl}-butan-2-one; 4-{4-[6-(4-Isobutoxymethyl-piperidin-1-yl)-5-nitro-pyrimidin-4-yloxy]-phenyl}-butan-2-one; {1-[6-(Benzo[1,3]dioxol-5-ylamino)-5-nitro-pyrimidin-4-yl]-piperidin-4-yl}-(4-fluoro-phenyl)-methanone; (2,3-Difluoro-phenyl)-{5-nitro-6-[4-(pyridin-2-ylsulfanyl)-piperidin-1-yl]-pyrimidin-4-yl}-amine; (2,4-Difluoro-phenyl)-{5-nitro-6-[4-(pyridin-2-ylsulfanyl)-piperidin-1-yl]-pyrimidin-4-yl}-amine; 1-{2-Nitro-3-[4-(3-oxo-butyl)-phenoxy]-phenyl})-piperidine-4-carboxylic acid ethyl ester; 1-[6-(4-Acetyl-phenoxy)-5-nitro-pyrimidin-4-yl]-piperidine-4-carboxylic acid ethyl ester; 3'-Nitro-2'-[4-(3-oxo-butyl)-phenoxy]-3,4,5,6-tetrahydro-2H-[1,4']bipyridinyl-4-carboxylic acid ethyl ester; 4-(4-{5-Nitro-6-[4-(pyridin-2-ylsulfanyl)-piperidin-1-yl]-pyrimidin-4-yloxy}-phenyl)-butan-2-one; 4-(4-{5-Nitro-6-[4-(2-trifluoromethyl-phenoxy)-piperidin-1-yl]-pyrimidin-4-yloxy}-phenyl)-butan-2-one; 4-(4-{6-[4-(3-Methyl-[1,2,4]oxadiazol-5-yl)-piperidin-1-yl]-5-nitro-pyrimidin-4-yloxy}-phenyl)-butan-2-one; 4-(2,4-Difluoro-phenoxy)-5-nitro-6-[4-(pyridin-2-ylsulfanyl)-piperidin-1-yl]-pyrimidine; 4-(4-{6-[4-(4-Fluoro-benzoyl)-piperidin-1-yl]-5-nitro-pyrimidin-4-yloxy}-phenyl)-butan-2-one; 4-(4-Methanesulfonyl-phenoxy)-5-nitro-6-[4-(pyridin-2-ylsulfanyl)-cyclohexyl]-pyrimidine; 4-(4-Methanesulfonyl-phenoxy)-5-nitro-6-[4-(pyridin-4-ylsulfanyl)-cyclohexyl]-pyrimidine; 4-(4-Methanesulfonyl-phenoxy)-5-nitro-6-(4-phenylsulfanyl-cyclohexyl)-pyrimidine; 1-{6-[(Benzo[1,3]dioxol-5-ylmethyl)-amino]-5-nitro-pyrimidin-4-yl}-piperidine-4-carboxylic acid ethyl ester; 1-{6-[4-(1,1-Dioxo-1λ⁶-thiomorpholin-4-ylmethyl)-phenylamino]-5-nitro-pyrimidin-4-yl}-piperidine-4-carboxylic acid ethyl ester; 1-[6-(4-Methanesulfonyl-phenylamino)-5-nitro-pyrimidin-4-yl]-piperidine-4-carboxylic acid ethyl ester; 1-[6-(4-Dimethylsulfamoyl-phenylamino)-5-nitro-pyrimidin-4-yl]-piperidine-4-carboxylic acid ethyl ester; 1-[6-(3-Methoxy-phenylamino)-5-nitro-pyrimidin-4-yl]-piperidine-4-carboxylic acid ethyl ester; 1-[6-(2-Methoxy-phenylamino)-5-nitro-pyrimidin-4-yl]-piperidine-4-carboxylic acid ethyl ester; 1-[6-(4-Methanesulfonyl-phenoxy)-5-nitro-pyrimidin-4-yl]-piperidine-4-carboxylic acid ethyl ester; 1-{6-[4-(2-Methoxycarbonyl-acetyl)-phenoxy]-5-nitro-pyrimidin-4-yl}-piperidine-4-carboxylic acid ethyl ester; 1-[6-(2-Amino-4-ethanesulfonyl-phenoxy)-5-nitro-pyrimidin-4-yl]-piperidine-4-carboxylic acid ethyl ester; 1-[6-(2,5-Dimethoxy-phenylamino)-5-nitro-pyrimidin-4-yl]-piperidine-4-carboxylic acid ethyl ester; (4-{5-Nitro-6-[4-(pyridin-2-ylsulfanyl)-piperidin-1-yl]-pyrimidin-4-ylamino}-phenyl)-phenyl-methanone; 1-[6-(4-Cyclohexyl-phenylamino)-5-nitro-pyrimidin-4-yl]-piperidine-4-carboxylic acid ethyl ester; 1-[5-Nitro-6-(4-[1,2,4]triazol-1-yl-phenylamino)-pyrimidin-4-yl]-piperidine-4-carboxylic acid ethyl ester; 1-[5-Nitro-6-(4-trifluoromethanesulfonyl-phenylamino)-pyrimidin-4-yl]-piperidine-4-carboxylic acid ethyl ester; 1-[5-Nitro-6-(4-[1,2,3]thiadiazol-4-yl-phenylamino)-pyrimidin-4-yl]-piperidine-4-carboxylic acid ethyl ester; [6-(4-Ethoxymethyl-piperidin-1-yl)-5-nitro-pyrimidin-4-yl]-(4-methanesulfonyl-phenyl)-amine; [5-Nitro-6-(4-propyl-piperidin-1-yl)-pyrimidin-4-yl]-(4-[1,2,4]triazol-1-yl-phenyl)-amine; {5-Nitro-6-[4-(pyridin-2-ylsulfanyl)-piperidin-1-yl]-pyrimidin-4-yl}-(4-[1,2,4]triazol-1-yl-phenyl)-amine; (2-Fluoro-phenyl)-{6-[4-(3-methyl-[1,2,4]oxadiazol-5-yl)-piperidin-1-yl]-5-nitro-pyrimidin-4-yl}-amine; (4-Methanesulfonyl-phenyl)-{6-[4-(3-methyl-[1,2,4]oxadiazol-5-yl)-piperidin-1-yl]-5-nitro-pyrimidin-4-yl}-amine; {6-[4-(3-Methyl-[1,2,4]oxadiazol-5-yl)-piperidin-1-yl]-5-nitro-pyrimidin-4-yl}-(4-[1,2,4]triazol-1-yl-phenyl)-amine; (4-Methanesulfonyl-phenyl)-{5-nitro-6-[4-(pyridin-2-ylsulfanyl)-piperidin-1-yl]-pyrimidin-4-yl}-amine; (3-Methoxy-phenyl)-{5-nitro-6-[4-(pyridin-2-ylsulfanyl)-piperidin-1-yl]-pyrimidin-4-yl}-amine; 1-[6-(Benzo[1,3]dioxol-5-ylamino)-5-nitro-pyrimidin-4-yl]-piperidine-4-carboxylic acid ethyl ester; 1-[6-(2-Fluoro-phenylamino)-5-nitro-pyrimidin-4-yl]-piperidine-4-carboxylic acid ethyl ester; 1-[6-(3-Fluoro-phenylamino)-5-nitro-pyrimidin-4-yl]-piperidine-4-carboxylic acid ethyl ester; 1-[6-(3,4-Dihydro-2H-benzo[b][1,4]dioxepin-7-ylamino)-5-nitro-pyrimidin-4-yl]-piperidine-4-carboxylic acid ethyl ester; 1-{6-[4-(Morpholine-4-sulfonyl)-phenylamino]-5-nitro-pyrimidin-4-yl}-piperidine-4-carboxylic acid ethyl ester; Benzo[1,3]dioxol-5-yl-[5-nitro-6-(4-propyl-piperidin-1-yl)-pyrimidin-4-yl]-amine; (4-Fluoro-phenyl)-{1-[5-nitro-6-(4-[1,2,4]triazol-1-yl-phenylamino)-pyrimidin-4-yl]-piperidin-4-yl}-methanone; [5-Nitro-6-(4-phenylsulfanyl-piperidin-1-yl)-pyrimidin-4-yl]-(4-[1,2,4]triazol-1-yl-phenyl)-amine; (4-Fluoro-phenyl)-{1-[6-(2-fluoro-phenylamino)-5-nitro-pyrimidin-4-yl]-piperidin-4-yl}-methanone; (4-Methanesulfonyl-phenyl)-[5-nitro-6-(4-phenylsulfanyl-piperidin-1-yl)-pyrimidin-4-yl]-amine; (4-Methanesulfonyl-phenyl)-{5-nitro-6-[4-(pyridin-2-yloxy)-piperidin-1-yl]-pyrimidin-4-yl}-amine; (4-Methanesulfonyl-phenyl)-{5-nitro-6-[4-(pyridin-4-ylsulfanyl)-piperidin-1-yl]-pyrimidin-4-yl}-amine; (4-Methanesulfonyl-phenyl)-{6-[4-(4-methoxy-phenylsulfanyl)-piperidin-1-yl]-5-nitro-pyrimidin-4-yl}-amine; 2-Methoxy-phenyl)-{5-nitro-6-[4-(pyridin-2-ylsulfanyl)-piperidin-1-yl]-pyrimidin-4-yl}-amine; (4-Methanesulfonyl-phenyl)-(5-nitro-6-{4-[3-(3-trifluoromethyl-phenyl)-[1,2,4]oxadiazol-5-yl]-piperidin-1-yl}-pyrimidin-4-yl)-amine; {6-[4-(3-Ethyl-[1,2,4]oxadiazol-5-yl)-piperidin-1-yl]-5-nitro-pyrimidin-4-yl}-(4-methanesulfonyl-phenyl)-amine; (6-{4-[5-(4-Fluoro-phenyl)-[1,3,4]oxadiazol-2-yl]-piperidin-1-yl}-5-nitro-pyrimidin-4-yl)-(4-methanesulfonyl-phenyl)-amine; (4-Methanesulfonyl-phenyl)-[5-nitro-6-(4-pyridin-2-ylmethyl-piperidin-1-yl)-pyrimidin-4-yl]-amine; 1-{6-[4-(2,5-Dioxo-imidazolidin-4-yl)-phenoxy]-5-nitro-pyrimidin-4- yl}-piperidine-4-carboxylic acid ethyl ester; 1-[5-Nitro-6-(4-propionyl-phenoxy)-pyrimidin-4-yl]-piperidine-4-carboxylic acid ethyl ester; 1-[5-Nitro-6-(4-[1,2,3]thiadiazol-4-yl-phenoxy)-pyrimidin-4-yl]-piperidine-4-carboxylic acid ethyl ester; 1-[6-[4-(3-Oxo-butyl)-phenoxy]-5-(2,2,2-trifluoro-acetylamino)-pyrimidin-4-yl]-piperidine-4-carboxylic acid ethyl ester; 1-[6-(2-Benzoyl-5-methoxy-phenoxy)-5-nitro-pyrimidin-4-yl]-piperidine-4-carboxylic acid ethyl ester; 3'-Nitro-4'-[4-(3-oxo-butyl)-phenoxy]-3,4,5,6-tetrahydro-2H-[1,2']bipyridinyl-4-carboxylic acid ethyl ester; 1-[6-(4-Dimethyl sulfamoyl-phenylamino)-5-nitro-pyrimidin-4-yl]-piperidine-4-carboxylic acid ethyl ester; 1-{6-[4-(4,5-Dichloro-imidazol-1-yl)-phenylamino]-5-nitro-pyrimidin-4-yl}-piperidine-4-carboxylic acid ethyl ester; Benzo[1,3]dioxol-5-yl-{5-nitro-6-[4-(pyridin-2-ylsulfanyl)-piperidin-1-yl]-pyrimidin-4-yl}-amine; (4-Fluoro-phenyl)-{1-[6-(2-fluoro-phenylamino)-5-nitro-pyrimidin-4-yl]-piperidin-4-yl}-methanone; (2,5-Difluoro-phenyl)-{5-nitro-6-[4-(pyridin-2-ylsulfanyl)-piperidin-1-yl]-pyrimidin-4-yl}-amine; 1-{5-Nitro-6-[4-(3-oxo-butyl)-phenoxy]-pyrimidin-4-yl}-piperidine-4-carboxylic acid ethyl ester; 4-[4-(3-Isopropyl-[1,2,4]oxadiazol-5-yl)-piperidin-1-yl]-6-(4-methanesulfonyl-phenoxy)-pyrimidine-5-carbonitrile; 5-[1,3]Dioxolan-2-yl-4-[4-(3-isopropyl-[1,2,4]oxadiazol-5-yl)-piperidin-1-yl]-6-(4-methanesulfonyl-phenoxy)-pyrimidine; 4-[4-(3-Isopropyl-[1,2,4]oxadiazol-5-yl)-piperidin-1-yl]-6-(4-methanesulfonyl-phenoxy)-pyrimidine-5-carbaldehyde; 5-[1,3]Dioxolan-2-yl-4-[4-(3-isopropyl-[1,2,4]oxadiazol-5-yl)-piperidin-1-yl]-6-(4-[1,2,3]thiadiazol-4-yl-phenoxy)-pyrimidine; 4-[4-(3-Isopropyl-[1,2,4]oxadiazol-5-yl)-piperidin-1-yl]-6-(4-[1,2,3]thiadiazol-4-yl-phenoxy)-pyrimidine-5-carbaldehyde; 4-[4-(3-Isopropyl-[1,2,4]oxadiazol-5-yl)-piperidin-1-yl]-6-(4-[1,2,3]thiadiazol-4-yl-phenoxy)-pyrimidine-5-carboxylic acid; [4-[4-(3-Isopropyl-[1,2,4]oxadiazol-5-yl)-piperidin-1-yl]-6-(4-[1,2,3]thiadiazol-4-yl-phenoxy)-pyrimidin-5-yl]-methanol; [4-[4-(3-Isopropyl-[1,2,4]oxadiazol-5-yl)-piperidin-1-yl]-6-(4-[1,2,3]thiadiazol-4-yl-phenoxy)-pyrimidin-5-ylmethyl]-dimethyl-amine; 4-[4-(3-Isopropyl-[1,2,4]oxadiazol-5-yl)-piperidin-1-yl]-6-(4-methylsulfanyl-phenylamino)-pyrimidine-5-carbonitrile; 4-[4-(3-Isopropyl-[1,2,4]oxadiazol-5-yl)-piperidin-1-yl]-6-(4-methanesulfinyl-phenylamino)-pyrimidine-5-carbonitrile; (4-Methanesulfonyl-phenyl)-{5-nitro-6-[4-(4-trifluoromethoxy-phenoxy)-piperidin-1-yl]-pyrimidin-4-yl}-amine; 4-[4-(3-Isopropyl-[1,2,4]oxadiazol-5-yl)-piperidin-1-yl]-6-(4-methanesulfonyl-phenylamino)-pyrimidine-5-carbonitrile; 1-{1-[6-(2-Fluoro-4-methanesulfonyl-phenylamino)-5-nitro-pyrimidin-4-yl]-piperidin-4-yl}-hexan-1-one; 1-{1-[6-(4-Methanesulfonyl-phenylamino)-5-nitro-pyrimidin-4-yl]-piperidin-4-yl}-hexan-1-one; {6-[4-(3-tert-Butyl-[1,2,4]oxadiazol-5-yl)-piperidin-1-yl]-5-nitro-pyrimidin-4-yl}-(2-fluoro-4-methanesulfonyl-phenyl)-amine; {6-[4-(3-tert-Butyl-[1,2,4]oxadiazol-5-yl)-piperidin-1-yl]-5-nitro-pyrimidin-4-yl}-(4-methanesulfonyl-phenyl)-amine; [6-(4-Benzofuran-2-yl-piperidin-1-yl)-5-nitro-pyrimidin-4-yl]-(4-methanesulfonyl-phenyl)-amine and 5-Nitro-4-(5-phenyl-[1,3,4]oxadiazol-2-ylsulfanyl)-6-[4-(pyridin-2-ylsulfanyl)-piperidin-1-yl]-pyrimidine.

Examples of GPR119 agonists are described in International Application No. PCT/US2004/005555 (published as WO 04/076413), the disclosure of which is herein incorporated by reference in its entirety. Disclosed in International Application No. PCT/US2004/005555 as a GPR119 agonist is a compound of Formula (II):

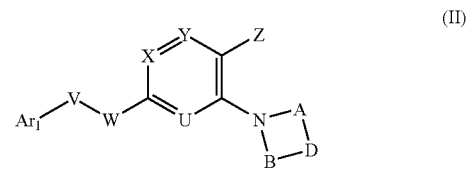

wherein:

A and B are independently $C_{1-3}$ alkylene optionally substituted with 1 to 4 methyl groups;

U is N or $CR_1$;

D is O, S, S(O), S(O)$_2$, $CR_2R_3$ or $NR_2$;

V is selected from the group consisting of $C_{1-3}$ alkylene, ethynylene and $C_{1-2}$ heteroalkylene optionally substituted with 1 to 4 substituents selected from the group consisting of $C_{1-3}$ alkyl, $C_{1-4}$ alkoxy, carboxy, cyano, $C_{1-3}$ haloalkyl and halogen; or V is absent;

W is —S(O)$_2$NR$_4$—, —NR$_4$—, —O—, —S—, —S(O)—, —S(O)$_2$—; or W is absent;

X is N or $CR_5$;

Y is N or $CR_6$;

Z is selected from the group consisting of H, $C_{1-5}$ acyl, $C_{1-5}$ acyloxy, $C_{1-4}$ alkoxy, $C_{1-6}$ alkyl, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{4-8}$ diacylamino, $C_{1-4}$ dialkylcarboxamide, $C_{1-4}$ dialkylthiocarboxamide, $C_{2-6}$ dialkylsulfonamide, $C_{1-4}$ dialkylsulfonylamino, formyl, $C_{1-4}$ haloalkoxy, $C_{1-4}$ haloalkyl, $C_{1-4}$ haloalkylcarboxamide, $C_{1-4}$ haloalkylsulfinyl, $C_{1-4}$ haloalkylsulfonyl, $C_{1-4}$ haloalkylthio, halogen, aryl, heteroaryl, hydroxyl, hydroxylamino, nitro and tetrazolyl; or Z is a group of Formula (IIA):

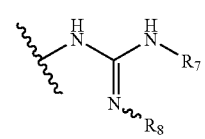

wherein:
$R_7$ is H, $C_{1-6}$ alkyl or $C_{3-6}$ cycloalkyl; and
$R_8$ is H, nitro or cyano;

$Ar_1$ is aryl or heteroaryl optionally substituted with $R_9$, $R_{10}$, $R_{11}$, $R_{12}$ and $R_{13}$;

$R_1$, $R_5$ and $R_6$ are independently selected from the group consisting of H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-6}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl and nitro;

$R_2$ is selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, carbo-$C_{1-6}$-alkoxy, carboxamide, carboxy, cyano, $C_{3-6}$-cycloalkyl, $C_{2-6}$ dialkylcarboxamide, $C_{1-4}$ haloalkoxy, $C_{1-4}$ haloalkyl, halogen, heteroaryl, hydroxyl and phenyl; and wherein $C_{1-8}$ alkyl, heteroaryl and phenyl are optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-heteroalkylene, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxy)amino and nitro; or $R_2$ is —$Ar_2$—$Ar_3$ wherein $Ar_2$ and $Ar_3$ are independently aryl or heteroaryl optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, carbo-$C_{1-6}$-alkoxy, carboxamide, carboxy, cyano, $C_{3-6}$-cycloalkyl, $C_{2-6}$ dialkylcarboxamide, $C_{1-4}$ haloalkoxy, $C_{1-4}$ haloalkyl, halogen, hydroxyl and nitro; or $R_2$ is a group of Formula (IIB):

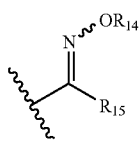

(IIB)

wherein:
$R_{14}$ is $C_{1-8}$ alkyl or $C_{3-6}$ cycloalkyl; and $R_{15}$ is F, Cl, Br or CN; or $R_2$ is a group of Formula (IIC):

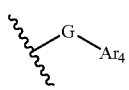

(IIC)

wherein:
G is C=O, $CR_{16}R_{17}$, O, S, S(O), S(O)$_2$; where $R_{16}$ and $R_{17}$ are independently H or $C_{1-8}$ alkyl; and
$Ar_4$ is phenyl or heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, hydroxyl, hydroxylamino and nitro;

$R_3$ is H, $C_{1-8}$ alkyl, $C_{1-4}$ alkoxy or hydroxyl;
$R_4$ is H or $C_{1-8}$ alkyl;
$R_9$ is selected from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, arylsulfonyl, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclicsulfonyl, heteroaryl, hydroxyl, nitro, $C_{4-7}$ oxo-cycloalkyl, phenoxy, phenyl, sulfonamide and sulfonic acid, and wherein $C_{1-5}$ acyl, $C_{1-4}$ alkoxy, $C_{1-8}$ alkyl, $C_{1-4}$ alkylsulfonamide, alkylsulfonyl, arylsulfonyl, heteroaryl, phenoxy and phenyl are optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro and phenyl; or $R_9$ is a group of Formula (IID):

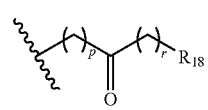

(IID)

wherein:
"p" and "r" are independently 0, 1, 2 or 3; and
$R_{18}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-6}$ cycloalkyl, $C_{2-6}$ dialkylcarboxamide, halogen, heteroaryl or phenyl, and wherein the heteroaryl or phenyl optionally substituted with 1 to 5 substituents selected independently from the group consisting of $C_{1-4}$ alkoxy, $C_{1-8}$ alkyl, amino, $C_{1-4}$ alkylamino, $C_{2-4}$ alkynyl, $C_{2-8}$ dialkylamino, halogen, $C_{1-4}$ haloalkoxy, $C_{1-4}$ haloalkyl and hydroxyl; and $R_{10}$-$R_{13}$ are independently selected form the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl and nitro; or two adjacent $R_{10}R_{11}$ groups form a 5, 6 or 7 membered cycloalkyl, cycloalkenyl or heterocyclic group with $Ar_1$ wherein the 5, 6 or 7 membered group is optionally substituted with halogen.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Specific examples of GPR119 agonists disclosed in International Application No. PCT/US2004/005555 include the following compounds according to Formula (II) (referred to herein as Group B1): 6'-[4-(2-Methoxycarbonyl-acetyl)-phenoxy]-3'-nitro-3,4,5,6-tetrahydro-2H-[1,2']bipyridinyl-4-carboxylic acid ethyl ester; 1-[4-(4-Acetyl-3'-nitro-3,4,5,6-tetrahydro-2H-[1,2']bipyridinyl-6'-yloxy)-phenyl]-ethanone; 6'-[4-(4-Hydroxy-benzenesulfonyl)-phenoxy]-3'-nitro-3,4,5,6-tetrahydro-2H-[1,2']bipyridinyl-4-carboxylic acid ethyl ester; 6'-(4-Imidazol-1-yl-phenoxy)-3'-nitro-3,4,5,6-tetrahydro-2H-[1,2']bipyridinyl-4-carboxylic acid ethyl ester; 6'-(4-Benzoyl-phenoxy)-3'-nitro-3,4,5,6-tetrahydro-2H-[1,2']bipyridinyl-4-carboxylic acid ethyl ester; 6'-[4-(2-Methoxy-ethyl)-phenoxy]-3'-nitro-3,4,5,6-tetrahydro-2H-[1,2']bipyridinyl-4-carboxylic acid ethyl ester; 6'-(4-Cyclopentyl-phenoxy)-3'-nitro-3,4,5,6-tetrahydro-2H-[1,2']bipyridinyl-4-carboxylic acid ethyl ester; 6'-(4'-Cyano-biphenyl-4-yloxy)-3'-nitro-3,4,5,6-tetrahydro-2H-[1,2']bipyridinyl-4-carboxylic acid ethyl ester; 3'-Nitro-6'-(4-sulfo-phenoxy)-3,4,5,6-tetrahydro-2H-[1,2']bipyridinyl-4-carboxylic acid ethyl ester; 3'-Nitro-6'-(4-pyrrol-1-yl-phenoxy)-3,4,5,6-tetrahydro-2H-[1,2']bipyridinyl-4-carboxylic acid ethyl ester; 6'-(4-Carbamoyl-phenoxy)-3'-nitro-3,4,5,6-tetrahydro-2H-[1,2']bipyridinyl-4-carboxylic acid ethyl ester; 3'-Nitro-6'-(4-[1,2,4]triazol-1-yl-phenoxy)-3,4,5,6-tetrahydro-2H-[1,2']bipyridinyl-4-carboxylic acid ethyl ester; 6'-(2-Amino-4-ethanesulfonyl-phenoxy)-3'-nitro-3,4,5,6-tetrahydro-2H-[1,2']bipyridinyl-4-carboxylic acid ethyl ester; 3'-Nitro-6'-[4-(4-oxo-cyclohexyl)-phenoxy]-3,4,5,6-tetrahydro-2H-[1,2']bipyridinyl-4-carboxylic acid ethyl ester; 6'-(4'-Methoxy-biphenyl-4-yloxy)-3'-nitro-3,4,5,6-tetrahydro-2H-[1,2']bipyridinyl-4-carboxylic acid ethyl ester; 3'-Nitro-6'-(4-[1,2,3]thiadiazol-4-yl-phenoxy)-3,4,5,6-tetrahydro-2H-[1,2']bipyridinyl-4-carboxylic acid ethyl ester; 6'-[4-(1,3-Dioxo-1,3-dihydro-isoindol-2-yl)-phenoxy]-3'-nitro-3,4,5,6-tetrahydro-2H-[1,2']bipyridinyl-4-carboxylic acid ethyl ester; 6'-[4-(2,5-Dioxo-imidazolidin-4-yl)-phenoxy]-3'-nitro-3,4,5,6-tetrahydro-2H-[1,2']bipyridinyl-4-carboxylic acid ethyl ester; 3'-Nitro-6'-[4-(3-oxo-butyl)-phenoxy]-3,4,5,6-tetrahydro-2H-[1,2']bipyridinyl-4-carboxylic acid ethyl ester; 3-[4-(3'-Nitro-4-propyl-3,4,5,6-tetrahydro-2H-[1,2']bipyridinyl-6'-yloxy)-phenyl]-3-oxo-propionic acid methyl ester; 4-[4-(3'-Nitro-4-propyl-3,4,5,6-tetrahydro-2H-[1,2']bipyridinyl-6'-yloxy)-phenyl]-butan-2-one; 4-{4-[3'-Nitro-4-(pyridin-2-ylsulfanyl)-3,4,5,6-tetrahydro-2H-[1,2']bipyridinyl-6'-yloxy]-phenyl}-butan-2-one; and 3'-Nitro-4-(pyridin-2-ylsulfanyl)-6'-(4-[1,2,4]triazol-1-yl-phenoxy)-3,4,5,6-tetrahydro-2H-[1,2']bipyridinyl.

Specific examples of GPR119 agonists disclosed in International Application No. PCT/US2004/005555 include the following compounds according to Formula (II) (referred to herein as Group B2): 1-[5-(4-Benzoyl-phenoxy)-2-nitro-phenyl]-piperidine-4-carboxylic acid ethyl ester; 1-{5-[4-(2-Methoxycarbonyl-acetyl)-phenoxy]-2-nitro-phenyl}-piperidine-4-carboxylic acid ethyl ester; 1-[5-(2-Amino-4-ethanesulfonyl-phenoxy)-2-nitro-phenyl]-piperidine-4-carboxylic acid ethyl ester; 1-{2-Nitro-5-[4-(3-oxo-butyl)-phenoxy]-phenyl}-piperidine-4-carboxylic acid ethyl ester; 4-{4-[4-Nitro-3-(4-propyl-piperidin-1-yl)-phenoxy]-phenyl}-butan-2-one; 1-{4-[4-Nitro-3-(4-propyl-piperidin-1-yl)-phenoxy]-phenyl}-ethanone; 3-{4-[4-Nitro-3-(4-propyl-piperidin-1-yl)-phenoxy]-phenyl}-3-oxo-propionic acid methyl ester; 5-Ethanesulfonyl-2-[4-nitro-3-(4-propyl-piperidin-1-yl)-phenoxy]-phenylamine; {4-[4-Nitro-3-(4-propyl-piperidin-1-yl)-phenoxy]-phenyl}-phenyl-methanone; 1-{4-Nitro-3-[4-(3-oxo-butyl)-phenoxy]-phenyl}-piperidine-4-carboxylic acid ethyl ester; 4-{4-[2-Nitro-5-(4-propyl-piperidin-1-yl)-phenoxy]-phenyl}-butan-2-one; 1-[3-(4-Benzoyl-phenoxy)-4-nitro-phenyl]-piperidine-4-carboxylic acid ethyl ester; {4-[2-Nitro-5-(4-propyl-piperidin-1-yl)-phenoxy]-phenyl}-phenyl-methanone; 1-{5-[4-(2-Carboxy-ethyl)-phenoxy]-2-nitro-phenyl}-piperidine-4-carboxylic acid ethyl ester; 1-{5-[4-(2-Carboxy-2-oxo-ethyl)-phenoxy]-2-nitro-phenyl}-piperidine-4-carboxylic acid ethyl ester; 1-[2-Nitro-5-(4-vinyl-phenoxy)-phenyl]-piperidine-4-carboxylic acid ethyl ester; 3-{4-[4-Nitro-3-(4-propyl-piperidin-1-yl)-phenoxy]-phenyl}-propionic acid; 3-{4-[4-Nitro-3-(4-propyl-piperidin-1-yl)-phenoxy]-phenyl}-2-oxo-propionic acid; 1-[2-Nitro-5-(4-vinyl-phenoxy)-phenyl]-4-propyl-piperidine; 1-{4-[4-Nitro-3-(4-propyl-piperidin-1-yl)-phenoxy]-phenyl}-butan-1-one; 1-{4-[4-Nitro-3-(4-propyl-piperidin-1-yl)-phenoxy]-phenyl}-pentan-1-one; 1-{4-[4-Nitro-3-(4-propyl-piperidin-1-yl)-phenoxy]-phenyl}-hexan-1-one; 4-{4-[3-(4-Methoxymethyl-piperidin-1-yl)-4-nitro-phenoxy]-phenyl}-butan-2-one; 1-{4-[3-(4-Methoxymethyl-piperidin-1-yl)-4-nitro-phenoxy]-phenyl}-ethanone; {4-[3-(4-Methoxymethyl-piperidin-1-yl)-4-nitro-phenoxy]-phenyl}-phenyl-methanone; 2-(3-Methyl-[1,2,4]oxadiazol-5-yl)-1-{4-[4-nitro-3-(4-propyl-piperidin-1-yl)-phenoxy]-phenyl}-ethanone; 4-(4-{3-[4-(3-Methyl-[1,2,4]oxadiazol-5-yl)-piperidin-1-yl]-4-nitro-phenoxy}-phenyl)-butan-2-one; 4-(4-{4-Nitro-3-[4-(pyridin-2-ylsulfanyl)-piperidin-1-yl]-phenoxy}-phenyl)-butan-2-one; 2-{1-[2-Nitro-5-(4-[1,2,4]triazol-1-yl-phenoxy)-phenyl]-piperidin-4-ylsulfanyl}-pyridine; 2-Methyl-5-{4-[4-nitro-3-(4-propyl-piperidin-1-yl)-phenoxy]-phenyl}-2H-pyrazol-3-ol; 2-[4-Nitro-3-(4-propyl-piperidin-1-yl)-phenoxy]-5-trifluoromethyl-pyridine; 5-Bromo-2-[4-nitro-3-(4-propyl-piperidin-1-yl)-phenoxy]-pyridine; 1-(4-{4-Nitro-3-[4-(pyridin-2-ylsulfanyl)-piperidin-1-yl]-phenoxy}-phenyl)-ethanone; 2-{1-[5-(4-Methanesulfonyl-phenoxy)-2-nitro-phenyl]-piperidin-4-ylsulfanyl}-pyridine; 1-{5-[4-(5-Methyl-[1,3,4]oxadiazol-2-yl)-phenoxy]-2-nitro-phenyl}-4-propyl-piperidine; 1-{5-[3-(3-Methyl-[1,2,4]oxadiazol-5-yl)-phenoxy]-2-nitro-phenyl}-4-propyl-piperidine.

Specific examples of GPR119 agonists disclosed in International Application No. PCT/US2004/005555 include the following compound according to Formula (II) (referred to herein as Group B3): 5-Bromo-1-[4-nitro-3-(4-propyl-piperidin-1-yl)-phenyl]-1H-pyridin-2-one.

Specific examples of GPR119 agonists disclosed in International Application No. PCT/US2004/005555 include the following compounds according to Formula (II) (referred to herein as Group B4): 6'-Benzenesulfonylamino-3'-nitro-3,4,5,6-tetrahydro-2H-[1,2']bipyridinyl-4-carboxylic acid ethyl ester; 6'-(Benzenesulfonyl-methyl-amino)-3'-nitro-3,4,5,6-tetrahydro-2H-[1,2']bipyridinyl-4-carboxylic acid ethyl ester; 6'-(Benzenesulfonyl-butyl-amino)-3'-nitro-3,4,5,6-tetrahydro-2H-[1,2']bipyridinyl-4-carboxylic acid ethyl ester; 6'-(5-Ethanesulfonyl-2-hydroxy-phenylamino)-3'-nitro-3,4,5,6-tetrahydro-2H-[1,2']bipyridinyl-4-carboxylic acid ethyl ester; 6'-(2-Bromo-4-trifluoromethyl-benzenesulfonylamino)-3'-nitro-3,4,5,6-tetrahydro-2H-[1,2']bipyridinyl-4-carboxylic acid ethyl ester; {4-[3'-Nitro-4-(pyridin-2-ylsulfanyl)-3,4,5,6-tetrahydro-2H-[1,2']bipyridinyl-6'-ylamino]-phenyl}-phenyl-methanone and [3'-Nitro-4-(pyridin-2-ylsulfanyl)-3,4,5,6-tetrahydro-2H-[1,2']bipyridinyl-6'-yl]-(4-[1,2,4]triazol-1-yl-phenyl)-amine.

Specific examples of GPR119 agonists disclosed in International Application No. PCT/US2004/005555 include the following compounds according to Formula (II) (referred to herein as Group B5): 1-[5-(4-Benzoyl-phenylamino)-2-nitro-phenyl]-piperidine-4-carboxylic acid ethyl ester and {4-[4-Nitro-3-(4-propyl-piperidin-1-yl)-phenylamino]-phenyl}-phenyl-methanone.

Examples of GPR119 agonists are described in International Application No. PCT/US2004/022327 (published as WO 05/007647), the disclosure of which is herein incorporated by reference in its entirety. Disclosed in International Application No. PCT/US2004/022327 as a GPR119 agonist is a compound of Formula (II):

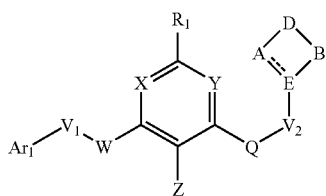

(III)

wherein:

A and B are each independently $C_{1-3}$ alkylene optionally substituted with 1 to 4 substituents selected from the group consisting of $C_{1-3}$ alkyl, $C_{1-4}$ alkoxy, carboxy, cyano, $C_{1-3}$ haloalkyl and halogen;

D is O, S, S(O), S(O)$_2$, CR$_2$R$_3$ or N—R$_2$;

E is N, C or CR$_4$;

--- is a single bond when E is N or CR$_4$, or a double bond when E is C;

V$_1$ is selected from the group consisting of $C_{1-3}$ alkylene, ethynylene and $C_{1-2}$ heteroalkylene optionally substituted with 1 to 4 substituents selected from the group consisting of $C_{1-3}$ alkyl, $C_{1-4}$ alkoxy, carboxy, cyano, $C_{1-3}$ haloalkyl and halogen; or V$_1$ is a bond;

V$_2$ is $C_{3-6}$ cycloalkylene or $C_{1-3}$ alkylene wherein each are optionally substituted with 1 to 4 substituents selected from the group consisting of $C_{1-3}$ alkyl, $C_{1-4}$ alkoxy, carboxy, cyano, $C_{1-3}$ haloalkyl and halogen; or V$_2$ is a bond;

W is NR$_5$, O, S, S(O) or S(O)$_2$; or W is absent;

Q is NR$_6$, O, S, S(O) or S(O)$_2$;

X is N or CR$_7$;

Y is N or CR$_8$;

Z is selected from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, $C_{1-2}$ alkylamino, $C_{2-4}$ dialkylamino, carbamimidoyl, carbo-$C_{1-6}$-alkoxy, carboxamide, carboxy, cyano, $C_{3-7}$ cycloalkyl, $C_{4-8}$ diacylamino, $C_{2-6}$ dialkylcarboxamide, $C_{2-6}$ dialkylthiocarboxamide, $C_{2-6}$ dialkylsulfonamide, $C_{2-6}$ dialkylsulfonylamino, formyl, $C_{1-4}$ haloalkoxy, $C_{1-4}$ haloalkyl, $C_{1-4}$ haloalkylcarboxamide, $C_{1-4}$ haloalkylsulfinyl, $C_{1-4}$ haloalkylsulfonyl, $C_{1-4}$ haloalkylthio, halogen, aryl, heterocyclic, heteroaryl, hydroxyl, hydroxycarbamimidoyl, hydroxylamino, nitro and tetrazolyl, wherein $C_{1-8}$ alkyl, $C_{3-7}$ cycloalkyl, and heterocyclic are each optionally substituted with 1, 2, 3 or 4 groups selected from the group consisting of $C_{1-5}$ acyl, $C_{1-5}$ acyloxy, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-2}$ alkylamino, $C_{2-4}$ dialkylamino, carbo-$C_{1-6}$-alkoxy, carboxamide, carboxy, cyano, formyl, $C_{1-4}$ haloalkoxy, $C_{1-4}$ haloalkylsulfinyl, $C_{1-4}$ haloalkylsulfonyl, $C_{1-4}$ haloalkylthio, halogen, hydroxyl, hydroxylamino and nitro, and wherein said $C_{1-7}$ alkyl is optionally substituted with amino; or Z is a group of Formula (IIIA):

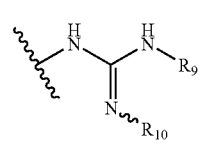

(IIIA)

wherein:

R$_9$ is H, $C_{1-8}$ alkyl or $C_{3-7}$ cycloalkyl; and

R$_{10}$ is H, nitro or nitrile;

Ar$_1$ is aryl or heteroaryl each optionally substituted with R$_{11}$, R$_{12}$, R$_{13}$, R$_{14}$, and R$_{15}$; wherein R$_{11}$ is selected from the group consisting of $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, arylsulfonyl, carbamimidoyl, carbo-$C_{1-6}$ alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, $C_{2-6}$ dialkylthiocarboxamide, guanidinyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclic-oxy, heterocyclicsulfonyl, heterocyclic-carbonyl, heteroaryl, heteroarylcarbonyl, hydroxyl, nitro, $C_{4-7}$ oxo-cycloalkyl, phenoxy, phenyl, sulfonamide, sulfonic acid, and thiol, and wherein $C_{1-5}$ acyl, $C_{1-6}$ acylsulfonamide, $C_{1-4}$ alkoxy, $C_{1-8}$ alkyl, $C_{1-4}$ alkylamino, $C_{1-6}$ alkylsulfonamide, $C_{1-4}$ alkylsulfonyl, $C_{1-4}$ alkylthio, arylsulfonyl, carbamimidoyl, $C_{2-6}$ dialkylamino, heterocyclic, heterocyclic-carbonyl, heteroaryl, phenoxy and phenyl are optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro, phenyl, and phosphonooxy, wherein said $C_{1-7}$ alkyl and $C_{1-4}$ alkylcarboxamide are each optionally substituted with 1 to 5 substituents selected from the group consisting of $C_{1-4}$ alkoxy and hydroxy; or R$_{11}$ is a group of Formula (IIIB):

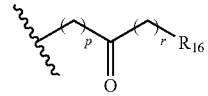

(IIIB)

wherein:

"p" and "r" are each independently 0, 1, 2 or 3; and R$_{16}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-7}$ cycloalkyl, $C_{2-6}$ dialkylcarboxamide, halogen, heteroaryl or phenyl, and wherein the heteroaryl or phenyl optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl; and $R_{12}$, $R_{13}$, $R_{14}$, and $R_{15}$ are each independently selected form the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl and nitro; or two adjacent groups selected from the group consisting of $R_{12}$, $R_{13}$, $R_{14}$ and $R_{15}$ together with the atoms to which they are attached form a 5-, 6- or 7-membered cycloalkyl, cycloalkenyl or heterocyclic group fused with $Ar_1$, wherein the 5-, 6- or 7-membered group is optionally substituted with halogen;

$R_1$, $R_7$ and $R_8$ are each independently selected from the group consisting of H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-7}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio and hydroxyl;

$R_2$ is selected from the group consisting of $C_{1-8}$ alkyl, amino, aryl, carboxamide, carboxy, cyano, $C_{3-6}$-cycloalkyl, $C_{1-4}$ haloalkoxy, $C_{1-4}$ haloalkyl, halogen, heteroaryl and hydroxyl; and wherein $C_{1-8}$ alkyl, aryl or heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-heteroalkylene, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro; or $R_2$ is —$Ar_2$—$Ar_3$ wherein $Ar_2$ and $Ar_3$ are each independently aryl or heteroaryl optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, $C_{1-4}$ alkylamino, carbo-$C_{1-6}$-alkoxy, carboxamide, carboxy, cyano, $C_{3-6}$-cycloalkyl, $C_{2-8}$ dialkylamino, $C_{2-6}$ dialkylcarboxamide, $C_{1-4}$ haloalkoxy, $C_{1-4}$ haloalkyl, halogen, hydroxyl and nitro; or $R_2$ is a group of Formula (IIIC):

wherein:

$R_{17}$ is H, $C_{1-8}$ alkyl, $C_{3-7}$ cycloalkyl, aryl, heteroaryl or $OR_{19}$; and $R_{18}$ is F, Cl, Br, CN or $NR_{20}R_{21}$; where $R_{19}$ is H, $C_{1-8}$ alkyl or $C_{3-7}$ cycloalkyl, and $R_{20}$ and $R_{21}$ are each independently H, $C_{1-8}$ alkyl, $C_{3-7}$ cycloalkyl, aryl or heteroaryl; or $R_2$ is a group of Formula (IIID):

wherein:

G is:

i) —C(O)—, —C(O)$NR_{23}$—, —C(O)O—, —OC(O)$NR_{23}$—, —$NR_{23}$C(O)O—, —OC(O)—, —C(S)—, —C(S)$NR_{23}$—, —C(S)O—, —OC(S)—, —$CR_{23}R_{24}$—, —O—, —S—, —S(O)— or —S(O)$_2$— when D is $CR_2R_3$, or ii) —$CR_{23}R_{24}$C(O)—, —C(O)—, —$CR_{23}R_{24}$C(O)$NR_{25}$—, —C(O)$NR_{23}$—, —C(O)O—, —C(S)—, —C(S)$NR_{23}$—, —C(S)O—, —$CR_{23}R_{24}$—, —S(O)$_2$—, or a bond when D is $NR_2$, wherein $R_{23}$, $R_{24}$ and $R_{25}$ are each independently H or $C_{1-8}$ alkyl; and $R_{22}$ is H, $C_{1-8}$ alkyl, $C_{2-6}$ alkynyl, $C_{3-7}$ cycloalkyl, phenyl, heteroaryl, or heterocyclic each optionally substituted with 1 to 5 substituents selected from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, heterocyclic, hydroxyl, hydroxylamino, nitro, phenyl, phenoxy, and sulfonic acid, wherein said $C_{1-7}$ alkyl, heteroaryl, phenyl and phenoxy are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino, and nitro;

$R_3$ is H, $C_{1-8}$ alkyl, $C_{1-4}$ alkoxy or hydroxyl; and $R_4$, $R_5$ and $R_6$ are each independently H, $C_{1-8}$ alkyl or $C_{3-7}$ cycloalkyl, wherein said $C_{1-8}$ alkyl is optionally substituted with $C_{1-4}$ alkoxy, $C_{3-7}$ cycloalkyl, or heteroaryl.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Specific examples of GPR119 agonists disclosed in International Application No. PCT/US2004/022327 include the following compounds according to Formula (III) (referred to herein as Group C1): 3-[6-(4-Methanesulfonyl-phenylamino)-5-nitro-pyrimidin-4-yloxymethyl]-pyrrolidine-1-carboxylic acid tert-butyl ester; 4-[5-Cyano-6-(6-methylsulfanyl-pyridin-3-ylamino)-pyrimidin-4-yloxy]-piperidine-1-carboxylic acid tert-butyl ester; 4-[5-Cyano-6-(6-methanesulfonyl-pyridin-3-ylamino)-pyrimidin-4-yloxy]-piperidine-1-carboxylic acid tert-butyl ester; [6-(1-Hexyl-piperidin-4-yloxy)-5-nitro-pyrimidin-4-yl]-(4-methanesulfonyl-phenyl)-amine; [6-(1-Cyclopropylmethyl-piperidin-4-yloxy)-5-nitro-pyrimidin-4-yl]-(4-methanesulfonyl-phenyl)-amine; 4-[6-(4-Methanesulfonyl-phenylamino)-5-nitro-pyrimidin-4-yloxy]-piperidine-1-carboxylic acid isopropyl ester; 4-[6-(4-Methanesulfonyl-phenylamino)-5-nitro-pyrimidin-4-yloxy]-piperidine-1-carboxylic acid 2-isopropyl-5-methyl-cyclohexyl ester; {4-[6-(4-Methanesulfonyl-phenylamino)-5-nitro-pyrimidin-4-yloxy]-piperidin-1-yl}-pyridin-3-yl-methanone; (2-Chloro-pyridin-3-yl)-{4-[6-(4-methanesulfonyl-phenylamino)-5-nitro-pyrimidin-4-yloxy]-piperidin-1-yl}-methanone; {4-[6-(4-Methanesulfonyl-phenylamino)-5-nitro-pyrimidin-4-yloxy]-piperidin-1-yl}-pyridin-2-yl-methanone; (4-Methanesulfonyl-phenyl)-[6-(1-methanesulfonyl-piperidin-4-yloxy)-5-nitro-pyrimidin-4-yl]-amine; (4-Methanesulfonyl-phenyl)-{5-nitro-6-[1-(propane-1-sulfonyl)-piperidin-4-yloxy]-pyrimidin-4-yl}-amine; {6-[1-(Butane-1-sulfonyl)-piperidin-4-yloxy]-5-nitro-pyrimidin-4-yl}-(4-methanesulfonyl-phenyl)-amine; (4-Methanesulfonyl-phenyl)-{5-nitro-6-[1-(thiophene-2-sulfonyl)-piperidin-4-yloxy]-pyrimidin-4-yl}-amine; (4-Methanesulfonyl-phenyl)-{6-[1-(1-methyl-1H-imidazole-4-sulfonyl)-piperidin-4-yloxy]-5-nitro-pyrimidin-4-yl}-amine; {6-[1-(2,4-Dimethyl-thiazole-5-sulfonyl)-piperidin-4-yloxy]-5-nitro-pyrimidin-4-yl}-(4-methanesulfonyl-phenyl)-amine; 4-[5-Cyano-6-(3-fluoro-4-methanesulfonyl-phenylamino)-pyrimidin-4-yloxy]-piperidine-1-carboxylic acid tert-butyl ester; 4-[6-(2-Fluoro-4-methanesulfonyl-phenylamino)-5-nitro-pyrimidin-4-yloxy]-piperidine-1-carboxylic acid tert-butyl ester; 4-[5-Cyano-6-(4-methanesulfonyl-phenylamino)-pyrimidin-4-yloxy]-piperidine-1-carboxylic acid tert-butyl ester; 4-[6-(6-Methanesulfonyl-pyridin-3-ylamino)-5-nitro-pyrimidin-4-yloxy]-piperidine-1-carboxylic acid tert-butyl ester; 4-[5-Acetyl-6-(6-methanesulfonyl-pyridin-3-ylamino)-pyrimidin-4-yloxy]-piperidine-1-carboxylic acid tert-butyl ester; 4-[5-Amino-6-(2-fluoro-4-methanesulfonyl-phenylamino)-pyrimidin-4-yloxy]-piperidine-1-carboxylic acid tert-butyl ester; 4-[5-Cyano-6-(4-methanesulfonyl-phenylamino)-pyrimidin-4-yloxy]-piperidine-1-carboxylic acid isopropyl ester; 4-[5-Cyano-6-(4-methanesulfonyl-phenylamino)-pyrimidin-4-yloxy]-piperidine-1-carboxylic acid ethyl ester; 4-[5-Cyano-6-(4-methanesulfonyl-phenylamino)-pyrimidin-4-yloxy]-piperidine-1-carboxylic acid isobutyl ester; 4-(4-Methanesulfonyl-phenylamino)-6-[1-(tetrahydro-furan-2-carbonyl)-piperidin-4-yloxy]-pyrimidine-5-carbonitrile; 4-[1-(3,3-Dimethyl-2-oxo-butyl)-piperidin-4-yloxy]-6-(4-methanesulfonyl-phenylamino)-pyrimidine-5-carbonitrile; 4-(4-Methanesulfonyl-phenylamino)-6-[1-(pyridine-3-carbonyl)-piperidin-4-yloxy]-pyrimidine-5-carbonitrile; 4-(1-Formyl-piperidin-4-yloxy)-6-(4-methanesulfonyl-phenylamino)-pyrimidine-5-carbonitrile and 4-(4-Methanesulfonyl-phenylamino)-6-[1-(pyridine-2-carbonyl)-piperidin-4-yloxy]-pyrimidine-5-carbonitrile.

Specific examples of GPR119 agonists disclosed in International Application No. PCT/US2004/022327 include the following compounds according to Formula (III) (referred to herein as Group C2): 4-[6-(4-Methanesulfonyl-phenylamino)-5-nitro-pyrimidin-4-yloxy]-piperidine-1-carboxylic acid tert-butyl ester; (4-Methanesulfonyl-phenyl)-[5-nitro-6-(piperidin-4-yloxy)-pyrimidin-4-yl]-amine: 1-{4-[6-(4-Methanesulfonyl-phenylamino)-5-nitro-pyrimidin-4-yloxy]-piperidin-1-yl}-3,3-dimethyl-butan-1-one; (4-Methanesulfonyl-phenyl)-[5-nitro-6-(1-pyridin-2-ylmethyl-piperidin-4-yloxy)-pyrimidin-4-yl]-amine; (4-Methanesulfonyl-phenyl)-[5-nitro-6-(1-pyridin-3-ylmethyl-piperidin-4-yloxy)-pyrimidin-4-yl]-amine; {6-[1-(3,3-Dimethyl-butyl)-piperidin-4-yloxy]-5-nitro-pyrimidin-4-yl}-(4-methanesulfonyl-phenyl)-amine; (4-Methanesulfonyl-phenyl)-{6-[1-(3-methyl-butyl)-piperidin-4-yloxy]-5-nitro-pyrimidin-4-yl}-amine; (4-Methanesulfonyl-phenyl)-[5-nitro-6-(3,4,5,6-tetrahydro-2H-[1,2']bipyridinyl-4-yloxy)-pyrimidin-4-yl]-amine; 4-[6-(4-Methanesulfonyl-phenylamino)-5-nitro-pyrimidin-4-yloxy]-piperidine-1-carboxylic acid ethyl ester; 1-{4-[6-(4-Methanesulfonyl-phenylamino)-5-nitro-pyrimidin-4-yloxy]-piperidin-1-yl}-3,3-dimethyl-butan-2-one; {6-[1-(2-Ethoxy-ethyl)-piperidin-4-yloxy]-5-nitro-pyrimidin-4-yl}-(4-methanesulfonyl-phenyl)-amine; 4-[6-(4-Methanesulfonyl-phenylamino)-5-nitro-pyrimidin-4-yloxymethyl]-piperidine-1-carboxylic acid tert-butyl ester; 4-{2-[6-(4-Methanesulfonyl-phenylamino)-5-nitro-pyrimidin-4-yloxy]-ethyl}-piperidine-1-carboxylic acid tert-butyl ester; 3-[6-(4-Methanesulfonyl-phenylamino)-5-nitro-pyrimidin-4-yloxy]-pyrrolidine-1-carboxylic acid tert-butyl ester and 3-[6-(4-Methanesulfonyl-phenylamino)-5-nitro-pyrimidin-4-yloxymethyl]-pyrrolidine-1-carboxylic acid tert-butyl ester.

Specific examples of GPR119 agonists disclosed in International Application No. PCT/US2004/022327 include the following compounds according to Formula (III) (referred to herein as Group C3): 4-[6-(4-Methanesulfonyl-phenylamino)-5-nitro-pyrimidin-4-ylamino]-piperidine-1-carboxylic acid tert-butyl ester; N-(4-Methanesulfonyl-phenyl)-5-nitro-N'-piperidin-4-yl-pyrimidine-4,6-diamine; 1-{4-[6-(4-Methanesulfonyl-phenylamino)-5-nitro-pyrimidin-4-ylamino]-piperidin-1-yl}-ethanone and 1-{4-[6-(4-Methanesulfonyl-phenylamino)-5-nitro-pyrimidin-4-ylamino]-piperidin-1-yl}-2,2-dimethyl-propan-1-one.

Specific examples of GPR119 agonists disclosed in International Application No. PCT/US2004/022327 include the following compounds according to Formula (III) (referred to herein as Group C4): 4-[6-(4-Cyano-2-fluoro-phenylamino)-5-ethynyl-pyrimidin-4-yloxy]-piperidine-1-carboxylic acid isopropyl ester; 4-[5-Ethynyl-6-(2-fluoro-4-[1,2,4]triazol-1-yl-phenylamino)-pyrimidin-4-yloxy]-piperidine-1-carboxylic acid isopropyl ester; 4-{5-Ethynyl-6-[1-(3-isopropyl-[1,2,4]oxadiazol-5-yl)-piperidin-4-yloxy]-pyrimidin-4- ylamino}-3-fluoro-benzonitrile; {5-Ethynyl-6-[1-(3-isopropyl-[1,2,4]oxadiazol-5-yl)-piperidin-4-yloxy]-pyrimidin-4-yl}-(2-fluoro-4-methanesulfonyl-phenyl)-amine; 4-{6-[2,5-Difluoro-4-(2-methanesulfonyl-ethyl)-phenylamino]-5-methyl-pyrimidin-4-yloxy}-piperidine-1-carboxylic acid isopropyl ester; 4-{6-[2-Fluoro-4-(2-sulfamoyl-ethyl)-phenylamino]-5-methyl-pyrimidin-4-yloxy}-piperidine-1-carboxylic, acid isopropyl ester; 4-{6-[6-(2-Fluoro-ethyl)-2-methyl-pyridin-3-ylamino]-5-methyl-pyrimidin-4-yloxy}-piperidine-1-carboxylic acid isopropyl ester; 4-{2-[4-Fluoro-6-(2-isopropoxy-ethyl)-pyridin-3-ylamino]-3-methyl-pyridin-4-yloxy}-piperidine-1-carboxylic acid isopropyl ester; 4-{6-[2,5-Difluoro-4-(2-[1,2,4]triazol-1-yl-ethyl)-phenylamino]-5-methyl-pyrimidin-4-yloxy}-piperidine-1-carboxylic acid isopropyl ester; 4-{5-Ethynyl-6-[2-fluoro-4-(4-methoxy-pyridin-2-yl)-phenylamino]-pyrimidin-4-yloxy}-piperidine-1-carboxylic acid isopropyl ester; 4-{6-[2-Fluoro-4-(2-propionylsulfamoyl-ethyl)-phenylamino]-5-methyl-pyrimidin-4-yloxy}-piperidine-1-carboxylic acid isopropyl ester; 4-{6-[2-Fluoro-4-(2-methanesulfonyl-ethyl)-phenylamino]-5-methyl-pyrimidin-4-yloxy}-piperidine-1-carboxylic acid isopropyl ester; and 4-{6-[2,3-Difluoro-4-(2-methanesulfonyl-ethyl)-phenylamino]-5-methyl-pyrimidin-4-yloxy}-piperidine-1-carboxylic acid isopropyl ester.

Specific examples of GPR119 agonists disclosed in International Application No. PCT/US2004/022327 include the following compounds according to Formula (III) (referred to herein as Group C5): 4-[5-Acetyl-6-(6-methanesulfonyl-pyridin-3-ylamino)-pyrimidin-4-yloxy]-piperidine-1-carboxylic acid isobutyl ester; 1-[4-(1-Benzyl-azetidin-3-yloxy)-6-(6-methanesulfonyl-pyridin-3-ylamino)-pyrimidin-5-yl]-ethanone; 4-[5-Cyano-6-(6-propylamino-pyridin-3-ylamino)-pyrimidin-4-yloxy]-piperidine-1-carboxylic acid isopropyl ester; 4-[5-Cyano-6-(2-fluoro-4-isopropylamino-phenylamino)-pyrimidin-4-yloxy]-piperidine-1-carboxylic acid isopropyl ester; 4-[5-Cyano-6-(2-fluoro-4-propylamino-phenylamino)-pyrimidin-4-yloxy]-piperidine-1-carboxylic acid isopropyl ester; 4-[5-Cyano-6-(2-fluoro-4-propoxy-phenylamino)-pyrimidin-4-yloxy]-piperidine-1-carboxylic acid isopropyl ester; 4-[5-Cyano-6-(6-propyl-pyridin-3-ylamino)-pyrimidin-4-yloxy]-piperidine-1-carboxylic acid isopropyl ester; 4-{5-Cyano-6-[4-(2-dimethylamino-ethylsulfanyl)-2-fluoro-phenylamino]-pyrimidin-4-yloxy}-piperidine-1-carboxylic acid isopropyl ester; 4-{5-Cyano-6-[4-(2-dimethylamino-ethanesulfonyl)-2-fluoro-phenylamino]-3-oxy-pyrimidin-4-yloxy}-piperidine-1-carboxylic acid isopropyl ester; 4-{5-Cyano-6-[2-fluoro-4-(4-methyl-piperazin-1-yl)-phenylamino]-pyrimidin-4-yloxy}-piperidine-1-carboxylic acid isopropyl ester; 4-{5-Cyano-6-[2-fluoro-4-(3-methyl-butylamino)-phenylamino]-pyrimidin-4-yloxy}-piperidine-1-carboxylic acid isopropyl ester; 4-[5-Cyano-6-(2-fluoro-4-morpholin-4-yl-phenylamino)-pyrimidin-4-yloxy]-piperidine-1-carboxylic acid isopropyl ester; 4-{5-Cyano-6-[4-(2-dimethylamino-ethylamino)-2-fluoro-phenylamino]-pyrimidin-4-yloxy}-piperidine-1-carboxylic acid isopropyl ester; 4-[5-Cyano-6-(4-dimethylamino-2-fluoro-phenylamino)-pyrimidin-4-yloxy]-piperidine-1-carboxylic acid isopropyl ester; 4-{5-Cyano-6-[2-fluoro-4-(2-pyrrolidin-1-yl-ethylamino)-phenylamino]-pyrimidin-4-yloxy}-piperidine-1-carboxylic acid isopropyl ester; 4-[6-(2-Fluoro-4-methanesulfonyl-phenylamino)-5-methyl-pyrimidin-4-yloxy]-piperidine-1-carboxylic acid isopropyl ester; 4-{5-Cyano-6-[2-fluoro-4-(2-morpholin-4-yl-ethylamino)-phenylamino]-pyrimidin-4-yloxy}-piperidine-1-carboxylic acid isopropyl ester; 4-[6-(2-Fluoro-4-iodo-phenylamino)-5-methyl-pyrimidin-4-yloxy]-piperidine-1-carboxylic acid isopropyl ester; 4-[5-Cyano-6-(2-fluoro-4-methanesulfonyl-phenylamino)-pyrimidin-4-yloxy]-piperidine-1-carboxylic acid isopropyl ester; 4-[6-(2-Fluoro-4-morpholin-4-yl-phenylamino)-5-methyl-pyrimidin-4-yloxy]-piperidine-1-carboxylic acid isopropyl ester; 4-[6-(2,5-Difluoro-4-propoxy-phenylamino)-5-methyl-pyrimidin-4-yloxy]-piperidine-1-carboxylic acid isopropyl ester; 4-[6-(2-Fluoro-4-propylamino-phenylamino)-5-methyl-pyrimidin-4-yloxy]-piperidine-1-carboxylic acid isopropyl ester; 4-{6-[2-Fluoro-4-(2-methoxy-ethylamino)-phenylamino]-5-methyl-pyrimidin-4-yloxy}-piperidine-1-carboxylic acid isopropyl ester; 4-(6-{2-Fluoro-4-[(tetrahydro-furan-2-ylmethyl)-amino]-phenylamino}-5-methyl-pyrimidin-4-yloxy)-piperidine-1-carboxylic acid isopropyl ester; 4-{6-[2-Fluoro-4-(2-methanesulfonyl-ethylamino)-phenylamino]-5-methyl-pyrimidin-4-yloxy}-piperidine-1-carboxylic acid isopropyl ester; 4-(6-{2-Fluoro-4-[(2-methanesulfonyl-ethyl)-methyl-amino]-phenylamino}-5-methyl-pyrimidin-4-yloxy)-piperidine-1-carboxylic acid isopropyl ester; 4-[6-(4-Bromo-2,5-difluoro-phenylamino)-5-methyl-pyrimidin-4-yloxy]-piperidine-1-carboxylic acid isopropyl ester; 4-[6-(4-Cyano-2-fluoro-phenylamino)-5-methyl-pyrimidin-4-yloxy]-piperidine-1-carboxylic acid isopropyl ester; 4-[6-(4-Cyano-2,5-difluoro-phenylamino)-5-methyl-pyrimidin-4-yloxy]-piperidine-1-carboxylic acid isopropyl ester; 4-[6-(2,5-Difluoro-4-morpholin-4-yl-phenylamino)-5-methyl-pyrimidin-4-yloxy]-piperidine-1-carboxylic acid isopropyl ester; 4-[6-(6-Chloro-2-methyl-pyridin-3-ylamino)-5-methyl-pyrimidin-4-yloxy]-piperidine-1-carboxylic acid isopropyl ester; 4-[5-Methyl-6-(2-methyl-6-morpholin-4-yloxy)-pyrimidin-4-yloxy]-piperidine-1-carboxylic acid isopropyl ester; 4-[5-(4,5-Dihydro-1H-imidazol-2-yl)-6-(2-fluoro-4-methanesulfonyl-phenylamino)-pyrimidin-4-yloxy]-piperidine-1-carboxylic acid isopropyl ester; (2-Fluoro-4-methanesulfonyl-phenyl)-{6-[1-(3-isopropyl-[1,2,4]oxadiazol-5-yl)-piperidin-4-yloxy]-5-methyl-pyrimidin-4-yl}-amine; 4-[6-(2-Fluoro-4-propoxy-phenylamino)-5-methyl-pyrimidin-4-yloxy]-piperidine-1-carboxylic acid isopropyl ester; 4-{6-[2-Fluoro-4-(2-methanesulfonyl-ethoxy)-phenylamino]-5-methyl-pyrimidin-4-yloxy}-piperidine-1-carboxylic acid isopropyl ester; 4-{6-[2-Fluoro-4-(2-methoxy-ethoxy)-phenylamino]-5-methyl-pyrimidin-4-yloxy}-piperidine-1-carboxylic acid isopropyl ester; 4-{6-[2-Fluoro-4-(2-isopropoxy-ethoxy)-phenylamino]-5-methyl-pyrimidin-4-yloxy}-piperidine-1-carboxylic acid isopropyl ester; 4-[6-(6-Chloro-4-methyl-pyridin-3-ylamino)-5-methyl-pyrimidin-4-yloxy]-piperidine-1-carboxylic acid isopropyl ester; 4-[6-(2-Fluoro-4-methanesulfonyl-phenylamino)-5-(N-hydroxycarbamimidoyl)-pyrimidin-4-yloxy]-piperidine-1-carboxylic acid isopropyl ester; 4-[5-Carbamimidoyl-6-(2-fluoro-4-methanesulfonyl-phenylamino)-pyrimidin-4-yloxy]-piperidine-1-carboxylic acid isopropyl ester; 4-{6-[2-Fluoro-4-(tetrahydro-furan-2-ylmethoxy)-phenylamino]-5-methyl-pyrimidin-4-yloxy}-piperidine-1-carboxylic acid isopropyl ester; 4-[5-Methyl-6-(4-methyl-6-morpholin-4-yl-pyridin-3-ylamino)-pyrimidin-4-yloxy]-piperidine-1-carboxylic acid isopropyl ester; 4-{6-[6-(2-Methoxy-ethoxy)-2-methyl-pyridin-3-ylamino]-5-methyl-pyrimidin-4-yloxy}-piperidine-1-carboxylic acid isopropyl ester; 4-{6-[6-(2-Methoxy-ethoxy)-4-methyl-pyridin-3-ylamino]-5-methyl-pyrimidin-4-yloxy}-piperidine-1-carboxylic acid isopropyl ester; 4-{6-[2,5-Difluoro-4-(2-methoxy-ethoxy)-phenylamino]-5-methyl-pyrimidin-4-yloxy}-piperidine-1-carboxylic acid isopropyl ester; 4-{6-[2-Fluoro-4-(2-isopropoxy-ethylsulfamoyl)-phenylamino]-5-methyl-pyrimidin-4-yloxy}-piperidine-1-carboxylic acid isopropyl ester; 4-{6-[2,5-Difluoro-4-(N-hydroxycarbamimidoyl)-phenylamino]-5-methyl-pyrimidin-4-yloxy}-piperidine-1-carboxylic acid isopropyl ester; 4-[6-(4-Carbamoyl-2,5-difluoro-phenylamino)-5-methyl-pyrimidin-4-yloxy]-piperidine-1-carboxylic acid isopropyl ester; 4-{6-[(2-Fluoro-4-methanesulfonyl-phenyl)-(2-methoxy-ethyl)-amino]-5-methyl-pyrimidin-4-yloxy}-piperidine-1-carboxylic acid isopropyl ester; 4-[6-(4-Carbamimidoyl-2,5-difluoro-phenylamino)-5-methyl-pyrimidin-4-yloxy]-piperidine-1-carboxylic acid isopropyl ester; 4-{6-[4-(2-Ethoxy-ethoxy)-2-fluoro-phenylamino]-5-methyl-pyrimidin-4-yloxy}-piperidine-1-carboxylic acid isopropyl ester; 4-{6-[2-Fluoro-4-(tetrahydro-pyran-4-yloxy)-phenylamino]-5-methyl-pyrimidin-4-yloxy}-piperidine-1-carboxylic acid isopropyl ester; 4-{6-[2-Fluoro-4-(2-hydroxy-ethoxy)-phenylamino]-5-methyl-pyrimidin-4-yloxy}-piperidine-1-carboxylic acid isopropyl ester; 1-{4-[6-(2-Fluoro-4-methanesulfonyl-phenylamino)-5-methyl-pyrimidin-4-yloxy]-piperidin-1-yl}-butan-1-one; 1-{4-[6-(2-Fluoro-4-methanesulfonyl-phenylamino)-5-methyl-pyrimidin-4-yloxy]-piperidin-1-yl}-pentan-1-one; 1-{4-[6-(2-Fluoro-4-methanesulfonyl-phenylamino)-5-methyl-pyrimidin-4-yloxy]-piperidin-1-yl}-3-methyl-butan-1-one; 4-{6-[2-Fluoro-4-(pyridin-2-ylmethoxy)-phenylamino]-5-methyl-pyrimidin-4-yloxy}-piperidine-1-carboxylic acid isopropyl ester; 4-[2-(2-Fluoro-4-methanesulfonyl-phenylamino)-3-methyl-pyridin-4-yloxy]-piperidine-1-carboxylic acid isopropyl ester; 4-[6-(6-Chloro-4-fluoro-pyridin-3-ylamino)-5-cyano-pyrimidin-4-yloxy]-piperidine-1-carboxylic acid isopropyl ester; and 4-[5-Amino-6-(2-fluoro-4-methanesulfonyl-phenylamino)-pyrimidin-4-yloxy]-piperidine-1-carboxylic acid isopropyl ester.

Specific examples of GPR119 agonists disclosed in International Application No. PCT/US2004/022327 include the following compound according to Formula (III) (referred to herein as Group C6): 4-({[6-(2-Fluoro-4-methanesulfonyl-phenylamino)-5-methyl-pyrimidin-4-yl]-isopropyl-amino}-methyl)-piperidine-1-carboxylic acid tert-butyl ester.

Specific examples of GPR119 agonists disclosed in International Application No. PCT/US2004/022327 include the following compounds according to Formula (III) (referred to herein as Group C7): 4-(2-Fluoro-4-methanesulfonyl-phenoxy)-6-[1-(3-methoxy-propyl)-piperidin-4-yloxy]-5-methyl-pyrimidine; 1-{4-[6-(2-Fluoro-4-methanesulfonyl-phenoxy)-5-methyl-pyrimidin-4-yloxy]-piperidin-1-yl}-3-methoxy-propan-2-ol; 4-{6-[2-Fluoro-4-(5-isopropoxymethyl-[1,2,4]oxadiazol-3-yl)-phenoxy]-5-methyl-pyrimidin-4-yloxy}-piperidine-1-carboxylic acid isopropyl ester; 4-{6-[2-Fluoro-4-(5-methoxy-pyridin-2-yl)-phenoxy]-5-methyl-pyrimidin-4-yloxy}-piperidine-1-carboxylic acid isopropyl ester; 4-{6-[6-(2-Cyclopropoxy-ethylamino)-2-methyl-pyridin-3-yloxy]-5-methyl-pyrimidin-4-yloxy}-piperidine-1-carboxylic acid isopropyl ester; 4-{6-[2-Fluoro-4-(pyridine-2-carbonyl)-phenoxy]-5-methyl-pyrimidin-4-yloxy}-piperidine-1-carboxylic acid isopropyl ester; 4-[6-(2-Fluoro-4-methanesulfonyl-phenoxy)-5-methanesulfonylamino-pyrimidin-4-yloxy]-piperidine-1-carboxylic acid isopropyl ester; 4-[6-(4-Methoxy-6'-methyl-3,4,5,6-tetrahydro-2H-[1,2']bipyridinyl-5'-yloxy)-5-methyl-pyrimidin-4-yloxy]-piperidine-1-carboxylic acid isopropyl ester; 1-{4-[6-(2-Fluoro-4-methanesulfonyl-phenoxy)-5-methyl-pyrimidin-4-yloxy]-piperidin-1-yl}-2-(4-trifluoromethoxy-phenoxy)-propan-1-one; 1-{4-[6-(2-Fluoro-4-methanesulfonyl-phenoxy)-5-methyl-pyrimidin-4-yloxy]-piperidin-1-yl}-2-(4-trifluoromethoxy-phenoxy)-ethanone; N-(4-Chloro-phenyl)-2-{4-[6-(2-fluoro-4-methanesulfonyl-phenoxy)-5-methyl-pyrimidin-4-yloxy]-piperidin-1-yl}-acetamide; N-(3-Chloro-phenyl)-2-{4-[6-(2-fluoro-4-methanesulfonyl-phenoxy)-5-methyl-pyrimidin-4-yloxy]-piperidin-1-yl}-acetamide; N-(3,5-Dichloro-phenyl)-2-{4-[6-(2-fluoro-4-methanesulfonyl-phenoxy)-5-methyl-pyrimidin-4-yloxy]-piperidin-1-yl}-acetamide; 2-{4-[6-(2-Fluoro-4-methanesulfonyl-phenoxy)-5-methyl-pyrimidin-4-yloxy]-piperidin-1-yl}-N-(4-trifluoromethyl-phenyl)-acetamide; 2-{4-[6-(2-Fluoro-4-methanesulfonyl-phenoxy)-5-methyl-pyrimidin-4-yloxy]-piperidin-1-yl}-N-phenyl-acetamide; 2-{4-[6-(2-Fluoro-4-methanesulfonyl-phenoxy)-5-methyl-pyrimidin-4-yloxy]-piperidin-1-yl}-N-(4-isopropyl-phenyl)-acetamide; 2-{4-[6-(2-Fluoro-4-methanesulfonyl-phenoxy)-5-methyl-pyrimidin-4-yloxy]-piperidin-1-yl}-N-(4-methoxy-phenyl)-acetamide; 2-{4-[6-(2-Fluoro-4-methanesulfonyl-phenoxy)-5-methyl-pyrimidin-4-yloxy]-piperidin-1-yl}-N-(3-trifluoromethyl-phenyl)-acetamide; 4-{6-[2-Fluoro-4-(3-methoxy-propane-1-sulfonyl)-phenoxy]-5-methyl-pyrimidin-4-yloxy}-piperidine-1-carboxylic acid isopropyl ester; 4-{6-[6-(2-Isopropoxy-ethyl)-2-methyl-pyridin-3-yloxy]-5-methyl-pyrimidin-4-yloxy}-piperidine-1-carboxylic acid isopropyl ester; 4-{5-Methyl-6-[2-methyl-6-(2-pyridin-2-yl-ethoxy)-pyridin-3-yloxy]-pyrimidin-4-yloxy}-piperidine-1-carboxylic acid isopropyl ester; 4-{6-[2-Fluoro-4-(thiophene-2-carbonyl)-phenoxy]-5-methyl-pyrimidin-4-yloxy}-piperidine-1-carboxylic acid isopropyl ester; 4-(6-{6-[(2-Isopropoxy-ethyl)-methyl-amino]-2-methyl-pyridin-3-yloxy}-5-methyl-pyrimidin-4-yloxy)-piperidine-1-carboxylic acid isopropyl ester; 4-{6-[6-(2-Isopropoxy-ethanesulfonyl)-2-methyl-pyridin-3-yloxy]-5-methyl-pyrimidin-4-yloxy}-piperidine-1-carboxylic acid isopropyl ester; 4-{6-[6-(2-Hydroxy-ethanesulfonyl)-2-methyl-pyridin-3-yloxy]-5-methyl-pyrimidin-4-yloxy}-piperidine-1-carboxylic acid isopropyl ester; 4-[6-(6-Amino-2-methyl-pyridin-3-yloxy)-5-methyl-pyrimidin-4-yloxy]-piperidine-1-carboxylic acid isopropyl ester; 4-(2-Fluoro-4-methanesulfonyl-phenoxy)-5-methyl-6-[1-(3-methyl-butyl)-piperidin-4-yloxy]-pyrimidine; 2-({4-[6-(2-Fluoro-4-methanesulfonyl-phenoxy)-5-methyl-pyrimidin-4-yloxy]-piperidin-1-yl}-1-morpholin-4-yl-ethanone; 1-(3,4-Dichloro-phenyl)-2-{4-[6-(2-fluoro-4-methanesulfonyl-phenoxy)-5-methyl-pyrimidin-4-yloxy]-piperidin-1-yl}-ethanone; 1-(3-Chloro-phenyl)-2-{4-[6-(2-fluoro-4-methanesulfonyl-phenoxy)-5-methyl-pyrimidin-4-yloxy]-piperidin-1-yl}-ethanone; 2-{4-[6-(2-Fluoro-4-methanesulfonyl-phenoxy)-5-methyl-pyrimidin-4-yloxy]-piperidin-1-yl}-1-thiophen-3-yl-ethanone; 2-{4-[6-(2-Fluoro-4-methanesulfonyl-phenoxy)-5-methyl-pyrimidin-4-yloxy]-piperidin-1-yl}-1-phenyl-ethanone; 1-(2,4-Dimethoxy-phenyl)-2-{4-[6-(2-fluoro-4-methanesulfonyl-phenoxy)-5-methyl-pyrimidin-4-yloxy]-piperidin-1-yl}-ethanone; 4-(2-Fluoro-4-methanesulfonyl-phenoxy)-5-methyl-6-[1-(4-methyl-pentyl)-piperidin-4-yloxy]-pyrimidine; 1-{4-[6-(2-Fluoro-4-methanesulfonyl-phenoxy)-5-methyl-pyrimidin-4-yloxy]-piperidin-1-yl}-3-isopropoxy-propan-1-one; 1-{4-[6-(2-Fluoro-4-methanesulfonyl-phenoxy)-5-methyl-pyrimidin-4-yloxy]-piperidin-1-yl}-4-isopropoxy-butan-1-one; 1-{4-[6-(2-Fluoro-4-methanesulfonyl-phenoxy)-5-methyl-pyrimidin-4-yloxy]-piperidin-1-yl}-3-hydroxy-propan-1-one; 2-{4-[6-(2-Fluoro-4-methanesulfonyl-phenoxy)-5-methyl-pyrimidin-4-yloxy]-piperidin-1-yl}-1-(5-pyridin-2-yl-thiophen-2-yl)-ethanone; 4-(2-Fluoro-4-methanesulfonyl-phenoxy)-5-methyl-6-[1-(5-methyl-hexyl)-piperidin-4-yloxy]-pyrimidine; 3-{4-[6-(2-Fluoro-4-methanesulfonyl-phenoxy)-5-methyl-pyrimidin-4-yloxy]-piperidin-1-yl}-3-oxo-propane-1-sulfonic acid; 2-{4-[6-(2-Fluoro-4-methanesulfonyl-phenoxy)-5-methyl-pyrimidin-4-yloxy]-piperidin-1-yl}-1-thiophen-2-yl-ethanone; 4-(2-Fluoro-4- methanesulfonyl-phenoxy)-5-methyl-6-(1-pentyl-piperidin-4-yloxy)-pyrimidine; 4-(1-Butyl-piperidin-4-yloxy)-6-(2-fluoro-4-methanesulfonyl-phenoxy)-5-methyl-pyrimidine; 4-{-4-[6-(2-Fluoro-4-methanesulfonyl-phenoxy)-5-methyl-pyrimidin-4-yloxy]-piperidin-1-yl}-cyclohexanecarboxylic acid; 1-(4-Diethylamino-phenyl)-2-{4-[6-(2-fluoro-4-methanesulfonyl-phenoxy)-5-methyl-pyrimidin-4-yloxy]-piperidin-1-yl}-ethanone; 2-{4-[6-(2-Fluoro-4-methanesulfonyl-phenoxy)-5-methyl-pyrimidin-4-yloxy]-piperidin-1-yl}-1-(2-methyl-4-phenyl-furan-3-yl)-ethanone; 4-(2-Fluoro-4-methanesulfonyl-phenoxy)-6-(1-hexyl-piperidin-4-yloxy)-5-methyl-pyrimidine; 4-{4-[6-(2-Fluoro-4-methanesulfonyl-phenoxy)-5-methyl-pyrimidin-4-yloxy]-piperidin-1-yl}-butyric acid; 1-{4-[6-(2-Fluoro-4-methanesulfonyl-phenoxy)-5-methyl-pyrimidin-4-yloxy]-piperidin-1-yl}-pentan-2-one; 1-{4-[6-(2-Fluoro-4-methanesulfonyl-phenoxy)-5-methyl-pyrimidin-4-yloxy]-piperidin-1-yl}-hexan-2-one; 1-{4-[6-(2-Fluoro-4-methanesulfonyl-phenoxy)-5-methyl-pyrimidin-4-yloxy]-piperidin-1-yl}-hexan-2-one; 1-{4-[6-(2-Fluoro-4-methanesulfonyl-phenoxy)-5-methyl-pyrimidin-4-yloxy]-piperidin-1-yl}-4-methyl-pentan-2-one; 1-{4-[6-(2-Fluoro-4-methanesulfonyl-phenoxy)-5-methyl-pyrimidin-4-yloxy]-piperidin-1-yl}-5-methyl-hexan-2-one; 1-{4-[6-(2-Fluoro-4-methanesulfonyl-phenoxy)-5-methyl-pyrimidin-4-yloxy]-piperidin-1-yl}-6-methyl-heptan-2-one; 5-{4-[6-(2-Fluoro-4-methanesulfonyl-phenoxy)-5-methyl-pyrimidin-4-yloxy]-piperidin-1-yl}-4-oxo-pentanoic acid; 5-{4-[6-(2-Fluoro-4-methanesulfonyl-phenoxy)-5-methyl-pyrimidin-4-yloxy]-piperidin-1-yl}-4-oxo-pentanenitrile; 1-{4-[6-(2-Fluoro-4-methanesulfonyl-phenoxy)-5-methyl-pyrimidin-4-yloxy]-piperidin-1-yl}-2-pyridin-2-yl-ethanone; 2-{4-[6-(2-Fluoro-4-methanesulfonyl-phenoxy)-5-methyl-pyrimidin-4-yloxy]-piperidin-1-yl}-1-pyridin-4-yl-ethanone; 2-{4-[6-(2-Fluoro-4-methanesulfonyl-phenoxy)-5-methyl-pyrimidin-4-yloxy]-piperidin-1-ylmethyl}-acrylic acid; 1-[1,4]Dioxan-2-yl-2-{4-[6-(2-fluoro-4-methanesulfonyl-phenoxy)-5-methyl-pyrimidin-4-yloxyl]-piperidin-1-yl}-ethanone; 1-(2,3-Dihydro-[1,4]dioxin-2-yl)-2-{4-[6-(2-fluoro-4-methanesulfonyl-phenoxy)-5-methyl-pyrimidin-4-yloxy]-piperidin-1-yl}-ethanone; 2-{4-[6-(2-Fluoro-4-methanesulfonyl-phenoxy)-5-methyl-pyrimidin-4-yloxy]-piperidin-1-yl}-1-p-tolyl-ethanone; 2-{4-[6-(2-Fluoro-4-methanesulfonyl-phenoxy)-5-methyl-pyrimidin-4-yloxy]-piperidin-1-yl}-1-(4-methoxy-phenyl)-ethanone; 1-(2-Chloro-phenyl)-2-{4-[6-(2-fluoro-4-methanesulfonyl-phenoxy)-5-methyl-pyrimidin-4-yloxy]-piperidin-1-yl}-ethanone; 3-(2-{4-[6-(2-Fluoro-4-methanesulfonyl-phenoxy)-5-methyl-pyrimidin-4-yloxy]-piperidin-1-yl}-acetyl)-benzonitrile; 1-(2,4-Dimethyl-phenyl)-2-{4-[6-(2-fluoro-4-methanesulfonyl-phenoxy)-5-methyl-pyrimidin-4-yloxy]-piperidin-1-yl}-ethanone; 1-(4-Chloro-3-methyl-phenyl)-2-{4-[6-(2-fluoro-4-methanesulfonyl-phenoxy)-5-methyl-pyrimidin-4-yloxy]-piperidin-1-yl}-ethanone; 1-(4-Difluoromethoxy-phenyl)-2-{4-[6-(2-fluoro-4-methanesulfonyl-phenoxy)-5-methyl-pyrimidin-4-yloxy]-piperidin-1-yl}-ethanone; 1-(2,3-Dihydro-benzo[1,4]dioxin-6-yl)-2-{4-[6-(2-fluoro-4-methanesulfonyl-phenoxy)-5-methyl-pyrimidin-4-yloxy]-piperidin-1-yl}-ethanone; 2-{4-[6-(2-Fluoro-4-methanesulfonyl-phenoxy)-5-methyl-pyrimidin-4-yloxy-piperidin-1-yl}-1-(5-phenyl-thiophen-2-yl)-ethanone; 2-{4-[6-(2-Fluoro-4-methanesulfonyl-phenoxy)-5-methyl-pyrimidin-4-yloxy]-piperidin-1-yl}-1-thiophen-2-yl-ethanone; {4-[6-(2-Fluoro-4-methanesulfonyl-phenoxy)-5-methyl-pyrimidin-4-yloxy]-piperidin-1-yl}-acetic acid ethyl ester; 1-{4-[6-(2-Fluoro-4-methanesulfonyl-phenoxy)-5-methyl-pyrimidin-4-yloxy]-piperidin-1-yl}-3-methoxy-propan-2-ol; 4-(2-Fluoro-4-methanesulfonyl-phenoxy)-6-[1-(4-methoxy-cyclohexyl)-piperidin-4-yloxy]-5-methyl-pyrimidin; 1-{4-[6-(2-Fluoro-4-methanesulfonyl-phenoxy)-5-methyl-pyrimidin-4-yloxy]-piperidin-1-yl}-hexan-1-one; 4-{6-[2-Fluoro-4-(2-isobutoxy-ethoxy)-phenoxy]-5-methyl-pyrimidin-4-yloxy}-piperidine-1-carboxylic acid isopropyl ester; 4-{6-[4-(2-Cyclopropoxy-ethoxy)-2-fluoro-phenoxy]-5-methyl-pyrimidin-4-yloxy}-piperidine-1-carboxylic acid isopropyl ester; 4-{6-[4-(2-Ethoxy-ethoxy)-2-fluoro-phenoxy]-5-methyl-pyrimidin-4-yloxy}-piperidine-1-carboxylic acid isopropyl ester; 4-{6-[2-Fluoro-4-(3-methoxy-propoxy)-phenoxy]-5-methyl-pyrimidin-4-yloxy}-piperidine-1-carboxylic acid isopropyl ester; 4-{6-[2-Fluoro-4-(2-pyridin-2-yl-ethoxy)-phenoxy]-5-methyl-pyrimidin-4-yloxy}-piperidine-1-carboxylic acid isopropyl ester; 4-{6-[2-Fluoro-4-(tetrahydro-pyran-4-yloxy)-phenoxy]-5-methyl-pyrimidin-4-yloxy}-piperidine-1-carboxylic acid isopropyl ester; 4-{6-[4-(2-tert-Butoxy-ethoxy)-2-fluoro-phenoxy]-5-methyl-pyrimidin-4-yloxy}-piperidine-1-carboxylic acid isopropyl ester; 4-[6-(2-Fluoro-4-sulfo-phenoxy)-5-methyl-pyrimidin-4-yloxy]-piperidine-1-carboxylic acid isopropyl ester; 4-[6-(2,5-Difluoro-4-trifluoromethoxy-phenoxy)-5-ethynyl-pyrimidin-4-yloxy]-piperidine-1-carboxylic acid isopropyl ester; 4-[6-(2,5-Difluoro-4-trifluoromethoxy-phenoxy)-5-prop-1-ynyl-pyrimidin-4-yloxy]-piperidine-1-carboxylic acid isopropyl ester; 4-[5-Ethynyl-6-(2-fluoro-4-methoxy-phenoxy)-pyrimidin-4-yloxy]-piperidine-1-carboxylic acid isopropyl ester; 4-[5-Ethynyl-6-(6-methoxy-4-methyl-pyridin-3-yloxy)-pyrimidin-4-yloxy]-piperidine-1-carboxylic acid isopropyl ester; 4-{5-Ethynyl-6-[6-(2-isopropoxy-ethyl)-2-methyl-pyridin-3-yloxy]-pyrimidin-4-yloxy}-piperidine-1-carboxylic acid isopropyl ester; 4-[6-(4-Cyano-2-fluoro-phenoxy)-5-ethynyl-pyrimidin-4-yloxy]-piperidine-1-carboxylic acid isopropyl ester; 4-[5-Ethynyl-6-(2-fluoro-4-[1,2,4]triazol-4-yl-phenoxy)-pyrimidin-4-yloxy]-piperidine-1-carboxylic acid isopropyl ester; 4-[5-Ethynyl-6-(2-fluoro-4-[1,2,4]triazol-1-yl-phenoxy)-pyrimidin-4-yloxy]-piperidine-1-carboxylic acid isopropyl ester; 1-{4-[5-Ethynyl-6-(2-fluoro-4-[1,2,4]triazol-1-yl-phenoxy)-pyrimidin-4-yloxy]-piperidin-1-yl}-3-pyridin-2-yl-propan-1-one; 4-{5-Ethynyl-6-[1-(3-isopropyl-[1,2,4]oxadiazol-5-yl)-piperidin-4-yloxy]-pyrimidin-4-yloxy}-3-fluoro-benzonitrile; 5-Ethynyl-4-(2-fluoro-4-methanesulfonyl-phenoxy)-6-[1-(3-isopropyl-[1,2,4]oxadiazol-5-yl)-piperidin-4-yloxy]-pyrimidine; 4-[1-(3-Ethyl-[1,2,4]oxadiazol-5-yl)-piperidin-4-yloxy]-5-ethynyl-6-(2-fluoro-4-methanesulfonyl-phenoxy)-pyrimidine; 4-[1-(3-Ethyl-[1,2,4]oxadiazol-5-yl)-piperidin-4-yloxy]-6-(2-fluoro-4-methanesulfonyl-phenoxy)-5-methyl-pyrimidine; 4-(2-Fluoro-4-methanesulfonyl-phenoxy)-5-methyl-6-[1-(3-methyl-[1,2,4]oxadiazol-5-yl)-piperidin-4-yloxy]-pyrimidine; 4-[6-(2-Fluoro-4-methanesulfonylamino-phenoxy)-5-methyl-pyrimidin-4-yloxy]-piperidine-1-carboxylic acid isopropyl ester; cis-{4-[6-(2-Fluoro-4-methanesulfonyl-phenoxy)-5-methyl-pyrimidin-4-yloxy]-cyclohexyl}-carbamic acid isopropyl ester; trans-{4-[6-(2-Fluoro-4-methanesulfonyl-phenoxy)-5-methyl-pyrimidin-4-yloxy]-cyclohexyl}-carbamic acid isopropyl ester; N-{4-[6-(2-Fluoro-4-methanesulfonyl-phenoxy)-5-methyl-pyrimidin-4-yloxy]-cyclohexyl}-3-methyl-butyramide; N-{4-[6-(2-Fluoro-4-methanesulfonyl-phenoxy)-5-methyl-pyrimidin-4-yloxy]-cyclohexyl}-isobutyramide; 4-{6-[2,5-Difluoro-4-(2-methanesulfonyl-ethyl)-phenoxy]-5-methyl-pyrimidin-4-yloxy}-piperidine-1-carboxylic acid isopropyl ester; 4-{6-[4-Fluoro-6-(2-methanesulfonyl-ethyl)-pyridin-3-yloxy]-5-methyl-pyrimidin-4-yloxy}-piperidine-1-carboxylic acid isopropyl ester; 4-{5-Cyclopropyl-6-[2,5-difluoro-4-(2-hydroxy-ethyl)-phenoxy]-pyrimidin-4-yloxy}-piperidine-1-carboxylic acid isopropyl ester; 4-(5-Cyclopropyl-6-{2,5-difluoro-4-[2-(4-methoxy-piperidin-1-yl)-ethyl]-phenoxy}-pyrimidin-4-yloxy)-piperidine-1-carboxylic acid isopropyl ester; 4-{6-[2,5-Difluoro-4-(2-morpholin-4-yl-ethyl)-phenoxy]-5-methyl-pyrimidin-4-yloxy}-piperidine-1-carboxylic acid isopropyl ester; 4-(6-{2-Fluoro-4-[2-(4-methoxy-piperidin-1-yl)-ethyl]-phenoxy}-5-methyl-pyrimidin-4-yloxy)-piperidine-1-carboxylic acid isopropyl ester; 4-{6-[6-(2-Fluoro-ethyl)-2-methyl-pyridin-3-yloxy]-5-methyl-pyrimidin-4-yloxy}-piperidine-1-carboxylic acid isopropyl ester; 4-{6-[2-Fluoro-4-(1-hydroxy-cyclopropyl methyl)-phenoxy]-5-methyl-pyrimidin-4-yloxy}-piperidine-1-carboxylic acid isopropyl ester; 4-{2-[2,5-Difluoro-4-(2-methanesulfonyl-ethyl)-phenoxy]-3-methyl-pyridin-4-yloxy}-piperidine-1-carboxylic acid isopropyl ester; (R)-4-(6-{2-Fluoro-4-[2-(3-methoxy-piperidin-1-yl)-ethyl]-phenoxy}-5-methyl-pyrimidin-4-yloxy)-piperidine-1-carboxylic acid isopropyl ester; (S)-4-(6-{2-Fluoro-4-[2-(3-methoxy-piperidin-1-yl)-ethyl]-phenoxy)}-5-methyl-pyrimidin-4-yloxy)-piperidine-1-carboxylic acid isopropyl ester; (R)-4-(5-Ethynyl-6-{2-fluoro-4-[2-(2-methoxy-piperidin-1-yl)-ethyl]-phenoxy}-pyrimidin-4-yloxy)-piperidine-1-carboxylic acid isopropyl ester; (S)-4-(2-{2-Fluoro-4-[2-(2-methoxy-piperidin-1-yl)-ethyl]-phenoxy}-3-methyl-pyridin-4-yloxy)-piperidine-1-carboxylic acid isopropyl ester; 4-{6-[4-Fluoro-6-(2-morpholin-4-yl-ethyl)-pyridin-3-yloxy]-5-methyl-pyrimidin-4-yloxy}-piperidine-1-carboxylic acid isopropyl ester; 4-{5-Ethynyl-6-[4-fluoro-6-(2-methanesulfonyl-ethyl)-pyridin-3-yloxy]-pyrimidin-4-yloxy}-piperidine-1-carboxylic acid isopropyl ester; 4-{2-[2,5-Difluoro-4-(2-isopropoxy-ethyl)-phenoxy]-3-methyl-pyridin-4-yloxy}-piperidine-1-carboxylic acid isopropyl ester; 4-{6-[2-Fluoro-4-(2-propionylsulfamoyl-ethyl)-phenoxy]-5-methyl-pyrimidin-4-yloxy}-piperidine-1-carboxylic acid isopropyl ester; 4-{6-[2-Fluoro-4-(2-sulfamoyl-ethyl)-phenoxy]-5-methyl-pyrimidin-4-yloxy}-piperidine-1-carboxylic acid isopropyl ester; 4-{6-[2,5-Difluoro-4-(2-sulfamoyl-ethyl)-phenoxy]-5-ethynyl-pyrimidin-4-yloxy}-piperidine-1-carboxylic acid isopropyl ester; 4-{6-[2,5-Difluoro-4-(2-[1,2,4]triazol-1-yl-ethyl)-phenoxy]-5-methyl-pyrimidin-4-yloxy}-piperidine-1-carboxylic acid isopropyl ester; 4-{6-[2,3-Difluoro-4-(2-methanesulfonyl-ethyl)-phenoxy]-5-methyl-pyrimidin-4-yloxy}-piperidine-1-carboxylic acid isopropyl ester; 4-(2-{2-Fluoro-4-[2-(6-methoxy-pyridin-2-yl)-ethyl]-phenoxy}-3-methyl-pyridin-4-yloxy)-piperidine-1-carboxylic acid isopropyl ester; 4-(6-{2-Fluoro-4-[2-(3-methoxy-pyridin-2-yl)-ethyl]-phenoxy}-5-methyl-pyrimidin-4-yloxy)-piperidine-1-carboxylic acid isopropyl ester; 4-[6-(3-Fluoro-1-oxy-pyridin-4-yloxy)-5-methyl-pyrimidin-4-yloxy]-piperidine-1-carboxylic acid isopropyl ester; 4-[6-(5'-Methoxy-6-methyl-[2,2']bipyridinyl-5-yloxy)-5-methyl-pyrimidin-4-yloxy]-piperidine-1-carboxylic acid isopropyl ester; 4-{5-Ethynyl-6-[2-fluoro-4-(4-methoxy-pyridin-2-yl)-phenoxy]-pyrimidin-4-yloxy}-piperidine-1-carboxylic acid isopropyl ester; 4-{6-[2-Fluoro-4-(3-methoxy-pyridin-2-yl)-phenoxy]-5-methyl-pyrimidin-4-yloxy}-piperidine-1-carboxylic acid isopropyl ester; 4-(6-{2,5-Difluoro-4-[2-(3-methoxy-piperidin-1-yl)-ethyl]-phenoxy}-5-methyl-pyrimidin-4-yloxy)-piperidine-1-carboxylic acid isopropyl ester; and 4-(6-({2,5-Difluoro-4-[2-(3-methoxy-piperidin-1-yl)-ethyl]-phenoxy}-5-ethynyl-pyrimidin-4-yloxy)-piperidine-1-carboxylic acid isopropyl ester.

Specific examples of GPR119 agonists disclosed in International Application No. PCT/US2004/022327 include the following compounds according to Formula (III) (referred to herein as Group C8): 4-[6-(2-Fluoro-4-morpholin-4-yl-phenoxy)-5-methyl-pyrimidin-4-yloxy]-piperidine-1-carboxylic acid isopropyl ester; {4-[6-(2-Fluoro-4-methanesulfonyl-phenoxy)-5-methyl-pyrimidin-4-yloxy]-piperidin-1-yl}-[6-(2-pyrrolidin-1-yl-ethyl)-pyridin-3-yl]-methanone; (6-Amino-pyridin-3-yl)-{4-[6-(2-fluoro-4-methanesulfonyl-phenoxy)-5-methyl-pyrimidin-4-yloxy]-piperidin-1-yl}-methanone; 4-[5-Ethyl-6-(2-fluoro-4-methanesulfonyl-phenoxy)-pyrimidin-4-yloxy]-piperidine-1-carboxylic acid isopropyl ester; 4-[6-(2-Fluoro-phenoxy)-5-methyl-pyrimidin-4-yloxy]-piperidine-1-carboxylic acid isopropyl ester; 4-{6-[6-(2-Isopropoxy-ethylamino)-2-methyl-pyridin-3-yloxy]-5-methyl-pyrimidin-4-yloxy}-piperidine-1-carboxylic acid isopropyl ester; 4-{6-[6-(2-Hydroxy-ethylsulfanyl)-2-methyl-pyridin-3-yloxy]-5-methyl-pyrimidin-4-yloxy}-piperidine-1-carboxylic acid isopropyl ester; 4-[5-Methyl-6-(2-methyl-6-pentyl-pyridin-3-yloxy)-pyrimidin-4-yloxy]-piperidine-1-carboxylic acid isopropyl ester; 2-{4-[6-(2-Fluoro-4-methanesulfonyl-phenoxy)-5-methyl-pyrimidin-4-yloxy]-piperidin-1-yl}-1-(3-fluoro-phenyl)-ethanone; 4-(2-Fluoro-4-methanesulfonyl-phenoxy)-5-methyl-6-[1-(2-pyridin-3-yl-ethyl)-piperidin-4-yloxy]-pyrimidine; 2-{4-[6-(2-Fluoro-4-methanesulfonyl-phenoxy)-5-methyl-pyrimidin-4-yloxy]-piperidin-1-yl}-1-(4-trifluoromethoxy-phenyl)-ethanone; 2-{4-[6-(2-Fluoro-4-methanesulfonyl-phenoxy)-5-methyl-pyrimidin-4-yloxy]-piperidin-1-yl}-1-pyridin-2-yl-ethanone; 4-{6-[6-(2-Methoxy-ethanesulfonyl)-2-methyl-pyridin-3-yloxy]-5-methyl-pyrimidin-4-yloxy}-piperidine-1-carboxylic acid isopropyl ester; 4-(2-Fluoro-4-methanesulfonyl-phenoxy)-6-[1-(3-isopropyl-[1,2,4]oxadiazol-5-yl)-piperidin-4-yloxy]-5-methyl-pyrimidine; 4-(6-{2-Fluoro-4-[(2-hydroxy-ethylcarbamoyl)-methyl]-phenoxy}-5-methyl-pyrimidin-4-yloxy)-piperidine-1-carboxylic acid isopropyl ester; 4-[6-(5-Iodo-pyridin-2-yloxy)-5-methyl-pyrimidin-4-yloxy]-piperidine-1-carboxylic acid isopropyl ester; 4-(6-{2-Fluoro-4-[N-(2-isopropoxy-ethyl)-carbamimidoyl]-phenoxy}-5-methyl-pyrimidin-4-yloxy)-piperidine-1-carboxylic acid isopropyl ester; 4-[6-(4-Carboxy-2-fluoro-phenoxy)-5-methyl-pyrimidin-4-yloxy]-piperidine-1-carboxylic acid isopropyl ester; 4-(4-Bromo-2-fluoro-phenoxy)-6-[1-(3-isopropyl-[1,2,4]oxadiazol-5-yl)-piperidin-4-yloxy]-5-methyl-pyrimidine; 4-[6-(5-Methanesulfonyl-pyridin-2-yloxy)-5-methyl-pyrimidin-4-yloxy]-piperidine-1-carboxylic acid isopropyl ester; 4-{6-[6-(2-Hydroxy-ethylamino)-2-methyl-pyridin-3-yloxy]-5-methyl-pyrimidin-4-yloxy}-piperidine-1-carboxylic acid isopropyl ester; 4-[5-Cyclopropyl-6-(2-fluoro-4-methanesulfonyl-phenoxy)-pyrimidin-4-yloxy]-piperidine-1-carboxylic acid isopropyl ester; 4-{6-[6-(2-Methanesulfonyl-ethylamino)-2-methyl-pyridin-3-yloxy]-5-methyl-pyrimidin-4-yloxy}-piperidine-1-carboxylic acid isopropyl ester; 4-{4-[6-(2-Fluoro-4-methanesulfonyl-phenoxy)-5-methyl-pyrimidin-4-yloxy]-piperidin-1-yl}-4-oxo-butyric acid; 2-{4-[6-(2-Fluoro-4-methanesulfonyl-phenoxy)-5-methyl-pyrimidin-4-yloxy]-piperidin-1-yl}-1-(3-trifluoromethyl-phenyl)-ethanone; 4-{6-[6-(2-Methoxy-ethylsulfanyl)-2-methyl-pyridin-3-yloxy]-5-methyl-pyrimidin-4-yloxy}-piperidine-1-carboxylic acid isopropyl ester; 1-(2,5-Dimethoxy-phenyl)-2-{4-[6-(2-fluoro-4-methanesulfonyl-phenoxy)-5-methyl-pyrimidin-4-yloxy]-piperidin-1-yl}ethanone; 2-{4-[6-(2-Fluoro-4-methanesulfonyl-phenoxy)-5-methyl-pyrimidin-4-yloxy]-piperidin-1-yl}-1-pyridin-2-yl-ethanone; 4-[6-(6-Chloro-2-methyl-pyridin-3-yloxy)-5-methyl-pyrimidin-4-yloxy]-piperidine-1-carboxylic acid isopropyl ester; 2-{4-[6-(2-Fluoro-4-methanesulfonyl-phenoxy)-5-methyl-pyrimidin-4-yloxy]-piperidin-1-yl}-1-(4-fluoro-phenyl)-ethanone; 2-{4-[6-(2-

Fluoro-4-methanesulfonyl-phenoxy)-5-methyl-pyrimidin-4-yloxy]-piperidin-1-yl}-1-(4-trifluoromethyl-phenyl)-ethanone; 1-{4-[6-(2-Fluoro-4-methanesulfonyl-phenoxy)-5-methyl-pyrimidin-4-yloxy]-piperidin-1-yl}-3,3-dimethyl-butan-2-one; 2-{4-[6-(2-Fluoro-4-methanesulfonyl-phenoxy)-5-methyl-pyrimidin-4-yloxy]-piperidin-1-yl}-1-pyridin-3-yl-ethanone; 1-{4-[6-(2-Fluoro-4-methanesulfonyl-phenoxy)-5-methyl-pyrimidin-4-yloxy]-piperidin-1-yl}-butan-2-one; 4-(6-{2-Fluoro-4-[(2-isopropoxy-ethylcarbamoyl)-methyl]-phenoxy}-5-methyl-pyrimidin-4-yloxy)-piperidine-1-carboxylic acid isopropyl ester; 2-{4-[6-(2-Fluoro-4-methanesulfonyl-phenoxy)-5-methyl-pyrimidin-4-yloxy)-piperidin-1]-yl}-1-(4-methanesulfonyl-phenyl)-ethanone; 1-(4-Chloro-phenyl)-2-{4-[6-(2-fluoro-4-methanesulfonyl-phenoxy)-5-methyl-pyrimidin-4-yloxy]-piperidin-1-yl}-ethanone; 4-(2-{4-[6-(2-Fluoro-4-methanesulfonyl-phenoxy)-5-methyl-pyrimidin-4-yloxy]-piperidin-1-yl}-acetyl)-benzonitrile; 1-(3,4-Difluoro-phenyl)-2-{4-[6-(2-fluoro-4-methanesulfonyl-phenoxy)-5-methyl-pyrimidin-4-yloxy]-piperidin-1-yl}-ethanone; 4-{6-[2-Fluoro-4-(2-isopropoxy-ethylcarbamoyl)-phenoxy]-5-methyl-pyrimidin-4-yloxy}-piperidine-1-carboxylic acid isopropyl ester; 1-{4-[6-(2-Fluoro-4-methanesulfonyl-phenoxy)-5-methyl-pyrimidin-4-yloxy]-piperidin-1-yl}-butan-1-one; 1-{4-[6-(2-Fluoro-4-methanesulfonyl-phenoxy)-5-methyl-pyrimidin-4-yloxy]-piperidin-1-yl}-pentan-1-one; 4-[6-(2,4-Difluoro-phenoxy)-5-methyl-pyrimidin-4-yloxy]-piperidine-1-carboxylic acid isopropyl ester; 1-{4-[6-(2-Fluoro-4-methanesulfonyl-phenoxy)-5-methyl-pyrimidin-4-yloxy]-piperidin-1-yl}-3-methyl-butan-1-one; 1-{4-[6-(2-Fluoro-4-methanesulfonyl-phenoxy)-5-methyl-pyrimidin-4-yloxy]-piperidin-1-yl}-4-methyl-pentan-1-one; 1-{4-[6-(2-Fluoro-4-methanesulfonyl-phenoxy)-5-methyl-pyrimidin-4-yloxy]-piperidin-1-yl}-5-methyl-hexan-1-one; 4-{6-[2-Fluoro-4-(2-methoxy-ethylcarbamoyl)-phenoxy]-5-methyl-pyrimidin-4-yloxy}-piperidine-1-carboxylic acid isopropyl ester; 4-[6-(2-Fluoro-4-methanesulfonyl-phenoxy)-5-methyl-pyrimidin-4-yloxy]-piperidine-1-carboxylic acid isopropyl ester; 4-[6-(4-Bromo-2-fluoro-phenoxy)-5-methyl-pyrimidin-4-yloxy]-piperidine-1-carboxylic acid isopropyl ester; 4-{6-[2-Fluoro-4-(methoxy-methyl-carbamoyl)-phenoxy]-5-methyl-pyrimidin-4-yloxy}-piperidine-1-carboxylic acid isopropyl ester; 1-{4-[6-(2-Fluoro-4-methanesulfonyl-phenoxy)-5-methyl-pyrimidin-4-yloxy]-piperidin-1-yl}-3-methoxy-propan-1-one; 4-[6-(4-Cyano-2-fluoro-phenoxy)-5-methyl-pyrimidin-4-yloxy]-piperidine-1-carboxylic acid isopropyl ester; 4-[5-(5-Aminomethyl-4,5-dihydro-oxazol-2-yl)-6-(2-fluoro-4-methanesulfonyl-phenoxy)-pyrimidin-4-yloxy]-piperidine-1-carboxylic acid isopropyl ester; 4-{6-[6-(2-Methoxy-ethylamino)-2-methyl-pyridin-3-yloxy]-5-methyl-pyrimidin-4-yloxy}-piperidine-1-carboxylic acid isopropyl ester; 4-{6-[6-(3-Methanesulfonyl-pyrrolidin-1-yl)-2-methyl-pyridin-3-yloxy]-5-methyl-pyrimidin-4-yloxy}-piperidine-1-carboxylic acid isopropyl ester; 4-[6-(6-Benzylamino-2-methyl-pyridin-3-yloxy)-5-methyl-pyrimidin-4-yloxy]-piperidine-1-carboxylic acid isopropyl ester; 4-[6-(4-Carbamoyl-2-fluoro-phenoxy)-5-methyl-pyrimidin-4-yloxy]-piperidine-1-carboxylic acid isopropyl ester; 4-{6-[2-Fluoro-4-(2-isopropoxy-ethylamino)-phenoxy]-5-methyl-pyrimidin-4-yloxy}-piperidine-1-carboxylic acid isopropyl ester; 4-(6-{2-Fluoro-4-[(tetrahydro-furan-2-ylmethyl)-amino]-phenoxy}-5-methyl-pyrimidin-4-yloxy)-piperidine-1-carboxylic acid isopropyl ester; 4-(6-{6-[(2-Methanesulfonyl-ethyl)-methyl-amino]-2-methyl-pyridin-3-yloxy}-5-methyl-pyrimidin-4-yloxy)-piperidine-1-carboxylic acid isopropyl ester; 4-[6-(2-Fluoro-4-hydroxycarbamoyl-phenoxy)-5-methyl-pyrimidin-4-yloxy]-piperidine-1-carboxylic acid isopropyl ester; 4-{6-[2-Fluoro-4-(2-pyrrolidin-1-yl-ethylcarbamoyl)-phenoxy]-5-methyl-pyrimidin-4-yloxy}-piperidine-1-carboxylic acid isopropyl ester; 4-{6-[2-Fluoro-4-(4-isopropyl-piperazine-1-carbonyl)-phenoxy]-5-methyl-pyrimidin-4-yloxy}-piperidine-1-carboxylic acid isopropyl ester; 4-{6-[2-Fluoro-4-(2-morpholin-4-yl-ethyl)-phenoxy]-5-methyl-pyrimidin-4-yloxy}-piperidine-1-carboxylic acid isopropyl ester; 4-{6-[2-Fluoro-4-(2-methanesulfonyl-ethyl)-phenoxy]-5-methyl-pyrimidin-4-yloxy}-piperidine-1-carboxylic acid isopropyl ester; 4-{6-[2-Fluoro-4-(2-hydroxy-ethyl)-phenoxy]-5-methyl-pyrimidin-4-yloxy}-piperidine-1-carboxylic acid isopropyl ester; 4-[6-(4-Carboxymethyl-2-fluoro-phenoxy)-5-methyl-pyrimidin-4-yloxy]-piperidine-1-carboxylic acid isopropyl ester; 4-[6-(4-Dimethylcarbamoylmethyl-2-fluoro-phenoxy)-5-methyl-pyrimidin-4-yloxy]-piperidine-1-carboxylic acid isopropyl ester; 4-[6-(2-Fluoro-4-sulfamoyl-phenoxy)-5-methyl-pyrimidin-4-yloxy]-piperidine-1-carboxylic acid isopropyl ester; 4-[6-(2-Fluoro-4-propionylsulfamoyl-phenoxy)-5-methyl-pyrimidin-4-yloxy]-piperidine-1-carboxylic acid isopropyl ester; 4-[5-Ethynyl-6-(2-fluoro-4-methanesulfonyl-phenoxy)-pyrimidin-4-yloxy]-piperidine-1-carboxylic acid isopropyl ester; 4-{6-[2-Fluoro-4-(2-phosphonooxy-ethyl)-phenoxy]-5-methyl-pyrimidin-4-yloxy}-piperidine-1-carboxylic acid isopropyl ester; 4-[5-Bromo-6-(2-fluoro-4-methanesulfonyl-phenoxy)-pyrimidin-4-yloxy]-piperidine-1-carboxylic acid isopropyl ester; 4-(6-{2-Fluoro-4-[2-(2-methanesulfonyl-pyrrolidin-1-yl)-2-oxo-ethyl]-phenoxy}-5-methyl-pyrimidin-4-yloxy)-piperidine-1-carboxylic acid isopropyl ester; 4-[6-(4-Carbamoylmethyl-2-fluoro-phenoxy)-5-methyl-pyrimidin-4-yloxy]-piperidine-1-carboxylic acid isopropyl ester; 4-[6-(2-Fluoro-4-{[(tetrahydro-furan-2-ylmethyl)-carbamoyl]-methyl}-phenoxy)-5-methyl-pyrimidin-4-yloxy]-piperidine-1-carboxylic acid isopropyl ester; 4-[6-(2-Fluoro-3-sulfamoyl-phenoxy)-5-methyl-pyrimidin-4-yloxy]-piperidine-1-carboxylic acid isopropyl ester; C-{4-[6-(2-Fluoro-4-methanesulfonyl-phenoxy)-5-methyl-pyrimidin-4-yloxy]-piperidin-1-yl}-C-(4-fluoro-phenyl)-methyleneamine; 3-tert-Butoxy-1-{4-[6-(2-fluoro-4-methanesulfonyl-phenoxy)-5-methyl-pyrimidin-4-yloxy]-piperidin-1-yl}-propan-1-one; 2-Ethoxy-1-{4-[6-(2-fluoro-4-methanesulfonyl-phenoxy)-5-methyl-pyrimidin-4-yloxy]-piperidin-1-yl}-ethanone; {4-[6-(2-Fluoro-4-methanesulfonyl-phenoxy)-5-methyl-pyrimidin-4-yloxy]-piperidin-1-yl}-(tetrahydro-furan-2-yl)-methanone; (S)-1-{4-[6-(2-Fluoro-4-methanesulfonyl-phenoxy)-5-methyl-pyrimidin-4-yloxy]-piperidin-1-yl}-3-methyl-2-methylamino-butan-1-one; 4-(6-{2-Fluoro-4-[2-(3-hydroxy-piperidin-1-yl)-2-oxo-ethyl]-phenoxy}-5-methyl-pyrimidin-4-yloxy)-piperidine-1-carboxylic acid isopropyl ester; 4-{6-[2-Fluoro-4-(2-morpholin-4-yl-2-oxo-ethyl)-phenoxy]-5-methyl-pyrimidin-4-yloxy}-piperidine-1-carboxylic acid isopropyl ester; 4-{6-[2-Fluoro-4-(2-imidazol-1-yl-ethyl)-phenoxy]-5-methyl-pyrimidin-4-yloxy}-piperidine-1-carboxylic acid isopropyl ester; 4-{6-[2-Fluoro-4-(2-[1,2,3]triazol-1-yl-ethyl)-phenoxy]-5-methyl-pyrimidin-4-yloxy}-piperidine-1-carboxylic acid isopropyl ester; (R)-1-{4-[6-(2-Fluoro-4-methanesulfonyl-phenoxy)-5-methyl-pyrimidin-4-yloxy]-piperidin-1-yl}-3-methyl-2-methylamino-butan-1-one; (S)-1-{4-[6-(2-Fluoro-4-methanesulfonyl-phenoxy)-5-methyl-pyrimidin-4-yloxy]-piperidin-1-yl}-3-hydroxy-butan-1-one; (R)—N-(1-{4-[6-(2-Fluoro-4-methanesulfonyl-phenoxy)-5-methyl-pyrimidin-4-yloxy]-piperidine-1-carbonyl}-2-methyl-propyl)-acetamide; (S)—N-(1-{4-[6-(2-Fluoro-4-methanesulfonyl-phenoxy)-5-methyl-pyrimidin-4-yloxy]- piperidine-1-carbonyl}-2-methyl-propyl)-acetamide; (R)—N-(2-{4-[6-(2-Fluoro-4-methanesulfonyl-phenoxy)-5-methyl-pyrimidin-4-yloxy]-piperidin-1-yl}-1-methyl-2-oxo-ethyl)-acetamide; (S)—N-(2-{4-[6-(2-Fluoro-4-methanesulfonyl-phenoxy)-5-methyl-pyrimidin-4-yloxy]-piperidin-1-yl}-1-methyl-2-oxo-ethyl)-acetamide; 4-[6-(2-Fluoro-4-methanesulfonyl-phenoxy)-5-methyl-pyrimidin-4-yloxy]-piperidine-1-carboxylic acid (S)-tetrahydro-furan-3-yl ester; 4-[6-(2-Fluoro-4-methanesulfonyl-phenoxy)-5-methyl-pyrimidin-4-yloxy]-piperidine-1-carboxylic acid (R)-tetrahydro-furan-3-yl ester; 4-[6-(2-Amino-4-ethanesulfonyl-phenoxy)-5-methyl-pyrimidin-4-yloxy]-piperidine-1-carboxylic acid isopropyl ester; 4-[6-(4-Methanesulfonyl-phenoxy)-5-methyl-pyrimidin-4-yloxy]-piperidine-1-carboxylic acid isopropyl ester; (1-{4-[6-(2-Fluoro-4-methanesulfonyl-phenoxy)-5-methyl-pyrimidin-4-yloxy]-piperidine-1-carbonyl}-2-methyl-propyl)-carbamic acid tert-butyl ester; 4-{6-[2-Fluoro-4-(6-methoxy-pyridin-3-yl)-phenoxy]-5-methyl-pyrimidin-4-yloxy}-piperidine-1-carboxylic acid isopropyl ester; 3-Amino-1-{4-[6-(2-fluoro-4-methanesulfonyl-phenoxy)-5-methyl-pyrimidin-4-yloxy]-piperidin-1-yl}-4-methyl-pentan-1-one; 2-Amino-1-{4-[6-(2-fluoro-4-methanesulfonyl-phenoxy)-5-methyl-pyrimidin-4-yloxy]-piperidin-1-yl}-3-methyl-butan-1-one; 4-{6-[2-Fluoro-4-(2-isopropoxy-ethoxy)-phenoxy]-5-methyl-pyrimidin-4-yloxy}-piperidine-1-carboxylic acid isopropyl ester; and 4-[5-Methyl-6-(4-sulfo-phenoxy)-pyrimidin-4-yloxy]-piperidine-1-carboxylic acid isopropyl ester.

Specific examples of GPR119 agonists disclosed in International Application No. PCT/US2004/022327 include the following compounds according to Formula (III) (referred to herein as Group C9): 4-({Cyclopropyl-[6-(2-fluoro-4-methanesulfonyl-phenoxy)-5-methyl-pyrimidin-4-yl]-amino}-methyl)-piperidine-1-carboxylic acid tert-butyl ester; 4-({Cyclopropyl-[6-(2-fluoro-4-methanesulfonyl-phenoxy)-5-methyl-pyrimidin-4-yl]-amino}-methyl)-piperidine-1-carboxylic acid isopropyl ester; 4-({[6-(2-Fluoro-4-methanesulfonyl-phenoxy)-5-methyl-pyrimidin-4-yl]-isopropyl-amino}-methyl)-piperidine-1-carboxylic acid isopropyl ester; and 4-({Cyclopropylmethyl-[6-(2-fluoro-4-methanesulfonyl-phenoxy)-5-methyl-pyrimidin-4-yl]-amino}-methyl)-piperidine-1-carboxylic acid isopropyl ester.

Specific examples of GPR119 agonists disclosed in International Application No. PCT/US2004/022327 include the following compound according to Formula (III) (referred to herein as Group C10): 4-[6-(2-Fluoro-4-methanesulfonyl-phenylamino)-5-methyl-pyrimidin-4-ylsulfanyl]-piperidine-1-carboxylic acid isopropyl ester.

Examples of GPR119 agonists are described in International Application No. PCT/US2004/022417 (published as WO 05/007658), the disclosure of each of which is herein incorporated by reference in its entirety. Disclosed in International Application No. PCT/US2004/022417 as a GPR119 agonist is a compound of Formula (IV):

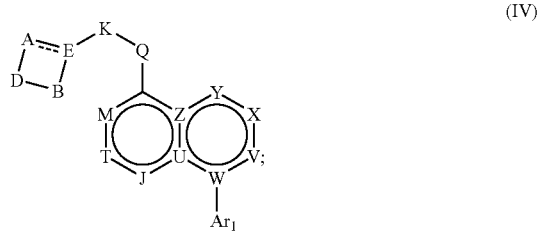

wherein:
A and B are each independently $C_{1-3}$ alkylene optionally substituted with 1 to 4 substituents selected from the group consisting of $C_{1-3}$ alkyl, $C_{1-4}$ alkoxy, carboxy, cyano, $C_{1-3}$ haloalkyl and halogen;
D is O, S, S(O), $S(O)_2$, $CR_1R_2$ or N—$R_2$, wherein $R_1$ is selected from the group consisting of H, $C_{1-8}$ alkyl, $C_{1-4}$ alkoxy, halogen and hydroxyl;
E is N, C or $CR_3$, wherein $R_3$ is H or $C_{1-8}$ alkyl;
--- is a single bond when E is N or $CR_3$, or a double bond when E is C;
K is a $C_{3-6}$ cycloalkylene or $C_{1-3}$ alkylene wherein each are optionally substituted with 1 to 4 substituents selected from the group consisting of $C_{1-3}$ alkyl, $C_{1-4}$ alkoxy, carboxy, cyano, $C_{1-3}$ haloalkyl and halogen; or K is a bond;
Q is $NR_4$, O, S, S(O) or $S(O)_2$, wherein $R_4$ is H or $C_{1-8}$ alkyl and the $C_{1-8}$ alkyl is optionally substituted with $C_{2-8}$ dialkylamine;
T is N or $CR_5$;
M is N or $CR_6$;
J is N or $CR_7$;
U is C or N;
V is N, $CR_8$ or V is a bond;
W is N or C;
X is O, S, N, $CR_9$ or $NR_{11}$;
Y is O, S, N, $CR_{10}$ or $NR_{12}$;
Z is C or N;
$R_5$, $R_6$, $R_7$, $R_8$, $R_9$ and $R_{10}$ are each independently selected from the group consisting of H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-6}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, hydroxylamino and nitro; wherein said $C_{2-6}$ alkenyl, $C_{1-8}$ alkyl, $C_{2-6}$ alkynyl and $C_{3-6}$ cycloalkyl are optionally substituted with 1, 2, 3 or 4 substituents selected from the group consisting of $C_{1-5}$ acyl, $C_{1-5}$ acyloxy, $C_{1-4}$ alkoxy, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro;
$R_{11}$ and $R_{12}$ are each independently selected from $C_{2-6}$ alkenyl, $C_{1-8}$ alkyl, $C_{2-6}$ alkynyl or $C_{3-6}$ cycloalkyl each optionally substituted with 1, 2, 3 or 4 substituents selected from the group consisting of $C_{1-5}$ acyl, $C_{1-5}$ acyloxy, $C_{1-4}$ alkoxy, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl; $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro;

Ar$_1$ is aryl or heteroaryl each optionally substituted with R$_{13}$, R$_{14}$, R$_{15}$, R$_{16}$, and R$_{17}$; wherein R$_{13}$ is selected from the group consisting of C$_{1-5}$ acyl, C$_{1-6}$ acylsulfonamide, C$_{1-5}$ acyloxy, C$_{2-6}$ alkenyl, C$_{1-4}$ alkoxy, C$_{1-8}$ alkyl, C$_{1-4}$ alkylamino, C$_{1-6}$ alkylcarboxamide, C$_{1-4}$ alkylthiocarboxamide, C$_{2-6}$ alkynyl, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylthioureyl, C$_{1-4}$ alkylureyl, amino, arylsulfonyl, carbamimidoyl, carbo-C$_{1-6}$ alkoxy, carboxamide, carboxy, cyano, C$_{3-7}$ cycloalkyl, C$_{3-7}$ cycloalkyloxy, C$_{2-6}$ dialkylamino, C$_{2-6}$ dialkylcarboxamide, C$_{2-6}$ dialkylthiocarboxamide, guanidinyl, halogen, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkylthio, heterocyclic, heterocyclic-oxy, heterocyclicsulfonyl, heterocyclic-carbonyl, heteroaryl, heteroarylcarbonyl, hydroxyl, nitro, C$_{4-7}$ oxo-cycloalkyl, phenoxy, phenyl, sulfonamide, sulfonic acid, and thiol, and wherein said C$_{1-5}$ acyl, C$_{1-6}$ acylsulfonamide, C$_{1-4}$ alkoxy, C$_{1-8}$ alkyl, C$_{1-4}$ alkylamino, C$_{1-6}$ alkylsulfonamide, C$_{1-4}$ alkylsulfonyl, C$_{1-4}$ alkylthio, arylsulfonyl, carbamimidoyl, C$_{2-6}$ dialkylamino, heterocyclic, heterocyclic-carbonyl, heteroaryl, phenoxy and phenyl are optionally substituted with 1 to 5 substituents selected independently from the group consisting of C$_{1-5}$ acyl, C$_{1-5}$ acyloxy, C$_{2-6}$ alkenyl, C$_{1-4}$ alkoxy, C$_{1-7}$ alkyl, C$_{1-4}$ alkylamino, C$_{1-4}$ alkylcarboxamide, C$_{2-6}$ alkynyl, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylureyl, carbo-C$_{1-6}$-alkoxy, carboxamide, carboxy, cyano, C$_{3-7}$ cycloalkyl, C$_{3-7}$ cycloalkyloxy, C$_{2-6}$ dialkylamino, C$_{2-6}$ dialkylcarboxamide, halogen, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkylthio, heteroaryl, heterocyclic, hydroxyl, nitro, phenyl, and phosphonooxy, and wherein said C$_{1-7}$ alkyl and C$_{1-4}$ alkylcarboxamide are each optionally substituted with 1 to 5 substituents selected from the group consisting of C$_{1-4}$ alkoxy and hydroxy; or R$_{13}$ is a group of Formula (IVA):

(IVA)

wherein:

"p" and "r" are independently 0, 1, 2 or 3; and

R$_{18}$ is H, C$_{1-5}$ acyl, C$_{2-6}$ alkenyl, C$_{1-8}$ alkyl, C$_{1-4}$ alkylcarboxamide, C$_{2-6}$ alkynyl, C$_{1-4}$ alkylsulfonamide, carbo-C$_{1-6}$-alkoxy, carboxamide, carboxy, cyano, C$_{3-7}$ cycloalkyl, C$_{2-6}$ dialkylcarboxamide, halogen, heteroaryl or phenyl, and wherein said heteroaryl or phenyl optionally substituted with 1 to 5 substituents selected independently from the group consisting of C$_{1-4}$ alkoxy, amino, C$_{1-4}$ alkylamino, C$_{2-6}$ alkynyl, C$_{2-8}$ dialkylamino, halogen, C$_{1-4}$ haloalkoxy, C$_{1-4}$ haloalkyl and hydroxyl;

R$_{14}$, R$_{15}$, R$_{16}$, and R$_{17}$ are each independently selected form the group consisting of H, C$_{1-5}$ acyl, C$_{1-5}$ acyloxy, C$_{2-6}$ alkenyl, C$_{1-4}$ alkoxy, C$_{1-8}$ alkyl, C$_{1-4}$ alkylcarboxamide, C$_{2-6}$ alkynyl, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylureyl, carbo-C$_{1-6}$-alkoxy, carboxamide, carboxy, cyano, C$_{3-7}$ cycloalkyl, C$_{2-6}$ dialkylcarboxamide, halogen, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkylthio, hydroxyl and nitro; or two adjacent R$_{14}$, R$_{15}$, R$_{16}$ and R$_{17}$ together with the atoms to which they are attached form a 5, 6 or 7 member cycloalkyl, cycloalkenyl or heterocyclic group fused with Ar$_1$ wherein the 5, 6 or 7 member group is optionally substituted with halogen; and R$_2$ is selected from the group consisting of C$_{1-8}$ alkyl, C$_{2-6}$ alkynyl, amino, aryl, carboxamide, carboxy, cyano, C$_{3-6}$-cycloalkyl, C$_{1-4}$ haloalkoxy, C$_{1-4}$ haloalkyl, halogen, heteroaryl and hydroxyl; and wherein said C$_{1-8}$ alkyl, aryl and heteroaryl are each optionally substituted with 1 to 5 substituents selected from the group consisting of C$_{1-5}$ acyl, C$_{1-5}$ acyloxy, C$_{1-4}$ alkoxy, C$_{1-8}$ alkyl, C$_{1-4}$ alkylamino, C$_{1-4}$ alkylcarboxamide, C$_{1-4}$ alkylthiocarboxamide, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylthioureyl, C$_{1-4}$ alkylureyl, amino, carbo-C$_{1-6}$-alkoxy, carboxamide, carboxy, cyano, C$_{3-6}$-cycloalkyl, C$_{3-6}$-cycloalkyl-C$_{1-3}$-heteroalkylene, C$_{2-8}$ dialkylamino, C$_{2-6}$ dialkylcarboxamide, C$_{2-6}$ dialkylthiocarboxamide, C$_{2-6}$ dialkylsulfonamide, C$_{1-4}$ alkylthioureyl, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkyl, C$_{1-4}$ haloalkylthio, halogen, heterocyclic, hydroxyl, hydroxylamino and nitro; or R$_2$ is —Ar$_2$—Ar$_3$ wherein Ar$_2$ and Ar$_3$ are each independently aryl or heteroaryl each optionally substituted with 1 to 5 substituents selected from the group consisting of H, C$_{1-5}$ acyl, C$_{1-5}$ acyloxy, C$_{1-4}$ alkoxy, C$_{1-8}$ alkyl, C$_{1-4}$ alkylcarboxamide, C$_{1-4}$ alkylthiocarboxamide, C$_{1-4}$ alkylsulfinyl, C$_{1-4}$ alkylsulfonyl, C$_{1-4}$ alkylthio, amino, C$_{1-4}$ alkylamino, carbo-C$_{1-6}$-alkoxy, carboxamide, carboxy, cyano, C$_{3-6}$-cycloalkyl, C$_{2-8}$ dialkylamino, C$_{2-6}$ dialkylcarboxamide, C$_{1-4}$ haloalkoxy, C$_{1-4}$ haloalkyl, halogen, hydroxyl and nitro; or R$_2$ is a group of Formula (IVB):

(IVB)

wherein:

R$_{19}$ is H, C$_{1-8}$ alkyl, C$_{3-7}$ cycloalkyl, aryl, heteroaryl or OR$_{21}$; and R$_{20}$ is F, Cl, Br, CN or NR$_{22}$R$_{23}$; where R$_{21}$ is H, C$_{1-8}$ alkyl or C$_{3-7}$ cycloalkyl, and R$_{22}$ and R$_{23}$ are independently H, C$_{1-8}$ alkyl, C$_{3-7}$ cycloalkyl, aryl or heteroaryl;

or

R$_2$ is a group of Formula (IVC):

(IVC)

wherein:

G is:

i) —C(O)—, —C(O)NR$_{25}$—, —NR$_{25}$C(O)—, —NR$_{25}$—, —NR$_{25}$C(O)O—, —OC(O)NR$_{25}$—,

—$CR_{25}R_{26}NR_{27}C(O)$—, —$CR_{25}R_{26}C(O)NR_{27}$—, —$C(O)O$—, —$OC(O)$—, —$C(S)$—, —$C(S)NR_{25}$—, —$C(S)O$—, —$OC(S)$—, —$CR_{25}R_{26}$—, —$O$—, —$S$—, —$S(O)$—, —$S(O)_2$— or a bond when D is $CR_2R_3$; or ii) —$CR_{25}R_{26}C(O)$—, —$C(O)$—, —$CR_{25}R_{26}C(O)NR_{27}$—, —$C(O)NR_{25}$—, —$C(O)O$—, —$C(S)$—, —$C(S)NR_{25}$—, —$C(S)O$—, —$CR_{25}R_{26}$—, —$S(O)_2$—, or a bond when D is $NR_2$;

wherein $R_{25}$, $R_{26}$ and $R_{27}$ are each independently H or $C_{1-8}$ alkyl; and $R_{24}$ is H, $C_{1-8}$ alkyl, $C_{3-7}$ cycloalkyl, phenyl, heteroaryl, or heterocyclic each optionally substituted with 1 to 5 substituents selected from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, heterocyclic, hydroxyl, hydroxylamino, nitro, phenyl, phenoxy, and sulfonic acid, wherein said $C_{1-4}$ alkoxy, $C_{1-7}$ alkyl, $C_{1-4}$ alkylamino, heteroaryl, phenyl and phenoxy are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino, nitro, and phenyl;

provided that Z and U are not both N.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Specific examples of GPR119 agonists disclosed in International Application No. PCT/US2004/022417 include the following compounds according to Formula (IV) (referred to herein as Group D1): 4-[1-(4-Methanesulfonyl-phenyl)-1H-pyrazolo[3,4-d]pyrimidin-4-yloxy]-piperidine-1-carboxylic acid tert-butyl ester; 4-[1-(4-Methanesulfonyl-phenyl)-3-methyl-1H-pyrazolo[3,4-d]pyrimidin-4-yloxy]-piperidine-1-carboxylic acid tert-butyl ester; 4-[1-(4-Methanesulfonyl-phenyl)-3,6-dimethyl-1H-pyrazolo[3,4-d]pyrimidin-4-yloxy]-piperidine-1-carboxylic acid tert-butyl ester; 4-[1-(4-Methanesulfonyl-phenyl)-1H-pyrazolo[3,4-d]pyrimidin-4-yloxy]-piperidine-1-carboxylic acid isobutyl ester; 4-[1-(4-Methanesulfonyl-phenyl)-1H-pyrazolo[3,4-d]pyrimidin-4-yloxy]-piperidine-1-carboxylic acid isopropyl ester; 1-(4-Methanesulfonyl-phenyl)-4-(piperidin-4-yloxy)-1H-pyrazolo[3,4-d]pyrimidine; {4-[1-(4-Methanesulfonyl-phenyl)-1H-pyrazolo[3,4-d]pyrimidin-4-yloxy]-piperidin-1-yl}-pyridin-3-yl-methanone; (3-Fluoro-phenyl)-{4-[1-(4-methanesulfonyl-phenyl)-1H-pyrazolo[3,4-d]pyrimidin-4-yloxy]-piperidin-1-yl}-methanone; (1-tert-Butyl-5-methyl-1H-pyrazol-4-yl)-{4-[1-(4-methanesulfonyl-phenyl)-1H-pyrazolo[3,4-d]pyrimidin-4-yloxy]-piperidin-1-yl}-methanone; (5-tert-Butyl-2-methyl-2H-pyrazol-3-yl)-{4-[1-(4-methanesulfonyl-phenyl)-1H-pyrazolo[3,4-d]pyrimidin-4-yloxy]-piperidin-1-yl}-methanone; 4-[1-(4-Methanesulfonyl-phenyl)-1H-pyrazolo[3,4-d]pyrimidin-4-ylamino]-piperidine-1-carboxylic acid tert-butyl ester; 4-[1-(4-Methanesulfonyl-phenyl)-1H-pyrazolo[3,4-d]pyrimidin-4-ylamino]-piperidine-1-carboxylic acid isopropyl ester; 4-[1-(4-Methanesulfonyl-phenyl)-1H-pyrazolo[3,4-d]pyrimidin-4-ylamino]-piperidine-1-carboxylic acid isobutyl ester; Furan-2-yl-{4-[1-(4-methanesulfonyl-phenyl)-1H-pyrazolo[3,4-d]pyrimidin-4-yloxy]-piperidin-1-yl}-methanone; {4-[1-(4-Methanesulfonyl-phenyl)-1H-pyrazolo[3,4-d]pyrimidin-4-yloxy]-piperidin-1-yl}-(1-methyl-1H-pyrrol-2-yl)-methanone; 2-{4-[1-(4-Methanesulfonyl-phenyl)-1H-pyrazolo[3,4-d]pyrimidin-4-yloxy]-piperidin-1-yl}-1-pyridin-3-yl-ethanone; 2-{4-[1-(4-Methanesulfonyl-phenyl)-1H-pyrazolo[3,4-d]pyrimidin-4-yloxy]-piperidin-1-yl}-1-pyridin-2-yl-ethanone; {4-[1-(4-Methanesulfonyl-phenyl)-1H-pyrazolo[3,4-d]pyrimidin-4-yloxy]-piperidin-1-yl}-(5-methyl-pyridin-3-yl)-methanone; {4-[1-(4-Methanesulfonyl-phenyl)-1H-pyrazolo[3,4-d]pyrimidin-4-yloxy]-piperidin-1-yl}-(2-methyl-pyridin-3-yl)-methanone; {4-[1-(4-Methanesulfonyl-phenyl)-1H-pyrazolo[3,4-d]pyrimidin-4-yloxy]-piperidin-1-yl}-(6-methyl-pyridin-3-yl)-methanone; {4-[1-(4-Methanesulfonyl-phenyl)-1H-pyrazolo[3,4-d]pyrimidin-4-yloxy]-piperidin-1-yl}-(5-methyl-isoxazol-3-yl)-methanone; 2-{4-[1-(4-Methanesulfonyl-phenyl)-1H-pyrazolo[3,4-d]pyrimidin-4-yloxy]-piperidin-1-yl}-1-thiophen-2-yl-ethanone; 4-(1-Benzyl-azetidin-3-yloxy)-1-(4-methanesulfonyl-phenyl)-1H-pyrazolo[3,4-d]pyrimidine; 3-[1-(4-Methanesulfonyl-phenyl)-1H-pyrazolo[3,4-d]pyrimidin-4-ylamino]-piperidine-1-carboxylic acid tert-butyl ester; 1-{4-[1-(4-Methanesulfonyl-phenyl)-1H-pyrazolo[3,4-d]pyrimidin-4-yloxy]-piperidin-1-yl}-3,3-dimethyl-butan-2-one; {4-[1-(4-Methanesulfonyl-phenyl)-1H-pyrazolo[3,4-d]pyrimidin-4-yloxy]-piperidin-1-yl}-pyrazin-2-yl-methanone; {4-[1-(4-Methanesulfonyl-phenyl)-1H-pyrazolo[3,4-d]pyrimidin-4-yloxy]-piperidin-1-yl}-(5-methyl-pyrazin-2-yl)-methanone; {4-[1-(4-Methanesulfonyl-phenyl)-1H-pyrazolo[3,4-d]pyrimidin-4-yloxy]-piperidin-1-yl}-pyrimidin-5-yl-methanone; {4-[1-(4-Methanesulfonyl-phenyl)-1H-pyrazolo[3,4-d]pyrimidin-4-yloxy]-piperidin-1-yl}-pyridazin-4-yl-methanone; {4-[1-(4-Methanesulfonyl-phenyl)-1H-pyrazolo[3,4-d]pyrimidin-4-yloxy]-piperidin-1-yl}-thiophen-2-yl-methanone; (3,4-Dimethyl-isoxazol-5-yl)-{4-[1-(4-methanesulfonyl-phenyl)-1-pyrazolo[3,4-d]pyrimidin-4-yloxy]-piperidin-1-yl}-methanone; 3-tert-Butoxy-1-{4-[1-(4-methanesulfonyl-phenyl)-1H-pyrazolo[3,4-d]pyrimidin-4-yloxy]-piperidin-1-yl}-propan-1-one; (3-{4-[1-(4-Methanesulfonyl-phenyl)-1H-pyrazolo[3,4-d]pyrimidin-4-yloxy]-piperidin-1-yl}-3-oxo-propyl)-methyl-carbamic acid tert-butyl ester; {4-[1-(4-Methanesulfonyl-phenyl)-1H-pyrazolo[3,4-d]pyrimidin-4-yloxy]-piperidin-1-yl}-(6-trifluoromethyl-pyridin-3-yl)-methanone; {(4-[1-(4-Methanesulfonyl-phenyl)-1H-pyrazolo[3,4-d]pyrimidin-4-ylamino]-cyclohexyl}-carbamic acid tert-butyl ester; N-[1-(4-Methanesulfonyl-phenyl)-1H-pyrazolo[3,4-d]pyrimidin-4-yl]-cyclohexane-1,4-diamine; {4-[1-(4-Methanesulfonyl-phenyl)-1H-pyrazolo[3,4-d]pyrimidin-4-yloxy]-piperidin-1-yl}-(4-methyl-[1,2,3]thiadiazol-5-yl)-methanone; (3,5-Dimethyl-isoxazol-4-yl)-{4-[1-(4-methanesulfonyl-phenyl)-1H-pyrazolo[3,4-d]pyrimidin-4-yloxy]-piperidin-1-yl}-methanone; (2,5-Dimethyl-2H-pyrazol-3-yl)-{4-[1-(4-methanesulfonyl-phenyl)-1H-pyrazolo[3,4-d]pyrimidin-4-yloxy]-piperidin-1-yl}-methanone; {4-[1-(4-Methanesulfonyl-phenyl)-1H- pyrazolo[3,4-d]pyrimidin-4-yloxy]-piperidin-1-yl}-(3-methyl-isoxazol-5-yl)-methanone; 4-[1-(4-Methanesulfonyl-phenyl)-1H-pyrazolo[3,4-d]pyrimidin-4-yloxy]-piperidine-1-carboxylic acid pyridin-4-ylamide; N-{4-[1-(4-Methanesulfonyl-phenyl)-1H-pyrazolo[3,4-d]pyrimidin-4-ylamino]-cyclohexyl}-nicotinamide; 3-tert-Butoxy-N-{4-[1-(4-methanesulfonyl-phenyl)-1H-pyrazolo[3,4-d]pyrimidin-4-ylamino]-cyclohexyl}-propionamide; {4-[1-(4-Methanesulfonyl-phenyl)-1H-pyrazolo[3,4-d]pyrimidin-4-ylamino]-cyclohexyl}-carbamic acid tert-butyl ester; (3,5-Dimethyl-isoxazol-4-yl)-{4-[1-(4-methanesulfonyl-phenyl)-1H-pyrazolo[3,5-d]pyrimidin-4-yloxy]-piperidin-1-yl}-methanone; 4-[1-(3,5-Bis-trifluoromethyl-phenyl)-1H-pyrazolo[3,4-d]pyrimidin-4-yloxy]-piperidine-1-carboxylic acid tert-butyl ester; 3-[1-(4-Methanesulfonyl-phenyl)-1H-pyrazolo[3,4-d]pyrimidin-4-yloxy]-azetidine-1-carboxylic acid isopropyl ester; 4-[1-(4-Methanesulfonyl-phenyl)-1H-pyrazolo[3,4-d]pyrimidin-4-yloxy]-piperidine-1-carboxylic acid butyl ester; 4-[1-(4-Methanesulfonyl-phenyl)-1H-pyrazolo[3,4-d]pyrimidin-4-yloxy]-piperidine-1-carboxylic acid propyl ester; 4-[1-(3-Fluoro-phenyl)-1H-pyrazolo[3,4-d]pyrimidin-4-yloxy]-piperidine-1-carboxylic acid tert-butyl ester; 4-[1-(2,4-Difluoro-phenyl)-1H-pyrazolo[3,4-d]pyrimidin-4-yloxy]-piperidine-1-carboxylic acid tert-butyl ester; {4-[1-(2,4-Difluoro-phenyl)-1H-pyrazolo[3,4-d]pyrimidin-4-ylamino]-cyclohexyl}-carbamic acid tert-butyl ester; {4-[1-(3-Fluoro-phenyl)-1H-pyrazolo[3,4-d]pyrimidin-4-ylamino]-cyclohexyl}-carbamic acid tert-butyl ester; N-[1-(4-Methanesulfonyl-phenyl)-1H-pyrazolo[3,4-d]pyrimidin-4-yl]-cyclohexane-1,4-diamine; {3-[1-(4-Methanesulfonyl-phenyl)-1H-pyrazolo[3,4-d]pyrimidin-4-ylamino]-piperidin-1-yl}-(6-methyl-pyridin-3-yl)-methanone; {3-[1-(4-Methanesulfonyl-phenyl)-1H-pyrazolo[3,4-d]pyrimidin-4-ylamino]-piperidin-1-yl}-(2-methyl-pyridin-3-yl)-methanone; {3-[1-(4-Methanesulfonyl-phenyl)-1H-pyrazolo[3,4-d]pyrimidin-4-ylamino]-piperidin-1-yl}-(5-methyl-pyridin-3-yl)-methanone; {3-[1-(4-Methanesulfonyl-phenyl)-1H-pyrazolo[3,4-d]pyrimidin-4-ylamino]-piperidin-1-yl}-pyridin-3-yl-methanone; {3-[1-(4-Methanesulfonyl-phenyl)-1H-pyrazolo[3,4-d]pyrimidin-4-ylamino]-piperidin-1-yl}-(1-methyl-1H-pyrrol-3-yl)-methanone; {4-[1-(4-Methanesulfonyl-phenyl)-1H-pyrazolo[3,4-d]pyrimidin-4-yloxy]-cyclohexyl}-carbamic acid tert-butyl ester; N-[1-(2,4-Difluoro-phenyl)-1H-pyrazolo[3,4-d]pyrimidin-4-yl]-cyclohexane-1,4-diamine; {4-[1-(4-Methanesulfonyl-phenyl)-1H-pyrazolo[3,4-d]pyrimidin-4-yloxy]-piperidin-1-yl}-(4-trifluoromethyl-pyridin-3-yl)-methanone; 4-[1-(4-Methanesulfonyl-phenyl)-1H-pyrazolo[3,4-d]pyrimidin-4-yloxy]-piperidine-1-carboxylic acid cyclohexyl ester; 4-[1-(4-Methanesulfonyl-phenyl)-1H-pyrazolo[3,4-d]pyrimidin-4-yloxy]-piperidine-1-carboxylic acid tetrahydro-pyran-4-yl ester; 4-[1-(4-Methanesulfonyl-phenyl)-1H-pyrazolo[3,4-d]pyrimidin-4-yloxy]-piperidine-1-carboxylic acid cyclopentyl, ester; 4-[1-(4-Methanesulfonyl-phenyl)-1H-pyrazolo[3,4-d]pyrimidin-4-yloxy]-piperidine-1-carboxylic acid tetrahydro-furan-3-yl ester; 4-[1-(4-Methanesulfonyl-phenyl)-1H-pyrazolo[3,4-d]pyrimidin-4-yloxy]-piperidine-1-carboxylic acid tetrahydro-furan-3-yl ester; 4-[1-(4-Methanesulfonyl-phenyl)-1H-pyrazolo[3,4-d]pyrimidin-4-yloxy]-piperidine-1-carboxylic acid tetrahydro-thiopyran-4-yl ester; 4-[1-(4-Methanesulfonyl-phenyl)-1H-pyrazolo[3,4-d]pyrimidin-4-yloxy]-piperidine-1-carboxylic acid cyclobutyl ester; (6-tert-Butyl-pyridin-3-yl)-{4-[1-(4-methanesulfonyl-phenyl)-1H-pyrazolo[3,4-d]pyrimidin-4-yloxy]-piperidin-1-yl}-methanone; (4-{[1-(4-Methanesulfonyl-phenyl)-1H-pyrazolo[3,4-d]pyrimidin-4-ylamino]-methyl}-cyclohexyl)-carbamic acid tert-butyl ester; N-{4-[1-(4-Methanesulfonyl-phenyl)-1H-pyrazolo[3,4-d]pyrimidin-4-ylamino]-cyclohexylmethyl}-nicotinamide; N-{4-[1-(4-Methanesulfonyl-phenyl)-1H-pyrazolo[3,4-d]pyrimidin-4-ylamino]-cyclohexylmethyl}-6-methyl-nicotinamide; 4-[1-(2-Fluoro-4-methanesulfonyl-phenyl)-1H-pyrazolo[3,4-d]pyrimidin-4-yloxy]-piperidine-1-carboxylic acid tert-butyl ester; 4-({[1-(4-Methanesulfonyl-phenyl)-1H-pyrazolo[3,4-d]pyrimidin-4-yl]-methyl-amino}-methyl)-piperidine-1-carboxylic acid tert-butyl ester; 4-{[1-(4-Methanesulfonyl-phenyl)-1H-pyrazolo[3,4-d]pyrimidin-4-ylamino]-methyl}-piperidine-1-carboxylic acid tert-butyl ester; 3-{[1-(4-Methanesulfonyl-phenyl)-1H-pyrazolo[3,4-d]pyrimidin-4-ylamino]-methyl}-piperidine-1-carboxylic acid tert-butyl ester; 4-({Ethyl-[1-(4-methanesulfonyl-phenyl)-1H-pyrazolo[3,4-d]pyrimidin-4-yl]-amino}-methyl)-piperidine-1-carboxylic acid tert-butyl ester; 4-{1-[2-(2-Dimethylamino-ethoxy)-4-methanesulfonyl-phenyl]-1H-pyrazolo[3,4-d]pyrimidin-4-yloxy}-piperidine-1-carboxylic acid tert-butyl ester; 3-[1-(2-Fluoro-4-methanesulfonyl-phenyl)-1H-pyrazolo[3,4-d]pyrimidin-4-ylamino]-piperidine-1-carboxylic acid tert-butyl ester; 4-[1-(4-Methanesulfonyl-phenyl)-1H-pyrazolo[3,4-d]pyrimidin-4-yloxy]-piperidine-1-carboxylic acid pyridin-3-ylmethyl esteracid tert-butyl ester; 4-[1-(4-Methanesulfonyl-phenyl)-1H-pyrazolo[3,4-d]pyrimidin-4-yloxy]-piperidine-1-carboxylic acid 2-pyridin-3-yl-ethyl ester; 4-[1-(4-Methanesulfonyl-phenyl)-1H-pyrazolo[3,4-d]pyrimidin-4-yloxy]-piperidine-1-carboxylic acid 3-pyridin-3-yl-propyl ester; 4-[1-(4-Methanesulfonyl-phenyl)-1H-pyrazolo[3,4-d]pyrimidin-4-yloxy]-piperidine-1-carboxylic acid 2-dimethylamino-ethyl ester; 4-{[1-(4-Methanesulfonyl-phenyl)-1H-pyrazolo[3,4-d]pyrimidin-4-yl]-methyl-amino}-piperidine-1-carboxylic acid tert-butyl ester; 4-[1-(2,4-Difluoro-phenyl)-1H-pyrazolo[3,4-d]pyrimidin-4-yloxy]-piperidine-1-carboxylic acid tert-butyl ester; 4-({Ethyl-[1-(2-fluoro-4-methanesulfonyl-phenyl)-1H-pyrazolo[3,4-d]pyrimidin-4-yl]-amino}-methyl)-piperidine-1-carboxylic acid isopropyl ester; 4-({Ethyl-[1-(2-fluoro-4-methanesulfonyl-phenyl)-1H-pyrazolo[3,4-d]pyrimidin-4-yl]-amino}-methyl)-piperidine-1-carboxylic acid tert-butyl ester; 4-[6-Dimethylamino-1-(4-methanesulfonyl-phenyl)-1H-pyrazolo[3,4-d]pyrimidin-4-yloxy]-piperidine-1-carboxylic acid tert-butyl ester; 1-(4-{[1-(4-Methanesulfonyl-phenyl)-1H-pyrazolo[3,4-d]pyrimidin-4-yl]-methyl-amino}-piperidin-1-yl)-3,3-dimethyl-butan-2-one; 4-{[1-(4-Methanesulfonyl-phenyl)-1H-pyrazolo[3,4-d]pyrimidin-4-yl]-methyl-amino}-piperidine-1-carboxylic acid cyclobutyl ester; and 4-[({1-[4-(2-Methanesulfonyl-ethyl)-phenyl]-1H-pyrazolo[3,4-d]pyrimidin-4-yl}-methyl-amino)-methyl]-piperidine-1-carboxylic acid tert-butyl ester.

Specific examples of GPR119 agonists disclosed in International Application No. PCT/US2004/022417 include the following compounds according to Formula (IV) (referred to herein as Group D2): 4-({[1-(2,5-Difluoro-phenyl)-1H-pyrazolo[3,4-d]pyrimidin-4-yl]-methyl-amino}-methyl)-piperidine-1-carboxylic acid tert-butyl ester; 2-{4-[1-(2-Fluoro-4-methanesulfonyl-phenyl)-1H-pyrazolo[3,4-d]pyrimidin-4-yloxy]-piperidin-1-yl}-1-(4-trifluoromethoxy-phenyl)-ethanone; 2-{4-[1-(2-Fluoro-4-methanesulfonyl-phenyl)-1H-pyrazolo[3,4-d]pyrimidin-4-yloxy]-piperidin-1-yl}-1-(3-fluoro-phenyl)-ethanone; 2-{4-[1-(2-Fluoro-4-methanesulfonyl-phenyl)-1H-pyrazolo[3,4-d]pyrimidin-4-yloxy]-piperidin-1-yl}-1-pyridin-2-yl-ethanone; (2,5-Dimethyl-furan-3-yl)-{4-[1-(4-methanesulfonyl-phenyl)-1H-pyrazolo[3,4-d]pyrimidin-4-yloxy]-piperidin-1-yl}-methanone; 4-({(2-Dimethylamino-ethyl)-[1-(4-methanesulfonyl-phenyl)-1H-pyrazolo[3,4-d]pyrimidin-4- yl]-amino}-methyl)-piperidine-1-carboxylic acid tert-butyl ester; 4-({(2-Dimethylamino-ethyl)-[1-(2-fluoro-4-methanesulfonyl-phenyl)-1H-pyrazolo[3,4-d]pyrimidin-4-yl]-amino}-methyl)-piperidine-1-carboxylic acid tert-butyl ester; 4-[1-(2-Dimethylamino-4-methanesulfonyl-phenyl)-1H-pyrazolo[3,4-d]pyrimidin-4-yloxy]-piperidine-1-carboxylic acid tert-butyl ester; 4-{2-Ethyl-[1-(4-methanesulfonyl-phenyl)-1H-pyrazolo[3,4-d]pyrimidin-4-yl]-amino}-ethyl)-piperazine-1-carboxylic acid tert-butyl ester; 4-[1-(4-Methanesulfonyl-phenyl)-1H-pyrazolo[3,4-d]pyrimidin-4-ylsulfanyl]-piperidine-1-carboxylic acid tert-butyl ester; 4-{2-[1-(4-Methanesulfonyl-phenyl)-1H-pyrazolo[3,4-d]pyrimidin-4-yloxy]-ethyl}-piperazine-1-carboxylic acid ethyl ester; 4-{2-[1-(4-Methanesulfonyl-phenyl)-1H-pyrazolo[3,4-d]pyrimidin-4-yloxy]-propyl}-piperazine-1-carboxylic acid ethyl ester; 4-[1-(4-Methanesulfonyl-phenyl)-1H-pyrazolo[3,4-d]pyrimidine-4-sulfanyl]-piperidine-1-carboxylic acid tert-butyl ester; 4-[1-(4-Methanesulfonyl-phenyl)-1H-pyrazolo[3,4-d]pyrimidine-4-sulfonyl]-piperidine-1-carboxylic acid tert-butyl ester; 4-[1-(2-Fluoro-4-methanesulfonyl-phenyl)-1H-pyrazolo[3,4-d]pyrimidin-4-ylsulfanyl]-piperidine-1-carboxylic acid tert-butyl ester; 4-[1-(2-Fluoro-4-methanesulfonyl-phenyl)-1H-pyrazolo[3,4-d]pyrimidin-4-ylsulfanyl]-piperidine-1-carboxylic acid butyl ester; 4-[1-(2-Fluoro-4-methanesulfonyl-phenyl)-1H-pyrazolo[3,4-d]pyrimidin-4-ylsulfanyl]-piperidine-1-carboxylic acid 2-methoxy-ethyl ester; 4-[1-(2-Fluoro-4-methanesulfonyl-phenyl)-1H-pyrazolo[3,4-d]pyrimidin-4-ylsulfanyl]-piperidine-1-carboxylic acid 3,3-dimethyl-butyl ester; 4-[1-(2-Fluoro-4-methanesulfonyl-phenyl)-1H-pyrazolo[3,4-d]pyrimidin-4-ylsulfanyl]-piperidine-1-carboxylic acid 4-methyl-pentyl ester; 4-[1-(2-Fluoro-4-methanesulfonyl-phenyl)-1H-pyrazolo[3,4-d]pyrimidin-4-ylsulfanyl]-piperidine-1-carboxylic acid cyclopropylmethyl ester; 4-[1-(2-Fluoro-4-methanesulfonyl-phenyl)-1H-pyrazolo[3,4-d]pyrimidin-4-ylsulfanyl]-piperidine-1-carboxylic acid cyclobutylmethyl ester; 4-[1-(2-Fluoro-4-methanesulfonyl-phenyl)-1H-pyrazolo[3,4-d]pyrimidin-4-ylsulfanyl]-piperidine-1-carboxylic acid 2-cyclopropyl-ethyl ester; (5-Bromo-furan-2-yl)-{4-[1-(2-fluoro-4-methanesulfonyl-phenyl)-1H-pyrazolo[3,4-d]pyrimidin-4-ylsulfanyl]-piperidin-1-yl}-methanone; {4-[1-(4-Methanesulfonyl-phenyl)-1H-pyrazolo[3,4-d]pyrimidin-4-yloxy]-piperidin-1-yl}-(5-morpholin-4-ylmethyl-furan-2-yl)-methanone; 4-[1-(4-Methanesulfonyl-phenyl)-1H-pyrazolo[3,4-d]pyrimidin-4-yloxy]-piperidine-1-carboxylic acid pentyl ester; 4-[1-(4-Methanesulfonyl-phenyl)-1H-pyrazolo[3,4-d]pyrimidin-4-yloxy]-piperidine-1-carboxylic acid 1-ethyl-propyl ester; 4-[1-(4-Methanesulfonyl-phenyl)-1H-pyrazolo[3,4-d]pyrimidin-4-yloxy]-piperidine-1-carboxylic acid 2-ethyl-butyl ester; 4-[1-(4-Methanesulfonyl-phenyl)-1H-pyrazolo[3,4-d]pyrimidin-4-yloxy]-piperidine-1-carboxylic acid cyclopentylmethyl ester; 4-[1-(4-Methanesulfonyl-phenyl)-1H-pyrazolo[3,4-d]pyrimidin-4-yloxy]-piperidine-1-carboxylic acid 2-pyrrolidin-1-yl-ethyl ester; 4-[1-(4-Methanesulfonyl-phenyl)-1H-pyrazolo[3,4-d]pyrimidin-4-yloxy]-piperidine-1-carboxylic acid 2-morpholin-4-ylethyl ester; 4-[1-(4-Methanesulfonyl-phenyl)-1H-pyrazolo[3,4-d]pyrimidin-4-yloxy]-piperidine-1-carboxylic acid ethyl ester; 4-[1-(4-Methanesulfonyl-phenyl)-1H-pyrazolo[3,4-d]pyrimidin-4-yloxy]-piperidine-1-carboxylic acid 2,2-dimethyl-propyl ester; (5-Butyl-pyridin-2-yl)-{4-[1-(4-methanesulfonyl-phenyl)-1H-pyrazolo[3,4-d]pyrimidin-4-yloxy]-piperidin-1-yl}-methanone; Ethyl-[1-(2-fluoro-4-methanesulfonyl-phenyl)-1H-pyrazolo[3,4-d]pyrimidin-4-yl]-(3,4,5,6-tetrahydro-2H-[1,2]bipyridinyl-4-ylmethyl)-amine; Ethyl-[1-(2-fluoro-4-methanesulfonyl-phenyl)-1H-pyrazolo[3,4-d]pyrimidin-4-yl]-(5'-trifluoromethyl-3,4,5,6-tetrahydro-2H-[1,2']bipyridinyl-4-ylmethyl)-amine; [1-(4-Methanesulfonyl-phenyl)-1H-pyrazolo[3,4-d]pyrimidin-4-yl]-(5'-trifluoromethyl-3,4,5,6-tetrahydro-2H-[1,2'] bipyridinyl-4-yl)-amine; 4-[1-(2-Fluoro-4-methanesulfonyl-phenyl)-1H-pyrazolo[3,4-d]pyrimidin-4-yloxy]-piperidine-1-carboxylic acid isopropyl ester; 5'-Fluoro-4-[1-(4-methanesulfonyl-phenyl)-1H-pyrazolo[3,4-d]pyrimidin-4-yloxy]-3,4,5,6-tetrahydro-2H-[1,2']bipyridinyl; 4-[1-(4-Methanesulfonyl-phenyl)-1H-pyrazolo[3,4-d]pyrimidin-4-yloxy]-5'-methyl-3,4,5,6-tetrahydro-2H-[1,2']bipyridinyl; 4-[1-(4-methanesulfonyl-phenyl)-1H-pyrazolo[3,4-d]pyrimidin-4-yloxy]-6'-trifluoromethyl-3,4,5,6-tetrahydro-2H-[1,2']bipyridinyl; [1-(2-Fluoro-4-methanesulfonyl-phenyl)-1H-pyrazolo[3,4-d]pyrimidin-4-yl]-[1-(3-isopropyl-[1,2,4]oxadiazol-5-ylmethyl)-pyrrolidin-3-yl]-amine; [1-(2-Fluoro-4-methanesulfonyl-phenyl)-1H-pyrazolo[3,4-d]pyrimidin-4-yl]-[1-(3-isopropyl-[1,2,4]oxadiazol-5-ylmethyl)-pyrrolidin-3-yl]-amine; (4-Ethyl-pyridin-2-yl)-{4-[1-(2-fluoro-4-methanesulfonyl-phenyl)-1H-pyrazolo[3,4-d]pyrimidin-4-yloxy]-piperidin-1-yl}-methanone; 1-(2-Fluoro-4-methanesulfonyl-phenyl)-4-[1-(3-isopropyl-[1,2,4]oxadiazol-5-ylmethyl)-pyrrolidin-3-yloxy]-1H-pyrazolo[3,4-d]pyrimidine; 1-(2-Fluoro-4-methanesulfonyl-phenyl)-4-[1-(3-isopropyl-[1,2,4]oxadiazol-5-ylmethyl)-piperidin-4-yloxy]-1H-pyrazolo[3,4-d]pyrimidine; (5'-Fluoro-3,4,5,6-tetrahydro-2H-[1,2']bipyridinyl-4-yl)-[1-(4-methanesulfonyl-phenyl)-1H-pyrazolo[3,4-d]pyrimidin-4-yl]-amine; (5-Bromo-pyridin-3-yl)-{4-[1-(2-fluoro-4-methanesulfonyl-phenyl)-1H-pyrazolo[3,4-d]pyrimidin-4-yloxy]-piperidin-1-yl}-methanone; 3-[1-(2-Fluoro-4-methanesulfonyl-phenyl)-1H-pyrazolo[3,4-d]pyrimidin-4-yloxy]-pyrrolidine-1-carboxylic acid tert-butyl ester; 3-[1-(4-Methanesulfonyl-phenyl)-1H-pyrazolo[3,4-d]pyrimidin-4-ylamino]-pyrrolidine-1-carboxylic acid tert-butyl ester; 3-[1-(2-Fluoro-4-methanesulfonyl-phenyl)-1H-pyrazolo[3,4-d]pyrimidin-4-ylamino]-pyrrolidine-1-carboxylic acid isopropyl ester; (6-Chloro-pyridin-3-yl)-{4-[1-(4-methanesulfonyl-phenyl)-1H-pyrazolo[3,4-d]pyrimidin-4-yloxy]-piperidin-1-yl}-methanone; (5-Chloro-pyridin-3-yl)-{4-[1-(4-methanesulfonyl-phenyl)-1H-pyrazolo[3,4-d]pyrimidin-4-yloxy]-piperidin-1-yl}-methanone; {4-[1-(4-Methanesulfonyl-phenyl)-1H-pyrazolo[3,4-d]pyrimidin-4-yloxy]-piperidin-1-yl}-(1-methyl-3-trifluoromethyl-1H-pyrazol-4-yl)-methanone; (2-Chloro-pyridin-4-yl)-{4-[1-(4-methanesulfonyl-phenyl)-1H-pyrazolo[3,4-d]pyrimidin-4-yloxy]-piperidin-1-yl}-methanone; (4-Hydroxy-3-methoxy-phenyl)-{4-[1-(4-methanesulfonyl-phenyl)-1H-pyrazolo[3,4-d]pyrimidin-4-yloxy]-piperidin-1-yl}-methanone; (4-Chloro-3-nitro-phenyl)-{4-[1-(4-methanesulfonyl-phenyl)-1H-pyrazolo[3,4-d]pyrimidin-4-yloxy]-piperidin-1-yl}-methanone; 1-{4-[1-(4-Methanesulfonyl-phenyl)-1H-pyrazolo[3,4-d]pyrimidin-4-yloxy]-piperidin-1-yl}-3-methyl-butan-1-one; {4-[1-(4-Methanesulfonyl-phenyl)-1H-pyrazolo[3,4-d]pyrimidin-4-yloxy]-piperidin-1-yl}-(6-pyrazol-1-yl-pyridin-3-yl)-methanone; (2-Hydroxy-pyridin-3-yl)-{4-[1-(4-methanesulfonyl-phenyl)-1H-pyrazolo[3,4-d]pyrimidin-4-yloxy]-piperidin-1-yl}-methanone; (5,6-Dichloro-pyridin-3-yl)-{4-[1-(4-methanesulfonyl-phenyl)-1H-pyrazolo[3,4-d]pyrimidin-4-yloxy]-piperidin-1-yl}-methanone; (5-Bromo-pyridin-3-yl)-{4-[1-(4-methanesulfonyl-phenyl)-1H-pyrazolo[3,4-d]pyrimidin-4-yloxy]-piperidin-1-yl}-methanone; 5-{4-[1-(4-Methanesulfonyl-phenyl)-1H-pyrazolo[3,4-d]pyrimidin-4-yloxy]-piperidine-1-carbonyl}-nicotinic acid; (1H-Imidazol-4-yl)-{4-[1-(4-methanesulfonyl-phenyl)-1H-pyrazolo[3,4-d]pyrimidin-4-yloxy]-piperidin-1-yl}-methanone; 3-[1-(4-

Methanesulfonyl-phenyl)-1H-pyrazolo[3,4-d]pyrimidin-4-yloxy]-pyrrolidine-1-carboxylic acid tert-butyl ester; {4-[1-(4-Methanesulfonyl-phenyl)-1H-pyrazolo[3,4-d]pyrimidin-4-yloxy]-piperidin-1-yl}-(6-pyrrolidin-1-yl-pyridin-3-yl)-methanone; (6-Isobutylamino-pyridin-3-yl)-{4-[1-(4-methanesulfonyl-phenyl)-1H-pyrazolo[3,4-d]pyrimidin-4-yloxy]-piperidin-1-yl}-methanone; (6-Ethylamino-pyridin-3-yl)-{4-[1-(4-methanesulfonyl-phenyl)-1H-pyrazolo[3,4-d]pyrimidin-4-yloxy]-piperidin-1-yl}-methanone; (6-Cyclobutylamino-pyridin-3-yl)-{4-[1-(4-methanesulfonyl-phenyl)-1H-pyrazolo[3,4-d]pyrimidin-4-yloxy]-piperidin-1-yl}-methanone; (6-Isopropylamino-pyridin-3-yl)-{4-[1-(4-methanesulfonyl-phenyl)-1H-pyrazolo[3,4-d]pyrimidin-4-yloxy]-piperidin-1-yl}-methanone; [6-(1-Ethyl-propylamino)-pyridin-3-yl]-{4-[1-(4-methanesulfonyl-phenyl)-1H-pyrazolo[3,4-d]pyrimidin-4-yloxy]-piperidin-1-yl}-methanone; {4-[1-(4-Methanesulfonyl-phenyl)-1H-pyrazolo[3,4-d]pyrimidin-4-yloxy]-piperidin-1-yl}-[6-(1-propyl-butylamino)-pyridin-3-yl]-methanone; 5-Benzyloxy-2-{4-[1-(4-methanesulfonyl-phenyl)-1H-pyrazolo[3,4-d]pyrimidin-4-yloxy]-piperidine-1-carbonyl}-pyran-4-one; Benzo[c]isoxazol-3-yl-{4-[1-(4-methanesulfonyl-phenyl)-1H-pyrazolo[3,4-d]pyrimidin-4-yloxy]-piperidin-1-yl}-methanone; (4-Chloro-pyridin-2-yl)-{4-[1-(1-(4-methanesulfonyl-phenyl)-1H-pyrazolo[3,4-d]pyrimidin-4-yloxy]-piperidin-1-yl}-methanone; (4-Iodo-pyridimin-2-yl)-{4-[1-(4-methanesulfonyl-phenyl)-1H-pyrazolo[3,4-d]pyrimidin-4-yloxy]-piperidin-1-yl}-methanone; 1-{4-[1-(4-Methanesulfonyl-phenyl)-1H-pyrazolo[3,4-d]pyrimidin-4-yloxy]-piperidin-1-yl}-butan-2-one; 2-(5-Bromo-pyridin-3-yl)-1-{4-[1-(4-methanesulfonyl-phenyl)-1H-pyrazolo[3,4-d]pyrimidin-4-yloxy]-piperidin-1-yl}-ethanone; (6-Fluoro-pyridin-2-yl)-{4-[1-(4-methanesulfonyl-phenyl)-1H-pyrazolo[3,4-d]pyrimidin-4-yloxy]-piperidin-1-yl}-methanone; (5-Fluoro-pyridin-2-yl)-{4-[1-(4-methanesulfonyl-phenyl)-1H-pyrazolo[3,4-d]pyrimidin-4-yloxy]-piperidin-1-yl}-methanone; (6-Chloro-pyridin-2-yl)-{4-[1-(4-methanesulfonyl-phenyl)-1H-pyrazolo[3,4-d]pyrimidin-4-yloxy]-piperidin-1-yl}-methanone; (2-Chloro-5-fluoro-pyridin-3-yl)-{4-[1-(4-methanesulfonyl-phenyl)-1H-pyrazolo[3,4-d]pyrimidin-4-yloxy]-piperidin-1-yl}-methanone; {4-[1-(4-Methanesulfonyl-phenyl)-1H-pyrazolo[3,4-d]pyrimidin-4-yloxy]-piperidin-1-yl}-[5-(2-methyl-pyrrolidin-1-ylmethyl)-pyridin-3-yl]-methanone; {4-[1-(4-Methanesulfonyl-phenyl)-1H-pyrazolo[3,4-d]pyrimidin-4-yloxy]-piperidin-1-yl}-(6-methyl-pyridin-2-yl)-methanone; 5-{4-[1-(4-Methanesulfonyl-phenyl)-1H-pyrazolo[3,4-d]pyrimidin-4-yloxy]-piperidine-1-carbonyl}-nicotinonitrile; {4-[1-(4-Methanesulfonyl-phenyl)-1H-pyrazolo[3,4-d]pyrimidin-4-yloxy]-piperidin-1-yl}-(4-methoxy-pyridin-2-yl)-methanone; (2-Fluoro-pyridin-4-yl)-{4-[1-(4-methanesulfonyl-phenyl)-1H-pyrazolo[3,4-d]pyrimidin-4-yloxy]-piperidin-1-yl}-methanone; (2-Fluoro-pyridin-3-yl)-{4-[1-(4-methanesulfonyl-phenyl)-1H-pyrazolo[3,4-d]pyrimidin-4-yloxy]-piperidin-1-yl}-methanone; (6-Fluoro-pyridin-3-yl)-{4-[1-(4-methanesulfonyl-phenyl)-1H-pyrazolo[3,4-d]pyrimidin-4-yloxy]-piperidin-1-yl}-methanone; {4-[1-(4-Methanesulfonyl-phenyl)-1H-pyrazolo[3,4-d]pyrimidin-4-yloxy]-piperidin-1-yl}-(4-methoxy-thiophen-3-yl)-methanone; 2-{4-[1-(4-Methanesulfonyl-phenyl)-1H-pyrazolo[3,4-d]pyrimidin-4-yloxy]-piperidine-1-carbonyl}-pyran-4-one; (5-Ethyl-pyridin-2-yl)-{4-[1-(2-fluoro-4-methanesulfonyl-phenyl)-1H-pyrazolo[3,4-d]pyrimidin-4-yloxy]-piperidin-1-yl}-methanone; (4-Ethoxy-phenyl)-{4-[1-(2-fluoro-4-methanesulfonyl-phenyl)-1H-pyrazolo[3,4-d]pyrimidin-4-yloxy]-piperidin-1-yl}-methanone; {4-[1-(4-Methanesulfonyl-phenyl)-1H-pyrazolo[3,4-d]pyrimidin-4-yloxy]-piperidin-1-yl}-(5-pyridin-2-yl-thiophen-2-yl)-methanone; (5-Amino-pyridin-2-yl)-{4-[1-(4-methanesulfonyl-phenyl)-1H-pyrazolo[3,4-d]pyrimidin-4-yloxy]-piperidin-1-yl}-methanone; (5-Amino-pyridin-2-yl)-{4-[1-(2-fluoro-4-methanesulfonyl-phenyl)-1H-pyrazolo[3,4-d]pyrimidin-4-yloxy]-piperidin-1-yl})-methanone; {4-[1-(2-Fluoro-4-methanesulfonyl-phenyl)-1H-pyrazolo[3,4-d]pyrimidin-4-yloxy]-piperidin-1-yl}-[5-(3-methyl-butylamino)-pyridin-2-yl]-methanone; {4-[1-(2-Fluoro-4-methanesulfonyl-phenyl)-1H-pyrazolo[3,4-d]pyrimidin-4-yloxy]-piperidin-1-yl}-(4-trifluoromethoxy-phenyl)-methanone; (5-Butyl-pyridin-2-yl)-{4-[1-(2-fluoro-4-methanesulfonyl-phenyl)-1H-pyrazolo[3,4-d]pyrimidin-4-yloxy]-piperidin-1-yl}-methanone; (5-Ethylamino-pyridin-2-yl)-{4-[1-(2-fluoro-4-methanesulfonyl-phenyl)-1H-pyrazolo[3,4-d]pyrimidin-4-yloxy]-piperidin-1-yl}-methanone; {4-[1-(2-Fluoro-4-methanesulfonyl-phenyl)-1H-pyrazolo[3,4-d]pyrimidin-4-yloxy]-piperidin-1-yl}-(5-isopropoxymethyl-pyridin-2-yl)-methanone; (4-Difluoromethoxy-phenyl)-{4-[1-(2-fluoro-4-methanesulfonyl-phenyl)-1H-pyrazolo[3,4-d]pyrimidin-4-yloxy]-piperidin-1-yl}-methanone; {4-[1-(2-Fluoro-4-methanesulfonyl-phenyl)-1H-pyrazolo[3,4-d]pyrimidin-4-yloxy]-piperidin-1-yl}-(5-isopropoxy-pyridin-2-yl)-methanone; 5-{4-[1-(4-Methanesulfonyl-phenyl)-1H-pyrazolo[3,4-d]pyrimidin-4-yloxy]-piperidine-1-carbonyl}-pyridine-2-carboxylic acid methyl ester; {4-[1-(4-Methanesulfonyl-phenyl)-1H-pyrazolo[3,4-d]pyrimidin-4-yloxy]-piperidin-1-yl}-acetic acid ethyl ester; {4-[1-(2-Fluoro-4-methanesulfonyl-phenyl)-1H-pyrazolo[3,4-d]pyrimidin-4-yloxy]-piperidin-1-yl}-(3-trifluoromethoxy-phenyl)-methanone; 1-(2-Fluoro-4-methanesulfonyl-phenyl)-4-[1-(3-isopropyl-[1,2,4]oxadiazol-5-yl)-piperidin-4-yloxy]-1H-pyrazolo[3,4-d]pyrimidine; 1-(4-Chloro-phenyl)-2-{4-[1-(4-methanesulfonyl-phenyl)-1H-pyrazolo[3,4-d]pyrimidin-4-yloxy]-piperidin-1-yl}-ethanone; 2-{4-[1-(4-Methanesulfonyl-phenyl)-1H-pyrazolo[3,4-d]pyrimidin-4-yloxy]-piperidin-1-yl}-1-(3-trifluoromethyl-phenyl)-ethanone; 4-[1-(2-Fluoro-4-methanesulfonyl-phenyl)-1H-pyrazolo[3,4-d]pyrimidin-4-yloxy]-5'-isopropoxy-3,4,5,6-tetrahydro-2H-[1,2']bipyridinyl; 1-(4-Methanesulfonyl-phenyl)-4-[1-(4-trifluoromethoxy-phenyl)-piperidin-4-yloxy]-1H-pyrazolo[3,4-d]pyrimidine; 1-(2-Fluoro-4-methanesulfonyl-phenyl)-4-[1-(4-trifluoromethoxy-phenyl)-piperidin-4-yloxy]-1H-pyrazolo[3,4-d]pyrimidine; 1-(4-Chloro-3-methyl-phenyl)-2-{4-[1-(4-methanesulfonyl-phenyl)-1H-pyrazolo[3,4-d]pyrimidin-4-yloxy]-piperidin-1-yl}-ethanone; 1-(3,4-Dichloro-phenyl)-2-{4-[1-(4-methanesulfonyl-phenyl)-1H-pyrazolo[3,4-d]pyrimidin-4-yloxy]-piperidin-1-yl}-ethanone; 5'-Bromo-4-[1-(4-methanesulfonyl-phenyl)-1H-pyrazolo[3,4-d]pyrimidin-4-yloxy]-3,4,5,6-tetrahydro-2H-[1,2']bipyridinyl; 1-(2-Fluoro-4-methanesulfonyl-phenyl)-4-[1-(3-trifluoromethoxy-phenyl)-piperidin-4-yloxy]-1H-pyrazolo[3,4-d]pyrimidine; 4-[1-(4-Methanesulfonyl-phenyl)-1H-pyrazolo[3,4-d]pyrimidin-4-yloxy]-5'-trifluoromethyl-3,4,5,6-tetrahydro-2H-[1,2']bipyridinyl; 1-(2,4-Dimethoxy-phenyl)-2-{4-[1-(4-methanesulfonyl-phenyl)-1H-pyrazolo[3,4-d]pyrimidin-4-yloxy]-piperidin-1-yl}-ethanone; 1-(4-Difluoromethoxy-phenyl)-2-{4-[1-(4-methanesulfonyl-phenyl)-1H-pyrazolo[3,4-d]pyrimidin-4-yloxy]-piperidin-1-yl}-ethanone; 1-(4-Diethylamino-phenyl)-2-{4-[1-(4-methanesulfonyl-phenyl)-1H-pyrazolo[3,4-d]pyrimidin-4-yloxy]-piperidin-1-yl}-ethanone; (2-{4-[1-(2-Fluoro-4-methanesulfonyl-phenyl)-1H-pyrazolo[3,4-d]pyrimidin-4-yloxy]-piperidin-1-yl}-5-methyl-pyrimidin-4-yl)-dimethyl-amine; 1-(2-Fluoro- 4-methanesulfonyl-phenyl)-4-[1-(5-methyl-4-pyrrolidin-1-yl-pyrimidin-2-yl)-piperidin-4-yloxy]-1H-pyrazolo[3,4-d]pyrimidine; 4-[1-(2-Fluoro-4-methanesulfonyl-phenyl)-1H-pyrazolo[3,4-d]pyrimidin-4-ylsulfanyl]-piperidine-1-carboxylic acid isopropyl ester; 4-[1-(2-Methyl-4-propylamino-phenyl)-1H-pyrazolo[3,4-d]pyrimidin-4-yloxy]-piperidine-1-carboxylic acid isopropyl ester; 4-[1-(4-Isopropylamino-2-methyl-phenyl)-1H-pyrazolo[3,4-d]pyrimidin-4-yloxy]-piperidine-1-carboxylic acid isopropyl ester; 4-[1-(2-Methyl-4-morpholin-4-yl-phenyl)-1H-pyrazolo[3,4-d]pyrimidin-4-yloxy]-piperidine-1-carboxylic acid isopropyl ester; 4-{1-[4-(2-Methoxy-ethylamino)-2-methyl-phenyl]-1H-pyrazolo[3,4-d]pyrimidin-4-yloxy}-piperidine-1-carboxylic acid isopropyl ester; 4-(1-{4-[(2-Methanesulfonyl-ethyl)-methyl-amino]-2-methyl-phenyl}-1H-pyrazolo[3,4-d]pyrimidin-4-yloxy)-piperidine-1-carboxylic acid isopropyl ester; 4-[1-(4-Bromo-phenyl)-1H-pyrazolo[3,4-d]pyrimidin-4-yloxy]-piperidine-1-carboxylic acid isopropyl ester; 4-[1-(4-Propylamino-phenyl)-1H-pyrazolo[3,4-d]pyrimidin-4-yloxy]-piperidine-1-carboxylic acid isopropyl ester; 4-[1-(4-Isopropylamino-phenyl)-1H-pyrazolo[3,4-d]pyrimidin-4-yloxy]-piperidine-1-carboxylic acid isopropyl ester; 4-(1-{4-[4-(2-Methanesulfonyl-ethyl)-piperazin-1-yl]-2-methyl-phenyl}-1H-pyrazolo[3,4-d]pyrimidin-4-yloxy}-piperidine-1-carboxylic acid isopropyl ester; 4-(1-{2-Methyl-4-[(tetrahydro-furan-2-ylmethyl)-amino]-phenyl}-1H-pyrazolo[3,4-d]pyrimidin-4-yloxy)-piperidine-1-carboxylic acid isopropyl ester; 4-[1-(4-Cyclopropylamino-2-methyl-phenyl)-1H-pyrazolo[3,4-d]pyrimidin-4-yloxy]-piperidine-1-carboxylic acid isopropyl ester; 4-{-[4-(2-Dimethylamino-ethylamino)-2-methyl-phenyl]-1H-pyrazolo[3,4-d]pyrimidin-4-yloxy}-piperidine-1-carboxylic acid isopropyl ester; 4-[1-(4-Morpholin-4-yl-phenyl)-1H-pyrazolo[3,4-d]pyrimidin-4-yloxy]-piperidine-1-carboxylic acid isopropyl ester; 4-({[1-(2-Fluoro-4-methanesulfonyl-phenyl)-1H-pyrazolo[3,4-d]pyrimidin-4-yl]-isopropyl-amino}-methyl)-piperidine-1-carboxylic acid tert-butyl ester; 4-[1-(2-Fluoro-4-morpholin-4-yl-phenyl)-1H-pyrazolo[3,4-d]pyrimidin-4-yloxy]-piperidine-1-carboxylic acid isopropyl ester; 4-[1-(2-Fluoro-4-isopropylamino-phenyl)-1H-pyrazolo[3,4-d]pyrimidin-4-yloxy]-piperidine-1-carboxylic acid isopropyl ester; 4-(1-{4-[(2-Methanesulfonyl-ethyl)-methyl-amino]-phenyl}-1H-pyrazolo[3,4-d]pyrimidin-4-yloxy)-piperidine-1-carboxylic acid isopropyl ester; 4-{1-[4-(2-Methoxy-ethylamino)-phenyl]-1H-pyrazolo[3,4-d]pyrimidin-4-yloxy}-piperidine-1-carboxylic acid isopropyl ester; 4-(1-{4-[(Tetrahydro-furan-2-ylmethyl)-amino]-phenyl}-1H-pyrazolo[3,4-d]pyrimidin-4-yloxy)-piperidine-1-carboxylic acid isopropyl ester; 4-(1-{4-[4-(2-Methanesulfonyl-ethyl)-piperazin-1-yl]-phenyl}-1H-pyrazolo[3,4-d]pyrimidin-4-yloxy)-piperidine-1-carboxylic acid isopropyl ester; 4-[1-(4-Amino-phenyl)-1H-pyrazolo[3,4-d]pyrimidin-4-yloxy]-piperidine-1-carboxylic acid isopropyl ester; 4-({[1-(2-Fluoro-4-methanesulfonyl-phenyl)-1H-pyrazolo[3,4-d]pyrimidin-4-yl]-isopropyl-amino}-methyl)-piperidine-1-carboxylic acid isopropyl ester; 4-[1-(5-Ethyl-pyrimidin-2-yl)-piperidin-4-ylsulfanyl]-1-(2-fluoro-4-methanesulfonyl-phenyl)-1H-pyrazolo[3,4-d]pyrimidine; 4-[1-(2-Fluoro-4-sulfamoyl-phenyl)-1H-pyrazolo[3,4-d]pyrimidin-4-yloxy]-piperidine-1-carboxylic acid isopropyl ester; 4-[1-(2-Fluoro-4-propionylsulfamoyl-phenyl)-1H-pyrazolo[3,4-d]pyrimidin-4-yloxy]-piperidine-1-carboxylic acid isopropyl ester; 4-[1-(4-Cyano-2-fluoro-phenyl)-1H-pyrazolo[3,4-d]pyrimidin-4-yloxy]-piperidine-1-carboxylic acid isopropyl ester; 1-(2,5-Difluoro-4-methoxy-phenyl)-4-[4-(3-isopropyl-[1,2,4]oxadiazol-5-yl)-cyclohexyloxy]-1H-pyrazolo[3,4-d]pyrimidine; 4-[1-(2,5-Difluoro-4-methanesulfonyl-phenyl)-1H-pyrazolo[3,4-d]pyrimidin-4-yloxy]-piperidine-1-carboxylic acid isopropyl ester; 4-[1-(4-Fluoro-6-methoxy-pyridin-3-yl)-1H-pyrazolo[3,4-d]pyrimidin-4-yloxy]-piperidine-1-carboxylic acid isopropyl ester; 4-[1-(6-Methoxy-2-methyl-pyridin-3-yl)-1H-pyrazolo[3,4-d]pyrimidin-4-yloxy]-piperidine-1-carboxylic acid isopropyl ester; 4-[1-(2,5-Difluoro-4-sulfamoyl-phenyl)-1H-pyrazolo[3,4-d]pyrimidin-4-yloxy]-piperidine-1-carboxylic acid isopropyl ester; 4-[1-(2-Fluoro-4-hydroxy-phenyl)-1H-pyrazolo[3,4-d]pyrimidin-4-yloxy]-piperidine-1-carboxylic acid isopropyl ester; 3-Fluoro-4-{4-[1-(3-isopropyl-[1,2,4]oxadiazol-5-yl)-piperidin-4-yloxy]-pyrazolo[3,4-d]pyrimidin-1-yl}-N-propionyl-benzenesulfonamide; 3-Fluoro-4-{4-[1-(3-isopropyl-[1,2,4]oxadiazol-5-yl)-piperidin-4-yloxy]-pyrazolo[3,4-d]pyrimidin-1-yl}-benzonitrile; 3-Fluoro-4-{4-[1-(3-isopropyl-[1,2,4]oxadiazol-5-yl)-piperidin-4-yloxy]-pyrazolo[3,4-d]pyrimidin-1-yl}-benzenesulfonamide; 1-(2,5-Difluoro-4-methanesulfonyl-phenyl)-4-[1-(3-isopropyl-[1,2,4]oxadiazol-5-yl)-piperidin-4-yloxy]-1H-pyrazolo[3,4-d]pyrimidine; 1-(4-Fluoro-6-methoxy-pyridin-3-yl)-4-[1-(3-isopropyl-[1,2,4]oxadiazol-5-yl)-piperidin-4-yloxy]-1H-pyrazolo[3,4-d]pyrimidine; 4-[1-(3-Isopropyl-[1,2,4]oxadiazol-5-yl)-piperidin-4-yloxy]-1-(6-methoxy-2-methyl-pyridin-3-yl)-1H-pyrazolo[3,4-d]pyrimidine; 2,5-Difluoro-4-{4-[1-(3-isopropyl-[1,2,4]oxadiazol-5-yl)-piperidin-4-yloxy]-pyrazolo[3,4-d]pyrimidin-1-yl}-benzenesulfonamide; 1-(2-Fluoro-4-methanesulfonyl-phenyl)-4-[4-(3-isopropyl-[1,2,4]oxadiazol-5-yl)-cyclohexyloxy]-1H-pyrazolo[3,4-d]pyrimidine; 3-Fluoro-4-{4-[4-(3-isopropyl-[1,2,4]oxadiazol-5-yl)-cyclohexyloxy]-pyrazolo[3,4-d]pyrimidin-1-yl}-N-propionyl-benzenesulfonamide; 3-Fluoro-4-{4-[4-(3-isopropyl-[1,2,4]oxadiazol-5-yl)-cyclohexyloxy]-pyrazolo[3,4-d]pyrimidin-1-yl}-benzonitrile; 3-Fluoro-4-{4-[4-(3-isopropyl-[1,2,4]oxadiazol-5-yl)-cyclohexyloxy]-pyrazolo[3,4-d]pyrimidin-1-yl}-benzenesulfonamide; 1-(2,5-Difluoro-4-methanesulfonyl-phenyl)-4-[4-(3-isopropyl-[1,2,4]oxadiazol-5-yl)-cyclohexyloxy]-1H-pyrazolo[3,4-d]pyrimidine; 1-(4-Fluoro-6-methoxy-pyridin-3-yl)-4-[4-(3-isopropyl-[1,2,4]oxadiazol-5-yl)-cyclohexyloxy]-1H-pyrazolo[3,4-d]pyrimidine; 4-[4-(3-Isopropyl-[1,2,4]oxadiazol-5-yl)-cyclohexyloxy]-1-(6-methoxy-2-methyl-pyridin-3-yl)-1H-pyrazolo[3,4-d]pyrimidine; 2,5-Difluoro-4-{4-[4-(3-isopropyl-[1,2,4]oxadiazol-5-yl)-cyclohexyloxy]-pyrazolo[3,4-d]pyrimidin-1-yl}-benzenesulfonamide; 4-[1-(2-Fluoro-4-methoxy-phenyl)-1H-pyrazolo[3,4-d]pyrimidin-4-yloxy]-piperidine-1-carboxylic acid isopropyl ester; 4-[1-(4-Difluoromethoxy-2-fluoro-phenyl)-1H-pyrazolo[3,4-d]pyrimidin-4-yloxy]-piperidine-1-carboxylic acid isopropyl ester; 4-[1-(2-Fluoro-4-trifluoromethoxy-phenyl)-1H-pyrazolo[3,4-d]pyrimidin-4-yloxy]-piperidine-1-carboxylic acid isopropyl ester; 4-[1-(2,5-Difluoro-4-methoxy-phenyl)-1H-pyrazolo[3,4-d]pyrimidin-4-yloxy]-piperidine-1-carboxylic acid isopropyl ester; 3-Fluoro-4-{4-[1-(3-isopropyl-[1,2,4]oxadiazol-5-yl)-piperidin-4-yloxy]-pyrazolo[3,4-d]pyrimidin-1-yl}-phenol; 1-(2-Fluoro-4-methoxy-phenyl)-4-[1-(3-isopropyl-[1,2,4]oxadiazol-5-yl)-piperidin-4-yloxy]-1H-pyrazolo[3,4-d]pyrimidine; 1-(4-Difluoromethoxy-2-fluoro-phenyl)-4-[1-(3-isopropyl-[1,2,4]oxadiazol-5-yl)-piperidin-4-yloxy]-1H-pyrazolo[3,4-d]pyrimidine; 1-(2-Fluoro-4-trifluoromethoxy-phenyl)-4-[1-(3-isopropyl-[1,2,4]oxadiazol-5-yl)-piperidin-4-yloxy]-1H-pyrazolo[3,4-d]pyrimidine; 1-(2,5-Difluoro-4-methoxy-phenyl)-4-[1-(3-isopropyl-[1,2,4]oxadiazol-5-yl)-piperidin-4-yloxy]-1H-pyrazolo[3,4-d]pyrimidine; 3-Fluoro-4-{4-[4-(3-isopropyl-

[1,2,4]oxadiazol-5-yl}-cyclohexyloxy]-pyrazolo[3,4-d]pyrimidin-1-yl)-phenol; 1-(2-Fluoro-4-methoxy-phenyl)-4-[4-(3-isopropyl-[1,2,4]oxadiazol-5-yl)-cyclohexyloxy]-1H-pyrazolo[3,4-d]pyrimidine; 1-(4-Difluoromethoxy-2-fluorophenyl)-4-[4-(3-isopropyl-[1,2,4]oxadiazol-5-yl)-cyclohexyloxy]-1H-pyrazolo[3,4-d]pyrimidine; and 1-(2-Fluoro-4-trifluoromethoxy-phenyl)-4-[4-(3-isopropyl-[1,2,4]oxadiazol-5-yl)-cyclohexyloxy]-1H-pyrazolo[3,4-d]pyrimidine.

Specific examples of GPR119 agonists disclosed in International Application No. PCT/US2004/022417 include the following compounds according to Formula (IV) (referred to herein as Group D3): 4-[9-(6-Methanesulfonyl-pyridin-3-yl)-9H-purin-6-yloxy]-piperidine-1-carboxylic acid isobutyl ester; {4-[9-(6-Methanesulfonyl-pyridin-3-yl)-9H-purin-6-yloxy]-piperidin-1-yl}-pyridin-3-yl-methanone; 4-[9-(4-Methanesulfonyl-phenyl)-9H-purin-6-yloxy]-piperidine-1-carboxylic acid tert-butyl ester; 4-[9-(6-Methanesulfonyl-pyridin-3-yl)-9H-purin-6-yloxy]-piperidine-1-carboxylic acid tert-butyl ester and 4-[9-(2-Fluoro-4-methanesulfonyl-phenyl)-9H-purin-6-yloxy]-piperidine-1-carboxylic acid tert-butyl ester.

Specific examples of GPR119 agonists disclosed in International Application No. PCT/US2004/022417 include the following compounds according to Formula (IV) (referred to herein as Group D4): 4-[9-(2-Fluoro-4-propionylsulfamoyl-phenyl)-9H-purin-6-yloxy]-piperidine-1-carboxylic acid isopropyl ester; 4-[9-(4-Cyano-2-fluoro-phenyl)-9H-purin-6-yloxy]-piperidine-1-carboxylic acid isopropyl ester; 4-[9-(2-Fluoro-4-sulfamoyl-phenyl)-9H-purin-6-yloxy]-piperidine-1-carboxylic acid isopropyl ester; 9-(2-Fluoro-4-methanesulfonyl-phenyl)-6-[1-(3-isopropyl-[1,2,4]oxadiazol-5-yl)-piperidin-4-yloxy]-9H-purine; 3-Fluoro-4-{6-[1-(3-isopropyl-[1,2,4]oxadiazol-5-yl)-piperidin-4-yloxy]-purin-9-yl}-N-propionyl-benzenesulfonamide; 3-Fluoro-4-(6-[1-(3-isopropyl-[1,2,4]oxadiazol-5-yl)-piperidin-4-yloxy]-purin-9-yl)-benzonitrile; 3-Fluoro-4-{6-[1-(3-isopropyl-[1,2,4]oxadiazol-5-yl)-piperidin-4-yloxy]-purin-9-yl}-benzenesulfonamide; 4-[9-(2,5-Difluoro-4-methanesulfonyl-phenyl)-9H-purin-6-yloxy]-piperidine-1-carboxylic acid isopropyl ester; 4-[9-(4-Fluoro-6-methoxy-pyridin-3-yl)-9H-purin-6-yloxy]-piperidine-1-carboxylic acid isopropyl ester; 4-[9-(6-Methoxy-2-methyl-pyridin-3-yl)-9H-purin-6-yloxy]-piperidine-1-carboxylic acid isopropyl ester; 4-[9-(2,5-Difluoro-4-sulfamoyl-phenyl)-9H-purin-6-yloxy]-piperidine-1-carboxylic acid isopropyl ester; 9-(2,5-Difluoro-4-methanesulfonyl-phenyl)-6-[1-(3-isopropyl-[1,2,4]oxadiazol-5-yl)-piperidin-4-yloxy]-9H-purine; 9-(4-Fluoro-6-methoxy-pyridin-3-yl)-6-[1-(3-isopropyl-[1,2,4]oxadiazol-5-yl)-piperidin-4-yloxy]-9H-purine; 6-[1-(3-Isopropyl-[1,2,4]oxadiazol-5-yl)-piperidin-4-yloxy]-9-(6-methoxy-2-methyl-pyridin-3-yl)-9H-purine; 2,5-Difluoro-4-{6-[1-(3-isopropyl-[1,2,4]oxadiazol-5-yl)-piperidin-4-yloxy]-purin-9-yl}-benzenesulfonamide; 9-(2-Fluoro-4-methanesulfonyl-phenyl)-6-[4-(3-isopropyl-[1,2,4]oxadiazol-5-yl)-cyclohexyloxy]-9H-purine; 3-Fluoro-4-{6-[4-(3-isopropyl-[1,2,4]oxadiazol-5-yl)-cyclohexyloxy]-purin-9-yl}-N-propionyl-benzenesulfonamide; 3-Fluoro-4-{6-[4-(3-isopropyl-[1,2,4]oxadiazol-5-yl)-cyclohexyloxy]-purin-9-yl}-benzonitrile; 3-Fluoro-4-{6-[4-(3-isopropyl-[1,2,4]oxadiazol-5-yl)-cyclohexyloxy]-purin-9-yl}-benzenesulfonamide; 9-(2,5-Difluoro-4-methanesulfonyl-phenyl)-6-[4-(3-isopropyl-[1,2,4]oxadiazol-5-yl)-cyclohexyloxy]-9H-purine; 9-(4-Fluoro-6-methoxy-pyridin-3-yl)-6-[4-(3-isopropyl-[1,2,4]oxadiazol-5-yl)-cyclohexyloxy]-9H-purine; 6-[4-(3-Isopropyl-[1,2,4]oxadiazol-5-yl)-cyclohexyloxy]-9-(6-methoxy-2-methyl-pyridin-3-yl)-9H-purine; and 2,5-Difluoro-4-{6-[4-(3-isopropyl-[1,2,4]oxadiazol-5-yl)-cyclohexyloxy)-purin-9-yl}-benzenesulfonamide.

Specific examples of GPR119 agonists disclosed in International Application No. PCT/US2004/022417 include the following compound according to Formula (IV) (referred to herein as Group D5): 4-[3-(4-Methanesulfonyl-phenyl)-3H-[1,2,3]triazolo[4,5-d]pyrimidin-7-yloxy]-piperidine-1-carboxylic acid tert-butyl ester.

Specific examples of GPR119 agonists disclosed in International Application No. PCT/US2004/022417 include the following compounds according to Formula (IV) (referred to herein as Group D6): 3-(2-Fluoro-4-methanesulfonyl-phenyl)-7-[1-(3-isopropyl-[1,2,4]oxadiazol-5-yl)-piperidin-4-yloxy]-3H-[1,2,3]triazolo[4,5-d]pyrimidine; 3-Fluoro-4-({7-[1-(3-isopropyl-[1,2,4]oxadiazol-5-yl)-piperidin-4-yloxy]-[1,2,3]triazolo[4,5-d]pyrimidin-3-yl}-N-propionyl-benzenesulfonamide; 3-Fluoro-4-{7-[1-(3-isopropyl-[1,2,4]oxadiazol-5-yl)-piperidin-4-yloxy]-[1,2,3]triazolo[4,5-d]pyrimidin-3-yl}-benzonitrile; 3-Fluoro-4-{7-[1-(3-isopropyl-[1,2,4]oxadiazol-5-yl)-piperidin-4-yloxy]-[1,2,3]triazolo[4,5-d]pyrimidin-3-yl}-benzenesulfonamide; 3-(2-Fluoro-4-methanesulfonyl-phenyl)-7-[4-(3-isopropyl-[1,2,4]oxadiazol-5-yl)-cyclohexyloxy]-3H-[1,2,3]triazolo[4,5-d]pyrimidine; 3-Fluoro-4-{7-[4-(3-isopropyl-[1,2,4]oxadiazol-5-yl)-cyclohexyloxy]-[1,2,3]triazolo[4,5-d]pyrimidin-3-yl}-N-propionyl-benzenesulfonamide; 3-Fluoro-4-{7-[4-(3-isopropyl-[1,2,4]oxadiazol-5-yl)-cyclohexyloxy]-[1,2,3]triazolo[4,5-d]pyrimidin-3-yl}-benzonitrile; 3-Fluoro-4-{7-[4-(3-isopropyl-[1,2,4]oxadiazol-5-yl)-cyclohexyloxy]-[1,2,3]triazolo[4,5-d]pyrimidin-3-yl}-benzenesulfonamide; 3-(2,5-Difluoro-4-methanesulfonyl-phenyl)-7-[4-(3-isopropyl-[1,2,4]oxadiazol-5-yl)-cyclohexyloxy]-3H-[1,2,3]triazolo[4,5-d]pyrimidine; 3-(4-Fluoro-6-methoxy-pyridin-3-yl)-7-[4-(3-isopropyl-[1,2,4]oxadiazol-5-yl)-cyclohexyloxy]-3H-[1,2,3]triazolo[4,5-d]pyrimidine; 7-[4-(3-Isopropyl-[1,2,4]oxadiazol-5-yl)-cyclohexyloxy]-3-(6-methoxy-2-methyl-pyridin-3-yl)-3H-[1,2,3]triazolo[4,5-d]pyrimidine; 2,5-Difluoro-4-{7-[4-(3-isopropyl-[1,2,4]oxadiazol-5-yl)-cyclohexyloxy]-[1,2,3]triazolo[4,5-d]pyrimidin-3-yl}-benzenesulfonamide; 4-[3-(2-Fluoro-4-methanesulfonyl-phenyl)-3H-[1,2,3]triazolo[4,5-d]pyrimidin-7-yloxy]-piperidine-1-carboxylic acid isopropyl ester; 4-[3-(2-Fluoro-4-propionylsulfamoyl-phenyl)-3H-[1,2,3]triazolo[4,5-d]pyrimidin-7-yloxy]-piperidine-1-carboxylic acid isopropyl ester; 4-[3-(4-Cyano-2-fluoro-phenyl)-3H-[1,2,3]triazolo[4,5-d]pyrimidin-7-yloxy]-piperidine-1-carboxylic acid isopropyl ester; 4-[3-(2-Fluoro-4-sulfamoyl-phenyl)-3H-[1,2,3]triazolo[4,5-d]pyrimidin-7-yloxy]-piperidine-1-carboxylic acid isopropyl ester; 4-[3-(2,5-Difluoro-4-methanesulfonyl-phenyl)-3H-[1,2,3]triazolo[4,5-d]pyrimidin-7-yloxy]-piperidine-1-carboxylic acid isopropyl ester; 4-[3-(4-Fluoro-6-methoxy-pyridin-3-yl)-3H-[1,2,3]triazolo[4,5-d]pyrimidin-7-yloxy]-piperidine-1-carboxylic acid isopropyl ester; 4-[3-(6-Methoxy-2-methyl-pyridin-3-yl)-3H-[1,2,3]triazolo[4,5-d]pyrimidin-7-yloxy]-piperidine-1-carboxylic acid isopropyl ester; 4-[3-(2,5-Difluoro-4-sulfamoyl-phenyl)-3H-[1,2,3]triazolo[4,5-d]pyrimidin-7-yloxy]-piperidine-1-carboxylic acid isopropyl ester; 3-(2,5-Difluoro-4-methanesulfonyl-phenyl)-7-[1-(3-isopropyl-[1,2,4]oxadiazol-5-yl)-piperidin-4-yloxy]-3H-[1,2,3]triazolo[4,5-d]pyrimidine; 3-(4-Fluoro-6-methoxy-pyridin-3-yl)-7-[1-(3-isopropyl-[1,2,4]oxadiazol-5-yl)-piperidin-4-yloxy]-3H-[1,2,3]triazolo[4,5-d]pyrimidine; 7-[1-(3-Isopropyl-[1,2,4]oxadiazol-5-yl)-piperidin-4-yloxy]-3-(6-methoxy-2-methyl-pyridin-3-yl)-3H-[1,2,3]triazolo[4,5-d]pyrimidine; and 2,5-Difluoro-4-{7-

[1-(3-isopropyl-[1,2,4]oxadiazol-5-yl)-piperidin-4-yloxy]-[1,2,3]triazolo[4,5-d]pyrimidin-3-yl}-benzenesulfonamide.

Specific examples of GPR119 agonists disclosed in International Application No. PCT/US2004/022417 include the following compound according to Formula (IV) (referred to herein as Group D7): 4-[3-(4-Methanesulfonyl-phenyl)-isoxazolo[4,5-d]pyrimidin-7-yloxy]-piperidine-1-carboxylic acid tert-butyl ester.

Specific examples of GPR119 agonists disclosed in International Application No. PCT/US2004/022417 include the following compounds according to Formula (IV) (referred to herein as Group D8): 4-({Ethyl-[3-(4-methanesulfonyl-phenyl)-isoxazolo[4,5-d]pyrimidin-7-yl]-amino}-methyl)-piperidine-1-carboxylic acid tert-butyl ester; 4-[3-(4-Methanesulfonyl-phenyl)-isoxazolo[4,5-d]pyrimidin-7-ylsulfanyl]-piperidine-1-carboxylic acid tert-butyl ester; and 4-[3-(4-Methanesulfonyl-phenyl)-isoxazolo[4,5-d]pyrimidin-7-yloxy]-piperidine-1-carboxylic acid isopropyl ester.

Specific examples of GPR119 agonists disclosed in International Application No. PCT/US2004/022417 include the following compound according to Formula (IV) (referred to herein as Group D9): 4-[8-(2-Fluoro-4-methanesulfonyl-phenyl)-[1,7]naphthyridin-4-yloxy]-piperidine-1-carboxylic acid isopropyl ester.

Specific examples of GPR119 agonists disclosed in International Application No. PCT/US2004/022417 include the following compounds according to Formula (IV) (referred to herein as Group D10): 4-[8-(2-Fluoro-4-methanesulfonyl-phenyl)-quinolin-4-yloxy]-piperidine-1-carboxylic acid isopropyl ester; 4-[8-(4-Methylsulfanyl-phenyl)-quinolin-4-yloxy]-piperidine-1-carboxylic acid isopropyl ester; 4-[8-(4-Methanesulfonyl-phenyl)-quinolin-4-yloxy]-piperidine-1-carboxylic acid isopropyl ester; 4-[8-(4-Isopropoxy-phenyl)-quinolin-4-yloxy]-piperidine-1-carboxylic acid isopropyl ester; 4-[8-(4-Bromo-2-fluoro-phenyl)-quinolin-4-yloxy]-piperidine-1-carboxylic acid isopropyl ester; 4-[8-(2-Fluoro-4-propionylsulfamoyl-phenyl)-quinolin-4-yloxy]-piperidine-1-carboxylic acid isopropyl ester; 4-[8-(4-Cyano-2-fluoro-phenyl)-quinolin-4-yloxy]-piperidine-1-carboxylic acid isopropyl ester; 4-[8-(2-Fluoro-4-sulfamoyl-phenyl)-quinolin-4-yloxy]-piperidine-1-carboxylic acid isopropyl ester; 4-[8-(2,5-Difluoro-4-methanesulfonyl-phenyl)-quinolin-4-yloxy]-piperidine-1-carboxylic acid isopropyl ester; 4-[8-(4-Fluoro-6-methoxy-pyridin-3-yl)-quinolin-4-yloxy]-piperidine-1-carboxylic acid isopropyl ester; 4-[8-(6-Methoxy-2-methyl-pyridin-3-yl)-quinolin-4-yloxy]-piperidine-1-carboxylic acid isopropyl ester; 4-[8-(2,5-Difluoro-4-sulfamoyl-phenyl)-quinolin-4-yloxy]-piperidine-1-carboxylic acid isopropyl ester; 2,5-Difluoro-4-{4-[1-(3-isopropyl-[1,2,4]oxadiazol-5-yl)-piperidin-4-yloxy]-quinolin-8-yl}-benzenesulfonamide; 4-[1-(3-Isopropyl-[1,2,4]oxadiazol-5-yl)-piperidin-4-yloxy]-8-(6-methoxy-2-methyl-pyridin-3-yl)-quinoline; 8-(4-Fluoro-6-methoxy-pyridin-3-yl)-4-[1-(3-isopropyl-[1,2,4]oxadiazol-5-yl)-piperidin-4-yloxy]-quinoline; 8-(2,5-Difluoro-4-methanesulfonyl-phenyl)-4-[1-(3-isopropyl-[1,2,4]oxadiazol-5-yl)-piperidin-4-yloxy]-quinoline; 3-Fluoro-4-{4-[1-(3-isopropyl-[1,2,4]oxadiazol-5-yl)-piperidin-4-yloxy]-quinolin-8-yl}-benzenesulfonamide; 3-Fluoro-4-{4-[1-(3-isopropyl-[1,2,4]oxadiazol-5-yl)-piperidin-4-yloxy]-quinolin-8-yl}-benzonitrile; 3-Fluoro-4-{4-[1-(3-isopropyl-[1,2,4]oxadiazol-5-yl)-piperidin-4-yloxy]-quinolin-8-yl}-N-propionyl-benzenesulfonamide; 8-(2-Fluoro-4-methanesulfonyl-phenyl)-4-[1-(3-isopropyl-[1,2,4]oxadiazol-5-yl)-piperidin-4-yloxy]-quinolin; 2,5-Difluoro-4-{4-[4-(3-isopropyl-[1,2,4]oxadiazol-5-yl)-cyclohexyloxy]-quinolin-8-yl}-benzenesulfonamide; 4-[4-(3-Isopropyl-[1,2,4]oxadiazol-5-yl)-cyclohexyloxy]-8-(6-methoxy-2-methyl-pyridin-3-yl)-quinoline; 8-(4-Fluoro-6-methoxy-pyridin-3-yl)-4-[4-(3-isopropyl-1-[1,2,4]oxadiazol-5-yl)-cyclohexyloxy]-quinoline; 8-(2,5-Difluoro-4-methanesulfonyl-phenyl)-4-[4-(3-isopropyl-[1,2,4]oxadiazol-5-yl)-cyclohexyloxy]-quinoline; 3-Fluoro-4-{4-[4-(3-isopropyl-[1,2,4]oxadiazol-5-yl)-cyclohexyloxy]-quinolin-8-yl}-benzenesulfonamide; 3-Fluoro-4-{4-[4-(3-isopropyl-[1,2,4]oxadiazol-5-yl)-cyclohexyloxy]-quinolin-8-yl}-benzonitrile; 3-Fluoro-4-{4-[4-(3-isopropyl-[1,2,4]oxadiazol-5-yl)-cyclohexyloxy]-quinolin-8-yl}-N-propionyl-benzenesulfonamide; and 8-(2-Fluoro-4-methanesulfonyl-phenyl)-4-[4-(3-isopropyl-[1,2,4]oxadiazol-5-yl)-cyclohexyloxy]-quinoline.

Specific examples of GPR119 agonists disclosed in International Application No. PCT/US2004/022417 include the following compounds according to Formula (IV) (referred to herein as Group D11): 4-[8-(2-Fluoro-4-methanesulfonyl-phenyl)-pyrido[3,4-d]pyrimidin-4-yloxy]-piperidine-1-carboxylic acid isopropyl ester; 4-[8-(2-Fluoro-4-propionylsulfamoyl-phenyl)-pyrido[3,4-d]pyrimidin-4-yloxy]-piperidine-1-carboxylic acid isopropyl ester; 4-[8-(4-Cyano-2-fluoro-phenyl)-pyrido[3,4-d]pyrimidin-4-yloxy]-piperidine-1-carboxylic acid isopropyl ester; 4-[8-(2-Fluoro-4-sulfamoyl-phenyl)-pyrido[3,4-d]pyrimidin-4-yloxy]-piperidine-1-carboxylic acid isopropyl ester; 4-[8-(2,5-Difluoro-4-methanesulfonyl-phenyl)-pyrido[3,4-d]pyrimidin-4-yloxy]-piperidine-1-carboxylic acid isopropyl ester; 4-[8-(4-Fluoro-6-methoxy-pyridin-3-yl)-pyrido[3,4-d]pyrimidin-4-yloxy]-piperidine-1-carboxylic acid isopropyl ester; 4-[8-(6-Methoxy-2-methyl-pyridin-3-yl)-pyrido[3,4-d]pyrimidin-4-yloxy]-piperidine-1-carboxylic acid isopropyl ester; 4-[8-(2,5-Difluoro-4-sulfamoyl-phenyl)-pyrido[3,4-d]pyrimidin-4-yloxy]-piperidine-1-carboxylic acid isopropyl ester; 8-(2-Fluoro-4-methanesulfonyl-phenyl)-4-[1-(3-isopropyl-[1,2,4]oxadiazol-5-yl)-piperidin-4-yloxy]-pyrido[3,4-d]pyrimidine; 3-Fluoro-4-{4-[1-(3-isopropyl-[1,2,4]oxadiazol-5-yl)-piperidin-4-yloxy]-pyrido[3,4-d]pyrimidin-8-yl}-N-propionyl-benzenesulfonamide; 3-Fluoro-4-{4-[1-(3-isopropyl-[1,2,4]oxadiazol-5-yl)-piperidin-4-yloxy]-pyrido[3,4-d]pyrimidin-8-yl}-benzonitrile; 3-Fluoro-4-{4-[1-(3-isopropyl-[1,2,4]oxadiazol-5-yl)-piperidin-4-yloxy]-pyrido[3,4-d]pyrimidin-8-yl}-benzenesulfonamide; 8-(2,5-Difluoro-4-methanesulfonyl-phenyl)-4-[1-(3-isopropyl-[1,2,4]oxadiazol-5-yl)-piperidin-4-yloxy]-pyrido[3,4-d]pyrimidine; 8-(4-Fluoro-6-methoxy-pyridin-3-yl)-4-[1-(3-isopropyl-[1,2,4]oxadiazol-5-yl)-piperidin-4-yloxy]-pyrido[3,4-d]pyrimidine; 4-[1-(3-Isopropyl-[1,2,4]oxadiazol-5-yl)-piperidin-4-yloxy]-8-(6-methoxy-2-methyl-pyridin-3-yl)-pyrido[3,4-d]pyrimidine; 2,5-Difluoro-4-{4-[1-(3-isopropyl-[1,2,4]oxadiazol-5-yl)-piperidin-4-yloxy]-pyrido[3,4-d]pyrimidin-8-yl}-benzenesulfonamide; 8-(2-Fluoro-4-methanesulfonyl-phenyl)-4-[4-(3-isopropyl-[1,2,4]oxadiazol-5-yl)-cyclohexyloxy]-pyrido[3,4-d]pyrimidine; 3-Fluoro-4-{4-[4-(3-isopropyl-[1,2,4]oxadiazol-5-yl)-cyclohexyloxy]-pyrido[3,4-d]pyrimidin-8-yl}-N-propionyl-benzenesulfonamide; 3-Fluoro-4-{4-[4-(3-isopropyl-[1,2,4]oxadiazol-5-yl)-cyclohexyloxy]-pyrido[3,4-d]pyrimidin-8-yl}-benzonitrile; 3-Fluoro-4-{4-[4-(3-isopropyl-[1,2,4]oxadiazol-5-yl)-cyclohexyloxy]-pyrido[3,4-d]pyrimidin-8-yl}-benzenesulfonamide; 8-(2,5-Difluoro-4-methanesulfonyl-phenyl)-4-[4-(3-isopropyl-[1,2,4]oxadiazol-5-yl)-cyclohexyloxy]-pyrido[3,4-d]pyrimidine; 8-(4-Fluoro-6-methoxy-pyridin-3-yl)-4-[4-(3-isopropyl-[1,2,4]oxadiazol-5-yl)-cyclohexyloxy]-pyrido[3,4-d]pyrimidine; 4-[4-(3-Isopropyl-[1,2,4]oxadiazol-5-yl)-cyclohexyloxy]-8-(6-methoxy-2-methyl-pyridin-3-yl)-pyrido[3,4-d]

pyrimidine; and 2,5-Difluoro-4-{4-[4-(3-isopropyl-[1,2,4] oxadiazol-5-yl)-cyclohexyloxy]-pyrido[3,4-d]pyrimidin-8-yl}-benzenesulfonamide.

Specific examples of GPR119 agonists disclosed in International Application No. PCT/US2004/022417 include the following compounds according to Formula (IV) (referred to herein as Group D12): 3-(2-Fluoro-4-methanesulfonyl-phenyl)-7-[4-(3-isopropyl-[1,2,4]oxadiazol-5-yl)-cyclohexyloxy]-pyrazolo[1,5-a]pyrimidine; 3-Fluoro-4-{7-[4-(3-isopropyl-[1,2,4]oxadiazol-5-yl)-cyclohexyloxy]-pyrazolo[1,5-a]pyrimidin-3-yl}-N-propionyl-benzenesulfonamide; 3-Fluoro-4-{7-[4-(3-isopropyl-[1,2,4]oxadiazol-5-yl]-cyclohexyloxy]-pyrazolo[1,5-a]pyrimidin-3-yl)-benzonitrile; 3-Fluoro-4-{7-[4-(3-isopropyl-[1,2,4]oxadiazol-5-yl)-cyclohexyloxy]-pyrazolo[1,5-a]pyrimidin-3-yl}-benzenesulfonamide; 3-(2,5-Difluoro-4-methanesulfonyl-phenyl)-7-[4-(3-isopropyl-[1,2,4]oxadiazol-5-yl)-cyclohexyloxy]-pyrazolo[1,5-a]pyrimidine; 3-(4-Fluoro-6-methoxy-pyridin-3-yl)-7-[4-(3-isopropyl-[1,2,4]oxadiazol-5-yl)-cyclohexyloxy]-pyrazolo[1,5-a]pyrimidine; 7-[4-(3-Isopropyl-[1,2,4]oxadiazol-5-yl)-cyclohexyloxy]-3-(6-methoxy-2-methyl-pyridin-3-yl)-pyrazolo[1,5-a]pyrimidine; 2,5-Difluoro-4-{7-[4-(3-isopropyl-[1,2,4] oxadiazol-5-yl)-cyclohexyloxy]-pyrazolo[1,5-a]pyrimidin-3-yl}-benzenesulfonamide; 4-[3-(2-Fluoro-4-methanesulfonyl-phenyl)-pyrazolo[1,5-a]pyrimidin-7-yloxy]-piperidine-1-carboxylic acid isopropyl ester; 4-[3-(2-Fluoro-4-propionylsulfamoyl-phenyl)-pyrazolo[1,5-a]pyrimidin-7-yloxy]-piperidine-1-carboxylic acid isopropyl ester; 4-[3-(4-Cyano-2-fluoro-phenyl)-pyrazolo[1,5-a]pyrimidin-7-yloxy]-piperidine-1-carboxylic acid isopropyl ester; 4-[3-(2-Fluoro-4-sulfamoyl-phenyl)-pyrazolo[1,5-a]pyrimidin-7-yloxy]-piperidine-1-carboxylic acid isopropyl ester; 4-[3-(2,5-Difluoro-4-methanesulfonyl-phenyl)-pyrazolo[1,5-a]pyrimidin-7-yloxy]-piperidine-1-carboxylic acid isopropyl ester; 4-[3-(4-Fluoro-6-methoxy-pyridin-3-yl)-pyrazolo[1,5-a]pyrimidin-7-yloxy]-piperidine-1-carboxylic acid isopropyl ester; 4-[3-(6-Methoxy-2-methyl-pyridin-3-yl)-pyrazolo[1,5-a]pyrimidin-7-yloxy]-piperidine-1-carboxylic acid isopropyl ester; 4-[3-(2,5-Difluoro-4-sulfamoyl-phenyl)-pyrazolo[1,5-a]pyrimidin-7-yloxy]-piperidine-1-carboxylic acid isopropyl ester; 3-(2-Fluoro-4-methanesulfonyl-phenyl)-7-[1-(3-isopropyl-[1,2,4]oxadiazol-5-yl)-piperidin-4-yloxy]-pyrazolo[1,5-a]pyrimidine; 3-Fluoro-4-{7-[1-(3-isopropyl-[1,2,4]oxadiazol-5-yl)-piperidin-4-yloxy]-pyrazolo[1,5-a]pyrimidin-3-yl}-N-propionyl-benzenesulfonamide; 3-Fluoro-4-{7-[1-(3-isopropyl-[1,2,4]oxadiazol-5-yl)-piperidin-4-yloxy]-pyrazolo[1,5-a]pyrimidin-3-yl}-benzonitrile; 3-Fluoro-4-{7-[1-(3-isopropyl-[1,2,4]oxadiazol-5-yl)-piperidin-4-yloxy]-pyrazolo[1,5-a]pyrimidin-3-yl}-benzenesulfonamide; 3-(2,5-Difluoro-4-methanesulfonyl-phenyl)-7-[1-(3-isopropyl-[1,2,4]oxadiazol-5-yl)-piperidin-4-yloxy]-pyrazolo[1,5-a]pyrimidine; 3-(4-Fluoro-6-methoxy-pyridin-3-yl)-7-[1-(3-isopropyl-[1,2,4]oxadiazol-5-yl)-piperidin-4-yloxy]-pyrazolo[1,5-a]pyrimidine; 7-[1-(3-isopropyl-[1,2,4] oxadiazol-5-yl)-piperidin-4-yloxy]-3-(6-methoxy-2-methyl-pyridin-3-yl)-pyrazolo[1,5-a]pyrimidin; 2,5-Difluoro-4-{7-[1-(3-isopropyl-[1,2,4]oxadiazol-5-yl)-piperidin-4-yloxy]-pyrazolo[1,5-a]pyrimidin-3-yl}-benzenesulfonamide; 4-[3-(2-Fluoro-4-methanesulfonyl-phenyl)-2-methyl-pyrazolo[1,5-a]pyrimidin-7-yloxy]-piperidine-1-carboxylic acid isopropyl ester; 4-[3-(2-Fluoro-4-propionylsulfamoyl-phenyl)-2-methyl-pyrazolo[1,5-a]pyrimidin-7-yloxy]-piperidine-1-carboxylic acid isopropyl ester; 4-[3-(4-Cyano-2-fluoro-phenyl)-2-methyl-pyrazolo[1,5-a]pyrimidin-7-yloxy]-piperidine-1-carboxylic acid isopropyl ester; 4-[3-(2-Fluoro-4-sulfamoyl]-phenyl)-2-methyl-pyrazolo[1,5-a]pyrimidin-7-yloxy)-piperidine-1-carboxylic acid isopropyl ester; 4-[3-(2,5-Difluoro-4-methanesulfonyl-phenyl)-2-methyl-pyrazolo[1,5-a]pyrimidin-7-yloxy]-piperidine-1-carboxylic acid isopropyl ester; 4-[3-(4-Fluoro-6-methoxy-pyridin-3-yl)-2-methyl-pyrazolo[1,5-a]pyrimidin-7-yloxy]-piperidine-1-carboxylic acid isopropyl ester; 4-[3-(6-Methoxy-2-methyl-pyridin-3-yl)-2-methyl-pyrazolo[1,5-a]pyrimidin-7-yloxy]-piperidine-1-carboxylic acid isopropyl ester; 4-[3-(2,5-Difluoro-4-sulfamoyl-phenyl)-2-methyl-pyrazolo[1,5-a]pyrimidin-7-yloxy]-piperidine-1-carboxylic acid isopropyl ester; 2,5-Difluoro-4-{7-[1-(3-isopropyl-[1,2,4]oxadiazol-5-yl)-piperidin-4-yloxy-2-methyl-pyrazolo 1,5-a]pyrimidin-3-yl}-benzenesulfonamide; 7-[1-(3-isopropyl-[1,2,4]oxadiazol-5-yl)-piperidin-4-yloxy]-3-(6-methoxy-2-methyl-pyridin-3-yl)-2-methyl-pyrazolo-[1,5-a]pyrimidine; 3-(4-Fluoro-6-methoxy-pyridin-3-yl)-7-[1-(3-isopropyl-[1,2,4]oxadiazol-5-yl)-piperidin-4-yloxy]-2-methyl-pyrazolo [1,5-a]pyrimidine; 3-(2,5-Difluoro-4-methanesulfonyl-phenyl)-7-[1-(3-isopropyl-[1,2,4]oxadiazol-5-yl)-piperidin-4-yloxy]-2-methyl-pyrazolo[1,5-a]pyrimidine; 3-Fluoro-4-{7-[1-(3-isopropyl-[1,2,4]oxadiazol-5-yl)-piperidin-4-yloxy]-2-methyl-pyrazolo[1,5-a]pyrimidin-3-yl}-benzenesulfonamide; 3-Fluoro-4-{7-[1-(3-isopropyl-[1,2,4] oxadiazol-5-yl)-piperidin-yloxy]-2-methyl-pyrazolo[1,5-a]pyrimidin-3-yl}-benzonitrile; 3-Fluoro-4-{7-[1-(3-isopropyl-[1,2,4]oxadiazol-5-yl)-piperidin-4-yloxy]-2-methyl-pyrazolo[1,5-a]pyrimidin-3-yl}-N-propionyl-benzenesulfonamide; 3-(2-Fluoro-4-methanesulfonyl-phenyl)-7-[1-(3-isopropyl-[1,2,4]oxadiazol-5-yl)-piperidin-4-yloxy]-2-methyl-pyrazolo[1,5-a]pyrimidine; 3-(2-Fluoro-4-methanesulfonyl-phenyl)-7-[4-(3-isopropyl-[1,2,4] oxadiazol-5-yl)-cyclohexyloxy]-2-methyl-pyrazolo[1,5-a] pyrimidine; 3-Fluoro-4-{7-[4-(3-isopropyl-[1,2,4] oxadiazol-5-yl)-cyclohexyloxy]-2-methyl-pyrazolo[1,5-a]pyrimidin-3-yl}-N-propionyl-benzenesulfonamide; 3-Fluoro-4-{7-[4-(3-isopropyl-[1,2,4]oxadiazol-5-yl]-cyclohexyloxy]-2-methyl-pyrazolo[1,5-a]pyrimidin-3-yl)-benzonitrile; 3-Fluoro-4-{7-[4-(3-isopropyl-[1,2,4]oxadiazol-5-yl)-cyclohexyloxy]-2-methyl-pyrazolo[1,5-a]pyrimidin-3-yl}-benzenesulfonamide; 3-(2,5-Difluoro-4-methanesulfonyl-phenyl)-7-[4-(3-isopropyl-[1,2,4]oxadiazol-5-yl)-cyclohexyloxy]-2-methyl-pyrazolo[1,5-a]pyrimidine; 3-(4-Fluoro-6-methoxy-pyridin-3-yl)-7-[4-(3-isopropyl-[1,2,4]oxadiazol-5-yl)-cyclohexyloxy]-2-methyl-pyrazolo[1,5-a]pyrimidine; 7-[4-(3-Isopropyl-[1,2,4]oxadiazol-5-yl)-cyclohexyloxy]-3-(6-methoxy-2-methyl-pyridin-3-yl)-2-methyl-pyrazolo[1,5-a]pyrimidine; and 2,5-Difluoro-4-{7-[4-(3-isopropyl-[1,2,4]oxadiazol-5-yl)-cyclohexyloxy]-2-methyl-pyrazolo[1,5-a]pyrimidin-3-yl}-benzenesulfonamide.

Specific examples of GPR119 agonists disclosed in International Application No. PCT/US2004/022417 include the following compounds according to Formula (IV) (referred to herein as Group D13): 4-[3-(2-Fluoro-4-methanesulfonyl-phenyl)-1-methyl-1H-pyrazolo[4,3-d]pyrimidin-7-yloxy]-piperidine-1-carboxylic acid isopropyl ester; 4-[3-(2-Fluoro-4-propionylsulfamoyl-phenyl)-1-methyl-1H-pyrazolo[4,3-d]pyrimidin-7-yloxy]-piperidine-1-carboxylic acid isopropyl ester; 4-[3-(4-Cyano-2-fluoro-phenyl)-1-methyl-1H-pyrazolo[4,3-d]pyrimidin-7-yloxy]-piperidine-1-carboxylic acid isopropyl ester; 4-[3-(2-Fluoro-4-sulfamoyl-phenyl)-1-methyl-1H-pyrazolo[4,3-d]pyrimidin-7-yloxy]-piperidine-1-carboxylic acid isopropyl ester; 4-[3-(2,5-Difluoro-4-methanesulfonyl-phenyl)-1-methyl-1H-pyrazolo[4,3-d]pyrimidin-7-yloxy]-piperidine-1-carboxylic acid isopropyl ester; 4-[3-(4-Fluoro-6-methoxy-pyridin-3-yl)-1- methyl-1H-pyrazolo[4,3-d]pyrimidin-7-yloxy]-piperidine-1-carboxylic acid isopropyl ester; 4-[3-(6-Methoxy-2-methyl-pyridin-3-yl)-1-methyl-1H-pyrazolo[4,3-d]pyrimidin-7-yloxy]-piperidine-1-carboxylic acid isopropyl ester; 4-[3-(2,5-Difluoro-4-sulfamoyl-phenyl)-1-methyl-1H-pyrazolo[4,3-d]pyrimidin-7-yloxy]-piperidine-1-carboxylic acid isopropyl ester; 3-(2-Fluoro-4-methanesulfonyl-phenyl)-7-[1-(3-isopropyl-[1,2,4]oxadiazol-5-yl)-piperidin-4-yloxy]-1-methyl-1H-pyrazolo[4,3-d]pyrimidine; 3-Fluoro-4-{7-[1-(3-isopropyl-[1,2,4]oxadiazol-5-yl)-piperidin-4-yloxy]-1-methyl-1H-pyrazolo[4,3-d]pyrimidin-3-yl}-N-propionyl-benzenesulfonamide; 3-Fluoro-4-(7-[1-(3-isopropyl-[1,2,4]oxadiazol-5-yl)-piperidin-4-yloxy]-1-methyl-1H-pyrazolo[4,3-d]pyrimidin-3-yl-benzonitrile; 3-Fluoro-4-{7-[1-(3-isopropyl-[1,2,4]oxadiazol-5-yl)-piperidin-4-yloxy]-1-methyl-1H-pyrazolo[4,3-d]pyrimidin-3-yl}-benzenesulfonamide; 3-(2,5-Difluoro-4-methanesulfonyl-phenyl)-7-[1-(3-isopropyl-[1,2,4]oxadiazol-5-yl)-piperidin-4-yloxy]-1-methyl-1H-pyrazolo[4,3-d]pyrimidine; 3-(4-Fluoro-6-methoxy-pyridin-3-yl)-7-[1-(3-isopropyl-[1,2,4]oxadiazol-5-yl)-piperidin-4-yloxy]-1-methyl-1H-pyrazolo[4,3-d]pyrimidine; 7-[1-(3-Isopropyl-[1,2,4]oxadiazol-5-yl)-piperidin-4-yloxy]-3-(6-methoxy-2-methyl-pyridin-3-yl)-1-methyl-1H-pyrazolo[4,3-d]pyrimidine; 2,5-Difluoro-4-{7-[1-(3-isopropyl-[1,2,4]oxadiazol-5-yl)-piperidin-4-yloxy]-1-methyl-1H-pyrazolo[4,3-d]pyrimidin-3-yl}-benzenesulfonamide; 3-(2-Fluoro-4-methanesulfonyl-phenyl)-7-[4-(3-isopropyl-[1,2,4]oxadiazol-5-yl)-cyclohexyloxy]-1-methyl-1H-pyrazolo[4,3-d]pyrimidine; 3-Fluoro-4-{7-[4-(3-isopropyl-[1,2,4]oxadiazol-5-yl)-cyclohexyloxy]-1-methyl-1H-pyrazolo[4,3-d]pyrimidin-3-yl}-N-propionyl-benzenesulfonamide; 3-Fluoro-4-{7-[4-(3-isopropyl-[1,2,4]oxadiazol-5-yl)-cyclohexyloxy]-1-methyl-1H-pyrazolo[4,3-d]pyrimidin-3-yl}-benzonitrile; 3-Fluoro-4-{7-[4-(3-isopropyl-[1,2,4]oxadiazol-5-yl)-cyclohexyloxy]-1-methyl-1H-pyrazolo[4,3-d]pyrimidin-3-yl}-benzenesulfonamide; 3-(2,5-Difluoro-4-methanesulfonyl-phenyl)-7-[4-(3-isopropyl-[1,2,4]oxadiazol-5-yl)-cyclohexyloxy]-1-methyl-1H-pyrazolo[4,3-d]pyrimidine; 3-(4-Fluoro-6-methoxy-pyridin-3-yl)-7-[4-(3-isopropyl-[1,2,4]oxadiazol-5-yl)-cyclohexyloxy]-1-methyl-1H-pyrazolo[4,3-d]pyrimidine; 7-[4-(3-Isopropyl-[1,2,4]oxadiazol-5-yl)-cyclohexyloxy]-3-(6-methoxy-2-methyl-pyridin-3-yl)-1-methyl-1H-pyrazolo[4,3-d]pyrimidine; and 2,5-Difluoro-4-{7-[4-(3-isopropyl-[1,2,4]oxadiazol-5-yl)-cyclohexyloxy]-1-methyl-1H-pyrazolo[4,3-d]pyrimidin-3-yl}-benzenesulfonamide.

Specific examples of GPR119 agonists disclosed in International Application No. PCT/US2004/022417 include the following compounds according to Formula (IV) (referred to herein as Group D14): 4-[3-(2-Fluoro-4-methanesulfonyl-phenyl)-2-methyl-2H-pyrazolo[4,3-d]pyrimidin-7-yloxy]-piperidine-1-carboxylic acid isopropyl ester; 4-[3-(2-Fluoro-4-propionylsulfamoyl-phenyl)-2-methyl-2H-pyrazolo[4,3-d]pyrimidin-7-yloxy]-piperidine-1-carboxylic acid isopropyl ester; 4-[3-(4-Cyano-2-fluoro-phenyl)-2-methyl-2H-pyrazolo[4,3-d]pyrimidin-7-yloxy]-piperidine-1-carboxylic acid isopropyl ester; 4-[3-(2-Fluoro-4-sulfamoyl-phenyl)-2-methyl-2H-pyrazolo[4,3-d]pyrimidin-7-yloxy]-piperidine-1-carboxylic acid isopropyl ester; 4-[3-(2,5-Difluoro-4-methanesulfonyl-phenyl)-2-methyl-2H-pyrazolo[4,3-d]pyrimidin-7-yloxy]-piperidine-1-carboxylic acid isopropyl ester; 4-[3-(4-Fluoro-6-methoxy-pyridin-3-yl)-2-methyl-2H-pyrazolo[4,3-d]pyrimidin-7-yloxy]-piperidine-1-carboxylic acid isopropyl ester; 4-[3-(6-Methoxy-2-methyl-pyridin-3-yl)-2-methyl-2H-pyrazolo[4,3-d]pyrimidin-7-yloxy]-piperidine-1-carboxylic acid isopropyl ester; 4-[3-(2,5-Difluoro-4-sulfamoyl-phenyl)-2-methyl-2H-pyrazolo[4,3-d]pyrimidin-7-yloxy]-piperidine-1-carboxylic acid isopropyl ester; 3-(2-Fluoro-4-methanesulfonyl-phenyl)-7-[1-(3-isopropyl-[1,2,4]oxadiazol-5-yl)-piperidin-4-yloxy]-2-methyl-2H-pyrazolo[4,3-d]pyrimidine; 3-Fluoro-4-{7-[1-(3-isopropyl-[1,2,4]oxadiazol-5-yl)-piperidin-4-yloxy]-2-methyl-2H-pyrazolo[4,3-d]pyrimidin-3-yl}-N-propionyl-benzenesulfonamide; 3-Fluoro-4-{7-[1-(3-isopropyl-[1,2,4]oxadiazol-5-yl)-piperidin-4-yloxy]-2-methyl-2H-pyrazolo[4,3-d]pyrimidin-3-yl}-benzonitrile; 3-Fluoro-4-{7-[1-(3-isopropyl-[1,2,4]oxadiazol-5-yl)-piperidin-4-yloxy]-2-methyl-2H-pyrazolo[4,3-d]pyrimidin-3-yl}-benzenesulfonamide; 3-(2,5-Difluoro-4-methanesulfonyl-phenyl)-7-[1-(3-isopropyl-[1,2,4]oxadiazol-5-yl)-piperidin-4-yloxy]-2-methyl-2H-pyrazolo[4,3-d]pyrimidine; 3-(4-Fluoro-6-methoxy-pyridin-3-yl)-7-[1-(3-isopropyl-[1,2,4]oxadiazol-5-yl)-piperidin-4-yloxy]-2-methyl-2H-pyrazolo[4,3-d]pyrimidine; 7-[1-(3-Isopropyl-[1,2,4]oxadiazol-5-yl)-piperidin-4-yloxy]-3-(6-methoxy-2-methyl-pyridin-3-yl)-2-methyl-2H-pyrazolo[4,3-d]pyrimidine; 2,5-Difluoro-4-{7-[1-(3-isopropyl-[1,2,4]oxadiazol-5-yl)-piperidin-4-yloxy]-2-methyl-2H-pyrazolo[4,3-d]pyrimidin-3-yl}-benzenesulfonamide; 3-(2-Fluoro-4-methanesulfonyl-phenyl)-7-[4-(3-isopropyl-[1,2,4]oxadiazol-5-yl)-cyclohexyloxy]-2-methyl-2H-pyrazolo[4,3-d]pyrimidine; 3-Fluoro-4-{7-[4-(3-isopropyl-[1,2,4]oxadiazol-5-yl)-cyclohexyloxy]-2-methyl-2H-pyrazolo[4,3-d]pyrimidin-3-yl}-N-propionyl-benzenesulfonamide; 3-Fluoro-4-{7-[4-(3-isopropyl-[1,2,4]oxadiazol-5-yl)-cyclohexyloxy]-2-methyl-2H-pyrazolo[4,3-d]pyrimidin-3-yl}-benzonitrile; 3-Fluoro-4-{7-[4-(3-isopropyl-[1,2,4]oxadiazol-5-yl)-cyclohexyloxy]-2-methyl-2H-pyrazolo[4,3-d]pyrimidin-3-yl}-benzenesulfonamide; 3-(2,5-Difluoro-4-methanesulfonyl-phenyl)-7-[4-(3-isopropyl-[1,2,4]oxadiazol-5-yl)-cyclohexyloxy]-2-methyl-2H-pyrazolo[4,3-d]pyrimidine; 3-(4-Fluoro-6-methoxy-pyridin-3-yl)-7-[4-(3-isopropyl-[1,2,4]oxadiazol-5-yl)-cyclohexyloxy]-2-methyl-2H-pyrazolo[4,3-d]pyrimidine; 7-[4-(3-Isopropyl-[1,2,4]oxadiazol-5-yl)-cyclohexyloxy]-3-(6-methoxy-2-methyl-pyridin-3-yl)-2-methyl-2H-pyrazolo[4,3-d]pyrimidine; and 2,5-Difluoro-4-{7-[4-(3-isopropyl-[1,2,4]oxadiazol-5-yl)-cyclohexyloxy]-2-methyl-2H-pyrazolo[4,3-d]pyrimidin-3-yl}-benzenesulfonamide.

Examples of GPR119 agonists are described in International Application No. PCT/US2005/019318 (published as WO 2005/121121), the disclosure of which is herein incorporated by reference in its entirety. Disclosed in International Application No. PCT/US2005/019318 as a GPR119 agonist is a compound of Formula (V):

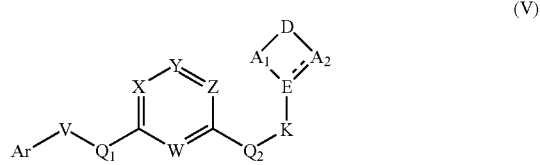

(V)

or N-oxide thereof;

wherein:

$A_1$ and $A_2$ are independently $C_{1-3}$ alkylene optionally substituted with one or more substituents selected independently from the group consisting of $C_{1-6}$ alkyl, $C_{1-6}$ alkoxy, and carboxy;

D is $CR_1R_2$ or $NR_2$, wherein $R_1$ is selected from the group consisting of H, $C_{1-6}$ alkyl, $C_{1-6}$ alkoxy, halogen and hydroxyl;

E is N, C or $CR_3$, wherein $R_3$ is H or $C_{1-6}$ alkyl;

--- is a single bond when E is N or $CR_3$, or a double bond when E is C;

K is absent, $C_{3-6}$ cycloalkylene, or $C_{1-3}$ alkylene group optionally substituted with one or more substituents selected independently from the group consisting of $C_{1-6}$ alkyl, $C_{1-6}$ alkoxy, carboxy, cyano, and halogen;

$Q_1$ is $NR_4$, O, S, S(O) or $S(O)_2$, wherein $R_4$ is H, $C_{1-6}$ acyl, $C_{1-6}$ alkyl, $C_{2-6}$ alkenyl, $C_{2-6}$ alkynyl, $C_{3-7}$ cycloalkyl, or $C_{3-7}$-cycloalkyl-$C_{1-3}$-alkylene, wherein said $C_{1-6}$ alkyl is optionally substituted with one or more substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-4}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthiocarboxamide, $C_{1-6}$ alkylthioureyl, $C_{1-6}$ alkylureyl, amino, di-$C_{1-6}$-alkylamino, $C_{1-6}$ alkoxycarbonyl, carboxamide, carboxy, cyano, $C_{3-6}$ cycloalkyl, di-$C_{1-6}$-alkylcarboxamide, di-$C_{1-4}$-alkylsulfonamide, di-$C_{1-6}$-alkylthiocarboxamido, $C_{1-6}$ haloalkoxy, $C_{1-4}$ haloalkyl, halogen, $C_{1-6}$ haloalkylsulfinyl, $C_{1-6}$ haloalkylsulfonyl, $C_{1-6}$ haloalkylthio, hydroxyl, hydroxylamino and nitro;

$Q_2$ is absent, $NR_5$, or O, wherein $R_5$ is H, $C_{1-6}$ acyl, $C_{1-6}$ alkyl, $C_{2-6}$ alkenyl, $C_{2-6}$ alkynyl, $C_{3-7}$ cycloalkyl, or $C_{3-7}$-cycloalkyl-$C_{1-3}$-alkylene, wherein said $C_{1-6}$ alkyl is optionally substituted with one or more substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthiocarboxamide, $C_{1-6}$ alkylthioureyl, $C_{1-6}$ alkylureyl, amino, di-$C_{1-6}$-alkylamino, $C_{1-6}$ alkoxycarbonyl, carboxamide, carboxy, cyano, $C_{3-6}$ cycloalkyl, di-$C_{1-6}$-alkylcarboxamide, di-$C_{1-6}$-alkylsulfonamide, di-$C_{1-6}$-alkylthiocarboxamido, $C_{1-6}$ haloalkoxy, $C_{1-6}$ haloalkyl, halogen, $C_{1-6}$ haloalkylsulfinyl, $C_{1-6}$ haloalkylsulfonyl, $C_{1-6}$ haloalkylthio, hydroxyl, hydroxylamino and nitro;

W is N or CH;

X is N or $CR_6$;

Y is N or $CR_7$;

Z is N or $CR_8$;

V is absent, $C_{1-3}$ heteroalkylene, or $C_{1-3}$ alkylene wherein each are optionally substituted with one or more substituents selected independently from the group consisting of $C_{1-3}$ alkyl, $C_{1-6}$ alkoxy, carboxy, cyano, $C_{1-3}$ haloalkyl, and halogen;

$R_6$, $R_7$, and $R_8$ are each independently selected from the group consisting of H; $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthiocarboxamide, $C_{1-6}$ alkylthioureyl, $C_{1-6}$ alkylureyl, amino, di-$C_{1-6}$-alkylamino, $C_{1-6}$ alkoxycarbonyl, carboxamide, carboxy, cyano, $C_{3-6}$ cycloalkyl, di-$C_{1-6}$-alkylcarboxamide, di-$C_{1-6}$-alkylsulfonamide, di-$C_{1-6}$-alkylthiocarboxamido, $C_{1-6}$ haloalkoxy, $C_{1-6}$ haloalkyl, halogen, $C_{1-6}$ haloalkylsulfinyl, $C_{1-6}$ haloalkylsulfonyl, $C_{1-6}$ haloalkylthio, hydroxyl, hydroxylamino and nitro, wherein said $C_{2-6}$ alkenyl, $C_{1-6}$ alkyl, $C_{2-6}$ alkynyl and $C_{3-6}$ cycloalkyl are each optionally substituted with one or more substituents independently selected from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthiocarboxamide, $C_{1-6}$ alkylthioureyl, amino, di-$C_{1-6}$-alkylamino, $C_{1-6}$ alkoxycarbonyl, carboxamide, carboxy, cyano, $C_{3-6}$ cycloalkyl, di-$C_{1-6}$-alkylcarboxamide, di-$C_{1-6}$-alkylsulfonamide, di-$C_{1-6}$-alkylthiocarboxamido, $C_{1-6}$ haloalkoxy, $C_{1-6}$ haloalkyl, halogen, $C_{1-6}$ haloalkylsulfinyl, $C_{1-6}$ haloalkylsulfonyl, $C_{1-6}$ haloalkylthio, hydroxyl, hydroxylamino and nitro;

Ar is aryl or heteroaryl optionally substituted with $R_9$-$R_{13}$;

$R_9$ is selected from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthiocarboxamide, $C_{1-6}$ alkylthioureyl, $C_{1-6}$ alkylureyl, amino, aryl, arylcarbonyl, arylsulfonyl, di-$C_{1-6}$-alkylamino, carbamimidoyl, $C_{1-6}$ alkoxycarbonyl, carboxamide, carboxy, cyano, $C_{3-6}$ cycloalkyl, di-$C_{1-6}$-alkylcarboxamide, di-$C_{1-6}$-alkylsulfonamide, di-$C_{1-6}$-alkylthiocarboxamido, guanidine, $C_{1-6}$ haloalkoxy, $C_{1-6}$ haloalkyl, halogen, $C_{1-6}$ haloalkylsulfinyl, $C_{1-6}$ haloalkylsulfonyl, $C_{1-6}$ haloalkylthio, heterocyclic, heterocyclicsulfonyl, heteroaryl, hydroxyl, hydroxylamino, nitro, $C_{3-6}$ oxo-cycloalkyl, phenoxy, sulfonamide, sulfonic acid and thiol; and wherein each available $R_9$ is optionally substituted with one or more substituents selected independently from the group consisting of $C_{1-6}$ acyl, $C_{1-6}$ acylsulfonamide, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthiocarboxamide, $C_{1-6}$ alkylthioureyl, $C_{1-6}$ alkylureyl, amino; aryl, arylcarbonyl, arylsulfonyl, di-$C_{1-6}$-alkylamino, $C_{1-6}$ alkoxycarbonyl, carboxamide, carboxy, cyano, $C_{3-6}$ cycloalkyl, di-$C_{1-6}$-alkylcarboxamide, di-$C_{1-6}$-alkylsulfonamide, di-$C_{1-6}$-alkylthiocarboxamido, $C_{1-6}$ haloalkoxy, $C_{1-6}$ haloalkyl, halogen, $C_{1-6}$ haloalkylsulfinyl, $C_{1-6}$ haloalkylsulfonyl, $C_{1-6}$ haloalkylthio, heteroaryl, heteroarylcarbonyl, heteroarylsulfonyl, heterocyclic, hydroxyl, hydroxylamino, and nitro;

$R_{10}$-$R_{13}$ are independently selected from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthiocarboxamide, $C_{1-6}$ alkylthioureyl, $C_{1-6}$ alkylureyl, amino, di-$C_{1-6}$-alkylamino, $C_{1-6}$ alkoxycarbonyl, carboxamide, carboxy, cyano, $C_{3-6}$ cycloalkyl, di-$C_{1-6}$-alkylcarboxamide, di-$C_{1-6}$-alkylsulfonamide, di-$C_{1-6}$-alkylthiocarboxamido, $C_{1-6}$ haloalkoxy, $C_{1-6}$ haloalkyl, halogen, $C_{1-6}$ haloalkylsulfinyl, $C_{1-6}$ haloalkylsulfonyl. $C_{1-6}$ haloalkylthio, hydroxyl, hydroxylamino, nitro, and thiol; or two adjacent groups together with the atoms to which they are bonded form a 5, 6 or 7 member cycloalkyl, cycloalkenyl or heterocyclic group wherein the 5, 6 or 7 member group is optionally substituted with halogen or oxo; and $R_2$ is selected from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthiocarboxamide, $C_{1-6}$ alkylthioureyl, $C_{1-6}$ alkylureyl, amino, aryl, arylcarbonyl, aryloxy, di-$C_{1-6}$-alkylamino, carbamimidoyl, $C_{1-6}$ alkoxycarbonyl, $C_{3-7}$-cycloalkoxycarbonyl, carboxamide, carboxy, cyano, $C_{3-6}$ cycloalkyl, di-$C_{1-6}$-alkylcarboxamide, di-$C_{1-6}$-alkylsulfonamide, di-$C_{1-6}$-alkylthiocarboxamido, guanidine, $C_{1-6}$ haloalkoxy, $C_{1-6}$ haloalkyl, halogen, $C_{1-6}$ haloalkylsulfinyl, $C_{1-6}$ haloalkylsulfonyl, $C_{1-6}$ haloalkylthio, heteroaryl, heteroaryl-$C_{1-3}$-alkylene, heteroarylcarbonyl, heteroaryloxy, heterocycliccarboxamide, hydroxyl, hydroxylamino and nitro; wherein each available $R_2$ is optionally substituted with one or more substituents selected independently from the group consisting of $C_{1-6}$ acyl, $C_{1-4}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthiocarboxamide, $C_{1-6}$ alkylthioureyl, $C_{1-6}$ alkylureyl, amino, aryl, di-$C_{1-6}$-alkylamino, $C_{1-6}$ alkoxycarbonyl, carboxamide, carboxy, cyano, $C_{3-6}$ cycloalkyl, di-$C_{1-6}$-alkylcarboxamide, di-$C_{1-6}$-alkylsulfonamide, di-$C_{1-6}$-alkylthiocarboxamido, $C_{1-6}$ haloalkoxy, $C_{1-6}$ haloalkyl, halogen, $C_{1-6}$ haloalkylsulfinyl, $C_{1-6}$ haloalkylsulfonyl, $C_{1-6}$ haloalkylthio, heterocyclic, heteroaryl, hydroxyl, hydroxylamino and nitro, and wherein $C_{1-6}$ alkyl is further optionally substituted with one or more substituents selected independently from the group consisting of $C_{1-6}$ acyl, $C_{1-6}$ alkoxy, $C_{1-6}$ alkylamino, $C_{1-6}$ alkylcarboxamide, $C_{1-6}$ alkylsulfonamide, $C_{1-6}$ alkylsulfinyl; $C_{1-6}$ alkylsulfonyl, $C_{1-6}$ alkylthio, $C_{1-6}$ alkylureyl, amino, di-$C_{1-6}$-alkylamino, $C_{1-6}$ alkoxycarbonyl, carboxamide, carboxy, cyano, $C_{3-6}$ cycloalkyl, di-$C_{1-6}$-alkylcarboxamide, di-$C_{1-6}$-alkylsulfonamide, $C_{1-6}$ haloalkoxy, $C_{1-6}$ haloalkyl, halogen, $C_{1-6}$ haloalkylsulfinyl, $C_{1-6}$ haloalkylsulfonyl, $C_{1-6}$ haloalkylthio, heterocyclic, hydroxyl, hydroxylamino and nitro.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Specific examples of GPR119 agonists disclosed in International Application No. PCT/US2005/019318 include the following compounds according to Formula (V) (referred to herein as Group E1): 4-[4-(3-Isopropyl-[1,2,4]oxadiazol-5-yl)-piperidin-1-yl]-6-(4-methanesulfonyl-phenoxy)-pyrimidine; {6-[4-(3-Isopropyl-[1,2,4]oxadiazol-5-yl)-piperidin-1-yl]-pyrimidin-4-yl}-(4-methanesulfonyl-phenyl)-amine; 4-{[6-(2-Fluoro-4-methanesulfonyl-phenylamino)-pyrimidin-4-yl]-methyl-amino}-piperidine-1-carboxylic acid tert-butyl ester; 4-({[6-(2-Fluoro-4-methanesulfonyl-phenylamino)-pyrimidin-4-yl]-methyl-amino}-methyl)-piperidine-1-carboxylic acid tert-butyl ester; 4-({[6-(4-Methanesulfonyl-phenylamino)-pyrimidin-4-yl]-methyl-amino}-methyl)-piperidine-1-carboxylic acid tert-butyl ester; 4-({[6-(2,5-Difluoro-benzylamino)-pyrimidin-4-yl]-methyl-amino}-methyl)-piperidine-1-carboxylic acid tert-butyl ester; 4-[({6-[(Benzo[1,3]dioxol-5-ylmethyl)-amino]-pyrimidin-4-yl}-methyl-amino)-methyl]-piperidine-1-carboxylic acid tert-butyl ester; (2-Fluoro-4-methanesulfonyl-phenyl)-{6-[4-(3-fluoro-phenoxy)-piperidin-1-yl]-pyrimidin-4-yl}-amine; 4-({Methyl-[6-(2-pyridin-4-yl-ethylamino)-pyrimidin-4-yl]-amino}-methyl)-piperidine-1-carboxylic acid tert-butyl ester; 4-({Methyl-[6-(2-pyridin-3-yl-ethylamino)-pyrimidin-4-yl]-amino}-methyl)-piperidine-1-carboxylic acid tert-butyl ester; 4-[(Methyl-{6-[(pyridin-3-ylmethyl)-amino]-pyrimidin-4-yl}-amino)-methyl]-piperidine-1-carboxylic acid tert-butyl ester; 4-[({6-[(2-Fluoro-4-methanesulfonyl-phenyl)-methyl-amino]-pyrimidin-4-yl}-methyl-amino)-methyl]-piperidine-1-carboxylic acid tert-butyl ester; 4-({[6-(2-Fluoro-4-methanesulfonyl-phenylamino)-pyrimidin-4-yl]-methyl-amino}-methyl)-piperidine-1-carboxylic acid isobutyl ester; 4-({[6-(4-Cyano-2-fluoro-phenylamino)-pyrimidin-4-yl]-methyl-amino}-methyl)-piperidine-1-carboxylic acid tert-butyl ester; 4-[({6-[4-(2-Methanesulfonyl-ethyl)-phenylamino]-pyrimidin-4-yl}-methyl-amino)-methyl]-piperidine-1-carboxylic acid tert-butyl ester; 4-({[6-(4-Ethylsulfanyl-phenylamino)-pyrimidin-4-yl]-methyl-amino}-methyl)-piperidine-1-carboxylic acid tert-butyl ester; 4-({[6-(4-Isopropylsulfanyl-phenylamino)-pyrimidin-4-yl]-methyl-amino}-methyl)-piperidine-1-carboxylic acid tert-butyl ester; 4-({[6-(4-Ethylsulfamoyl-phenylamino)-pyrimidin-4-yl]-methyl-amino}-methyl)-piperidine-1-carboxylic acid tert-butyl ester; 4-({Methyl-[6-(4-methylsulfamoyl-phenylamino)-pyrimidin-4-yl]-amino}-methyl)-piperidine-1-carboxylic acid tert-butyl ester; 4-({[6-(4-Dimethylsulfamoyl-phenylamino)-pyrimidin-4-yl]-methyl-amino}-methyl)-piperidine-1-carboxylic acid tert-butyl ester; 4-({Methyl-[6-(4-methylsulfamoylmethyl-phenylamino)-pyrimidin-4-yl]-amino}-methyl)-piperidine-1-carboxylic acid tert-butyl ester; 4-({Methyl-[6-(4-sulfamoyl-phenylamino)-pyrimidin-4-yl]-amino}-methyl)-piperidine-1-carboxylic acid tert-butyl ester; 4-({Methyl-[6-(4-[1,2,4]triazol-1-yl-phenylamino)-pyrimidin-4-yl]-amino}-methyl)-piperidine-1-carboxylic acid tert-butyl ester; 4-({Methyl-[6-(4-[1,2,4]triazol-1-ylmethyl-phenylamino)-pyrimidin-4-yl]-amino}-methyl)-piperidine-1-carboxylic acid tert-butyl ester; 4-[(Methyl-(6-[4-(2-[1,2,4]triazol-1-yl-ethyl)-phenylamino]-pyrimidin-4-yl)-amino)-methyl]-piperidine-1-carboxylic acid tert-butyl ester; 4-({[6-(Benzo[1,3]dioxol-5-ylamino)-pyrimidin-4-yl]-methyl-amino}-methyl)-piperidine-1-carboxylic acid tert-butyl ester; 4-({[6-(6-Methanesulfonyl-pyridin-3-ylamino)-pyrimidin-4-yl]-methyl-amino}-methyl)-piperidine-1-carboxylic acid tert-butyl ester; 4-({[6-(3,5-Dimethoxy-phenylamino)-pyrimidin-4-yl]-methyl-amino}-methyl)-piperidine-1-carboxylic acid tert-butyl ester; 4-[(Methyl-{6-[4-(2-oxo-oxazolidin-4-ylmethyl)-phenylamino]-pyrimidin-4-yl}-amino)-methyl]-piperidine-1-carboxylic acid tert-butyl ester; 4-[({6-[4-(1,1-Dioxo-1λ6-thiomorpholin-4-ylmethyl)-phenylamino]-pyrimidin-4-yl}-methyl-amino)-methyl]-piperidine-1-carboxylic acid tert-butyl ester; 4-({Methyl-[6-(4-pyrazol-1-yl-phenylamino)-pyrimidin-4-yl]-amino}-methyl)-piperidine-1-carboxylic acid tert-butyl ester; 4-({[6-(2,2-Difluoro-benzo[1,3]dioxol-5-ylamino)-pyrimidin-4-yl]-methyl-amino}-methyl)-piperidine-1-carboxylic acid tert-butyl ester; 4-({Methyl-[6-(4-trifluoromethanesulfonyl-phenylamino)-pyrimidin-4-yl]-amino}-methyl)-piperidine-1-carboxylic acid tert-butyl ester; 4-[(Methyl-{6-[4-(morpholine-4-sulfonyl)-phenylamino]-pyrimidin-4-yl}-amino)-methyl]-piperidine-1-carboxylic acid tert-butyl ester; 4-[(Methyl-{6-[2-(pyridine-2-carbonyl)-phenylamino]-pyrimidin-4-yl}-amino)-methyl]-piperidine-1-carboxylic acid tert-butyl ester; 4-({[6-(2-Fluoro-5-methanesulfonyl-phenylamino)-pyrimidin-4-yl]-methyl-amino}-methyl)-piperidine-1-carboxylic acid tert-butyl ester; N-Ethyl-3-fluoro-4-[6-(methyl-piperidin-4-ylmethyl-amino)-pyrimidin-4-ylamino]-benzenesulfonamide; 3-Fluoro-N-isopropyl-4-[6-(methyl-piperidin-4-ylmethyl-amino)-pyrimidin-4-ylamino]-benzenesulfonamide; 4-({[6-(3,4-Difluoro-phenylamino)-pyrimidin-4-yl]-methyl-amino}-methyl)-piperidine-1-carboxylic acid tert-butyl ester; 4-({[6-(2,6-Difluoro-phenylamino)-pyrimidin-4-yl]-methyl-amino}-methyl)-piperidine-1-carboxylic acid tert-butyl ester; 4-({[6-(2,5-Difluoro-phenylamino)-pyrimidin-4- yl]-methyl-amino}-methyl)-piperidine-1-carboxylic acid tert-butyl ester; 4-({[6-(2,3-Difluoro-phenylamino)-pyrimidin-4-yl]-methyl-amino}-methyl)-piperidine-1-carboxylic acid tert-butyl ester; 4-({Methyl-[6-(2,3,5-trifluoro-phenylamino)-pyrimidin-4-yl]-amino}-methyl)-piperidine-1-carboxylic acid tert-butyl ester; 4-({[6-(2-Fluoro-phenylamino)-pyrimidin-4-yl]-methyl-amino}-methyl)-piperidine-1-carboxylic acid tert-butyl ester; 4-({[6-(2-Fluoro-4-methyl-phenylamino)-pyrimidin-4-yl]-methyl-amino}-methyl)-piperidine-1-carboxylic acid tert-butyl ester; 4-({[6-(3-Chloro-2-fluoro-phenylamino)-pyrimidin-4-yl]-methyl-amino}-methyl)-piperidine-1-carboxylic acid tert-butyl ester; 4-({[6-(2,4-Difluoro-phenylamino)-pyrimidin-4-yl]-methyl-amino}-methyl)-piperidine-1-carboxylic acid tert-butyl ester; 4-[(Methyl-(6-[2-(1-oxy-pyridin-3-yl)-ethylamino]-pyrimidin-4-yl)-amino)-methyl]-piperidine-1-carboxylic acid tert-butyl ester; 4-[(Methyl-(6-[2-(1-oxy-pyridin-3-yl)-ethylamino]-pyrimidin-4-yl)-amino)-methyl]-piperidine-1-carboxylic acid isobutyl ester; 4-({[6-(2,5-Difluoro-phenylamino)-pyrimidin-4-yl]-methyl-amino}-methyl)-piperidine-1-carboxylic acid isobutyl ester; 4-({[6-(4-Cyano-2-fluoro-phenylamino)-pyrimidin-4-yl]-methyl-amino}-methyl)-piperidine-1-carboxylic acid isobutyl ester; 4-[({6-[2-(2-Fluoro-phenoxy)-ethylamino]-pyrimidin-4-yl}-methyl-amino)-methyl]-piperidine-1-carboxylic acid tert-butyl ester; 4-({[6-(2-Fluoro-phenoxy)-pyrimidin-4-yl]-methyl-amino}-methyl)-piperidine-1-carboxylic acid tert-butyl ester; 4-({[6-(2,5-Difluoro-phenoxy)-pyrimidin-4-yl]-methyl-amino}-methyl)-piperidine-1-carboxylic acid tert-butyl ester; 4-[({6-[2-(2-Chloro-phenoxy)-ethylamino]-pyrimidin-4-yl}-methyl-amino)-methyl]-piperidine-1-carboxylic acid tert-butyl ester; 4-({[6-(2-Chloro-phenoxy)-pyrimidin-4-yl]-methyl-amino}-methyl)-piperidine-1-carboxylic acid tert-butyl ester; 4-[({6-[2-(4-Fluoro-phenoxy)-propylamino]-pyrimidin-4-yl}-methyl-amino)-methyl]-piperidine-1-carboxylic acid tert-butyl ester; 4-({[6-(4-Ethylsulfamoyl-2-fluoro-phenylamino)-pyrimidin-4-yl]-methyl-amino}-methyl)-piperidine-1-carboxylic acid tert-butyl ester; 4-({[6-(2-Fluoro-4-isopropylsulfamoyl-phenylamino)-pyrimidin-4-yl]-methyl-amino}-methyl)-piperidine-1-carboxylic acid tert-butyl ester; 4-({[6-(4-Cyano-2,5-difluoro-phenylamino)-pyrimidin-4-yl]-methyl-amino}-methyl)-piperidine-1-carboxylic acid tert-butyl ester; 4-({[6-(4-Bromo-2,5-difluoro-phenylamino)-pyrimidin-4-yl]-methyl-amino}-methyl)-piperidine-1-carboxylic acid tert-butyl ester; 4-({[6-(5-Carboxy-2-fluoro-phenylamino)-pyrimidin-4-yl]-methyl-amino}-methyl)-piperidine-1-carboxylic acid tert-butyl ester; 4-({[6-(6-Methoxy-pyridin-3-ylamino)-pyrimidin-4-yl]-methyl-amino}-methyl)-piperidine-1-carboxylic acid tert-butyl ester; 4-({[6-(2,6-Dimethoxy-pyridin-3-ylamino)-pyrimidin-4-yl]-methyl-amino}-methyl)-piperidine-1-carboxylic acid tert-butyl ester; 6-{6-[(1-tert-Butoxycarbonyl-piperidin-4-ylmethyl)-methyl-amino]-pyrimidin-4-ylamino}-nicotinic acid; 4-({[6-(6-Acetylamino-pyridin-3-ylamino)-pyrimidin-4-yl]-methyl-amino}-methyl)-piperidine-1-carboxylic acid tert-butyl ester; 4-({[6-(5-Fluoro-pyridin-2-ylamino)-pyrimidin-4-yl]-methyl-amino}-methyl)-piperidine-1-carboxylic acid tert-butyl ester; 4-({[6-(4-Cyano-2-ethyl-phenylamino)-pyrimidin-4-yl]-methyl-amino}-methyl)-piperidine-1-carboxylic acid tert-butyl ester; 4-({[6-(4-Butyryl-phenylamino)-pyrimidin-4-yl]-methyl-amino}-methyl)-piperidine-1-carboxylic acid tert-butyl ester; 4-({[6-(5-Bromo-3-methyl-pyridin-2-ylamino)-pyrimidin-4-yl]-methyl-amino}-methyl)-piperidine-1-carboxylic acid tert-butyl ester; 4-({[6-(3-Bromo-5-methyl-pyridin-2-ylamino)-pyrimidin-4-yl]-methyl-amino}-methyl)-piperidine-1-carboxylic acid tert-butyl ester; 4-({Methyl-[6-(5-trifluoromethyl-pyridin-2-ylamino)-pyrimidin-4-yl]-amino}-methyl)-piperidine-1-carboxylic acid tert-butyl ester; 4-({[6-(4-Bromo-2-fluoro-phenylamino)-pyrimidin-4-yl]-methyl-amino}-methyl)-piperidine-1-carboxylic acid tert-butyl ester; 4-({[6-(3-Carboxy-4-fluoro-phenylamino)-pyrimidin-4-yl]-methyl-amino}-methyl)-piperidine-1-carboxylic acid tert-butyl ester; 4-({[6-(4-Ethoxycarbonyl-2-fluoro-phenylamino)-pyrimidin-4-yl]-methyl-amino}-methyl)-piperidine-1-carboxylic acid isobutyl ester; 4-({[6-(4-Carboxy-2-fluoro-phenylamino)-pyrimidin-4-yl]-methyl-amino}-methyl)-piperidine-1-carboxylic acid isobutyl ester; 4-({[6-(4-Cyano-2-fluoro-phenylamino)-pyrimidin-4-yl]-methyl-amino}-methyl)-piperidine-1-carboxylic acid isopropyl ester; 4-({[6-(4-Cyano-2-fluoro-phenylamino)-pyrimidin-4-yl]-methyl-amino}-methyl)-piperidine-1-carboxylic acid butyl ester; 4-({[6-(4-Cyano-2-fluoro-phenylamino)-pyrimidin-4-yl]-methyl-amino}-methyl)-piperidine-1-carboxylic acid cyclopropylmethyl ester; (4-[6-(2-Fluoro-4-methanesulfonyl-phenylamino)-pyrimidin-4-yl]-piperazin-1-yl)-acetic acid ethyl ester; (2-Fluoro-4-methanesulfonyl-phenyl)-(6-[4-(3-isopropyl-[1,2,4]oxadiazol-5-ylmethyl)-piperazin-1-yl]-pyrimidin-4-yl)-amine; 4-({[6-(2,5-Difluoro-4-hydroxy-phenylamino)-pyrimidin-4-yl]-methyl-amino}-methyl)-piperidine-1-carboxylic acid isobutyl ester; 4-({[6-(4-Ethylcarbamoyl-2-fluoro-phenylamino)-pyrimidin-4-yl]-methyl-amino}-methyl)-piperidine-1-carboxylic acid isobutyl ester; 4-[({6-[2-Fluoro-4-(N-hydroxycarbamimidoyl)-phenylamino]-pyrimidin-4-yl}-methyl-amino)-methyl]-piperidine-1-carboxylic acid isobutyl ester: 4-({[6-(2-Fluoro-4-methanesulfonyl-phenylamino)-pyrimidin-4-yl]-methyl-amino}-methyl)-piperidine-1-carboxylic acid 3-methyl-butyl ester; 4-({[6-(2,5-Difluoro-4-methanesulfonyl-phenylamino)-pyrimidin-4-yl]-methyl-amino}-methyl)-piperidine-1-carboxylic acid tert-butyl ester; 4-({[6-(2-Fluoro-4-methanesulfonyl-phenylamino)-pyrimidin-4-yl]-methyl-amino}-methyl)-piperidine-1-carboxylic acid isopropyl ester; (5-Butyl-pyridin-2-yl)-[4-({[6-(2-fluoro-4-methanesulfonyl-phenylamino)-pyrimidin-4-yl]-methyl-amino}-methyl)-piperidin-1-yl]-methanone; N-(2-Fluoro-4-methanesulfonyl-phenyl)-N'-(5'-fluoro-3,4,5,6-tetrahydro-2H-[1,2']bipyridinyl-4-ylmethyl)-N'-methyl-pyrimidine; -4,6-diamine; 4-({[6-(4-Carbamimidoyl-2-fluoro-phenylamino)-pyrimidin-4-yl]-methyl-amino}-methyl)-piperidine-1-carboxylic acid isobutyl ester; 4-({[6-(2-Fluoro-4-methanesulfonyl-phenylamino)-pyrimidin-4-yl]-methyl-amino}-methyl)-piperidine-1 carboxylic acid cyclobutyl ester; 4-[6-(2-Fluoro-4-methanesulfonyl-phenylamino)-pyrimidin-4-ylamino]-piperidine-1-carboxylic acid tert-butyl ester; N-(2-Fluoro-4-methanesulfonyl-phenyl)-N'-[1-(3-isopropyl-[1,2,4]oxadiazol-5-ylmethyl)-piperidin-4-ylmethyl]-N'-methyl-pyrimidine; -4,6-diamine; 4-({[6-(2-Fluoro-4-methanesulfonyl-phenylamino)-pyrimidin-4-yl]-methyl-amino}-methyl)-piperidine-1-carboxylic acid 1-ethyl-propyl ester; 4-({Ethyl-[6-(2-fluoro-4-methanesulfonyl-phenylamino)-pyrimidin-4-yl]-amino}-methyl)-piperidine-1-carboxylic acid tert-butyl ester; 4-({Ethyl-[6-(2-fluoro-4-methanesulfonyl-phenylamino)-pyrimidin-4-yl]-amino}-methyl)-piperidine-1-carboxylic acid isopropyl ester; 4-({[6-(4-Cyano-2,5-difluoro-phenylamino)-pyrimidin-4-yl]-ethyl-amino}-methyl)-piperidine-1-carboxylic acid isopropyl ester; 4-({[6-(4-Amino-2,5-difluoro-phenoxy)-pyrimidin-4-yl]-ethyl-amino}-methyl)-piperidine-1-carboxylic acid tert-butyl ester; 4-({[6-(2,5-Difluoro-4-methoxy-phenylamino)-pyrimidin-4-yl]-ethyl-amino}-methyl)-piperidine-1-carboxylic acid tert-butyl ester; 4-({[6-(2,5-Difluoro-4- methanesulfonyl-phenylamino)-pyrimidin-4-yl]-ethyl-amino}-methyl)-piperidine-1-carboxylic acid tert-butyl ester; 4-({Ethyl-[6-(2,4,5-trifluoro-phenylamino)-pyrimidin-4-yl]-amino}-methyl)-piperidine-1-carboxylic acid tert-butyl ester; (2-Fluoro-4-methanesulfonyl-phenyl)-{6-[4-(3-isopropyl-[1,2,4]oxadiazol-5-yl)-piperidin-1-yl]-pyrimidin-4-yl}-amine; 4-[(Ethyl-{6-[4-(N-ethylcarbamimidoyl)-2,5-difluoro-phenylamino]-pyrimidin-4-yl}-amino)-methyl]-piperidine-1-carboxylic acid isopropyl ester; 4-({[6-(4-Bromo-2,5-difluoro-phenylamino)-pyrimidin-4-yl]-ethyl-amino}-methyl)-piperidine-1-carboxylic acid tert-butyl ester; 4-[({6-[5-(2-Amino-ethylamino)-4-cyano-2-fluoro-phenylamino]-pyrimidin-4-yl}-ethyl-amino)-methyl]-piperidine-1-carboxylic acid isopropyl ester; {1-[6-(2-Fluoro-4-methanesulfonyl-phenylamino)-pyrimidin-4-yl]-piperidin-4-yl}-acetic acid methyl ester; 3-{4-[6-(2-Fluoro-4-methanesulfonyl-phenylamino)-pyrimidin-4-yl]-piperazin-1-yl}-propionic acid ethyl ester; (2-Fluoro-4-methanesulfonyl-phenyl)-(6-[4-(4-isobutyl-phenyl)-piperidin-1-yl]-pyrimidin-4-yl)-amine; (2-Fluoro-4-methanesulfonyl-phenyl)-{6-[4-(4-isopropyl-phenyl)-piperidin-1-yl]-pyrimidin-4-yl}-amine; {6-[4-(3-Cyclopropylmethyl-[1,2,4]oxadiazol-5-yl)-piperidin-1-yl]-pyrimidin-4-yl}-(2-fluoro-4-methanesulfonyl-phenyl)-amine; (2-Fluoro-4-methanesulfonyl-phenyl)-{6-[4-(3-isobutyl-[1,2,4]oxadiazol-5-yl)-piperidin-1-yl]-pyrimidin-4-yl}-amine; (2-Fluoro-4-methanesulfonyl-phenyl)-{6-[4-(4-isopropoxy-phenyl)-piperazin-1-yl]-pyrimidin-4-yl}-amine; (2-Fluoro-4-methanesulfonyl-phenyl)-{6-[4-(4-isopropoxy-phenyl)-piperidin-1-yl]-pyrimidin-4-yl}-amine; (2-Fluoro-4-methanesulfonyl-phenyl)-{6-[4-(5-isopropoxy-pyridin-2-yl)-piperazin-1-yl]-pyrimidin-4-yl}-amine; {6-[4-(3-Dimethylaminomethyl-[1,2,4]oxadiazol-5-yl)-piperidin-1-yl]-pyrimidin-4-yl}-(2-fluoro-4-methanesulfonyl-phenyl)-amine; (2-Fluoro-4-methanesulfonyl-phenyl)-(6-{4-[2-(3-isopropyl-[1,2,4]oxadiazol-5-yl)-ethyl]-piperazin-1-yl}-pyrimidin-4-yl)-amine; (2-Fluoro-4-methanesulfonyl-phenyl)-{6-[4-(5-isopropoxy-pyridin-2-yloxy)-piperidin-1-yl]-pyrimidin-4-yl}-amine; (2-Fluoro-4-methanesulfonyl-phenyl)-(6-[4-(3-pyridin-3-yl-[1,2,4]oxadiazol-5-yl)-piperidin-1-yl]-pyrimidin-4-yl)-amine; 2,5-Difluoro-4-{6-[4-(4-isopropoxy-phenyl)-piperazin-1-yl]-pyrimidin-4-ylamino}-benzonitrile; 4-{[6-(2-Fluoro-4-methanesulfonyl-phenylamino)-pyrimidin-4-ylamino]-methyl}-piperidine-1-carboxylic acid tert-butyl ester; 4-{[6-(2-Fluoro-4-methanesulfonyl-phenylamino)-pyrimidin-4-ylamino]-methyl}-piperidine-1-carboxylic acid isopropyl ester; 4-({[6-(2-Fluoro-4-methanesulfonyl-phenylamino)-pyrimidin-4-yl]-isopropyl-amino}-methyl)-piperidine-1-carboxylic acid tert-butyl ester; 4-({[4-(2-Fluoro-4-methanesulfonyl-phenylamino)-pyridin-2-yl]-methyl-amino}-methyl)-piperidine-1-carboxylic acid isobutyl ester; and 4-({[2-(2-Fluoro-4-methanesulfonyl-phenylamino)-pyridin-4-yl]-methyl-amino}-methyl)-piperidine-1-carboxylic acid isobutyl ester.

Specific examples of GPR119 agonists disclosed in International Application No. PCT/US2005/019318 include the following compounds according to Formula (V) (referred to herein as Group E2): 4-[6-(2-Fluoro-4-methanesulfonyl-phenylamino)-pyrimidin-4-yloxy]-piperidine-1-carboxylic acid tert-butyl ester; (2-Fluoro-4-methanesulfonyl-phenyl)-{6-[1-(3-isopropyl-[1,2,4]oxadiazol-5-ylmethyl)-piperidin-4-yloxy]-pyrimidin-4-yl}-amine; 4-[6-(2-Fluoro-4-methanesulfonyl-phenylamino)-pyrimidin-4-yloxy]-piperidine-1-carboxylic acid isopropyl ester; (6-Chloro-pyridin-2-yl)-{4-[6-(2-fluoro-4-methanesulfonyl-phenylamino)-pyrimidin-4-yloxy]-piperidin-1-yl}-methanone; (6-Bromo-pyridin-2-yl)-{4-[6-(2-fluoro-4-methanesulfonyl-phenylamino)-pyrimidin-4-yloxy]-piperidin-1-yl}-methanone; {4-[6-(2-Fluoro-4-methanesulfonyl-phenylamino)-pyrimidin-4-yloxy]-piperidin-1-yl}-(6-methyl-pyridin-2-yl)-methanone; {4-[6-(2-Fluoro-4-methanesulfonyl-phenylamino)-pyrimidin-4-yloxy]-piperidin-1-yl}-(6-fluoro-pyridin-2-yl)-methanone; {4-[6-(2-Fluoro-4-methanesulfonyl-phenylamino)-pyrimidin-4-yloxy]-piperidin-1-yl}-pyridin-2-yl-methanone; (5-Bromo-pyridin-3-yl)-{4-[6-(2-fluoro-4-methanesulfonyl-phenylamino)-pyrimidin-4-yloxy]-piperidin-1-yl}-methanone; {4-[6-(2-Fluoro-4-methanesulfonyl-phenylamino)-pyrimidin-4-yloxy]-piperidin-1-yl}-(5-methyl-pyridin-3-yl)-methanone; (5,6-Dichloro-pyridin-3-yl)-{4-[6-(2-fluoro-4-methanesulfonyl-phenylamino)-pyrimidin-4-yloxy]-piperidin-1-yl}-methanone; 4-[6-(4-Cyano-2,5-difluoro-phenylamino)-pyrimidin-4-yloxy]-piperidine-1-carboxylic acid tert-butyl ester; 4-[6-(2,5-Difluoro-4-methanesulfonyl-phenylamino)-pyrimidin-4-yloxy]-piperidine-1-carboxylic acid tert-butyl ester; 4-[6-(2,4,5-Trifluoro-phenylamino)-pyrimidin-4-yloxy]-piperidine-1-carboxylic acid tert-butyl ester; 4-[6-(4-Bromo-2,5-difluoro-phenylamino)-pyrimidin-4-yloxy]-piperidine-1-carboxylic acid tert-butyl ester; 4-[6-(3-Fluoro-4-methyl-phenylamino)-pyrimidin-4-yloxy]-piperidine-1-carboxylic acid tert-butyl ester; 4-[6-(3-Hydroxy-4-methoxy-phenylamino)-pyrimidin-4-yloxy]-piperidine-1-carboxylic acid tert-butyl ester; 4-[6-(6-Cyano-pyridin-3-ylamino)-pyrimidin-4-yloxy]-piperidine-1-carboxylic acid tert-butyl ester; 4-[6-(3-Chloro-4-cyano-phenylamino)-pyrimidin-4-yloxy]-piperidine-1-carboxylic acid tert-butyl ester; 4-[6-(6-Chloro-pyridin-3-ylamino)-pyrimidin-4-yloxy]-piperidine-1-carboxylic acid tert-butyl ester; 4-[6-(3-Fluoro-4-methoxy-phenylamino)-pyrimidin-4-yloxy]-piperidine-1-carboxylic acid tert-butyl ester; 4-[6-(3,4-Dimethoxy-phenylamino)-pyrimidin-4-yloxy]-piperidine-1-carboxylic acid tert-butyl ester; 4-[6-(2,3-Dihydro-benzo[1,4]dioxin-6-ylamino)-pyrimidin-4-yloxy]-piperidine-1-carboxylic acid tert-butyl ester; 4-[6-(4-Cyano-2,5-difluoro-phenylamino)-pyrimidin-4-yloxy]-piperidine-1-carboxylic acid isopropyl ester; 4-[6-(4-Cyano-5-ethylamino-2-fluoro-phenylamino)-pyrimidin-4-yloxy]-piperidine-1-carboxylic acid tert-butyl ester; 4-[6-(4-Ethoxy-2,5-difluoro-phenylamino)-pyrimidin-4-yloxy]-piperidine-1-carboxylic acid isopropyl ester; 4-[6-(4-Ethylsulfanyl-phenylamino)-pyrimidin-4-yloxy]-piperidine-1-carboxylic acid tert-butyl ester; 4-[6-(4-Isopropylsulfanyl-phenylamino)-pyrimidin-4-yloxy]-piperidine-1-carboxylic acid tert-butyl ester; (5-Butyl-pyridin-2-yl)-{4-[6-(2-fluoro-4-methanesulfonyl-phenylamino)-pyrimidin-4-yloxy]-piperidin-1-yl}-methanone; 4-[6-(5-Chloro-3-methyl-pyridin-2-ylamino)-pyrimidin-4-yloxy]-piperidine-1-carboxylic acid tert-butyl ester; 4-[6-(6-Acetylamino-4-methyl-pyridin-3-ylamino)-pyrimidin-4-yloxy]-piperidine-1-carboxylic acid tert-butyl ester; 4-[6-(5-Fluoro-4-methyl-pyridin-2-ylamino)-pyrimidin-4-yloxy]-piperidine-1-carboxylic acid tert-butyl ester; 4-[6-(6-Methoxy-5-methyl-pyridin-3-ylamino)-pyrimidin-4-yloxy]-piperidine-1-carboxylic acid tert-butyl ester; 4-[6-(6-Methoxy-2-methyl-pyridin-3-ylamino)-pyrimidin-4-yloxy]-piperidine-1-carboxylic acid tert-butyl ester; 4-[6-(6-Fluoro-5-methyl-pyridin-3-ylamino)-pyrimidin-4-yloxy]-piperidine-1-carboxylic acid tert-butyl ester; 4-[6-(2-Chloro-6-methyl-pyridin-3-ylamino)-pyrimidin-4-yloxy]-piperidine-1-carboxylic acid tert-butyl ester; 4-[6-(4-Methyl-pyridin-3-ylamino)-pyrimidin-4-yloxy]-piperidine-1-carboxylic acid tert-butyl ester; 4-[6-(2-Methyl-pyridin-3-ylamino)-pyrimidin-4-yloxy]-piperidine-1-carboxylic acid tert-butyl ester; 4-[6-(6-Chloro-2-methyl-pyridin-3-ylamino)-pyrimidin-4-yloxy]-piperidine-1-carboxylic acid tert-butyl ester; 4-[6-(6-Fluoro-pyridin-3-ylamino)-pyrimidin-4-yloxy]-piperidine-1-carboxylic acid tert-butyl ester; 4-[6-(2-Chloro-4-methyl-pyridin-3-ylamino)-pyrimidin-4-yloxy]-piperidine-1-carboxylic acid tert-butyl ester; 4-[6-(6-Methoxy-pyridin-3-ylamino)-pyrimidin-4-yloxy]-piperidine-1-carboxylic acid tert-butyl ester; 4-[6-(5-Fluoro-pyridin-2-ylamino)-pyrimidin-4-yloxy]-piperidine-1-carboxylic acid tert-butyl ester; 4-[6-(2-Fluoro-pyridin-3-ylamino)-pyrimidin-4-yloxy]-piperidine-1-carboxylic acid tert-butyl ester; 4-[6-(6-Chloro-5-methyl-pyridin-3-ylamino)-pyrimidin-4-yloxy]-piperidine-1-carboxylic acid tert-butyl ester; 4-[6-(2-Methyl-pyridin-4-ylamino)-pyrimidin-4-yloxy]-piperidine-1-carboxylic acid tert-butyl ester; 4-[6-(2-Methoxy-pyridin-3-ylamino)-pyrimidin-4-yloxy]-piperidine-1-carboxylic acid tert-butyl ester; 4-[6-(2,5-Difluoro-phenylamino)-pyrimidin-4-yloxy]-piperidine-1-carboxylic acid tert-butyl ester; 4-[6-(4-Chloro-2-fluoro-phenylamino)-pyrimidin-4-yloxy]-piperidine-1-carboxylic acid tert-butyl ester; 4-[6-(2,5-Difluoro-phenylamino)-pyrimidin-4-yloxy]-piperidine-1-carboxylic acid isopropyl ester; 4-[6-(6-Methoxy-pyridin-3-ylamino)-pyrimidin-4-yloxy]-piperidine-1-carboxylic acid isopropyl ester; 4-[6-(4-Cyano-3-methoxy-phenylamino)-pyrimidin-4-yloxy]-piperidine-1-carboxylic acid isopropyl ester; 4-[6-(3-Fluoro-4-hydroxy-phenylamino)-pyrimidin-4-yloxy]-piperidine-1-carboxylic acid isopropyl ester; 4-[6-(6-Ethoxy-pyridin-3-ylamino)-pyrimidin-4-yloxy]-piperidine-1-carboxylic acid isopropyl ester; 4-[6-(2,5-Difluoro-4-isopropoxy-phenylamino)-pyrimidin-4-yloxy]-piperidine-1-carboxylic acid isopropyl ester; (2-Fluoro-4-methanesulfonyl-phenyl)-[6-(5'-isopropoxy-3,4,5,6-tetrahydro-2H-[1,2']bipyridinyl-4-yloxy)-pyrimidin-4-yl]-amine; (2-Fluoro-4-methanesulfonyl-phenyl)-{6-[1-(3-isopropyl-[1,2,4]oxadiazol-5-yl)-piperidin-4-yloxy]-pyrimidin-4-yl}-amine; 4-[6-(4-Cyano-2-fluoro-phenylamino)-pyrimidin-4-yloxy]-piperidine-1-carboxylic acid isopropyl ester; 4-[6-(Pyridin-3-ylamino)-pyrimidin-4-yloxy]-piperidine-1-carboxylic acid isopropyl ester; 4-[6-(Pyridin-4-ylamino)-pyrimidin-4-yloxy]-piperidine-1-carboxylic acid isopropyl ester; 4-[6-(2,5-Difluoro-4-propoxy-phenylamino)-pyrimidin-4-yloxy]-piperidine-1-carboxylic acid isopropyl ester; 4-[6-(4-Ethylamino-2-fluoro-phenylamino)-pyrimidin-4-yloxy]-piperidine-1-carboxylic acid isopropyl ester; 4-[6-(4-Dimethylamino-2-fluoro-phenylamino)-pyrimidin-4-yloxy]-piperidine-1-carboxylic acid isopropyl ester; 4-[6-(2-Fluoro-4-propylamino-phenylamino)-pyrimidin-4-yloxy]-piperidine-1-carboxylic acid isopropyl ester; 4-[6-(2-Fluoro-4-isopropylamino-phenylamino)-pyrimidin-4-yloxy]-piperidine-1-carboxylic acid isopropyl ester; 4-[6-(2-Methyl-6-propylamino-pyridin-3-ylamino)-pyrimidin-4-yloxy]-piperidine-1-carboxylic acid isopropyl ester; 4-[6-(2-Methyl-pyridin-3-ylamino)-pyrimidin-4-yloxy]-piperidine-1-carboxylic acid isopropyl ester; 4-[6-(6-Isopropylamino-2-methyl-pyridin-3-ylamino)-pyrimidin-4-yloxy]-piperidine-1-carboxylic acid isopropyl ester; 4-[6-(2-Methyl-6-propoxy-pyridin-3-ylamino)-pyrimidin-4-yloxy]-piperidine-1-carboxylic acid isopropyl ester; 4-[6-(4-Iodo-2-methyl-phenylamino)-pyrimidin-4-yloxy]-piperidine-1-carboxylic acid isopropyl ester; 4-[6-(2-Fluoro-4-iodo-phenylamino)-pyrimidin-4-yloxy]-piperidine-1-carboxylic acid isopropyl ester; 4-{6-[Methyl-(2-methyl-4,5,6,7-tetrahydro-2H-indazol-3-yl)-amino]-pyrimidin-4-yloxy}-piperidine-1-carboxylic acid isopropyl ester; 4-[6-(2-Methyl-2H-pyrazol-3-ylamino)-pyrimidin-4-yloxy]-piperidine-1-carboxylic acid isopropyl ester; 4-[6-(2-Phenyl-2H-pyrazol-3-ylamino)-pyrimidin-4-yloxy]-piperidine-1-carboxylic acid isopropyl ester; 4-[6-(5-tert-Butyl-1H-pyrazol-3-ylamino)-pyrimidin-4-yloxy]-piperidine-1-carboxylic acid isopropyl ester; 4-[6-(5-p-Tolyl-1H-pyrazol-3-ylamino)-pyrimidin-4-yloxy]-piperidine-1-carboxylic acid isopropyl ester; 4-[6-(6-Methoxy-5-methyl-pyridin-3-ylamino)-pyrimidin-4-yloxy]-piperidine-1-carboxylic acid isopropyl ester; 4-[6-(4-Methyl-pyridin-3-ylamino)-pyrimidin-4-yloxy]-piperidine-1-carboxylic acid isopropyl ester; 4-[6-(4-Acetylamino-3-methyl-phenylamino)-pyrimidin-4-yloxy]-piperidine-1-carboxylic acid isopropyl ester; 4-[6-(3-Chloro-4-fluoro-phenylamino)-pyrimidin-4-yloxy]-piperidine-1-carboxylic acid isopropyl ester; 4-[6-(3,5-Dimethoxy-phenylamino)-pyrimidin-4-yloxy]-piperidine-1-carboxylic acid isopropyl ester; 4-[6-(6-Ethyl-pyridin-2-ylamino)-pyrimidin-4-yloxy]-piperidine-1-carboxylic acid isopropyl ester; 4-[6-(5-Methyl-pyridin-2-ylamino)-pyrimidin-4-yloxy]-piperidine-1-carboxylic acid isopropyl ester; 4-[6-(2-Methyl-quinolin-6-ylamino)-pyrimidin-4-yloxy]-piperidine-1-carboxylic acid isopropyl ester; 4-[6-(2-Methylsulfanyl-benzothiazol-6-ylamino)-pyrimidin-4-yloxy]-piperidine-1-carboxylic acid isopropyl ester; 4-[6-(6-Morpholin-4-yl-pyridin-3-ylamino)-pyrimidin-4-yloxy]-piperidine-1-carboxylic acid isopropyl ester; 4-[6-(4-Benzenesulfonyl-thiophen-3-ylamino)-pyrimidin-4-yloxy]-piperidine-1-carboxylic acid isopropyl ester; 4-[6-(4-Piperidin-1-yl-phenylamino)-pyrimidin-4-yloxy]-piperidine-1-carboxylic acid isopropyl ester; 4-[6-(3-Trifluoromethoxy-phenylamino)-pyrimidin-4-yloxy]-piperidine-1-carboxylic acid isopropyl ester; 4-[6-(5-Oxo-5,6,7,8-tetrahydro-naphthalen-2-ylamino)-pyrimidin-4-yloxy]-piperidine-1-carboxylic acid isopropyl ester; 4-[6-(6-Methyl-1H-pyrazolo[3,4-b]pyridin-3-ylamino)-pyrimidin-4-yloxy]-piperidine-1-carboxylic acid isopropyl ester; 4-[6-(5-Cyano-pyridin-2-ylamino)-pyrimidin-4-yloxy]-piperidine-1-carboxylic acid isopropyl ester; 4-[6-(4-Bromo-2,5-difluoro-phenylamino)-pyrimidin-4-yloxy]-piperidine-1-carboxylic acid isopropyl ester; 4-[6-(4-Trifluoromethyl-pyridin-2-ylamino)-pyrimidin-4-yloxy]-piperidine-1-carboxylic acid isopropyl ester; 4-[6-(5-Methyl-1H-pyrazol-3-ylamino)-pyrimidin-4-yloxy]-piperidine-1-carboxylic acid isopropyl ester; 4-[6-(5-Cyclopropyl-1H-pyrazol-3-ylamino)-pyrimidin-4-yloxy]-piperidine-1-carboxylic acid isopropyl ester; 4-[6-(2,6-Dimethyl-pyridin-3-ylamino)-pyrimidin-4-yloxy]-piperidine-1-carboxylic acid isopropyl ester; 4-[6-(4-Cyano-2-methyl-phenylamino)-pyrimidin-4-yloxy]-piperidine-1-carboxylic acid isopropyl ester; 4-[6-(4-Methoxy-2-methyl-phenylamino)-pyrimidin-4-yloxy]-piperidine-1-carboxylic acid isopropyl ester; 4-[6-(2,4-Dimethoxy-phenylamino)-pyrimidin-4-yloxy]-piperidine-1-carboxylic acid isopropyl ester; 4-{6-[Acetyl-(2-fluoro-4-methanesulfonyl-phenyl)-amino]-pyrimidin-4-yloxy}-piperidine-1-carboxylic acid isopropyl ester; 4-[6-(5-Carbamoyl-pyridin-2-ylamino)-pyrimidin-4-yloxy]-piperidine-1-carboxylic acid isopropyl ester; 4-{6-[4-(3,4-Difluoro-phenyl)-thiazol-2-ylamino]-pyrimidin-4-yloxy}-piperidine-1-carboxylic acid isopropyl ester; 4-[6-(5-Oxo-1-phenyl-4,5-dihydro-1H-pyrazol-3-ylamino)-pyrimidin-4-yloxy]-piperidine-1-carboxylic acid isopropyl ester; 4-[6-(3-Oxazol-5-yl-phenylamino)-pyrimidin-4-yloxy]-piperidine-1-carboxylic acid isopropyl ester; 4-[6-(5-Trifluoromethyl-pyridin-2-ylamino)-pyrimidin-4-yloxy]-piperidine-1-carboxylic acid isopropyl ester; 4-[6-(4-Chloro-2-trifluoromethoxy-phenylamino)-pyrimidin-4-yloxy]-piperidine-1-carboxylic acid isopropyl ester; 4-{6-[(5-Pyridin-2-yl-thiophen-2-ylmethyl)-amino]-pyrimidin-4-yloxy}-piperidine-1-carboxylic acid isopropyl ester; 4-{6-[5-(4-Chloro-phenyl)-2H-pyrazol-3-ylamino]-pyrimidin-4-yloxy}-piperidine-1-carboxylic acid isopropyl ester; 4-[6-(1-Oxo-indan-5-ylamino)-pyrimidin-4-yloxy]-piperidine-1- carboxylic acid isopropyl ester; 4-{6-[5-(1-Methyl-pyrrolidin-2-yl)-pyridin-2-ylamino]-pyrimidin-4-yloxy}-piperidine-1-carboxylic acid isopropyl ester; 4-[6-(6-Methoxy-2-methyl-pyridin-3-ylamino)-pyrimidin-4-yloxy]-piperidine-1-carboxylic acid isopropyl ester; 4-[6-(5-Bromo-3-methyl-pyridin-2-ylamino)-pyrimidin-4-yloxy]-piperidine-1-carboxylic acid isopropyl ester; 4-[6-(2-Chloro-6-methyl-pyridin-3-ylamino)-pyrimidin-4-yloxy]-piperidine-1-carboxylic acid isopropyl ester; 4-[6-(2-Ethynyl-phenylamino)-pyrimidin-4-yloxy]-piperidine-1-carboxylic acid isopropyl ester; 4-[6-(4-Bromo-2-trifluoromethoxy-phenylamino)-pyrimidin-4-yloxy]-piperidine-1-carboxylic acid isopropyl ester; 4-[6-(3-Iodo-4-methyl-phenylamino)-pyrimidin-4-yloxy]-piperidine-1-carboxylic acid isopropyl ester; 4-[6-(2-Fluoro-5-methyl-phenylamino)-pyrimidin-4-yloxy]-piperidine-1-carboxylic acid isopropyl ester; 4-{6-[5-(4-Methoxy-phenyl)-[1,3,4]thiadiazol-2-ylamino]-pyrimidin-4-yloxy}-piperidine-1-carboxylic acid isopropyl ester; 4-[6-(3,5-Dimethyl-isoxazol-4-ylamino)-pyrimidin-4-yloxy]-piperidine-1-carboxylic acid isopropyl ester; 4-[2-(2,5-Difluoro-4-propoxy-phenylamino)-pyridin-4-yloxy]-piperidine-1-carboxylic acid isopropyl ester; 4-[6-(2,5-Difluoro-4-propylamino-phenylamino)-pyrimidin-4-yloxy]-piperidine-1-carboxylic acid isopropyl ester; 4-[6-(2,5-Difluoro-4-morpholin-4-yl-phenylamino)-pyrimidin-4-yloxy]-piperidine-1-carboxylic acid isopropyl ester; 4-[6-(2-Methyl-4-propylamino-phenylamino)-pyrimidin-4-yloxy]-piperidine-1-carboxylic acid isopropyl ester; 4-{6-[2,5-Difluoro-4-(4-methyl-piperazin-1-yl)-phenylamino]-pyrimidin-4-yloxy}-piperidine-1-carboxylic acid isopropyl ester; 4-{6-[2,5-Difluoro-4-(2-pyrrolidin-1-yl-ethoxy)-phenylamino]-pyrimidin-4-yloxy}-piperidine-1-carboxylic acid isopropyl ester; 4-{6-[4-(2-Dimethylamino-ethoxy)-2,5-difluoro-phenylamino]-pyrimidin-4-yloxy}-piperidine-1-carboxylic acid isopropyl ester; 4-{6-[2,5-Difluoro-4-(2-morpholin-4-yl-ethoxy)-phenylamino]-pyrimidin-4-yloxy}-piperidine-1-carboxylic acid isopropyl ester; 4-[6-(2,4-Difluoro-phenylamino)-pyrimidin-4-yloxy]-piperidine-1-carboxylic acid isopropyl ester; 4-[6-(2,4,5-Trifluoro-phenylamino)-pyrimidin-4-yloxy]-piperidine-1-carboxylic acid isopropyl ester; 4-[6-(4-Methanesulfonyl-phenylamino)-pyrimidin-4-yloxy]-piperidine-1-carboxylic acid isopropyl ester; 4-{6-[Acetyl-(4-methanesulfonyl-phenyl)-amino]-pyrimidin-4-yloxy}-piperidine-1-carboxylic acid isopropyl ester; (2,5-Difluoro-4-propoxy-phenyl)-{6-[1-(5-isopropyl-[1,2,4]oxadiazol-3-yl)-piperidin-4-yloxy]-pyrimidin-4-yl}-amine; 4-{6-[2,5-Difluoro-4-(morpholin-4-ylamino)-phenylamino]-pyrimidin-4-yloxy}-piperidine-1-carboxylic acid isopropyl ester; 4-{6-[2,5-Difluoro-4-(2-methoxy-ethylamino)-phenylamino]-pyrimidin-4-yloxy}-piperidine-1-carboxylic acid isopropyl ester; 4-(6-{2,5-Difluoro-4-[(tetrahydro-furan-2-ylmethyl)-amino]-phenylamino}-pyrimidin-4-yloxy)-piperidine-1-carboxylic acid isopropyl ester; 4-[6-(4-Butylamino-2,5-difluoro-phenylamino)-pyrimidin-4-yloxy]-piperidine-1-carboxylic acid isopropyl ester; 4-({6-[2,5-Difluoro-4-(3-methyl-butylamino)-phenylamino]-pyrimidin-4-yloxy}-piperidine-1-carboxylic acid isopropyl ester; 4-[6-(2-Fluoro-4-methanesulfonyl-phenylamino)-2-methyl-pyrimidin-4-yloxy]-piperidine-1-carboxylic acid isopropyl ester; 4-{6-[2,5-Difluoro-4-(2-morpholin-4-yl-ethylamino)-phenylamino]-pyrimidin-4-yloxy}-piperidine-1-carboxylic acid isopropyl ester; 4-{6-[2-(2,5-Difluoro-phenoxy)-ethylamino]-pyrimidin-4-yloxy}-piperidine-1-carboxylic acid isopropyl ester; 4-[6-(2,5-Difluoro-phenoxy)-pyrimidin-4-yloxy]-piperidine-1-carboxylic acid isopropyl ester; 4-[6-(4-Bromo-2-fluoro-phenoxy)-pyrimidin-4-yloxy]-piperidine-1-carboxylic acid isopropyl ester; 4-[6-(2-Fluoro-4-morpholin-4-yl-phenoxy)-pyrimidin-4-yloxy]-piperidine-1-carboxylic acid isopropyl ester; 4-{6-[2,5-Difluoro-4-(tetrahydro-furan-2-ylmethoxy)-phenylamino]-pyrimidin-4-yloxy}-piperidine-1-carboxylic acid isopropyl ester; 4-[6-(2-Fluoro-4-methanesulfonyl-phenylamino)-pyridin-2-yloxy]-piperidine-1-carboxylic acid tert-butyl ester; 4-[5-(2-Fluoro-4-methanesulfonyl-phenylamino)-pyridin-3-yloxy]-piperidine-1-carboxylic acid tert-butyl ester; 4-[6-(2-Fluoro-4-methanesulfonyl-phenylamino)-pyridin-2-yloxy]-piperidine-1-carboxylic acid isopropyl ester; 4-[4-(2-Fluoro-4-methanesulfonyl-phenylamino)-pyridin-2-yloxy]-piperidine-1-carboxylic acid isopropyl ester; 4-[4-(2,5-Difluoro-4-propoxy-phenylamino)-pyridin-2-yloxy]-piperidine-1-carboxylic acid isopropyl ester; and 4-[2-(2-Fluoro-4-methanesulfonyl-phenylamino)-pyridin-4-yloxy]-piperidine-1-carboxylic acid isopropyl ester; 4-[2-(2,5-Difluoro-4-propoxy-phenylamino)-pyridin-4-yloxy]-piperidine-1-carboxylic acid isopropyl ester.

Examples of GPR119 agonists are described in International. Application No. PCT/GB2004/050046 (published as WO 2005/061489), the disclosure of which is herein incorporated by reference in its entirety. Disclosed in International Application No. PCT/GB2004/050046 as a GPR119 agonist is a compound of Formula (VI):

$R^1$-A-V—B—$R^2$      (VI)

wherein:

V is a 5-membered heteroaryl ring containing up to four heteroatoms selected from O, N and S, optionally substituted by $C_{1-4}$ alkyl;

A is —CH=CH— or $(CH_2)_n$;

B is —CH=CH— or $(CH_2)_n$, where one of the $CH_2$ groups may be replaced by O, $NR^5$, $S(O)_m$, C(O) or $C(O)NR^{12}$;

n is independently 0, 1, 2 or 3;

m is independently 0, 1 or 2;

$R^1$ is 3- or 4-pyridyl, 4- or 5-pyrimidinyl or 2-pyrazinyl, any of which may be optionally substituted by one or more substituents selected from halo, $C_{1-4}$ alkyl, $C_{1-4}$ fluoroalkyl, $C_{2-4}$ alkenyl, $C_{2-4}$ alkynyl, $C_{3-7}$ cycloalkyl, aryl, $OR^6$, CN, $NO_2$, $S(O)_mR^6$, $CON(R^6)_2$, $N(R^6)_2$, $NR^{10}COR^6$, $NR^{10}SO_2R^6$, $SO_2N(R^6)_2$, a 4- to 7-membered heterocyclyl group or a 5- or 6-membered heteroaryl group;

$R^2$ is 4- to 7-membered cycloalkyl substituted by $R^3$, C(O)$OR^3$, $C(O)R^3$ or $S(O)_2R^3$, or 4- to 7-membered heterocyclyl, containing one or two nitrogen atoms which is unsubstituted or substituted by $C(O)OR^4$, $C(O)R^3$, $S(O)_2R^3$, $C(O)NHR^4$, $P(O)(OR^{11})_2$ or a 5- or 6-membered nitrogen containing heteroaryl group;

$R^3$ is $C_{3-8}$ alkyl, $C_{3-8}$ alkenyl or $C_{3-8}$ alkynyl, any of which may be optionally substituted with up to 5 fluoro or chloro atoms, and may contain a $CH_2$ group that may be replaced by O, or $C_{3-7}$ cycloalkyl, aryl, heterocyclyl, heteroaryl, $C_{1-4}$ alkyl$C_{3-7}$ cycloalkyl, $C_{1-4}$ alkylaryl, $C_{1-4}$ alkylheterocyclyl or $C_{1-4}$ alkylheteroaryl, any of which may be optionally substituted with one or more substituents selected from halo, $C_{1-4}$ alkyl, $C_{1-4}$ fluoroalkyl, $OR^6$, CN, $CO_2C_{1-4}$ alkyl, $N(R^6)_2$ and $NO_2$;

$R^4$ is $C_{2-8}$ alkyl, $C_{2-8}$ alkenyl or $C_{2-8}$ alkynyl, any of which may be optionally substituted with up to 5 fluoro or chloro atoms, and may contain a $CH_2$ group that may be replaced by O, or $C_{3-7}$ cycloalkyl, aryl, heterocyclyl, heteroaryl, $C_{1-4}$ alkyl$C_{3-7}$ cycloalkyl, $C_{1-4}$ alkylaryl, $C_{1-4}$ alkylheterocyclyl or $C_{1-4}$ alkylheteroaryl, any of which may be substituted with one or more substituents selected from halo, $C_{1-4}$ alkyl, $C_{1-4}$ fluoroalkyl, $OR^6$, CN, $CO_2C_{1-4}$ alkyl, $N(R^6)_2$ and $NO_2$;

R⁵ is hydrogen, C(O)R⁷, S(O)₂R⁸, $C_{3-7}$ cycloalkyl or $C_{1-4}$ alkyl optionally substituted by OR⁶, $C_{3-7}$ cycloalkyl, aryl, heterocyclyl or heteroaryl, wherein the cyclic groups may be substituted with one or more substituents selected from halo, $C_{1-2}$ alkyl, $C_{1-2}$ fluoroalkyl, OR⁶, CN, N(R⁶)₂ and NO₂;

R⁶ are independently hydrogen, $C_{1-4}$ alkyl, $C_{3-7}$ cycloalkyl, aryl, heterocyclyl or heteroaryl, wherein the cyclic groups may be substituted with one or more substituents selected from halo, $C_{1-4}$ alkyl, $C_{1-4}$ fluoroalkyl, OR⁹, CN, SO₂CH₃, N(R¹⁰)₂ and NO₂; or a group (N(R¹⁰)₂ may form a 4- to 7-membered heterocyclic ring optionally containing a further heteroatom selected from O and NR¹⁰;

R⁷ is hydrogen, $C_{1-4}$ alkyl, OR⁶, N(R⁶)₂, aryl or heteroaryl;
R⁸ is $C_{1-4}$ alkyl, $C_{1-4}$-fluoroalkyl, aryl or heteroaryl;
R⁹ is hydrogen, $C_{1-2}$ alkyl or $C_{1-2}$ fluoroalkyl;
R¹⁰ is hydrogen or $C_{1-4}$ alkyl;
R¹¹ is phenyl; and
R¹² is hydrogen, $C_{1-4}$ alkyl or $C_{3-7}$ cycloalkyl.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Specific examples of GPR119 agonists disclosed in International Application No. PCT/GB2004/050046 include the following compounds according to Formula (VI) (referred to herein as Group F1): 4-(3-Pyridin-4-yl-[1,2,4]oxadiazol-5-ylmethoxy)piperidine-1-carboxylic acid tert-butyl ester; 4-(3-Pyridin-4-yl-[1,2,4]oxadiazol-5-yl)piperidine-1-carboxylic acid tert-butyl ester; 3-(3-Pyridin-4-yl-[1,2,4]oxadiazol-5-ylmethoxy)piperidine-1-carboxylic acid tert-butyl ester; 4-[5-(4-Pentylcyclohexylmethyl)-[1,2,4]oxadiazol-3-yl]pyridine; trans-2-Chloro-4-[5-(4-pentylcyclohexane)-[1,2,4]oxadiazol-3-yl]pyridine; trans-4-[5-(4-Pentylcyclohexane)-[1,2,4]oxadiazol-3-ylmethyl]pyridine; 4-(3-Pyridin-4-ylmethyl-[1,2,4]oxadiazol-5-yl)piperidine-1-carboxylic acid tert-butyl ester; trans-3-[5-(4-Pentylcyclohexyl)-[1,2,4]oxadiazol-3-ylmethyl]pyridine; 4-[5-(4-Butylcyclohexane)-[1,2,4]oxadiazol-3-yl]pyridine; 4-[5-(4-n-Propylcyclohexyl)-[1,2,4]oxadiazol-3-yl]pyridine; trans-4-[5-(4-Pentylcyclohexane)-[1,2,4]oxadiazol-3-yl]pyridine; 4-[2-(3-Pyridin-4-yl-[1,2,4]oxadiazol-5-yl)-ethyl]piperidine-1-carboxylic acid tert-butyl ester; 4-(3-Pyridin-4-yl-[1,2,4]oxadiazol-5-ylmethyl)piperidine-1-carboxylic acid tert-butyl ester; 3-[5-(4-Propylcyclohexyl)-[1,2,4]oxadiazol-3-yl]pyridine; 3-[5-(4-Butylcyclohexane)-[1,2,4]oxadiazol-3-yl]pyridine; trans-4-[3-(4-Pentylcyclohexyl)-[1,2,4]oxadiazol-5-yl]pyridine-2-carboxylic acid methylamide; trans-4-[5-(4-(4-Pentylcyclohexyl)-[1,2,4]oxadiazol-3-yl]pyridine-2-carboxylic acid amide; trans-4-[3-(4-Pentylcyclohexyl)-[1,2,4]oxadiazol-5-yl]pyridine; trans-2-Chloro-4-[3-(4-pentylcyclohexyl)-[1,2,4]oxadiazol-5-yl]pyridine; trans-3-[3-(4-Pentylcyclohexyl)-[1,2,4]oxadiazol-5-yl]pyridine; trans-2-Methyl-3-[3-(4-pentylcyclohexyl)-[1,2,4]oxadiazol-5-yl]pyridine; trans-2-Chloro-6-methyl-4-[3-(4-pentylcyclohexyl)-[1,2,4]oxadiazol-5-yl]pyridine; trans-4-[3-(4-Pentylcyclohexyl)-[1,2,4]oxadiazol-5-yl]pyridine-2-carbonitrile; trans-2-Chloro-3-[3-(4-pentylcyclohexyl)-[1,2,4]oxadiazol-5-yl]pyridine; trans-2-Chloro-6-methyl-3-[3-(4-pentylcyclohexyl)-[1,2,4]oxadiazol-5-yl]pyridine; trans-2-Methyl-5-[3-(4-pentylcyclohexyl)-[1,2,4]oxadiazol-5-yl]pyridine; trans-3-Methyl-5-[3-(4-pentylcyclohexyl)-[1,2,4]oxadiazol-5-yl]pyridine; trans-2,6-Dichloro-4-[3-(4-pentylcyclohexyl)-[1,2,4]oxadiazol-5-yl]pyridine; trans-2-Chloro-6-methoxy-4-[3-(4-pentylcyclohexyl)-[1,2,4]oxadiazol-5-yl]pyridine; trans-5-[3-(4-Pentylcyclohexyl)-[1,2,4]oxadiazol-5-yl]-2-[1,2,4]triazol-1-ylpyridine; 2-[3-(4-Pentylcyclohexyl)-[1,2,4]oxadiazol-5-yl]pyrazine; 4-[3-(4-Pentylcyclohexyl)-[1,2,4]oxadiazol-5-yl]pyridine; trans-5-[[3-(4-Pentylcyclohexyl)-[1,2,4]oxadiazol-5-yl]pyridine-2-carbonitrile; trans-5-Chloro-2-methylsulfanyl-4-(3-(4-pentylcyclohexyl)-[1,2,4]oxadiazol-5-yl]pyrimidine; trans-2-Fluoro-5-[3-(4-pentylcyclohexyl)-[1,2,4]oxadiazol-5-yl]pyridine; trans-2-Fluoro-4-[3-(4-pentylcyclohexyl)-[1,2,4]oxadiazol-5-yl]pyridine; trans-2-Imidazol-1-yl-5-[3-(4-pentylcyclohexyl)-[1,2,4]oxadiazol-5-yl]pyridine; trans-2-Methyl-4-[3-(4-pentylcyclohexyl)-[1,2,4]oxadiazol-5-yl]pyridine; trans-3-Methyl-4-[3-(4-pentylcyclohexyl)-[1,2,4]oxadiazol-5-yl]pyridine; trans-4-{2-[3-(4-Pentylcyclohexyl)-[1,2,4]oxadiazol-5-yl]vinyl}pyridine; 4-(5-Pyridin-4-yl-[1,2,4]oxadiazol-3-ylmethoxy)piperidine-1-carboxylic acid tert-butyl ester; 4-[5-(2-Cyanopyridin-4-yl)-[1,2,4]oxadiazol-3-ylmethoxy]piperidine-1-carboxylic acid tert-butyl ester; (E)-4-[5-(2-Pyridin-3-yl-vinyl)-[1,2,4]oxadiazol-3-ylmethoxy]piperidine-1-carboxylic acid tert-butyl ester; (E)-4-[5-(2-Pyridin-3-yl-vinyl)-[1,2,4]oxadiazol-3-yl]piperidine-1-carboxylic acid tert-butyl ester; (E)-4-[5-(2-Pyridin-3-yl-vinyl)-[1,2,4]oxadiazol-3-ylmethyl]piperidine-1-carboxylic acid tert-butyl ester; (E)-4-[5-(2-Pyridin-4-yl-vinyl)-[1,2,4]oxadiazol-3-yl]piperidine-1-carboxylic acid tert-butyl ester; 4-[5-(2-Pyridin-4-yl-ethyl)-[1,2,4]oxadiazol-3-yl]-piperidine-1-carboxylic acid tert-butyl ester; 4-{5-[2-(2-Cyanopyridin-4-yl)ethyl]-[1,2,4]oxadiazol-3-yl}piperidine-1-carboxylic acid tert-butyl ester; 4-(5-[2-(2-Cyanopyridin-4-yl)ethyl]-[1,2,4]oxadiazol-3-ylmethoxy)piperidine-1-carboxylic acid tert-butyl ester; 4-(5-[2-(2-Cyanopyridin-4-yl)ethyl]-[1,2,4]oxadiazol-3-ylmethyl)piperidine-1-carboxylic acid tert-butyl ester; 4-(5-Piperidin-4-yl-[1,2,4]oxadiazol-3-yl)pyridine; 4-(3-Pyridin-4-yl-[1,2,4]oxadiazol-5-yl)piperidine-1-carboxylic acid isobutyl ester; 4-(3-Pyridin-4-yl-[1,2,4]oxadiazol-5-yl)piperidine-1-carboxylic acid 2-methoxyethyl ester; 4-(3-Pyridin-4-yl-[1,2,4]oxadiazol-5-yl)piperidine-1-carboxylic acid ethyl ester; 3,3-Dimethyl-1-[4-(3-pyridin-4-yl-[1,2,4]oxadiazol-5-yl)piperidin-1-yl]butan-1-one; 2-Cyclopentyl-1-[4-(3-pyridin-4-yl-[1,2,4]oxadiazol-5-yl)piperidin-1-yl]ethanone; 4-{5-[1-(Butane-1-sulfonyl)piperidin-4-yl]-[1,2,4]oxadiazol-5-yl}pyridine; 4-(3-Pyridin-4-yl-[1,2,4]oxadiazol-5-yl)piperidine-1-carboxylic acid propylamide; 4-(3-Pyridin-4-yl-[1,2,4]oxadiazol-5-yl)piperidine-1-carboxylic acid tert-butylamide; 4-(3-Pyridin-4-yl-[1,2,4]oxadiazol-5-ylmethoxy)piperidine-1-carboxylic acid cyclopentyl ester; 4-(3-Pyridin-4-yl-[1,2,4]oxadiazol-5-ylmethoxy)piperidine-1-carboxylic acid benzyl ester; 4-(3-Pyridin-4-yl-[1,2,4]oxadiazol-5-ylmethoxy)piperidine-1-carboxylic acid isobutyl ester; 4-(3-Pyridin-4-yl-[1,2,4]oxadiazol-5-ylmethoxy)piperidine-1-carboxylic acid ethyl ester; 4-(3-Pyridin-4-yl-[1,2,4]oxadiazol-5-ylmethoxy)piperidine-1-carboxylic acid cycloheptyl ester; 4-(3-Pyridin-4-yl-[1,2,4]oxadiazol-5-ylmethoxy)piperidine-1-carboxylic acid methyl ester; 4-(3-Pyridin-4-yl-[1,2,4]oxadiazol-5-ylmethoxy)piperidine-1-carboxylic acid 2-methoxy-ethyl ester; 4-(3-Pyridin-4-yl-[1,2,4]oxadiazol-5-ylmethoxy)piperidine-1-carboxylic acid isopropyl ester; 4-(3-Pyridin-4-yl-[1,2,4]oxadiazol-5-ylmethoxy)piperidine-1-carboxylic acid 4-methoxy-phenyl ester; 4-(3-Pyridin-4-yl-[1,2,4]oxadiazol-5-ylmethoxy)piperidine-1-carboxylic acid 2,2,2-trichloroethyl ester; 4-(3-Pyridin-4-yl-[1,2,4]oxadiazol-5-ylmethoxy)piperidine-1-carboxylic acid 4-chloro-phenyl ester; 4-(3-Pyridin-4-yl-[1,2,4]oxadiazol-5-ylmethoxy)piperidine-1- carboxylic acid phenyl ester; 4-(3-Pyridin-4-yl-[1,2,4]oxadiazol-5-ylmethoxy)piperidine-1-carboxylic acid 2-ethyl-hexyl ester; 4-(3-Pyridin-4-yl-[1,2,4]oxadiazol-5-ylmethoxy)piperidine-1-carboxylic acid propyl ester; 4-(3-Pyridin-4-yl-[1,2,4]oxadiazol-5-ylmethoxy)piperidine-1-carboxylic acid hexyl ester; 4-(3-Pyridin-4-yl-[1,2,4]oxadiazol-5-ylmethoxy)piperidine-1-carboxylic acid (1R,2S,5R)-2-isopropyl-5-methylcyclohexyl ester; 4-(3-Pyridin-4-yl-[1,2,4]oxadiazol-5-ylmethoxy)piperidine-1-carboxylic acid (1S,2R,5S)-2-isopropyl-5-methylcyclohexyl ester; 4-(3-Pyridin-4-yl-[1,2,4]oxadiazol-5-ylmethoxy)piperidine-1-carboxylic acid 2,2-dimethylpropyl ester; 4-(3-Pyridin-4-yl-[1,2,4]oxadiazol-5-ylmethoxy)piperidine-1-carboxylic acid naphthalen-1-yl ester; 4-(3-Pyridin-4-yl-[1,2,4]oxadiazol-5-ylmethoxy)piperidine-1-carboxylic acid 2-methoxy-phenyl ester; 4-(3-Pyridin-4-yl-[1,2,4]oxadiazol-5-ylmethoxy)piperidine-1-carboxylic acid 3-trifluoromethylphenyl ester; 4-(3-Pyridin-4-yl-[1,2,4]oxadiazol-5-ylmethoxy)piperidine-1-carboxylic acid prop-2-ynyl ester; 4-(3-Pyridin-4-yl-[1,2,4]oxadiazol-5-ylmethoxy)piperidine-1-carboxylic acid but-2-ynyl ester; 4-(3-Pyridin-4-yl-[1,2,4]oxadiazol-5-ylmethoxy)piperidine-1-carboxylic acid pentyl ester; 4-(3-Pyridin-4-yl-[1,2,4]oxadiazol-5-ylmethoxy)piperidine-1-carboxylic acid p-tolyl ester; 4-(3-Pyridin-4-yl-[1,2,4]oxadiazol-5-ylmethoxy)piperidine-1-carboxylic acid 2-chloro-phenyl ester; 4-(3-Pyridin-4-yl-[1,2,4]oxadiazol-5-ylmethoxy)piperidine-1-carboxylic acid naphthalen-2-yl ester; 4-(3-Pyridin-4-yl-[1,2,4]oxadiazol-5-ylmethoxy)piperidine-1-carboxylic acid butyl ester; 4-(3-Pyridin-4-yl-[1,2,4]oxadiazol-5-ylmethoxy)piperidine-1H-carboxylic acid 4-methoxycarbonyl-phenyl ester; 4-(3-Pyridin-4-yl-[1,2,4]oxadiazol-5-ylmethoxy)piperidine-1-carboxylic acid 4-fluoro-phenyl ester; 3-Methyl-1-[4-(3-pyridin-4-yl-[1,2,4]oxadiazol-5-ylmethoxy)piperidin-1-yl]-butan-1-one; Phenyl-[4-(3-pyridin-4-yl-[1,2,4]oxadiazol-5-ylmethoxy)piperidin-1-yl]methanone; 1-[4-(3-Pyridin-4-yl-[1,2,4]oxadiazol-5-ylmethoxy)piperidin-1-yl]butan-1-one; 2,2-Dimethyl-1-[4-(3-pyridin-4-yl-[1,2,4]oxadiazol-5-ylmethoxy)piperidin-1-yl]propan-1-one; Cyclopentyl-[4-(3-pyridin-4-yl-[1,2,4]oxadiazol-5-ylmethoxy)piperidin-1-yl]methanone; [4-(3-Pyridin-4-yl-[1,2,4]oxadiazol-5-ylmethoxy)piperidin-1]-yl-p-tolylmethanone; 3,3-Dimethyl-1-[4-(3-pyridin-4-yl-[1,2,4]oxadiazol-5-ylmethoxy)piperidin-1-yl]butan-1-one; 4-(5-[1-(Butane-1-sulfonyl)piperidin-4-yloxymethyl]-[1,2,4]oxadiazol-3-yl)pyridine; 4-{5-[1-(Propane-1-sulfonyl)piperidin-4-yloxymethyl]-[1,2,4]oxadiazol-3-yl}pyridine; 4-(3-Pyridin-4-yl-[1,2,4]oxadiazol-5-ylmethoxy)piperidine-1-carboxylic acid tert-butylamide; 4-(3-Pyridin-4-yl-[1,2,4]oxadiazol-5-ylmethoxy)piperidine-1-carboxylic acid o-tolylamide; trans-4-(3-Pyridin-4-yl-[1,2,4]oxadiazol-5-yl)cyclohexanecarboxylic acid propyl ester; trans-4-(3-Pyridin-4-yl-[1,2,4]oxadiazol-5-yl)cyclohexanecarboxylic acid butyl ester; trans-4-(3-Pyridin-4-yl-[1,2,4]oxadiazol-5-yl)cyclohexanecarboxylic acid isobutyl ester; trans-4-[5-(4-Propoxymethylcyclohexyl)-[1,2,4]oxadiazol-3-yl]pyridine; trans-4-[5-(4-Butoxymethylcyclohexyl)-[1,2,4]oxadiazol-3-yl]pyridine; cis-4-[5-(3-Butoxymethylcyclopentyl)-[1,2,4]oxadiazol-3-yl]pyridine; cis-4-[5-(3-Propoxymethylcyclopentyl)-[1,2,4]oxadiazol-3-yl]pyridine; cis-4-[5-(3-Butoxymethylcyclohexyl)-[1,2,4]oxadiazol-3-yl]pyridine; 4-(3-Pyridin-4-yl-[1,2,4]oxadiazol-5-ylmethoxy)-3,4,5,6-tetrahydro-2H-[1,3]bipyridinyl; 2-[4-(3-Pyridin-4-yl-[1,2,4]oxadiazol-5-ylmethoxy)piperidin-1-yl]pyrazine; 2-[4-(3-Pyridin-4-yl-[1,2,4]oxadiazol-5-ylmethoxy)piperidin-1-yl]pyrimidine; (4-Pentylcyclohexyl)-(3-pyridin-4-yl-[1,2,4]oxadiazol-5-ylmethyl)amine; (4-Pentylcyclohexyl-methyl)-(3-pyridin-4-yl-[1,2,4]oxadiazol-5-ylmethyl)amine; 4-[(3-Pyridin-4-yl-[1,2,4]oxadiazol-5-ylmethyl)amino]piperidine-1-carboxylic acid tert-butyl ester; 4-[3-Pyridin-4-yl-[1,2,4]oxadiazol-5-ylmethyl)amino]methyl)-piperidine-1-carboxylic acid tert-butyl ester; 4-{([5-(2-Cyanopyridin-4-yl)-[1,2,4]oxadiazol-3-ylmethyl]amino}-piperidine-1-carboxylic acid tert-butyl ester; Methyl-(4-pentylcyclohexyl)-(3-pyridin-4-yl-[1,2,4]oxadiazol-5-ylmethyl)amine; Methyl-(4-pentylcyclohexylmethyl)-(3-pyridin-4-yl-[1,2,4]oxadiazol-5-ylmethyl)amine; 4-[Methyl-(3-pyridin-4-yl-[1,2,4]oxadiazol-5-ylmethyl)amino]piperidine-1-carboxylic acid tert-butyl ester; 4-[Ethyl-(3-pyridin-4-yl-[1,2,4]oxadiazol-5-ylmethyl)amino]piperidine-1-carboxylic acid tert-butyl ester; 4-[Propyl-(3-pyridin-4-yl-[1,2,4]oxadiazol-5-ylmethyl)amino]piperidine-1-carboxylic acid tert-butyl ester; 4-[Cyclopropylmethyl-(3-pyridin-4-yl-[1,2,4]oxadiazol-5-ylmethyl)amino]piperidine-1-carboxylic acid tert-butyl ester; 4-[Butyl-(3-pyridin-4-yl-[1,2,4]oxadiazol-5-ylmethyl)amino]piperidine-1-carboxylic acid tert-butyl ester; 4-{[Methyl-(3-pyridin-4-yl-[1,2,4]oxadiazol-5-ylmethyl)amino]methyl}-piperidine-1-carboxylic acid tert-butyl ester; 4-{[Ethyl-(3-pyridin-4-yl-[1,2,4]oxadiazol-5-ylmethyl)amino]methyl}-piperidine-1-carboxylic acid tert-butyl ester; 4-{[5-(2-Cyanopyridin-4-yl)-[1,2,4]oxadiazol-3-ylmethyl]ethylamino}-piperidine-1-carboxylic acid tert-butyl ester; 4-[Methyl-(3-pyridin-4-yl-[1,2,4]oxadiazol-5-ylmethyl)amino]piperidine-1-carboxylic acid cyclopentyl ester; 4-{[Methyl-(3-pyridin-4-yl-[1,2,4]oxadiazol-5-ylmethyl)amino]methyl}-piperidine-1-carboxylic acid 2,2,2-trichloroethyl ester; 4-(3-Pyridin-4-yl-[1,2,4]oxadiazol-5-ylmethoxymethyl)piperidine-1-carboxylic acid tert-butyl ester; 4-(3-Pyridin-4-yl-[1,2,4]oxadiazol-5-ylmethyl)piperazine-1-carboxylic acid tert-butyl ester; 4-(3-Pyridin-4-yl-[1,2,4]oxadiazol-5-ylmethylsulfanyl)piperidine-1-carboxylic acid tert-butyl ester; 4-(3-Pyridin-4-yl-[1,2,4]oxadiazol-5-ylmethanesulfonyl)piperidine-1-carboxylic acid tert-butyl ester; 4-(5-Pyridin-4-yl-[1,3,4]oxadiazol-2-ylmethoxy)piperidine-1-carboxylic acid tert-butyl ester; 3-Pyridin-4-yl-[1,2,4]oxadiazole-5-carboxylic acid (4-pentylcyclohexyl) amide; [4-(3-Pyridin-4-yl-[1,2,4]oxadiazol-5-ylmethoxy)piperidin-1-yl]phosphonic acid diphenyl ester; 4-(4-Pyridin-4-yl-thiazol-2-ylmethoxy)piperidine-1-carboxylic acid tert-butyl ester; 4-(2-Pyridin-4-yl-thiazol-4-ylmethyl)piperidine-1-carboxylic acid tert-butyl ester; trans-4-[5-(4-Pentylcyclohexyl)-[1,3,4]thiadiazol-2-yl]pyridine; 4-(5-Pyridin-4-yl-[1,3,4]thiadiazol-2-ylmethoxy)piperidine-1-carboxylic acid tert-butyl ester; 4-(5-Pyridin-4-yl-4H-[1,2,4]triazol-3-ylmethoxy)piperidine-1-carboxylic acid tert-butyl ester; 4-[2-(5-Pyridin-4-yl-isoxazol-3-yl)ethyl]piperidine-1-carboxylic acid tert-butyl ester; 4-(5-Pyridin-4-yl-isoxazol-3-ylmethoxy)piperidine-1-carboxylic acid tert-butyl ester; 4-(5-Pyridin-4-yl-isoxazol-3-ylmethyl)piperidine-1-carboxylic acid tert-butyl ester; 4-[2-(1-Methyl-5-pyridin-4-yl-1H-pyrazol-3-yl)ethyl]piperidine-1-carboxylic acid tert-butyl ester; 4-[2-(2-Methyl-5-pyridin-4-yl-2H-pyrazol-3-yl)ethyl]-piperidine-1-carboxylic acid tert-butyl ester; (E)-4-{5-[2-(2-Cyanopyridin-4-yl)vinyl]-[1,2,4]oxadiazol-3-yl}piperidine-1-carboxylic acid tert-butyl ester; 4-(5-[2-(2H-Tetrazol-5-yl)pyridine-4-yl]-[1,2,4]oxadiazol-3-ylmethoxy)-piperidine-1-carboxylic acid tert-butyl ester; 4-[5-(2-Cyanopyridin-4-yl)-[1,2,4]oxadiazol-3-ylmethoxy]piperidine-1-carboxylic acid isopropyl ester; and 4-[5-(2-Cyanopyridin-4-yl)-[1,2,4]oxadiazol-3-ylmethoxy]piperidine-1-carboxylic acid phenyl ester.

Examples of GPR119 agonists are described in International Application No. PCT/US06/00567 (published as WO 2006/083491), the disclosure of which is herein incorporated by reference in its entirety. Disclosed in International Application No. PCT/US06/00567 as a GPR119 agonist is a compound of Formula (VII):

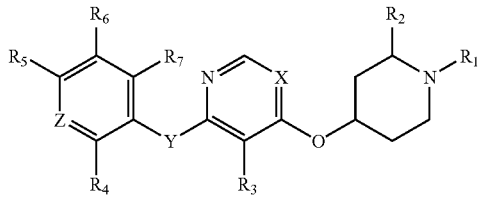

(VII)

wherein:
X is N or CR$_8$ wherein R$_8$ is H or halogen;
Y is NH or O;
Z is CH or N;
R$_1$ is carbo-C$_{1-6}$-alkoxy, oxadiazolyl or pyrimidinyl wherein said carbo-C$_{1-6}$-alkoxy, oxadiazolyl and pyrimidinyl are each optionally substituted with 1 or 2 substituents selected independently from the group consisting of C$_{1-4}$ alkyl, C$_{1-4}$ alkoxy and C$_{3-5}$ cycloalkyl;
R$_2$ is H or C$_{1-4}$ alkyl;
R$_3$ is C$_{1-4}$ alkoxy, O—C$_{2-4}$ alkynyl or hydroxyl;
R$_4$ is selected from the group consisting of H, C$_{1-4}$ alkoxy, C$_{1-4}$ alkyl, C$_{2-4}$ alkynyl and halogen;
R$_5$ is selected from the group consisting of C$_{1-4}$ acylsulfonamide, C$_{1-4}$ alkoxy, C$_{1-4}$ alkyl, C$_{1-4}$ alkylamino, C$_{1-4}$ alkylsulfonyl, C$_{1-4}$ alkylthio, cyano, heterocyclyl, di-C$_{1-4}$-dialkylamino and sulfonamide, wherein said C$_{1-4}$ alkoxy, C$_{1-4}$ alkyl, C$_{1-4}$ alkylamino, C$_{1-4}$ alkylsulfonyl, C$_{1-4}$ alkylthio, di-C$_{1-4}$-dialkylamino and heterocyclyl are each optionally substituted with 1 or 2 substituents selected independently from the group consisting of C$_{2-4}$ alkynyl, C$_{1-4}$ alkoxy, C$_{1-4}$ alkylcarboxamide, C$_{1-4}$ alkylsulfonyl, C$_{3-5}$ cycloalkyl, C-s cycloalkyloxy, di-C$_{1-4}$-alkylcarboxamide, hydroxyl and phosphonooxy, wherein said C$_{1-4}$ alkylcarboxamide is optionally substituted with hydroxyl; or
R$_5$ is a group of Formula (VIIA):

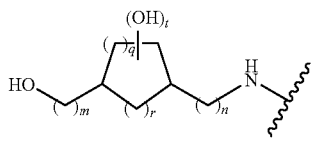

(VIIA)

wherein "m", "n" and "q" are each independently 0, 1, 2 or 3; "r" is 0, 1 or 2; and "t" is 0 or 1;
R$_6$ is H or halogen; and
R$_7$ is H or C$_{1-4}$ alkyl.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Specific examples of GPR119 agonists disclosed in International Application No. PCT/US06/00567 include the following compounds according to Formula (VII) (referred to herein as Group G1): 4-[6-(4-Methanesulfonyl-2-methoxyphenylamino)-5-methoxy-pyrimidin-4-yloxy]-piperidine-1-carboxylic acid isopropyl ester; 4-{5-Methoxy-6-[6-(2-methoxy-ethyl)-2-methyl-pyridin-3-ylamino]-pyrimidin-4-yloxy}-piperidine-1-carboxylic acid isopropyl ester; 4-{6-[6-(2-Methanesulfonyl-ethyl)-2-methyl-pyridin-3-ylamino]-5-methoxy-pyrimidin-4-yloxy}-piperidine-1-carboxylic acid 1-cyclopropyl-ethyl ester; 4-[6-(2-Fluoro-4-methanesulfonyl-phenylamino)-5-methoxy-pyrimidin-4-yloxy]-piperidine-1-carboxylic acid isopropyl ester; 4-[6-(4-Cyano-2-fluoro-phenylamino)-5-methoxy-pyrimidin-4-yloxy]-piperidine-1-carboxylic acid isopropyl ester; 4-{6-[6-(2-Hydroxy-ethyl)-2-methyl-pyridin-3-ylamino]-5-methoxy-pyrimidin-4-yloxy}-piperidine-1-carboxylic acid isopropyl ester; 4-{6-[6-(2-Methanesulfonyl-ethyl)-2-methyl-pyridin-3-ylamino]-5-methoxy-pyrimidin-4-yloxy}-piperidine-1-carboxylic acid isopropyl ester; 4-{5-Methoxy-6-[6-(2-methoxy-ethylamino)-2-methyl-pyridin-3-ylamino]-pyrimidin-4-yloxy}-piperidine-1-carboxylic acid isopropyl ester; 4-{6-[6-(2-Methanesulfonyl-ethoxy)-2-methyl-pyridin-3-ylamino]-5-methoxy-pyrimidin-4-yloxy}-piperidine-1-carboxylic acid isopropyl ester; 4-{6-[6-(2-Hydroxy-propylamino)-2-methyl-pyridin-3-ylamino]-5-methoxy-pyrimidin-4-yloxy}-piperidine-1-carboxylic acid isopropyl ester; 4-{6-[6-(3-Hydroxy-propyl)-2-methyl-pyridin-3-ylamino]-5-methoxy-pyrimidin-4-yloxy}-piperidine-1-carboxylic acid isopropyl ester; 4-{5-Methoxy-6-[2-methyl-6-(3-phosphonooxy-propyl)-pyridin-3-ylamino]-pyrimidin-4-yloxy}-piperidine-1-carboxylic acid isopropyl ester; 4-{6-[6-(2-Methanesulfonyl-ethylamino)-2-methoxy-pyridin-3-ylamino]-5-methoxy-pyrimidin-4-yloxy}-piperidine-1-carboxylic acid isopropyl ester; 4-{6-[6-(2-Methanesulfonyl-propylamino)-2-methyl-pyridin-3-ylamino]-5-methoxy-pyrimidin-4-yloxy}-piperidine-1-carboxylic acid isopropyl ester; 4-[6-(6-Dimethylcarbamoylmethyl-2-methyl-pyridin-3-ylamino)-5-methoxy-pyrimidin-4-yloxy]-piperidine-1-carboxylic acid isopropyl ester; 4-(6-{2-Fluoro-4-[(2-hydroxy-ethylcarbamoyl)-methyl]-phenylamino}-5-methoxy-pyrimidin-4-yloxy)-piperidine-1-carboxylic acid isopropyl ester; 4-{6-[6-(2-Methanesulfonyl-ethylamino)-pyridin-3-ylamino]-5-methoxy-pyrimidin-4-yloxy}-piperidine-1-carboxylic acid isopropyl ester; 4-{6-[2-Fluoro-4-(2-hydroxy-ethylsulfanyl)-phenylamino]-5-methoxy-pyrimidin-4-yloxy}-piperidine-1-carboxylic acid isopropyl ester; 4-{6-[6-(2,3-Dihydroxy-propylamino)-2-methyl-pyridin-3-ylamino]-5-methoxy-pyrimidin-4-yloxy}-piperidine-1-carboxylic acid isopropyl ester; 4-{6-[6-(2,3-Dihydroxy-propylamino)-2-methyl-pyridin-3-ylamino]-5-methoxy-pyrimidin-4-yloxy}-piperidine-1-carboxylic acid isopropyl ester; 4-{6-[6-(2-Hydroxy-ethoxy)-2-methyl-pyridin-3-ylamino]-5-methoxy-pyrimidin-4-yloxy}-piperidine-1-carboxylic acid isopropyl ester; 4-{5-Methoxy-6-[2-methyl-6-(2-phosphonooxy-ethoxy)-pyridin-3-ylamino]-pyrimidin-4-yloxy}-piperidine-1-carboxylic acid isopropyl ester; 4-{6-[6-(3-Hydroxy-propoxy)-2-methyl-pyridin-3-ylamino]-5-methoxy-pyrimidin-4-yloxy}-piperidine-1-carboxylic acid isopropyl ester; and 4-{5-Methoxy-6-[2-methyl-6-(3-phosphonooxy-propoxy)-pyridin-3-ylamino]-pyrimidin-4-yloxy}-piperidine-1-carboxylic acid isopropyl ester.

Specific examples of GPR119 agonists disclosed in International Application No. PCT/US06/00567 include the following compounds according to Formula (VII) (referred to herein as Group G2): 4-[2-(2-Fluoro-4-propoxy-phenylamino)-3-methoxy-pyridin-4-yloxy]-piperidine-1-carboxylic acid isopropyl ester; 4-{2-[2-Fluoro-4-(2-hydroxy-ethyl)-phenylamino]-3-methoxy-pyridin-4-yloxy}-piperidine-1-carboxylic acid isopropyl ester; 4-[5-Fluoro-2-(2-fluoro-4- methanesulfonyl-phenylamino)-3-methoxy-pyridin-4-yloxy]-piperidine-1-carboxylic acid isopropyl ester; 4-{2-[2-Ethyl-4-(2-methanesulfonyl-ethyl)-phenylamino]-3-methoxy-pyridin-4-yloxy}-2-methyl-piperidine-1-carboxylic acid isopropyl ester; 4-{5-Fluoro-2-[6-(2-hydroxy-ethoxy)-2-methyl-pyridin-3-ylamino]-3-methoxy-pyridin-4-yloxy}-piperidine-1-carboxylic acid isopropyl ester; 4-{2-[2-Fluoro-4-(2-methanesulfonyl-ethyl)-phenylamino]-3-methoxy-pyridin-4-yloxy}-piperidine-1-carboxylic acid isopropyl ester; 4-(2-[6-(2-Hydroxy-ethylamino)-2-methyl-pyridin-3-ylamino]-3-methoxy-pyridin-4-yloxy)-piperidine-1-carboxylic acid isopropyl ester; 4-[2-(4-Cyano-2-fluoro-phenylamino)-3-methoxy-pyridin-4-yloxy]-piperidine-1-carboxylic acid isopropyl ester; 4-[2-(2-Chloro-4-cyano-phenylamino)-3-methoxy-pyridin-4-yloxy]-piperidine-1-carboxylic acid isopropyl ester; 4-{2-[6-(2-Methanesulfonyl-ethyl)-2-methoxy-pyridin-3-ylamino]-3-methoxy-pyridin-4-yloxy}-piperidine-1-carboxylic acid isopropyl ester; 4-{2-[6-(2-Methanesulfonyl-ethyl)-2-methyl-pyridin-3-ylamino]-3-methoxy-pyridin-4-yloxy}-piperidine-1-carboxylic acid isopropyl ester; 4-{2-[6-(2-Hydroxy-ethyl)-2-methyl-pyridin-3-ylamino]-3-methoxy-pyridin-4-yloxy}-piperidine-1-carboxylic acid isopropyl ester; 4-{2-[6-(3-Hydroxy-butyl)-2-methoxy-pyridin-3-ylamino]-3-methoxy-pyridin-4-yloxy}-piperidine-1-carboxylic acid isopropyl ester; 4-{2-[2-Fluoro-4-(2-hydroxy-ethoxy)-phenylamino]-3-methoxy-pyridin-4-yloxy}-piperidine-1-carboxylic acid isopropyl ester; 4-{3-Ethoxy-2-[2-fluoro-4-(2-phosphonooxy-ethyl)-phenylamino]-pyridin-4-yloxy}-piperidine-1-carboxylic acid isopropyl ester; 4-[3-Methoxy-2-(2-methoxy-4-propionylsulfamoyl-phenylamino)-pyridin-4-yloxy]-piperidine-1-carboxylic acid isopropyl ester; 4-[2-(2,5-Difluoro-4-propoxy-phenylamino)-3-methoxy-pyridin-4-yloxy]-piperidine-1-carboxylic acid isopropyl ester; (2-Fluoro-4-methanesulfonyl-phenyl)-{4-[1-(5-isopropyl-[1,2,4]oxadiazol-3-yl)-piperidin-4-yloxy]-3-methoxy-pyridin-2-yl}-amine; (2-Fluoro-4-methanesulfonyl-phenyl)-(3-methoxy-4-[1-(5-methoxy-pyrimidin-2-yl)-piperidin-4-yloxy]-pyridin-2-yl)-amine; 4-{2-[6-(2-Cyclopropoxy-ethyl)-2-methyl-pyridin-3-ylamino]-3-methoxy-pyridin-4-yloxy}-piperidine-1-carboxylic acid isopropyl ester; 4-[2-(2-Chloro-4-methanesulfonyl-phenylamino)-5-fluoro-3-methoxy-pyridin-4-yloxy]-piperidine-1-carboxylic acid isopropyl ester; 4-[3-Ethoxy-2-(4-methanesulfonyl-2-methoxy-phenylamino)-pyridin-4-yloxy]-piperidine-1-carboxylic acid isopropyl ester; 4-[2-(5-Fluoro-2-methyl-4-propoxy-phenylamino)-3-methoxy-pyridin-4-yloxy]-piperidine-1-carboxylic acid isopropyl ester; 4-{2-[6-(2-Methanesulfonyl-ethyl)-2-methyl-pyridin-3-ylamino]-3-methoxy-pyridin-4-yloxy}-piperidine-1-carboxylic acid isopropyl ester; 4-[2-(2-Fluoro-4-methanesulfonyl-phenylamino)-3-hydroxy-pyridin-4-yloxy]-piperidine-1-carboxylic acid isopropyl ester; 4-[2-(2-Chloro-4-propoxy-phenylamino)-3-methoxy-pyridin-4-yloxy]-piperidine-1-carboxylic acid isopropyl ester; 4-{3-Methoxy-2-[2-methyl-6-(2-phosphonooxy-ethyl)-pyridin-3-ylamino]-pyridin-4-yloxy}-piperidine-1-carboxylic acid isopropyl ester; 4-{2-[6-(2-Methanesulfonyl-ethylamino)-2-methyl-pyridin-3-ylamino]-3-methoxy-pyridin-4-yloxy}-piperidine-1-carboxylic acid isopropyl ester; 4-(2-{6-[(2-Methanesulfonyl-ethyl)-methyl-amino]-2-methyl-pyridin-3-ylamino}-3-methoxy-pyridin-4-yloxy)-piperidine-1-carboxylic acid isopropyl ester; 4-{2-[6-(3-Methanesulfonyl-pyrrolidin-1-yl)-2-methyl-pyridin-3-ylamino]-3-methoxy-pyridin-4-yloxy}-piperidine-1-carboxylic acid isopropyl ester; 4-[2-(3-Methanesulfonyl-6'-methyl-3,4,5,6-tetrahydro-2H-[1,2']bipyridinyl-5'-ylamino)-3-methoxy-pyridin-4-yloxy]-piperidine-1-carboxylic acid isopropyl ester; 4-{2-[6-(3-Methanesulfonyl-azetidin-1-yl)-2-methyl-pyridin-3-ylamino]-3-methoxy-pyridin-4-yloxy}-piperidine-1-carboxylic acid isopropyl ester; 4-[3-Ethynyloxy-2-(2-fluoro-4-methanesulfonyl-phenylamino)-pyridin-4-yloxy]-piperidine-1-carboxylic acid isopropyl ester; 4-{2-[2-Fluoro-4-(2-phosphonooxy-ethanesulfonyl)-phenylamino]-3-methoxy-pyridin-4-yloxy}-piperidine-1-carboxylic acid isopropyl ester; 4-[2-(4-Ethanesulfonyl-2-fluoro-phenylamino)-3-methoxy-pyridin-4-yloxy]-piperidine-1-carboxylic acid sec-butyl ester; 4-{2-[6-(2,3-Dihydroxy-propylamino)-4-methyl-pyridin-3-ylamino]-3-methoxy-pyridin-4-yloxy}-piperidine-1-carboxylic acid isopropyl ester; 4-{2-[6-(2-Hydroxy-ethylsulfanyl)-pyridin-3-ylamino]-3-methoxy-pyridin-4-yloxy}-piperidine-1-carboxylic acid isopropyl ester; 4-{2-[2-Fluoro-4-(2-hydroxy-ethanesulfonyl)-phenylamino]-3-methoxy-pyridin-4-yloxy}-piperidine-1-carboxylic acid isopropyl ester; 4-{2-[6-(2-Hydroxy-ethoxy)-2-methyl-pyridin-3-ylamino]-3-methoxy-pyridin-4-yloxy}-piperidine-1-carboxylic acid isopropyl ester; 4-{3-Methoxy-2-[2-methyl-6-(2-phosphonooxy-ethoxy)-pyridin-3-ylamino]-pyridin-4-yloxy}-piperidine-1-carboxylic acid isopropyl ester; 4-{2-[6-(3-Hydroxy-propoxy)-2-methyl-pyridin-3-ylamino]-3-methoxy-pyridin-4-yloxy}-piperidine-1-carboxylic acid isopropyl ester; 4-{3-Methoxy-2-[2-methyl-6-(3-phosphonooxy-propoxy)-pyridin-3-ylamino]-pyridin-4-yloxy}-piperidine-1-carboxylic acid isopropyl ester; 4-[3-Methoxy-2-(2-methoxy-4-sulfamoyl-phenylamino)-pyridin-4-yloxy]-piperidine-1-carboxylic acid isopropyl ester; 4-{2-[2-Fluoro-4-(3-phosphonooxy-propyl)-phenylamino]-3-methoxy-pyridin-4-yloxy}-piperidine-1-carboxylic acid isopropyl ester; 4-{2-[6-(2-Hydroxy-ethyl)-2-methyl-pyridin-3-ylamino]-3-methoxy-pyridin-4-yloxy}-piperidine-1-carboxylic acid isopropyl ester; 4-{3-Methoxy-2-[2-methyl-6-(2-phosphonooxy-ethyl)-pyridin-3-ylamino]-pyridin-4-yloxy}-piperidine-1-carboxylic acid isopropyl ester; 4-{2-[6-(3-Hydroxy-propyl)-2-methyl-pyridin-3-ylamino]-3-methoxy-pyridin-4-yloxy}-piperidine-1-carboxylic acid isopropyl ester; and 4-{3-Methoxy-2-[2-methyl-6-(3-phosphonooxy-propyl)-pyridin-3-ylamino]-pyridin-4-yloxy}-piperidine-1-carboxylic acid isopropyl ester.

Specific examples of GPR119 agonists disclosed in International Application No. PCT/US06/00567 include the following compounds according to Formula (VII) (referred to herein as Group G3): 4-[6-(2,6-Dimethyl-pyridin-3-ylamino)-5-methoxy-pyrimidin-4-yloxy]-piperidine-1-carboxylic acid isopropyl ester; 4-[6-(6-Methanesulfonyl-2-methyl-pyridin-3-ylamino)-5-methoxy-pyrimidin-4-yloxy]-piperidine-1-carboxylic acid isopropyl ester; 4-[6-(6-Methanesulfonyl-4-methyl-pyridin-3-ylamino)-5-methoxy-pyrimidin-4-yloxy]-piperidine-1-carboxylic acid isopropyl ester; 4-[5-Methoxy-6-(2-methyl-6-propylsulfanyl-pyridin-3-ylamino)-pyrimidin-4-yloxy]-piperidine-1-carboxylic acid isopropyl ester; 4-(5-Methoxy-6-[2-methyl-6-(propane-1-sulfonyl)-pyridin-3-ylamino]-pyrimidin-4-yloxy)-piperidine-1-carboxylic acid isopropyl ester; 4-[6-(6-Ethylsulfanyl-2-methyl-pyridin-3-ylamino)-5-methoxy-pyrimidin-4-yloxy]-piperidine-1-carboxylic acid isopropyl ester; 4-[6-(6-Ethanesulfonyl-2-methyl-pyridin-3-ylamino)-5-methoxy-pyrimidin-4-yloxy]-piperidine-1-carboxylic acid isopropyl ester; 4-[6-(6-Isopropylsulfanyl-2-methyl-pyridin-3-ylamino)-5-methoxy-pyrimidin-4-yloxy]-piperidin-1-carboxylic acid isopropyl ester; 4-{5-Methoxy-6-[2-methyl-6-(propane-2-sulfonyl)-pyridin-3-ylamino]-pyrimidin-4-yloxy}-piperidine-1-carboxylic acid isopropyl ester; 4-{6-[6-(2-Hydroxy-ethanesulfonyl)-2-methyl-pyridin-3-ylamino]-5-methoxy-pyrimidin-4-yloxy}-piperidine-1- carboxylic acid isopropyl ester; 4-[5-Hydroxy-6-(6-methanesulfonyl-2-methyl-pyridin-3-ylamino)-pyrimidin-4-yloxy]-piperidine-1-carboxylic acid isopropyl ester; 4-[5-Ethoxy-6-(6-methanesulfonyl-2-methyl-pyridin-3-ylamino)-pyrimidin-4-yloxy]-piperidine-1-carboxylic acid isopropyl ester; 4-[5-Isopropoxy-6-(6-methanesulfonyl-2-methyl-pyridin-3-ylamino)-pyrimidin-4-yloxy]-piperidine-1-carboxylic acid isopropyl ester; 4-[6-(6-Methanesulfonyl-2-methyl-pyridin-3-ylamino)-5-propoxy-pyrimidin-4-yloxy]-piperidine-1-carboxylic acid isopropyl ester; 4-[6-(6-Methanesulfonyl-2-methyl-pyridin-3-ylamino)-5-methoxy-pyrimidin-4-yloxy]-piperidine-1-carboxylic acid 1-ethyl-propyl ester; 4-[6-(6-Methanesulfonyl-2-methyl-pyridin-3-ylamino)-5-methoxy-pyrimidin-4-yloxy]-piperidine-1-carboxylic acid sec-butyl ester; 4-[6-(6-Cyano-4-methyl-pyridin-3-ylamino)-5-methoxy-pyrimidin-4-yloxy]-piperidine-1-carboxylic acid isopropyl ester; 4-[6-(6-Hydroxymethyl-4-methyl-pyridin-3-ylamino)-5-methoxy-pyrimidin-4-yloxy]-piperidine-1-carboxylic acid isopropyl ester; {6-[1-(3-Isopropyl-[1,2,4]oxadiazol-5-yl)-piperidin-4-yloxy]-5-methoxy-pyrimidin-4-yl}-(6-methanesulfonyl-2-methyl-pyridin-3-yl)-amine; 4-[6-(6-Methanesulfonyl-2,4-dimethyl-pyridin-3-ylamino)-5-methoxy-pyrimidin-4-yloxy]-piperidine-1-carboxylic acid isopropyl ester; and 4-{6-[6-(1-Methanesulfonyl-1-methyl-ethyl)-2-methyl-pyridin-3-ylamino]-5-methoxy-pyrimidin-4-yloxy}-piperidine-1-carboxylic acid isopropyl.

Examples of GPR119 agonists are described in International Application No. PCT/GB2005/050264 (published as WO 2006/067531), the disclosure of which is herein incorporated by reference in its entirety. Disclosed in International Application No. PCT/GB2005/050264 as a GPR119 agonist is a compound of Formula (VIII):

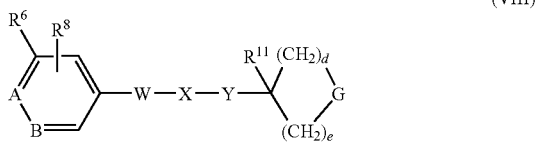

(VIII)

wherein:
one of A and B is nitrogen and the other is $CR^1$;
W and Y are independently a bond, an unbranched or a branched $C_{1-3}$ alkylene or an unbranched or a branched $C_{2-3}$ alkenylene;
X is selected from $CH_2$, O, S, CH(OH), CH(halogen), C(O), C(O)O, C(O)S, SC(O), $C(O)CH_2S$, $C(O)CH_2C(OH)$, $C(O)CH_2C(O)$, OC(O), $NR^5$, $CH(NR^5R^{55})$, C(O)$NR^2$, S(O) and S(O)$_2$;
G is $CHR^3$, $N-C(O)OR^4$, $N-C(O)NR^4R^5$, $N-C_{1-4}$alkylene-$C(O)OR^4$, $N-C(O)C(O)OR^4$, $N-S(O)_2R^4$, $N-C(O)R^4$ or $N-P(O)(O-Ph)_2$; or N-heterocyclyl or N-heteroaryl, either of which may optionally be substituted by one or two groups selected from $C_{1-4}$alkyl, $C_{1-4}$alkoxy or halogen;
$R^1$ is hydrogen, halogen, cyano, $C(O)NH_2$, $C_{1-4}$alkyl, $SO_2C_{1-4}$alkyl, $SOC_{1-4}$alkyl or $SC_{1-4}$alkyl;
$R^2$ is hydrogen or $C_{1-4}$alkyl;
$R^3$ is $C_{3-6}$alkyl;
$R^4$ is $C_{1-8}$alkyl, $C_{2-8}$alkenyl or $C_{2-8}$alkynyl, any of which may be optionally substituted by one or more halo atoms, $NR^5R^{55}$, $OR^5$, $C(O)OR^5$, $OC(O)R^5$ or cyano, and may contain a $CH_2$ group that is replaced by O or S; or a $C_{3-7}$cycloalkyl, aryl, heterocyclyl, heteroaryl, $C_{1-4}$alkylene$C_{3-7}$cycloalkyl, $C_{1-4}$alkylenearyl, $C_{1-4}$alkyleneheterocyclyl or $C_{1-4}$alkyleneheteroaryl, any of which may be substituted with one or more substituents selected from halo, $C_{1-4}$alkyl, $C_{1-4}$fluoroalkyl, $OR^5$, CN, $NR^5R^{55}$, $SO_2Me$, $NO_2$ or $C(O)OR^5$;
$R^5$ and $R^{55}$ are independently hydrogen or $C_{1-4}$alkyl; or taken together $R^5$ and $R^{55}$ may form a 5 or 6 membered heterocyclic ring;
$R^6$ is hydrogen, halogen, CN, $C_{1-4}$alkyl, $C_{1-4}$alkoxy, ethynyl, $C(O)NR^7R^{77}$ or $C_{1-4}$alkyleneS(O)$_f$;
$R^7$ and $R^{77}$ are independently hydrogen or $C_{1-4}$alkyl; or taken together $R^7$ and $R^{77}$ may form a 5 or 6 membered heterocyclic ring;
$R^8$ is hydrogen, halogen, CN, $C_{1-4}$alkyl or $C_{1-4}$alkoxy;
$R^{11}$ is hydrogen or hydroxy;
d is 0, 1, 2 or 3;
e is 1, 2, 3, 4 or 5;
with the proviso that d+e is 2, 3, 4 or 5; and
f is 0, 1 or 2.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Specific examples of GPR119 agonists disclosed in International Application No. PCT/GB2005/050264 include the following compounds according to Formula (VIII) (referred to herein as Group H1): 4-(3-Pyridin-4-ylpropylsulfanylcarbonyl)piperidine-1-carboxylic acid tert-butyl ester; 4-Pentylcyclohexane carbothioic acid S-(3-pyridin-4-ylpropyl) ester; 4-(2-Pyridin-4-ylethylsulfanylcarbonyl)piperidine-1-carboxylic acid tert-butyl ester; 4-Pentylcyclohexane carbothioic acid S-(2-pyridin-4-ylethyl) ester; 4-(Pyridine-4-carbonylsulfanyl)piperidine-1-carboxylic acid tert-butyl ester; (E)-4-(3-Pyridin-4-ylacryloylsulfanyl)piperidine-1-carboxylic acid tert-butyl ester; 4-(3-Pyridin-4-ylpropionylsulfanyl)piperidine-1-carboxylic acid tert-butyl ester; 4-(Pyridine-4-carbonylsulfanylmethyl)piperidine-1-carboxylic acid tert-butyl ester; 4-(3-Pyridin-4-ylpropionylsulfanylmethyl)piperidine-1-carboxylic acid tert-butyl ester; 4-(2-Pyridin-4-ylacetoxymethyl)piperidine-1-carboxylic acid tert-butyl ester; 4-(2-Pyridin-4-ylacetoxy)piperidine-1-carboxylic acid tert-butyl ester; 4-[3-(2-Pyridin-4-ylacetoxy)propyl]piperidine-1-carboxylic acid tert-butyl ester; Isonicotinic acid 3-(1-tert-butoxycarbonylpiperidin-4-yl)propyl ester; (E)-4-(3-Pyridin-4-ylacryloyloxymethyl)piperidine-1-carboxylic acid tert-butyl ester; (E)-4-(3-Pyridin-4-ylacryloyloxy)piperidine-1-carboxylic acid tert-butyl ester; (E)-4-[3-(3-Pyridin-4-ylacryloyloxy)propyl]piperidine-1-carboxylic acid tert-butyl ester; 4-(2-Pyridin-4-ylethoxycarbonylmethyl)piperidine-1-carboxylic acid tert-butyl ester; Piperidine-1,4-dicarboxylic acid 1-tert-butyl ester 4-(2-pyridin-4-ylethyl) ester; Piperidine-1,4-dicarboxylic acid 1-tert-butyl ester 4-(3-pyridin-4-ylpropyl) ester; (E)-4-[Methyl(3-pyridin-4-ylacryloyl)amino]piperidine-1-carboxylic acid tert-butyl ester; 4-(2-[Methyl(pyridine-4-carbonyl)amino]ethyl)piperidine-1-carboxylic acid tert-butyl ester; 4-[Methyl(pyridine-4-carbonyl)amino]piperidine-1-carboxylic acid tert-butyl ester; 4-{2-[Methyl(2-pyridin-4-ylacetyl)amino]ethyl}piperidine-1-carboxylic acid tert-butyl ester; 4-{2-[Methyl(3-pyridin-4-ylacryloyl)amino]ethyl}piperidine-1-carboxylic acid tert-butyl ester; 4-{[Methyl-(3-pyridin-4-ylacryloyl)amino]methyl}piperidine-1-carboxylic acid tert-butyl ester; 4-(2-Pyridin-4-ylethylsulfanylmethyl)

piperidine-1-carboxylic acid tert-butyl ester; 4-(2-Pyridin-4-ylethylsulfanyl)piperidine-1-carboxylic acid tert-butyl ester; 4-[2-(2-Pyridin-4-ylethylsulfanyl)ethyl]piperidine-1-carboxylic acid tert-butyl ester; 4-(3-Pyridin-4-ylpropylsulfanylmethyl)piperidine-1-carboxylic acid tert-butyl ester; 4-(3-Pyridin-4-ylpropylsulfanyl)piperidine-1-carboxylic acid tert-butyl ester; 4-[2-(3-Pyridin-4-ylpropylsulfanyl)ethyl]piperidine-1-carboxylic acid tert-butyl ester; 4-(2-Pyridin-4-ylethoxymethyl)piperidine-1-carboxylic acid tert-butyl ester; 4-(3-Pyridin-4-ylpropoxymethyl)piperidine-1-carboxylic acid tert-butyl ester; 4-[2-(3-Pyridin-4-ylpropoxy)ethyl]piperidine-1-carboxylic acid tert-butyl ester; 4-[2-(2-Pyridin-4-ylethoxy)ethyl]piperidine-1-carboxylic acid tert-butyl ester; 4-[3-(2-Cyanopyridin-4-yl)propoxymethyl]piperidine-1-carboxylic acid tert-butyl ester; 4-{2-[3-(2-Cyanopyridin-4-yl)propoxy]ethyl}piperidine-1-carboxylic acid tert-butyl ester; 4-[3-Pyridin-4-ylmethoxy)propyl]piperidine-1-carboxylic acid tert-butyl ester; 4-[2-(2-Bromopyridin-4-ylmethoxy)ethyl]piperidine-1-carboxylic acid tert-butyl ester; 4-(3-Pyridin-4-ylpropoxy)piperidine-1-carboxylic acid tert-butyl ester; 4-[3-(pyridin-4-yloxy)propyl]piperidine-1-carboxylic acid tert-butyl ester; 4-[2-(Pyridin-4-ylmethoxy)ethyl]piperidine-1-carboxylic acid tert-butyl ester; 4-(2-Oxo-2-pyridin-4-ylethylsulfanylmethyl)piperidine-1-carboxylic acid tert-butyl ester; 4-(3-Pyridin-4-ylpropane-1-sulfonyl)piperidine-1-carboxylic acid tert-butyl ester; 4-(3-Pyridin-4-ylpropane-1-sulfinyl)piperidine-1-carboxylic acid tert-butyl ester; 4-(3-Pyridin-4-ylpropane-1-sulfonylmethyl)piperidine-1-carboxylic acid ten-butyl ester; 4-(3-Pyridin-4-ylpropane-1-sulfinylmethyl)piperidine-1-carboxylic acid tert-butyl ester; 4-[2-(3-Pyridin-4-ylpropane-1-sulfonyl)ethyl]piperidine-1-carboxylic acid tert-butyl ester; 4-[2-(3-Pyridin-4-ylpropane-1-sulfinyl)ethyl]piperidine-1-carboxylic acid tert-butyl ester; 4-(2-Pyridin-4-ylethanesulfonylmethyl)piperidine-1-carboxylic acid tert-butyl ester; (E)-4-(2-Oxo-4-pyridin-4-ylbut-3-enyl)piperidine-1-carboxylic acid tert-butyl ester; (E)-4-(4-Pyridin-4-ylbut-3-enyl)piperidine-1-carboxylic acid tert-butyl ester; (Z)-4-(4-Pyridin-4-ylbut-3-enyl)piperidine-1-carboxylic acid tert-butyl ester; (E)-4-(3-Pyridin-4-ylallyl)piperidine-1-carboxylic acid tert-butyl ester; (Z)-4-(3-Pyridin-4-ylallyl)piperidine-1-carboxylic acid tert-butyl ester; 4-(4-Pyridin-4-ylbutyl)piperidine-1-carboxylic acid tert-butyl ester; 4-(3-Pyridin-4-ylpropyl)piperidine-1-carboxylic acid tert-butyl ester; 4-(2-Methyl-3-pyridin-4-ylpropyl)piperidine-1-carboxylic acid tert-butyl ester; (E)-4-[4-(2-Cyanopyridin-4-yl)but-3-enyl]piperidine-1-carboxylic acid tert-butyl ester; 4-[4-(2-Cyanopyridin-4-yl)butyl]piperidine-1-carboxylic acid tert-butyl ester; 4-[3-(2-Cyanopyridin-4-yl)propyl]piperidine-1-carboxylic acid tert-butyl ester; 4-[2-(2-Cyanopyridin-4-ylmethoxy)ethyl]piperidine-1-carboxylic acid tert-butyl ester; 4-(4-Pyridin-4-ylbutyl)piperidine-1-carboxylic acid tert-butylamide; 4-(4-Pyridin-4-ylbutyl)piperidine-1-carboxylic acid tert-butylmethylamide; 4-(4-Pyridin-4-yl-butyl)piperidine-1-carboxylic acid 2,2,2-trichloroethyl ester; 4-(4-Pyridin-4-ylbutyl)piperidine-1-carboxylic acid isobutyl ester; 4-(4-Pyridin-4-ylbutyl)piperidine-1-carboxylic acid 4-methoxyphenyl ester; 4-(4-Pyridin-4-ylbutyl)piperidine-1-carboxylic acid 2,2-dimethylpropyl ester; 4-(4-Pyridin-4-ylbutyl)piperidine-1-carboxylic acid phenyl ester; 4-(4-Pyridin-4-ylbutyl)piperidine-1-carboxylic acid cyclopentyl ester; 4-(4-Pyridin-4-ylbutyl)piperidine-1-carboxylic acid 2-chlorobenzyl ester; 4-(4-Pyridin-4-ylbutyl)piperidine-1-carboxylic acid p-tolyl ester; 4-(4-Pyridin-4-ylbutyl)piperidine-1-carboxylic acid propyl ester; 4-(4-Pyridin-4-ylbutyl)piperidine-1-carboxylic acid hexyl ester; 4-(4-Pyridin-4-ylbutyl)piperidine-1-carboxylic acid prop-2-ynyl ester; 4-(4-Pyridin-4-ylbutyl)piperidine-1-carboxylic acid naphthalen-1-yl ester; 4-(4-Pyridin-4-ylbutyl)piperidine-1-carboxylic acid 4-fluorophenyl ester; 4-(4-Pyridin-4-ylbutyl)piperidine-1-carboxylic acid 4-methoxycarbonylphenyl ester; 4-(4-Pyridin-4-ylbutyl)piperidine-1-carboxylic acid 4-nitrophenyl ester; 4-(4-Pyridin-4-ylbutyl)piperidine-1-carboxylic acid isopropyl ester; 4-(4-Pyridin-4-ylbutyl)piperidine-1-carboxylic acid 4-chlorophenyl ester; 4-(4-Pyridin-4-ylbutyl)piperidine-1-carboxylic acid 3-trifluoromethylphenyl ester; 4-(4-Pyridin-4-ylbutyl)piperidine-1-carboxylic acid 2-chlorophenyl ester; 4-(4-Pyridin-4-ylbutyl)piperidine-1-carboxylic acid 2-methoxyphenyl ester; 4-(4-Pyridin-4-yl-butyl)piperidine-1-carboxylic acid but-2-ynyl ester, 4-(4-Pyridin-4-ylbutyl)piperidine-1-carboxylic acid naphthalen-2-yl ester; 4-(4-Pyridin-4-ylbutyl)piperidine-1-carboxylic acid pentyl ester; 4-(4-Pyridin-4-ylbutyl)piperidine-1-carboxylic acid o-tolyl ester; 4-(4-Pyridin-4-ylbutyl)piperidine-1-carboxylic acid 2-cyano-1,1-dimethylethyl ester; 4-(4-Pyridin-4-ylbutyl)piperidine-1-carboxylic acid 2,2,2-trifluoroethyl ester; 4-(4-Pyridin-4-ylbutyl)piperidine-1-carboxylic acid cyclobutyl ester; 4-(4-Pyridin-4-ylbutyl)piperidine-1-carboxylic acid cyclohexyl ester; 4-(4-Pyridin-4-ylbutyl)piperidine-1-carboxylic acid 2-methylsufanylethyl ester; 4-(4-Pyridin-4-ylbutyl)piperidine-1-carboxylic acid tetrahydrofuran-2-ylmethyl ester; 2-[4-(4-Pyridin-4-ylbutyl)piperidin-1-yl]propionic acid ethyl ester; [4-(4-Pyridin-4-ylbutyl)piperidin-1-yl]acetic acid ethyl ester; [4-(4-Pyridin-4-ylbutyl)piperidin-1-yl]acetic acid tert-butyl ester; Oxo-[4-(4-pyridin-4-ylbutyl)piperidin-1-yl]acetic acid methyl ester; 2-[4-(4-Pyridin-4-ylbutyl)piperidin-1-yl]pyrimidine; 4-(4-Pyridin-4-ylbutyl)-3,4,5,6-tetrahydro-2H-[1,2']bipyridinyl; 4-(2,4-Dioxo-4-pyridin-4-ylbutyl)piperidine-1-carboxylic acid tert-butyl ester; 4-(3,5-Dioxo-5-pyridin-4-yl-pentyl)piperidine-1-carboxylic acid tert-butyl ester; 4-[1-(2-Cyanopyridin-4-yl)vinyloxycarbonylmethyl]piperidine-1-carboxylic acid tert-butyl ester; 4-(2-Hydroxy-4-pyridin-4-ylbutyl)piperidine-1-carboxylic acid tert-butyl ester; 4-(2-Hydroxy-4-pyridin-4-ylbutyl)piperidine-1-carboxylic acid tert-butyl ester; 4-(2-Hydroxy-4-oxo-4-pyridin-4-ylbutyl)piperidine-1-carboxylic acid tert-butyl ester; 4-[4-(2-Cyanopyridin-4-yl)-2-hydroxy-4-oxobutyl]piperidine-1-carboxylic acid tert-butyl ester; 4-(1-Hydroxy-4-pyridin-4-ylbutyl)piperidine-1-carboxylic acid tert-butyl ester; (Z)-4-(4-Oxo-4-pyridin-4-ylbut-2-enyl)piperidine-1-carboxylic acid tert-butyl ester; 4-(4-Oxo-4-pyridin-4-ylbutyl)piperidine-1-carboxylic acid tert-butyl ester; 4-(4-hydroxy-4-pyridin-4-ylbutyl)piperidine-1-carboxylic acid tert-butyl ester; 4-[4-(2-Cyanopyridin-4-yl)-2-hydroxybutyl]piperidine-1-carboxylic acid tert-butyl ester; 4-[4-(2-Cyanopyridin-4-yl)-4-hydroxybutyl]piperidine-1-carboxylic acid tert-butyl ester; 4-[4-(2-Cyanopyridin-4-yl)-1-hydroxybutyl]piperidine-1-carboxylic acid tert-butyl ester; 4-(2-Oxo-4-pyridin-4-ylbutyl)piperidine-1-carboxylic acid tert-butyl ester; 4-(3-Oxo-4-pyridin-4-ylbutyl)piperidine-1-carboxylic acid tert-butyl ester; 4-(4-Pyridin-4-yl-butyryl)piperidine-1-carboxylic acid tert-butyl ester; 4-[4-(2-Cyanopyridin-4-yl)-2-oxobutyl]piperidine-1-carboxylic acid tert-butyl ester; 4-[4-(2-Cyanopyridin-4-yl)butyryl]piperidine-1-carboxylic acid tert-butyl ester; 4-[4-(2-Cyanopyridin-4-yl)butyryl]piperidine-1-carboxylic acid tert-butyl ester; 4-(3-Methylamino-4-pyridin-4-ylbutyl)piperidine-1-carboxylic acid tert-butyl ester; 4-(1-Methylamino-4-pyridin-4-ylbutyl)piperidine-1-carboxylic acid tert-butyl ester; 4-[4-(2-Cyanopyridin-4-yl)-4-methylaminobutyl]piperidine-1-carboxylic acid tert-butyl ester; 4-[4-(2-Cyano-pyridin-4-yl)-2-methylamino-butyl]piperidine-1-carboxylic acid tert-butyl ester; 4-(1-Dimethylamino-4-pyridin-4-ylbutyl)piperidine-1-carboxylic acid tert-butyl ester; 4-[4-(2-Cyanopyridin-4-yl)-4-dimethylaminobutyl]-piperidine-1-carboxylic acid tert-butyl ester; 4-[4-(2-Cyanopyridin-4-yl)-2-dimethylaminobutyl]-piperidine-1-carboxylic acid tert-butyl ester; 4-[2-(2-Carbamoylpyridin-4-ylmethoxy)ethyl]piperidine-1-carboxylic acid tert-butyl ester; 4-[2-(2-Ethynylpyridin-4-ylmethoxy)ethyl]piperidine-1-carboxylic acid tert-butyl ester; 4-[(E)-4-(2-Methylpyridin-4-yl)but-3-enyl]piperidine-1-carboxylic acid ter-butyl ester; 4-[(Z)-4-(2-Methylpyridin-4-yl)but-3-enyl]piperidine-1-carboxylic acid tert-butyl ester; 4-[4-(2-Methylpyridin-4-yl)butyl]piperidine-1-carboxylic acid tert-butyl ester; 4-Hydroxy-4-[4-(2-methylpyridin-4-yl)butyl]piperidine-1-carboxylic acid ter-butyl ester.

Examples of GPR119 agonists are described in International Application No. PCT/GB2005/050265 (published as WO 2006/067532), the disclosure of which is herein incorporated by reference in its entirety. Disclosed in International Application No. PCT/GB2005/050265 as a GPR119 agonist is a compound of Formula (IX):

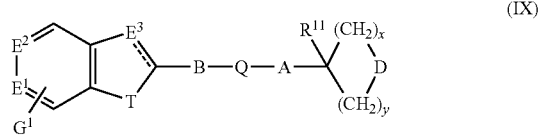

or an N-oxide thereof,
wherein:
one of $E^1$ and $E^2$ is N and the other is N or $C-G^2$;
the dashed line together with the solid line forms an optional double bond;
when the dashed line together with the solid line forms a double bond $E^3$ is $CR^8$ or N, and when it is a single bond $E^3$ is $CHR^8$, O or $NR^2$;
T is O, S, $NR^2$, $(CH_2)_2$, or $E^4=E^5$, where $E^4$ and $E^5$ are independently CH or N;
B is a bond, $-CH_2=CH_2-$ or $(CH_2)_j$;
j is 1, 2 or 3;
Q is a bond, C(O)S, or a 5- or 6-membered heteroaromatic ring;
A is $(CH_2)_n$, where one $CH_2$ group may be replaced by O, S, C(O), CH(OH)CH(Hal) $CH(NR^2R^3)$, S(O), $S(O)_2$ or $NR^3$; two $CH_2$ groups may be replaced by CH=CH, C(O)O, C(O)S, SC(O), $C(O)NR^2$ or OC(O); or three $CH_2$ groups may be replaced by $C(O)CH_2S$, $C(O)CH_2C(OH)$ or $C(O)CH_2C(O)$;
n is 0, 1, 2, 3, 4, 5, or 6;
$G^1$ and $G^2$ are independently hydrogen, halogen, $CF_3$, $C_{1-4}$alkoxy, $NR^4R^{44}$, $SO_2C_{1-4}$alkyl, $SOC_{1-4}$alkyl, $SC_{1-4}$alkyl or cyano; or $C_{1-4}$alkyl, $C_{2-4}$alkenyl, or $C_{2-4}$alkynyl, optionally substituted by hydroxy, $NR^4R^{44}$, oxo or $C_{1-4}$alkoxy;
D represents $CHR^9$ or $NR^1$;
$R^1$ is $C(O)OR^5$, $C(O)R^5$, $S(O)_2R^5$, $C(O)NR^5R^{10}$, $C(O)NR^5R^{55}$, $C_{1-4}$alkylene-$C(O)OR^5$, $C(O)C(O)OR^5$, $S(O)_2R^5$, $C(O)R^5$ or $P(O)(O-Ph)_2$; or heterocyclyl or heteroaryl, either of which may optionally be substituted by one or two groups selected from $C_{1-4}$alkyl, $C_{1-4}$alkoxy, $C_{1-4}$alkyl-OH, halogen, $C_{1-4}$-fluoroalkyl, heterocyclyl, $C(O)OC_{1-4}$alkyl;
$R^2$ and $R^3$ are independently hydrogen or $C_{1-4}$alkyl;
$R^4$ and $R^{44}$ are independently hydrogen, $C_{1-4}$alkyl, $C_{3-7}$cycloalkyl, or aryl, which may optionally be substituted with 1 or 2 substituents selected from halo, $C_{1-4}$alkyl, $CF_3$, $C_{1-4}$alkoxy, cyano, and $S(O)_2Me$; or, taken together, $R^4$ and $R^{44}$ may form a 5- or 6-membered heterocyclic ring;
$R^5$ and $R^{55}$ are independently $C_{1-8}$alkyl, $C_{2-8}$alkenyl or $C_{2-8}$alkynyl, any of which may be optionally substituted by one or more halo atoms, $NR^6R^{66}$, $OR^6$, $C(O)OR^6$, $OC(O)R^6$ or cyano, and may contain a $CH_2$ group that is replaced by O or S; or a $C_{3-7}$cycloalkyl, aryl, heterocyclyl, heteroaryl, $C_{1-4}$alkyleneC$_{3-7}$cycloalkyl, $C_{1-4}$alkylenearyl, $C_{1-4}$alkyleneheterocyclyl or $C_{1-4}$alkyleneheteroaryl, any of which may be substituted with one or more substituents selected from halo, $C_{1-4}$alkyl, $C_{1-4}$fluoroalkyl, $OR^7$, CN, $NR^7R^{77}$, $SO_2Me$, $NO_2$ or $C(O)OR^7$;
$R^6$, $R^{66}$, $R^7$, and $R^{77}$ each independently are hydrogen or $C_{1-4}$alkyl; or, taken together, $R^6$ and $R^{66}$ or $R^7$ and $R^{77}$ may form a 5- or 6-membered heterocyclic ring;
$R^8$ is hydrogen, hydroxy, $C_{1-4}$alkoxy or benzyloxy;
$R^9$ is $C_{3-6}$alkyl
$R^{10}$ is hydrogen or $C_{1-4}$alkyl;
$R^{11}$ is hydrogen or hydroxy;
x is 0, 1, 2 or 3; and
y is 1, 2, 3, 4 or 5;
with the proviso that x+y is 2, 3, 4 or 5.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Specific examples of GPR119 agonists disclosed in International Application No. PCT/GB2005/050265 include the following compounds according to Formula (IX) (referred to herein as Group I1): 4-(Furo[3,2-c]pyridine-2-carbonylsulfanyl)piperidine-1-carboxylic acid tert-butyl ester; 4-([1,6]Naphthyridine-2-carbonylsulfany)-piperidine-1-carboxylic acid tert-butyl ester; 4-([1,7]Naphthyridine-3-carbonylsulfanyl)-piperidine-1-carboxylic acid tert-butyl ester; 4-(6-Chloro-1H-pyrrolo[3,2-c]pyridine-2-carbonylsulfanyl)-piperidine-1-carboxylic acid tert-butyl ester; 4-(1H-Pyrrolo[2,3-c]pyridine-2-carbonylsulfanyl)-piperidine-1-carboxylic acid tert-butyl ester; 4-(5-Chloro-1H-pyrrolo[2,3-c]pyridine-2-carbonylsulfanyl)-piperidine-1-carboxylic acid tert-butyl ester; 4-([1,6]Naphthyridine-2-carbonylsulfanylmethyl)-piperidine-1-carboxylic acid tert-butyl ester; 4-(1H-Pyrrolo[2,3-c]pyridine-2-carbonylsulfanylmethyl)-piperidine-1-carboxylic acid tert-butyl ester; 4-(Furo[3,2-c]pyridine-2-carbonylsulfanylmethyl)-piperidine-1-carboxylic acid tert-butyl ester; 4-(6-Chloro-1H-pyrrolo[3,2-c]pyridine-2-carbonylsulfanylmethyl)-piperidine-1-carboxylic acid tert-butyl ester; 4-(5-Chloro-1H-pyrrolo[2,3-c]pyridine-2-carbonylsulfanylmethyl)-piperidine-1-carboxylic acid tert-butyl ester; 4-([1,7]Naphthyridine-3-carbonylsulfanylmethyl)-piperidine-1-carboxylic acid tert-butyl ester; 4-[2-(Furo[3,2-c]pyridin-2-ylmethoxy)ethyl]piperidine-1-carboxylic acid tert-butyl ester; 4-(Furo[3,2-c]pyridin-2-ylmethoxy)piperidine-1-carboxylic acid tert-butyl ester; 4-(Furo[3,2-c]pyridin-2-ylmethoxymethyl)-piperidine-1-carboxylic acid tert-butyl ester; 4-[3-(Furo[3,2-c]pyridin-2-ylmethoxy)propyl]-piperidine-1-carboxylic acid tert-butyl ester; 4-[4-(Furo[3,2-c]pyridin-2-ylmethoxy)butyl]-piperidine-1-carboxylic acid tert-butyl ester; 4-(2-Furo[3,2-c]pyridin-2-ylethyl)piperidine-1-carboxylic acid tert-butyl ester; 4-(3-Furo[3,2-c]pyridin-2-ylpropyl)piperidine-1-carboxylic acid tert-butyl ester; 4-(2-Furo[2,3-c]pyridin-2-ylethyl)piperidine-1-carboxylic acid tert-butyl ester; 4-(2-Oxazolo[4,5-c]pyridin-2-yl-2-oxo-ethyl)piperidine-1-carboxylic acid tert-butyl ester; 4-(2-Chloro-2-oxazolo[4,5-c]pyridin-2-ylethyl)piperidine-1-carboxylic acid tert-butyl ester; 4-(2-Oxazolo[4,5-c]pyridin-2-yl-ethyl)piperidine-1-carboxylic acid tert-butyl ester; 4-[5-(4-Hydroxymethyl furo[3,2-c]pyridin-2-yl)-[1,2,4]oxadiazol-3-ylmethoxy]-piperidine-1-carboxylic acid tert-butyl ester; 4-[5-(4-Methoxymethylfuro[3,2-c]pyridine-2-yl)-[1,2,4]oxadiazole-3-ylmethoxy]piperidine-1-carboxylic acid tert-butyl ester; 4-[5-(4-Dimethylaminomethylfuro[3,2-c]pyridine-2-yl)-[1,2,4]oxadiazole-3-ylmethoxy]piperidine-1-carboxylic acid tert-butyl ester; 4-[5-(4-Pyrrolidin-1-ylmethylfuro[3,2-c]pyridine-2-yl)-[1,2,4]oxadiazole-3-ylmethoxy]-piperidine-1-carboxylic acid tert-butyl ester; 4-[5-(4-Formylfuro[3,2-c]pyridine-2-yl)-[1,2,4]oxadiazole-3-ylmethoxy]piperidine-1-carboxylic acid tert-butyl ester; 4-([(5-Furo[3,2-c]pyridin-2-yl-[1,2,4]oxadiazol-3-ylmethyl)amino]methyl)-piperidine-1-carboxylic acid tert-butyl ester; 4-[5-Furo[3,2-c]pyridin-2-yl-[1,2,4]oxadiazol-3-ylmethyl)amino]piperidine-1-carboxylic acid tert-butyl ester; 4-[(3-Furo[3,2-c]pyridin-2-yl-[1,2,4]oxadiazol-5-ylmethyl)amino]piperidine-1-carboxylic acid tert-butyl ester; 4-[Ethyl(5-furo[3,2-c]pyridin-2-yl-[1,2,4]oxadiazol-3-ylmethyl)amino]-piperidine-1-carboxylic acid tert-butyl ester; 4-[(5-Furo[3,2-c]pyridine-2-yl-[1,2,4]oxadiazol-3-ylmethyl)propylamino]-piperidine-1-carboxylic acid tert-butyl ester; 4-(5-Furo[3,2-c]pyridine-2-yl-[1,2,4]oxadiazol-3-ylmethyl)methylamino)-piperidine-1-carboxylic acid tert-butyl ester; 4-[(3-Furo[3,2-c]pyridine-2-yl-[1,2,4]oxadiazol-5-ylmethyl)methylamino]-piperidine-1-carboxylic acid tert-butyl ester; 4-[Ethyl(3-furo[3,2-c]pyridin-2-yl-[1,2,4]oxadiazol-5-ylmethyl)amino]-piperidine-1-carboxylic acid tert-butyl ester; 4-(5-Thieno[2,3-c]pyridin-2-yl-[1,2,4]oxadiazol-3-yl)piperidine-1-carboxylic acid tert-butyl ester; 4-(5-Thieno[3,2-c]pyridin-2-yl-[1,2,4]oxadiazol-3-ylmethoxy)piperidine-1-carboxylic acid tert-butyl ester; 4-(5-Furo[3,2-c]pyridin-2-yl-[1,2,4]oxadiazol-3-yl)piperidine-1-carboxylic acid tert-butyl ester; 4-(5-Furo[3,2-c]pyridin-2-yl-[1,2,4]oxadiazol-3-ylmethoxy)piperidine-1-carboxylic acid tert-butyl ester; 4-(5-Thieno[2,3-c]pyridin-2-yl-[1,2,4]oxadiazol-3-ylmethoxy)piperidine-1-carboxylic acid tert-butyl ester; 4-(5-Thieno[2,3-c]pyridin-2-yl-[1,2,4]oxadiazol-3-ylmethyl)piperidine-1-carboxylic acid tert-butyl ester; 4-(5-Thieno[3,2-c]pyridin-2-yl-[1,2,4]oxadiazol-3-ylmethyl)piperidine-1-carboxylic acid tert-butyl ester; 4-(5-Furo[3,2-c]pyridin-2-yl-[1,2,4]oxadiazol-3-ylmethyl)piperidine-1-carboxylic acid tert-butyl ester; 4-(5-Thieno[3,2-c]pyridin-2-yl-[1,2,4]oxadiazol-3-yl)-piperidine-1-carboxylic acid tert-butyl ester; 4-(5-[1,7]Naphthyridin-3-yl-[1,2,4]oxadiazol-3-ylmethoxy)piperidine-1-carboxylic acid tert-butyl ester; 4-(5-[1,7]Naphthyridin-3-yl-[1,2,4]oxadiazol-3-yl)-piperidine-1-carboxylic acid tert-butyl ester; 4-(5-[1,7]Naphthyridin-3-yl-[1,2,4]oxadiazol-3-ylmethyl)piperidine-1-carboxylic acid tert-butyl ester; 4-[5-(1-Methyl-1H-pyrrolo[2,3-c]pyridin-2-yl)-[1,2,4]oxadiazol-3-ylmethyl]piperidine-1-carboxylic acid tert-butyl ester; 4-[5-(1H-Pyrrolo[2,3-c]pyridin-2-yl)-[1,2,4]oxadiazol-3-ylmethoxy]piperidine-1-carboxylic acid tert-butyl ester; 4-[5-(1H-Pyrrolo[2,3-c]pyridin-2-yl)-[1,2,4]oxadiazol-3-ylmethyl]piperidine-1-carboxylic acid tert-butyl ester; 4-(5-Furo[2,3-c]pyridin-2-yl-[1,2,4]oxadiazol-3-ylmethoxy)piperidine-1-carboxylic acid tert-butyl ester; 4-(5-Furo[2,3-c]pyridin-2-yl-[1,2,4]oxadiazol-3-yl)piperidine-1-carboxylic acid tert-butyl ester; 4-[5-(1H-Pyrrolo[2,3-c]pyridin-2-yl)-[1,2,4]oxadiazol-3-yl]-piperidine-1-carboxylic acid tert-butyl ester; 4-[5-(7,8-Dihydro-isoquinolin-6-yl)-[1,2,4]oxadiazol-3-ylmethoxy]piperidine-1-carboxylic acid tert-butyl ester; 4-[5-(4-Chlorofuro[3,2-c]pyridin-2-yl)-[1,2,4]oxadiazol-3-ylmethyl]piperidine-1-carboxylic acid tert-butyl ester; 4-[5-(4-Chlorofuro[3,2-c]pyridin-2-yl)-[1,2,4]oxadiazol-3-ylmethoxy]piperidine-1-carboxylic acid tert-butyl ester; 4-(3-Furo[3,2-c]pyridin-2-yl-[1,2,4]oxadiazol-5-ylmethyl)piperidine-1-carboxylic acid tert-butyl ester; 4-(3-Furo[3,2-c]pyridin-2-yl-[1,2,4]oxadiazol-5-ylmethoxy)piperidine-1-carboxylic acid tert-butyl ester; (3S)-3-(3-Furo[3,2-c]pyridin-2-yl-[1,2,4]oxadiazol-5-ylmethoxy)pyrrolidine-1-carboxylic acid tert-butyl ester; (3R)-3-(3-Furo[3,2-c]pyridin-2-yl-[1,2,4]oxadiazol-5-ylmethoxy)pyrrolidine-1-carboxylic acid tert-butyl ester; 3-(3-Furo[3,2-c]pyridin-2-yl-[1,2,4]oxadiazol-5-ylmethoxy)azetidine-1-carboxylic acid tert-butyl ester; 3-[2-(3-Furo[3,2-c]pyridin-2-yl-[1,2,4]oxadiazol-5-yl)-ethoxy]azetidine-1-carboxylic acid tert-butyl ester; 4-(5-Furo[3,2-c]pyridin-2-yl-[1,2,4]oxadiazol-3-ylmethyl)piperidine-1-carboxylic acid propyl ester; 4-(5-Furo[3,2-c]pyridin-2-yl-[1,2,4]oxadiazol-3-ylmethyl)piperidine-1-carboxylic acid isopropyl ester; 4-(5-Furo[3,2-c]pyridin-2-yl-[1,2,4]oxadiazol-3-ylmethyl)piperidine-1-carboxylic acid ethyl ester; 4-(5-Furo[3,2-c]pyridin-2-yl-[1,2,4]oxadiazol-3-ylmethyl)piperidine-1-carboxylic acid isobutyl ester; 4-(5-Furo[3,2-c]pyridin-2-yl-[1,2,4]oxadiazol-3-ylmethyl)piperidine-1-carboxylic acid cyclopropylmethyl ester; 4-(5-Furo[3,2-c]pyridin-2-yl-[1,2,4]oxadiazol-3-ylmethyl)piperidine-1-carboxylic acid 2-methoxycarbonyl-2-methylpropyl ester; 4-(5-Furo[3,2-c]pyridin-2-yl-[1,2,4]oxadiazol-3-ylmethyl)piperidine-1-carboxylic acid (S)-sec-butyl ester; 4-(5-Furo[3,2-c]pyridin-2-yl-[1,2,4]oxadiazol-3-ylmethyl)piperidine-1-carboxylic acid cyclobutyl ester; 4-(5-Furo[3,2-c]pyridin-2-yl-[1,2,4]oxadiazol-3-ylmethyl)piperidine-1-carboxylic acid 1-methoxycarbonyl-1-methylethyl ester; 4-(5-Furo[3,2-c]pyridin-2-yl-[1,2,4]oxadiazol-3-ylmethyl)piperidine-1-carboxylic acid 1-methyl-cyclobutyl ester; 4-(5-Furo[3,2-c]pyridin-2-yl-[1,2,4]oxadiazol-3-ylmethyl)piperidine-1-carboxylic acid (R)-tetrahydrofuran-2-ylmethyl ester; 4-(5-Furo[3,2-c]pyridin-2-yl-[1,2,4]oxadiazol-3-ylmethyl)piperidine-1-carboxylic acid 2-ethoxy-ethyl ester; 4-(5-Furo[3,2-c]pyridin-2-yl-[1,2,4]oxadiazol-3-ylmethyl)piperidine-1-carboxylic acid 1-methyl-cyclopropyl ester; 2-[3-(1-Pyrimidin-2-ylpiperidin-4-ylmethyl)-[1,2,4]oxadiazol-5-yl]furo[3,2-c]pyridine; 4-(5-Furo[3,2-c]pyridin-2-yl-[1,2,4]oxadiazol-3-ylmethyl)piperidine-1-carboxylic acid 1-carboxy-1-methylethyl ester; 4-(5-Furo[3,2-c]pyridin-2-yl-[1,2,4]oxadiazol-3-ylmethyl)piperidine-1-carboxylic acid 2-carboxy-2-methylpropyl ester; 4-[5-(5-Oxyfuro[3,2-c]pyridin-2-yl)-[1,2,4]oxadiazol-3-ylmethyl]piperidine-1-carboxylic acid tert-butyl ester; 4-[2-(5-Oxyfuro[3,2-c]pyridin-2-yl)ethyl]piperidine-1-carboxylic acid tert-butyl ester; 4-[5-(4-Cyanofuro[3,2-c]pyridin-2-yl)-[1,2,4]oxadiazol-3-ylmethyl]piperidine-1-carboxylic acid tert-butyl ester; 4-[2-(4-Cyanofuro[3,2-c]pyridin-2-ylmethoxy)-ethyl]piperidine-1-carboxylic acid tert-butyl ester; 4-[2-(4-Cyanofuro[3,2-c]pyridin-2-yl)ethyl]-piperidine-1-carboxylic acid tert-butyl ester; 4-[5-(7-Cyanofuro[2,3-c]pyridin-2-yl)-[1,2,4]oxadiazol-3-ylmethoxy]piperidine-1-carboxylic acid tert-butyl ester; 4-[5-(4-Cyanofuro[3,2-c]pyridin-2-yl)-[1,2,4]oxadiazol-3-ylmethoxy]piperidine-1-carboxylic acid tert-butyl ester; 4-[(5-(4-Cyanothieno[3,2-c]pyridin-2-yl)-[1,2,4]oxadiazol-3-ylmethoxy]piperidine-1-carboxylic acid tert-butyl ester; 4-[5-(4-Cyanofuro[3,2-c]pyridin-2-yl)-[1,2,4]oxadiazol-3-ylmethyl]piperidine-1-carboxylic acid propyl ester; 4-[5-(4-Cyanofuro[3,2-c]pyridin-2-yl)-[1,2,4]oxadiazol-3-ylmethyl]piperidine-1-carboxylic acid isopropyl ester; 4-[5-(4-Cyanofuro[3,2-c]pyridin-2-yl)-[1,2,4]oxadiazol-3-ylmethyl]piperidine-1-carboxylic acid isobutyl ester; 4-[5-

(4-Cyanofuro[3,2-c]pyridin-2-yl)-[1,2,4]oxadiazol-3-ylmethyl]piperidine-1-carboxylic acid ethyl ester; 4-[5-(4-Cyanofuro[3,2-c]pyridin-2-yl)-[1,2,4]oxadiazol-3-ylmethyl]piperidine-1-carboxylic acid cyclobutyl ester; 4-[5-(4-Cyanofuro[3,2-c]pyridin-2-yl)-[1,2,4]oxadiazol-3-ylmethyl]piperidine-1-carboxylic acid tetrahydropyran-4-yl ester; 4-[5-(4-Cyanofuro[3,2-c]pyridin-2-yl)-[1,2,4]oxadiazol-3-ylmethyl]piperidine-1-carboxylic acid (R)-sec-butyl ester; 4-[5-(4-Cyanofuro[3,2-c]pyridin-2-yl)-[1,2,4]oxadiazol-3-ylmethyl]piperidine-1-carboxylic acid tetrahydrofuran-2-ylmethyl ester; 4-[5-(4-Cyanofuro[3,2-c]pyridin-2-yl)-[1,2,4]oxadiazol-3-ylmethyl]piperidine-1-carboxylic acid (R)-tetrahydrofuran-2-ylmethyl ester; 4-[5-(4-Cyanofuro[3,2-c]pyridin-2-yl)-[1,2,4]oxadiazol-3-ylmethyl]piperidine-1-carboxylic acid (R)-tetrahydrofuran-3-yl ester; 4-[5-(4-Cyanofuro[3,2-c]pyridin-2-yl)-[1,2,4]oxadiazol-3-ylmethyl]piperidine-1-carboxylic acid tetrahydrothiopyran-4-yl ester; 4-[5-(4-Cyanofuro[3,2-c]pyridin-2-yl)-[1,2,4]oxadiazol-3-ylmethyl]piperidine-1-carboxylic acid 1-methoxycarbonyl-1-methylethyl ester; 4-[5-(4-Cyanofuro[3,2-c]pyridin-2-yl)-[1,2,4]oxadiazol-3-ylmethyl]piperidine-1-carboxylic acid methoxycarbonylmethyl ester; 4-[5-(4-Cyanofuro[3,2-c]pyridin-2-yl)-[1,2,4]oxadiazol-3-ylmethyl]piperidine-1-carboxylic acid cyclopropylmethyl ester; 4-[5-(4-Cyanofuro[3,2-c]pyridin-2-yl)-[1,2,4]oxadiazol-3-ylmethyl]piperidine-1-carboxylic acid 3-ethoxy-propyl ester; 4-[5-(4-Cyanofuro[3,2-c]pyridin-2-yl)-[1,2,4]oxadiazol-3-ylmethyl]piperidine-1-carboxylic acid (S)-sec-butyl ester; 4-[5-(4-Cyanofuro[3,2-c]pyridin-2-yl)-[1,2,4]oxadiazol-3-ylmethyl]piperidine-1-carboxylic acid 3-methyl-oxetan-3-ylmethyl ester; 4-[5-(4-Cyanofuro[3,2-c]pyridin-2-yl)-[1,2,4]oxadiazol-3-ylmethyl]piperidine-1-carboxylic acid 2-ethoxy-ethyl ester; 4-[5-(4-Cyanofuro[3,2-c]pyridin-2-yl)-[1,2,4]-oxadiazol-3-ylmethyl]piperidine-1-carboxylic acid 2-methoxy-1-methylethyl ester; 4-[5-(4-Cyanofuro[3,2-c]pyridin-2-yl)-[1,2,4]oxadiazol-3-ylmethyl]piperidine-1-carboxylic acid tetrahydrofuran-3-ylmethyl ester; 4-[5-(4-Cyanofuro[3,2-c]pyridin-2-yl)-[1,2,4]oxadiazol-3-ylmethyl]piperidine-1-carboxylic acid (S)-tetrahydrofuran-3-yl ester; 4-[5-(4-Cyanofuro[3,2-c]pyridin-2-yl)-[1,2,4]oxadiazol-3-ylmethyl]piperidine-1-carboxylic acid tetrahydropyran-2-ylmethyl ester; 4-[5-(4-Cyanofuro[3,2-c]pyridin-2-yl)-[1,2,4]oxadiazol-3-ylmethyl]piperidine-1-carboxylic acid 1-methyl-cyclopropyl ester; 4-[5-(4-Cyanofuro[3,2-c]pyridin-2-yl)-[1,2,4]oxadiazol-3-ylmethyl]piperidine-1-carboxylic acid 1-methyl-cyclobutyl ester; 4-[5-(4-Cyanofuro[3,2-c]pyridin-2-yl)-[1,2,4]oxadiazol-3-ylmethyl]piperidine-1-carboxylic acid 1-cyclopropylethyl ester; 4-[5-(4-Cyanofuro[3,2-c]pyridin-2-yl)-[1,2,4]oxadiazol-3-ylmethyl]piperidine-1-carboxylic acid 1-methyl-cyclopropylmethyl ester; 4-[5-(4-Cyanofuro[3,2-c]pyridin-2-yl)-[1,2,4]oxadiazol-3-ylmethyl]piperidine-1-carboxylic acid 2-methyl-cyclopropylmethyl ester; 4-[5-(4-Cyanofuro[3,2-c]pyridin-2-yl)[1,2,4]oxadiazol-3-ylmethyl]piperidine-1-carboxylic acid 3-methoxypropyl ester; 4-[5-(4-Cyanofuro[3,2-c]pyridin-2-yl)-[1,2,4]oxadiazol-3-ylmethyl]piperidine-1-carboxylic acid 3-acetoxypropyl ester; 4-[5-(4-Cyanofuro[3,2-c]pyridin-2-yl)-[1,2,4]oxadiazol-3-ylmethyl]piperidine-1-carboxylic acid oxetan-3-yl ester; 4-[5-(4-Cyanofuro[3,2-c]pyridin-2-yl)-[1,2,4]oxadiazol-3-ylmethyl]piperidine-1-carboxylic acid 1-oxo-hexahydro-1$\lambda^4$-thiopyran-4-yl ester; 4-[5-(4-Cyanofuro[3,2-c]pyridin-2-yl)-[1,2,4]oxadiazol-3-ylmethyl]piperidine-1-carboxylic acid 1,1-dioxo-hexahydro-1$\lambda^6$-thiopyran-4-yl ester; 4-[5-(3-Benzyloxyfuro[3,2-c]pyridin-2-yl)-[1,2,4]oxadiazol-3-ylmethyl]-piperidine-1-carboxylic acid tert-butyl ester; 4-[5-(3-Hydroxyfuro[3,2-c]pyridin-2-yl)-[1,2,4]oxadiazol-3-ylmethyl]-piperidine-1-carboxylic acid tert-butyl ester; 4-[5-(4-Methylfuro[3,2-c]pyridin-2-yl)-[1,2,4]oxadiazol-3-ylmethyl]piperidine-1-carboxylic acid tert-butyl ester; 4-[5-(7-Iodofuro[3,2-c]pyridin-2-yl)-[1,2,4]oxadiazol-3-ylmethyl]piperidine-1-carboxylic acid tert-butyl ester; 4-Chloro-2-[3-(1-pyrimidin-2-ylpiperidin-4-yloxymethyl)-[1,2,4]oxadiazol-5-yl]furo[3,2-c]pyridine; 2-(3-((1-(3-Methoxypyridin-2-yl)piperidin-4-yl)methyl)-[1,2,4]-oxadiazol-5-yl)furo[3,2-c]pyridine; Ethyl 6-(4-((5-(furo[3,2-c]pyridin-2-yl)-[1,2,4]-oxadiazol-3-yl)methyl)piperidin-1-yl) nicotinate; 2-{3-[1-(4,6-Dimethyl-pyrimidin-2-yl)piperidin-4-ylmethyl]-[1,2,4]oxadiazol-5-yl}-furo[3,2-c]pyridine; 4-(5-Furo[3,2-c]pyridin-2-yl-[1,2,4]oxadiazol-3-ylmethyl)-3,4,5,6-tetrahydro-2H-[1,2']bipyridinyl-3'-carboxylic acid ethyl ester; 2-[4-(5-Furo[3,2-c]pyridin-2-yl-[1,2,4]oxadiazol-3-ylmethyl)piperidin-1-yl]-quinoline; 1-[4-(5-Furo[3,2-c]pyridin-2-yl-[1,2,4]oxadiazol-3-ylmethyl)piperidin-1-yl] isoquinoline; 2-[3-(1-Pyrazin-2-yl-piperidin-4-ylmethyl)-[1,2,4]oxadiazol-5-yl]-furo[3,2-c]pyridine; 2-{3-[1-(4-Methoxy-pyrimidin-2-yl)-piperidin-4-ylmethyl]-[1,2,4]oxadiazol-5-yl}-furo[3,2-c]pyridine; [4-(5-Furo[3,2-c]pyridin-2-yl-[1,2,4]oxadiazol-3-ylmethyl)-3,4,5,6-tetrahydro-2H-[1,2']bipyridinyl-5'-yl]-methanol; 2-{3-[1-(5-Ethyl-pyrimidin-2-yl)-piperidin-4-ylmethyl]-[1,2,4] oxadiazol-5-yl}-furo[3,2-c]pyridine; 2'-Chloro-4-(5-furo[3,2-c]pyridin-2-yl-[1,2,4]oxadiazol-3-ylmethyl-3,4,5,6-tetrahydro-2H-[1,4']bipyridinyl; 4'-Chloro-4-(5-furo[3,2-c]pyridin-2-yl-[1,2,4]oxadiazol-3-ylmethyl)-3,4,5,6-tetrahydro-2H-[1,2']bipyridinyl; 2-[4-(5-Furo[3,2-c]pyridin-2-yl-[1,2,4]oxadiazol-3-ylmethyl)piperidin-1-yl]-quinoxaline; 4-(5-Furo[3,2-c]pyridin-2-yl-[1,2,4]oxadiazol-3-ylmethyl)-6'-methyl-3,4,5,6-tetrahydro-2H-[1,2']bipyridinyl; 2-{3-[1-(6-Methyl-pyridazin-3-yl)piperidin-4-ylmethyl]-[1,2,4]oxadiazol-5-yl}furo[3,2-c]pyridine; [4-(5-Furo[3,2-c]pyridin-2-yl-[1,2,4]oxadiazol-3-ylmethyl)-3,4,5,6-tetrahydro-2H-[1,2']bipyridinyl-4'-yl]-methanol; 4-(5-Furo[3,2-c]pyridin-2-yl-[1,2,4]oxadiazol-3-ylmethyl)-5'-methyl-3,4,5,6-tetrahydro-2H-[1,2']bipyridinyl; 4-(5-Furo[3,2-c]pyridin-2-yl-[1,2,4]oxadiazol-3-ylmethyl)-4'-methyl-3,4,5,6-tetrahydro-2H-[1,2']bipyridinyl; 2-{3-[1-(5-Propyl-pyrimidin-2-yl)-piperidin-4-ylmethyl]-[1,2,4]oxadiazol-5-yl}-furo[3,2-c]pyridine; 2-{3-[1-(1H-Benzoimidazol-2-yl)-piperidin-4-ylmethyl]-[1,2,4]oxadiazol-5-yl}furo[3,2-c] pyridine; 4-(5-Furo[3,2-c]pyridin-2-yl-[1,2,4]oxadiazol-3-ylmethyl)-3,4,5,6-tetrahydro-2H-[1,2']bipyridinyl; 2-{3-[1-(Furo[3,2-c]pyridin-4-yl)piperidin-4-ylmethyl]-[1,2,4]oxadiazol-5-yl}-furo[3,2-c]pyridine; 2-{3-[1-(2-Chloropyrimidin-4-yl)piperidin-4-ylmethyl]-[1,2,4]oxadiazol-5-yl}furo[3,2-c]pyridine; 2-{3-[1-(4-Morpholin-4-yl-pyrimidin-2-yl)-piperidin-4-ylmethyl]-[1,2,4]oxadiazol-5-yl}-furo[3,2-c]pyridine; 2-{3-[1-(4-Trifluoromethyl-phenyl)-piperidin-4-ylmethyl]-[1,2,4]oxadiazol-5-yl}furo [3,2-c]pyridine.

Examples of GPR119 agonists are described in International Application No. PCT/GB2005/050266 (published as WO 2006/070208), the disclosure of which is herein incorporated by reference in its entirety. Disclosed in International Application No. PCT/GB2005/050266 as a GPR119 agonist is a compound of Formula (X):

wherein:

V is phenyl or a 6-membered heteroaryl ring containing up to three N atoms;

A is —CH=CH— or $(CH_2)_n$;

B is —CH=CH— or $(CH_2)_n$, where one of the $CH_2$ groups may be replaced by O, $NR^5$, $S(O)_m$, $C(O)$ or $C(O)NR^{12}$;

n is independently 0, 1, 2 or 3;
m is independently 0.1 or 2;

$R^1$ is 3- or 4-pyridyl, 4- or 5-pyrimidinyl or 2-pyrazinyl, any of which may be optionally substituted by one or more substituents selected from halo, $C_{1-4}$ alkyl, $C_{1-4}$ fluoroalkyl, $C_{2-4}$ alkenyl, $C_{2-4}$-alkynyl, $C_{3-7}$ cycloalkyl, aryl, $OR^6$, CN, $NO_2$, $S(O)_mR^6$, $CON(R^6)_2$, $N(R^6)_2$, $NR^{10}COR^6$, $NR^{10}SO_2R^6$, $SO_2N(R^6)_2$, a 4- to 7-membered heterocyclyl group or a 5- or 6-membered heteroaryl group;

$R^2$ is 4- to 7-membered cycloalkyl substituted by $R^3$, C(O)OR$^3$, $C(O)R^3$ or $S(O)_2R^3$, or 4- to 7-membered heterocyclyl, containing one or two nitrogen atoms which is unsubstituted or substituted by $C(O)OR^4$, $C(O)R^3$, $S(O)_2 R^3$, $C(O)NHR^4$, $P(O)(OR^{11})_2$ or a 5- or 6-membered nitrogen containing heteroaryl group;

$R^3$ is $C_{3-8}$ alkyl, $C_{3-8}$ alkenyl or $C_{3-8}$ alkynyl, any of which may be optionally substituted with up to 5 fluoro or chloro atoms, and may contain a $CH_2$ group that may be replaced by O, or $C_{3-7}$ cycloalkyl, aryl, heterocyclyl, heteroaryl, $C_{1-4}$ alkyl$C_{3-7}$ cycloalkyl, $C_{1-4}$ alkylaryl, $C_{1-4}$ alkylheterocyclyl or $C_{1-4}$ alkylheteroaryl, any of which may be optionally substituted with one or more substituents selected from halo, $C_{1-4}$ alkyl, $C_{1-4}$ fluoroalkyl, $OR^6$, CN, $CO_2C_{1-4}$ alkyl, $N(R^6)_2$ and $NO_2$;

$R^4$ is $C_{2-8}$ alkyl, $C_{2-8}$ alkenyl or $C_{2-8}$ alkynyl, any of which may be optionally substituted with up to 5 fluoro or chloro atoms, and may contain a $CH_2$ group that may be replaced by O, or $C_{3-7}$ cycloalkyl, aryl, heterocyclyl, heteroaryl, $C_{1-4}$ alkyl$C_{3-7}$ cycloalkyl, $C_{1-4}$ alkylaryl, $C_{1-4}$ alkylheterocyclyl or $C_{1-4}$ alkylheteroaryl, any of which may be substituted with one or more substituents selected from halo, $C_{1-4}$ alkyl, $C_{1-4}$ fluoroalkyl, $OR^6$, CN, $CO_2C_{1-4}$ alkyl, $N(R^6)_2$ and $NO_2$;

$R^5$ is hydrogen, $C(O)R^7$, $S(O)_2R^8$, $C_{3-7}$ cycloalkyl or $C_{1-4}$ alkyl optionally substituted by $OR^6$, $C_{3-7}$ cycloalkyl, aryl, heterocyclyl or heteroaryl, wherein the cyclic groups may be substituted with one or more substituents selected from halo, $C_{1-2}$ alkyl, $C_{1-2}$ fluoroalkyl, $OR^6$, CN, $N(R^6)_2$ and $NO_2$;

$R^6$ are independently hydrogen, $C_{1-4}$ alkyl, $C_{3-7}$ cycloalkyl, aryl, heterocyclyl or heteroaryl, wherein the cyclic groups may be substituted with one or more substituents selected from halo, $C_{1-4}$ alkyl, $C_{1-4}$ fluoroalkyl, $OR^9$, CN, $SO_2CH_3$, $N(R^{10})_2$ and $NO_2$; or a group $N(R^{10})_2$ may form a 4- to 7-membered heterocyclic ring optionally containing a further heteroatom selected from O and $NR^{10}$;

$R^7$ is hydrogen, $C_{1-4}$ alkyl, $OR^6$, $N(R^6)_2$, aryl or heteroaryl;
$R^8$ is $C_{1-4}$ alkyl, $C_{1-4}$ fluoroalkyl, aryl or heteroaryl;
$R^9$ is hydrogen, $C_{1-2}$ alkyl or $C_{1-2}$ fluoroalkyl;
$R^{10}$ is hydrogen or $C_{1-4}$ alkyl;
$R^{11}$ is phenyl; and
$R^{12}$ is hydrogen, $C_{1-4}$ alkyl or $C_{3-7}$ cycloalkyl.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Specific examples of GPR119 agonists disclosed in International Application No. PCT/GB2005/050266 include the following compounds according to Formula (X) (referred to herein as Group J1): 4-{[Methyl-(2-pyridin-4-ylpyrimidin-4-yl)-amino]methyl}piperidine-1-carboxylic acid tert-butyl ester; 4-([Methyl-(2-pyridin-4-ylpyrimidin-4-ylmethyl)amino]methyl)piperidine-1-carboxylic acid tert-butyl ester; 4-[([2,4']Bipyridinyl-6-ylmethylmethylamino)methyl]piperidine-1-carboxylic acid tert-butyl ester.

Examples of GPR119 agonists are described in International Application No. PCT/JP02/09350 (published as WO 03/026661), the disclosure of which is herein incorporated by reference in its entirety. Disclosed GPR119 agonist in International Application No. PCT/JP02/09350 is a compound of Formula (XI):

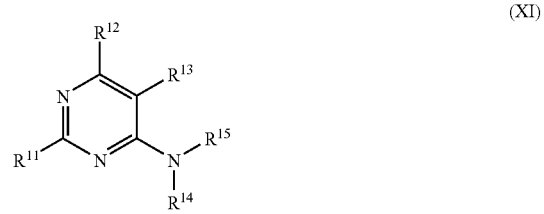

(XI)

wherein:
— $R^{11}$ is a group represented by formula -$A^{11}$-$D^{11}$; wherein $A^{11}$ is a single bond, lower alkylene, or lower alkenylene; and wherein $D^{11}$ is an aryl, cycloalkyl, aromatic heterocycle, or a non-aromatic heterocycle, each of which may be substituted;
$R^{12}$ is —H or a lower alkyl, which may be substituted by one or more groups selected from the group consisting of aryl, halogen, —O-lower alkyl, and —OH;
$R^{13}$ is —H, methyl, or fluoro;
$R^{14}$ is —H or a lower alkyl, which may be substituted by one or more halogens; and
—$R^{15}$ is a group represented by formula -$A^{15}$-$D^{15}$; wherein $A^{15}$ is a single bond, lower alkylene, or lower alkenylene, each of which may be substituted; and wherein $D^{15}$ is —H; —O— lower alkyl; an amino, which may be substituted by one or two groups selected from the group consisting of lower alkyl and aryl; or an aryl, cycloalkyl, aromatic heterocycle, or non-aromatic heterocycle, each of which may be substituted.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Examples of GPR119 agonists are described in International Application No. PCT/JP02/09350 (published as WO 03/026661), the disclosure of which is herein incorporated by reference in its entirety. Disclosed GPR119 agonist in International Application No. PCT/JP02/09350 is a compound of Formula (XII):

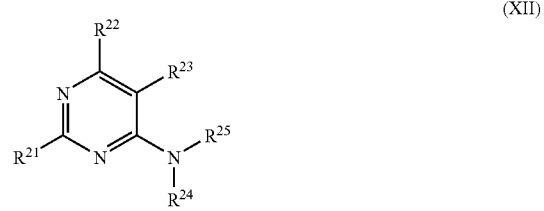

(XII)

wherein:
R²¹ is an aryl or aromatic heterocycle, each of which may be substituted;
R²² is methyl or ethyl;
R²³ is —H or fluoro;
R²⁴ is —H; and
R²⁵ is a lower alkyl or cycloalkyl, each of which may be substituted.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Specific examples of GPR119 agonists disclosed in International Application No. PCT/JP02/09350 are the following compounds according to Formula (XII) (referred to herein as Group L1): 3-(2-{[2-(4-bromophenyl)-6-methylpyrimidine-4-yl]amino}ethyl)pyrrolidine 1-oxide; 2-{[2-(3-chloro-4-fluorophenyl)-6-ethylpyrimidine-4-yl]amino}ethanol; 3-(2-{[6-methyl-2-(3,4,5-trifluorophenyl)pyrimidine-4-yl]amino}ethyl)pyridine 1-oxide; 3-(2-{[2-(4-bromophenyl)-5-fluoro-6-methylpyrimidine-4-yl]amino}ethyl)pyridine 1-oxide; 3-(2-{[2-(2,1,3-benzoxadiazol-5-yl)-6-methylpyrimidine-4-yl]amino}ethyl)pyridine 1-oxide; 3-(2-{[6-ethyl-2-(3,4,5-trifluorophenyl)pyrimidine-4-yl]amino}ethyl)pyridine 1-oxide; 2-{[6-ethyl-2-(3,4,5-trifluorophenyl)pyrimidine-4-yl]amino}ethanol; 3-2-{[2-(2,5-difluorophenyl)-6-methylpyrimidine-4-yl]amino}ethyl) pyridine 1-oxide; 3-(2-{[2-(2,1,3-benzoxadiazol-5-yl)-6-ethylpyrimidine-4-yl]amino}ethyl)pyridine 1-oxide; 3-(2-{[2-(4-chloro-2-fluorophenyl)-6-methylpyrimidine-4-yl]amino}ethyl)pyridine 1-oxide; 3-(2-{[2-(4-chloro-3-fluorophenyl)-6-methylpyrimidine-4-yl]amino}ethyl) pyridine 1-oxide; 3-(2-{[2-(5-bromo-2-fluorophenyl)-6-methylpyrimidine-4-yl]amino}ethyl)pyridine 1-oxide; 3-(2-{[6-ethyl-2-(2,3,5-trifluorophenyl)pyrimidine-4-yl]amino}ethyl)pyridine 1-oxide; 3-(2-{[6-methyl-2-(2,3,5-trifluorophenyl)pyrimidine-4-yl]amino}ethyl)pyridine 1-oxide.

Examples of GPR119 agonists are described in International Application No. PCT/JP2005/018412 (published as WO 2006/040966), the disclosure of which is herein incorporated by reference in its entirety. Disclosed GPR119 agonist in International Application No. PCT/JP2005/018412 is a compound of Formula (XIII):

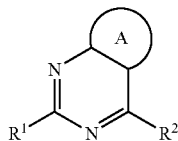

(XIII)

wherein:
A is a ring selected from the group consisting of group X¹ and group X², wherein the carbon atoms comprised by this ring can be substituted by one or more groups selected from the group consisting of, lower alkyl, —O-lower alkyl, halogen, carboxyl, —CO₂-lower alkyl and carbamoyl;

group X¹ comprises

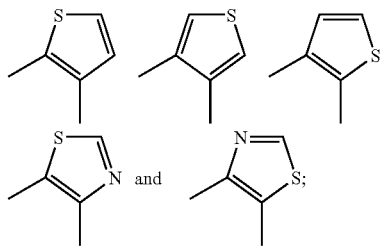

group X² comprises

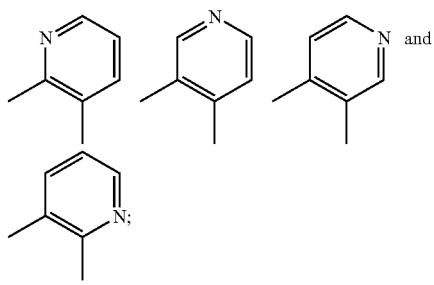

—R¹ is phenyl substituted by a least one halogen; wherein this phenyl may have further substituents; and wherein when A is a ring selected from group X², —R¹ represents a phenyl substituted by at least three halogens;
—R² is a group represented by Formula (XIIIA)

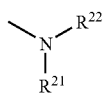

(XIIIA)

or an optionally substituted cyclic amino; wherein —R²¹ and —R²² are the same or different and represent —H, lower alkyl, lower alkenyl, lower alkynyl, cycloalkyl, phenyl, aromatic heterocycle, non-aromatic heterocycle or —O-lower alkyl, wherein each of these groups is optionally substituted; and wherein if A is a ring selected from the group X¹, —R² represents an optionally substituted cyclic amino.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Specific examples of GPR119 agonists disclosed in International Application No. PCT/JP2005/018412 are the following compounds according to Formula (XIII) (referred to herein as Group M1): 4-azepane-1-yl-2-(4-chloro-2,5-difluorophenyl)thieno[3,2-d]pyrimidine; 2-(4-chloro-5-fluoro-2-piperidine-1-yl phenyl)-7-methyl-4-piperidine-1-ylthieno [3,2-d]pyrimidine; [2-(4-azepane-1-ylthieno[3,2-d] pyrimidine-2-yl)-5-chloro-4-fluorophenyl]dimethylamine; 2-{5-[2-(4-chloro-2,5-difluorophenyl)thieno[3,2-d]pyrimidine-4-yl]-4,5,6,7-tetrahydro-2H-pyrazolo[4,3-c]pyridine-2-yl}ethanol; 2-{5-[2-(4-chloro-2,5-difluorophenyl)thieno[3,2-d]pyrimidine-4-yl]-4,5,6,7-tetrahydro-2H-pyrazolo[4,3-c]pyridine-1-yl}ethanol; {1-[2-(4-chloro-2,5-difluorophenyl)thieno[3,2-d]pyrimidine-4-yl]piperidine-3-yl}acetic acid; {1-[2-(4-chloro-2,5-difluorophenyl)thieno[3,2-d]pyrimidine-4-yl]piperidine-4-ylidene}acetic acid; 2-(4-chloro-2,5-difluorophenyl)-4-piperazine-1-ylthieno[3,2-d]pyrimidine; 1-[2-(4-chloro-2,5-difluorophenyl)thieno[3,2-d]pyrimidine-4-yl]piperidine-4-one; 2-{4-[2-(4-chloro-2,5-difluorophenyl)thieno[3,2-d]pyrimidine-4-yl]piperazine-1-yl}-2-oxoethanol; ethyl{4-[2-(4-chloro-2,5-difluorophenyl)thieno[3,2-d]pyrimidine-4-yl]piperazine-1-yl)}(oxo)acetate; 4-(4-acetyl-3-methylpiperazine-1-yl)-2-(4-chloro-2,5-difluorophenyl)thieno[3,2-d]pyrimidine; 2-{1-[2-(4-chloro-2,5-difluorophenyl)thieno[3,2-d]pyrimidine-4-yl]piperidine-4-yl}acetamide; 1-[2-(4-chloro-2,5-difluorophenyl)thieno[3,2-d]pyrimidine-4-yl]azepane-4-ol; 1-[2-(4-chloro-2,5-difluorophenyl)thieno[3,2-d]pyrimidine-4-yl]azepane-4-carbonitrile; (S)-3-{4-[2-(4-chloro-2,5-difluorophenyl)thieno[3,2-d]pyrimidine-4-yl]piperazine-1-yl}propane-1,2-diol; 1-[2-(4-chloro-2,5-difluorophenyl)thieno[3,2-d]pyrimidine-4-yl]azepane-4-one oxime; 1-[2-(4-chloro-2,5-difluorophenyl)thieno[3,2-d]pyrimidine-4-yl]azepane-4-carboxylate; ethyl({-[2-(4-chloro-2,5-difluorophenyl)thieno[3,2-d]pyrimidine-4-yl}oxy)acetate; (4RS,5SR)-1-[2-(4-chloro-2,5-difluorophenyl)thieno[3,2-d]pyrimidine-4-yl]azepane-4,5-diol; {4-[2-(4-chloro-2,5-difluorophenyl)thieno[3,2-d]pyrimidine-4-yl]piperazine-2-yl}methanol; 7-[2-(4-chloro-2,5-difluorophenyl)thieno[3,2-d]pyrimidine-4-yl]tetrahydroimidazo[1,5-a]piperazine-1,3(2H,5H)-dione; 2-[2-(4-chloro-2,5-difluorophenyl)thieno[3,2-d]pyrimidine-4-yl]tetrahydropyrrolo[1,2-a]piperazine-6,8(2H,7H)-dione; 4-azepane-1-yl-2-(4-chloro-2,5-difluorophenyl)thieno[3,2-d]pyrimidine-6-carboxylate; {1-[2-(4-chloro-2,5-difluorophenyl)thieno[3,2-d]pyrimidine-4-yl]piperidine-4-yl}acetonitrile; 2-(4-chloro-2,5-difluorophenyl)-4-[4-(1H-tetrazol-5-ylmethyl)piperidine-1-yl]thieno[3,2-d]pyrimidine; 4-azepane-1-yl-2-(4-chloro-5-fluoro-2-methoxyphenyl)thieno[3,2-d]pyrimidine.

Examples of GPR119 agonists are described in International Application No. PCT/JP2005/019000 (published as WO 2006/043490), the disclosure of which is herein incorporated by reference in its entirety. Disclosed GPR119 agonist in International Application No. PCT/JP2005/019000 is a compound of Formula (XIV):

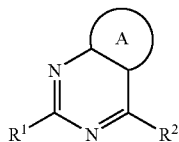

(XIV)

wherein:
A is a ring selected from the group consisting of group $X^1$, group $X^2$, group $X^3$ and group $X^4$, wherein the carbon atoms comprised by this ring may be substituted by one or more groups, selected from the group consisting of, lower alkyl, —O-lower alkyl, halogen, carboxyl, —CO$_2$-lower alkyl and carbamoyl, and wherein the sulfur atoms comprised by this ring may be oxidized;

group $X^1$ is a group comprising

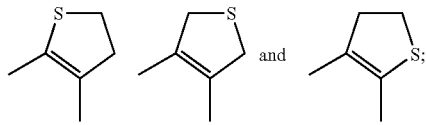

group $X^2$ is a group comprising

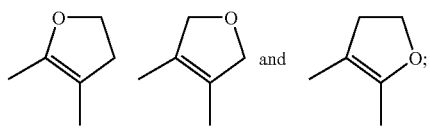

group $X^3$ is a group comprising

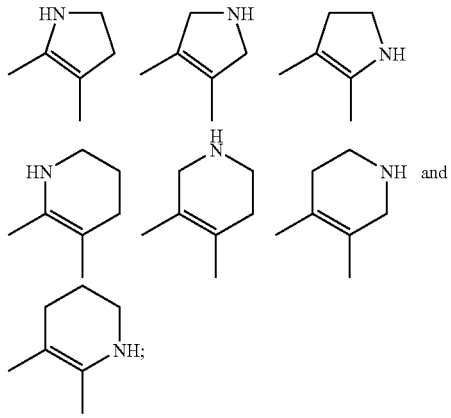

group $X^4$ is a group comprising

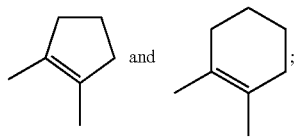

—$R^1$ is a group selected from (1) to (3) below:
  (1) Phenyl substituted by at least one halogen, wherein this phenyl may have further substituents;
  (2) Cyclopropyl, cyclobutyl, cyclopentyl, cyclohexyl, or cycloheptyl, each of which may be substituted;
  (2) Pyridyl, pyridazinyl, pyrimidinyl, pyrazinyl, pyrrolyl, thienyl, thiazolyl, oxazolyl, imidazolyl, isothiazolyl, isooxazolyl, pyrazolyl, or furyl substituted by at least one halogen; wherein these rings may be substituted by one or more halogens, which are the same or different; and wherein these rings are bonded via a carbon atom comprised by these rings to position 2 of the pyrimidine ring in the Formula (XIV);
wherein when A is a ring selected from group $X^4$, —$R^1$ represents a phenyl that is substituted by at least three halogens;

—R² is the group represented by a Formula (XIVA)

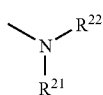
(XIVA)

or an optionally substituted cyclic amino;
wherein —R²¹ and —R²² are the same or different and represent —H, lower alkyl, lower alkenyl, lower alkynyl, cycloalkyl, phenyl, aromatic heterocycle, non-aromatic heterocycle or —O-lower alkyl, wherein each of these groups may be substituted;
wherein when A is a ring selected from group X² or group X³, —R² represents an optionally substituted cyclic amino.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Specific examples of GPR119 agonists disclosed in International Application No. PCT/JP2005/019000 are the following compounds according to Formula (XIV) (referred to herein as Group N1): (R)-2-(4-chloro-2,5-difluorophenyl)-4-(3-methylpiperidin-1-yl)-5,7-dihydrothieno[3,4-d]pyrimidine-6,6-dioxide; 4-{1-[2-(4-chloro-2,5-difluorophenyl)-6,7-dihydro-5H-cyclopenta[d]pyrimidin-4-yl]piperidin-4-yl}butanic acid; {1-[2-(4-chloro-2,5-difluorophenyl)-6,6-dioxo-5,7-dihydrothieno[3,4-d]pyrimidin-4-yl]piperidin-4-ylidine}acetic acid; 2-(4-chloro-2,5-difluorophenyl)-4-piperazin-1-yl-5,7-dihydrothieno[3,4-d]pyrimidine; 2-{4-[2-(4-chloro-2,5-difluorophenyl)-5,7-dihydrothieno[3,4-d]pyrimidin-4-yl]piperazin-1-yl}-2-oxoethanol; 2-(4-chloro-2,5-difluorophenyl)-4-[4-(methylsulfonyl)piperazin-1-yl]-5,7-dihydrothieno[3,4-d]pyrimidine; [1-(2-cyclopentyl-6,6-dioxo-5,7-dihydrothieno[3,4-d]pyrimidin-4-yl)piperidin-4-yl]acetamide; 1-{2-[2,5-difluoro-4-(methylthio)phenyl]-6,6-dioxide-5,7-dihydrothieno[3,4-d]pyrimidin-4-yl}-1,4-diazepane-5-one; 4-[6,6-dioxide-4-(5-oxo-1,4-diazepan-1-yl)-5,7-dihydrothieno[3,4-d]pyrimidin-2-yl]-2,5-difluorobenzonitrile; 3-{1-[2-(4-chloro-2,5-difluorophenyl)-6,6-dioxide-5,7-dihydrothieno[3,4-d]pyrimidin-4-yl]piperidin-4-yl}propane-1-ol; 2-({1-[2-(4-chloro-2,5-difluorophenyl)-6,6-dioxide-5,7-dihydrothieno[3,4-d]pyrimidin-4-yl]piperidin-4-yl}amino)ethanol; 2-{8-[2-(4-chloro-2,5-difluorophenyl)-6,6-dioxide-5,7-dihydrothieno[3,4-d]pyrimidin-4-yl]-2,8-diazaspiro[4.5]deca-2-yl)}ethanol; (2Z)-3-{1-[2-(4-chloro-2,5-difluorophenyl)-6,6-dioxide-5,7-dihydrothieno[3,4-d]pyrimidin-4-yl]piperidin-4-yl}prop-2-en-1-ol; (4R,5S)-1-[2-(4-chloro-2,5-difluorophenyl)-6,6-dioxide-5,7-dihydrothieno[3,4-d]pyrimidin-4-yl]azepane-4,5-diol; N-(2-aminoethyl)-N-[2-(4-chloro-2,5-difluorophenyl)-6,6-dioxide-5,7-dihydrothieno[3,4-d]pyrimidin-4-yl]-β-alanine; {1-[2-(4-chloro-2,5-difluorophenyl)-6,6-dioxide-5,7-dihydrothieno[3,4-d]pyrimidin-4-yl]piperidin-4-yl}acetonitrile; 1-[2-(4-chloro-2,5-difluorophenyl)-6,6-dioxide-5,7-dihydrothieno[3,4-d]pyrimidin-4-yl]piperidin-4-yl(2-hydroxyethyl)methyl carbamate; 1-{-[2-(4-chloro-2,5-difluorophenyl)-6,6-dioxide-5,7-dihydrothieno[3,4-d]pyrimidin-4-yl]piperidin-4-yl}pyrrolidin-2-one; 3-{1-[2-(4-chloro-2,5-difluorophenyl)-6,6-dioxide-5,7-dihydrothieno[3,4-d]pyrimidin-4-yl]piperidin-4-yl}-1,3-oxazolidin-2-one; 4-[2-(4-chloro-2,5-difluorophenyl)-6,6-dioxide-5,7-dihydrothieno[3,4-d]pyrimidin-4-yl]-N-ethylpiperazine-1-carboxamide; 2-(4-chloro-2,5-difluorophenyl)-N-cyclohexane-3-en-1-yl-5,7-dihydrothieno[3,4-d]pyrimidine-4-amine 6,6-dioxide; 3-{1-[2-(4-chloro-2,5-difluorophenyl)-6,6-dioxide-5,7-dihydrothieno[3,4-d]pyrimidin-4-yl]-4-hydroxypiperidin-4-yl}propyl acetate.

Examples of GPR119 agonists are described in International Application No. PCT/GB2006/050176 (published as WO 2007/003960), the disclosure of which is herein incorporated by reference in its entirety.

Examples of GPR119 agonists are described in International Application No. PCT/GB2006/050177 (published as WO 2007/003961), the disclosure of which is herein incorporated by reference in its entirety:

Examples of GPR119 agonists are described in International Application No. PCT/GB2006/050178 (published as WO 2007/003962), the disclosure of which is herein incorporated by reference in its entirety.

Examples of GPR119 agonists are described in International Application No. PCT/GB2006/050182 (published as WO 2007/003964), the disclosure of which is herein incorporated by reference in its entirety.

In one aspect of the present invention, the GPR119 agonist is a compound of Formula (I).

In one aspect of the present invention, the GPR119 agonist is a compound of Formula (II).

In one aspect of the present invention, the GPR119 agonist is a compound of Formula (III).

In one aspect of the present invention, the GPR119 agonist is a compound of Formula (IV).

In one aspect of the present invention, the GPR119 agonist is a compound of Formula (V).

In one aspect of the present invention, the GPR119 agonist is a compound of Formula (VI).

In one aspect of the present invention, the GPR119 agonist is a compound of Formula (VI), provided that the compound is not identical to 4-(5-piperidin-4-yl-[1,2,4]oxadiazol-3-yl)pyridine, 4-(3-pyridin-4-yl-[1,2,4]oxadiazol-5-yl)piperidine-1-carboxylic acid butyl ester, 4-[5-(4-butylcyclohexyl)-[1,2,4]oxadiazol-3-yl]pyridine, 3-[5-(4-butylcyclohexyl)-[1,2,4]oxadiazol-3-yl]pyridine, or 3-[5-(4-propylcyclohexyl)-[1,2,4]oxadiazol-3-yl]pyridine, In one aspect of the present invention, the GPR119 agonist is a compound of Formula (VII).

In one aspect of the present invention, the GPR119 agonist is a compound of Formula (VIII).

In one aspect of the present invention, the GPR119 agonist is a compound of Formula (IX).

In one aspect of the present invention, the GPR119 agonist is a compound of Formula (X).

In one aspect of the present invention, the GPR119 agonist is a compound of Formula (XI).

In one aspect of the present invention, the GPR119 agonist is a compound of Formula (XII).

In one aspect of the present invention, the GPR119 agonist is a compound of Formula (XII), provided that when in Formula (XII) R²² is methyl and R²³ is —H, R²⁵ in Formula (XII) is not: an unsubstituted lower alkyl; ethyl or propyl, each of which is substituted by a dimethylamino or a diisopropylamino; methyl substituted by a carbamoyl, which is substituted by two identical or different groups selected from the group consisting of lower alkyl and phenyl; or methyl substituted by phenyl, which may be substituted.

In one aspect of the present invention, the GPR119 agonist is a compound of Formula (XII), provided that the compound is not identical to 6-methyl-N-(2-morpholine-4-ylethyl)-2-phenylpyrimidine-4-amine, 6-methyl-2-(4-methoxyphenyl)-N-(2-morpholine-4-ylethyl)pyrimidine-4-amine, 2-{[6-methyl-2-(6-methylpyridine-2-yl)pyrimidine-4-yl]amino}ethanol, 2-{[2-(4-bromophenyl)-6-methylpyrimidine-4-yl]amino}ethanol, or [2-(4-bromophenyl)-6-methylpyrimidine-4-yl](cyclohexyl)amino.

In one aspect of the present invention, the GPR119 agonist is a compound of Formula (XIII).

In one aspect of the present invention, the GPR119 agonist is a compound of Formula (XIV).

In one aspect of the present invention, the GPR119 agonist is a compound of Formula (XIV), provided that the compound is not identical to 2-(2-fluorophenyl)-N,N-dimethyl-5,7-dihydrothieno[3,4-d]pyrimidine-4-amine or 2-cyclopropyl-4-piperazin-1-yl-5,7-dihydrothieno[3,4-d]pyrimidine.

In one aspect of the present invention, the GPR119 agonist is a compound selected from Group A1, Group B1, Group B2, Group B3, Group B4, Group B5, Group C1, Group C2, Group C3, Group C4, Group C5, Group C6, Group C7, Group C8, Group C9, Group C10, Group D1, Group D2, Group D3, Group D4, Group D5, Group D6, Group D7, Group D8, Group D9, Group D10, Group D11, Group D12, Group D13, Group D14, Group E1, Group E2, Group F1, Group G1, Group G2, Group G3, Group H1, Group I1, Group J1, Group L1, Group M1, or Group N1.

In one aspect, the GPR119 agonist is selected from the left column of Table D. It is expressly contemplated that each individual GPR119 agonist from the left column of Table D is a separate embodiment within the scope of the present invention.

In one aspect, the GPR119 agonist is selected from any set of compounds selected from the left column of Table D.

In one aspect, the GPR119 agonist is identical to a compound disclosed in International Application No. PCT/US2004/001267 (published as WO 04/065380).

In one aspect, the GPR119 agonist is identical to a compound disclosed in International Application No. PCT/US2004/005555 (published as WO 04/076413).

In one aspect, the GPR119 agonist is identical to a compound disclosed in International Application No. PCT/US2004/022327 (published as WO 05/007647).

In one aspect, the GPR119 agonist is identical to a compound disclosed in International Application No. PCT/US2004/022417 (published as WO 05/007658).

In one aspect, the GPR119 agonist is identical to a compound disclosed in International Application No. PCT/US2005/019318 (published as WO 2005/121121).

In one aspect, the GPR119 agonist is identical to a compound disclosed in International Application No. PCT/GB2004/050046 (published as WO 2005/061489).

In one aspect, the GPR119 agonist is identical to a compound disclosed in International Application No. PCT/US06/00567 (published as WO 2006/083491).

In one aspect, the GPR119 agonist is identical to a compound disclosed in International Application No. PCT/GB2005/050264 (published as WO 2006/067531).

In one aspect, the GPR119 agonist is identical to a compound disclosed in International Application No. PCT/GB2005/050265 (published as WO 2006/067532).

In one aspect, the GPR119 agonist is identical to a compound disclosed in International Application No. PCT/GB2005/050266 (published as WO 2006/070208).

In one aspect, the GPR119 agonist is identical to a compound disclosed in International Application No. PCT/JP02/09350 (published as WO 03/026661).

In one aspect, the GPR119 agonist is identical to a compound disclosed in International Application No. PCT/JP2005/018412 (published as WO 06/040966).

In one aspect, the GPR119 agonist is identical to a compound disclosed in International Application No. PCT/JP2005/019000 (published as WO 2006/043490).

In one aspect, the GPR119 agonist is identical to a compound disclosed in International Application No. PCT/GB2006/050176 (published as WO 2007/003960).

In one aspect, the GPR119 agonist is identical to a compound disclosed in International Application No. PCT/GB2006/050177 (published as WO 2007/003961).

In one aspect, the GPR119 agonist is identical to a compound disclosed in International Application No. PCT/GB2006/050178 (published as WO 2007/003962).

In one aspect, the GPR119 agonist is identical to a compound disclosed in International Application No. PCT/GB2006/050182 (published as WO 2007/003964).

Other examples of GPR119 agonists may be found in International Application No. PCT/JP02/09350 (published as WO 03/026661), the disclosure of which is herein incorporated by reference in its entirety. GPR119 agonists disclosed in International Application No. PCT/JP02/09350 include but are not limited to the compounds in Table A.

TABLE A

| Cmpd No. | Chemical Structure | Chemical Name |
|---|---|---|
| 1A | 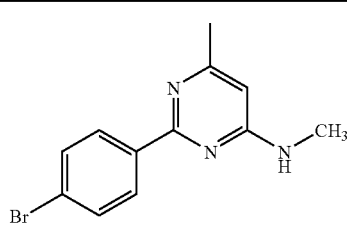 | [2-(4-Bromo-phenyl)-6-methyl-pyrimidin-4-yl]-methyl-amine |

TABLE A-continued

| Cmpd No. | Chemical Structure | Chemical Name |
| --- | --- | --- |
| 2A | 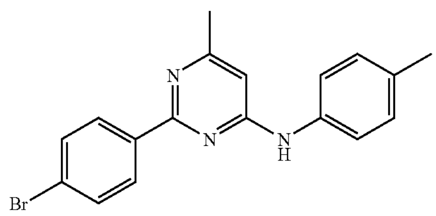 | [2-(4-Bromo-phenyl)-6-methyl-pyrimidin-4-yl]-p-tolyl-amine |
| 3A | 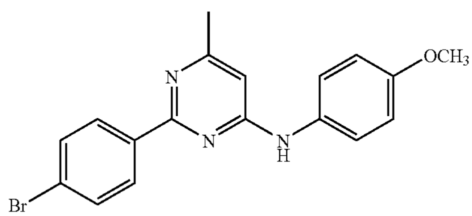 | [2-(4-Bromo-phenyl)-6-methyl-pyrimidin-4-yl]-(4-methoxy-phenyl)-amine |
| 4A | 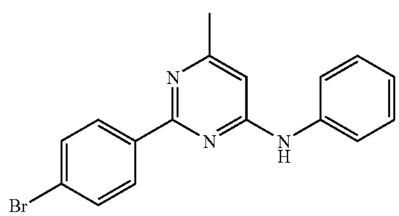 | [2-(4-Bromo-phenyl)-6-methyl-pyrimidin-4-yl]-phenyl-amine |
| 5A | 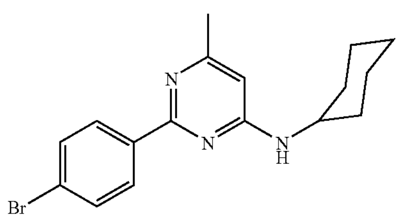 | [2-(4-Bromo-phenyl)-6-methyl-pyrimidin-4-yl]-cyclohexyl-amine |
| 6A | 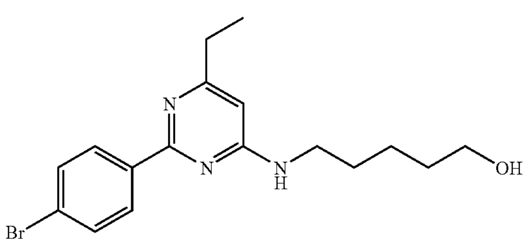 | 5-[2-(4-Bromo-phenyl)-6-ethyl-pyrimidin-4-ylamino]-pentan-1-ol |
| 7A | 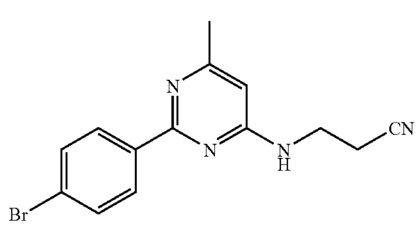 | 3-[2-(4-Bromo-phenyl)-6-methyl-pyrimidin-4-ylamino]-propionitrile |

TABLE A-continued

| Cmpd No. | Chemical Structure | Chemical Name |
|---|---|---|
| 8A | 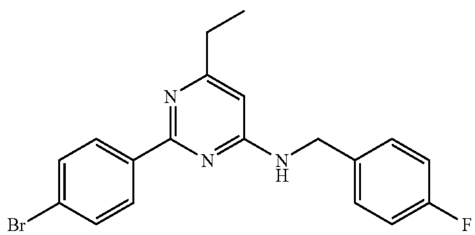 | [2-(4-Bromo-phenyl)-6-ethyl-pyrimidin-4-yl]-(4-fluoro-benzyl)-amine |
| 9A | 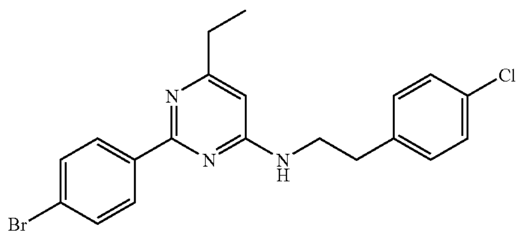 | [2-(4-Bromo-phenyl)-6-ethyl-pyrimidin-4-yl]-[2-(4-chloro-phenyl)-ethyl]-amine |
| 10A | 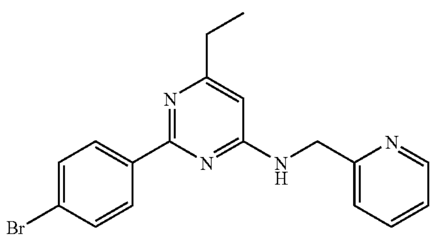 | [2-(4-Bromo-phenyl)-6-ethyl-pyrimidin-4-yl]-pyridin-2-ylmethyl-amine |
| 11A | 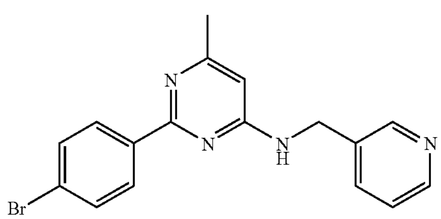 | [2-(4-Bromo-phenyl)-6-methyl-pyrimidin-4-yl]-pyridin-3-ylmethyl-amine |
| 12A | 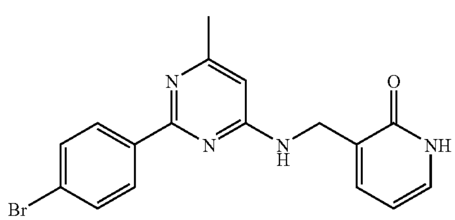 | 3-{[2-(4-Bromo-phenyl)-6-methyl-pyrimidin-4-ylamino]-methyl}-1H-pyridin-2-one |
| 13A | 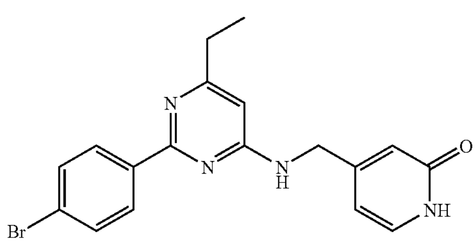 | 4-{[2-(4-Bromo-phenyl)-6-ethyl-pyrimidin-4-ylamino]-methyl}-1H-pyridin-2-one |

TABLE A-continued

| Cmpd No. | Chemical Structure | Chemical Name |
|---|---|---|
| 14A | 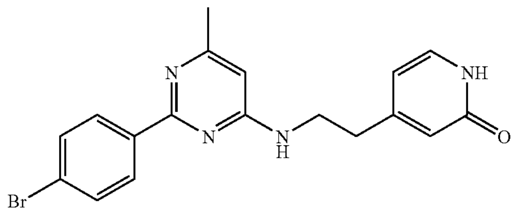 | 4-{2-[2-(4-Bromo-phenyl)-6-methyl-pyrimidin-4-ylamino]-ethyl}-1H-pyridin-2-one |
| 15A | 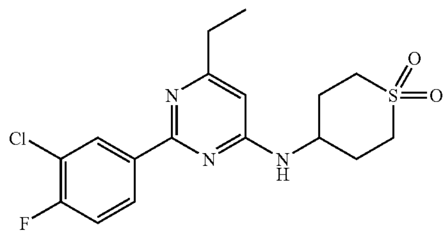 | [2-(3-Chloro-4-fluoro-phenyl)-6-ethyl-pyrimidin-4-yl]-(1,1-dioxo-hexahydro-1l6-thiopyran-4-yl)-amine |
| 16A | 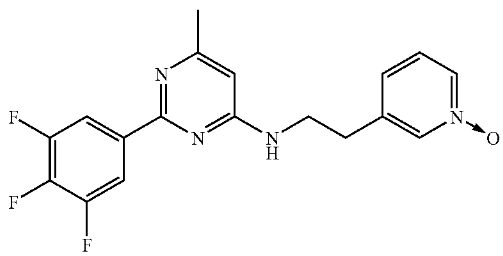 | [6-Methyl-2-(3,4,5-trifluoro-phenyl)-pyrimidin-4-yl]-[2-(1-oxy-pyridin-3-yl)-ethyl]-amine |
| 17A | 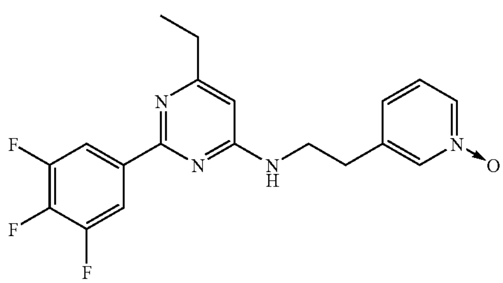 | [6-Ethyl-2-(3,4,5-trifluoro-phenyl)-pyrimidin-4-yl]-[2-(1-oxy-pyridin-3-yl)-ethyl]-amine |
| 18A | 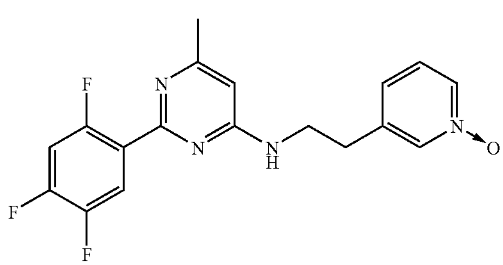 | [6-Methyl-2-(2,4,5-trifluoro-phenyl)-pyrimidin-4-yl]-[2-(1-oxy-pyridin-3-yl)-ethyl]-amine |
| 19A | 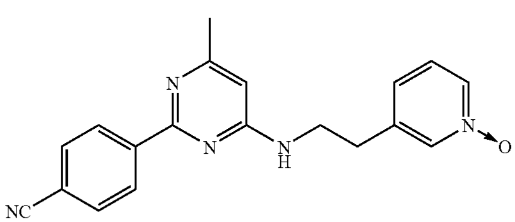 | 4-{4-Methyl-6-[2-(1-oxy-pyridin-3-yl)-ethylamino]-pyrimidin-2-yl}-benzonitrile |

TABLE A-continued

| Cmpd No. | Chemical Structure | Chemical Name |
|---|---|---|
| 20A | 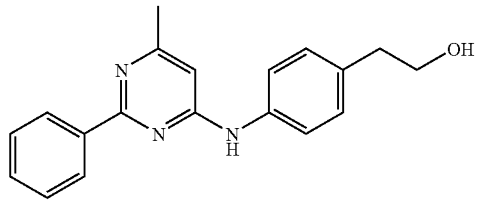 | 2-[4-(6-Methyl-2-phenyl-pyrimidin-4-ylamino)-phenyl]-ethanol |
| 21A | 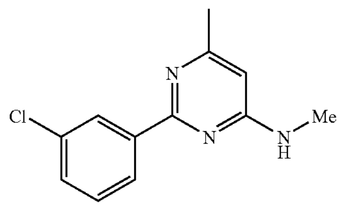 | [2-(3-Chloro-phenyl)-6-methyl-pyrimidin-4-yl]-methyl-amine |
| 22A | 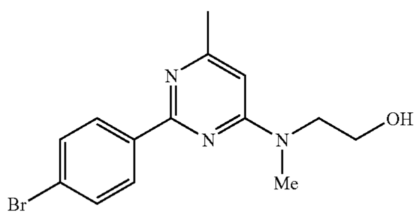 | 2-{[2-(4-Bromo-phenyl)-6-methyl-pyrimidin-4-yl]-methyl-amino}-ethanol; compound with methane |

Examples of GPR119 agonists may be found in International Application JP 2004269468, the disclosure of which is herein incorporated by reference in its entirety. GPR119 agonists disclosed in JP 2004269468 include but are not limited to the compounds in Table B.

TABLE B

| Cmpd No. | Chemical Structure | Chemical Name |
|---|---|---|
| 1B | 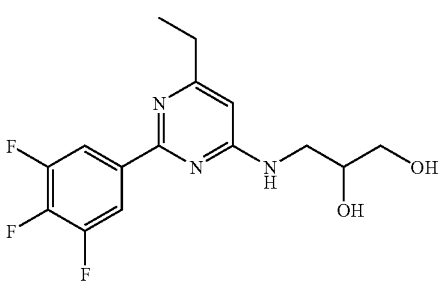 | 3-[6-Ethyl-2-(3,4,5-trifluoro-phenyl)-pyrimidin-4-ylamino]-propane-1,2-diol |
| 2B | 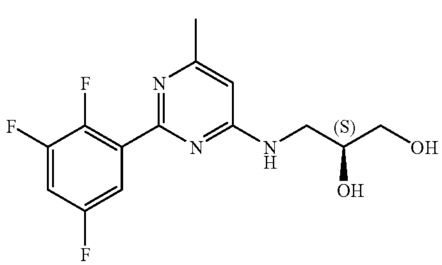 | (S)-3-[6-Methyl-2-(2,3,5-trifluoro-phenyl)-pyrimidin-4-ylamino]-propane-1,2-diol |

TABLE B-continued

| Cmpd No. | Chemical Structure | Chemical Name |
| --- | --- | --- |
| 3B | 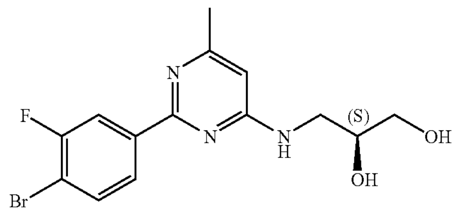 | [2-(4-Bromo-3-fluoro-phenyl)-6-methyl-pyrimidin-4-ylamino]-propane-1,2-diol |
| 4B | 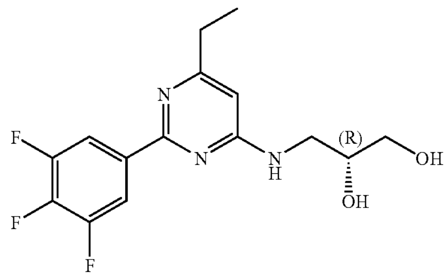 | (R)-3-[6-Ethyl-2-(3,4,5-trifluoro-phenyl)-pyrimidin-4-ylamino]-propane-1,2-diol |
| 5B | 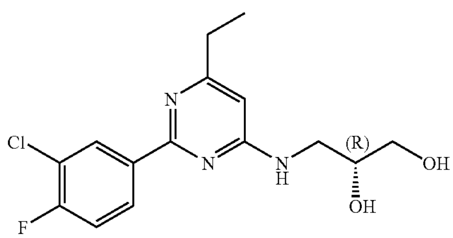 | (R)-3-[2-(3-Chloro-4-fluoro-phenyl)-6-ethyl-pyrimidin-4-ylamino]-propane-1,2-diol |
| 6B | 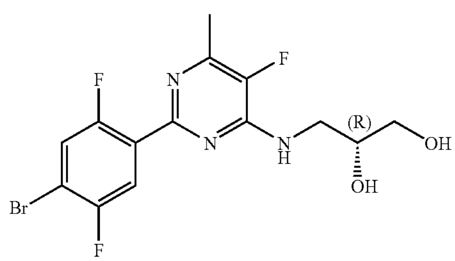 | (R)-3-[2-(4-Bromo-2,5-difluoro-phenyl)-5-fluoro-6-methyl-pyrimidin-4-ylamino]-propane-1,2-diol |
| 7B | 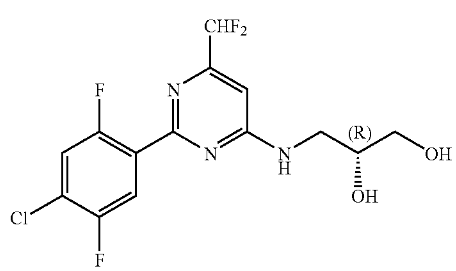 | (R)-3-[2-(4-Chloro-2,5-difluoro-phenyl)-6-difluoromethyl-pyrimidin-4-ylamino]-propane-1,2-diol |

Examples of GPR119 agonists may be found in International Application JP 2004269469, the disclosure of which is herein incorporated by reference in its entirety. GPR119 agonists disclosed in JP 2004269469 include but are not limited to the compounds in Table C.

TABLE C

| Cmpd No. | Chemical Structure | Chemical Name |
|---|---|---|
| 1C | 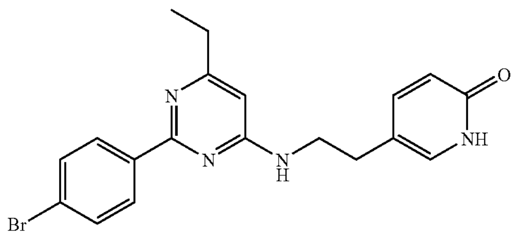 | 5-{2-[2-(4-Bromo-phenyl)-6-ethyl-pyrimidin-4-ylamino]-ethyl}-1H-pyridin-2-one |
| 2C | 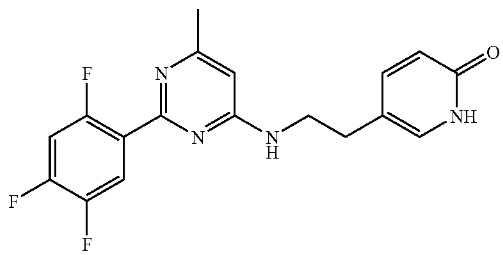 | 5-{2-[6-Methyl-2-(2,4,5-trifluoro-phenyl)-pyrimidin-4-ylamino]-ethyl}-1H-pyridin-2-one |
| 3C | 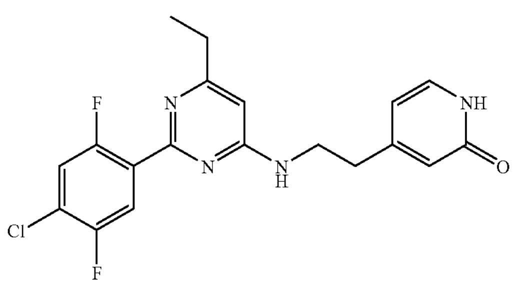 | 4-{2-[2-(4-Chloro-2,5-difluoro-phenyl)-6-ethyl-pyrimidin-4-ylamino]-ethyl}-1H-pyridin-2-one |
| 4C | 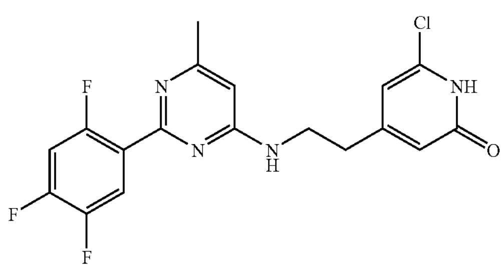 | 6-Chloro-4-{2-[6-methyl-2-(2,4,5-trifluoro-phenyl)-pyrimidin-4-ylamino]-ethyl}-1H-pyridin-2-one |
| 5C | 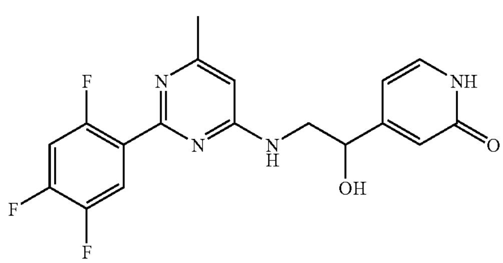 | 4-{1-Hydroxy-2-[6-methyl-2-(2,4,5-trifluoro-phenyl)-pyrimidin-4-ylamino]-ethyl}-1H-pyridin-2-one |

TABLE C-continued

| Cmpd No. | Chemical Structure | Chemical Name |
|---|---|---|
| 6C | 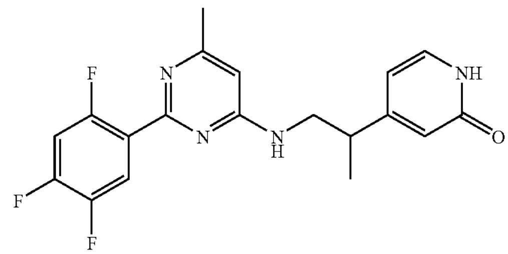 | 4-{1-Methyl-2-[6-methyl-2-(2,4,5-trifluoro-phenyl)-pyrimidin-4-ylamino]-ethyl}-1H-pyridin-2-one |

In one aspect, the GPR119 agonist is identical to a compound disclosed in WO 03/026661.

In one aspect, the GPR119 agonist is a compound selected from Table A.

In one aspect, the GPR119 agonist is identical to a compound disclosed in JP 2004269468.

In one aspect, the GPR119 agonist is a compound selected from Table B.

In one aspect, the GPR119 agonist is identical to a compound disclosed in JP 2004269469.

In one aspect, the GPR119 agonist is a compound selected from Table C.

In one aspect of the present invention, the GPR119 agonist has an $EC_{50}$ of less than about 10 μM, less than about 1 μM, less than about 100 nM, less than about 75 nM, less than about 50 nM, less than about 25 nM, less than about 20 nM, less than about 15 nM, less than about 10 nM, less than about 5 nM, less than about 4 nM, less than about 3 nM, less than about 2 nM, or less than about 1 nM. In certain embodiments, the GPR119 agonist has an $EC_{50}$ of less than about 50 nM, less than about 25 nM, less than about 20 nM, less than about 15 nM, less than about 10 nM, less than about 5 nM, less than about 4 nM, less than about 3 nM, less than about 2 nM, or less than about 1 nM.

In one aspect of the present invention, the GPR119 agonist is a selective GPR119 agonist, wherein the selective GPR119 agonist has a selectivity for GPR119 over corticotrophin-releasing factor-1 (CRF-1) receptor of at least about 10-fold, of at least about 100-fold, or of at least about 1000-fold. In one aspect of the present invention, the GPR119 agonist is a selective GPR119 agonist, wherein the selective GPR119 agonist has a selectivity for GPR119 over corticotrophin-releasing factor-1 (CRF-1) receptor of at least about 100-fold.

In one aspect of the present invention, the GPR119 agonist is a small molecule.

In one aspect of the present invention, the GPR119 agonist is orally active.

It is expressly contemplated that a GPR119 agonist of the invention is an agonist of an endogenous GPR119.

In one aspect of the present invention, the GPR119 agonist is an agonist of human GPR119 (e.g., human GPR119, GenBank® Accession No. AAP72125 and alleles thereof).

In one aspect of the present invention, any one or more GPR119 agonist can be excluded from any embodiment of the present invention.

DPP-IV Inhibitors

The class of DPP-IV inhibitors useful in the novel therapeutic combinations of the present invention include compounds which exhibit an acceptably high affinity for DPP-IV. The DPP-IV inhibitor or pharmaceutically acceptable salt may be any DPP-IV inhibitor, and in particular embodiment a selective dipeptidyl peptidase inhibitor, and in further particular embodiment a selective DPP-IV inhibitor.

Examples of DPP-IV inhibitors are described in International Application No. PCT/US02/21349 (published as WO 03/004498), the disclosure of which is herein incorporated by reference in its entirety. Disclosed in International Application No. PCT/US02/21349 as a DPP-IV inhibitor is a compound of Formula (XIX):

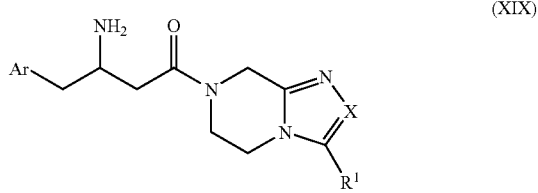

(XIX)

wherein:

Ar is phenyl which is unsubstituted or substituted with 1-5 of $R^3$, wherein $R^3$ is independently selected from the group consisting of:
(1) halogen,
(2) $C_{1-6}$alkyl, which is linear or branched and is unsubstituted or substituted with 1-5 halogens,
(3) $OC_{1-6}$alkyl, which is linear or branched and is unsubstituted or substituted with 1-5 halogens, and
(4) CN;

X is selected from the group consisting of:
(1) N, and
(2) $CR^2$;

$R^1$ and $R^2$ are independently selected from the group consisting of:
(1) hydrogen,
(2) CN,
(3) $C_{1-10}$alkyl, which is linear or branched and which is unsubstituted or substituted with 1-5 halogens or phenyl, which is unsubstituted or substituted with 1-5 substituents independently selected from halogen, CN, OH, $R^4$, $OR^4$, $NHSO_2R^4$, $SO_2R^4$, $CO_2H$, and $CO_2C_{1-6}$alkyl, wherein the $CO_2C_{1-6}$alkyl is linear or branched,
(4) phenyl which is unsubstituted or substituted with 1-5 substituents independently selected from halogen, CN, OH, $R^4$, $OR^4$, $NHSO_2R^4$, $SO_2R^4$, $CO_2H$, and $CO_2C_{1-6}$alkyl, wherein the $CO_2C_{1-6}$alkyl is linear or branched, and (5) a 5- or 6-membered heterocycle which may be saturated or unsaturated comprising 1-4 heteroatoms independently selected from N, S and O, the heterocycle being unsubstituted or substituted with 1-3 substituents independently selected from oxo, OH, halogen, $C_{1-6}$alkyl, and $OC_{1-6}$alkyl, wherein the $C_{1-6}$alkyl and $OC_{1-6}$alkyl are linear or branched and optionally substituted with 1-5 halogens;

$R^4$ is $C_{1-6}$alkyl, which is linear or branched and which is unsubstituted or substituted with 1-5 groups independently selected from halogen, $CO_2H$, and $CO_2C_{1-6}$alkyl, wherein the $CO_2C_{1-6}$alkyl is linear or branched.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Specific examples of DPP-IV inhibitors disclosed in International Application No. PCT/US02/21349 include the following compounds according to Formula (XIX) (referred to herein, as Group S1): 7-[(3R)-3-Amino-4-(3,4-difluorophenyl)butanoyl]-2-(trifluoromethyl)-5,6,7,8-tetrahydroimidazo[1,2-α]pyrazine; 7-[(3R)-3-Amino-4-(2,5-difluorophenyl)butanoyl]-2-(trifluoromethyl)-5,6,7,8-tetrahydroimidazo[1,2-α]pyrazine; 7-[(3R)-3-Amino-4-(2,4,5-trifluorophenyl)butanoyl]-2-(trifluoromethyl)-5,6,7,8-tetrahydroimidazo[1,2-α]pyrazine; 7-[3(R)-3-Amino-4-(3,4-difluorophenyl(butanoyl]-5,6,7,8-tetrahydroimidazo[1,2-α]pyrazine; 7-[(3R)-3-Amino-4-(3,4-difluorophenyl)butanoyl]-3-ethyl-5,6,7,8-tetrahydro-1,2,4-triazolo[4,3-α]pyrazine; 7-[(3R)-3-Amino-4-(2,5-difluorophenyl)butanoyl]-3-(trifluoromethyl)-5,6,7,8-tetrahydro 1,2,4-triazolo[4,3-α]pyrazine; 7-[(3R)-3-Amino-4-(2,4,5-trifluorophenyl)butanoyl]-3-(trifluoromethyl)-5,6,7,8-tetrahydro-1,2,4-triazolo[4,3-α]pyrazine.

Examples of DPP-IV inhibitors are described in International Application No. PCT/EP99/09708 (published as WO 00/34241), the disclosure of which is herein incorporated by reference in its entirety. Disclosed in International Application No. PCT/EP99/09708 as a DPP-IV inhibitor is a compound of Formula (XX):

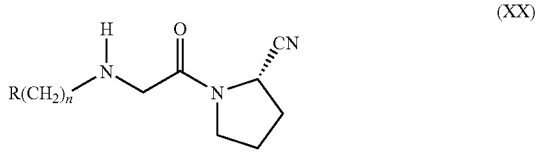

(XX)

wherein:

R is substituted adamantyl; and n is 0 to 3.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Specific examples of DPP-IV inhibitors disclosed in International Application No. PCT/EP99/09708 include the following compounds according to Formula (XX) (referred to herein as Group T1): pyrrolidine, 1-[[(3,5-dimethyl-1-adamantyl)amino]-acetyl]-2-cyano-, (S)—; pyrrolidine, 1-[[(3-ethyl-1-adamantyl)amino]acetyl]-2-cyano-, (S)—; pyrrolidine, 1-[[(3-methoxy-1-adamantyl)amino]-acetyl]-2-cyano-, (S)—; pyrrolidine, 1-[[[3-[[(t-butylamino)carbonyl]oxy]-1-adamantyl]amino]acetyl]-2-cyano-, (S)—; pyrrolidine, 1-[[[3-[[[(4-methoxyphenyl)amino]carbonyl]oxy]-1-adamantyl]amino]acetyl]-2-cyano-, (S)—; pyrrolidine, 1-[[[3-[[(phenylamino)carbonyl]oxy]-1-adamantyl]amino]acetyl]-2-cyano-, (S)—; pyrrolidine, 1-[[(5-hydroxy-2-adamantyl)amino]-acetyl]-2-cyano-, (S)—; pyrrolidine; 1-[[(3-acetyloxy-1-adamantyl)amino]-acetyl]-2-cyano-, (S)—; pyrrolidine, 1-[[[3-[[[(diisopropyl)amino]carbonyl]oxy]-1-adamantyl]amino]acetyl]-2-cyano-, (S)—; pyrrolidine, 1-[[[3-[[[(cyclohexyl)amino]carbonyl]oxy]-1-adamantyl]amino]acetyl]-2-cyano-, (S)—; pyrrolidine, 1-[[(3-ethoxy-1-adamantyl)amino]acetyl]-2-cyano-, (S)—.

Examples of DPP-IV inhibitors are described in International Application No. PCT/US01/07151 (published as WO 01/68603), the disclosure of which is herein incorporated by reference in its entirety. Disclosed in International Application No. PCT/US01/07151 as a DPP-IV inhibitor is a compound of Formula (XXI):

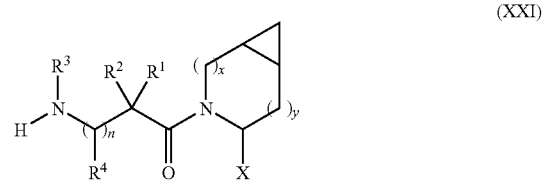

(XXI)

wherein:

x is 0 or 1 and y is 0 or 1, provided that x=1 when y=0 and x=0 when y=1;

n is 0 or 1;

X is H or CN;

$R^1$, $R^2$, $R^3$ and $R^4$ are the same or different and are independently selected from hydrogen, alkyl, alkenyl, alkynyl, cycloalkyl, cycloalkylalkyl, bicycloalkyl, tricycloalkyl, alkylcycloalkyl, hydroxyalkyl, hydroxyalkylcycloalkyl, hydroxycycloalkyl, hydroxybicycloalkyl, hydroxytricycloalkyl, bicycloalkylalkyl, alkylthioalkyl, arylalkylthioalkyl, cycloalkenyl, aryl, aralkyl, heteroaryl, heteroarylalkyl, cycloheteroalkyl or cycloheteroalkylalkyl; all optionally substituted through available carbon atoms with 1, 2, 3, 4 or 5 groups selected from hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkenylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfinyl, aminosulfonyl, alkylsulfinyl, sulfonamido or sulfonyl;

and $R^1$ and $R^3$ may optionally be taken together to form —$(CR^5R^6)_m$— where m is 2 to 6, and $R^5$ and $R^6$ are the same or different and are independently selected from hydroxy, alkoxy, H, alkyl, alkenyl, alkynyl, cycloalkyl, halo, amino, substituted amino, cycloalkylalkyl, cycloalkenyl, aryl, arylalkyl, heteroaryl, heteroarylalkyl, cycloheteroalkyl, cycloheteroalkylalkyl, alkylcarbonylamino, arylcarbonylamino, alkoxycarbonylamino, aryloxycarbonylamino, alkoxycarbonyl, aryloxycarbonyl, or alkylaminocarbonylamino, or $R^1$ and $R^4$ may optionally be taken together to form —$(CR^7R^8)_p$—wherein p is 2 to 6, and $R^7$ and $R^8$ are the same or different and are independently selected from hydroxy, alkoxy, cyano, H, alkyl, alkenyl, alkynyl, cycloalkyl, cycloalkylalkyl, cycloalkenyl, halo, amino, substituted amino, aryl, arylalkyl, heteroaryl, heteroarylalkyl, cycloheteroalkyl, cycloheteroalkylalkyl, alkylcarbonylamino, arylcarbonylamino, alkoxycarbonylamino, aryloxycarbonylamino, alkoxycarbonyl, aryloxycarbonyl, or alkylaminocarbonylamino, or optionally $R^1$ and $R^3$ together with

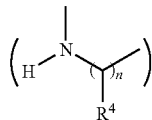

form a 5 to 7 membered ring containing a total of 2 to 4 heteroatoms selected from N, O, S, SO, or $SO_2$;

or optionally $R^1$ and $R^3$ together with

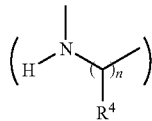

form a 4 to 8 membered cycloheteroalkyl ring wherein the cycloheteroalkyl ring has an optional aryl ring fused thereto or an optional 3 to 7 membered cycloalkyl ring fused thereto.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Examples of DPP-IV inhibitors are described in International Application No. PCT/US2004/042209 (published as WO 2005/095381), the disclosure of which is herein incorporated by reference in its entirety. Disclosed in International Application No. PCT/US2004/042209 as a DPP-IV inhibitor is a compound of Formula (XXII):

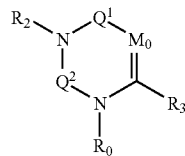

(XXII)

wherein:

$M_0$ is —C-LX, N or $CR_4$;

$Q^1$ and $Q^2$ are each independently selected from the group consisting of CO, CS, SO, $SO_2$, and C=$NR_9$;

$R_0$ is $R_1$ or -LX, with the proviso that only one of $R_0$ and $M_0$ is -LX;

$R_1$ is hydrogen or is selected from the group consisting of halo, perhalo($C_{1-10}$)alkyl, amino, cyano, thio, ($C_{1-10}$)alkyl, cycloalkyl, heterocycloalkyl, arylalkyl, heteroarylalkyl, aryl, heteroaryl, carbonyl($C_{1-3}$)alkyl, thiocarbonyl($C_{1-3}$)alkyl, sulfonyl($C_{1-3}$)alkyl, sulfinyl $C_{(1-3)}$alkyl, imino($C_{1-3}$)alkyl, hydroxy, alkoxy, aryloxy, heteroaryloxy, carbonyl group, imino group, sulfonyl group and sulfinyl group, each substituted or unsubstituted;

$R_2$ is hydrogen or selected from the group consisting of ($C_{1-10}$)alkyl, $C_{(3-12)}$cycloalkyl, ($C_{3-12}$)cycloalkyl($C_{1-5}$)alkyl, hetero($C_{3-12}$)cycloalkyl($C_{1-5}$)alkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, hetero($C_{4-12}$)bicycloaryl($C_{1-5}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, amino, aryl, heteroaryl, hydroxy, alkoxy, aryloxy, heteroaryloxy, carbonyl group, imino group, sulfonyl group and sulfinyl group, each substituted or unsubstituted;

$R_3$ is selected from the group consisting of perhalo($C_{1-10}$) alkyl, amino, ($C_{1-10}$)alkyl, cycloalkyl, heterocycloalkyl, arylalkyl, heteroarylalkyl, aryl, heteroaryl, carbonyl($C_{1-3}$)alkyl, thiocarbonyl($C_{1-3}$)alkyl, sulfonyl($C_{1-3}$) alkyl, sulfinyl($C_{1-3}$)alkyl, imino($C_{1-3}$)alkyl, hydroxy, alkoxy, aryloxy, heteroaryloxy, carbonyl group, imino group, sulfonyl group and sulfinyl group, each substituted or unsubstituted, and a substituted or unsubstituted 3, 4, 5, 6 or 7 membered ring;

$R_4$ is hydrogen or is selected from the group consisting of halo, perhalo($C_{1-10}$)alkyl, amino, cyano, thio, ($C_{1-10}$)alkyl, cycloalkyl, heterocycloalkyl, arylalkyl, heteroarylalkyl, aryl, heteroaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, hydroxy, alkoxy, aryloxy, heteroaryloxy, carbonyl group, imino group, sulfonyl group and sulfinyl group, each substituted or unsubstituted;

$R_9$ is hydrogen or is selected from the group consisting of alkyl, cycloalkyl, heterocycloalkyl, arylalkyl, heteroarylalkyl, bicycloaryl, and heterobicycloaryl, each substituted or unsubstituted;

L is a linker providing 1, 2 or 3 atom separation between X and the ring to which L is attached, wherein the atoms of the linker providing the separation are selected from the group consisting of carbon, oxygen, nitrogen, and sulfur; and X is selected from the group consisting of ($C_{1-10}$)alkyl, ($C_{3-12}$)cycloalkyl, hetero($C_{3-12}$)cycloalkyl, aryl($C_{1-10}$) alkyl, heteroaryl($C_{1-5}$)alkyl, ($C_{9-12}$)bicycloaryl, hetero ($C_{4-12}$)bicycloaryl, carbonyl($C_{1-3}$)alkyl, thiocarbonyl ($C_{1-3}$)alkyl, sulfonyl($C_{1-3}$)alkyl, sulfinyl($C_{1-3}$)alkyl, imino($C_{1-3}$)alkyl, amino, aryl, heteroaryl, hydroxy, alkoxy, aryloxy, heteroaryloxy, alkenyl, alkynyl, carbonyl group, cyano, imino group, sulfonyl group and sulfinyl group, each substituted or unsubstituted.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Specific examples of DPP-IV inhibitors disclosed in International Application No. PCT/US2004/042209 include the following compounds according to Formula (XXII) (referred to herein as Group V1): 2-(6-Chloro-2,4-dioxo-3,4-dihydro-2H-pyrimidin-1-ylmethyl)-benzonitrile; 2-(6-Chloro-3-methyl-2,4-dioxo-3,4-dihydro-2H-pyrimidin-1-ylmethyl)-benzonitrile; 2-{6-[3-Amino-piperidin-1-yl]-3-methyl-2,4-dioxo-3,4-dihydro-2H-pyrimidin-1-ylmethyl}-benzonitrile; 2-{6-[3-Amino-piperidin-1-yl]-3-ethyl-2,4-dioxo-3,4-dihydro-2H-pyrimidin-1-ylmethyl}benzonitrile; 2-{6-[3-Amino-piperidin-1-yl]-2,4-dioxo-3,4-dihydro-2H-pyrimidin-1-ylmethyl}-benzonitrile; 2-{6-[3-Amino-piperidin-1-yl]-5-chloro-3-methyl-2,4-dioxo-3,4-dihydro-2H-pyrimidin-1-ylmethyl}-benzonitrile; 6-[3-Amino-piperidin-1-yl]-1-(2-bromo-benzyl)-1H-pyrimidine-2,4-dione; 6-[3-Amino-piperidin-1-yl]-1-(2-iodo-benzyl)-1H-pyrimidine-2,4-dione; 6-[3-Amino-piperidin-1-yl]-1-(2-bromo-5-fluoro-benzyl)-3-methyl-1H-pyrimidine-2,4-dione; 6-[3-Amino-piperidin-1-yl]-1-(2-chloro-5-fluoro-benzyl)-3-methyl-1H-pyrimidine-2,4-dione; 6-[3-Amino-piperidin-1-yl]-1-(2-chloro-4-fluoro-benzyl)-3-methyl-1H-pyrimidine-2,4-dione; 6-[3-Amino-piperidin-1-yl]-1-(2-bromo-benzyl)-3-methyl-1H-pyrimidine-2,4-dione; 2-{6-[Azepan-3(±)-ylamino]-3-methyl-2,4-dioxo-3,4-dihydro-2H-pyrimidin-1-ylmethyl}-benzonitrile; 2-{6-[3(±)-Amino-azepan-1-yl]-3-methyl-2,4-dioxo-3,4-dihydro-2H-pyrimidin-1-ylmethyl}-benzonitrile; 2-{6-(2-Amino-ethylamino)-3-ethyl-2,4-dioxo-3,4-dihydro-2H-pyrimidin-1-ylmethyl}-benzonitrile; 2-{6-[3-Amino-piperidin-1-yl]-3-(3-cyano-benzyl)-2,4-dioxo-3,4-dihydro-2H-pyrimidin-1-ylmethyl}-benzonitrile; 2-{6-[3-Amino-piperidin-1-yl]-3-(2-cyano-benzyl)-2,4-dioxo-3,4-dihydro-2H-pyrimidin-1-ylmethyl}-benzonitrile; 2-{6-[3-Amino-piperidin-1-yl]-3-(4-cyano-benzyl)-2,4-dioxo-3,4-dihydro-2H-pyrimidin-1-ylmethyl}benzonitrile; 2-[6-(3-Amino-piperidin-1-yl)-3-(1H-benzoimidazol-2-ylmethyl)-2,4-dioxo-3,4-dihydro-2H-pyrimidin-1-ylmethyl]-benzonitrile; 2-{6-[3-Amino-piperidin-1-yl]-2,4-dioxo-3-(4-pyrazol-1-yl-benzyl)-3,4-dihydro-2H-pyrimidin-1-ylmethyl}-benzonitrile; 2-{6-[3-Amino-piperidin-1-yl]-2,4-dioxo-3-(3-pyrrol-1-yl-benzyl)-3,4-dihydro-2H-pyrimidin-1-ylmethyl}-benzonitrile; 6-[3-Amino-piperidin-1-yl]-3-(2-cyano-benzyl)-2,6-dioxo-3,6-dihydro-2H-pyrimidin-1-ylmethyl]-thiophene-3-carbonitrile; 3-{4-[3-Amino-piperidin-1-yl]-3-(2-cyano-benzyl)-2,6-dioxo-3,6-dihydro-2H-pyrimidin-1-ylmethyl}-benzoic acid methyl ester; 3-{4-[3-Amino-piperidin-1-yl]-3-(2-cyano-benzyl)-2,6-dioxo-3,6-dihydro-2H-pyrimidin-1-ylmethyl}-benzoic acid; 6-[3-Amino-piperidin-1-yl]-1,3-bis-(2-bromo-5-fluoro-benzyl)-1H-pyrimidine-2,4-dione; 2-{6-[3(R)-Amino-piperidin-1-yl]-5-chloro-2,4-dioxo-3,4-dihydro-2H-pyrimidin-1-ylmethyl}-benzonitrile; 6-[3(R)-Amino-piperidin-1-yl]-1-(2,5-di-chloro-benzyl)-3-methyl-1H-pyrimidine-2,4-dione; 6-[3(R)-Amino-piperidin-1-yl]-1-(2-chloro-3,6-di-fluoro-benzyl)-3-methyl-1H-pyrimidine-2,4-dione; (R)-2-((6-(3-amino-3-methylpiperidin-1-yl)-3-methyl-2,4-dioxo-3,4-dihydropyrimidin-1(2H)-yl)methyl)-4-fluorobenzonitrile; 2-[6-(3-Amino-piperidin-1-yl)-3-methyl-2,4-dioxo-3,4-dihydro-2H-pyrimidin-1-ylmethyl]-4-fluoro-benzonitrile.

Specific examples of DPP-IV inhibitors disclosed in International Application No. PCT/US2004/042209 include the following compounds according to Formula (XXII) (referred to herein as Group V2): 2-{6-[3(R)-Amino-piperidin-1-yl]-3-methyl-2,4-dioxo-3,4-dihydro-2H-pyrimidin-1-ylmethyl}benzonitrile; 2-{6-[3(R)-Amino-piperidin-1-yl]-3-ethyl-2,4-dioxo-3,4-dihydro-2H-pyrimidin-1-ylmethyl}-benzonitrile; 2-{6-[3(R)-Amino-piperidin-1-yl]-2,4-dioxo-3,4-dihydro-2H-pyrimidin-1-ylmethyl}-benzonitrile; 2-{6-[3(R)-Amino-piperidin-1-yl]-5-chloro-3-methyl-2,4-dioxo-3,4-dihydro-2H-pyrimidin-1-ylmethyl}-benzonitrile; 6-[3(R)-Amino-piperidin-1-yl]-1-(2-bromo-benzyl)-1H-pyrimidine-2,4-dione; 6-[3(R)-Amino-piperidin-1-yl]-1-(2-iodo-benzyl)-1H-pyrimidine-2,4-dione; 6-[3(R)-Amino-piperidin-1-yl]-1-(2-bromo-5-fluoro-benzyl)-3-methyl-1H-pyrimidine-2,4-dione; 6-{[3(R)-Amino-piperidin-1-yl]-1-(2-chloro-5-fluoro-benzyl)-3-methyl-1H-pyrimidine-2,4-dione; 6-[3(R)-Amino-piperidin-1-yl]-1-(2-chloro-4-fluoro-benzyl)-3-methyl-1H-pyrimidine-2,4-dione; 6-[3(R)-Amino-piperidin-1-yl]-1-(2-bromo-benzyl)-3-methyl-1H-pyrimidine-2,4-dione; 2-{6-[3(R)-Amino-piperidin-1-yl]-3-(3-cyano-benzyl)-2,4-dioxo-3,4-dihydro-2H-pyrimidin-1-ylmethyl}-benzonitrile; 2-{6-[3(R)-Amino-piperidin-1-yl]-3-(2-cyano-benzyl)-2,4-dioxo-3,4-dihydro-2H-pyrimidin-1-ylmethyl}-benzonitrile; 2-{6-[3(R)-Amino-piperidin-1-yl]-3-(4-cyano-benzyl)-2,4-dioxo-3,4-dihydro-2H-pyrimidin-1-ylmethyl}-benzonitrile; 2-[6-(3-Amino-piperidin-1-yl)-3-(1H-benzoimidazol-2-ylmethyl)-2,4-dioxo-3,4-dihydro-2H-pyrimidin-1-ylmethyl]-benzonitrile; 2-{6-[3(R)-Amino-piperidin-1-yl]-2,4-dioxo-3-(4-pyrazol-1-yl-benzyl)-3,4-dihydro-2H-pyrimidin-1-ylmethyl}-benzonitrile; 2-{6-[3(R)-Amino-piperidin-1-yl]-2,4-dioxo-3-(3-pyrrol-1-yl-benzyl)-3,4-dihydro-2H-pyrimidin-1-ylmethyl}-benzonitrile; 6-[3(R)-Amino-piperidin-1-yl]-3-(2-cyano-benzyl)-2,6-dioxo-3,6-dihydro-2H-pyrimidin-1-ylmethyl]-thiophene-3-carbonitrile; 3-{4-[3(R)-Amino-piperidin-1-yl]-3-(2-cyano-benzyl)-2,6-dioxo-3,6-dihydro-2H-pyrimidin-1-ylmethyl}-benzoic acid methyl ester; 3-{4-[3(R)-Amino-piperidin-1-yl]-3-(2-cyano-benzyl)-2,6-dioxo-3,6-dihydro-2H-pyrimidin-1-ylmethyl}-benzoic acid; 6-[3(R)-Amino-piperidin-1-yl]-1,3-bis-(2-bromo-5-fluoro-benzyl)-1H-pyrimidine-2,4-dione; 2-[6-(3(R)-Amino-piperidin-1-yl)-3-methyl-2,4-dioxo-3,4-dihydro-2H-pyrimidin-1-ylmethyl]-4-fluoro-benzonitrile.

Examples of DPP-IV inhibitors are described in Villhauer et al., J Med Chem (2003) 46:2774-2789, for LAF237; Ahren et al, J Clin Endocrinol Metab (2004) 89:2078-2084; Villhauer et al., J Med Chem (2002) 45:2362-2365 for NVP-DPP728; Ahren et al, Diabetes Care (2002) 25:869-875 for NVP-DPP728; Peters et al., Bioorg Med Chem Lett (2004) 14:1491-1493; Caldwell et al., Bioorg Med Chem Lett (2004) 14:1265-1268; Edmondson et al., Bioorg Med Chem Lett (2004) 14:5151-5155; and Abe et al., J Nat Prod (2004) 67:999-1004; the disclosure of each of which is herein incorporated by reference in its entirety.

Specific examples of DPP-IV inhibitors include, but are not limited to, dipeptide derivatives or dipeptide mimetics such as alanine-pyrrolidide, isoleucine-thiazolidide, and the pseudosubstrate N-valyl prolyl, O-benzoyl hydroxylamine, as described e.g. in U.S. Pat. No. 6,303,661, the disclosure of which is herein incorporated by reference in its entirety.

Examples of DPP-IV inhibitors may be found in U.S. Pat. Nos. 7,074,794, 7,060,722, 7,053,055, 7,026,316, 7,022,718, 6,949,515, 6,897,222, 6,869,947, 6,867,205, 6,861,440, 6,849,622, 6,812,350, 6,803,357, 6,800,650, 6,727,261, 6,716,843, 6,710,040, 6,706,742, 6,645,995, 6,617,340, 6,699,871, 6,573,287, 6,432,969, 6,395,767, 6,380,398, 6,303,661, 6,242,422, 6,166,063, 6,100,234, 6,040,145, the disclosure of each of which is herein incorporated by reference in its entirety. Examples of DPP-IV inhibitors may be found in U.S. Pat. Appl. Nos. 2006142576, 2006135767, 2006135512, 2006111336, 2006074087, 2006069116, 2006052382, 2006046978, 2006040963, 2006039974, 2006024313, 2006014764, 2005059724, 2005059716, 2005043292, 2005038020, 2005032804, 2005004205, 2004259903, 2004259902, 2004259883, 2004254226, 2004242898, 2004229926, 2004180925, 2004176406, 2004138214, 2004116328, 2004110817, 2004106656, 2004097510, 2004087587, 2004082570, 2004077645, 2004072892, 2004063935, 2004034014, 2003232788, 2003225102, 2003216450, 2003216382, 2003199528, 2003195188, 2003162820, 2003149071, 2003134802, 2003130281, 2003130199, 2003125304, 2003119750, 2003119738, 2003105077, 2003100563, 2003087950, 2003078247, 2002198205, 2002183367, 2002103384, 2002049164, 2002006899, the disclosure of each of which is herein incorporated by reference in, its entirety.

Examples of DPP-IV inhibitors may be found in International Applications WO 2006/071762, wo 2006/071752, WO 2006/068978, WO 2006/068163, WO 2006/058628, WO 2006/058064, WO 2006/040625, WO 2006/039325, WO 2006/033848, WO 2006/030847, WO 2006/027204, WO 2006/023750, WO 2006/020017, WO 2006/015699, WO 2006/015691, WO 2006/013104, WO 2006/012441, WO 2006/012395, WO 2006/011035, WO 2006/009886, WO 2005/123685, WO 2005/121131, WO 2005/121089, WO 2005/120494, WO 2005/118555, WO 2005/116029, WO 2005/116014, WO 2005/115982, WO 2005/108382, WO 2005/106011, WO 2005/100334, WO 2005/095339, WO 2005/094323, WO 2005/087235, WO 2005/082849, WO 2005/082348, WO 2005/079795, WO 2005/075426, WO 2005/072530, WO 2005/063750, WO 2005/058849, WO 2005/049022, WO 2005/047297, WO 2005/044195, WO 2005/042533, WO 2005/042488, WO 2005/040095, WO 2005/037828, WO 2005/037779, WO 2005/034940, WO 2005/033099, WO 2005/032590, WO 2005/030751. WO 2005/030127, WO 2005/026148, WO 2005/025554, WO 2005/023762, WO 2005/020920, WO 05/19168, WO 05/12312, WO 05/12308, WO 05/12249, WO 05/11581, WO 05/09956, WO 05/03135, WO 05/00848, WO 05/00846, WO 04/112701, WO 04/111051, WO 04/111041, WO 04/110436, WO 04/110375, WO 04/108730, WO 04/104216, WO 04/104215, WO 04/103993, WO 04/103276, WO 04/99134, WO 04/96806, WO 04/92128, WO 04/87650, WO 04/87053, WO 04/85661, WO 04/85378, WO 04/76434, WO 04/76433, WO 04/71454, WO 04/69162, WO 04/67509, WO 04/64778, WO 04/58266, WO 04/52362, WO 04/52850, WO 04/50022, WO 04/50658, WO 04/48379, WO 04/46106, WO 04/43940, WO 04/41820, WO 04/41795, WO 04/37169, WO 04/37181, WO 04/33455, WO 04/32836, WO 04/20407, WO 04/18469, WO 04/18468, WO 04/18467, WO 04/14860, WO 04/09544, WO 04/07468, WO 04/07446, WO 04/04661, WO 04/00327, WO 03/106456, WO 03/104229, WO 03/101958, WO 03/101448, WO 03/99279, WO 03/95425, WO 03/84940, WO 03/82817, WO 03/80633, WO 03/74500, WO 03/72556, WO 03/72528, WO 03/68757, WO 03/68748, WO 03/57666, WO 03/57144, WO 03/55881, WO 03/45228, WO 03/40174, WO 03/38123, WO 03/37327, WO 03/35067, WO 03/35057, WO 03/24965, WO 03/24942, WO 03/22871, WO 03/15775, WO 03/04498, WO 03/04496, WO 03/02530, WO 03/02596, WO 03/02595, WO 03/02593, WO 03/02553, WO 03/02531, WO 03/00181, WO 03/00180, WO 03/00250, WO 02/83109, WO 02/83128, WO 02/76450, WO 02/68420, WO 02/62764, WO 02/55088, WO 02/51836, WO 02/38541, WO 02/34900, WO 02/30891, WO 02/30890, WO 02/14271, WO 02/02560, WO 01/97808, WO 01/96295, WO 01/81337, WO 01/81304, WO 01/68603, WO 01/55105, WO 01/52825, WO 01/34594, WO 00/71135, WO 00/69868, WO 00/56297, WO 00/56296, WO 00/34241, WO 00/23421, WO 00/10549, WO 99/67278, WO 99/62914, WO 0.99/61431, WO 99/56753, WO 99/25719, WO 99/16864, WO 98/50066, WO 98/50046, WO 98/19998, WO 98/18763, WO 97/40832, WO 95/29691, WO 95/15309, WO 93/10127, WO 93/08259, WO 91/16339, EP 1671649, EP 1667524, EP 1664031, EP 1659123, EP 1658066, EP 1638970, EP 1638968, EP 1638950, EP 1635818, EP 1627870, EP 1625122, EP 1624874, EP 1517907, EP 1513808, EP 1492777, EP 1490335, EP 1489088, EP 1480961, EP 1476435, EP 1476429, EP 1469873, EP 1465891, EP 1463727, EP 1461337, EP 1450794, EP 1446116, EP 1442049, EP 1441719, EP 1426366, EP 1412357, EP1406873, EP 1406872, EP 1406622, EP 1404675, EP 1399420, EP 1399471, EP 1399470, EP 1399469, EP 1399433, EP 1399154, EP 1385508, EP 1377288, EP 1355886, EP 1354882, EP 1338592, EP 1333025, EP 1323710, EP 1304327, EP 1301187, EP 1296974, EP 1280797, EP 1282600, EP 1261586, EP 1258476, EP 1254113, EP 1248604, EP 1245568, EP 1215207, EP 1228061, EP 1137635, EP 1123272, EP 1104293, EP 1082314, EP 1050540, EP 1043328, EP 0995440, EP 0980249, EP 0975359, EP 0731789, EP 0641347, EP 0610317, EP 0528858, CA 2466870, CA 2433090, CA 2339537, CA 2289125. CA 2289124, CA 2123128, DD 296075, DE 19834591, DE 19828113, DE 19823831, DE 19616486, DE 10333935, DE 10327439, DE 10256264, DE 10251927, DE 10238477, DE 10238470, DE 10238243, DE 10143840, FR 2824825, FR 2822826, JP2005507261, JP 2005505531, JP 2005502624, JP 2005500321, JP 2005500308, JP2005023038, JP 2004536115, JP 2004535445, JP 2004535433, JP 2004534836, JP 2004534815, JP 2004532220, JP 2004530729, JP 2004525929, JP 2004525179, JP 2004522786, JP 2004521149, JP 2004503531, JP 2004315496, JP 2004244412, JP 2004043429, JP 2004035574, JP 2004026820, JP 2004026678, JP 2004002368, JP 2004002367, JP 2003535898, JP 2003535034, JP 2003531204, JP 2003531191, JP 2003531118, JP 2003524591, JP 2003520849, JP 2003327532, JP 2003300977, JP 2003238566, JP 2002531547, JP 2002527504, JP 2002517401, JP 2002516318, JP 2002363157, JP 2002356472, JP 2002356471, JP, 2002265439, JP 2001510442, JP 2000511559, JP 2000327689, JP 2000191616, JP 1998182613, JP 1998081666, JP 1997509921, JP 1995501078, JP 1993508624, the disclosure of each of which is herein incorporated by reference in its entirety.

In one aspect of the present invention, the DPP-IV inhibitor is valine-pyrrolidide (Deacon et al, Diabetes (1998) 47:764769; the disclosure of which is herein incorporated by reference in its entirety).

In one aspect of the present invention, the DPP-IV inhibitor is 3-(L-Isoleucyl)thiazolidine (isoleucine-thiazolidide). Isoleucine-thiazolidide may be found in JP 2001510442, WO 97/40832, U.S. Pat. No. 6,303,661, and DE 19616486, the disclosure of each of which is herein incorporated by reference in its entirety. Isoleucine-thiazolidide is described as an orally active and selective DPP-IV inhibitor [Pederson et al, Diabetes (1998) 47:1253-1258; the disclosure of which is herein incorporated by reference in its entirety].

In one aspect of the present invention, the DPP-IV inhibitor is 1-[2-[5-cyanopyridin-2-yl)amino]ethylamino]acetyl-2-cyano-(S)-pyrrolidine (NVP-DPP728). NVP-DPP728 may be found in WO 98/19998 and JP 2000511559, the disclosure of each of which is herein incorporated by reference in its entirety. NVP-DPP728 is described as an orally active and selective DPP-IV inhibitor [Villhauer et al, J Med Chem (2002) 45:2362-2365].

In one aspect of the present invention, the DPP-IV inhibitor is 3(R)-Amino-1-[3-(trifluoromethyl)-5,6,7,8-tetrahydro[1,2,4]triazolo[4,3-a]pyrazin-7-yl]-4-(2,4,5-trifluorophenyl)butan-1-one (MK-0431; sitagliptin). MK-0431 may be found in EP 1412357, WO 03/04498, U.S. Pat. No. 6,699,871, and US 2003100563, the disclosure of each of which is herein incorporated by reference in its entirety. MK-0431 is described as an orally active and selective DPP-IV inhibitor [Weber et al, Diabetes (2004) 53(Suppl. 2):A151, 633-P (Abstract), the disclosure of which is herein incorporated by reference in its entirety].

In one aspect of the present invention, the DPP-IV inhibitor is (1-[[3-hydroxy-1-adamantyl)amino]acetyl]-2-cyano-(S)-pyrrolidine (LAF237; vildagliptin). LAF237 may be found in U.S. Pat. No. 6,166,063, WO 00/34241, EP 1137635, and JP 2002531547, the disclosure of each of which is herein incorporated by reference in its entirety. LAF237 is described as an orally active and selective DPP-IV inhibitor [Villhauer et al, J Med Chem (2003) 46:2774-2789].

In one aspect of the present invention, the DPP-IV inhibitor is (1S,3S,5S)-2-[2(S)-Amino-2-(3-hydroxyadamantan-1-yl)acetyl]-2-azabicyclo[3.1.0]hexane-3-carbonitrile (BMS-477118; saxagliptin).

In one aspect of the present invention, the DPP-IV inhibitor is [1-[2(S)-Amino-3-methylbutyryl]pyrrolidin-2(R)-yl]boronic acid (PT-100).

In one aspect of the present invention, the DPP-IV inhibitor is GSK-823093.

In one aspect of the present invention, the DPP-IV inhibitor is PSN-9301.

In one aspect of the present invention, the DPP-IV inhibitor is T-6666.

In one aspect of the present invention, the DPP-IV inhibitor is SYR-322 (alogliptin).

In one aspect of the present invention, the DPP-IV inhibitor is SYR-619.

In one aspect of the present invention, the DPP-IV inhibitor is CR-14023.

In one aspect of the present invention, the DPP-IV inhibitor is CR-14025.

In one aspect of the present invention, the DPP-IV inhibitor is CR-14240.

In one aspect of the present invention, the DPP-IV inhibitor is CR-13651.

In one aspect of the present invention, the DPP-IV inhibitor is NNC-72-2138.

In one aspect of the present invention, the DPP-IV inhibitor is NN-7201.

In one aspect of the present invention, the DPP-IV inhibitor is PHX-1149.

In one aspect of the present invention, the DPP-IV inhibitor is PHX-1004.

In one aspect of the present invention, the DPP-IV inhibitor is SNT-189379.

In one aspect of the present invention, the DPP-IV inhibitor is GRC-8087.

In one aspect of the present invention, the DPP-IV inhibitor is PT-630.

In one aspect of the present invention, the DPP-IV inhibitor is SK-0403.

In one aspect of the present invention, the DPP-IV inhibitor is GSK-825964.

In one aspect of the present invention, the DPP-IV inhibitor is TS-021.

In one aspect of the present invention, the DPP-IV inhibitor is GRC-8200.

In one aspect of the present invention, the DPP-IV inhibitor is GRC-8116.

In one aspect of the present invention, the DPP-IV inhibitor is FE107542.

In one aspect of the present invention, the DPP-IV inhibitor is (2R)-4-oxo-4-[3-(trifluoromethyl)-5,6-dihydro[1,2,4]triazolo[4,3-A]pyrazin-7(8H)-yl]-1-(2,4,5-trifluorophenyl)butan-2-amine.

In one aspect of the present invention, the DPP-IV inhibitor is sitagliptin.

In one aspect of the present invention, the DPP-IV inhibitor is Januvia™ (sitagliptin phosphate).

In one aspect of the present invention, the DPP-IV inhibitor is (3R)-4-[(3R)-3-Amino-4-(2,4,5-trifluorophenyl)butanoyl]-3-(2,2,2-trifluoroethyl)-1,4-diazepan-2-one.

In one aspect of the present invention, the DPP-IV inhibitor is selected from the right column of Table D. It is expressly contemplated that each individual DPP-IV inhibitor from the right column of Table D is a separate embodiment within the scope of the present invention.

In one aspect of the present invention, the DPP-IV inhibitor is selected from any set of compounds selected from the right column of Table D.

In one aspect of the present invention, the DPP-IV inhibitor is a compound of Formula (XIX).

In one aspect of the present invention, the DPP-IV inhibitor is a compound of Formula (XX).

In one aspect of the present invention, the DPP-IV inhibitor is a compound of Formula (XXI).

In one aspect of the present invention, the DPP-IV inhibitor is a compound of Formula (XXII).

In one aspect of the present invention, the DPP-IV inhibitor is a compound selected from Group S1, Group T1, Group V1, or Group V2.

In one aspect of the present invention, the DPP-IV inhibitor is identical to a compound disclosed in International Application No. PCT/US02/21349 (published as WO 03/004498).

In one aspect of the present invention, the DPP-IV inhibitor is identical to a compound disclosed in International Application No. PCT/EP99/09708 (published as WO 00/34241).

In one aspect of the present invention, the DPP-IV inhibitor is identical to a compound disclosed in International Application No. PCT/US01/07151 (published as WO 01/68603).

In one aspect of the present invention, the DPP-IV inhibitor is identical to a compound disclosed in International Application No. PCT/US2004/042209 (published as WO 2005/095381).

In one aspect of the present invention, the DPP-IV inhibitor has an $IC_{50}$ of less than about 10 μM, less than about 1 μM, less than about 100 nM, less than about 75 nM, less than about 50 nM, less than about 25 nM, less than about 20 nM, less than about 15 nM, less than about 10 nM, less than about 5 nM, less than about 4 nM, less than about 3 nM, less than about 2 nM, or less than about 1 nM. In certain embodiments, the DPP-IV inhibitor has an $IC_{50}$ of less than about 50 nM, less than about 25 nM, less than about 20 nM, less than about 15 nM, less than about 10 nM, less than about 5 nM, less than about 4 nM, less than about 3 nM, less than about 2 nM, or less than about 1 nM.

In one aspect of the present invention, the DPP-IV inhibitor is a selective DPP-IV inhibitor, wherein the selective DPP-IV inhibitor has a selectivity for human plasma DPP-IV over one or more of PPCE, DPP-II, DPP-8 and DPP-9 of at least about 10-fold, and in particular embodiment of at least about 100-fold, and in further particular embodiment of at least about 1000-fold.

In one aspect of the present invention, the DPP-IV inhibitor is a small molecule.

In one aspect of the present invention, the DPP-IV inhibitor is orally active.

In one aspect of the present invention, the DPP-IV inhibitor is an inhibitor of human DPP-IV.

In one aspect of the present invention, any one or more DPP-IV inhibitor can be excluded from any embodiment of the present invention.

Combination of GPR119 Agonist and DPP-IV Inhibitor

By way of illustration and not limitation, an exemplary combination of GPR119 agonist and DPP-IV inhibitor in accordance with the present invention is provided by selecting a GPR119 agonist from the left column of Table D and a DPP-IV inhibitor from the right column of Table D. It is expressly contemplated that each individual combination of GPR119 agonist and DPP-IV inhibitor provided by selecting a GPR119 agonist from the left column of Table D and a DPP-IV inhibitor from the right column of Table D is a separate embodiment within the scope of the present invention.

TABLE D

| GPR119 Agonist | DPP-IV Inhibitor |
|---|---|
| [6-(4-Benzenesulfonyl-piperidin-1-yl)-5-nitro-pyrimidin-4-yl]-(4-methanesulfonyl-phenyl)-amine | valine-pyrrolidide |
| {4-[6-(4-Methanesulfonyl-phenylamino)-5-nitro-pyrimidin-4-yl]-piperazin-1-yl}-acetic acid ethyl ester | 3-(L-Isoleucyl)thiazolidine (isoleucine-thiazolidide) |
| (2-Fluoro-4-methanesulfonyl-phenyl)-{6-[4-(3-isopropyl-[1,2,4]oxadiazol-5-yl)-piperidin-1-yl]-5-nitro-pyrimidin-4-yl)-amine | 1-[2-[5-cyanopyridin-2-yl)amino]ethylamino]acetyl-2-cyano-(S)-pyrrolidine (NVP-DPP728) |
| 6'-[4-(2-Methoxycarbonyl-acetyl)-phenoxy]-3-nitro-3,4,5,6-terahydro-2H-[1,2']bipyridinyl-4-carboxylic acid ethyl ester | 3(R)-Amino-1-[3-(trifluoromethyl)-5,6,7,8-tetrahydro[1,2,4]triazolo[4,3-a]pyrazin-7-yl]-4-(2,4,5-trifluorophenyl)butan-1-one (MK-0431; sitagliptin) |
| 1-[4-(4-Acetyl-3'-nitro-3,4,5,6-tetrahydro-2H-[1,2']bipyridinyl -6'-yloxy)-phenyl]-ethanone | (1-[[3-hydroxy-1-adamantyl)amino]acetyl]-2-cyano-(S)-pyrrolidin (LAF237; vildagliptin) |
| 6'-[4-(4-Hydroxy-benzenesulfonyl)-phenoxy]-3-nitro-3 4,5,6-tetrahydro-2H-[1,2']bipyridinyl-4-carboxylic acid ethyl ester | (1S,3S,5S)-2-[2(S)-Amino-2-(3-hydroxyadamantan-1-yl)acetyl]-2-azabicyclo[3.1.0]hexane-3-carbonitrile (BMS-477118; saxagliptin) |
| 1-[5-(4-Benzoyl-phenoxy)-2-nitro-phenyl]-piperidine-4-carboxylic acid ethyl ester | [1-[2(S)-Amino-3-methylbutyryl]pyrrolidin-2(R)-yl]boronic acid (PT-100) |
| 1-[5-[4-(2-Methoxycarbonyl-acetyl)-phenoxy]-2-nitro-phenyl)-piperidine-4-carboxylic acid ethyl ester | GSK-823093 |
| 1-[5-(2-Amino-4-ethanesulfonyl-phenoxy)-2-nitro-phenyl)-piperidine-4-carboxylic acid ethyl ester | PSN-9301 |
| 5-Bromo-1-[4-nitro-3-(4-propyl-piperidin-1-yl)-phenyl]-1H-pyridin-2-one | T-6666 |
| 6'-Benzenesulfonylamino-3'-nitro-3,4,5,6-tetrahydro-2H-[1,2']bipyridinyl-4-carboxylic acid ethyl ester | SYR-322 (alogliptin) |
| 6'-(Benzenesulfonyl-methyl-amino)-3'-nitro-3,4,5,6-tetrahydro-2H-[1,2']bipyridinyl-4-carboxylic acid ethyl ester | SYR-619 |
| 6'-(Benzenesulfonyl-butyl-amino)-3-nitro-3,4,5,6-tetrahydro-2H-[1,2']bipyridinyl-4-carboxylic acid ethyl ester | CR-14023 |
| 1-[5-(4-Benzoyl-phenylamino)-2-nitro-phenyl]-piperidine-4-carboxylic acid ethyl ester | CR-14025 |
| {4-[4-Nitro-3-(4-propyl-piperidin-1-yl)-phenylamino)-phenyl}-phenyl-methanone | CR-14240 |
| 3-[6-(4-Mehanesulfonyl-phenylamino)-5-nitro-pyrimidin-4-yloxymethyl]-pyrrolidine-1-carboxylic acid tert-butyl ester | CR-13651 |
| 4-[5-Cyano-6-(6-methylsulfanyl-pyridin-3-ylamino)-pyrimidin-4-yloxy) | NNC-72-2138 |

TABLE D-continued

| GPR119 Agonist | DPP-IV Inhibitor |
| --- | --- |
| piperidine-1-carboxylic acid tert-butyl ester | |
| 4-[5-Cyano-6-(6-methanesulfonyl-pyridin-3-ylamino)-pyrimidin-4-yloxy]-piperidine-1-carboxylic acid tert-butyl ester | NN-7201 |
| 4-[6-(4-Methanesulfonyl-phenylamino)-5-nitro-pyrimidin-4-yloxyl-piperidine-1-carboxylic acid tert-butyl ester | PHX-1149 |
| (4-Methanesulfonyl-phenyl)-[5-nitro-6-(piperidin-4-yloxy)-pyrimidin-4-yl]-amine | PHX-1004 |
| 1-{4-[6-(4-Methanesulfonyl-phenylamino)-5-nitro-pyrimidin-4-yloxy]-piperidin-1-yl}-3,3-dimethyl-butan-1-one | SNT-189379 |
| 4-[6-(4-Methanesulfonyl-phenylamino)-5-nitro-pyrimidin-4-ylamino]-piperidine-1-carboxylic acid tert-butyl ester | GRC-8087 |
| N-(4-Methanesulfonyl-phenyl)-5-nitro-N'-piperidin-4-yl-pyrimidine-4,6-diamine | PT-630 |
| 1-{4-[6-(4-Methanesulfonyl-phenylamino)-5-nitro-pyrimidin-4-ylamino]-piperidin-1-yl}-ethanone | SK-0403 |
| 4-[6-(4-Cyano-2-fluoro-phenylamino)-5-ethynyl-pyrimidin-4-yloxy]-piperidine-1-carboxylic acid isopropyl ester | GSK-825964 |
| 4-[5-Ethynyl-6-(2-fluoro-4-[1,2,4]triazol-1-yl-phenylamino)-pyrimidin-4-yloxy]-piperidine-1-carboxylic acid isopropyl ester | 8-(3-Aminopiperidin-1-yl)-N2,7-dibenzyl-1-methylguanine trifluoroacetate |
| 4-{5-Ethynyl-6-[1-(3-isopropyl-[1,2,4]oxadiazol-5-yl)-piperidin-4-yloxy]-pyrimidin-4-ylamino}-3-fluoro-benzonitrile | N-[2-[2-[8-(3-Aminopiperidin-1-yl)-7-(2-butynyl)-3-methylxanthir 1-yl]acetyl]phenyl]formamide |
| 4-[5-Acetyl-6-(6-methanesulfonyl-pyridin-3-ylamino)-pyrimidin-4-yloxy]-piperidine-1-carboxylic acid isobutyl ester | 8-[3(R)-Aminopiperidin-1-yl]-7-(2-butynyl)-3-methyl-1-(quinazolin-2-ylmethyl)xanthine |
| 1-[4-(1-Benzyl-azetidin-3-yloxy)-6-(6-methanesulfonyl-pyridin-3-ylamino)-pyrimidin-5-yl]-ethanone | 8-(3-Aminopiperidin-1-yl)-1-(benzo[c]-1,8-naphthyridin-6-ylmethyl)-7-(2-butynyl)-3-methylxanthine |
| 4-[5-Cyano-6-(6-propylamino-pyridin-3-ylamino)-pyrimidin-4-yloxy]-piperidine-1-carboxylic acid isopropyl ester | 2-[8-[3(R)-Aminopiperidin-1-yl]-7-(2-butynyl)-3-methylxanthin-1-yl]-N-(2-pyridyl)acetamide |
| 4-(2-Fluoro-4-methanesulfonyl-phenylamino)-5-methyl-pyrimidin-4-yl]-isopropyl-amino}-methyl)-piperidine-1-carboxylic acid tert-butyl ester | 2-(3-Aminopiperidin-1-yl)-3-(2-butynyl)-5-(quinoxalin-6-ylmethyl; 4,5-dihydro-3H-imidazo[4,5-d]pyridazin-4-one |
| 4-(2-Fluoro-4-methanesulfonyl-phenoxy)-6-[1-(3-methoxy-propyl)-piperidin-4-yloxy]-5-methyl-pyrimidine | (1S, 3S, 5S)-2-[2(S)-Amino-4,4-dimethyl pentanoyl]-2-azabicyclo[3.1.0]hexane-3(S)-carbonitrile trifluoroacetate |
| 1-{4-[6-(2-Fluoro-4-methanesulfonyl-phenoxy)-5-methyl-pyrimidin-4-yloxy]-piperidin-1-yl}-3-methoxy-propan-2-ol | N1-(1-Cyanoethyl)-N1,3-dimethyl-L-valinamide |
| 4-{6-[2-Fluoro-4-(5-isopropoxymethyl-[1,2,4]oxadiazol-3-yl)-phenoxy]-5-methyl-pyrimidin-4-yloxy)-piperidine-1-carboxlic acid isopropyl ester | (1S, 3S, 5S)-2-[2(S)-Amino-2-[1-(3,3-dimethylbuyryl)piperidin-4-yl]acetyl]-2-azabicyclo[3.1.0]hexane-3-carbonitrile |
| 4-[6-(2-Fluoro-4-morpholin-4-yl-phenoxy)-5-methyl-pyrimidin-4-yloxy]-piperidine-1-carboxylic acid isopropyl ester | 2-[7-(2-Butynyl)-1-(2-phenylethyl)-8-(1-piperazinyl)xanthin-3-yl]-N-(2-propynyl)acetamide hydrochloride |
| {4-[6-(2-Fluoro-4-methanesulfonyl-phenoxy)-5-methyl-pyrimidin-4-yloxy]-piperidin-1-yl}-[6-(2-pyrrolidin-1-yl-ethyl)-pyridin-3-yl]-methanone | 2-[7-(2-Butynyl)-1-(3-cyanobenzyl)-6-oxo-8-(1-piperazinyl)-6,7-dihydro-1H-purin-2-yloxy]-N-methylbenzamide trifluoroacetate |
| (6-Amino-pyridin-3-yl)-{4-[6-(2-fluoro-4-methanesulfonyl-phenoxy)-5-methyl-pyrimidin-4-yloxy]-piperidin-1-yl}-methanone | 2-[3-(2-Butynyl)-4-oxo-2-(1-piperazinyl)-4,5-dihydro-3H-imidazo[4,5-d]pyridazin-5-ylmethyl]benzonitrile trifluoroacetate |

TABLE D-continued

| GPR119 Agonist | DPP-IV Inhibitor |
| --- | --- |
| 4-({Cyclopropyl-[6-(2-fluoro-4-methanesulfonyl-phenoxy)-5-methyl-pyrimidin-4-yl]-amino}-methyl)-piperidine-1-carboxylic acid tert-butyl ester | N-[1(S)-[2(S)-Cyanopyrrolidin-1-ylcarbonyl]-4-(pyrazin-2-ylcarboxamido)butyl]carbamic acid 1-acetoxyethyl ester |
| 4-({Cyclopropyl-[6-(2-fluoro-4-methanesulfonyl-phenoxy)-5-methyl-pyrimidin-4-yl]-amino)-methyl)-piperidine-1-carboxylic acid isopropyl ester | 2(S),4-Diamino-1-(4-thiomorpholinyl)butan-1-one |
| 4-({[6-(2-Fluoro-4-methanesulfonyl-phenoxy)-5-methyl-pyrimidin-4-yl]-isopropyl-amino}-methyl)-piperidine-1-carboxytic acid isopropyl ester | 1-[Perhydroindol-2(S)-ylcarbonyl]azetidine-2(S)-carbonitrile |
| 4-[6-(2-Fluoro-4-methanesulfonyl-phenylamino)-5-methyl-pyrimidin-4-ylsulfanyl]-piperidine-1-carboxylic acid isopropyl ester | 1-(2-Benzothiazolyl)-1-[1-[(2S, 3aS, 7aS)-perhydroindol-2-ylcarbonyl]pyrrolidin-2(S)-yl]methanone hydrochloride |
| 4-[1-(4-Methanesulfonyl-phenyl)-1H-pyrazolo[3,4-d]pyrimidin-4-yloxy]-piperidine-1-carboxylic acid tert-butyl ester | 1-[2(S)-Amino-2-cyclohexylacetyl]-4-methylazetidine-2-carbonitril hydrochloride |
| 4-[1-(4-Methanesulfonyl-phenyl)-3-methyl-1H-pyrazolo[3,4-d]pyrimidin-4-yloxy]-piperidine-1-carboxylic acid tert-butyl ester | 6-[2-[2-[5(S)-Cyano-4,5-dihydro-1H-pyrazol-1-yl]-2-oxoethylamino]ethylamino]pyridine-3-carbonitrile |
| 4-[1-(4-Mechanesulfonyl-phenyl)-3,6-dimethyl-1H-pyrazolo[3,4-d]pyrimidin-4-yloxy]-piperidine-1-carboxylic acid tert-butyl ester | 6-[2-[2-[2(S)-Cyano-4(S)-fluoropyrrolidin-1-yl]-2-oxoethylamino]2-methylpropylamino]-N,N-dimethylpyridine-3-sulfonamide |
| 4-({[1-(2,5-Difluoro-phenyl)-1H-pyrazolo[3,4-d]pyrimidin-4-yl]-methyl-amino)-methyl)-piperidine-1-carboxylic acid tert-butyl ester | trans-N-[4-[1(S)-Amino-2-[3(S)-fluoropyrrolidin-1-yl]-2-oxoethyl]cyclohexyl]-2,4-difluorobenzenesulfonamide |
| 2-{4-[1-(2-Fluoro-4-methanesulfonyl-phenyl)-1H-pyrazolo[3,4-d]pyrimidin-4-yloxy]-piperidin-1-yl}-1-(4-trifluoromethoxy-phenyl)-ethanone | 2(S)-Amino-1-(1-pyrrolidinyl)-2-(4-(thiazol-2-ylamino)cyclohexyl]ethanone trifluoroacetate |
| 2-{4-[1-(2-Fluoro-4-methanesulfonyl-phenyl)-1H-pyrazolo[3,4-d]pyrimidin-4-yloxy]-piperidin-1-yl}-1-(3-fluoro-phenyl)-ethanone | N-[(1R,3R)-3-[1(S)-Amino-2-oxo-2-(1-pyrrolidinyl)ethyl]cyclopentyl]-4-(methylsulfonyl)benzenesulfonamide |
| 4-[9-(6-Methanesulfonyl-pyridin-3-yl)-9H-purin-6-yloxy]-piperidine-1-carboxylic acid isobutyl ester | 3(R)-Amino-1-(6-benzyl-3-methyl-5,6,7,8-tetrahydroimidazo[1,2-a]pyrazin-7-yl)-4-(3,4-difluorophenyl)butan-1-one |
| (4-[9-(6-Methanesulfonyl-pyridin-3-yl)-9H-purin-6-yloxy]-piperidin-1-yl}-pyridin-3-yl-methanone | trans-N-[4-[1(S)-Amino-2-oxo-2-(1-pyrrolidinyl)ethyl]cyclohexyl]-2,4-difluorobenzenesulfonamide |
| 4-[9-(4-Methanesulfonyl-phenyl)-9H-purin-6-yloxy)-piperidine-1-carboxylic acid tert-butyl ester | 3(R)-Amino-4-(2,5-difluorophenyl)-1-[4-hydroxy-2-(trifluoromethyl)-5,6,7,8-tetrahydropyrido[3,4-d]pyrimidin-7-yl]butan-1-one |
| 4-[9-(2-Fluoro-4-propionylsulfamoyl-phenyl)-9H-purin-6-yloxy]-piperidine-1-carboxylic acid isopropyl ester | N-[(1R,3R)-3-[1(S)-Amino-2-oxo-2-(1-pyrrolidinyl)ethyl]cyclopentyl]-2-(methylsulfonamido)ethanesulfonamide |
| 4-[9-(4-Cyano-2-fluoro-phenyl)-9H-purin-6-yloxy)-piperidine-1-carboxylic acid isopropyl ester | 2-[4-[3(R)-Amino-4-(2-fluorophenyl)butyryl]-3(R)-benzylpiperazin 1-yl]-N-[3-(methylsulfonamido)phenyl]acetamide |
| 4-[9-(2-Fluoro-4-sulfamoyl-phenyl)-9H-purin-6-yloxy]-piperidine-1-carboxylic acid isopropyl ester | 3(R)-Amino-1-(3-thiazolidinyl)-4-(2,4,5-trifluorophenyl)butan-1-one |
| 4-[3-(4-Methanesulfonyl-phenyl)-3H-[1,2,3]triazolo[4,5-d]pyrimidin-7-yloxy]-piperidine-1-carboxylic acid tert-butyl ester | 4-[3(R)-Amino-4-(2,4,5-trifluorophenyl)butyryl]-3(R)-methyl-1,4-diazepan-2-one |
| 3-(2-Fluoro-4-methanesulfonyl-phenyl)-7-[1-(3-isopropyl-[1,2,4]oxadiazol-5-yl)-piperidin-4-yloxy]-3H-[1,2,3]triazolo[4,5-d]pyrimidine | 3(S)-Amino-4-(3,3-difluoropyrrolidin-1-yl)-N,N-dimethyl-4-oxo-2(S)-[4-([1,2,4]triazolo[1,5-a]pyridin-6-yl)phenyl]butyramide |
| 3-Fluoro-4-{7-[1-(3-isopropyl-[1,2,4]oxadiazol-5-yl)-piperidin-4-yloxy]-[1,2,3]triazolo[4,5-d]pyrimidin-3-yl}-N-propionyl-benzenesulfonamide | 3(R)-Amino-1-[2-(trifluoromethyl)-5,6,7,8-tetrahydro[1,2,4]triazolo[1,5-a]pyrazine-7-yl]-4-(2,4,5-trifluorophenyl)butanone hydrochloride |
| 3-Fluoro-4-{7-[1-(3-isopropyl-[1,2,4]oxadiazol-5-yl)-piperidin-4-yloxyl-(1,2,3]triazolo[4,5-d]pyrimidin-3-yl}-benzonitrile | 2(S)-Amino-3(S)-(4-fluorophenyl)-1-(3-thiazolidinyl)butan-1-one |

TABLE D-continued

| GPR119 Agonist | DPP-IV Inhibitor |
|---|---|
| 4-[3-(4-Methanesulfonyl-phenyl)-isoxazolo[4,5-d]pyrimidin-7-yloxy]-piperidine-1-carboxylic acid tert-butyl ester | 7-[3(R)-Amino-4-(2,5-difluorophenyl)butyryl]-5,6,7,8-tetrahydroimidazo[1,2-a]pyrazine-2-carboxylic acid ethyl ester |
| 4-({Ethyl-[3-(4-methanesulfonyl-phenyl)-isoxazolo[4,5-d]pyrimidin-7-yl]-amino}-methyl)-piperidine-1-carboxylic acid tert-butyl ester | 3(R)-Amino-1-(8-chloro-1,2,3,4-tetrahydropyrazino[1,2-a]benzimidazol-2-yl)-4-(2,5-difluorophenyl)butan-1-one trifluoroacetate |
| 4-[3-(4-Methanesulfonyl-phenyl)-isoxazolo[4,5-d]pyrimidin-7-ylsulfanyl]-piperidine-1-carboxylic acid tert-butyl ester | 3(R)-Amino-4-(2,5-difluorophenyl)-1-[2-(4-fluorophenyl)-4,5,6,7-tetrahydrothiazolo[4,5-c]pyridin-5-yl]buttan-1-one |
| 4-[3-(4-Methanesulfonyl-phenyl)-isoxazolo[4,5-d]pyrimidin-7-yloxy]-piperidine-1-carboxylic acid isopropyl ester | 2-[4-[2-[3(R)-Amino-4-(2-fluorophenyl)butyryl]-1,2,3,4-tetrahydroisoquinolin-3-ylcarboxamidomethyl]phenyl]acetic acid |
| 4-[8-(2-Fluoro-4-methanesulfonyl-phenyl)-[1,7]naphthyridin-4-yloxy]-piperidine-1-carboxylic acid isopropyl ester | 3(S)-Amino-2-oxopiperidin-1-ylphosphonic diamide hydrochloride |
| 4-[8-(2-Fluoro-4-methanesulfonyl-phenyl)-quinolin-4-yloxy]-piperidine-1-carboxylic acid isopropyl ester | 2-[2-(5-Nitropyridin-2-ylamino)ethylamino]-1-(1-pyrrolidinyl)ehanone dihydrochloride |
| 4-[8-(4-Methylsulfanyl-phenyl)-quinolin-4-yloxy]-piperidine-1-carboxylic acid isopropyl ester | 2-[8-(3-Aminopiperidin-1-yl)-1,3-dimethylxanthin-7-ylmethyl]benzonitrile hemisuccinate |
| 4-[8-(4-Methanesulfonyl-phenyl)-quiriolin-4-yloxy]-piperidine-1-carboxylic acid isopropyl ester | 2(S)-Amino-2-cyclohexyl-1-(3,3,4,4-tetrafluoropyrrolidin-1-yl)ethanone hydrochloride |
| 4-[8-(2-Fluoro-4-methanesulfonyl-phenyl)-pyrido[3,4-d]pyrimidin-4-yloxy]-piperidine-1-carboxylic acid isopropyl ester | 2(S)-Amino-2-cyclohexyl-1-(3-fluoropyrrolidin-1-yl)ethanone |
| 4-[8-(2-Fluoro-4-propionylsulfamoyl-phenyl)-pyrido[3,4-d]pyrimidin-4-yloxy]-piperidine-1-carboxylic acid isopropyl ester | 2-Amino-1-cyclopentyl-3-methylpentan-1-one hydrochloride |
| 4-[8-(4-Cyano-2-fluoro-phenyl)-pyridol[3,4-d]pyrimidin-4-yloxy]-piperidine-1-carboxylic acid isopropyl ester | 4-Amino-5-oxo-5-(1-pyrrolidinyl)pentanamide |
| 3-(2-Fluoro-4-methanesuifonyl-phenyl)-7-(4-(3-isopropyl-[1,2,4]oxadiazol-5-yl)-cyclohexyloxy]-pyrazolo[1,5-a]pyrimidine | 1-[2-[1,1-Dimethyl-2-(6-phenylpyridin-2-ylamino]ethylamino]acetyl]pyrrolidine-2(S)-carbonitrile hydrochloride |
| 3-Fluoro-4-(7-[4-(3-isopropyl-[1,2,4]oxadiazol-5-yl)-cyclohexyloxy]-pyrazolo[1,5-a]pyrimidin-3-yl}-N-propionyl-benzenesulfonamide | (7R*,8S*,13bS*)-7-Butyl-11,12-dimethoxy-,3,4,4a,6,7,8,9,9a,13b-decahydro-1H-pyrido[1,2-f]phenanthridin-8-amine |
| 3-Fluoro-4-(7-[4-(3-isopropyi-[1,2,4]oxadiazol-5-yl)-cyclohexyloxy]-pyrazolo[1,5-a]pyrimidin-3-yl}-benzonitrile | 5-(Aminomehyl)-6-(2,4-dichlorophenyl)-2-(3,5-dimethoxyphenyl)pyrimidin-4-amine |
| 4-[3-(2-Fluoro-4-methanesulfonyl-phenyl)-1-methyl-1H-pyrazolo[4,3-d]pyrimidin-7-yloxy]-piperidine-1-carboxylic acid isopropyl ester | 3-(Aminomethyl)-4-(2,4-dichlorophenyl)-7,8-dimethoxy-5H-indeno(1,2-b]pyridin-2-amine |
| 4-[3-(2-Fluoro-4-propionylsulfamoyl-phenyl)-1-methyl-1H-pyrazolo[4,3-d]pyrimidin-7-yloxy]-piperidine-1-carboxylic acid isopropyl ester | 5-(Aminomethyl)-6-(2,4-dichlorophenyl)-N2-(2-methoxyethyl)-N2 methylpyrimidine-2,4-diamine |
| 4-[3-(4-Cyano-2-fluoro-phenyl)-1-methyl-1H-pyrazolo(4,3-d]pyrimidin-7-yloxy]-piperidine-1-carboxylic acid isopropyl ester | 4,4-Difluoro-1-[2-[exo-8-(2-pyrimidinyl)-8-azabicyclo[3.2.1]oct-3 ylamino]acetyl]pyrrolidine-2(S)-carbonitrile |
| 4-[3-(2-Fluoro-4-mehanesulfonyl-phenyl)-2-methyl-2H-pyrazolo[4,3-d]pyrimidin-7-yloxy]-piperidine-1-carboxylic acid isopropyl ester | exo-3-[2-[8-(2-Pyrimidinyl)-8-azabicyclo[3.2.1]oct-3-ylamino]acetyl]thiazolidine-4(R)-carbonitrile. |
| 4-[3-(2-Fluoro-4-propionylsulfamoyl-phenyl)-2-methyl-2H-pyrazolo[4,3-d]pyrimidin-7-yloxy]-piperidine-1-carboxylic acid isopropyl ester | 1-[2- [3-(2,3-Dihydro-1H-isoindol-2-yl)-1,1-dimethyl-3-oxopropylamino]acetyl]pyrrolidine-2(S)-carbonitrile |
| 4-[3-(4-Cyano-2-fluoro-phenyl)-2-methyl-2H-pyrazolo[4,3-d]pyrimidin-7-yloxy]-piperidine-1-carboxylic acid isopropyl ester | 8-(3-Aminoperhydroazepin-1-yl)-3-methyl-7-(2-methylbenzyl)-2,3,6,7-tetrahydro-1H-purine-2,6-dione |

TABLE D-continued

| GPR119 Agonist | DPP-IV Inhibitor |
|---|---|
| 4-[4-(3-Isopropyl-[1,2,4]oxadiazol-5-yl)-piperidin-1-yl]-6-(4-mehanesulfonyl-phenoxy)-pyrimidine | 8-[3(R)-Aminopiperidin-1-yl]-7-(5-fluoro-2-methylbenzyl)-1,3-dimethylxanthine |
| {6-[4-(3-Isopropyl-[1,2,4]oxadiazo-5-yl)-piperidin-1-yl]-pyrimidin-4-yl)-(4-methanesulfonyl-phenyl)-amine | 2-[2-(3-Aminopiperidin-1-yl)-6,7-dimethoxy-4-oxo-3,4-dihydroquinazolin-3-ylmethyl]benzonitrile |
| 4-{[6-(2-Fluoro-4-methanesulfonyl-phenylamino)-pyrimidin-4-yl]-methyl-amino)-piperidine-]-carboxylic acid tert-butyl ester | 1-[2(S)-Amino-3,3-di methylbutyryl]-4(S)-fluoropyrrolidine-2(S)-carbonitrile hydrochloride |
| 4-[6-(2-Fluoro-4-methanesulfonyl-phenylamino)-pyrimidin-4-yloxy]-piperidine-1-carboxylic acid tert-butyl ester | 2-[3-(Aminomethyl)-4-butoxy-2-(2,2-dimethylpropyl)-1-oxo-1,2-dihydroisoquinolin-6-yloxy]acecamide hydrochloride |
| (2-Fluoro-4-methanesulfonyl-phenyl)-(6-[1-(3-isopropyl-[1,2,4]oxadiazol-5-ylmethyl)-piperidin-4-yloxy]-pyrimidin-4-yl}-amine; 4-[6-(2-Fluoro-4-methanesulfonyl-phenylamino)-pyrimidin-4-yloxy]-piperidine-1-carboxylic acid isopropyl ester | 3-(3-Chloroimidazo[1,2-a]pyridin-2-ylmethylsulfonyl)-N,N-dimethyl-1H-1,2,4-triazole-1-carboxamide |
| (6-Chloro-pyridin-2-yl)-{4-[6-(2-fluoro-4-methanesulfonyl-phenylamino)-pyrimidin-4-yloxy]-piperidin-1-yl}-methanone | 6-Chloro-2-isobutyl-4-phenylquinolin-3-ylmethylamine |
| [2-(4-Bromo-phenyl)-6-methyl-pyrimidin-4-yl]-methyl-amine | trans-1-[2-[4-(1,3-Dioxo-2,3-dihydro-1H-isoindol-2-yl)cyclohexylamino]acetyl]pyrrolidine-2(S)-carbonitrile hydrochloride |
| [2-(4-Bromo-phenyl)-6-methyl-pyrimidin-4-yl]-p-tolyl-amine | trans-4-[2-[4(R)-Cyanothiazolidin-3-yl]-2-oxoethylamino]-N,N-dimethylcyclohexanecarboxamide hydrochloride |
| [2-(4-Bromo-phenyl)-6-methyl-pyrimidin-4-yl]-(4-methoxy-phenyl)-amine | N-(5-Chloropyridin-2-yl)-2-[4-[1-[2-(4-cyanothiazolidin-3-yl)-2-oxoethyl]hydrazino]piperidin-1-yl]acetamide tris(trifluoroacetate) |
| [2-(4-Bromo-phenyl)-6-methyl-pyrimidin-4-yl]-phenyl-amine | 6-[2-[2-[2(S)-Cyanoazetidin-1-yl]-2-oxoethylamino]ethylamino]pyridine-3-carbonicrile dihydrochloride |
| [2-(4-Bromo-phenyl)-6-methyl-pyrimidin-4-yl]-cyclohexyl-amine | 4(S)-Fluoro-1-[2-[1-(2-hydroxyacetyl)-4-methylpiperidin-4-ylamino]acetyl]pyrrolidine-2(S)-carbonitrile fumarate |
| 5-[2-(4-Bromo-phenyl)-6-ethyl-pyrimidin-4-ylamino]-pentan-1-ol | TS-021 |
| 3-[2-(4-Bromo-phenyl)-6-methyl-pyrimidin-4-ylamino]-propionitrile | GRC-8200 |
| [2-(4-Bromo-phenyl)-6-ethyl-pyrimidin-4-yl]-(4-fluoro-benzyl)-amine | GRC-8116 |
| [2-(4-Bromo-phenyl)-6-ethyl-pyrimidin-4-yl]-[2-(4-chloro-phenyl)-ethyl]-amine | FE107542 |
| [2-(4-Bromo-phenyl)-6-ethyl-pyrimidin-4-yl]-pyridin-2-ylmethyl-amine |  |
| (2-(4-Bromo-phenyl)-6-methyl-pyrimidin-4-yl]-pyridin-3-ylmethyl-amine |  |
| 3-{[2-(4-Bromo-phenyl)-6-methyl-pyrimidin-4-ylamino]-methyl}-1H-pyridin-2-one |  |

TABLE D-continued

| GPR119 Agonist | DPP-IV Inhibitor |
|---|---|
| 4-{[2-(4-Bromo-phenyl)-6-ethyl-pyrimidin-4-ylamino]-methyl}-1H-pyridin-2-one | |
| 4-{2-[2-(4-Bromo-phenyl)-6-methyl-pyrimidin-4-ylamino]-ethyl-1H-pyridin-2-one | |
| [2-(3-Chloro-4-fluoro-phenyl)-6-ethyl-pyrimidin-4-yl]-(1,1-dioxo-hexahydro-1l6-thiopyran-4-yl)-amine | |
| [6-Methyl-2-(3,4,5-trifluoro-phenyl)-pyrimidin-4-yl]-[2-(1-oxy-pyridin-3-yl)-ethyl]-amine | |
| [6-Ethyl-2-(3,4,5-trifluoro-phenyl)-pyrimidin-4-yl]-[2-(1-oxy-pyridin-3-yl)-ethyl]-amine | |
| [6-Methyl-2-(2,4,5-trifluoro-phenyl)-pyrimidin-4-yl]-[2-(1-oxy-pyridin-3-yl)-ethyl]-amine | |
| 4-{4-Methyl-6-[2-(1-oxy-pyridin-3-yl)-ethylamino]-pyrimidin-2-yl}-benzonitrile | |

TABLE D-continued

| GPR119 Agonist | DPP-IV Inhibitor |
|---|---|
| 2-[4-(6-Methyl-2-phenyl-pyrimidin-4-ylamino)-phenyl]-ethanol | |
| [2-(3-Chloro-phenyl)-6-methyl-pyrimidin-4-yl]-methyl-amine | |
| 2-{[2-(4-Bromo-phenyl)-6-methyl-pyrimidin-4-yl]-methyl-amino}-ethanol; compound with methane | |
| 3-[6-Ethyl-2-(3,4,5-trifluoro-phenyl)-pyrimidin-4-ylamino]-propane-1,2-diol | |
| (S)-3-[6-Methyl-2-(2,3,5-trifluoro-phenyl)-pyrimidin-4-ylamino]-propane-1,2-diol | |
| (S)-3-[2-(4-Bromo-3-fluoro-phenyl)-6-methyl-pyrimidin-4-ylamino]-propane-1,2-diol | |
| (R)-3-[6-Ethyl-2-(3,4,5-trifluoro-phenyl)-pyrimidin-4-ylamino]-propane-1,2-diol | |
| (R)-3-[2-(3-Chloro-4-fluoro-phenyl)-6-ethyl-pyrimidin-4-ylamino]-propane-1,2-diol | |

TABLE D-continued

| GPR119 Agonist | DPP-IV Inhibitor |
|---|---|
| (R)-3-[2-(4-Bromo-2,5-difluoro-phenyl)-5-fluoro-6-methyl-pyrimidin-4-ylamino]-propane-1,2-diol | |
| (R)-3-[2-(4-Chloro-2,5-difluoro-phenyl)-6-difluoromethyl-pyrimidin-4-ylamino]-propane-1,2-diol | |
| 5-{2-[2-(4-Bromo-phenyl)-6-ethyl-pyrimidin-4-ylamino]-ethyl}-1H-pyridin-2-one | |
| 5-{2-[6-Methyl-2-(2,4,5-trifluoro-phenyl)-pyrimidin-4-ylamino]-ethyl}-1H-pyridin-2-one | |
| 4-{2-[2-(4-Chloro-2,5-difluoro-phenyl)-6-ethyl-pyrimidin-4-ylamino]-ethyl}-1H-pyridin-2-one | |
| 6-Chloro-4-{2-[6-methyl-2-(2,4,5-trifluoro-phenyl)-pyrimidin-4-ylamino]-ethyl}-1H-pyridin-2-one | |
| 4-{1-Hydroxy-2-[6-methyl-2-(2,4,5-trifluoro-phenyl)-pyrimidin-4-ylamino]-ethyl}-1H-pyridin-2-one | |

TABLE D-continued

| GPR119 Agonist | DPP-IV Inhibitor |
|---|---|
| 4-{1-Methyl-2-[6-methyl-2-(2,4,5-trifluoro-phenyl)-pyrimidin-4-ylamino]-ethyl}-1H-pyridin-2-one | 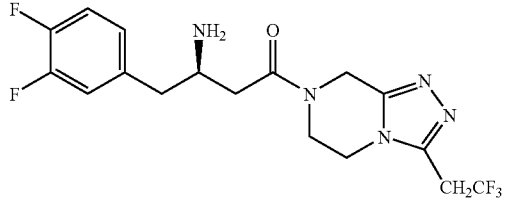 |
| 4-(3-Pyridin-4-yl-[1,2,4]oxadiazol-5-ylmethoxy)piperidine-1-carboxylic acid tert-butyl ester | 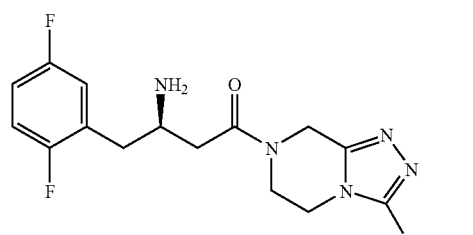 |
| 4-[5-(2-Cyanopyridin-4-yl)-[1,2,4]oxadiazol-3-ylmethoxy]piperidine-1-carboxylic acid tert-butyl ester | 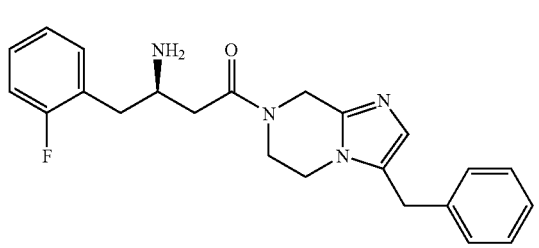 |
| 4-(3-Pyridin-4-yl-[1,2,4]oxadiazol-5-ylmethoxy)piperidine-1-carboxylic acid cyclopentyl ester | 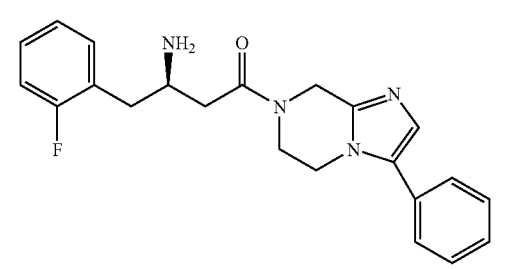 |
| 4-(3-Pyridin-4-yl-[1,2,4]oxadiazol-5-ylmethoxy)piperidine-1-carboxylic acid 2,2,2-trichloroethyl ester | 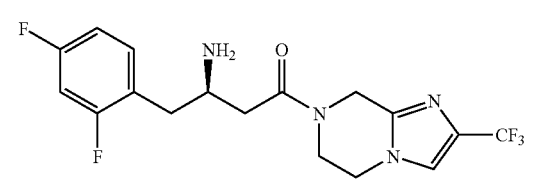 |
| 4-[Ethyl-(3-pyridin-4-yl-[1,2,4]oxadiazol-5-ylmethyl)amino]piperidine-1-carboxylic acid tert-butyl ester | 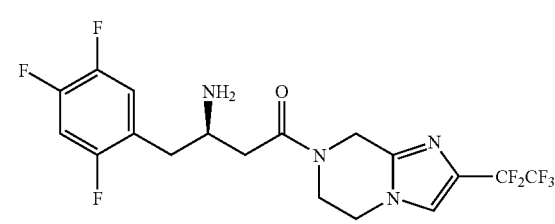 |
| 4-[Methyl-(3-pyridin-4-yl-[1,2,4]oxadiazol-5-ylmethyl)amino]piperidine-1-carboxylic acid cyclopentyl ester | 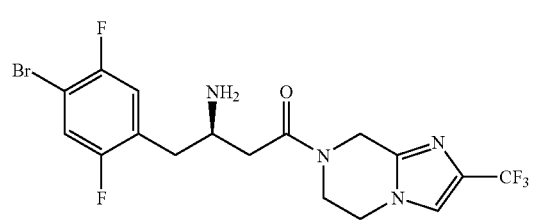 |

TABLE D-continued

| GPR119 Agonist | DPP-IV Inhibitor |
|---|---|
| 4-{[Methyl-(3-pyridin-4-yl-[1,2,4]oxadiazol-5-ylmethyl)amino]methyl}piperidine-1-carboxylic acid 2,2,2-trichloroethyl ester | |
| 4-[5-(4-Butyl-cyclohexyl)-[1,2,4]oxadiazol-3-yl)-pyridine (PSN375963) | |
| 4-(3-Pyridin-4-yl-[1,2,4]oxadiazol-5-ylmethoxy)-piperidine-1-carboxylic acid tert-butyl ester (PSN632408) | |
| 4-[6-(6-Methanesulfonyl-2-methyl-pyridin-3-ylamino)-5-methoxy-pyrimidin-4-yloxy]-piperidine-1-carboxylic acid isopropyl ester | |
| {6-[1-(3-Isopropyl-[1,2,4]oxadiazol-5-yl)-piperidin-4-yloxy]-5-methoxy-pyrimidin-4-yl}-(6-methanesulfonyl-2-methyl-pyridin-3-yl)-amine | |
| 4-[6-(6-Methanesulfonyl-4-methyl-pyridin-3-ylamino)-5-methoxy-pyrimidin-4-yloxy]-piperidine-1-carboxylic acid isopropyl ester | |
| 4-{[Methyl-(2-pyridin-4-ylpyrimidin-4-yl)-amino]methyl}piperidine-1-carboxylic acid tert-butyl ester | |

TABLE D-continued

| GPR119 Agonist | DPP-IV Inhibitor |
| --- | --- |
| 4-{[Methyl-(2-pyridin-4-ylpyrimidin-4-ylmethyl)amino]methyl}piperidine-1-carboxylic acid tert-butyl ester | (structure shown) |
| 4-[(([2,4']Bipyridinyl-6-ylmethylmethylamino)methyl]piperidine-1-carboxylic acid tert-butyl ester | (structure shown) |

(2R)-4-oxo-4-[3-(trifluoromethyl)-5,6-dihydro[1,2,4]triazolo[4,3-A]pyrazin-7(8H)-yl]-1-(2,4,5-trifluoropbenyl)butan-2-amine
(3R)-4-[(3R)-3-Amino-4-(2,4,5-trifluorophenyl)butanoyl]-3-(2,2,2-trifluoroethyl)-1,4-diazepan-2-one Additionally, compounds of the invention, including those illustrated in Table D, encompass all pharmaceutically acceptable salts, solvates, and hydrates thereof. See, e.g., Berge et al (1977), Journal of Pharmaceutical Sciences 66:1-19; and Polymorphism in Pharmaceutical Solids (1999) Brittain, ed., Marcel Dekker, Inc.; the disclosure of each of which is herein incorporated by reference in its entirety.

Composition/Formulation and Methods of Treatment

A GPR119 agonist optionally in combination with a DPP-IV inhibitor according to the present invention and including the combination therapy relating to a GPR119 agonist in combination with a DPP-IV inhibitor described above can be formulated into pharmaceutical compositions and medicaments for use in accordance with the present invention using techniques well known in the art. Proper formulation is dependent on the route of administration chosen.

As relates to therapies of the present invention, namely therapies relating to a GPR119 agonist optionally in combination with a DPP-IV inhibitor and including the combination therapy relating to a GPR119 agonist and a DPP-IV inhibitor described above, the compounds according to the invention can be administered in any suitable way. Suitable routes of administration include oral, nasal, rectal, transmucosal, transdermal, or intestinal administration, parenteral delivery, including intramuscular, subcutaneous, intramedullary injections, as well as intrathecal, direct intraventricular, intravenous, intraperitoneal, intranasal, intrapulmonary (inhaled) or intraocular injections using methods known in the art. Other suitable routes of administration are aerosol and depot formulation. Sustained release formulations, particularly depot, of the invented medicaments are expressly contemplated. In certain preferred embodiments, the compounds according to the present invention are administered orally. The compounds according to the present invention can be made up in solid or liquid form, such as tablets, capsules, powders, syrups, elixirs and the like, aerosols, sterile solutions, suspensions or emulsions, and the like. In certain embodiments, one or both of the GPR119 agonist and the DPP-IV inhibitor are administered orally.

Formulations for oral administration may be in the form of aqueous solutions and suspensions, in addition to solid tablet and capsule formulations. The aqueous solutions and suspensions may be prepared from sterile powders or granules. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants are well and widely known in the art.

It will be appreciated that the GPR119 agonist and the DPP-IV inhibitor may be present as a combined preparation for simultaneous, separate or sequential use for the treatment or prevention of a condition characterized by low bone mass, such as osteoporosis, and for increasing bone mass in an individual. Such combined preparations may be, for example, in the form of a twin pack.

It will therefore be further appreciated that the invention contemplates a product comprising or consisting essentially of a GPR119 agonist and a DPP-IV inhibitor as a combined preparation for simultaneous, separate or sequential use in the treatment or prevention of a condition characterized by low bone mass, such as osteoporosis, and for increasing bone mass in an individual.

A combination of the present invention comprising or consisting essentially of a GPR119 agonist and a DPP-IV inhibitor can be prepared by mixing the GPR119 agonist and the DPP-IV inhibitor either all together or independently with a pharmaceutically acceptable carrier, excipient, binder, diluent, etc. as described herein, and administering the mixture or mixtures either orally or non-orally as a pharmaceutical composition(s).

It will therefore be further appreciated that the GPR119 agonist and the DPP-IV inhibitor or pharmaceutical composition can be administered in separate dosage forms or in a single dosage form.

It is further appreciated that when the GPR119 agonist and the DPP-IV inhibitor are in separate dosage forms, GPR119 agonist and DPP-IV inhibitor can be administered by different routes.

Pharmaceutical compositions of the GPR119 agonist and DPP-IV inhibitor, either individually or in combination, may be prepared by methods well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Suitable pharmaceutically acceptable carriers are available to those in the art [see, e.g., Remington: The Science and Practice of Pharmacy, (Gennaro et al., eds.), 20$^{th}$ Edition, 2000, Lippincott Williams & Wilkins; and Handbook of Pharmaceutical Excipients (Rowe et al., eds), 4$^{th}$ Edition, 2003, Pharmaceutical Press; the disclosure of each of which is herein incorporated by reference in its entirety]. Proper formulation is dependent upon, the route of administration chosen. The term "carrier" material or "excipient" material herein means any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improved appearance of the composition. Acceptable excipients include stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials, such as cellulose esters of alkanoic acids and cellulose alkyl esters, low melting wax cocoa butter or powder, polymers, such as polyvinyl-pyrrolidone, polyvinyl alcohol, and polyethylene glycols, and other pharmaceutically acceptable materials. The components of the pharmaceutical composition can be encapsulated or tableted for convenient administration.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

As relates to the combination therapy described above, when the GPR119 agonist and the DPP-IV inhibitor are in separate dosage forms, it is understood that a pharmaceutically acceptable carrier used for the GPR119 agonist formulation need not be identical to a pharmaceutically acceptable carrier used for the DPP-IV inhibitor formulation.

Dragee cores are provided with suitable coatings. For this purpose, concentrated sugar solutions may be used which may optionally contain gum Arabic, talc; polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid, polyethylene glycols, cremophor, capmul, medium or long chain mono-, di- or triglycerides. Stabilizers may be added in these formulations, also.

Additionally, a GPR119 agonist and the combination of a GPR119 agonist with a DPP-IV inhibitor may be delivered using a sustained-release system. Various sustained-release materials have been established and are well known to those skilled in the art. Sustained-release tablets or capsules are particularly preferred. For example, a time delay material such as glyceryl monostearate or glyceryl distearate may be employed. The dosage form may also be coated by the techniques described in the U.S. Pat. Nos. 4,256,108, 4,166,452, and 4,265,874 to form osmotic therapeutic tablets for controlled release.

It is expressly contemplated that therapies of the present invention, namely therapies relating to a GPR119 agonist optionally in combination with a DPP-IV inhibitor and including the combination therapy relating to a GPR119 agonist and a DPP-IV inhibitor described above, may be administered or provided alone or in combination with one or more other pharmaceutically or physiologically acceptable compound. In one aspect of the present invention, the other pharmaceutically or physiologically acceptable compound is not a GPR119 agonist and is not a DPP-IV inhibitor. In one aspect of the present invention, the other pharmaceutically or physiologically acceptable compound is a pharmaceutical agent selected from the group consisting of calcium, vitamin D, estrogen, tibolone, selective estrogen receptor modulator (SERM; e.g., raloxifene, tamoxifen), biphosphonate (e.g., etidronate, alendronate, risedronate), calcitonin, 1α-hydroxylated metabolite of vitamin D, fluoride, thiazide, anabolic steroid, ipriflavone, vitamin K, parathyroid hormone (PTH), strontium, statin, osteoprotererin, EP4 receptor selective agonist, cannabinoid receptor type 2 (CB2) selective agonist, and p38 MAP kinase inhibitor. (See, e.g., World Health Organization Technical Report Series 921 (2003), Prevention and Management of Osteoporosis.)

In a combination therapy according to the present invention, the GPR119 agonist according to the present invention and the DPP-IV inhibitor according to the present invention can be administered simultaneously or at separate intervals. When administered simultaneously the GPR119 agonist and the DPP-IV inhibitor can be incorporated into a single pharmaceutical composition or into separate compositions, e.g., the GPR119 agonist in one composition and the DPP-IV inhibitor in another composition. Each of these compositions may be formulated with common excipients, diluents or carriers, and compressed into tablets, or formulated elixirs or solutions; and as sustained relief dosage forms and the like. The GPR119 agonist and DPP-IV inhibitor may be administered via different routes. For example, the GPR119 agonist may be administered orally via tablet and the DPP-IV inhibitor may be administered via inhalation.

When separately administered, therapeutically effective amounts of the GPR119 agonist and the DPP-IV inhibitor according to the present invention are administered on a different schedule. One may be administered before the other as long as the time between the two administrations falls within a therapeutically effective interval. A therapeutically effective interval is a period of time beginning when one of either (a) the GPR119 agonist or (b) the DPP-IV inhibitor is administered to an individual and ending at the limit of the beneficial effect in the treatment of the combination of (a) and (b).

In one aspect, the present invention features a composition comprising or consisting essentially of an amount of a GPR119 agonist according to the present invention. In one aspect, the present invention features a pharmaceutical composition comprising or consisting essentially of an amount of a GPR119 agonist according to the present invention and at least one pharmaceutically acceptable carrier.

In one aspect, the present invention features a combination comprising or consisting essentially of a combination of an amount of a GPR119 agonist according to the present invention and an amount of a DPP-IV inhibitor according to the present invention. In one aspect, the present invention features a pharmaceutical combination comprising or consisting essentially of a combination of an amount of a GPR119 agonist according to the present invention and an amount of a DPP-IV inhibitor according to the present invention, together with at least one pharmaceutically acceptable carrier.

In one aspect, the present invention features a composition comprising or consisting essentially of an amount of a GPR119 agonist according to the present invention. In one aspect, the present invention features a pharmaceutical composition comprising or consisting essentially of an amount of a GPR119 agonist according to the present invention and at least one pharmaceutically acceptable carrier. The present invention also relates to a dosage form of the composition or of the pharmaceutical composition wherein the GPR119 agonist is in an amount sufficient to give an effect in treating or preventing a condition characterized by low bone mass, such as osteoporosis, and/or in increasing bone mass in an individual.

In one aspect, the present invention features a composition comprising or consisting essentially of a combination of an amount of a GPR119 agonist according to the present invention and an amount of a DPP-IV inhibitor according to the present invention. In one aspect, the present invention features a pharmaceutical composition comprising or consisting essentially of a combination of an amount of a GPR119 agonist according to the present invention and an amount of a DPP-IV inhibitor according to the present invention, together with at least one pharmaceutically acceptable carrier. The present invention also relates to a dosage form of the composition or of the pharmaceutical composition wherein the GPR119 agonist and the DPP-IV inhibitor are in amounts sufficient to give an effect in treating or preventing a condition characterized by low bone mass, such as osteoporosis, and/or in increasing bone mass in an individual.

In one aspect, the present invention features a composition comprising or consisting essentially of a combination of an amount of a GPR119 agonist according to the present invention and an amount of a DPP-IV inhibitor according to the present invention. In one aspect, the present invention features a pharmaceutical composition comprising or consisting essentially of a combination of an amount of a GPR119 agonist according to the present invention and an amount of a DPP-IV inhibitor according to the present invention, together with at least one pharmaceutically acceptable carrier. The present invention also relates to a dosage form of the composition or of the pharmaceutical composition wherein the GPR119 agonist and the DPP-IV inhibitor are in amounts sufficient to give an effect in treating or preventing a condition characterized by low bone mass, such as osteoporosis, and/or in increasing bone mass in an individual, and wherein the amount of the GPR119 agonist alone and the amount of the DPP-IV inhibitor alone are not therapeutically effective in treating or preventing a condition characterized by low bone mass, such as osteoporosis, and/or in increasing bone mass in the individual.

In one aspect, the present invention features a composition comprising or consisting essentially of a combination of an amount of a GPR119 agonist according to the present invention and an amount of a DPP-IV inhibitor according to the present invention. In one aspect, the present invention features a pharmaceutical composition comprising or consisting essentially of a combination of an amount of a GPR119 agonist according to the present invention and an amount of a DPP-IV inhibitor according to the present invention, together with at least one pharmaceutically acceptable carrier. The present invention also relates to a dosage form of the composition or of the pharmaceutical composition wherein the GPR119 agonist and the DPP-IV inhibitor are in amounts sufficient to give an effect in treating or preventing a condition characterized by low bone mass, such as osteoporosis, and/or in increasing bone mass in an individual, and wherein the effect is a synergistic effect.

In one aspect, the present invention relates to a composition comprising or consisting essentially of a combination of an amount of a GPR119 agonist according to the present invention and an amount of a DPP-IV inhibitor according to the present invention. In one aspect, the present invention relates to a pharmaceutical composition comprising or consisting essentially of a combination of an amount of a GPR119 agonist according to the present invention and an amount of a DPP-IV inhibitor according to the present invention, together with at least one pharmaceutically acceptable carrier. The present invention also relates to a dosage form of the composition or of the pharmaceutical composition wherein the GPR119 agonist and the DPP-IV inhibitor are in amounts sufficient to give an effect in treating or preventing a condition characterized by low bone mass, such as osteoporosis, and/or in increasing bone mass in an individual, wherein the effect is a synergistic effect, and wherein the amount of the GPR119 agonist alone and the amount of the DPP-IV inhibitor alone are not therapeutically effective in treating or preventing a condition characterized by low bone mass, such as osteoporosis, and/or in increasing bone mass in the individual.

In one aspect, the present invention relates to a composition comprising or consisting essentially of a combination of an amount of a GPR119 agonist according to the present invention and an amount of a DPP-IV inhibitor according to the present invention. In one aspect, the present invention relates to a pharmaceutical composition comprising or consisting essentially of a combination of an amount of a GPR119 agonist according to the present invention and an amount of a DPP-IV inhibitor according to the present invention, together with at least one pharmaceutically acceptable carrier. The present invention also relates to a dosage form of the composition or of the pharmaceutical composition wherein the GPR119 agonist and the DPP-IV inhibitor are in amounts sufficient to give an effect in treating or preventing a condition characterized by low bone mass, such as osteoporosis, and/or in increasing bone mass in an individual, wherein the effect given by the combination of the amount of the GPR119 agonist and the amount of the DPP-IV inhibitor is greater than the effect given by the amount of the GPR119 agonist alone and the effect given by the amount of the DPP-IV inhibitor alone.

In one aspect, the present invention features a composition comprising or consisting essentially of an amount of a GPR119 agonist according to the present invention. In one aspect, the present invention features a pharmaceutical composition comprising or consisting essentially of an amount of a GPR119 agonist according to the present invention and at least one pharmaceutically acceptable carrier. The present invention also relates to a dosage form of the composition or of the pharmaceutical composition wherein the GPR119 agonist is in an amount sufficient to give an effect in increasing a GIP level in an individual.

In one aspect, the present invention features a composition comprising or consisting essentially of a combination of an amount of a GPR119 agonist according to the present invention and an amount of a DPP-IV inhibitor according to the present invention. In one aspect, the present invention features a pharmaceutical composition comprising or consisting essentially of a combination of an amount of a GPR119 agonist according to the present invention and an amount of a DPP-IV inhibitor according to the present invention, together with at least one pharmaceutically acceptable carrier. The present invention also relates to a dosage form of the composition or of the pharmaceutical composition wherein the GPR119 agonist and the DPP-IV inhibitor are in amounts sufficient to give an effect in increasing a GIP level in an individual.

In one aspect, the present invention features a composition comprising or consisting essentially of a combination of an amount of a GPR119 agonist according to the present invention and an amount of a DPP-IV inhibitor according to the present invention. In one aspect, the present invention features a pharmaceutical composition comprising or consisting essentially of a combination of an amount of a GPR119 agonist according to the present invention and an amount of a DPP-IV inhibitor according to the present invention, together with at least one pharmaceutically acceptable carrier. The present invention also relates to a dosage form of the composition or of the pharmaceutical composition wherein the GPR119 agonist and the DPP-IV inhibitor are in amounts sufficient to give an effect in increasing a GIP level in a subject, and wherein the amount of the GPR119 agonist alone and the amount of the DPP-IV inhibitor alone are not therapeutically effective in increasing a GIP level in the individual.

In one aspect, the present invention features a composition comprising or consisting essentially of a combination of an amount of a GPR119 agonist according to the present invention and an amount of a DPP-IV inhibitor according to the present invention. In one aspect, the present invention features a pharmaceutical composition comprising or consisting essentially of a combination of an amount of a GPR119 agonist according to the present invention and an amount of a DPP-IV inhibitor according to the present invention, together with at least one pharmaceutically acceptable carrier. The present invention also relates to a dosage form of the composition or of the pharmaceutical composition wherein the GPR119 agonist and the DPP-IV inhibitor are in amounts sufficient to give an effect in increasing a GIP level in an individual, and wherein the effect is a synergistic effect.

In one aspect, the present invention relates to a composition comprising or consisting essentially of a combination of an amount of a GPR119 agonist according to the present invention and an amount of a DPP-IV inhibitor according to the present invention. In one aspect, the present invention relates to a pharmaceutical composition comprising or consisting essentially of a combination of an amount of a GPR119 agonist according to the present invention and an amount of a DPP-IV inhibitor according to the present invention, together with at least one pharmaceutically acceptable carrier. The present invention also relates to a dosage form of the composition or of the pharmaceutical composition wherein the GPR119 agonist and the DPP-IV inhibitor are in amounts sufficient to give an effect in increasing a GIP level in a subject, wherein the effect is a synergistic effect, and wherein the amount of the GPR119 agonist alone and the amount of the DPP-IV inhibitor alone are not therapeutically effective in increasing a GIP level in the individual.

In one aspect, the present invention relates to a composition comprising or consisting essentially of a combination of an amount of a GPR119 agonist according to the present invention and an amount of a DPP-IV inhibitor according to the present invention. In one aspect, the present invention relates to a pharmaceutical composition comprising or consisting essentially of a combination of an amount of a GPR119 agonist according to the present invention and an amount of a DPP-IV inhibitor according to the present invention, together with at least one pharmaceutically acceptable carrier. The present invention also relates to a dosage form of the composition or of the pharmaceutical composition wherein the GPR119 agonist and the DPP-IV inhibitor are in amounts sufficient to give an effect in increasing a GIP level in a subject, wherein the effect given by the combination of the amount of the GPR119 agonist and the amount of the DPP-IV inhibitor is greater than the effect given by the amount of the GPR119 agonist alone and the effect given by the amount of the DPP-IV inhibitor alone.

Pharmaceutical compositions suitable for use in the present invention include compositions wherein the active ingredients are contained in an amount to achieve their intended purpose. In some embodiments, a pharmaceutical composition of the present invention is understood to be useful for treating or preventing a condition characterized by low bone mass, such as osteoporosis, or for increasing bone mass in an individual. Conditions characterized by low bone mass are according to the present invention. In some embodiments, a pharmaceutical composition of the present invention is understood to be useful for increasing a GIP level in an individual. As relates to the present invention, determination of the amount of a GPR119 agonist or of the amount of a combination of a GPR119 agonist with a DPP-IV inhibitor sufficient to achieve an intended purpose according to the invention is well within the capability of those skilled in the art, especially in light of the detailed disclosure provided herein.

The data obtained from animal studies, including but not limited to studies using mice, rats, rabbits, pigs, and non-human primates, can be used in formulating a range of dosage for use in humans. In general, one skilled in the art understands how to extrapolate in vivo data obtained in an animal model system to another, such as a human. In some circumstances, these extrapolations may merely be based on the weight of the animal model in comparison to another, such as a human; in other circumstances, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis is conducted or on whether further active compounds are administered in addition to the compounds of the present invention and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

An exemplary animal model system is the rat ovariectomy (OVX) bone loss model. The ovariectomized rat is an excellent preclinical animal model that correctly emulates the important clinical feature of the estrogen depleted human skeleton and the response of therapeutic agents. In this model, a therapeutic efficacy is achieved when the bone loss associated with ovariectomy is partially or completely prevented. (See, e.g., Bollag et al, Mol Cell Endocrinol (2001) 177:35-41; and Jee et al, J Musculoskel Neuron Interact (2001) 1:193-207.) In certain embodiments, therapeutic efficacy is achieved when the bone loss associated with ovariectomy is at least about 10% prevented, at least about 20% prevented, at least about 30% prevented, at least about 40% prevented, at least about 50% prevented, at least about 60% prevented, at least about 70% prevented, at least about 75% prevented, at least about 80% prevented, at least about 85% prevented, at least about 90% prevented, at least about 95% prevented, or 100% prevented.

An additional exemplary animal model system is increase of a blood GIP level after glucose challenge in mice. In certain embodiments, the blood GIP level is a plasma GIP level. In certain embodiments, the GIP level is a glucose-independent GIP level. In certain embodiments, the GIP level is a glucose-dependent GIP level. In certain embodiments, the GIP is total GIP. In certain embodiments, the total GIP is measured using a centrally or C-terminally directed assay. In certain embodiments, the GIP is bioactive GIP. In certain embodiments, the bioactive GIP is measured using an N-terminal-specific assay. In certain embodiments, the bioactive GIP has activity for promoting bone formation. In certain embodiments, therapeutic efficacy is achieved when the blood GIP level is increased by at least about 10%, at least about 25%, at least about 50%, at least about 100%, at least about 150%, at least about 200%, at least about 300%, at least about 400%, or at least about 500%.

Dosage amount and interval may be adjusted in order to provide an intended therapeutic effect. It will be appreciated that the exact dosage of a GPR119 agonist or DPP-IV inhibitor in accordance with the present invention will vary depending on the GPR119 agonist, the combination of a GPR119 agonist and a DPP-IV inhibitor, its potency, the mode of administration, the age and weight of the patient and the severity of the condition to be treated. The exact formulation, route of administration and dosage can be chosen by the individual physician in view of the patient's condition. By way of illustration and not limitation, an amount of a GPR119 agonist and/or an amount of a DPP-IV inhibitor in accordance with the present invention is less than about 0.001 mg/kg body weight, less than about 0.005 mg/kg body weight, less than about 0.01 mg/kg body weight, less than about 0.05 mg/kg body weight, less than about 0.1 mg/kg body weight, less than about 0.5 mg/kg body weight, less than about 1 mg/kg body weight, less than about 5 mg/kg body weight, less than about 10 mg/kg body weight, less than about 50 mg/kg body weight, or less than about 100 mg/kg body weight. In certain embodiments, an amount of a GPR119 agonist and/or an amount of a DPP-IV inhibitor in accordance with the present invention is less than about 0.001-100 mg/kg body weight, less than about 0.001-50 mg/kg body weight, less than about 0.001-10 mg/kg body weight, less than about 0.001-5 mg/kg body weight, less than about 0.001-1 mg/kg body weight, less than about 0.001 to 0.5 mg/kg body weight, less than about 0.001-0.1 mg/kg body weight, less than about 0.001-0.05 mg/kg body weight, less than about 0.001-0.01 mg/kg body weight, or less than about 0.001-0.005 mg/kg body weight.

It is expressly contemplated that a GPR119 agonist and a combination of a GPR119 agonist and a DPP-IV inhibitor can be used in methods of preventing bone loss (e.g., methods of preventing a decrease in bone mass), methods of inhibiting bone loss (e.g., methods of inhibiting a decrease in bone mass), methods of maintaining bone mass, and methods of promoting bone formation (e.g., methods of increasing bone mass) in an individual.

A preferred dosage range for an amount of a GPR119 agonist which can be administered on a daily or regular basis to achieve desired results is 0.001-100 mg/kg (mpk) body mass. Other preferred dosage range is 0.001-30 mg/kg body mass. Other preferred dosage range is 0.001-10 mg/kg body mass. Other preferred dosage range is 0.001-3.0 mg/kg body mass. Other preferred dosage range is 0.001-1.0 mg/kg body mass. Other preferred dosage range is 0.001-0.3 mg/kg body mass. Other preferred dosage range is 0.001-0.1 mg/kg body mass. Other preferred dosage range is 0.001-0.03 mg/kg body mass. Other preferred dosage range is 0.001-0.01 mg/kg body mass. Of course, these daily dosages can be delivered or administered in small amounts periodically during the course of a day. It is noted that these dosage ranges are only preferred ranges and are not meant to be limiting to the invention.

A preferred dosage range for an amount of a GPR119 agonist used in combination with a DPP-IV inhibitor for which a combination can be administered on a daily or regular basis to achieve desired results is 0.001-100 mg/kg body mass. Other preferred dosage range is 0.001-30 mg/kg body mass. Other preferred dosage range is 0.001-10 mg/kg body mass. Other preferred dosage range is 0.001-3.0 mg/kg body mass. Other preferred dosage range is 0.001-1.0 mg/kg body mass. Other preferred dosage range is 0.001-0.3 mg/kg body mass. Other preferred dosage range is 0.001-0.1 mg/kg body mass. Other preferred dosage range is 0.001-0.03 mg/kg body mass. Other preferred dosage range is 0.001-0.01 mg/kg body mass. Of course, these daily dosages can be delivered or administered in small amounts periodically during the course of a day. It is noted that these dosage ranges are only preferred ranges and are not meant to be limiting to the invention.

A preferred dosage range for an amount of a. DPP-IV inhibitor used in combination with a GPR119 agonist for which a combination can be administered on a daily or regular basis to achieve desired results is 0.001-100 mg/kg body mass. Other preferred dosage range is 0.001-30 mg/kg body mass. Other preferred dosage range is 0.001-10 mg/kg body mass. Other preferred dosage range is 0.001-3.0 mg/kg body mass. Other preferred dosage range is 0.001-1.0 mg/kg body mass. Other preferred dosage range is 0.001-0.3 mg/kg body mass. Other preferred dosage range is 0.001-0.1 mg/kg body mass. Other preferred dosage range is 0.001-0.03 mg/kg body mass. Other preferred dosage range is 0.001-0.01 mg/kg body mass. Of course, these daily dosages can be delivered or administered in small amounts periodically during the course of a day. It is noted that these dosage ranges are only preferred ranges and are not meant to be limiting to the invention.

It is expressly contemplated that, a GPR119 agonist or a combination of a GPR119 agonist and a DPP-IV inhibitor can be administered on a daily or regular basis to achieve an increased level of GIP in an individual. In certain embodiments, a GPR119 agonist or a combination of a GPR119 agonist and a DPP-IV inhibitor is administered on a daily or regular basis to achieve an increased blood (e.g., plasma or serum) level of GIP in an individual. In certain embodiments, a GPR119 agonist or a combination of a GPR119 agonist and a DPP-IV inhibitor is administered on a daily or regular basis to achieve an increased blood (e.g., plasma or serum) level of GIP in an individual that is 110% to 1000%, 110% to 900%, 110% to 800%, 110% to 700%, 110% to 600%, 110% to 500%, 110% to 400%, 110% to 300%, 110% to 200%, or 110% to 150% a normal blood level of GIP (e.g., a normal pre-meal plasma GIP level or a plasma GIP level between the normal pre-meal and post-meal plasma GIP levels) in an individual or the blood level of GIP in the individual prior to treatment. In certain embodiments, a GPR119 agonist or a combination of a GPR119 agonist and a DPP-IV inhibitor is administered on a daily or regular basis to achieve an increased blood (e.g., plasma or serum) level of GIP in an individual that is 150% to 1000%, 150% to 900%, 150% to 800%, 150% to 700%, 150% to 600%, 150% to 500%, 150% to 400%, 150% to 300%, or 150% to 200% a normal blood level of GIP (e.g., a normal pre-meal plasma GIP level or a plasma GIP level between the normal pre-meal and post-meal plasma GIP levels) in an individual or the blood level of GIP in the individual prior to treatment. In certain embodiments, a GPR119 agonist or a combination of a GPR119 agonist and a DPP-IV inhibitor is administered on a daily or regular basis to achieve an increased blood (e.g., plasma or serum) level of GIP in an individual that is 200% to 1000%, 200% to 900%, 200% to 800%, 200% to 700%, 200% to 600%, 200% to 500%, 200% to 400%, or 200% to 300% a normal blood level of GIP (e.g., a normal pre-meal plasma GIP level or a plasma GIP level between the normal pre-meal and post-meal plasma GIP levels) in an individual or the blood level of GIP in the individual prior to treatment. In certain embodiments, a GPR119 agonist or a combination of a GPR119 agonist and a DPP-IV inhibitor is administered on a daily or regular basis to achieve an increased blood (e.g., plasma or serum) level of GIP in an individual that is 250% to 1000%, 250% to 900%, 250% to 800%, 250% to 700%, 250% to 600%, 250% to 500%, 250% to 400%, or 250% to 300% a normal blood level of GIP (e.g., a normal pre-meal plasma GIP level or a plasma GIP level between the normal pre-meal and post-meal plasma GIP levels) in an individual or the blood level of GIP in the individual prior to treatment. In certain embodiments, a GPR119 agonist or a combination of a GPR119 agonist and a DPP-IV inhibitor is administered on a daily or regular basis to achieve an increased blood (e.g., plasma or serum) level of GIP in an individual that is 300% to 1000%, 300% to 900%, 300% to 800%, 300% to 700%, 300% to 600%, 300% to 500%, or 300% to 400% a normal blood level of GIP (e.g., a normal pre-meal plasma GIP level or a plasma GIP level between the normal pre-meal and post-meal plasma GIP levels) in an individual or the blood level of GIP in the individual prior to treatment. In certain embodiments, a GPR119 agonist or a combination of a GPR119 agonist and a DPP-IV inhibitor is administered on a daily or regular basis to achieve an increased blood (e.g., plasma or serum) level of GIP in an individual that is 400% to 1000%, 400% to 900%, 400% to 800%, 400% to 700%, 400% to 600%, or 400% to 500% a normal blood level of GIP (e.g., a normal pre-meal plasma GIP level or a plasma GIP level between the normal pre-meal and post-meal plasma GIP levels) in an individual or the blood level of GIP in the individual prior to treatment. In certain embodiments, a GPR119 agonist or a combination of a GPR119 agonist and a DPP-IV inhibitor is administered on a daily or regular basis to achieve an increased blood (e.g., plasma or serum) level of GIP in an individual that is 500% to 1000%, 500% to 900%, 500% to 800%, 500% to 700%, or 500% to 600% a normal blood level of GIP (e.g., a normal pre-meal plasma GIP level or a plasma GIP level between the normal pre-meal and post-meal plasma GIP levels) in an individual or the blood level of GIP in the individual prior to treatment. In certain embodiments, the blood (e.g., plasma or serum) level of GIP is a blood (e.g., plasma or serum) level of total GIP. In certain embodiments, the blood (e.g., plasma or serum) level of GIP is a blood (e.g., plasma or serum) level of bioactive (active) GIP. It is noted that these ranges of increased blood level of GIP are exemplary ranges and are not meant to be limiting to the invention.

It is expressly contemplated that a GPR119 agonist or a combination of a GPR119 agonist and a DPP-IV inhibitor can be administered on a daily or regular basis to achieve an increased level of GIP in an individual. In certain embodiments, a GPR119 agonist or a combination of a GPR119 agonist and a DPP-IV inhibitor is administered on a daily or regular basis to achieve an increased blood (e.g., plasma or serum) level of GIP in an individual. In certain embodiments, a GPR119 agonist or a combination of a GPR119 agonist and a DPP-IV inhibitor is administered on a daily or regular basis to achieve a blood (e.g., plasma or serum) level of GIP in an individual within a concentration range that is 100 pg/ml to 2000 pg/ml, 100 pg/ml to 1900 pg/ml, 100 pg/ml to 1800 pg/ml, 100 pg/ml to 1700 pg/ml, 100 pg/ml to 1600 pg/ml, 100 pg/ml to 1500 pg/ml, 100 pg/ml to 1400 pg/ml, 100 pg/ml to 1300 pg/ml, 100 pg/ml to 1200 pg/ml, 100 pg/ml to 1100 pg/ml, 100 pg/ml to 1000 pg/ml, 100 pg/ml to 900 pg/ml, 100 pg/ml to 800 pg/ml, 100 pg/ml to 700 pg/ml, 100 pg/ml to 600 pg/ml, 100 pg/ml to 500 pg/ml, 100 pg/ml to 400 pg/ml, 100 pg/ml to 300 pg/ml, or 100 pg/ml to 200 pg/ml. In certain embodiments, a GPR119 agonist or a combination of a GPR119 agonist and a DPP-IV inhibitor is administered on a daily or regular basis to achieve a blood (e.g., plasma or serum) level of GIP in an individual within a concentration range that is 200 pg/ml to 2000 pg/ml, 200 pg/ml to 1900 pg/ml, 200 pg/ml to 1800 pg/ml, 200 pg/ml to 1700 pg/ml, 200 pg/ml to 1600 pg/ml, 200 pg/ml to 1500 pg/ml, 200 pg/ml to 1400 pg/ml, 200 pg/ml to 1300 pg/ml, 200 pg/ml to 1200 pg/ml, 200 pg/ml to 1100 pg/ml, 200 pg/ml to 1000 pg/ml, 200 pg/ml to 900 pg/ml, 200 pg/ml to 800 pg/ml, 200 pg/ml to 700 pg/ml, 200 pg/ml to 600 pg/ml, 200 pg/ml to 500 pg/ml, 200 pg/ml to 400 pg/ml, or 200 pg/ml to 300 pg/ml. In certain embodiments, a GPR119 agonist or a combination of a GPR119 agonist and a DPP-IV inhibitor is administered on a daily or regular basis to achieve a blood (e.g., plasma or serum) level of GIP in an individual within a concentration range that is 300 pg/ml to 2000 pg/ml, 300 pg/ml to 1900 pg/ml, 300 pg/ml to 1800 pg/ml, 300 pg/ml to 1700 pg/ml, 300 pg/ml to 1600 pg/ml, 300 pg/ml to 1500 pg/ml, 300 pg/ml to 1400 pg/ml, 300 pg/ml to 1300 pg/ml, 300 pg/ml to 1200 pg/ml, 300 pg/ml to 1100 pg/ml, 300 pg/ml to 1000 pg/ml, 300 pg/ml to 900 pg/ml, 300 pg/ml to 800 pg/ml, 300 pg/ml to 700 pg/ml, 300 pg/ml to 600 pg/ml, 300 pg/ml to 500 pg/ml, or 300 pg/ml to 400 pg/ml. In certain embodiments, a GPR119 agonist or a combination of a GPR119 agonist and a DPP-IV inhibitor is administered on a daily or regular basis to achieve a blood (e.g., plasma or serum) level of GIP in an individual within a concentration range that is 400 pg/ml to 2000 pg/ml, 400 pg/ml to 1900 pg/ml, 400 pg/ml to 1800 pg/ml, 400 pg/ml to 1700 pg/ml, 400 pg/ml to 1600 pg/ml, 400 pg/ml to 1500 pg/ml, 400 pg/ml to 1400 pg/ml, 400 pg/ml to 1300 pg/ml, 400 pg/ml to 1200 pg/ml, 400 pg/ml to 1100 pg/ml, 400 pg/ml to 1000 pg/ml, 400 pg/ml to 900 pg/ml, 400 pg/ml to 800 pg/ml, 400 pg/ml to 700 pg/ml, 400 pg/ml to 600 pg/ml, or 400 pg/ml to 500 pg/ml. In certain embodiments, a GPR119 agonist or a combination of a GPR119 agonist and a DPP-IV inhibitor is administered on a daily or regular basis to achieve a blood (e.g., plasma or serum) level of GIP in an individual within a concentration range that is 500 pg/ml to 2000 pg/ml, 500 pg/ml to 1900 pg/ml, 500 pg/ml to 1800 pg/ml, 500 pg/ml to 1700 pg/ml, 500 pg/ml to 1600 pg/ml, 500 pg/ml to 1500 pg/ml, 500 pg/ml to 1400 pg/ml, 500 pg/ml to 1300 pg/ml, 500 pg/ml to 1200 pg/ml, 500 pg/ml to 1100 pg/ml, 500 pg/ml to 1000 pg/ml, 500 pg/ml to 900 pg/ml, 500 pg/ml to 800 pg/ml, 500 pg/ml to 700 pg/ml, or 500 pg/ml to 600 pg/ml. In certain embodiments, a GPR119 agonist or a combination of a GPR119 agonist and a DPP-IV inhibitor is administered on a daily or regular basis to achieve a blood (e.g., plasma or serum) level of GIP in an individual within a concentration range that is 600 pg/ml to 2000 pg/ml, 600 pg/ml to 1900 pg/ml, 600 pg/ml to 1800 pg/ml, 600 pg/ml to 1700 pg/ml, 600 pg/ml to 1600 pg/ml, 600 pg/ml to 1500 pg/ml, 600 pg/ml to 1400 pg/ml, 600 pg/ml to 1300 pg/ml, 600 pg/ml to 1200 pg/ml, 600 pg/ml to 1100 pg/ml, 600 pg/ml to 1000 pg/ml, 600 pg/ml to 900 pg/ml, 600 pg/ml to 800 pg/ml, or 600 pg/ml to 700 pg/ml. In certain embodiments, a GPR119 agonist or a combination of a GPR119 agonist and a DPP-IV inhibitor is administered on a daily or regular basis to achieve a blood (e.g., plasma or serum) level of GIP in an individual within a concentration range that is 700 pg/ml to 2000 pg/ml, 700 pg/ml to 1900 pg/ml, 700 pg/ml to 1800 pg/ml, 700 pg/ml to 1700 pg/ml, 700 pg/ml to 1600 pg/ml, 700 pg/ml to 1500 pg/ml, 700 pg/ml to 1400 pg/ml, 700 pg/ml to 1300 pg/ml, 700 pg/ml to 1200 pg/ml, 700 pg/ml to 1100 pg/ml, 700 pg/ml to 1000 pg/ml, 700 pg/ml to 900 pg/ml, or 700 pg/ml to 800 pg/ml. In certain embodiments, a GPR119 agonist or a combination of a GPR119 agonist and a DPP-IV inhibitor is administered on a daily or regular basis to achieve a blood (e.g., plasma or serum) level of GIP in an individual within a concentration range that is 800 pg/ml to 2000 pg/ml, 800 pg/ml to 1900 pg/ml, 800 pg/ml to 1800 pg/ml, 800 pg/ml to 1700 pg/ml, 800 pg/ml to 1600 pg/ml, 800 pg/ml to 1500 pg/ml, 800 pg/ml to 1400 pg/ml, 800 pg/ml to 1300 pg/ml, 800 pg/ml to 1200 pg/ml, 800 pg/ml to 1100 pg/ml, 800 pg/ml to 1000 pg/ml, or 800 pg/ml to 900 pg/ml. In certain embodiments, a GPR119 agonist or a combination of a GPR119 agonist and a DPP-IV inhibitor is administered on a daily or regular basis to achieve a blood (e.g., plasma or serum) level of GIP in an individual within a concentration range that is 900 pg/ml to 2000 pg/ml, 900 pg/ml to 1900 pg/ml, 900 pg/ml to 1800 pg/ml, 900 pg/ml to 1700 pg/ml, 900 pg/ml to 1600 pg/ml, 900 pg/ml to 1500 pg/ml, 900 pg/ml to 1400 pg/ml, 900 pg/ml to 1300 pg/ml, 900 pg/ml to 1200 pg/ml, 900 pg/ml to 1100 pg/ml, or 900 pg/ml to 1000 pg/ml. In certain embodiments, the blood (e.g., plasma or serum) level of GIP is a blood (e.g., plasma or serum) level of total GIP. In certain embodiments, the blood (e.g., plasma or serum) level of GIP is a blood (e.g., plasma or serum) level of bioactive (active) GIP. In certain embodiments, a GPR119 agonist or a combination of a GPR119 agonist and a DPP-IV inhibitor is administered on a daily or regular basis to achieve a blood (e.g., plasma or serum) level of GIP in an individual within a concentration range that is 1000 pg/ml to 2000 pg/ml, 1000 pg/ml to 1900 pg/ml, 1000 pg/ml to 1800 pg/ml, 1000 pg/ml to 1700 pg/ml, 1000 pg/ml to 1600 pg/ml, 1000 pg/ml to 1500 pg/ml, 1000 pg/ml to 1400 pg/ml, 1000 pg/ml to 1300 pg/ml, 1000 pg/ml to 1200 pg/ml, or 1000 pg/ml to 1100 pg/ml. In certain embodiments, the blood (e.g., plasma or serum) level of GIP is a blood (e.g., plasma or serum) level of total GIP. In certain embodiments, the blood (e.g., plasma or serum) level of GIP is a blood (e.g., plasma or serum) level of bioactive (active) GIP. It is noted that these ranges of blood GIP concentration are exemplary ranges and are not meant to be limiting to the invention.

In certain embodiments, a GPR119 agonist or a combination of a GPR119 agonist and a DPP-IV inhibitor is administered on a daily or regular basis to achieve an increased level of GIP in an individual in a manner that does not lead to down-regulation or to substantial down-regulation of the GIP receptor (decreased levels of GIP receptor protein) in bone (e.g., in femur) (e.g., in osteoblasts). In certain embodiments, the level of GIP receptor protein in bone is decreased by less than about 90%, less than about 80%, less than about 70%, less than about 60%, less than about 50%, less than about 40%, less than about 30%, less than about 25%, less than about 20%, less than about 15%, less than about 10%, less than about 5%, or less than about 2.5%. In certain embodiments, the level of GIP receptor protein in bone is decreased by less than about 25%, less than about 20%, less than about 15%, less than about 10%, less than about 5%, or less than about 2.5%. In certain embodiments, the level of GIP receptor protein in bone is decreased by less than about 10%, less than about 5%, or less than about 2.5%. In certain embodiments, the level of GIP receptor protein in bone is not decreased. In certain embodiments, the blood (e.g., plasma or serum) level of GIP is a blood (e.g., plasma or serum) level of total GIP. In certain embodiments, the blood (e.g., plasma or serum) level of GIP is a blood (e.g., plasma or serum) level of bioactive (active) GIP. Suitable animals models (e.g., mouse, rat) for assessing an effect of a GIP level on down-regulation of the GIP receptor in bone are known in the art. Methods for determining down-regulation of the GIP receptor in bone are known to the skilled artisan and include, e.g., Western blot using an antibody to the GIP receptor. See, e.g., Xie et, al, Bone, 2007.

In certain embodiments, the GPR119 agonist is a GPR119 partial agonist.

In certain embodiments, the GPR119 agonist is a nonendogenous GPR119 agonist.

In certain embodiments, administration of a GPR119 agonist or a combination of a GPR119 agonist and a DPP-IV inhibitor is oral.

In certain embodiments related to a combination of a GPR119 agonist and a DPP-IV inhibitor, the GPR119 agonist and the DPP-IV inhibitor are administered in separate dosage forms or in a single dosage form.

In certain embodiments, a GPR119 agonist or a combination of a GPR119 agonist and a DPP-IV inhibitor is administered in a manner that achieves elevation of GIP in an individual in a pulsatile or episodic fashion. Pulsatile or episodic elevation of GIP shall mean that blood (e.g., plasma or serum) levels of GIP rise from a baseline level to a peak level and return to the baseline level at least one time per day. In certain embodiments, the baseline level of plasma GIP is approximately a normal pre-meal plasma GIP level. In certain embodiments, the baseline level of plasma GIP is between the normal pre-meal and post-meal plasma GIP levels. The skilled artisan would be aware of how to effect pulsatile or episodic elevation of GIP in an individual. In certain embodiments, pulsatile or episodic elevation is achieved by administering a GPR119 agonist or a combination of a GPR119 agonist and a DPP-IV inhibitor in a manner such that an effect for elevating GIP resulting from the preceding dose completely dissipates before a subsequent dose is administered. In certain embodiments, pulsatile or episodic elevation of GIP is achieved by administering a GPR119 agonist or a combination of a GPR119 agonist and a DPP-IV inhibitor when plasma glucose levels rise (e.g., after ingestion of a meal). In certain embodiments, the blood (e.g., plasma or serum) level of GIP is a blood (e.g., plasma or serum) level of total GIP. In certain embodiments, the blood (e.g., plasma or serum) level of GIP is, a blood (e.g., plasma or serum) level of bioactive (active) GIP.

It is expressly contemplated that the dosage interval can relate to the time at which a meal is ingested. In certain embodiments, a GPR119 agonist or a combination of a GPR119 agonist and a DPP-IV inhibitor is administered before, during or after a meal. In certain embodiments, a GPR119 agonist or a combination of a GPR119 agonist and a DPP-TV inhibitor is administered before a meal. In certain embodiments, a GPR119 agonist or a combination of a GPR119 agonist and a DPP-IV inhibitor is administered 120 minutes or less prior to a meal. In certain embodiments, a GPR119 agonist or a combination of a GPR119 agonist and a DPP-IV inhibitor is administered 90 minutes or less prior to a meal. In certain embodiments, a GPR119 agonist or a combination of a GPR119 agonist and a DPP-IV inhibitor is administered 60 minutes or less prior to a meal. In certain embodiments, a GPR119 agonist or a combination of a GPR119 agonist and a DPP-IV inhibitor is administered 30 minutes or less prior to a meal. In certain embodiments, a GPR119 agonist or a combination of a GPR119 agonist and a DPP-IV inhibitor is administered 15 minutes or less prior to a meal. In certain embodiments, a GPR119 agonist or a combination of a GPR119 agonist and a DPP-IV inhibitor is administered during a meal. In certain embodiments, a GPR119 agonist or a combination of a GPR119 agonist and a DPP-IV inhibitor is administered after a meal. In certain embodiments, a GPR119 agonist or a combination of a GPR119 agonist and a DPP-IV inhibitor is administered 120 minutes or less after a meal. In certain embodiments, a GPR119 agonist or a combination of a GPR119 agonist and a DPP-IV inhibitor is administered 90 minutes or less after a meal. In certain embodiments, a GPR119 agonist or a combination of a GPR119 agonist and a DPP-IV inhibitor is administered 60 minutes or less after a meal. In certain embodiments, a GPR119 agonist or a combination of a GPR119 agonist and a DPP-IV inhibitor is administered 30 minutes or less after a meal. In certain embodiments, a GPR119 agonist or a combination of a GPR119 agonist and a DPP-IV inhibitor is administered 15 minutes or less after a meal. It is noted that these time intervals are exemplary time intervals and are not meant to be limiting to the invention. In certain embodiments, administration is oral. In certain embodiments related to a combination of a GPR119 agonist and a DPP-IV inhibitor, the GPR119 agonist and the DPP-IV inhibitor are administered in separate dosage forms or in a single dosage form. In certain embodiments, the meal is a daily meal such as breakfast, lunch, dinner and the like. In certain embodiments, the meal is a regularly scheduled daily meal such as breakfast, lunch, dinner and the like. In certain embodiments, a GPR119 agonist or a combination of a GPR119 agonist and a DPP-IV inhibitor is administered before, during or after one or more daily meals such as breakfast, lunch, dinner and the like. In certain embodiments, a GPR119 agonist or a combination of a GPR119 agonist and a DPP-IV inhibitor is administered before, during or after one or more regularly scheduled daily meals such as breakfast, lunch, dinner and the like.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. In certain embodiments, salts derived from inorganic bases include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When, the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In certain embodiments, such acids include citric, hydrobromic, hydrochloric, maleic, phosphoric, sulfuric, fumaric, and tartaric acids.

Dosage amount and interval may be adjusted individually to provide plasma levels of a GPR119 agonist according to the present invention and/or of a DPP-IV inhibitor according to the present invention which achieve an intended therapeutic effect. It is expressly contemplated, e.g., that the dosage interval of a GPR119 agonist either alone or in combination with a DPP-IV inhibitor can be adjusted to coincide with meals taken by the individual, such as at the time of one or more regular meals (e.g., at breakfast and/or at lunch and/or at dinner, and the like). Dosage intervals can also be determined using the value for a selected range of GPR119 agonist concentration or the value for a selected range of DPP-IV inhibitor concentration so as to achieve the intended therapeutic effect. A GPR119 agonist and/or a DPP-IV inhibitor should be administered using a regimen that maintains plasma levels within the selected range of GPR119 agonist concentration and/or DPP-IV inhibitor concentration, respectively, for 10-90% of the time, in particular embodiment between 30-99% of the time, and in further particular embodiment between 50-90% of the time. In cases of local administration or selective uptake, the range of GPR119 agonist concentration and/or the range of DPP-IV inhibitor concentration providing the intended therapeutic effect may not be related to plasma concentration.

The amount of composition administered will, of course, be dependent on the individual being treated, on the individual's weight, the severity of the affliction, the manner of administration, and the judgement of the prescribing physician.

In one aspect, the present invention accordingly features a method of treating or preventing a condition characterized by low bone mass, such as osteoporosis, or of increasing bone mass comprising administering to an individual in need thereof a therapeutically effective amount of a composition comprising or consisting essentially of an amount of a GPR119 agonist according to the present invention. In certain embodiments, the composition is a pharmaceutical composition.

In one aspect, the present invention accordingly features a method of treating or preventing a condition characterized by low bone mass, such as osteoporosis, or of increasing bone mass comprising administering to an individual in need thereof a therapeutically effective amount of a composition comprising or consisting essentially of an amount of a GPR119 agonist according to the present invention and an amount of a DPP-IV inhibitor according to the present invention. In certain embodiments, the composition is a pharmaceutical composition.

In one aspect, the present invention relates to a method of treating or preventing a condition characterized by low bone mass, such as osteoporosis, or of increasing bone mass comprising administering to an individual in need thereof a therapeutically effective amount of a composition comprising or consisting essentially of an amount of a GPR119 agonist according to the present invention and an amount of a DPP-IV inhibitor according to the present invention. In a related aspect, the present invention features said method wherein the GPR119 agonist and the DPP-IV inhibitor are administered in amounts sufficient to give an effect in treating or preventing a condition characterized by low bone mass, such as osteoporosis, and/or in increasing bone mass in an individual, wherein the amount of the GPR119 agonist alone and the amount of the DPP-IV inhibitor alone are not therapeutically effective in treating or preventing a condition characterized by low bone mass, such as osteoporosis, and/or in increasing bone mass in the individual. In certain embodiments, the composition is a pharmaceutical composition.

In one aspect, the present invention relates to a method of treating or preventing a condition characterized by low bone mass, such as osteoporosis, or of increasing bone mass comprising administering to an individual in need thereof a therapeutically effective amount of a composition comprising or consisting essentially of an amount of a GPR119 agonist according to the present invention and an amount of a DPP-IV inhibitor according to the present invention. In a related aspect, the present invention features said method wherein the GPR119 agonist and the DPP-IV inhibitor are administered in amounts sufficient to give an effect in treating or preventing a condition characterized by low bone mass, such as osteoporosis, and/or in increasing bone mass in an individual, wherein the effect is a synergistic effect. In certain embodiments, the composition is a pharmaceutical composition.

In one aspect, the present invention relates to a method of treating or preventing a condition characterized by low bone mass comprising administering to an individual in need thereof a therapeutically effective amount of a composition comprising or consisting essentially of an amount of a GPR119 agonist according to the present invention and an amount of a DPP-IV inhibitor according to the present invention. In a related aspect, the present invention features said method wherein the GPR119 agonist and the DPP-IV inhibitor are administered in amounts sufficient to give an effect in treating or preventing a condition characterized by low bone mass, such as osteoporosis, and/or in increasing bone mass in an individual, wherein the effect is a synergistic effect, and wherein the amount of the GPR119 agonist alone and the amount of the DPP-IV inhibitor alone are not therapeutically effective in treating or preventing a condition characterized by low bone mass, such as osteoporosis, and/or in increasing bone mass in an individual. In certain embodiments, the composition is a pharmaceutical composition.

In one aspect, the present invention relates to a method of treating or preventing a condition characterized by low bone mass comprising administering to an individual in need thereof a therapeutically effective amount of a composition comprising or consisting essentially of an amount of a GPR119 agonist according to the present invention and an amount of a DPP-IV inhibitor according to the present invention. In a related aspect, the present invention features said method wherein the GPR119 agonist and the DPP-IV inhibitor are administered in amounts sufficient to give an effect in treating or preventing a condition characterized by low bone mass, such as osteoporosis, and/or in increasing bone mass in an individual, wherein the effect given by the combination of the amount of a GPR119 agonist and the amount of the DPP-IV inhibitor is greater than the effect given by the amount of the GPR119 agonist alone and the effect given by the amount of the DPP-IV inhibitor alone. In certain embodiments, the composition is a pharmaceutical composition.

In one aspect, the present invention relates to a method of treating or preventing a condition characterized by low bone mass, such as osteoporosis, or of increasing bone mass comprising administering to an individual in need thereof a therapeutically effective amount of a composition comprising or consisting essentially of an amount of a GPR119 agonist according to the present invention. In a related aspect, the present invention features said method wherein the GPR119 agonist is administered in an amount sufficient to give an effect in increasing a GIP level in the individual. In certain, embodiments, the composition is a pharmaceutical composition.

In one aspect, the present invention relates to a method of treating or preventing a condition characterized by low bone mass, such as osteoporosis, or of increasing bone mass comprising administering to an individual in need thereof a therapeutically effective amount of a composition comprising or consisting essentially of an amount of a GPR119 agonist according to the present invention and an amount of a DPP-IV inhibitor according to the present invention. In a related aspect, the present invention features said method wherein the GPR119 agonist and the DPP-IV inhibitor are administered in amounts sufficient to give an effect in increasing a GIP level in the individual. In certain embodiments, the composition is a pharmaceutical composition.

In one aspect, the present invention relates to a method of treating or preventing a condition characterized by low bone mass, such as osteoporosis, or of increasing bone mass comprising administering to an individual in need thereof a therapeutically effective amount of a composition comprising or consisting essentially of an amount of a GPR119 agonist according to the present invention and an amount of a DPP-IV inhibitor according to the present invention. In a related aspect, the present invention features said method wherein the GPR119 agonist and the DPP-IV inhibitor are administered in amounts sufficient to give an effect in increasing a GIP level in the individual, and wherein the amount of the GPR119 agonist alone and the amount of the DPP-IV inhibitor alone are not therapeutically effective in increasing a GIP level in the individual. In certain embodiments, the composition is a pharmaceutical composition.

In one aspect, the present invention relates to a method of treating or preventing a condition characterized by low bone mass, such as osteoporosis, or of increasing bone mass comprising administering to an individual in need thereof a therapeutically effective amount of a composition comprising or consisting essentially of an amount of a GPR119 agonist according to the present invention and an amount of a DPP-IV inhibitor according to the present invention. In a related aspect, the present invention features said method wherein the GPR119 agonist and the DPP-IV inhibitor are administered in amounts sufficient to give an effect in increasing a GIP level in the individual, and wherein the effect is a synergistic effect. In certain embodiments, the composition is a pharmaceutical composition.

In one aspect, the present invention relates to a method of treating or preventing a condition characterized by low bone mass comprising administering to an individual in need thereof a therapeutically effective amount of a composition comprising or consisting essentially of an amount of a GPR119 agonist according to the present invention and an amount of a DPP-IV inhibitor according to the present invention. In a related aspect, the present invention features said method wherein the GPR119 agonist and the DPP-IV inhibitor are administered in amounts sufficient to give an effect in increasing a GIP level in the individual, wherein the effect is a synergistic effect, and wherein the amount of the GPR119 agonist alone and the amount of the DPP-IV inhibitor alone are not therapeutically effective in increasing a GIP level in the individual. In certain embodiments, the composition is a pharmaceutical composition.

In one aspect, the present invention relates to a method of treating or preventing a condition characterized by low bone mass comprising administering to an individual in need thereof a therapeutically effective amount of a composition comprising or consisting essentially of an amount of a GPR119 agonist according to the present invention and an amount of a DPP-IV inhibitor according to the present invention. In a related aspect, the present invention features said method wherein the GPR119 agonist and the DPP-IV inhibitor are administered in amounts sufficient to give an effect in increasing a GIP level in the individual, wherein the effect given by the combination of the amount of the GPR119 agonist and the amount of the DPP-IV inhibitor is greater than the effect given by the amount of the GPR119 agonist alone and the effect given by the amount of the DPP-IV inhibitor alone. In certain embodiments, the composition is a pharmaceutical composition.

In certain embodiments, the GIP level is a blood or plasma total GIP level. In certain embodiments, the GIP level is a blood or plasma bioactive GIP level.

Therapies of the present invention are useful for increasing bone formation in an individual.

Therapies of the present invention, namely therapies relating to a GPR119 agonist optionally in combination with a DPP-IV inhibitor and including the combination therapy relating to a GPR119 agonist and a DPP-IV inhibitor described above are useful in treating or preventing a condition characterized by low bone mass in an individual and in increasing bone mass in an individual.

In certain embodiments, the individual receiving a therapy of the present invention, namely a therapy relating to a GPR119 agonist optionally in combination with a DPP-IV inhibitor and including the combination therapy relating to a GPR119 agonist and a DPP-IV inhibitor described above is a human and a participant in a study reviewed by a governmental agency charged with marketing approval for a drug. In certain, embodiments, the study is a clinical trial. In certain embodiments, the governmental agency is the Food and Drug Administration of the United States.

Conditions characterized by low bone mass include but are not limited to osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height. In certain embodiments, the condition characterized by low bone mass is osteoporosis. In certain embodiments, the condition characterized by low bone mass is osteoporosis. In certain embodiments, osteoporosis is primary osteoporosis. In certain embodiments, osteoporosis is secondary osteoporosis. Conditions characterized by low bone mass also include but are not limited to long-term complications of osteoporosis such as curvature of the spine, loss of height and prosthetic surgery. It is understood that conditions characterized by low bone mass can be included in embodiments individually or in any combination. In certain embodiments, the condition characterized by low bone mass is primary osteoporosis.

In certain embodiments, the individual in need of increased bone mass has a bone mineral density (BMD) of greater than 1 (T-score<−1), greater than or equal to 1.5 (T-score≦−1.5), greater than or equal to 2 (T-score≦−2) or greater than or equal to 2.5 (T-score≦−2.5) standard deviations below the young adult reference mean. In certain embodiments, the individual in need of increased bone mass is in need of treatment of bone fracture. In certain embodiments, the individual in need of treatment of a bone fracture has a traumatic bone fracture, a long-term bone fracture, or an osteoporotic bone fracture. In certain embodiments, the individual is in need of treatment for a bone disease. In certain embodiments, the individual in need of treatment for a bone disease has osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, or loss of height. In certain embodiments, the individual in need of treatment for a bone disease has osteoporosis. In certain embodiments, osteoporosis is primary osteoporosis. In certain embodiments, osteoporosis is secondary osteoporosis. Destructive bone disorders that can be treated according to the invention include but are not limited to osteoporosis, primary osteoporosis, secondary osteoporosis, osteoarthritis, and osteolytic lesions such as those caused by neoplastic disease, radiotherapy, or chemotherapy.

Therapies of the present invention, namely therapies relating to a GPR119 agonist optionally in combination with a DPP-IV inhibitor and including the combination therapy relating to a GPR119 agonist and a DPP-IV inhibitor described above are additionally useful in the treatment of bone fracture. In certain embodiments, the individual in need of treatment of a bone fracture has a traumatic bone fracture, a long-term bone fracture, or an osteoporotic bone fracture.

Therapies of the present invention, namely therapies relating to a GPR119 agonist optionally in combination with a DPP-IV inhibitor and including the combination therapy relating to a GPR119 agonist and a DPP-IV inhibitor described above are additionally useful in the treatment of a bone disease. In certain embodiments, the individual in need of treatment for a bone disease has osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, or loss of height. In certain embodiments, the individual in need of treatment for a bone disease has osteoporosis. In certain embodiments, osteoporosis is primary osteoporosis. In certain embodiments, osteoporosis is secondary osteoporosis. Destructive bone disorders that can be treated according to the invention include but are not limited to osteoporosis, primary osteoporosis, secondary osteoporosis, osteoarthritis, and osteolytic lesions such as those caused by neoplastic disease, radiotherapy, or chemotherapy.

Therapies of the present invention, namely therapies relating to a GPR119 agonist optionally in combination with a DPP-IV inhibitor and including the combination therapy relating to a GPR119 agonist and a DPP-IV inhibitor described above are additionally useful in enhancing bone healing following facial reconstruction, maxillary reconstruction, mandibular reconstruction, periodontal disease or tooth extraction, enhancing long bone extension, enhancing prosthetic ingrowth or increasing bone synostosis in an individual.

In certain embodiments, the individual is a vertebrate. In certain embodiments, the individual that is a vertebrate is a fish, an amphibian, a reptile, a bird or a mammal. In certain embodiments, the individual or vertebrate is a mammal. In certain embodiments, the individual or vertebrate that is a mammal is a mouse, a rat, a hamster, a rabbit, a pig, a dog, a cat, a horse, a cow, a sheep, a goat, a non-human mammal, a non-human primate or a human. In certain embodiments, the individual is a human. In certain embodiments, the human is a post-menopausal woman or a man over the age of 50.

Kits

Also provided by the subject invention are kits for practicing the subject methods, as described above.

In certain embodiments, the kits at least include a composition comprising a GPR119 agonist and instructions for using the components of the kit to practice the subject methods, e.g., methods of treating or preventing a condition characterized by low bone mass, such as osteoporosis, methods of increasing bone mass in an individual, etc. In certain embodiments, the GPR119 agonist is in dosage form. In certain embodiments, the composition is a pharmaceutical composition.

In certain embodiments, the kits at least include a composition comprising a GPR119 agonist and a composition comprising a DPP-IV inhibitor and instructions for using the components of the kit to practice the subject methods, e.g., methods of treating or preventing a condition characterized by low bone mass, such as osteoporosis, methods of increasing bone mass in an individual, etc. In certain embodiments, the GPR119 agonist and/or the DPP-IV is in dosage form. In certain embodiments, the composition comprising a GPR119 agonist and the composition comprising a DPP-IV inhibitor are pharmaceutical compositions.

In certain embodiments, the kits at least include a composition comprising a GPR119 agonist in combination with a DPP-IV inhibitor and instructions for using the components of the kit to practice the subject methods, e.g., methods of treating or preventing a condition characterized by low bone mass, such as osteoporosis, methods of increasing bone mass in an individual, etc. In certain embodiments, the GPR119 agonist in combination with the DPP-IV inhibitor is in dosage form. In certain embodiments, the composition is a pharmaceutical composition.

It is expressly contemplated that the instructions may at least include (as separate or combined instructions) one or both of dosage information and educational information for using the components of the kit to practice the subject methods. Educational material may relate to safer practice of the subject methods, greater compliance with practice of the subject methods, etc. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Without further elaboration, it is believed that one skilled in the art can, using the preceding description, practice the present invention to its fullest extent. The foregoing detailed description is given for clearness of understanding only, and no unnecessary limitation should be understood therefrom, as modifications within the scope of the invention may become apparent to those skilled in the art.

This application claims the benefit of priority from the following provisional applications, filed via U.S. Express mail with the United States Patent and Trademark Office on the indicated dates: U.S. Provisional No. 60/791,613, filed Apr. 11, 2006; U.S. Provisional No. 60/834,737, filed Jul. 31, 2006; and U.S. Provisional No. 60/851,244, filed Oct. 12, 2006; the disclosures of each of which are incorporated herein by reference in their entireties.

Throughout this application, various publications, patents and patent applications are cited. The disclosures of these publications, patents and patent applications referenced in this application are herein incorporated by reference in their entirety into the present disclosure. Citation herein by Applicant of a publication, patent, or patent application is not an admission by Applicant of said publication, patent, or patent application as prior art.

EXAMPLES

Without further elaboration, it is believed that one skilled in the art can, using the preceding description, practice the present invention to its fullest extent. The following detailed examples are to be construed as merely illustrative, and not limitations of the preceding disclosure in any way whatsoever. Those skilled in the art will promptly recognize appropriate variations from the procedures.

Example 1

Pharmacodynamic Analysis of an Effect of Administration of GPR119 Agonist on Blood GIP Level in Wild-Type Mice A. C57blk/6 male mice were fasted for 18 hours, and randomly assigned into fourteen groups with n=6 for each group. Mice were administered per orally with vehicle (PET; 80% PEG400, 10% ethanol, 10% Tween80) or with a GPR119 agonist in accordance with the present invention (Compound 1Z; (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine) at 20 mg/kg, as indicated in FIG. 1A. Thirty minutes after treatment, a glucose bolus at 3 g/kg were delivered per orally, and plasma were collected at 0 (no glucose bolus), 2, 5, 10, 20, 40 and 60 minutes after glucose bolus. Plasma GIP levels were determined by using a rodent GIP ELISA kit purchased from Linco Research Laboratory [Rat/Mouse Gastric Inhibitory Polypeptide (Total) ELISA Catalog #EZRMGIP-55K], following instructions provided by the supplier. From the results shown in FIG. 1A, it is apparent that administration of the GPR119 agonist increased both a glucose-dependent and a glucose-independent level of GIP in the blood of the mice. Compound 1Z stimulated plasma total GIP in the mice. Compound 1Z is identical to a compound disclosed in International Patent Application No. PCT/US2004/001267 (published as WO 2004/065380).

B. C57blk/6 male mice were fasted for 18 hours, and randomly assigned into fourteen groups with n=6 for each group. Mice were administered per orally with vehicle (20% hydroxypropyl-β-cyclodextrin (HPCD)) or with a GPR119 agonist in accordance with the present invention (Compound 3Z) at 10 mg/kg, as indicated in FIG. 1B. Thirty minutes after treatment, a glucose bolus at 3 g/kg were delivered per orally, and plasma were collected at 0 (no glucose bolus), 5, 10, 20, 60 and 120 minutes after glucose bolus. Plasma GIP levels were determined by using a rodent GIP ELISA kit purchased from Linco Research Laboratory [Rat/Mouse Gastric Inhibitory Polypeptide (Total) ELISA Catalog #EZRMGIP-55K], following instructions provided by the supplier. Statistical analysis was performed using Excel program. Mean values of GIP concentration were calculated based on results with six mice in each group and shown as mean±SEM. From the results shown in FIG. 1B, it is apparent that administration of the GPR119 agonist increased both a glucose-dependent and a glucose-independent level of GIP in the blood of the mice. Compound 3Z stimulated plasma total GIP in the mice. Compound 3Z is identical to a compound disclosed in International Patent Application No. PCT/US2004/022327 (published as WO 2005/007647).

C. C57blk/6 male mice were fasted for 18 hours, and randomly assigned into fourteen groups with n=6 for each group. Mice were administered per orally with vehicle (20% hydroxypropyl-β-cyclodextrin (HPCD)) or with a GPR119 agonist in accordance with the present invention (Compound 3Z) at 1, 3, or 10 mg/kg. Thirty minutes after treatment, a glucose bolus at 3 g/kg was delivered per orally, and plasma were collected at 0 (no glucose bolus) or 5 minutes after glucose bolus. Plasma GIP levels were determined by using a rodent GIP ELISA kit purchased from Linco Research Laboratory [Rat/Mouse Gastric Inhibitory Peptide (Total) ELISA Catalog #EZRMGIP-55K], following instructions provided by the supplier. Statistical analysis was performed using Excel program. Mean values of GIP concentration were calculated based on results with six mice in each group and are shown in FIG. 1C. From FIG. 1C, it is apparent that the GPR119 agonist (Compound 3Z) stimulated plasma total GIP in the mice in a dose-dependent manner. Compound 3Z is identical to a compound disclosed in International Patent Application No. PCT/US2004/022327 (published as WO 2005/007647).

Example 2

Figure 2B:
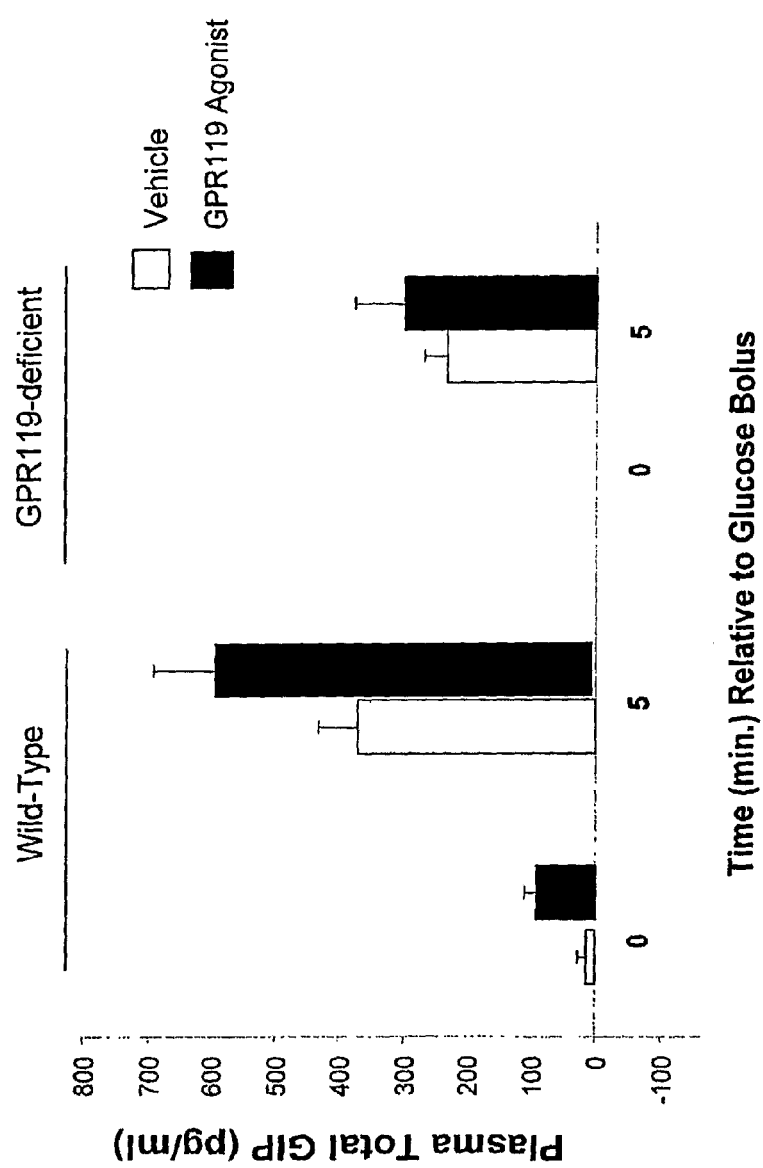
FIG. 2 shows an effect of administration of GPR119 agonist on blood GIP level in GPR119-deficient (knockout) mice compared to wild-type mice. A. The comparison was carried out using Compound 1Z as the GPR119 agonist. B. The comparison was carried out using Compound 2Z as the GPR119 agonist.

Effect of Administration of GPR119 Agonist on Blood GIP Level in GPR119-Deficient (Knockout) Mice Compared to Wild-Type Mice A. GPR119-deficient male mice and wild-type littermates were fasted for 18 hours. Mice were administered per orally with vehicle (PET; 80% PEG400, 10% ethanol, 10% Tween80) or with a GPR119 agonist in accordance with the present invention (Compound 1Z; (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine) at 20 mg/kg, as indicated (n=5). Thirty minutes after treatment, blood (100 microliter) was collected via retro orbital vein of the eye (time 0) followed by a glucose bolus at 3 g/kg (per orally). Five minutes after delivering glucose, another blood sample (100 microliter) was collected (time 5 minutes). Plasma were collected after centrifugation and GIP levels were determined by using a rodent GIP ELISA kit purchased from Linco Research Laboratory [Rat/Mouse Gastric Inhibitory Polypeptide (Total) ELISA Catalog #EZRMGIP-55K], following instructions provided by the supplier. From the results shown in FIG. 2A, it is apparent that functional GPR119 receptor was necessary for the administered GPR119 agonist to increase a glucose-independent level and a glucose-dependent level of GIP in the blood of the mice. Compound 1Z stimulated plasma total GIP in the wild-type mice. Compound 1Z is identical to a compound disclosed in International Patent Application No. PCT/US2004/001267 (published as WO 2004/065380).

B. GPR119-deficient male mice and wild-type littermates were fasted for 18 hours. Mice were administered per orally with vehicle (40% hydroxypropyl-β-cyclodextrin (HPCD)) or with a GPR119 agonist in accordance with the present invention (Compound 2Z) at 30 mg/kg, as indicated (n=5). Thirty minutes after treatment, blood (100 microliter) was collected via retro orbital vein of the eye (time 0) followed by a glucose bolus at 3 g/kg (per orally). Five minutes after delivering glucose, another blood sample (100 microliter) was collected (time 5 minutes). Plasma were collected after centrifugation and GIP levels were determined by using a rodent GIP ELISA kit purchased from Linco Research Laboratory [Rat/Mouse Gastric Inhibitory Polypeptide (Total) ELISA Catalog #EZRMGIP-55K], following instructions provided by the supplier. Mean values of GIP concentration were calculated based on results with five mice in each group. From the results shown in FIG. 2B, it is apparent that functional GPR119 receptor was necessary for the administered GPR119 agonist to increase a glucose-independent level and a glucose-dependent level of GIP in the blood of the mice. Compound 2Z stimulated plasma total GIP in the wild-type mice. Compound 2Z is identical to a compound disclosed in International Patent Application No. PCT/US2004/022417 (published as WO 2005/007658).

Example 3

Effect of Administration of GPR119 Agonist in Combination with DPP-IV Inhibitor on Blood GIP Level in Wild-Type Mice An amount of a GPR119 agonist in combination with an amount of a DPP-IV inhibitor in accordance with the present invention can be shown to increase a level of GIP in the blood of an individual using the in vivo assay described below.

C57blk/6 male mice are fasted for 18 hours, and randomly assigned into fourteen groups with n=6 for each group. Mice are administered per orally with vehicle (PET; 80% PEG400, 10% ethanol, 10% Tween80) or an amount of a GPR119 agonist in combination with an amount of a DPP-IV inhibitor. The experimental groups are analogous to those of Example 1 above. Each of the combined GPR119 agonist and DPP-IV inhibitor is used at an amount between 0.001 mg/kg body weight and 100 mg/kg body weight. Thirty minutes after treatment, a glucose bolus at 3 g/kg is delivered per orally, and plasma is collected at 0 (no glucose bolus), 2, 5, 10, 20, 40 and 60 minutes after glucose bolus. Plasma GIP levels are determined by using a rodent GIP ELISA kit purchased from Linco Research Laboratory [Rat/Mouse Gastric Inhibitory Polypeptide (Total) ELISA Catalog #EZRMGIP-55K], following instructions provided by the supplier.

The assay may in related version include additional experimental groups wherein the mice are injected with the amount of the GPR119 agonist alone and/or additional experimental groups wherein the mice are injected with the amount of the DPP-IV inhibitor alone.

It can be shown that a GPR119 agonist and a DPP-IV inhibitor can be provided in amounts sufficient for the combination to give an effect in increasing a blood GIP level in the individual, wherein the amount of the GPR119 agonist alone and the amount of the DPP-IV inhibitor alone are not therapeutically effective in increasing a blood GIP level in the individual using the foregoing in vivo assay.

It can be shown that a GPR119 agonist and a DPP-IV inhibitor can be provided in amounts sufficient for the combination to give an effect in increasing a blood GIP level in the individual, wherein the effect is a synergistic effect using the foregoing in vivo assay.

It can be shown that a GPR119 agonist and a DPP-IV inhibitor can be provided in amounts sufficient for the combination to give an effect in increasing a blood GIP level in the individual, wherein the effect is a synergistic effect, and wherein the amount of the GPR119 agonist alone and the amount of a DPP-IV inhibitor alone are not therapeutically effective in increasing a blood GIP level in the individual using the foregoing in vivo assay.

It can be shown that a GPR119 agonist and a DPP-IV inhibitor can be provided in amounts sufficient for the combination to give an effect in increasing a blood GIP level in the individual, wherein the effect given by the combination of the GPR119 agonist and the DPP-IV inhibitor is greater than the effect given by the amount of the GPR119 agonist alone and the effect given by the amount of the DPP-IV inhibitor alone using the foregoing in vivo assay.

Example 4

Pharmacodynamic Analysis of an Effect of Administration of GPR119 Agonist in Combination with DPP-IV Inhibitor on Blood GIP Level in Wild-Type Mice An amount of a GPR119 agonist in combination with an amount of a DPP-IV inhibitor in accordance with the present invention was shown to increase a level of GIP in the blood of an individual using the in vivo assay of Example 3, supra.

C57blk/6 male mice were fasted for 18 hours, and randomly assigned into twenty-four groups with n=6 for each group. Mice were administered per orally with vehicle (PET; 80% PEG400, 10% ethanol, 10% Tween80), with a DPP-IV inhibitor in accordance with the present invention (AR247810) alone at 1 mg/kg, or with a combination of a GPR119 agonist ((2-Fluoro-4-methanesulfonyl-phenyl)-{6-[4-(3-isopropyl-[1,2,4]oxadiazol-5-yl]-piperidin-1-yl]-5-nitro-pyrimidin-4-yl}-amine) at 10 mg/kg and the DPP-IV inhibitor (AR247810) at 1 mg/kg in accordance with the present invention, as indicated in FIG. 3. Thirty minutes after treatment, a glucose bolus at 3 g/kg were delivered per orally, and plasma were collected at 0 minute, (no glucose bolus), 5 minutes, 10 minutes, 20 minutes, 40 minutes, 60 minutes, 90 minutes, and 120 minutes after glucose bolus. Plasma total GIP levels were determined by using a rodent GIP ELISA kit purchased from Linco Research Laboratory [Rat/Mouse Gastric Inhibitory Polypeptide (Total) ELISA Catalog #EZRM-GIP-55K], following instructions provided by the supplier.

From the results shown in FIG. 3, it is apparent that administration of the amount of the GPR119 agonist in combination with the amount of the DPP-IV inhibitor in accordance with the present invention consistently gave an effect in increasing a level of GIP in the blood of in the mice greater than the effect given by the amount of the DPP-IV inhibitor alone.

Example 5

Effect of Administration of GPR119 Agonist on Bone Mass in Ovariectomized Rats

A GPR119 agonist in accordance with the present invention can be shown to be effective in treating or preventing a condition characterized by low bone mass, such as osteoporosis, and/or in increasing bone mass in an individual using the in vivo ovariectomized (OVX) rat model described below [see, e.g., Bollag et al, Mol Cell Endocrinol (2001) 177:35-41].

Twenty virgin female OVX and 20 virgin non-OVX Sprague-Dawley rats (150-175 g), age 8 weeks, are purchased from Harlan Sprague-Dawley, Inc. (Indianapolis, Ind.). Animals are fed ad libitum on a normal commercial pellet diet, Teklab Rodent diet (1.46% calcium), with free access to water. The rats are randomly divided into four weight-matched experimental groups and selected to receive per orally vehicle or a GPR119 agonist in accordance with the present invention. Treatment is continued on a daily basis for 6 weeks.

1. Control. Ten non-OVX rats are administered per orally vehicle.
2. Control+Treatment. Ten non-OVX rats are administered per orally GPR119 agonist.
3. OVX. Ten OVX rats are administered per orally vehicle.
4. OVX+Treatment. Ten OVX rats are administered per orally GPR119 agonist.

The rats are weighed daily and length measured at baseline and again at 6 weeks. Dual energy X-ray absorptiometry (DXA) using a Hologic QDR 1000/W (Waltham, Mass.) is performed on all animals prior to initiation of treatment and at 6 weeks, and data is analyzed using the software Rat Whole Body version 5.53. Bone mineral density (BMD) is determined at the spine.

The percent change in vertebral bone density after 6 weeks of treatment is determined. It is shown that administration of a GPR119 agonist attenuates the negative effects of ovariectomy on vertebral bone density. Attenuation of the negative effects of ovariectomy on vertebral bone density is indicative of the treatment having efficacy in treating or preventing a condition characterized by low bone mass, such as osteoporosis, and/or in increasing bone mass in an individual.

Example 6

Effect of Administration of GPR119 Agonist in Combination with DPP-IV Inhibitor on Bone Mass in Ovariectomized Rats A GPR119 agonist in combination with a DPP-IV inhibitor in accordance with the present invention can be shown to be effective in treating or preventing a condition characterized by low bone mass, such as osteoporosis, and/or in increasing bone mass in an individual using the in vivo ovariectomized (OVX) rat model described below [see, e.g., Bollag et al, Mol Cell Endocrinol (2001) 177:35-41].

Twenty virgin female OVX and 20 virgin non-OVX Sprague-Dawley rats (150-175 g), age 8 weeks, are purchased from Harlan Sprague-Dawley, Inc. (Indianapolis, Ind.). Animals are fed ad libitum on a normal commercial pellet diet, Teklab Rodent diet (1.46% calcium), with free access to water. The rats are randomly divided into four weight-matched experimental groups and selected to receive per orally vehicle or a GPR119 agonist in combination with a DPP-IV inhibitor in accordance with the present invention. Treatment is continued on a daily basis for 6 weeks.

1. Control. Ten non-OVX rats are administered per orally vehicle.
2. Control+Treatment. Ten non-OVX rats are administered per orally GPR119 agonist in combination with DPP-IV inhibitor.

3. OVX. Ten OVX rats are administered per orally vehicle.
4. OVX+Treatment. Ten OVX rats are administered per orally GPR119 agonist in combination with DPP-IV inhibitor.

The rats are weighed daily and length measured at baseline and again at 6 weeks. Dual energy X-ray absorptiometry (DXA) using a Hologic QDR 1000/W (Waltham, Mass.) is performed on all animals prior to initiation of treatment and at 6 weeks, and data is analyzed using the software Rat Whole Body version 5.53.

The percent change in vertebral bone density after 6 weeks of treatment is determined. It is shown that administration of a GPR119 agonist attenuates the negative effects of ovariectomy on vertebral bone density. Attenuation of the negative effects of ovariectomy on vertebral bone density is indicative of the treatment having efficacy in treating or preventing a condition characterized by low bone mass, such as osteoporosis, and/or in increasing bone mass in an individual.

The assay may in related version include additional experimental groups wherein the mice are injected with the amount of the GPR119 agonist alone and/or additional experimental groups wherein the mice are injected with the amount of the DPP-IV inhibitor alone.

It can be shown that a GPR119 agonist and a DPP-IV inhibitor can be provided in amounts sufficient for the combination to give an effect in attenuating the negative effects of ovariectomy on vertebral bone density, wherein the amount of the GPR119 agonist alone and the amount of the DPP-IV inhibitor alone are not therapeutically effective in attenuating the negative effects of ovariectomy on vertebral bone density using the in vivo assay described above.

It can be shown that a GPR119 agonist and a DPP-IV inhibitor can be provided in amounts sufficient for the combination to give an effect in attenuating the negative effects of ovariectomy on vertebral bone density, wherein the effect is a synergistic effect using the in vivo assay described above.

It can be shown that a GPR119 agonist and a DPP-IV inhibitor can be provided in amounts sufficient for the combination to give an effect in attenuating the negative effects of ovariectomy on vertebral bone density, wherein the effect is a synergistic effect, and wherein the amount of the GPR119 agonist alone and the amount of a DPP-IV inhibitor alone are not therapeutically effective in attenuating the negative effects of ovariectomy on vertebral bone density using the in vivo assay described above.

It can be shown that a GPR119 agonist and a DPP-IV inhibitor can be provided in amounts sufficient for the combination to give an effect in attenuating the negative effects of ovariectomy on vertebral bone density, wherein the effect given by the combination of the GPR119 agonist and the DPP-IV inhibitor is greater than the effect given by the amount of the GPR119 agonist alone and the effect given by the amount of the DPP-IV inhibitor alone using the in vivo assay described above.

Example 7

Effect of Administration of GPR119 Agonist on Bone Fracture Healing

A GPR119 agonist in accordance with the present invention can be shown to be effective in treatment of bone fracture using the in vivo assay described below.

Fracture Technique

Sprague-Dawley rats at 3 months of age are anesthetized with Ketamine. A 1 cm incision is made on the anteromedial aspect of the proximal part of the right tibia or femur. The following describes the tibial surgical technique. The incision is carried through to the bone, and a 1 mm hole is drilled 4 mm proximal to the distal aspect of the tibial tuberosity 2 mm medial to the anterior ridge. Intramedullary nailing is performed with a 0.8 mm stainless steel tube (maximum load 36.3 N, maximum stiffness 61.8 N/mm, tested under the same conditions as the bones). No reaming of the medullary canal is performed. A standardized closed fracture is produced 2 mm above the tibiofibular junction by three-point bending using specially designed adjustable forceps with blunt jaws. To minimize soft tissue damage, care is taken not to displace the fracture. The skin is closed with monofilament nylon sutures. The operation is performed under sterile conditions. Radiographs of all fractures are taken immediately after nailing, and rats with fractures outside the specified diaphyseal area or with displaced nails are excluded. The remaining animals are divided randomly into the following groups with 10-12 animals per each subgroup per time point for testing the fracture healing. The rats are administered on a daily basis per orally with vehicle or with a GPR119 agonist. The GPR119 agonist is used at an amount between 0.001 mg/kg body weight and 100 mg/kg body weight. Treatment is continued for 10, 20, 40 and 80 days.

At 10, 20, 40 and 80 days, 10-12 rats from each group are anesthetized with Ketamine and sacrificed by exsanguination. Both tibiofibular bones are removed by dissection and all soft tissue is stripped. Bones from 5-6 rats for each group are stored in 70% ethanol for histological analysis, and bones from another 5-6 rats for each group are stored in a buffered Ringer's solution (+4° C., pH 7.4) for radiographs and biomechanical testing which is performed.

Histological Analysis

The methods for histological analysis of fractured bone have been previously published by Mosekilde and Bak [Bone (1993) 14:19-27]. Briefly, the fracture site is sawed 8 mm to each side of the fracture line, embedded undecalcified in methymethacrylate, and cut frontals sections on a Reichert-Jung Polycut microtome in 8 µm thick. Masson-Trichome stained mid-frontal sections (including both tibia and fibula) are used for visualization of the cellular and tissue response to fracture healing with and without treatment. Sirius red stained sections are used to demonstrate the characteristics of the callus structure and to differentiate between woven bone and lamellar bone at the fracture site. The following measurements are performed: (1) fracture gap—measured as the shortest distance between the cortical bone ends in the fracture, (2) callus length and callus diameter, (3) total bone volume area of callus, (4) bony tissue per tissue area inside the callus area, (5) fibrous tissue in the callus, and (6) cartilage area in the callus.

Biomechanical Analysis

The methods for biomechanical analysis have been previously published by Bak and Andreassen [Calcif Tissue Int (1989) 45:292-297]. Briefly, radiographs of all fractures are taken prior to the biomechanical test. The mechanical properties of the healing fractures are analyzed by a destructive three- or four-point bending procedure. Maximum load, stiffness, energy at maximum load, deflection at maximum load, and maximum stress are determined.

Example 8

Effect of Administration of GPR119 Agonist in Combination with DPP-IV Inhibitor on Bone Fracture Healing A GPR119 agonist in combination with a DPP-IV inhibitor in accordance with the present invention can be shown to be effective in treatment of bone fracture using the in vivo assay described below.

It can be shown that a GPR119 agonist and a DPP-IV inhibitor can be provided in amounts sufficient for the combination to give an effect in treating bone fracture in the individual, wherein the amount of the GPR119 agonist alone and the amount of the DPP-IV inhibitor alone are not therapeutically effective in treating bone fracture in the individual using the in vivo assay described below.

It can be shown that a GPR119 agonist and a DPP-IV inhibitor can be provided in amounts sufficient for the combination to give an effect in treating bone fracture in the individual, wherein the effect is a synergistic effect using the in vivo assay described below.

It can be shown that a GPR119 agonist and a DPP-IV inhibitor can be provided in amounts sufficient for the combination to give an effect in treating bone fracture in the individual, wherein the effect is a synergistic effect, and wherein the amount of the GPR119 agonist alone and the amount of a DPP-IV inhibitor alone are not therapeutically effective in treating bone fracture in the individual using the in vivo assay described below.

It can be shown that a GPR119 agonist and a DPP-IV inhibitor can be provided in amounts sufficient for the combination to give an effect in treating bone fracture in the individual, wherein the effect given by the combination of the GPR119 agonist and the DPP-IV inhibitor is greater than the effect given by the amount of the GPR119 agonist alone and the effect given by the amount of the DPP-IV inhibitor alone using the in vivo assay described below.

Fracture Technique

Sprague-Dawley rats at 3 months of age are anesthetized with Ketamine. A 1 cm incision is made on the anteromedial aspect of the proximal part of the right tibia or femur. The following describes the tibial surgical technique. The incision is carried through to the bone, and a 1 mm hole is drilled 4 mm proximal to the distal aspect of the tibial tuberosity 2 mm medial to the anterior ridge. Intramedullary nailing is performed with a 0.8 mm stainless steel tube (maximum load 36.3 N, maximum stiffness 61.8 N/mm, tested under the same conditions as the bones). No reaming of the medullary canal is performed. A standardized closed fracture is produced 2 mm above the tibiofibular junction by three-point bending using specially designed adjustable forceps with blunt jaws. To minimize soft tissue damage, care is taken not to displace the fracture. The skin is closed with monofilament nylon sutures. The operation is performed under sterile conditions. Radiographs of all fractures are taken immediately after nailing, and rats with fractures outside the specified diaphyseal area or with displaced nails are excluded. The remaining animals are divided randomly into the following groups with 10-12 animals per each subgroup per time point for testing the fracture healing. The rats are administered on a daily basis per orally with vehicle or with a GPR119 agonist in combination with a DPP-IV inhibitor. Each of the combined GPR119 agonist and DPP-IV inhibitor is used at an amount between 0.001 mg/kg body weight and 100 mg/kg body weight. Thirty minutes later, a glucose bolus at 3 g/kg is delivered per orally. Treatment is continued for 10, 20, 40 and 80 days.

At 10, 20, 40 and 80 days, 10-12 rats from each group are anesthetized with Ketamine and sacrificed by exsanguination. Both tibiofibular bones are removed by dissection and all soft tissue is stripped. Bones from 5-6 rats for each group are stored in 70% ethanol for histological analysis, and bones from another 5-6 rats for each group are stored in a buffered Ringer's solution (+4° C., pH 7.4) for radiographs and biomechanical testing which is performed.

Histological Analysis

The methods for histological analysis of fractured bone have been previously published by Mosekilde and Bak [Bone (1993) 14:19-27]. Briefly, the fracture site is sawed 8 mm to each side of the fracture line, embedded undecalcified in methymethacrylate, and cut frontals sections on a Reichert-Jung Polycut microtome in 8 μm thick. Masson-Trichome stained mid-frontal sections (including both tibia and fibula) are used for visualization of the cellular and tissue response to fracture healing with and without treatment. Sirius red stained sections are used to demonstrate the characteristics of the callus structure and to differentiate between woven bone and lamellar bone at the fracture site. The following measurements are performed: (1) fracture gap—measured as the shortest distance between the cortical bone ends in the fracture, (2) callus length and callus diameter, (3) total bone volume area of callus, (4) bony tissue per tissue area inside the callus area, (5) fibrous tissue in the callus, and (6) cartilage area in the callus.

Biomechanical Analysis

The methods for biomechanical analysis have been previously published by Bak and Andreassen [Calcif Tissue Int (1989) 45:292-297]. Briefly, radiographs of all fractures are taken prior to the biomechanical test. The mechanical properties of the healing fractures are analyzed by a destructive three- or four-point bending procedure. Maximum load, stiffness, energy at maximum load, deflection at maximum load, and maximum stress are determined.

Example 9

Melanophore Assay for GPR119 Agonist Activity

Melanophores are maintained in culture as reported by Potenza et al [Pigment Cell Research (1992) 5:372-378] and transfected with an expression vector encoding a GPR119 receptor (e.g., human GPR119, GenBank® Accession No. AAP72125 and alleles thereof) using electroporation. Following electroporation, the transfected cells are plated into 96 well plates for the assay. The cells are then allowed to grow for 48 hours in order to both recover from the electroporation procedure and attain maximal receptor expression levels.

On the assay day, the growth medium on the cells is replaced with serum-free buffer containing 10 nM melatonin. The melatonin acts via an endogenous Gi-coupled GPCR in the melanophores to lower intracellular cAMP levels. In response to lowered cAMP levels, the melanophores translocate their pigment to the center of the cell. The net effect of this is a significant decrease in the absorbance reading of the cell monolayer in the well, measured at 600-650 nM.

After a 1-hour incubation in melatonin, the cells become completely pigment-aggregated. At this point a baseline absorbance reading is collected. Serial dilutions of test compounds are then added to the plate, and compounds having GPR119 agonist activity produce increases in intracellular cAMP levels. In response to these increased cAMP levels, the melanophores translocate their pigment back into the cell periphery. After one hour, stimulated cells are fully pigment-dispersed. The cell monolayer in the dispersed state absorbs much more light in the 600-650 nm range. The measured increase in absorbance compared to the baseline reading allows one to quantitate the degree of receptor stimulation and plot a dose-response curve.

Materials and methods relating to melanophore assay are found in U.S. Pat. Nos. 5,462,856 and 6,051,386, the disclosure of each of which is herein incorporated by reference in its entirety.

Example 10

In Vitro Assay for Inhibition of DPP-IV Activity

Compounds can be evaluated for inhibition of DPP-IV activity using, e.g., the in vitro fluorescent assay described by Leiting et at (Biochem J (2003) 371:525-532). In this assay, DPP-IV is assayed continuously in 100 mM Hepes buffer (pH 7.5) and 0.1 mg/ml of BSA in a total volume of 100 μl for 30 min at 37° C., and read using a Spectramax Gemini plate reader (Molecular Devices, Sunnyvale, Calif.). The fluorogenic peptide Gly-Pro-AMC (where AMC stands for 7-amino-4-methylcoumarin; obtained from Bachem, Torrance, Calif.) is used as DPP-IV substrate. $IC_{50}$ values for compounds being evaluated are obtained at 50 μM Gly-Pro-AMC, the $K_m$ level of Gly-Pro-AMC concentration.

The protease inhibitory activities of DPP-IV inhibitors can be readily determined by methods known to those of ordinary skill in the art since suitable in vitro assays for measuring protease activity and the inhibition thereof by test compounds are known.

In other exemplary in vitro assay for DPP-IV inhibition, solutions of test compounds in varying concentrations (≦10 mM final concentration) are prepared in Dimethyl Sulfoxide (DMSO) and then diluted into assay buffer comprising: 20 mM Tris, pH 7.4; 20 mM KCl; and 0.1 mg/mL BSA. Human DPP-IV (0.1 nM final concentration) is added to the dilutions and pre-incubated for 10 minutes at ambient temperature before the reaction is initiated with A-P-7-amido-4-trifluoromethylcoumarin (AP-AFC; 10 μM final concentration). The total volume of the reaction mixture is 10-100 μL depending on assay formats used (384 or 96 well plates). The reaction is followed kinetically (excitation λ=400 nm; emission λ=505 nm) for 5-10 minutes or an end-point is measured after 10 minutes. Inhibition constants ($IC_{50}$) are calculated from the enzyme progress curves using standard mathematical models.

Compounds can also be evaluated for inhibition of DPP-IV activity for a fee by a company that provides the service. By way of example, $IC_{50}$ values for DPP-IV inhibition can be obtained for such compounds through MDS Pharma Services (Catalog #163910; King of Prussia, Pa.) in in vitro assay using recombinant human DPP-IV.

DPP-IV can be human DPP-IV. DPP-IV can be recombinant human DPP-IV.

Example 11

Whole Cell Adenylyl Cyclase Assay for GPR119 Agonist Activity

Cyclic AMP measurements are done with a Flash Plate™ Adenylyl Cyclase kit (New England Nuclear) according to the supplier's protocol. HEK293 cells are plated in 15-cm tissue culture dish at $12 \times 10^6$ cells per dish in regular growth medium (DMEM/10% FBS). On the next day, 10 μg of either empty vector DNA or expression plasmid DNA are transfected into cells with lipofectamine (Invitrogen, Carlsbad, Calif.) according to manufacturer's protocol. After 24 hours in culture, transfected cells are harvested in GIBCO cell dissociation buffer (Cat #13151-014), pelleted by centrifugation for 5 minutes at 1,100 rpm, and carefully re-suspended into an appropriate volume of Assay Buffer (50% 1×PBS and 50% Stimulation Buffer) to give a final cell count at $2 \times 10^6$ cells/ml. Test compounds are prepared in 50 μl Assay Buffer at desired assay concentration where indicated, and pipetted into wells of the 96-well Flash Plate. The cell suspension prepared above was then added (50 μl per well). After an incubation time of 60 minutes at room temperature, 100 μl of Detection Mix containing tracer [$^{125}$I]-cAMP is then added to the wells. Plates are incubated for additional 2 hours followed by counting in a Wallac MicroBeta scintillation counter. Values of cAMP/well are extrapolated from a standard cAMP curve which is included on each assay plate.

An increase in cAMP level in GPR119-transfected HEK293 cells over that in HEK293 cells transfected with empty vector is indicative of a test compound being a compound that stimulates GPR119 receptor functionality.

While the foregoing specification teaches the principles of the present invention, with examples provided for the purpose of illustration, it will be understood that the practice of the invention encompasses all of the usual variations, adaptions, or modifications, as come within the scope of the following claims and its equivalents.

What is claimed is:

1. A method of treating a condition selected from the group consisting of primary osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height, comprising administering to an individual in need thereof a therapeutically effective amount of a GPR119 agonist.

2. A method of treating a condition selected from the group consisting of primary osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height, comprising administering to an individual in need thereof a therapeutically effective amount of a pharmaceutical composition comprising a GPR119 agonist and a pharmaceutically acceptable carrier.

3. A method of treating bone fracture comprising administering to an individual in need thereof a therapeutically effective amount of a GPR119 agonist.

4. A method of treating bone fracture comprising administering to an individual in need thereof a therapeutically effective amount of a pharmaceutical composition comprising a GPR119 agonist and a pharmaceutically acceptable carrier.

5. The method of claim 3, wherein the individual has a traumatic bone fracture, a long-term bone fracture, or an osteoporotic bone fracture.

6. A method of enhancing bone healing following facial reconstruction, maxillary reconstruction, mandibular reconstruction, periodontal disease or tooth extraction, enhanced long bone extension, enhanced prosthetic ingrowth or increased bone synostosis comprising administering to an individual in need thereof a therapeutically effective amount of a GPR119 agonist.

7. A method of enhancing bone healing following facial reconstruction, maxillary reconstruction, mandibular reconstruction, periodontal disease or tooth extraction, enhanced long bone extension, enhanced prosthetic ingrowth or increased bone synostosis comprising administering to an individual in need thereof a therapeutically effective amount of a pharmaceutical composition comprising a GPR119 agonist and a pharmaceutically acceptable carrier.

8. The method of claim 1, wherein the GPR119 agonist is administered in an amount sufficient to increase a GIP level in the individual.

9. The method of claim 1, wherein the individual is a human.

10. The method of claim 1, wherein the GPR119 agonist is an agonist of human GPR119.

11. The method of claim 1, wherein the GPR119 agonist is a small molecule.

12. The method of claim 1, wherein the GPR119 agonist has an $EC_{50}$ of less than about 10 μM.

13. A method of treating a condition characterized by low bone mass comprising administering to an individual in need thereof a therapeutically effective amount of a GPR119 agonist and a DPP-IV inhibitor.

14. A method of treating a condition characterized by low bone mass comprising administering to an individual in need thereof a therapeutically effective amount of a pharmaceutical composition comprising a GPR119 agonist and a DPP-IV inhibitor and a pharmaceutically acceptable carrier.

15. The method of claim 13, wherein the condition characterized by low bone mass is selected from the group consisting of osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height.

16. A method of increasing bone mass comprising administering to an individual in need thereof a therapeutically effective amount of a GPR119 agonist and a DPP-IV inhibitor.

17. A method of increasing bone mass comprising administering to an individual in need thereof a therapeutically effective amount of a pharmaceutical composition comprising a GPR119 agonist and a DPP-IV inhibitor and a pharmaceutically acceptable carrier.

18. The method of claim 16, wherein the individual has a bone mineral density (BMD) greater than 1 standard deviations (T-score<−1) below the young adult reference mean.

19. A method of treating bone fracture comprising administering to an individual in need thereof a therapeutically effective amount of a GPR119 agonist and a DPP-IV inhibitor.

20. A method of treating bone fracture comprising administering to an individual in need thereof a therapeutically effective amount of a pharmaceutical composition comprising a GPR119 agonist and a DPP-IV inhibitor and a pharmaceutically acceptable carrier.

21. The method of claim 19, wherein the individual has a traumatic bone fracture, a long-term bone fracture, or an osteoporotic bone fracture.

22. A method of treating a bone disease comprising administering to an individual in need thereof a therapeutically effective amount of a GPR119 agonist and a DPP-IV inhibitor.

23. A method of treating a bone disease comprising administering to an individual in need thereof a therapeutically effective amount of a pharmaceutical composition comprising a GPR119 agonist and a DPP-IV inhibitor and a pharmaceutically acceptable carrier.

24. The method of claim 22, wherein the bone disease is selected from the group consisting of osteopenia, osteoporosis, rheumatoid arthritis, osteoarthritis, periodontal disease, alveolar bone loss, osteotomy bone loss, childhood idiopathic bone loss, Paget's disease, bone loss due to metastatic cancer, osteolytic lesions, curvature of the spine, and loss of height.

25. A method of enhancing bone healing following facial reconstruction, maxillary reconstruction, mandibular reconstruction, periodontal disease or tooth extraction, enhanced long bone extension, enhanced prosthetic ingrowth or increased bone synostosis comprising administering to an individual in need thereof a therapeutically effective amount of a GPR119 agonist and a DPP-IV inhibitor.

26. A method of enhancing bone healing following facial reconstruction, maxillary reconstruction, mandibular reconstruction, periodontal disease or tooth extraction, enhanced long bone extension, enhanced prosthetic ingrowth or increased bone synostosis comprising administering to an individual in need thereof a therapeutically effective amount of a pharmaceutical composition comprising a GPR119 agonist and a DPP-IV inhibitor and a pharmaceutically acceptable carrier.

27. The method of claim 13, wherein the GPR119 agonist and the DPP-IV inhibitor are administered in amounts sufficient to increase a GIP level in the individual.

28. The method of claim 13, wherein the individual is a human.

29. The method of claim 13, wherein the GPR119 agonist is an agonist of human GPR119 and/or the DPP-IV inhibitor is an inhibitor of human DPP-IV.

30. The method of claim 13, wherein the GPR119 agonist is a small molecule and/or the DPP-IV inhibitor is a small molecule.

31. The method of claim 13, wherein the GPR119 agonist has an $EC_{50}$ of less than about 10 μM and/or the DPP-IV inhibitor has an $IC_{50}$ of less than about 10 μM.

32. The method of claim 1, wherein the condition is primary osteoporosis.

33. The method of claim 1, wherein the condition is rheumatoid arthritis.

34. The method of claim 1, wherein the condition is osteoarthritis.

35. The method of claim 1, wherein the condition is bone loss due to metastatic cancer.

36. The method of claim 1, wherein the GPR119 agonist is a selective GPR119 agonist.

37. The method of claim 1, wherein the GPR119 agonist has a selectivity for GPR119 over corticotrophin releasing factor-1 (CRF-1) receptor of at least about 100-fold.

38. The method of claim 1, wherein the GPR119 agonist has an EC50 of less than about 1 μM.

39. The method of claim 1, wherein the GPR119 agonist has an EC50 of less than about 100 nM.

40. The method of claim 1, wherein the GPR119 agonist is orally active.

41. The method of claim 1, wherein the GPR119 agonist is orally active and has an EC50 of less than about 100 nM.

42. The method of claim 3, wherein the GPR119 agonist is administered in an amount sufficient to increase a GIP level in the individual.

43. The method of claim 3, wherein the individual is a human.

44. The method of claim 3, wherein the GPR119 agonist is an agonist of human GPR119.

45. The method of claim 3, wherein the GPR119 agonist is a small molecule.

46. The method of claim 3, wherein the GPR119 agonist has an $EC_{50}$ of less than about 10 μM.

47. The method of claim 3, wherein the GPR119 agonist is a selective GPR119 agonist.

48. The method of claim 3, wherein the GPR119 agonist has a selectivity for GPR119 over corticotrophin releasing factor-1 (CRF-1) receptor of at least about 100-fold.

49. The method of claim 3, wherein the GPR119 agonist has an EC50 of less than about 1 μM.

50. The method of claim 3, wherein the GPR119 agonist has an EC50 of less than about 100 nM.

51. The method of claim 3, wherein the GPR119 agonist is orally active.

52. The method of claim 3, wherein the GPR119 agonist is orally active and has an EC50 of less than about 100 nM.

53. The method of claim 6, wherein the GPR119 agonist is administered in an amount sufficient to increase a GIP level in the individual.

54. The method of claim 6, wherein the individual is a human.

55. The method of claim 6, wherein the GPR119 agonist is an agonist of human GPR119.

56. The method of claim 6, wherein the GPR119 agonist is a small molecule.

57. The method of claim 6, wherein the GPR119 agonist has an $EC_{50}$ of less than about 10 μM.

58. The method of claim 6, wherein the GPR119 agonist is a selective GPR119 agonist.

59. The method of claim 6, wherein the GPR119 agonist has a selectivity for GPR119 over corticotrophin releasing factor-1 (CRF-1) receptor of at least about 100-fold.

60. The method of claim 6, wherein the GPR119 agonist has an EC50 of less than about 1 μM.

61. The method of claim 6, wherein the GPR119 agonist has an EC50 of less than about 100 nM.

62. The method of claim 6, wherein the GPR119 agonist is orally active.

63. The method of claim 6, wherein the GPR119 agonist is orally active and has an EC50 of less than about 100 nM.

64. The method of claim 13, wherein the GPR119 agonist is a selective GPR119 agonist.

65. The method of claim 13, wherein the GPR119 agonist has a selectivity for GPR119 over corticotrophin releasing factor-1 (CRF-1) receptor of at least about 100-fold.

66. The method of claim 13, wherein the GPR119 agonist has an EC50 of less than about 1 μM.

67. The method of claim 13, wherein the GPR119 agonist has an EC50 of less than about 100 nM.

68. The method of claim 13, wherein the GPR119 agonist is orally active.

69. The method of claim 13, wherein the GPR119 agonist is orally active and has an EC50 of less than about 100 nM.

70. The method of claim 13, wherein the DPP-IV inhibitor is a selective DPP-IV inhibitor.

71. The method of claim 13, wherein the DPP-IV inhibitor is orally active.

72. The method of claim 13, wherein the DPP-IV inhibitor has an IC50 of less than about 10 μM.

73. The method of claim 13, wherein the DPP-IV inhibitor has an IC50 of less than about 1 μM.

74. The method of claim 13, wherein the DPP-IV inhibitor has an IC50 of less than about 100 nM.

75. The method of claim 13, wherein the DPP-IV inhibitor is orally active and has an IC50 of less than about 100 nM.

76. The method of claim 13, wherein the DPP-IV inhibitor is an inhibitor of human DPP-IV.

77. The method of claim 13, wherein the GPR119 agonist is orally active and has an EC50 of less than about 100 nM, and the DPP-IV inhibitor is orally active and has an IC50 of less than about 100 nM.

78. The method of claim 13, wherein the GPR119 agonist has a selectivity for GPR119 over corticotrophin releasing factor-1 (CRF-1) receptor of at least about 100-fold, and the DPP-IV inhibitor has a selectivity for human plasma DPP-IV over one or more of PPCE, DPP-II, DPP-8 and DPP-9 of at least 100-fold.

79. The method of claim 13, wherein the DPP-IV inhibitor is:

MK-0431: 3(R)-Amino-1-[3-(trifluoromethyl)-5,6,7,8-tetrahydro[1,2,4]triazolo[4,3-a]pyrazin-7-yl]-4-(2,4,5-trifluorophenyl)butan-1-one;

LAF237: (1-[[3-hydroxy-1-adamantyl)amino]acetyl]-2-cyano-(S)-pyrrolidine; or

BMS-477118: (1S,3S,5S)-2-[2(S)-Amino-2-(3-hydroxy-adamantan-1-yl)acetyl]-2 azabicyclo[3.1.0]hexane-3-carbonitrile.

80. The method of claim 15, wherein the condition is osteoporosis.

81. The method of claim 15, wherein the condition is rheumatoid arthritis.

82. The method of claim 15, wherein the condition is osteoarthritis.

83. The method of claim 15, wherein the condition is bone loss due to metastatic cancer.

84. The method of claim 16, wherein the GPR119 agonist is a selective GPR119 agonist.

85. The method of claim 16, wherein the GPR119 agonist has a selectivity for GPR119 over corticotrophin releasing factor-1 (CRF-1) receptor of at least about 100-fold.

86. The method of claim 16, wherein the GPR119 agonist has an EC50 of less than about 1 μM.

87. The method of claim 16, wherein the GPR119 agonist has an EC50 of less than about 100 nM.

88. The method of claim 16, wherein the GPR119 agonist is orally active.

89. The method of claim 16, wherein the GPR119 agonist is orally active and has an EC50 of less than about 100 nM.

90. The method of claim 16, wherein the GPR119 agonist and the DPP-IV inhibitor are administered in amounts sufficient to increase a GIP level in the individual.

91. The method of claim 16, wherein the individual is a human.

92. The method of claim 16, wherein the GPR119 agonist is an agonist of human GPR119 and/or the DPP-IV inhibitor is an inhibitor of human DPP-IV.

93. The method of claim 16, wherein the GPR119 agonist is a small molecule and/or the DPP-IV inhibitor is a small molecule.

94. The method of claim 16, wherein the GPR119 agonist has an $EC_{50}$ of less than about 10 μM and/or the DPP-IV inhibitor has an $IC_{50}$ of less than about 10 μM.

95. The method of claim 16, wherein the DPP-IV inhibitor is a selective DPP-IV inhibitor.

96. The method of claim 16, wherein the DPP-IV inhibitor is orally active.

97. The method of claim 16, wherein the DPP-IV inhibitor has an IC50 of less than about 10 μM.

98. The method of claim 16, wherein the DPP-IV inhibitor has an IC50 of less than about 1 μM.

99. The method of claim 16, wherein the DPP-IV inhibitor has an IC50 of less than about 100 nM.

100. The method of claim 16, wherein the DPP-IV inhibitor is orally active and has an IC50 of less than about 100 nM.

101. The method of claim 16, wherein the DPP-IV inhibitor is an inhibitor of human DPP-IV.

102. The method of claim 16, wherein the GPR119 agonist is orally active and has an EC50 of less than about 100 nM, and the DPP-IV inhibitor is orally active and has an IC50 of less than about 100 nM.

103. The method of claim 16, wherein the GPR119 agonist has a selectivity for GPR119 over corticotrophin releasing factor-1 (CRF-1) receptor of at least about 100-fold, and the DPP-IV inhibitor has a selectivity for human plasma DPP-IV over one or more of PPCE, DPP-II, DPP-8 and DPP-9 of at least 100-fold.

104. The method of claim 16, wherein the DPP-IV inhibitor is:
MK-0431: 3(R)-Amino-1-[3-(trifluoromethyl)-5,6,7,8-tetrahydro[1,2,4]triazolo[4,3-a]pyrazin-7-yl]-4-(2,4,5-trifluorophenyl)butan-1-one;
LAF237: (1-[[3-hydroxy-1-adamantyl)amino]acetyl]-2-cyano-(S)-pyrrolidine; or
BMS-477118: (1S,3S,5S)-2-[2(S)-Amino-2-(3-hydroxy-adamantan-1-yl)acetyl]-2 azabicyclo[3.1.0]hexane-3-carbonitrile.

105. The method of claim 19, wherein the GPR119 agonist is a selective GPR119 agonist.

106. The method of claim 19, wherein the GPR119 agonist has a selectivity for GPR119 over corticotrophin releasing factor-1 (CRF-1) receptor of at least about 100-fold.

107. The method of claim 19, wherein the GPR119 agonist has an EC50 of less than about 1 µM.

108. The method of claim 19, wherein the GPR119 agonist has an EC50 of less than about 100 nM.

109. The method of claim 19, wherein the GPR119 agonist is orally active.

110. The method of claim 19, wherein the GPR119 agonist is orally active and has an EC50 of less than about 100 nM.

111. The method of claim 19, wherein the GPR119 agonist and the DPP-IV inhibitor are administered in amounts sufficient to increase a GIP level in the individual.

112. The method of claim 19, wherein the individual is a human.

113. The method of claim 19, wherein the GPR119 agonist is an agonist of human GPR119 and/or the DPP-IV inhibitor is an inhibitor of human DPP-IV.

114. The method of claim 19, wherein the GPR119 agonist is a small molecule and/or the DPP-IV inhibitor is a small molecule.

115. The method of claim 19, wherein the GPR119 agonist has an $EC_{50}$ of less than about 10 µM and/or the DPP-IV inhibitor has an $IC_{50}$ of less than about 10 µM.

116. The method of claim 19, wherein the DPP-IV inhibitor is a selective DPP-IV inhibitor.

117. The method of claim 19, wherein the DPP-IV inhibitor is orally active.

118. The method of claim 19, wherein the DPP-IV inhibitor has an IC50 of less than about 10 µM.

119. The method of claim 19, wherein the DPP-IV inhibitor has an IC50 of less than about 1 µM.

120. The method of claim 19, wherein the DPP-IV inhibitor has an IC50 of less than about 100 nM.

121. The method of claim 19, wherein the DPP-IV inhibitor is orally active and has an IC50 of less than about 100 nM.

122. The method of claim 19, wherein the DPP-IV inhibitor is an inhibitor of human DPP-IV.

123. The method of claim 19, wherein the GPR119 agonist is orally active and has an EC50 of less than about 100 nM, and the DPP-IV inhibitor is orally active and has an IC50 of less than about 100 nM.

124. The method of claim 19, wherein the GPR119 agonist has a selectivity for GPR119 over corticotrophin releasing factor-1 (CRF-1) receptor of at least about 100-fold, and the DPP-IV inhibitor has a selectivity for human plasma DPP-IV over one or more of PPCE, DPP-II, DPP-8 and DPP-9 of at least 100-fold.

125. The method of claim 19, wherein the DPP-IV inhibitor is:
MK-0431: 3(R)-Amino-1-[3-(trifluoromethyl)-5,6,7,8-tetrahydro[1,2,4]triazolo[4,3-a]pyrazin-7-yl]-4-(2,4,5-trifluorophenyl)butan-1-one;
LAF237: (1-[[3-hydroxy-1-adamantyl)amino]acetyl]-2-cyano-(S)-pyrrolidine; or
BMS-477118: (1S,3S,5S)-2-[2(S)-Amino-2-(3-hydroxy-adamantan-1-yl)acetyl]-2 azabicyclo[3.1.0]hexane-3-carbonitrile.

126. The method of claim 22, wherein the GPR119 agonist is a selective GPR119 agonist.

127. The method of claim 22, wherein the GPR119 agonist has a selectivity for GPR119 over corticotrophin releasing factor-1 (CRF-1) receptor of at least about 100-fold.

128. The method of claim 22, wherein the GPR119 agonist has an EC50 of less than about 1 µM.

129. The method of claim 22, wherein the GPR119 agonist has an EC50 of less than about 100 nM.

130. The method of claim 22, wherein the GPR119 agonist is orally active.

131. The method of claim 22, wherein the GPR119 agonist is orally active and has an EC50 of less than about 100 nM.

132. The method of claim 22, wherein the GPR119 agonist and the DPP-IV inhibitor are administered in amounts sufficient to increase a GIP level in the individual.

133. The method of claim 22, wherein the individual is a human.

134. The method of claim 22, wherein the GPR119 agonist is an agonist of human GPR119 and/or the DPP-IV inhibitor is an inhibitor of human DPP-IV.

135. The method of claim 22, wherein the GPR119 agonist is a small molecule and/or the DPP-IV inhibitor is a small molecule.

136. The method of claim 22, wherein the GPR119 agonist has an $EC_{50}$ of less than about 10 µM and/or the DPP-IV inhibitor has an $IC_{50}$ of less than about 10 µM.

137. The method of claim 22, wherein the DPP-IV inhibitor is a selective DPP-IV inhibitor.

138. The method of claim 22, wherein the DPP-IV inhibitor is orally active.

139. The method of claim 22, wherein the DPP-IV inhibitor has an IC50 of less than about 10 µM.

140. The method of claim 22, wherein the DPP-IV inhibitor has an IC50 of less than about 1 µM.

141. The method of claim 22, wherein the DPP-IV inhibitor has an IC50 of less than about 100 nM.

142. The method of claim 22, wherein the DPP-IV inhibitor is orally active and has an IC50 of less than about 100 nM.

143. The method of claim 22, wherein the DPP-IV inhibitor is an inhibitor of human DPP-IV.

144. The method of claim 22, wherein the GPR119 agonist is orally active and has an EC50 of less than about 100 nM, and the DPP-IV inhibitor is orally active and has an IC50 of less than about 100 nM.

145. The method of claim 22, wherein the GPR119 agonist has a selectivity for GPR119 over corticotrophin releasing factor-1 (CRF-1) receptor of at least about 100-fold, and the DPP-IV inhibitor has a selectivity for human plasma DPP-IV over one or more of PPCE, DPP-II, DPP-8 and DPP-9 of at least 100-fold.

146. The method of claim 22, wherein the DPP-IV inhibitor is:
MK-0431: 3(R)-Amino-1-[3-(trifluoromethyl)-5,6,7,8-tetrahydro[1,2,4]triazolo[4,3-a]pyrazin-7-yl]-4-(2,4,5-trifluorophenyl)butan-1-one;
LAF237: (1-[[3-hydroxy-1-adamantyl)amino]acetyl]-2-cyano-(S)-pyrrolidine; or
BMS-477118: (1S,3S,5S)-2-[2(S)-Amino-2-(3-hydroxy-adamantan-1-yl)acetyl]-2 azabicyclo[3.1.0]hexane-3-carbonitrile.

147. The method of claim 24, wherein the condition is osteoporosis.

148. The method of claim 24, wherein the condition is rheumatoid arthritis.

149. The method of claim 24, wherein the condition is osteoarthritis.

150. The method of claim 24, wherein the condition is bone loss due to metastatic cancer.

151. The method of claim 25, wherein the GPR119 agonist is a selective GPR119 agonist.

152. The method of claim 25, wherein the GPR119 agonist has a selectivity for GPR119 over corticotrophin releasing factor-1 (CRF-1) receptor of at least about 100-fold.

153. The method of claim 25, wherein the GPR119 agonist has an EC50 of less than about 1 μM.

154. The method of claim 25, wherein the GPR119 agonist has an EC50 of less than about 100 nM.

155. The method of claim 25, wherein the GPR119 agonist is orally active.

156. The method of claim 25, wherein the GPR119 agonist is orally active and has an EC50 of less than about 100 nM.

157. The method of claim 25, wherein the GPR119 agonist and the DPP-IV inhibitor are administered in amounts sufficient to increase a GIP level in the individual.

158. The method of claim 25, wherein the individual is a human.

159. The method of claim 25, wherein the GPR119 agonist is an agonist of human GPR119 and/or the DPP-IV inhibitor is an inhibitor of human DPP-IV.

160. The method of claim 25, wherein the GPR119 agonist is a small molecule and/or the DPP-IV inhibitor is a small molecule.

161. The method of claim 25, wherein the GPR119 agonist has an $EC_{50}$ of less than about 10 μM and/or the DPP-IV inhibitor has an $IC_{50}$ of less than about 10 μM.

162. The method of claim 25, wherein the DPP-IV inhibitor is a selective DPP-IV inhibitor.

163. The method of claim 25, wherein the DPP-IV inhibitor is orally active.

164. The method of claim 25, wherein the DPP-IV inhibitor has an IC50 of less than about 10 μM.

165. The method of claim 25, wherein the DPP-IV inhibitor has an IC50 of less than about 1 μM.

166. The method of claim 25, wherein the DPP-IV inhibitor has an IC50 of less than about 100 nM.

167. The method of claim 25, wherein the DPP-IV inhibitor is orally active and has an IC50 of less than about 100 nM.

168. The method of claim 25, wherein the DPP-IV inhibitor is an inhibitor of human DPP-IV.

169. The method of claim 25, wherein the GPR119 agonist is orally active and has an EC50 of less than about 100 nM, and the DPP-IV inhibitor is orally active and has an IC50 of less than about 100 nM.

170. The method of claim 25, wherein the GPR119 agonist has a selectivity for GPR119 over corticotrophin releasing factor-1 (CRF-1) receptor of at least about 100-fold, and the DPP-IV inhibitor has a selectivity for human plasma DPP-IV over one or more of PPCE, DPP-II, DPP-8 and DPP-9 of at least 100-fold.

171. The method of claim 25, wherein the DPP-IV inhibitor is:
MK-0431: 3(R)-Amino-1-[3-(trifluoromethyl)-5,6,7,8-tetrahydro[1,2,4]triazolo[4,3-a]pyrazin-7-yl]-4-(2,4,5-trifluorophenyl)butan-1-one;
LAF237: (1-[[3-hydroxy-1-adamantyl)amino]acetyl]-2-cyano-(S)-pyrrolidine; or
BMS-477118: (1S,3S,5S)-2-[2(S)-Amino-2-(3-hydroxy-adamantan-1-yl)acetyl]-2 azabicyclo[3.1.0]hexane-3-carbonitrile.

* * * * *

UNITED STATES PATENT AND TRADEMARK OFFICE
CERTIFICATE OF CORRECTION

PATENT NO. : 7,816,364 B2  Page 1 of 1
APPLICATION NO. : 11/989038
DATED : October 19, 2010
INVENTOR(S) : Zhi-Liang Chu et al.

It is certified that error appears in the above-identified patent and that said Letters Patent is hereby corrected as shown below:

ON THE TITLE PAGE:

Item (54), line 1, delete "GRP119" and insert -- GPR119 --.

IN THE SPECIFICATIONS:

Column 1, line 1, delete "GRP119" and insert -- GPR119 --.

Signed and Sealed this

Twenty-first Day of December, 2010

David J. Kappos
*Director of the United States Patent and Trademark Office*